(12) United States Patent
Chotani et al.

(10) Patent No.: US 8,470,581 B2
(45) Date of Patent: Jun. 25, 2013

(54) REDUCTION OF CARBON DIOXIDE EMISSION DURING ISOPRENE PRODUCTION BY FERMENTATION

(75) Inventors: Gopal K. Chotani, Cupertino, CA (US); Alex Nielsen, Rungsted Kyst (DK); Karl J. Sanford, Cupertino, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 592 days.

(21) Appl. No.: 12/560,317

(22) Filed: Sep. 15, 2009

(65) Prior Publication Data

US 2010/0167370 A1 Jul. 1, 2010

Related U.S. Application Data

(60) Provisional application No. 61/097,200, filed on Sep. 15, 2008.

(51) Int. Cl.
*C12N 1/20* (2006.01)
*C12P 21/00* (2006.01)

(52) U.S. Cl.
USPC ....................................... 435/252.3; 435/70.1

(58) Field of Classification Search
None
See application file for complete search history.

(56) References Cited

U.S. PATENT DOCUMENTS

| | | | |
|---|---|---|---|
| 4,570,029 A | 2/1986 | Kulprathipanja et al. | |
| 4,652,527 A | 3/1987 | Stirling | |
| 4,683,202 A | 7/1987 | Mullis | |
| 4,703,007 A | 10/1987 | Mulholland et al. | |
| 5,849,970 A | 12/1998 | Fall et al. | |
| 5,874,276 A | 2/1999 | Fowler et al. | |
| 6,022,725 A | 2/2000 | Fowler et al. | |
| 6,106,888 A | 8/2000 | Dale et al. | |
| 6,176,176 B1 | 1/2001 | Dale et al. | |
| 6,268,328 B1 | 7/2001 | Mitchinson et al. | |
| 7,132,527 B2 | 11/2006 | Payne et al. | |
| 7,241,587 B2 | 7/2007 | Dodge et al. | |
| 7,262,041 B2 | 8/2007 | Baldwin et al. | |
| 2009/0203102 A1* | 8/2009 | Cervin et al. ................. | 435/167 |
| 2010/0048964 A1 | 2/2010 | Calabria et al. | |
| 2010/0113846 A1* | 5/2010 | McAuliffe et al. ............ | 585/16 |
| 2010/0167370 A1* | 7/2010 | Chotani et al. ................ | 435/167 |
| 2010/0196977 A1* | 8/2010 | Chotani et al. ................ | 435/158 |
| 2011/0014672 A1* | 1/2011 | Chotani et al. ................ | 435/167 |
| 2011/0159557 A1* | 6/2011 | Beck et al. .................... | 435/146 |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| WO | WO-95/04134 A1 | 2/1995 |
| WO | WO-96/35796 A1 | 11/1996 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2005/001036 A2 | 1/2005 |
| WO | WO-2005/001036 C1 | 1/2005 |
| WO | WO-2008/003078 A2 | 1/2008 |
| WO | WO-2008/003078 A3 | 1/2008 |
| WO | WO-2008/003078 A8 | 1/2008 |
| WO | WO-2009/076676 A2 | 6/2009 |
| WO | WO-2009/076676 A3 | 6/2009 |
| WO | WO-2010/003007 A2 | 1/2010 |
| WO | WO-2010/003007 A3 | 1/2010 |

OTHER PUBLICATIONS

Alexopoulos, C.J. (1962). *Introductory Mycology*, Wiley: New York, NY, pp. ix-x, (Table of contents only).
Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia*," *J. Biol. Chem.* 264(32):19169-19175.
Ausubel, F.M. et al. eds. (1994). Current Protocols in Molecular Biology, John Wiley and Sons, Inc., pp. 1-7, (Table of Contents Only).
Bellion, E. et al. (1993). "Methylamine Utilization in Yeast and Bacteria: Studies Using in vivo NMR," Chapter 32 *in Microbial Growth $C_1$ Compounds*, Muerrell, J.C. et al. eds, Intercept Ltd: Andover, UK, pp. 415-432.
Bennett, J.W. et al. eds. (1991). "Gene Cloning and Analysis," Chapter 3 *in More Gene Manipulations in Fungi*, Academic Press, San Diego, CA pp. 70-76.
Boel, E. et al. (1984). "Two Different Types of Intervening Sequences in the Glucoamylase Gene from *Aspergillus niger*," *The EMBO Journal* 3(7):1581-1585.
Bouvier, F. et al. (2005). "Biogenesis, Molecular Regulation and Function of Plant Isoprenoids," *Progress in Lipid Res.* 44:357-429.
Campbell, E.I. et al. (1989). "Improved Transformation Efficiency of *Aspergillus niger* Using the Homologus *niaD* Gene for Nitrate Reductase," *Curr. Genet.* 16:53-56.
Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Crueger, W. et al. (1989). *Biotechnology: A Textbook of Industrial Microbiology*, Second Edition, Brock, T.D. ed., Sinauer Associates, Inc.: Sunderland, MA, pp. vii-x (Table of contents Only).
Dhe-Paganon, S. et al. (1994). "Mechanism of Mevalonate Pyrophosphate Decarboxylase: Evidence for a Carbocationic Transition State," *Biochemistry* 33(45):13355-13362.
Finkelstein, D.B. (1992). "Transformation," Chapter 6 *in Biotechnology of Filamentous Fungi*, Butterworth-Heinemann: Boston, MA, pp. 113-156.

(Continued)

*Primary Examiner* — Anand Desai
(74) *Attorney, Agent, or Firm* — Morrison & Foerster LLP

(57) ABSTRACT

The present invention provides methods for increasing the amount of isoprene produced by cultured cells with only a minimal increase in carbon dioxide emitted, thereby resulting in process having a greater yield of isoprene relative to carbon dioxide. In addition, the present invention provides compositions that include the cultured cells or isoprene produced there from.

16 Claims, 195 Drawing Sheets

OTHER PUBLICATIONS

GenBank Accession No. AAQ84170, last updated on Feb. 15, 2005, located at < http://www.ncbi.nlm.nih.gov/protein/AAQ84170>, last visited on Dec. 22, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. CAC35696, last updated Apr. 15, 2005, located at <http://www.ncbi.nlm.nih.gov/protein/CAC35696>, last visited on Nov. 1, 2011, 2 pages.

GenBank Accession No. NC_003901.1, last updated May 11, 2011, located at <http://www.ncbi.nlm.nih.gov/nuccore/NC_003901.1>, last visited on Oct. 27, 2011, 360 pages.

Gerhardt, P. et al. eds. (1994). Methods for General and Molecular Bacteriology, American Society for Microbiology: Washington, D.C., p. v, (Table of Contents Only).

Gottschalk, G. (1986). Bacterial Metabolism, Second Edition, Springer Verlag: New York, NY, pp. xi-xiii, (Table of Contents Only).

Gräwert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chormatograph," *Atmos. Environ.* 27A(16):2689-2692.

Hale, W.G. et al. (1991). The Harper Collins Dictionary of Biology, Ehrlich, E. ed., Harper Perennial: New York, NY, 2 pages.

Harkki, A. et al. (Jun. 1989). "A Novel Fungal Expression System: Secretion of Active Calf Chymosin From the Filamentous Fungus *Trichoderma ressei*," *Bio. Technol.* 7:596-603.

Harkki, A. et al. (Mar. 1991). "Genetic Engineering of *Trichoderma* to Produce Strains with Novel Cellulase Profiles," *Enzyme Microb. Technol.* 13:277-233.

Hedl, M. et al. (Apr. 2002). "*Enterococcus faecalis* Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol.* 184(8):2116-2122.

Hoeffler, J-F. et al. (2002). "Isoprenoid Biosynthesis via the Methylerythritol Phosphate Pathway. Mechanistic Investigations of the 1-Deoxy-$_D$-Xylulose 5-Phosphate Reductoisimerase," *Eur. J. Biochem.* 269:4446-4457.

Hunter, B.K. (1985). "Formaldehyde Metabolism by *Escherichia coli*. Carbon and Solvent Deuterium Incoproration into Glycerol, 1,2-Propanediol, and 1,3-Propanediol," *Biochemistry* 24(15):4148-4155.

Ilmen, M. et al. (Apr. 1997). "Regulation of Cellulase Gene Expression in the Filamentous Fungus *Trichoderma reesei*," *Appl. Environ. Microbiol.* 63(4):1298-1306.

Julsing, M.K. et al. (2007). "Functional Analysis of Genes Involved in the Biosynthesis of Isoprene in *Bacillus subtilis*," *Applied Microbiol. Biotechnol.* 75:1377-1384.

Kelly, J.M. et al. (1985). "Transformation of *Aspergillus niger* by the amdS Gene of *Asperfillus nidulans*," *The EMBO Journal* 4(2):475-479.

Kinghorn, J.R. et al. (1992). Applied Molecular Genetics of Filamentous Fungi, Blackie Academic Professional and Chapman and Hall: London, 3 pages, (Table of Contents Only).

Koga, Y. et al. (Mar. 2007). "Biosynthesis of Ether-Type Polar Lipids in Archaea and Evolutionary Considerations," *Microbiology and Molecular Biology Reviews* 71(1):97-120.

Kreigler, M. (1990). Gene Transfer and Expression: A Laboratory Manual, W.H. Freeman and Company: New York, NY, pp. vii-x, (Table of Contents Only.).

Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-$_D$-Erythritol," *PNAS* 97(3):1062-1067.

Maury, J. et al. (2005). "Microbial Isoprenoid Production: An Example of Green Chemistry through Metabolic Engineering," *Adv. Biochem. Engin/Biotechnol.* 100:19-51.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Neidhardt, F.C. et al. (Sep. 1974). "Culture Medium for Enterobacteria," *J. Bacteriology* 119(3):736-747.

Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Pourquie, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.

Rohdih, F. et al. (Jun. 6, 2000). "Biosynthesis of Terpenoids: 4-Diphosphocytidyl-2C-Methyl-$_D$-Erythritol Synthase of *Arabidopsis thaliana*," *PNAS* 97(12):6451-6456.

Sambrook, J. et al. (1989). Molecular Cloning: A Laboratory Manual, 2nd edition, Cold Spring Harbor Laboratory Press: New York, NY, pp. xi-xxxviii (Table of Contents Only).

Schnitzler, J.-P. et al. (2005, e-pub. Jul. 29, 2005). "Biochemical Properties of Isoprene Synthase in Poplar (*Populus x canescens*)," *Planta* 222(5):777-786.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Ceullulases of *Trichoderma ressei* Wild Type and Mutants During Controlled Fermentations," *Appl. Microbiol. Biotechnol.* 20(1):46-53.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sprenger, G.A. et al. (Nov. 1997). "Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol," *PNAS* 94:12857-12862.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.

Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell Biol.* 11(2):620-631.

Van Den Hondel, C.A.M.J.J. et al. (1991). "Heterologous Gene Expression in Filamentous Fungi," Chapter 18 *in More Gene Manipulations in Fungi*, Bennet, J.W. et al. eds., Academic Press, Inc.: San Diego, CA, pp. 396-428.

Withers, S.T. et al. (Oct. 2007, e-pub. Aug. 10, 2007). "Identification of Isopentenol Biosynthetic from *Bacillus subtilis* by a Screening Method Based on Isorpenoid Precursor Toxicity," *Appl. Environ Microbiol.* 73(19):6277-6283.

Yamada, K. et al. (1989). "Production of Glycerol from Methanol by a Mutant Strain of *Candida boidinii* No. 2201," *Agric. Biol. Chem.* 53(2):541-543.

Yelton, M.M. et al. (Mar. 1984). "Transformation of *Aspergillus nidulans* by Using a *trpC* Plasmid," *PNAS* 81:1470-1474.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

* cited by examiner

Figure 1

1-
*at*gtgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggatttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttcccgattaaccagctgatgtatgtc
taa*ctgcag*
(SEQ ID NO:1)

Figure 3A 1-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattataaaaattaaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggatttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtcTAActgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctcccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcgggcaggacgcccgccataaactgccaggcatcaaattaagcagaaggccatcctg
acggatggcctttttgcgtttctacaaactcttttttgtttattttttctaaatacattcaaatat
gtatccgctcatgagacaataaccctgataaatgcttcaataatattgaaaaaggaagagtatg
agtattcaacatttccgtgtcgcccttattcccttttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatactttagattga
tttaaaacttcatttttaatttaaaaggatctaggtgaagatccttttgataatctcatgacc
aaaatcccttaacgtgagttttcgttccactgagcgtcagacccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccaggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A

1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatcttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataattttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtccagcgctctacagcatcggtgaacagttgcagttcgtccagagtgc
cataaacgtcatacacgtcatcgatgatcgtcaccagaccaaacatttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtcttttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacgggaatta
tgctcggtaatctgagtaaattgagaagaggtcgcacacatatgacgaccttcgatatggccgc
tgctgtgatgatgatgatgatgatgatgatggccatggtatatctccttcttaaagttaa
acaaaattatttctagagggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggcccgtggccggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaccttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctcccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaaccccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgattttctct
ggtcccgccgcatccataccgccagttgtttaccctcacaacgttccagtaaccgggcatgttc
atcatcagtaacccgtatcgtgagcatcctctctcgtttcatcggtatcattaccccatgaac
agaaatcccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgttttccataggctccgccccctgacgagcatcacaaaaatcgacgctcaagtcaga

Figure 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggttttttttgtttgcaagcagcagattacg
cgcagaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaagggaataa
gggcgacacggaaatgttgaatactcatactcttccttttcaatattattgaagcatttatca
gggttattgtctcatgagcggatacatatttgaatgtatttagaaaaataaacaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A 1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaataaggaggaataaa
ccatgtgtgcgacctcttctcaatttactcagattaccgagcataatcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaagacatcattaaagccctggaaaacatcgtactgctggacgaaaacaaaaagaacaaa
tctgacctgcacgcaaccgctctgtctttcgtctgctgcgtcagcacggtttcgaggtttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtaccttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtccgctggt
ggaccgagatgggcctggctagcaaactggattttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgactttatggcactctggacgaactgcaac
tgttcaccgatgctgtagagcgctgggacgttaacgctattaaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttacttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatcccccttcgccagctggcgtaatagcgaagaggcccgcac
cgatcgcccttcccaacagttgcgcagcctgaatggcgaatggcgcctgatgcggtatttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaagccagcc
tttcatgatatctcccaatttgtgtagggcttattatgcacgcttaaaaataataaagcag
acttgacctgatagtttggctgtgagcaattatgtgcttagtcatctaacgcttgagttaagc
cgcgccgcgaagcggcgtcggcttgaacgaattgttagacattatttgccgactaccttggtga
tctcgccttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

Figure 7B

```
cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgattttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatctttttacaccgttttcatctgtgca
tatggacagttttcccttgatatgtaacggtgaacagttgttctacttttgtttgttagtctt
gatgcttcactgatagatacaagagccataagaacctcagatccttccgtatttagccagtatg
ttctctagtgtggttcgttgttttgcgtgagccatgagaacgaaccattgagatcatacttac
tttgcatgtcactcaaaaattttgcctcaaaactggtgagctgaattttttgcagttaaagcatc
gtgtagtgttttcttagtccgttatgtaggtaggaatctgatgtaatggttgttggtattttg
tcaccattcatttttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaatttttttaactggaaaagataaggcaat
atctcttcactaaaaactaattctaattttcgcttgagaacttggcatagtttgtccactgga
aaatctcaaagcctttaaccaaaggattcctgatttccacagttctcgtcatcagctctctggt
tgcttttagctaatacaccataagcattttccctactgatgttcatcatctgagcgtattggtta
taagtgaacgataccgtccgttcttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtccttttcctttgagttgtgggtatctgta
```

Figure 7C

Aattctgctagacctttgctggaaaacttgtaaattctgctagaccctctgtaaattccgctag
acctttgtgtgtttttttttgtttatattcaagtggttataatttatagaataaagaaagaataa
aaaaagataaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtcttttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)

Figure 9
A.
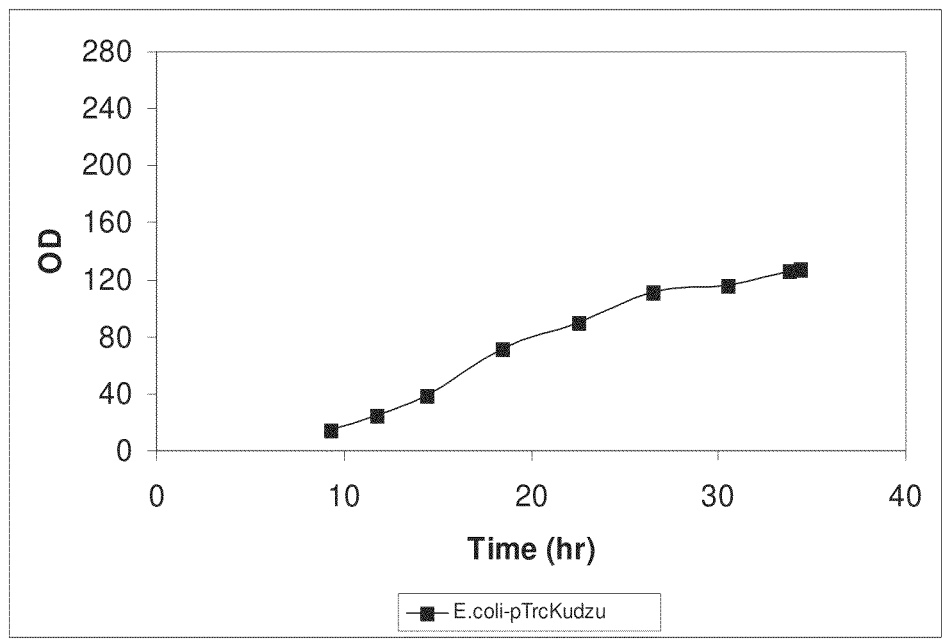
B.
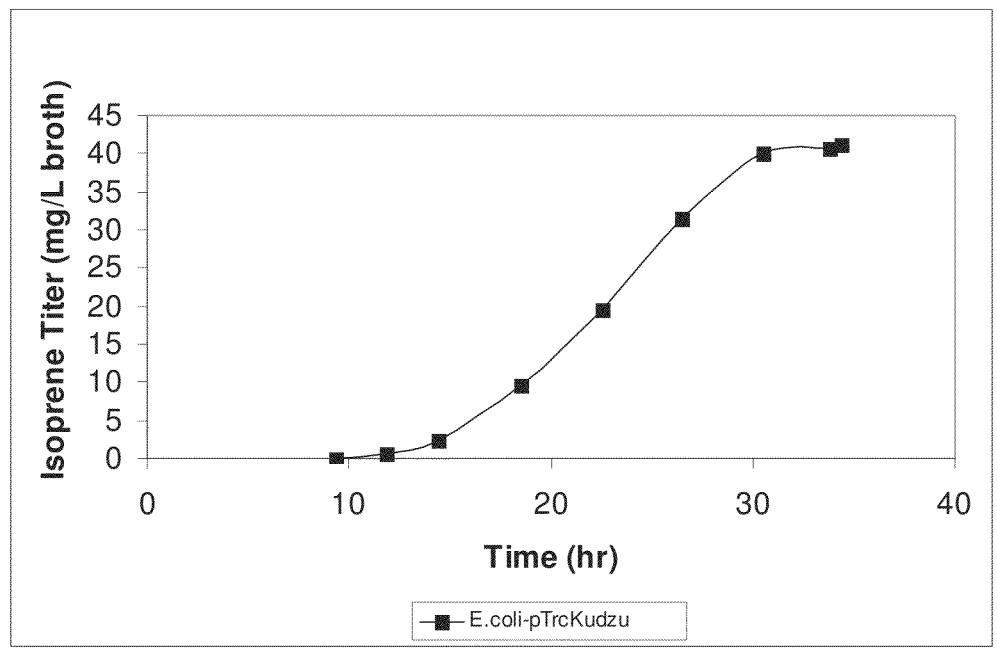

Figure 12A

1-
gaattgctccattttcttctgctatcaaaataacagactcgtgattttccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataattttttcattctatcccttttctgtaaagtttattttcagaatacttttatcatc
atgctttgaaaaaatatcacgataatatccattgttctcacggaagcacacgcaggtcatttga
acgaattttttcgacaggaatttgccgggactcaggagcatttaacctaaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgttttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtaccttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgacccttttcccgattaaccagctgatgtatgtctaa
aaaaaaccggccttggccccgccggttttttattattttttcttcctccgcatgttcaatccgct
ccataatcgacggatggctccctctgaaaattttaacgagaaacggcgggttgacccggctcag
tcccgtaacggccaagtcctgaaacgtctcaatcgccgcttccggtttccggtcagctcaatg
ccgtaacggtcggcggcgttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

Figure 12B

```
gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaagaaggatatggatctggagctgtaata
taaaaaccttcttcaactaacggggcaggttagtgacattagaaaaccgactgtaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaattttcctgctgtaataatgggtagaaggtaattacta
ttattattgatatttaagttaaacccagtaaatgaagtccatggaataatagaaagagaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcaccttgtcactaagaaaataaa
tgcagggtaaaatttatatccttcttgttttatgtttcggtataaaacactaatatcaatttct
gtggttatactaaaagtcgtttgttggttcaaataatgattaaatatctcttttctcttccaat
tgtctaaatcaattttattaaagttcatttgatatgcctcctaaattttatctaaagtgaatt
taggaggcttacttgtctgctttcttcattagaatcaatccttttttaaagtcaatattactgt
aacataaatatatattttaaaaatatcccactttatccaattttcgtttgttgaactaatgggt
gctttagttgaagaataaagaccacattaaaaatgtggtcttttgtgttttttaaaggatttt
gagcgtacgcgaaaaatcctttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattccttttcagataattttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataattttccgttcccaattccacattgcaataatagaaaatccatcttcatcggct
ttttcgtcatcatctgtatgaatcaaatcgccttcttctgtgtcatcaaggtttaatttttat
gtatttcttttaacaaaccaccataggagattaaccttttacggtgtaaaccttcctccaaatc
agacaaacgtttcaaattcttttcttcatcatcggtcataaaatccgtatcctttacaggatat
tttgcagtttcgtcaattgccgattgtatatccgatttatatttattttcggtcgaatcattt
gaacttttacatttggatcatagtctaatttcattgcctttttccaaaattgaatccattgttt
```

Figure 12C

```
ttgattcacgtagttttctgttattctaaaataagttggttccacacataccattacatgcatg
tgctgattataagaattatctttattatttattgtcacatccgttgcacgcataaaaccaacaa
gatttttattaatttttttatattgcatcattcggcgaaatccttgagccatatctgtcaaact
cttatttaattcttcgccatcataaacattttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaccacactcgataccactttctttc
gcctgtttcacgattttgtttatactctaatatttcagcacaatcttttactctttcagccttt
ttaaattcaagaatatgcagaagttcaaagtaatcaacattagcgattttcttttctctccatg
gtctcacttttccacttttttgtcttgtccactaaaacccttgattttcatctgaataaatgct
actattaggacacataatattaaaagaaaccccatctatttagttatttgtttagtcacttat
aactttaacagatggggttttctgtgcaaccaattttaagggttttcaatactttaaaacaca
tacataccaacacttcaacgcacctttcagcaactaaaataaaaatgacgttatttctatatgt
atcaagataagaaagaacaagttcaaaaccatcaaaaaaagacacctttcaggtgcttttttt
attttataaactcattccctgatctcgacttcgttcttttttacctctcggttatgagttagt
tcaaattcgttcttttaggttctaaatcgtgttttcttggaattgtgctgttttatcctttta
ccttgtctacaaacccctttaaaaacgttttttaaaggcttttaagccgtctgtacgttccttaag
```

(SEQ ID NO:57)

Figure 13

```
ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
```
(SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCAACC TCCCATTTCC TCCTTACGGC CCGATAGCGA
 301 TCGTCTTTCC CTCGCTATCA CTCGCTACCG GCCCTCCTC TGCACCGTAA CCTCCTACGT
 361 ATTTACCATA TCATAAAGTT TTTTCCGACG CTTATCGCTG ACCCCTGTC GCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```
(SEQ ID NO:11)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA ATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:12)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```
(SEQ ID NO:13)

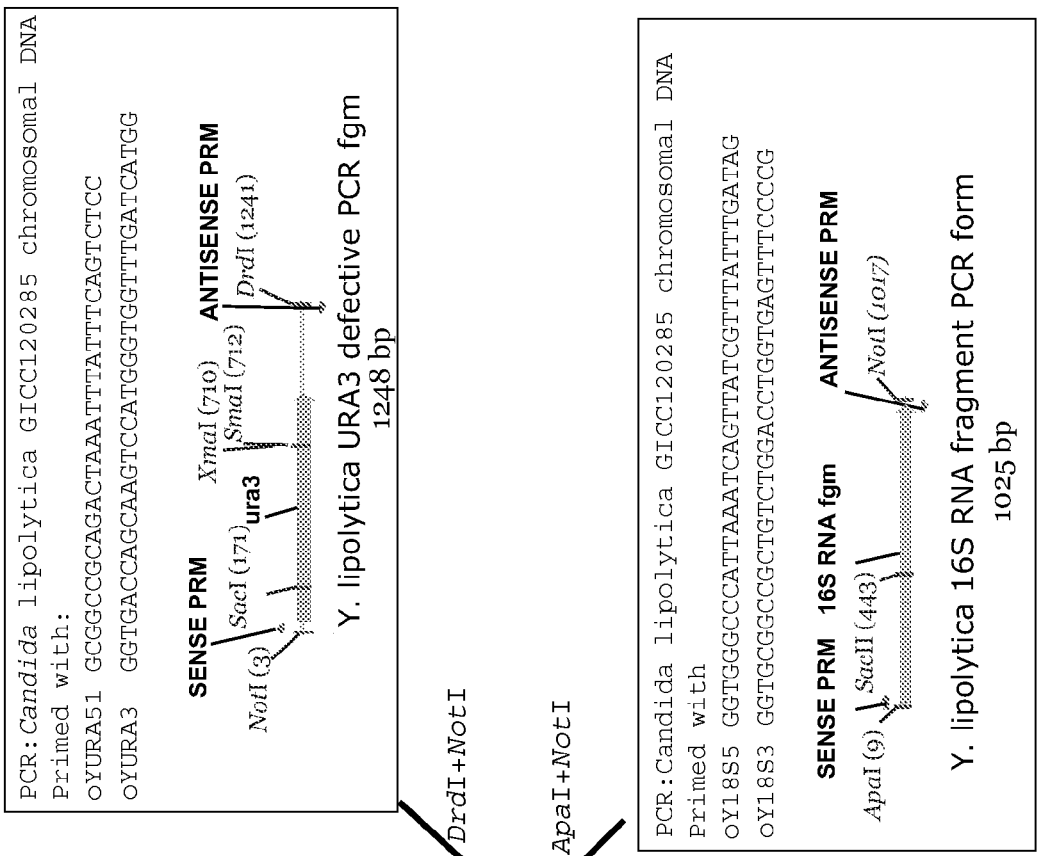
Figure 18A1

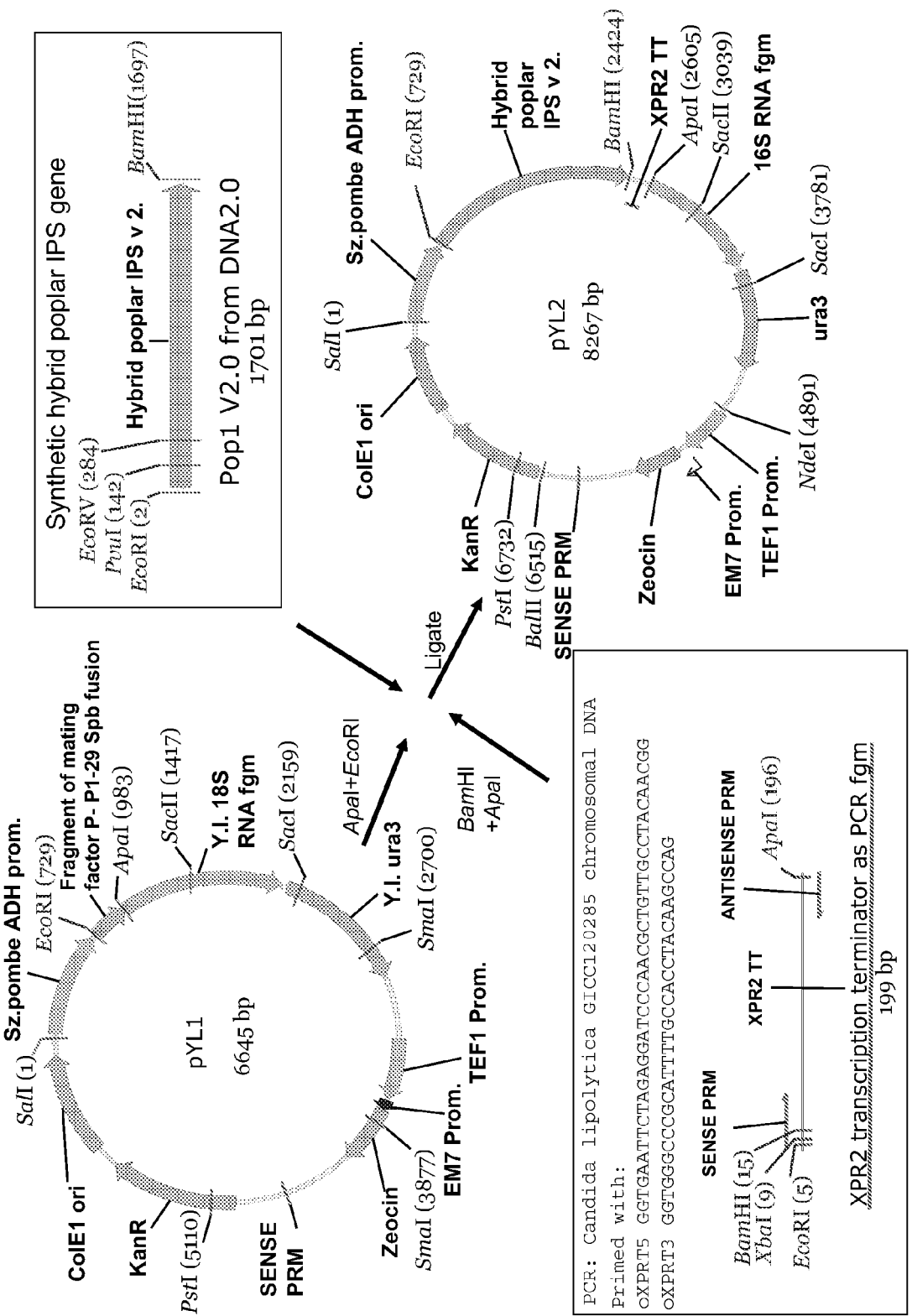
Figure 18A2

Figure 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgacccatgccgaactcagaagtg
aaacgccgtagcgccgatggtagtgtgggtctcccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggccttttttgcgtttctacaaactcttttgtttattttctaaatacattcaaatat
gtatccgcttaaccggaattgccagctggggcgccctctggtaaggttgggaagccctgcaaag
taaactggatggctttctcgccgccaaggatctgatggcgcagggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttcttttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatccttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccaggggaaacgcctggtatctttatagtcc
tgtcgggtttcgccacctctgacttgagcgtcgattttgtgatgctcgtcagggggcggagc
ctatggaaaaacgccagcaacgcggcctttttacggttcctggccttttgctggccttttgctc
acatgttcttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaaaccttcgcggtatggcatgatagcgcccggaaga

Figure 22B

```
gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaagacatcattaaagccctggaaaacatcgtactgctggac
gaaaacaaaagaacaaatctgacctgcacgcaaccgctctgtcttccgtctgctgcgtcagc
acggtttcgaggtttctcaggatgttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtacctttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta
```

Figure 22C

```
tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgacccttttccgattaaccagctgatgtatgtctaactgcatcgccctt
aggaggtaaaaaaaatgactgccgacaacaatagtatgcccatggtgcagtatctagttacg
ccaaattagtgcaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaaggcgctattactgcggc
ggtgagaaaactagatcatgaattaggtattccagaagatgaaactaagacaaggggtaagttt
cacttttttaaacagaatccattacatggcaccaagcaatgaaccatggggtgaacatgaaattg
attacatcctatttataagatcaacgctaaagaaaacttgactgtcaacccaaacgtcaatga
agttagagacttcaaatggggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctgggcttatcaccacgctaaagaacatgc
gcgacctgaaaggcccgcagttcctgcatatcatgaccaaaaaggtcgtggttatgaaccggc
agaaaaagacccgatcactttccacgccgtgcctaaatttgatcctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgacctttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
```

Figure 22D

```
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
```
(SEQ ID NO:20)

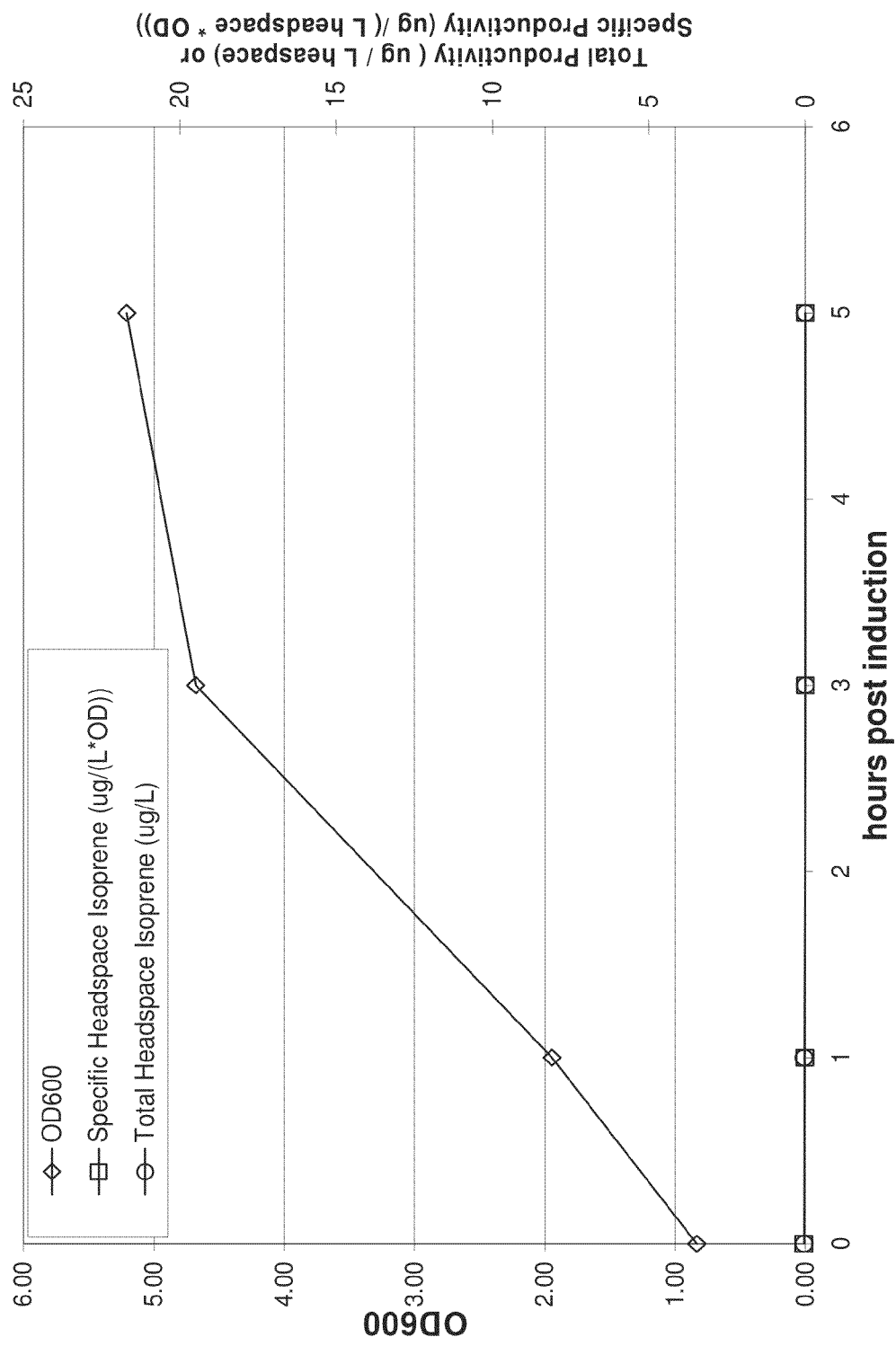

Figure 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaagaggtatatattaat
gtatcgattaaataaggaggaataaaccatggatccgagctcggatccactagtaacggccgcc
agtgtgctggaattcgcccttaggaggtaaaaaacatgtcattaccgttcttaacttctgcac
cgggaaaggttattattttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgccccatgccaagaatattaagttttctttaaagt
ctactttacccatcggtgctggttgggctcaagcgcctctatttctgtatcactggccttagc
tatggcctacttggggggttaataggatctaatgacttggaaaagctgtcagaaacgataag
catatagtgaatcaatgggccttcataggtgaaagtgtattcacggtacccttcaggaatag
ataacgctgtggccacttatggtaatgccctgctatttgaaaagactcacataatggaacaat
aaacacaaacaattttaagttcttagatgatttcccagccattccaatgatcctaacctatact
agaattccaaggtctacaaagatcttgttgctcgcgttcgtgtgttggtcaccgagaaatttc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaagaaattgcaagatgattttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaagtaaacaatttaaag
atggggagtggctgtaccatataagtcctaaaagtggcttcattcctgtttcgataggcggatc
taagaaccctttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctggctcctcggcaggtttagtcacagttttaactacagctttggcc
tcctttttgtatcggacctggaaaataatgtagacaaatatagagaagttattcataatttag
cacaagttgctcattgtcaagctcagggtaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatgggcgatattaagaatggttcagaaac
agtaaaactggtccagaaggtaaaaaattggtatgattcgcatatgccagaaagcttgaaaata

Figure 25B

```
tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaataactaaagaatctggtgccgatatcgaacctcccgtacaaactagcttattggatgatt
gccagaccttaaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactggggtgttaggaaagaaaaagatccggaaactt
atcttgataaataacttaaggtagctgcatgcagaattcgcccttaaggaggaaaaaaaaatga
ccgtttacacagcatccgttaccgcacccgtcaacatcgcaacccttaagtattggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aaccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaggatgtgagttccactcagggtatgcaattgac
cgtggcaacctccgaactatttaaagaaagaattgaacatgtcgtaccaaagagatttgaagtc
atgcgtaaagccattgttgaaaagatttcgccacctttgcaaaggaaacaatgatggattcca
actctttccatgccacatgtttggactcttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttatttttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatggggtgaacatgaaattgattaca
tcctattttataagatcaacgctaagaaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaattcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg
```

Figure 25C atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtcttccgtctgctgcgtcagcac
ggtttcgaggtttctcaggatgttttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatccaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgacccttcccgattaaccagctgatgtatgtctaactgcagctggtacca
tatgggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtgggtctcccatgcgagagtagggaactgccaggcatcaaataaaac
gaaaggctcagtcgaaagactgggccttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
tttttgcgtttctacaaactcttttgtttattttctaaatacattcaaatatgtatccgctt
aaccggaattgccagctggggcgccctctggtaaggttgggaagccctgcaaagtaaactggat
ggctttctcgccgccaaggatctgatggcgcagggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttcttttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcagggctcgcgcc
agccgaactgttcgccaggctcaaggcgagcatgcccgacggcgaggatctcgtcgtgacccat

Figure 25D ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagacccgtagaaaagatcaaggatcttcttgagatccttt
ttttctgcgcgtaatctgctgcttgcaaacaaaaaaccaccgctaccagcggtggtttgtttg
ccggatcaagagctaccaactcttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacgggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccagggggaaacgcctggtatctttatagtcctgtcgggt
ttcgccacctctgacttgagcgtcgattttgtgatgctcgtcagggggcggagcctatggaa
aaacgccagcaacgcggccttttacggttcctggccttttgctggccttttgctcacatgttc
tttcctgcgttatcccctgattctgtggataaccgtattaccgcctttgagtgagctgataccg
ctcgccgcagccgaacgaccgagcgcagcgagtcagtgagcgaggaagcggaagagcgcctgat
gcggtatttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaaccttcgcggtatggcatgatagcgcccggaagagagtcaat
tcagggtggtgaatgtgaaaccagtaacgttatacgatgtcgcagagtatgccggtgtctctta
tcagaccgtttcccgcgtggtgaaccaggccagccacgtttctgcgaaaacgcgggaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctggggcaaaccagcgtggaccgcttgctgcaactctctcagggccaggcggtgaagggca
atcagctgttgcccgtctcactggtgaaagaaaaaccaccctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg (SEQ ID NO:33)

Figure 27A

5'-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttattttggcgaaacaattgattcaattaggagaagcggaagtttt
aattgctggcggattgagaatatgtcccaagcacctaaattacaacgttttaattacgaaaca
gaaagctacgatgcgccttttctagtatgatgtatgatggattaacggatgcctttagtggtc
aggcaatgggcttaactgctgaaaatgtggccgaaaagtatcatgtaactagagaagagcaaga
tcaattttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagttttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaagaaaagaaata
tggagtggcttctttatgtatcggcggtggcttaggactcgctatgctactagagagacctcag
caaaaaaaaacagccgatttttatcaaatgagtcctgaggaacgcctggcttctcttcttaatg
aaggccagatttctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgttttttacgatgttgcagatcccgagtcattgattgataaactacaagtaagagaa
gcggaagttttcaacaagcagagttaagttatccatctatcgttaaacggggcggcggcttaa
gagatttgcaatatcgtacttttgatgaatcatttgtatctgtcgactttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaggacacatggctctacaagcacgttctttagcgatgacggtcggagctact
ggtaaagaagttgaggcagtcgctcaacaattaaaacgtcaaaaaacgatgaaccaagaccgag
ccatggctatttaaatgatttaagaaaacaataaaggaggtaaaaaaacatgacaattgggat

Figure 27B

```
tgataaaattagttttttgtgcccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaacctttcgctcgctctttcgaaatcaaggaagcttgtt
acggagcaacagcaggcttacagttagctaagaatcacgtagccttacatccagataaaaagt
cttggtcgtagcggcagatattgcaaaatatggcttaaattctggcggtgagcctacacaagga
gctggggcggttgcaatgttagttgctagtgaaccgcgcattttggctttaaagaggataatg
tgatgctgacgcaagatatctatgacttttggcgtccaacaggccacccgtatcctatggtcga
tggtcctttgtcaaacgaaacctacatccaatcttttgcccaagtctgggatgaacataaaaa
cgaaccggtcttgattttgcagattatgatgctttagcgttccatattccttacacaaaaatgg
gcaaaaaagccttattagcaaaaatctccgaccaaactgaagcagaacaggaacgaattttagc
ccgttatgaagaaagtatcgtctatagtcgtcgcgtaggaaacttgtatacgggttcactttat
ctgggactcatttcccttttagaaaatgcaacgactttaaccgcaggcaatcaaattggtttat
tcagttatggttctggtgctgtcgctgaattttcactggtgaattagtagctggttatcaaaa
tcatttacaaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgacccatgccgaactcagaagtgaa
acgccgtagcgccgatggtagtgtggggtctccccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggccttttttgcgtttctacaaactctttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagattttaatgcggatgttgcgattacttcgccaactattgcgataacaagaaaaagc
cagccttccatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttggcgcgattttccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
```

Figure 27C

```
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgacccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttttccccacggggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttttacaccgttttcatct
gtgcatatggacagttttccctttgatatgtaacggtgaacagttgttctacttttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaattttttgcagttaaa
gcatcgtgtagtgttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaattttcgcttgagaacttggcatagtttgtcca
ctggaaaatctcaaagccttaaccaaaggattcctgatttccacagttctcgtcatcagctct
ctggttgctttagctaatacaccataagcattttccctactgatgttcatcatctgagcgtatt
ggttataagtgaacgataccgtccgttcttccttgtagggttttcaatcgtggggttgagtag
tgccacacagcataaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaacttgtaaattctgctagaccctctgtaaattcc
gctagacctttgtgtgtttttttgtttatattcaagtggttataatttatagaataaagaaag
aataaaaaagataaaagaatagatcccagccctgtgtataactcactactttagtcagttcc
gcagtattacaaaggatgtcgcaaacgctgtttgctcctctacaaaacagaccttaaaaccct
aaaggcttaagtagcaccctcgcaagctcgggcaaatcgctgaatattccttttgtctccgacc
```

Figure 27D

Atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Figure 29A

5'-
tgtaacctttgctttcaaatgagtagaaataatgcacatccatgtttgtatcgtgcaaataaag
tgtttcatccgtaggaaaaaatgactttagtatctgttccgcttttctgatgaaatgtgctcc
ccgacaaaattgaatgaatcatggacatttgctggctttgatacagcgaaagcagccgttccta
tgttatatatcggatttaacagcaggacaaaaaacaccatgacagccatcgtcacccacttatt
cacacgcacataaacctttcctgacttttggaacagatgatagctcatcaaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatcccatccgggtattccttccaatacgaaagaaactaaaaa
tcatttgtacgatcggcaaactgacaacagcaaggtcgaacgtataaaacttacccttccgcc
atgatcacgcggcatcagcatatagtgaaaagccgtcagcagcacatatccgtataacaaaaaa
tgcagcagcggcagcagttcttttccgtcctctcttaagtaagcgctggtgaagtttgttgatt
gcacctggtgaataagttcaacagacactcccgccagcagcacaatccgcaatataacacccgc
caagaacattgtgcgctgccggtttattttgggatgatgcaccaaaagatataagcccgccaga
acaacaattgaccattgaatcagcagggtgctttgtctgcttaatataaaataacgttcgaaat
gcaatacataatgactgaataactccaacacgaacaacaactccatttttcttctgctatcaaaa
taacagactcgtgattttccaaacgagctttcaaaaaagcctctgccccttgcaaatcggatgc
ctgtctataaaattcccgatattggttaaacagcggcgcaatgcggccgcatctgatgtcttt
gcttggcgaatgttcatcttatttcttcctccctctcaataatttttttcattctatccctttttc
tgtaaagtttattttttcagaatacttttatcatcatgctttgaaaaaatatcacgataatatcc
attgttctcacggaagcacacgcaggtcatttgaacgaattttttcgacaggaatttgccggga
ctcaggagcatttaacctaaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaatgggtctactaaaatattattccatctattac
aataaattcacagaatagtcttttaagtaagtctactctgaatttttttaaaaggagagggtaa
agagtgtcattaccgttcttaacttctgcaccgggaaaggttattatttttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagttttctttaaagtctactttacccatcggtgctgggttgggctcaa
gcgcctctatttctgtatcactggccttagctatggcctacttgggggggttaataggatctaa
tgacttggaaaagctgtcagaaaacgataagcatatagtgaatcaatgggccttcataggtgaa
aagtgtattcacggtaccccttcaggaatagataacgctgtggccacttatggtaatgccctgc
tatttgaaaaagactcacataatggaacaataaacacaaacaattttaagttcttagatgattt
cccagccattccaatgatcctaacctatactagaattccaaggtctacaaagatcttgttgct
cgcgttcgtgtgttggtcaccgagaaatttcctgaagttatgagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctctttgactttgtt
acgaagagacattactcaagagcaaattgacagcttcaaaaagaaattgcaagatgattttagt

Figure 29B

```
tacgagacatttgaaacagacttgggtgggactggctgctgtttgttaagcgcaaaaaatttga
ataaagatcttaaaatcaaatccctagtattccaattatttgaaaataaaactaccacaaagca
acaaattgacgatctattattgccaggaaacacgaatttaccatggacttcataaaaggagagg
gtgtcagagttgagagccttcagtgcccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaaccctttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
cttttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
ataactaaagaatctggtgccgatatcgaacctcccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagattttctaaggt
tcaatggctggatgtaactcaggctgactggggtgttaggaaagaaaaagatccggaaacttat
cttgataaataaaaggagagggtgaccgtttacacagcatccgttaccgcacccgtcaacatcg
caacccttaagtattggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaagggctctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaggatgtga
gttccactcagggtatgcaattgaccgtggcaacctccgaactatttaaagaaagaattgaaca
tgtcgtaccaaagagatttgaagtcatgcgtaaagccattgttgaaaaagatttcgccacctt
gcaaaggaaacaatgatggattccaactcttccatgccacatgtttggactcttt ccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggcttt caaccatcaatttgaatcatctaactttactgc
acgtgaattggatcttgagttgcaaaaggatgttgccagagtgattttaactcaagtcggttca
ggcccacaagaaacaaacgaatctttgattgacgcaaagactggtctaccaaaggaataaaagg
agagggtgactgccgacaacaatagtatgccccatggtgcagtatctagttacgccaaattagt
```

Figure 29C

```
gcaaaaccaaacacctgaagacattttggaagagtttcctgaaattattccattacaacaaaga
cctaatacccgatctagtgagacgtcaaatgacgaaagcggagaaacatgtttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttattttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaaggggtaagtttcactttttaa
acagaatccattacatggcaccaagcaatgaaccatggggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaccggccttggccccgccg
gttttttattattttcttcctccgcatgttcaatccgctccataatcgacggatggctccctc
tgaaaattttaacgagaaacggcgggttgacccggctcagtccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaat
acttcggaaacatttaaaaaataaccttattggtacttacatgtttggatcaggagttgagagt
ggactaaaaccaaatagtgatcttgacttttagtcgtcgtatctgaaccattgacagatcaaa
gtaaagaaatacttatacaaaaattagacctatttcaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccattttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacataggggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgcttttctgatg
aaatgtgctccccgacaaaattgaatgaatcatggacatttgctggctttgatacagcgaaagc
agccgttcctatgttatatatcggatttaacagcaggacaaaaaacaccatgacagccatcgtc
acccacttattcacacgcacataaaccttcctgacttttggaacagatgatagctcatcaaaa
atcccgccattgccaaataaatcgtatatggcattactgcaccataatcttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
ccctttccgccatgatcacgcggcatcagcatatagtgaaaagccgtcagcagcacatatccgt
ataacaaaaatgcagcagcggcagcagttcttttccgtcctctcttaagtaagcgctggtgaa
gtttgttgattgcacctggtgaataagttcaacagacactcccgccagcagcacaatccgcaat
ataacacccgccaagaacattgtgcgctgccggttttatttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt
```

Figure 29D

Ataaaagctaatgattcagtccacataattgatagacgaattctgctacaggtcacgtggctat
gtgaaggatcgcgcgtccagttaagagcaaaaacattgacaaaaaaatttatttatgctaaaat
ttactattaatatatttgtatgtataataagattctcctggccaggggaatcttattttttgtg
gaggatcatttcatgaggaaaaatgagtccagcttaacgtctctaatttcagcttttgcccgtg
catatcacagccgatatgacacacctcttattttgatgattttatcgcaaaagatctcattaa
cgaaaagagtttatcgacatcagtaaaaatatgattcaagaaatatcgttttcaacaaagag
atcgccgaacgtcttcaaaatgatcctgaaaaatattaaatgggttgcacaaatccagctgt
ctccaacgccctagcacgtgcttcttattgtgaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcatttgttcctatggatttcaccaaaac
gttttcgtatgatctctcttagatgaaggatttaaaaacacaaaaacattcttcagccttctc
ggagtgtcttattatgtaacacgggaagaaatgcaagcttgatcagcaatttattttctcatg
tcccgcctggaagctctattgtttttgattatgcggacgaaacacttttacagcaaaagggac
gtcgaatcgagttgaacatatggtgaagatggctgccgcaagcggggaaccgatgaaatcatgt
ttcacttatcaagagattgaacatctg
(SEQ ID NO:47)

Figure 31A

5'-
tagaaaaactcatcgagcatcaaatgaaactgcaatttattcatatcaggattatcataccat
attttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaggacaattacaaacaggaatcgagtgcaaccggcgcaggaacactgccagcg
catcaacaatattttcacctgaatcaggatattcttctaatacctggaacgctgttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttcccgttgaatatggctcatattcttccttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacaccccttgtttgcctggcggcagtagcgcggtggtcccacctgac
cccatgccgaactcagaagtgaaacgccgtagcgccgatggtagtgtggggactcccatgcga
gagtagggaactgccaggcatcaaataaaacgaaaggctcagtcgaaagactgggcctttcgcc
cgggctaattagggggtgtcgcccttagtcgctgaacatgtgctctgtttctaccgagaacgt
ttccttcactgagacggaaaccgaggcacgtcgtagcgcgaactacgagccgaatagctgggac
tacgattcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctccgttggtggcgccgtgtgggcctggc
gaccaaactgcacttcgctaaggaccgcctgattgagtcttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgaccttgacgattatttcggcaatgcctggaaatccagctctggccgctg
caactgatcttcgcttattgcggttgtccaaaacatcaaaaggaggaaattgaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

Figure 31B

```
ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgcttttttctcatttataaggttaaataattctcatatatcaagcaaagt
gacaggcgcccttaaatattctgacaaatgctctttccctaaactcccccataaaaaacccg
ccgaagcgggttttttacgttatttgcggattaacgattactcgttatcagaaccgcccaggggg
cccgagcttaagactggccgtcgttttacaacacagaaagagtttgtagaaacgcaaaaaggcc
atccgtcaggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtgggctaactacggctacactagaagaacagtatttggtatctgcgctctgctga
agccagttaccttcggaaaaagagttggtagctcttgatccggcaaacaaaccaccgctggtag
cggtggttttttgtttgcaagcagcagattacgcgcagaaaaaaggatctcaagaagatcct
ttgatcttttctacggggtctgacgctcagtggaacgacgcgcgcgtaactcacgttaagggat
tttggtcatgagcttgcgccgtcccgtcaagtcagcgtaatgctctgcttt
```
(SEQ ID NO:48)

Figure 33A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
taccagcgtgatctgcgtgaaacctcccgttggtggcgccgtgtgggcctggcgaccaaactg
cacttcgctaaggaccgcctgattgagtcttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaggtgaaaacatcctgccgtacctgactaa
agcgtgggcggatctgtgtaacgcttttctgcaagaagcgaaatggctgtataacaaatccact
ccgaccttttgacgattatttcggcaatgcctggaaatccagctctggcccgctgcaactgatct
tcgcttatttttgcggttgtccaaaacatcaaaaaggaggaaattgaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttt
gcgtttctacaaactcttttgtttatttttctaaatacattcaaatatgtatccgctcatgag
acaataaccctgataaatgcttcaataatattgaaaaggaagagtatgagtattcaacatttc

Figure 33B

```
cgtgtcgcccttattccctttttgcggcattttgccttcctgttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgctttttgcacaacatggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagacccgtagaaaagatcaaaggatcttcttgagatcctt
ttttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccaggggaaacgcctggtatctttatagtcctgtcggg
tttcgccacctctgacttgagcgtcgatttttgtgatgctcgtcaggggggcggagcctatgga
aaaacgccagcaacgcggccttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc
```

Figure 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

Figure 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaaccttttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaagaacaaatctgacctgcacgcaaccgctctgtctttccgtctgct
gcgtcagcacggttttcgaggtttctcaggatgttttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagaccgcagtttggtg
aatgtcgcaaagctgttactaaaatgtttggtctggtgacgatcatcgatgacgtgtatgacgt

Figure 35B

```
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttcctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgacccttttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgttttctggtcatgatgaggagcaaattaagttaatgaatgaaattgtattgttttgga
ttgggacgataatgctattggtgccggtaccaagaaagtttgtcatttaatggaaaatattgaa
aagggtttactacatcgtgcattctccgtctttattttcaatgaacaaggtgaattacttttac
aacaaagagccactgaaaaaataactttccctgatctttggactaacacatgctgctctcatcc
actatgtattgatgacgaattaggtttgaaggtaagctagacgataagattaagggcgctatt
actgcggcggtgagaaaactagatcatgaattaggtattccagaagatgaaactaagacaaggg
gtaagtttcacttttttaaacagaatccattacatggcaccaagcaatgaaccatggggtgaaca
tgaaattgattacatcctatttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgacccatgccgaact
cagaagtgaaacgccgtagcgccgatggtagtgtggggtctccccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggccttttgcgtttctacaaactcttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcagggatcaagctct
gatcaagagacaggatgaggatcgtttcgcatgattgaacaagatggattgcacgcaggttctc
cggccgcttgggtggagaggctattcggctatgactgggcacaacagacaatcgctgctctga
tgccgccgtgttccggctgtcagcgcaggggcgcccggttcttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctatgggcgaagt
gccggggcaggatctcctgtcatctcaccttgctcctgccgagaaagtatccatcatggctgat
```

Figure 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaggat
cttcttgagatcctttttttctgcgcgtaatctgctgcttgcaaacaaaaaaaccaccgctacc
agcggtggtttgtttgccggatcaagagctaccaactcttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccaggggaaacgcctggtatctt
tatagtcctgtcgggtttcgccacctctgacttgagcgtcgattttgtgatgctcgtcagggg
ggcggagcctatggaaaaacgccagcaacgcggccttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:50)

Figure 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaaccttttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaagacatcattaaagccctggaaaacatcgtac
tgctggacgaaaacaaaagaacaaatctgacctgcacgcaaccgctctgtctttccgtctgct
gcgtcagcacggtttcgaggttctcaggatgttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

Figure 37B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttcctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgacccttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacacccgtttgaccaattgatttgggatg
tggggcatcaggcttatccgcataaaattttgaccggacgccgcgacaaaatcggcaccatccg
tcagaaaggcggtctgcacccgttccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggctttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgacctttt
gctgcgggtctggcgattggtggtacaaaccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

Figure 37C

```
gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggccttttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggccttttttgcgtttctacaaa
ctcttttttgtttattttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttcttttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagacccgtagaaaagatcaaggatcttcttgagatccttttttttctgcgcgtaatctg
ctgcttgcaaacaaaaaaaccaccgctaccagcggtggtttgtttgccggatcaagagctacca
actcttttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccagggggaaacgcctggtatctttatagtcctgtcgggtttcgccacctctgacttg
agcgtcgattttgtgatgctcgtcaggggggcggagcctatggaaaaacgccagcaacgcggc
cttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
```
(SEQ ID NO:51)

Figure 39A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagccttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcagggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagataagagccataagaacct
cagatccttccgtatttagccagtatgttctctagtgtggttcgttgttttgcgtgagccatg
agaacgaaccattgagatcatacttactttgcatgtcactcaaaaattttgcctcaaaactggt
gagctgaattttgcagttaaagcatcgtgtagtgttttcttagtccgttatgtaggtaggaa
tctgatgtaatggttgttggtattttgtcaccattcattttatctggttgttctcaagttcgg

Figure 39B

```
ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaattttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtaggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgctcacggctctggcagtgaatgggggtaaatggcactacaggcgccttttatggattc
atgcaaggaaactacccataatacaagaaagcccgtcacgggcttctcagggcgttttatggc
gggtctgctatgtggtgctatctgacttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct
```

Figure 39C

```
atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgacccttttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctcccatgcgaga
gtagggaactgccaggcatcaaataaaacgaaggctcagtcgaaagactgggcctttcgtttt
atctgttgtttgtcggtaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactcttttgtttatttt
tctaaatacattcaaatatgtatccgctcatgagacaataaccctgataaatgcttcaataat
```
(SEQ ID NO:52)

Figure 41A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagccttttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatcttttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgttttccaggtacttggagaaagccgggataattttgttgttggaccatttcgcct
cttgcagaaaggctttgcacagttcacgccagcttttcgtcagataggacaggttgttatgacc
tttctcttttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctcttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttcttttttgttttcgtccagcagtacgatgttttccagggctttaatgatgtctttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaattttaataataaagtta
atcgataattccggtcgagtgcccacacagattgtctgataaattgttaaagagcagtgccgct
tcgcttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 41B tgatgccgcatagttaagccagccccgacacccgccaacacccgctgacgagcttagtaaagcc
ctcgctagattttaatgcggatgttgcgattacttcgccaactattgcgataacaagaaaaagc
cagccttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactactt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacgaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgattttttccccacgggaggcgtcactggctccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatcttttacaccgttttcatct
gtgcatatggacagttttcccttttgatatgtaacggtgaacagttgttctacttttgtttgtta
gtcttgatgcttcactgatagatacaagagccataagaacctcagatccttccgtatttagcca
gtatgttctctagtgtggttcgttgttttgcgtgagccatgagaacgaaccattgagatcata
cttactttgcatgtcactcaaaaattttgcctcaaaactggtgagctgaattttgcagttaaa
gcatcgtgtagtgtttttcttagtccgttatgtaggtaggaatctgatgtaatggttgttggta
ttttgtcaccattcattttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc

Figure 41C cttgtgagttttcttttgtgttagttcttttaataaccactcataaatcctcatagagtatttg
ttttcaaaagacttaacatgttccagattatattttatgaattttttaactggaaaagataag
gcaatatctcttcactaaaaactaattctaattttcgcttgagaacttggcatagtttgtcca
ctggaaaatctcaaagccttttaaccaaaggattcctgatttccacagttctcgtcatcagctct
ctggttgctttagctaatacaccataagcattttccctactgatgttcatcatctgagcgtatt
ggttataagtgaacgataccgtccgttcttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgatttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgttttttttgtttatattcaagtggttataatttatagaataaagaaag
aataaaaaagataaaagaatagatcccagccctgtgtataactcactactttagtcagttcc
gcagtattacaaaaggatgtcgcaaacgctgtttgctcctctacaaaacagaccttaaaaccct
aaaggcttaagtagcaccctcgcaagctcgggcaaatcgctgaatattccttttgtctccgacc
atcaggcacctgagtcgctgtcttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgacttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

Figure 43A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaagccagccttcatgatatatctcccaattgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctcaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttcctttgatatgtaacggtgaaca
gttgttctactttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaaattttgcctcaaaactggt
gagctgaattttgcagttaaagcatcgtgtagtgttttcttagtccgttatgtaggtaggaa
tctgatgtaatggttgttggtattttgtcaccattcattttatctggttgttctcaagttcgg

Figure 43B

```
ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttttaactggaaaagataaggcaatatctcttcactaaaaactaattctaattttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgatttttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgtttttttgtttatattcaagtggtt
ataatttatagaataaagaaagaataaaaaaagataaaaagaatagatcccagccctgtgtata
actcactactttagtcagttccgcagtattacaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtcttttcgtgacattcagttc
gctgcgctcacggctctggcagtgaatgggggtaaatggcactacaggcgccttttatggattc
atgcaaggaaactacccataatacaagaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggatttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct
```

Figure 43C atctgacgaaaagctggcgtgaactgtgcaaagcctttctgcaagaggcgaaatggtccaacaa
caaaattatcccggcttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgtttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttatttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcacttttaaacagaatccattacatggcaccaagca
atgaaccatgggtgaacatgaaattgattacatcctatttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgacccatgccgaactcagaagtgaaacgccgtagcgccgatggtagtgtggggtctccc
atgcgagagtagggaactgccaggcatcaaataaaacgaaaggctcagtcgaaagactggcct
ttcgttttatctgttgtttgtcggtgaacgctctcctgagtaggacaaatccgccgggagcgga
tttgaacgttgcgaagcaacggcccggagggtggcgggcaggacgccgccataaactgccagg
catcaaattaagcagaaggccatcctgacggatggccttttgcgttctacaaactcttttttg
tttattttctaaatacattcaaatatgtatccgctcatgagacaataaccctgataaatgctt
caataat (SEQ ID NO:54)

Figure 45A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaggcccagtct
ttcgactgagccttt cgttttatttgatgcctggcagttccctactctcgcatggggagaccc
acactaccatcggcgctacggcgtttcacttctgagttcggcatggggtcaggtgggaccaccg
cgctactgccgccaggcaaattctgtttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagttttt gttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagttttt ccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagattttt gaatagctcggcaaaccgccgctacttttcg
gcaaacaaccgctggagggatcaaatttaggcacggcgtggaaagtgatcgggtcttttt ctgc
cggttcataaccacgaccttttt tggtcatgatatgcaggaactgcgggcctttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctcttt aattggcggcacgccagagaaaactttttt cccgccttcgcgcagtgaagag
taaagcttaccggaaagcagctgtgccagatggttgttgagcgcgccgacattttcggaaatcg
acatttcattgtcgttgagaataccagcatatcaggacggatatcgcccgcgtgattcatcgc
ttcaaacgccatgcctgcggtaatcgcgccatcgccaatgacacagacggtgcggcgattttt g
ccttcttttt cggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaattttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgttttttt acctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcagggtggagtcgctaacgcgttcacg

Figure 45B

```
attcatcttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
agcccgggataattttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtccagcgctctacagcatcggtgaacagttgcagttcgtccagagtgccataaac
gtcatacacgtcatcgatgatcgtcaccagaccaaacatttagtaacagctttgcgacattca
ccaaactgcgggtctggcgccatacccagtgcccagaaataaacttccatcaggcggtcgcgta
caaaatccagtttgctagccaggccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttcttttgttttcgtccagcagt
acgatgttttccagggctttaatgatgtctttttcaaatttgtaggtcagacccaggcgctgca
catcgtcgatcagctccagcagggacagcggctgggtgtctacacggttgatcatgcagcgaac
ttcttcctccagtttggtcgcttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaattttaataataaagttaatcgataattccggtcgagtgcccacac
agattgtctgataaattgttaaagagcagtgccgcttcgcttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagatttaatgcggatgttgcg
attacttcgccaactattgcgataacaagaaaagccagccttcatgatatctcccaattt
gtgtagggcttattatgcacgcttaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc
```

Figure 45C

```
cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtacccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgaccccggatgaagtggttcgcatcctcggttttct
ggaaggcgagcatcgtttgttcgcccagcttctgtatggaacgggcatgcggatcagtgaggt
ttgcaactgcgggtcaaggatctggatttcgatcacggcacgatcatcgtgcgggagggcaagg
gctccaaggatcgggccttgatgttacccgagagcttggcacccagcctgcgcgagcagggga
ttaattcccacgggttttgctgcccgcaaacgggctgttctggtgttgctagtttgttatcaga
atcgcagatccggcttcagccggtttgccggctgaaagcgctatttcttccagaattgccatga
tttttttccccacggggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatcttttttacaccgttttcatctgtgcatatggacagttttcctttgata
tgtaacggtgaacagttgttctacttttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaattttgcagttaaagcatcgtgtagtgtttttcttagtccgt
tatgtaggtaggaatctgatgtaatggttgttggtattttgtcaccattcattttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatattttatgaatttttttaactggaaaagataaggcaatatctcttcactaaaaactaattc
taattttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtccttttcctttgagttgtgggtatctgtaaattctgctagacctttgctgga
aaacttgtaaattctgctagaccctctgtaaattccgctagacctttgtgttttttttgttt
atattcaagtggttataatttatagaataaagaagaataaaaaagataaaagaatagatcc
cagccctgtgtataactcactactttagtcagttccgcagtattacaaaggatgtcgcaaacg
ctgtttgctcctctacaaaacagacttaaaacctaaaggcttaagtagcaccctcgcaagct
cgggcaaatcgctgaatattccttttgtctccgaccatcaggcacctgagtcgctgtcttttc
```

Figure 45D

```
Gtgacattcagttcgctgcgctcacggctctggcagtgaatgggggtaaatggcactacaggcg
cctttatggattcatgcaaggaaactacccataatacaagaaaagcccgtcacgggcttctca
gggcgttttatggcgggtctgctatgtggtgctatctgacttttgctgttcagcagttcctgc
cctctgattttccagtctgaccacttcggattatcccgtgacaggtcattcagactggctaatg
cacccagtaaggcagcggtatcatcaacaggctta
```
(SEQ ID NO:55)

5'-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatcccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaagggaataagggcgacacggaaatgttgaatactcatactcttcctttttc
aatattattgaagcatttatcagggttattgtctcatgagcggatacatatttgaatgtattta
gaaaaataaacaatagggttccgcgcacatttccccgaaaagtgccacctgacgtctaagaa
accattattcatgacattaacctataaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaagaga
aaaagcattttcaggtataggtgttttgggaaacaatttccccgaaccattatatttctctaca
tcagaaaggtataaatcataaaactctttgaagtcattctttacaggagtccaaataccagaga
atgttttagatacaccatcaaaaattgtataaagtggctctaacttatcccaataacctaactc
tccgtcgctattgtaaccagttctaaaagctgtatttgagtttatcacccttgtcactaagaaa
ataaatgcagggtaaaatttatatccttcttgttttatgtttc

Figure 51B ggtataaaacactaatatcaatttctgtggttatactaaaagtcgtttgttggttcaaataatg
attaaatatctcttttctcttccaattgtctaaatcaattttattaaagttcatttgatatgcc
tcctaaattttatctaaagtgaatttaggaggcttacttgtctgctttcttcattagaatcaa
tcctttttaaaagtcaatattactgtaacataaatatatattttaaaaatatcccactttatc
caattttcgtttgttgaactaatgggtgctttagttgaagaataaaagacctatgcggtgtgaa
ataccgcacagatgcgtaaggagaaaataccgcatcaggcgccattcgccattcaggctgcgca
actgttggaagggcgatcggtgcgggcctcttcgctattacgccagctggcgaaaggggatg
tgctgcaaggcgattaagttgggtaacgccagggttttcccagtcacgacgttgtaaaacgacg
gccagtgccaagcttgcatgcctgcactccattttcttctgctatcaaaataacagactcgtga
ttttccaaacgagctttcaaaaagcctctgccccttgcaaatcggatgcctgtctataaaatt
cccgatattggttaaacagcggcgcaatggcggccgcatctgatgtctttgcttggcgaatgtt
catcttatttcttcctccctctcaataattttttcattctatcccttttctgtaaagtttattt
ttcagaatacttttatcatcatgctttgaaaaaatatcacgataatatccattgttctcacgga
agcacacgcaggtcatttgaacgaattttttcgacaggaatttgccgggactcaggagcatta
acctaaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaatgggtctactaaaatattattccatctattacaataaattcacaga
atagtcttttaagtaagtctactctgaattttttaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttattttggcgaaacaattgattcaattaggagaagcggaagttttaa
ttgctggcgggattgagaatatgtcccaagcacctaaattacaacgttttaattacgaaacaga
aagctacgatgcgccttttctagtatgatgtatgatggattaacggatgcctttagtggtcag
gcaatgggcttaactgctgaaaatgtggccgaaaagtatcatgtaactagagaagagcaagatc
aattttctgtacattcacaattaaaagcagctcaagcacaagcagaagggatattcgctgacga
aatagccccattagaagtatcaggaacgcttgtggagaaagatgaagggattcgccctaattcg
agcgttgagaagctaggaacgcttaaaacagttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaacagccgatttatcaaatgagtcctgaggaacgcctggcttctcttcttaatgaa
ggccagatttctgctgatacaaaaaagaatttgaaaatacggctttatcttcgcagattgcca
atcatatgattgaaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgttttttacgatgttgcagatcccgagtcattgattgataaactacaagtaagagaagc
ggaagttttcaacaagcagagttaagttatccatctatcgttaaacggggcggcggcttaaga
gatttgcaatatcgtacttttgatgaatcatttgtatctgtcgacttttagtagatgttaagg
atgcaatgggggcaaatatcgttaacgctatgttggaaggtgtg

Figure 51C

```
gccgagttgttccgtgaatggtttgcggagcaaaagatttttattcagtattttaagtaattatg
ccacggagtcggttgttacgatgaaaacggctattccagtttcacgtttaagtaaggggagcaa
tggccgggaaattgctgaaaaattgttttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaggacacatggctctacaagcacgttctttagcg
atgacggtcggagctactggtaaagaagttgaggcagtcgctcaacaattaaaacgtcaaaaaa
cgatgaaccaagaccgagccatggctatttttaaatgatttaagaaaacaataaaaggagagggt
gacaattgggattgataaaattagttttttttgtgccccttatttattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcattttggctttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgatttttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcatttcccttttagaaaatgcaacgactttaaccgcaggcaatc
aaattggtttattcagttatggttctggtgctgtcgctgaattttcactggtgaattagtagc
tggttatcaaaatcatttacaaaagaaactcatttagcactgctggataatcggacagaactt
tctatcgctgaatatgaagccatgtttgcagaactttagacacagacattgatcaaacgttag
aagatgaattaaaatatagtatttctgctattaataataccgttcgttcttatcgaaactaaaa
aaaaccggccttggccccgccggttttttattattttttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
```

(SEQ ID NO:56)

Figure 62
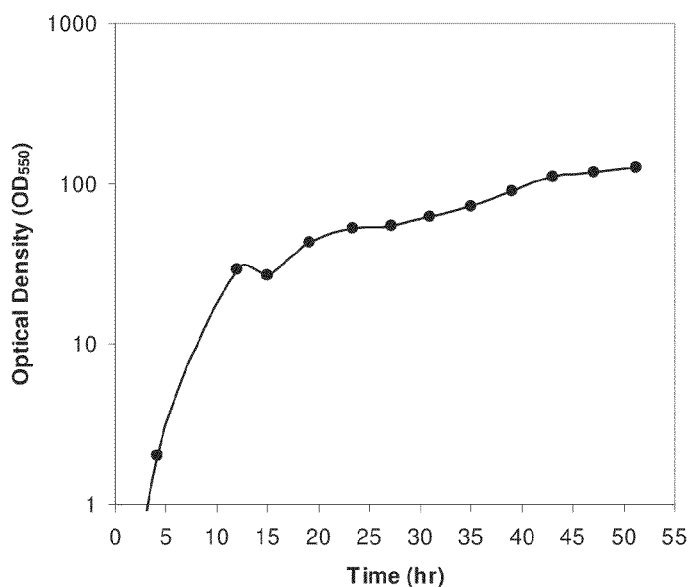
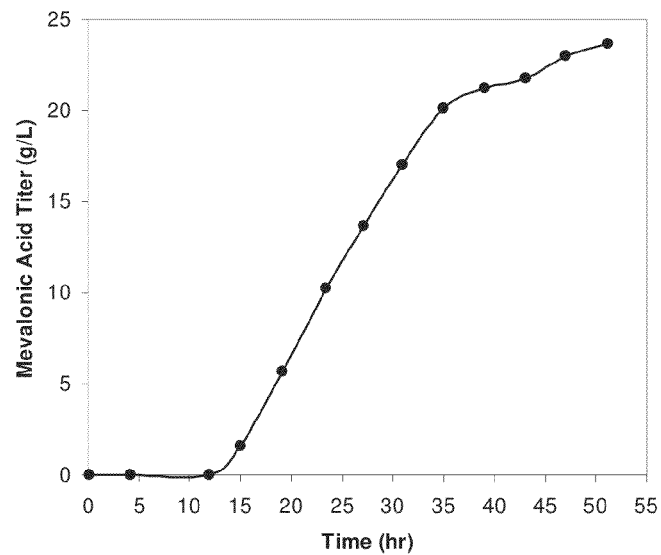
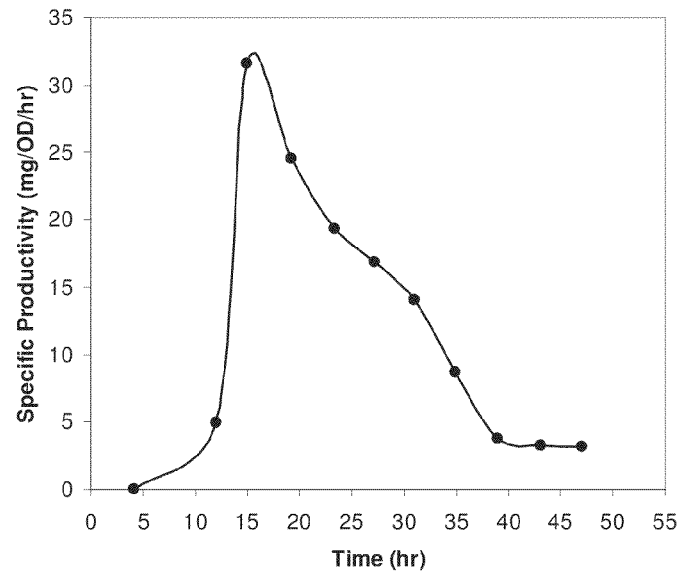

Figure 65
A
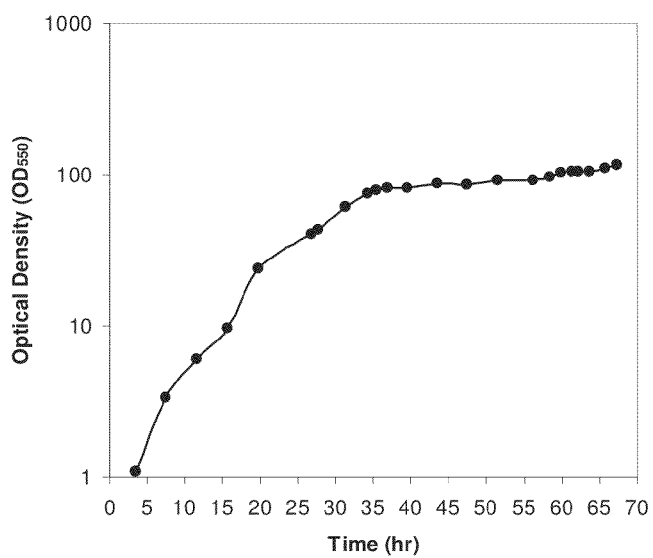
B
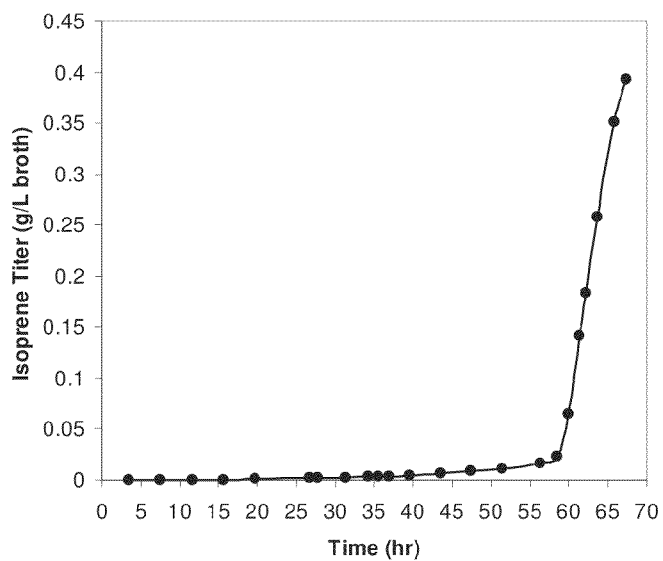
C
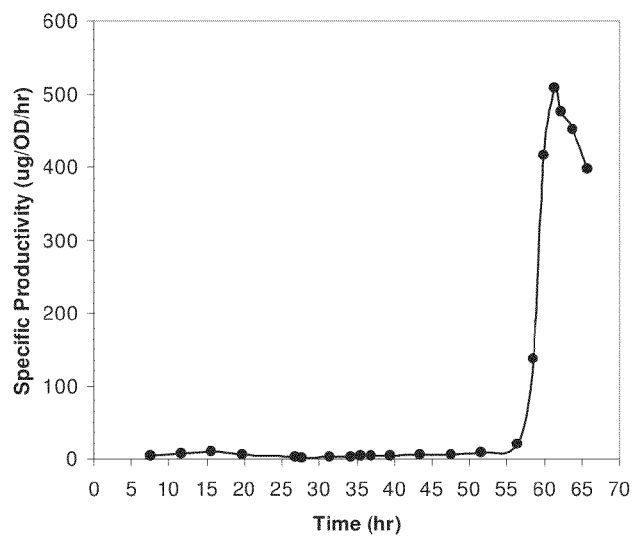

Figure 66
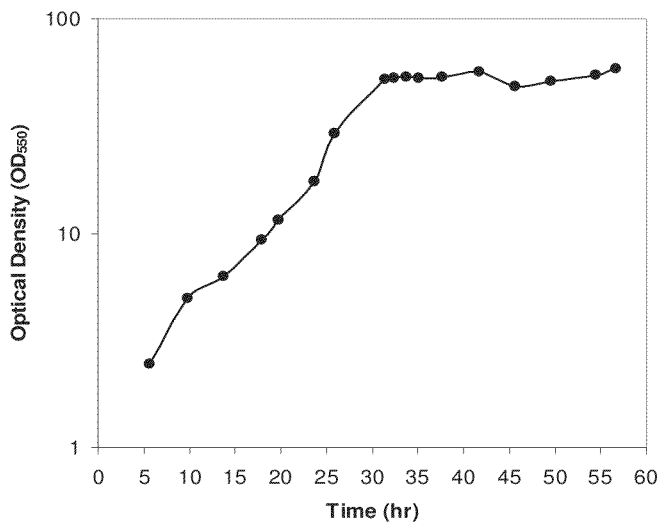
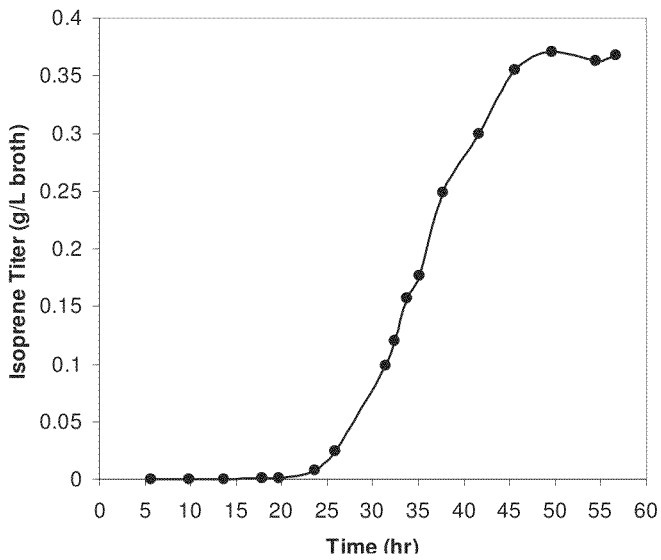
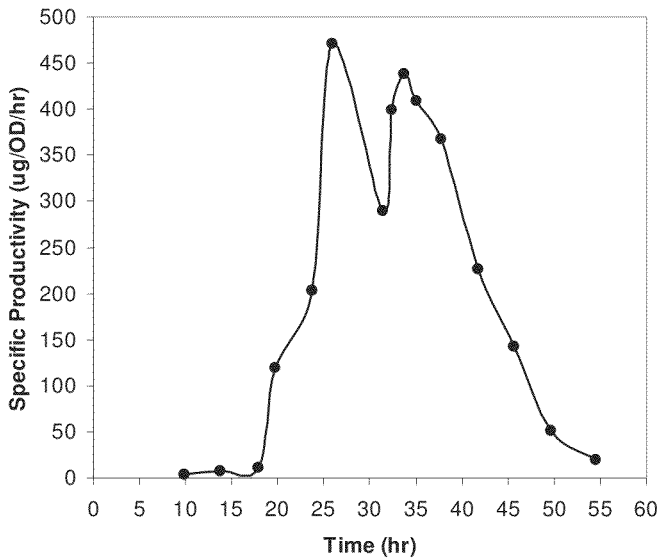

Figure 75A

| Fuel Conc. (wt.%) | Oxidizer Conc. (wt.%) | Fuel Makeup | Oxidizer Makeup | | | Concentration at Deflagration | | | | | | | |
|---|---|---|---|---|---|---|---|---|---|---|---|---|---|
| | | Isoprene (wt. %) | H₂O (wt. %) | O₂ (wt. %) | N₂ (wt. %) | Molar Concentration based on 100g of sample | | | | | Volumetric Concentrations based on ideal gas law | | |
| | | | | | | Isoprene (mole) | H₂O (mole) | O₂ (mole) | N₂ (mole) | Total (mole) | Isoprene (vol. %) | O₂ (vol. %) | N₂ (vol. %) | H₂O (vol. %) |

| Fuel Conc. (wt.%) | Oxidizer Conc. (wt.%) | Isoprene (wt. %) | H₂O (wt. %) | O₂ (wt. %) | N₂ (wt. %) | Isoprene (mole) | H₂O (mole) | O₂ (mole) | N₂ (mole) | Total (mole) | Isoprene (vol. %) | O₂ (vol. %) | N₂ (vol. %) | H₂O (vol. %) |
|---|---|---|---|---|---|---|---|---|---|---|---|---|---|---|
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.33 | 14.10 | 84.58 | 0.00 |
| 3.10 | 96.90 | 100 | 0 | 17 | 83 | 4.56 | 0.00 | 51.48 | 287.24 | 343.28 | 1.33 | 15.00 | 83.68 | 0.00 |
| 3.10 | 96.90 | 100 | 0 | 21 | 79 | 4.56 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 13.50 | 86.50 | 100 | 0 | 21 | 79 | 19.85 | 0.00 | 56.77 | 244.05 | 320.67 | 6.19 | 17.70 | 76.11 | 0.00 |

Figure 76A

| Fuel Conc. (wt.%) | Oxidizer Conc. (wt.%) | Fuel Makeup | Oxidizer Makeup | | | Concentration at Deflagration | | | | | | | |
|---|---|---|---|---|---|---|---|---|---|---|---|---|---|
| | | | | | | Molar Concentration based on 100g of sample | | | | Volumetric Concentrations based on ideal gas law | | | |
| | | Isoprene (wt. %) | $H_2O$ (wt. %) | $O_2$ (wt. %) | $N_2$ (wt. %) | Isoprene (mole) | $H_2O$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.252 | 96.748 | 100 | 4 | 12 | 84 | 4.78 | 21.50 | 36.28 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.88 | 350.58 | 1.38 | 14.66 | 77.84 | 6.13 |
| 3.276 | 96.724 | 100 | 4 | 21 | 75 | 4.82 | 21.49 | 63.48 | 259.08 | 348.87 | 1.38 | 18.19 | 74.26 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.98 |
| 9.400 | 90.600 | 100 | 4 | 17 | 79 | 13.82 | 20.13 | 48.13 | 255.62 | 337.71 | 4.09 | 14.25 | 75.69 | 5.96 |
| 13.300 | 86.700 | 100 | 4 | 21 | 75 | 19.56 | 19.27 | 56.90 | 232.23 | 327.95 | 5.96 | 17.35 | 70.81 | 5.87 |

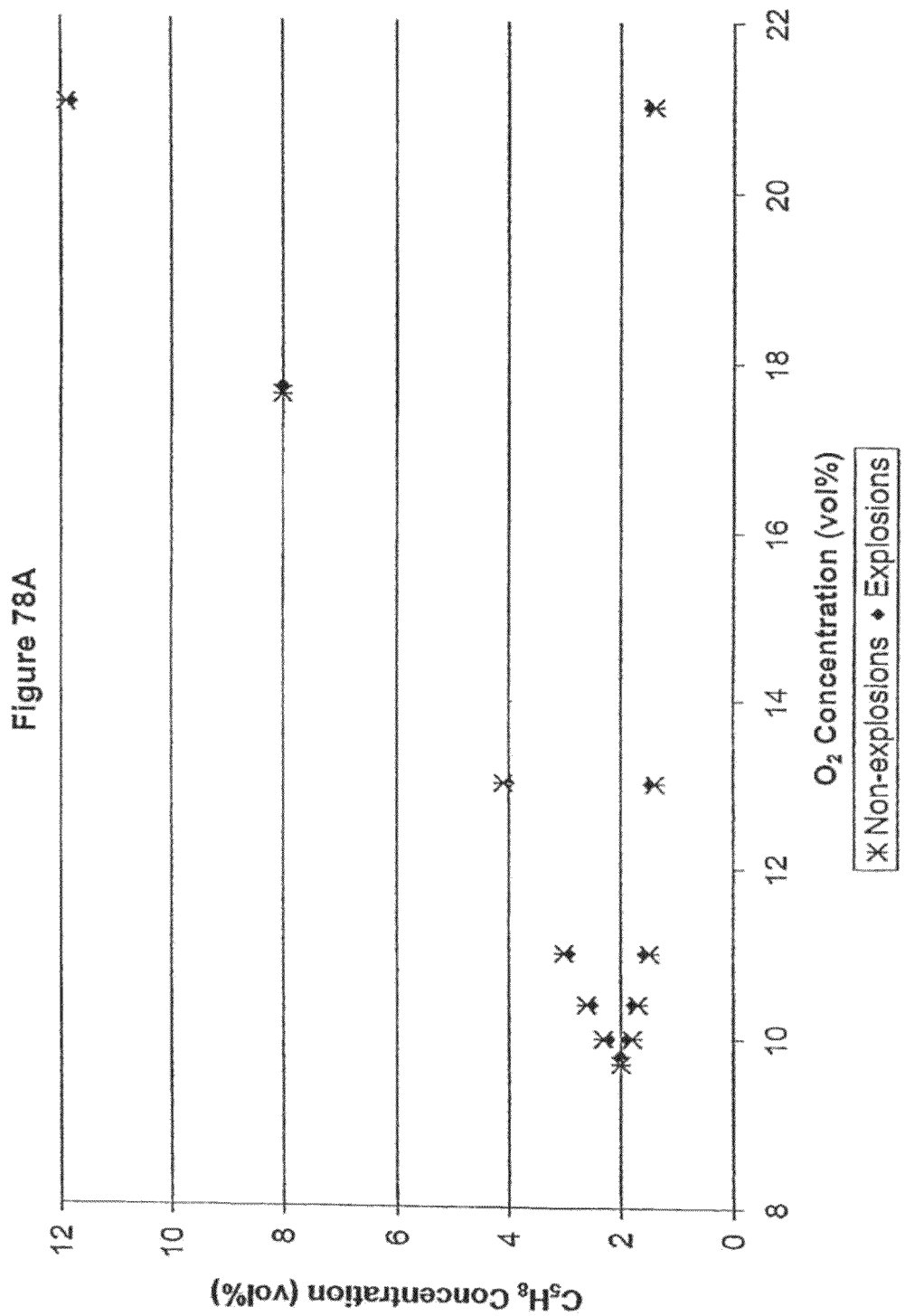

Figure 78B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

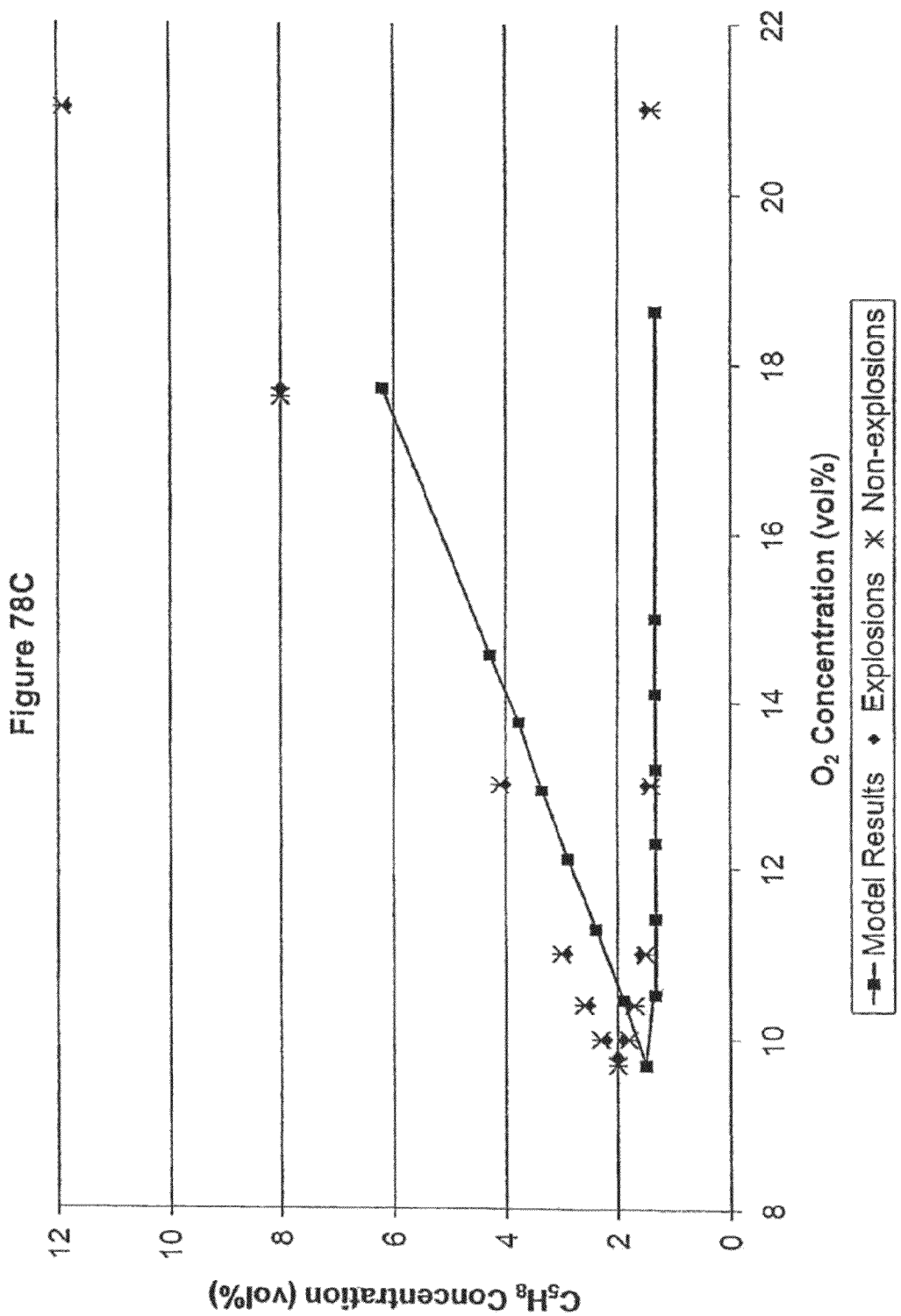

Figure 79B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

Figure 80A

TEST SERIES 1

| Test | Data File Name | Temp °C | Initial Pressure bara | Partial Pressures | | | Concentrations | | | Result | Pex bara |
|---|---|---|---|---|---|---|---|---|---|---|---|
| | | | | $C_5H_8$ mbar | $N_2$ mbar | $O_2$ mbar | $C_5H_8$ vol. % | $N_2$ vol. % | $O_2$ vol. % | | |
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.31 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.81 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 29 | 874 | 112 | 2.9 | 86.1 | 11.0 | Non-Explosion | 1.08 |
| 39 | T11130722 | 40 | 1.014 | 29 | 873 | 112 | 2.9 | 86.1 | 11.0 | Explosion | 1.1 |

Figure 80B

| Test | Data File Name | Temp °C | Initial Pressure bara | Partial Pressures | | | Concentrations | | | Result | Pex bara |
|---|---|---|---|---|---|---|---|---|---|---|---|
| | | | | $C_5H_8$ mbar | $N_2$ mbar | $O_2$ mbar | $C_5H_8$ vol. % | $N_2$ vol. % | $O_2$ vol. % | | |
| 40 | T11130723 | 40 | 1.014 | 30 | 872 | 112 | 3.0 | 86.0 | 11.0 | Non-Explosion | 1.08 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.05 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 884 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.06 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.08 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp °C | Initial Pressure bara | Partial Pressures | | | | Concentrations | | | | Result | Pex bara |
|---|---|---|---|---|---|---|---|---|---|---|---|---|---|
| | | | | $H_2O$ mbar | $C_5H_8$ mbar | $N_2$ mbar | $O_2$ mbar | $H_2O$ vol. % | $C_5H_8$ vol. % | $N_2$ vol. % | $O_2$ vol. % | | |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non-explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.06 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.68 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.8 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

Figure 86B gcggccgcgcccttgacgatgccacatcctgagcaaataattcaaccactaattgtgagcggataacacaaggaggaaacagccatggtat
cctgttctgcgccgggtaagatttacctgttcggtgaacacgccgtagtttatggcgaaactgcaattgcgtgtgcggtggaactgcgtaccc
gtgttcgcgcgcggaactcaatgactctatcactattcagagccagatcggccgcaccggtctggatttcgaaaagcacccttatgtgtctgcgg
taattgagaaaatgcgcaaatctattcctattaacggtgttttcttgaccgtcgattccgacatcccggtgggctccggtctgggtagcagcgc
agccgttactatcgcgtcattggtgcgctgaacgagctgttcggctttggcctcagcctgcaagaaatcgctaaactgggccacgaaatcg
aaattaaagtacagggtgccgcgtccccaaccgatacgtatgtttctaccttcggcggcgtggttaccatcccggaacgtcgcaaactgaaa
actccggactgcggcattgtgattggcgataccggcgttttctcctccaccaaagagttagtagctaacgtacgtcagctgcgcgaaagctac
ccggatttgatcgaaccgctgatgacctctattggcaaaatctctcgtatcggcgaacaactggttctgtctggcgactacgcatccatcggcc
gcctgatgaacgtcaaccagggtctcctggacgccctgggcgttaacatcttagaactgagccagctgatctattccgctcgtgcggcaggt
gcgtttggcgctaaaatcacgggcgctggcggcggtggctgtatggttgcgctgaccgctccggaaaaatgcaaccaagtggcagaagc
ggtagcaggcgctggcggtaaagtgactatcactaaaccgaccgagcaaggtctgaaagtagattaagccttgacttaatagctgcttatttc
gcccttatggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggttatatgta
ctctggcaaagttgcggcgcacgtctatgccactctgccggaagctgataccttacgtaatcttcggcccgaaccacaccggctacggtagc
cctgtctctgtgagccgtgaaacttggaagaccccgttgggcaatatcgatgttgacctggaactggcggacggcttcctgggttccatcgta
gatgcggatgaactcggtcacaaatacgaacactctatcgaagttcagctgccgtttctgcaataccgttttgaacgcgatttcaaaattctgcc
aatctgcatgggtatgcaagacgaagaaaccgcggtcgaagtaggtaacctgctggcggatctgatcagcgagtccggtaaacgtgctgt
gatcatcgcaagctctgatttcacccactatgagacggctgaacgtgccaaagaaatcgattccgaagttattgattctatcctgaactttgaca
tctctggcatgtacgatcgcctgtatcgccgtaacgcctctgtttgcggttacggcccgatcaccgctatgctgacggcaagcaaaaagctg
ggcggctctcgtgcgactttgctgaaatacgcaaacagccggtgacgtgtccggtgataaagacgctgtggtgggctacgccgccatcatcg
ttgagtaagctgattaaaggttgaacagataggatttcgtcatggatcctacaaggaggaaaaaaacatgaatgcttctaatgaaccggtgatt
ctgaaactgggtggctctgctattaccgacaaaggtgcctacgaaggcgtagttaaggaagctgatttgctgcgcatcgcacaggaagttag
cggtttccgtggcaagatgatcgtggttcatggtgctggtagcttcggccatacgtacgcgaagaaatacggcctggaccgtaccttcgacc
cagagggcgcaattgttactcatgaatctgttaaaaagctcgcctccaaagttgtaggtgctctgaatagcttcggcgtgcgtgctatcgcggt
gcatcctatggactgcgcagtatgccgtaacggtcgtatcgaaacgatgtatctggactccatcaagttaatgctggaaaaaggtctggtgcc
ggttctgcacggcgacgtcgcaatggatattgaactgggcacttgtatcctgtccggtgatcaaatcgttccttacctggccaaagaactggg
tatctcccgcctcggcctgggcagcgcagaggatggtgtgctggatatggagggcaaacctgtaccggaaatcaccccagaaactttcga
agagttccgccactgcatcggtggttctggttctactgatgtaaccggtggcatgctgggcaaagtgctggaacttctggaattgagcaaaaa
ttcttccattactagctacattttcaacgctggtaaagcagacaacatctaccgctttctgaatggtgagtccatcggcactcgcatcagcccgg
acaagcgtgtttaagctagttattaacctaaatgctctaaaccagttatgagctctacaaggaggaaaaaaacatgattaacactaccagccgc
cgcaaaattgaacacctgaaactctgcgcagaatcccgggttgaagcgcgtcaggtatctgccggctttgaagacgttactctgatccaccg
cgctttaccggagctgaacatggatgaactggaccctcagcgttgatttcctgggtaaacgcatcaaagcgccgttcctgattgcgtctatcac
gggtggtcacccagataccatcccggttaacgctgcgctggcagctgctgctgaggagctgggtgttggcatcggcgttggctctcagcgc
gcggccattgatgatccgagccaggaagacagcttccgtgtagtgcgtgatgaagccccagatgcgtttgtttatggcaacgtcggcgcag
cacagatccgtcagtatggtgttgaaggtgttgaaaaactgatcgaaatgattgacgcagatgccttggcaatccacctgaactttctgcaag
aagcggtccaaccggaaggtgaccgcgacgcgaccggttgcctggacatgattaccgaaatttgctctcagattaaaactccggtaatcgt
gaaagaaaccggtgcaggcattagccgtgaagatgcgattctgttccagaaagctggcgtgagcgcaatcgacgttggcggcgcgggcg
gcacctcctgggctggcgtcgaggtctaccgtgctaaagaaagccgtgactctgttagcgagcgtttaggtgagctgttttgggatttcggca
ttccgacggtagcttctctgattgaatcccgcgtttccttgccgctgatcgcaaccggcggtatccgtaacggtctggacattgctaaaagcatt
gctctcggcgcaagcgctgccagccgcctctgccgttcgttggtccgtccctggagggcaaagaatccgttgtacgtgtgctgagctgca
tgctggaagaatttaaagcagcaatgttttgtgcggttgcggcaacatcaaaga

Figure 86C cctgcacaactctccagtagtggtaactggttggacccgcgaatacctggagcagcgcggttttaacgttaaggacctctccctgccgggca
acgctctgtaagcttcaacgcgtctacaaataaaaaaggcacgtcagatgacgtgcctttttcttgtctaga
(SEQ ID NO:102)

Figure 87B gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagccgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaaccatgtgtgcgacctcttctcaatttactcagattaccgagcataattcccgtcgttccgcaaa
ctatcagccaaacctgtggaatttcgaattcctgcaatccctggagaacgacctgaaagtggaaaagctggaggagaaagcgaccaaact
ggaggaagaagttcgctgcatgatcaaccgtgtagacacccagccgctgtccctgctggagctgatcgacgatgtgcagcgcctgggtct
gacctacaaatttgaaaaagacatcattaaagccctggaaaacatcgtactgctggacgaaaacaaaaagaacaaatctgacctgcacgca
accgctctgtctttccgtctgctgcgtcagcacggtttcgaggtttctcaggatgtttttgagcgtttcaaggataaagaaggtggtttcagcggt
gaactgaaaggtgacgtccaaggcctgctgagcctgtatgaagcgtcttacctgggtttcgagggtgagaacctgctggaggaggcgcgt
accttttccatcacccacctgaagaacaacctgaaagaaggcattaataccaaggttgcagaacaagtgagccacgccctggaactgccat
atcaccagcgtctgcaccgtctggaggcacgttggttcctggataaatacgaaccgaaagaaccgcatcaccagctgctgctggagctggc
gaagctggatttaacatggtacagaccctgcaccagaaagagctgcaagatctgtcccgctggtggaccgagatgggcctggctagcaa
actggattttgtacgcgaccgcctgatggaagtttatttctgggcactgggtatggcgccagacccgcagtttggtgaatgtcgcaaagctgtt
actaaaatgtttggtctggtgacgatcatcgatgacgtgtatgacgtttatggcactctggacgaactgcaactgttcaccgatgctgtagagc
gctgggacgttaacgctattaacaccctgccggactatatgaaactgtgttttcctggcactgtacaacaccgttaacgacacgtcctattctatt
ctgaaagagaaaggtcataacaacctgtcctatctgacgaaaagctggcgtgaactgtgcaaagcctttctgcaagaggcgaaatggtcca
acaacaaaattatcccggctttctccaagtacctggaaaacgccagcgtttcctcctccggtgtagcgctgctggcgccgtcttactttccgta
tgccagcagcaggaagacatctccgaccacgcgctgcgttccctgaccgacttccatggtctggtgcgttctagctgcgttatcttccgcctg
tgcaacgatctggccacctctgcggcggagctggaacgtggcgagactaccaattctatcattagctacatgcacgaaaacgatggtacca
gcgaggaacaggcccgcgaagaactgcgtaaactgatcgacgccgaatggaaaaagatgaatcgtgaacgcgttagcgactccaccctg
ctgcctaaagcgttcatggaaatcgcagttaacatggcacgtgtttcccactgcacctaccagtatggcgatggtctgggtcgcccagactac
gcgactgaaaaccgcatcaaactgctgctgattgacccttcccgattaaccagctgatgtatgtctaactgcataaaggaggtaaaaaaaca
tggtatcctgttctgcgccgggtaagatttacctgttcggtgaacacgccgtagtttatggcgaaactgcaattgcgtgtgcggtggaactgcg
tacccgtgttcgcgcggaactcaatgactctatcactattcagagccagatcggccgcaccggtctggatttcgaaaagcacccttatgtgtct
gcggtaattgagaaaatgcgcaaatctattcctattaacggtgttttcttgaccgtcgattccgacatcccggtgggctccggtctgggtagca
gcgcagccgttactatcgcgtctattggtgcgctgaacgagctgttcggctttggcctcagcctgcaagaaatcgctaaactgggccacgaa
atcgaaattaaagtacagggtgccgcgtccccaaccgatacgtatgtttctaccttcggcggcgtggttaccatcccggaacgtcgcaaact
gaaaactccggactgcggcattgtgattggcgataccggcgttttctcctccaccaaagagttagtagctaacgtacgtcagctgcgcgaaa
gctacccggatttgatcgaaccgctgatgacctctattggcaaaatctctcgtatcggcgaacaactggttctgtctggcgactacgcatccat
cggccgcctgatgaacgtcaaccagggtctcctggacgccctgggcgttaacatcttagaactgagccagctgatctattccgctcgtgcgg
caggtgcgtttggcgctaaaatcacgggcgctggcggcggtggctgtatggttgcgctgaccgctccggaaaaatgcaaccaagtggcag
aagcggtagcaggcgctggcggtaaagtgactatcactaaaccgaccgagcaaggtctgaaagtagattaaagtctagttaaagtttaaac
ggtctccagcttggctgttttggcggatgagagaagattttcagcctgatacagattaaatcagaacgcagaagcggtctgataaaacagaat
ttgcctggcggcagtagcgcggtggtcccacctgaccccatgccgaactcagaagtgaaacgccgtagcgccgatggtagtgtggggtct
ccccatgcgagagtagggaactgccaggcatcaaataaaacgaaaggctcagtcgaaagactgggcctttcgttttatctgttgtttgtcggt
gaacgctctcctgagtaggacaaatccgccgggagcggatttgaacgttgcgaagcaacggcccggagggtggcgggcaggacgccc
gccataaactgccaggcatcaaattaagcagaaggccatcctgacggatggccttttgcgtttctacaaactctttttgtttatttttctaaataca
ttcaaatatgtatccgcttaaccggaattgccagctggggcgccctctggtaaggttgggaagccctgcaaagtaaactggatggctttctcg
ccgccaaggatctgatggcgcaggggatcaagctctgatcaagagacaggatgaggatcgtttcgcatgattgaacaagatggattgcac
gcaggttctccggccgcttgggtggagaggctattcggctatgactgggcacaa

Figure 87C cagacaatcggctgctctgatgccgccgtgttccggctgtcagcgcaggggcgcccggttcttttgtcaagaccgacctgtccggtgccct
gaatgaactgcaagacgaggcagcgcggctatcgtggctggccacgacgggcgttccttgcgcagctgtgctcgacgttgtcactgaagc
gggaagggactggctgctattgggcgaagtgccggggcaggatctcctgtcatctcaccttgctcctgccgagaaagtatccatcatggct
gatgcaatgcggcggctgcatacgcttgatccggctacctgcccattcgaccaccaagcgaaacatcgcatcgagcgagcacgtactcgg
atggaagccggtcttgtcgatcaggatgatctggacgaagagcatcagggggctcgcgccagccgaactgttcgccaggctcaaggcgag
catgcccgacggcgaggatctcgtcgtgacccatggcgatgcctgcttgccgaatatcatggtggaaaatggccgctttctggattcatcga
ctgtggccggctgggtgtggcggaccgctatcaggacatagcgttggctacccgtgatattgctgaagagcttggcggcgaatgggctga
ccgcttcctcgtgcttacggtatcgccgctcccgattcgcagcgcatcgccttctatcgccttcttgacgagttcttctgacgcatgaccaaaa
tcccttaacgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggcttcagcag
agcgcagataccaaatactgtccttctagtgtagccgtagttaggccaccacttcaagaactctgtagcaccgcctacatacctcgctctgcta
atcctgttaccagtggctgctgccagtggcgataagtcgtgtcttaccgggttggactcaagacgatagttaccggataaggcgcagcggtc
gggctgaacggggggttcgtgcacacagcccagcttggagcgaacgacctacaccgaactgagatacctacagcgtgagctatgagaaa
gcgccacgcttcccgaaggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggcggagc
ctatggaaaaacgccagcaacgcggcctttttacggttcctggccttttgctggccttttgctcacatgttctttcctgcgttatcccctgattctgt
ggataaccgtattaccgcctttgagtgagctgataccgctcgccgcagccgaacgaccgagcgcagcgagtcagtgagcgaggaagcg
gaagagcgcctgatgcggtattttctccttacgcatctgtgcggtatttcacaccgcatatggtgcactctcagtacaatctgctctgatgccgc
atagttaagccagtatacactccgctatcgctacgtgactgggtcatggctgcgccccgacacccgccaacacccgctgacgcgccctgac
gggcttgtctgctcccggcatccgcttacagacaagctgtgaccgtctccgggagctgcatgtgtcagaggttttcaccgtcatcaccgaaa
cgcgcgaggcagcagatcaattcgcgcgcgaaggcgaagcggcatgcatttacgttgacaccatcgaatggtgcaaaacctttcgcggta
tggcatgatagcgcccggaagagagtcaattcaggtggtgaatgtgaaaccagtaacgttatacgatgtcgcagagtatgccggtgtctct
tatcagaccgtttcccgcgtggtgaaccaggccagccacgtttctgcgaaaacgcgggaaaaagtggaagcggcgatggcggagctgaa
ttacattcccaaccgcgtggcacaacaactggcgggcaaacagtcgttgctgattggcgttgccacctccagtctggccctgcacgcgccg
tcgcaaattgtcgcggcgattaaatctcgcgccgatcaactgggtgccagcgtggtggtcgatggtagaacgaagcggcgtcgaagcct
gtaaagcggcggtgcacaatcttctcgcgcaacgcgtcagtgggctgatcattaactatccgctggatgaccaggatgccattgctgtggaa
gctgcctgcactaatgttccggcgttatttcttgatgtctctgaccagacacccatcaacagtattattttctcccatgaagacggtacgcgactg
ggcgtggagcatctggtcgcattgggtcaccagcaaatcgcgctgttagcggggcccattaagttctgtctcggcgcgtctgcgtctggctgg
ctggcataaatatctcactcgcaatcaaattcagccgatagcggaacgggaaggcgactggagtgccatgtccggttttcaacaaaccatgc
aaatgctgaatgagggcatcgttcccactgcgatgctggttgccaacgatcagatggcgctgggcgcaatgcgcgccattaccgagtccg
ggctgcgcgttggtgcggatatctcggtagtgggatacgacgataccgaagacagctcatgttatatcccgccgtcaaccaccatcaaaca
ggattttcgcctgctggggcaaaccagcgtggaccgcttgctgcaactctctcagggccaggcggtgaagggcaatcagctgttgcccgtc
tcactggtgaaaagaaaaaccaccctggcgcccaatacgcaaaccgcctctccccgcgcgttggccgattcattaatgcagctggcacga
caggtttcccgactggaaagcgggcagtgagcgcaacgcaattaatgtgagttagcgcgaattgatctg
(SEQ ID NO:103)

MCM376 - MVK from M. mazei archeal Lower in pET200D
6647 bp

Figure 88B aagggcgagctcaacgatccggctgctaacaaagcccgaaaggaagctgagttggctgctgccaccgctgagcaataactagcataacc
ccttgggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaaccccctatttgttt
atttttctaaatacattcaaatatgtatccgctcatgagacaataaccctgataaatgcttcaataatattgaaaaaggaagagtatgattgaacaa
gatggattgcacgcaggttctccggccgcttggtggagaggctattcggctatgactgggcacaactgacaatcggctgctctgatgccg
ccgtgttccggctgtcagcgcaggggcgcccggttcttttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagga
tgatctggacgaagagcatcaggggctcgcgccagccgaactgttcgccaggctcaaggcgcgcatgcccgacggcgaggatctcgtc
gtgacacatggcgatgcctgcttgccgaatatcatggtggaaaatggccgcttttctggattcatcgactgtggccggctgggtgtggcgga
ccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgagcgggactctgggggttcgaaatgaccgaccaagcgac
gcctaactgtcagaccaagtttactcatatatactttagattgatttaaaacttcattttttaatttaaaaggatctaggtgaagatccttttttgataatct
catgaccaaaatcccttaacgtgagttttcgttccactgagcgtcagaccccgtagaaaagatcaaaggatcttcttgagatccttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttttgtgatgctcgtcagg
ggggcggagcctatggaaaaacgccagcaacgcggccttttacggttcctggccttttgctggccttttgctcacatgttctttcctgcgttat
cccctgattctgtggataaccgtattaccgcctttgagtgagctgataccgctcgccgcagccgaacgaccgagcgcagcgagtcagtgag
cgaggaagcggaagagcgcctgatgcggtattttctccttacgcatctgtgcggtatttcacaccgcaatggtgcactctcagtacaatctgct
ctgatgccgcatagttaagccagtatacactccgctatcgctacgtgactgggtcatggctgcgccccgacacccgccaacacccgctgac
gcgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcctccgtgt
aagggggatttctgttcatgggggtaatgataccgatgaaacgagagaggatgctcacgatacgggttactgatgatgaacatgcccggtta
ctggaacgttgtgagggtaaacaactggcggtatggatgcggcgggaccagagaaaaatcactcagggtcaatgccagcgcttcgttaat
acagatgtaggtgttccacagggtagccagcagcatcctgcgatgcagatccggaacataatggtgcagggcgctgacttccgcgtttcca
gactttacgaaacacggaaaccgaagaccattcatgttgttgctcaggtcgcagacgttttgcagcagcagtcgcttcacgttcgctcgcgta
tcggtgattcattctgctaaccagtaaggcaaccccgccagcctagccgggtcctcaacgacaggagcacgatcatgcgcacccgtggcc
aggacccaacgctgcccgagatgcgccgcgtgcggctgctggagatggcggacgcgatggatatgttctgccaagggttggtttgcgcat
tcacagttctccgcaagaattgattggctccaattcttggagtggtgaatccgttagcgaggtgccgccggcttccattcaggtcgaggtggc
ccggctccatgcaccgcgacgcaacgcggggaggcagacaaggtatagggcggcgcctacaatccatgccaacccgttccatgtgctc
gccgaggcggcataaatcgccgtgacgatcagcggtccaatgatcgaagttaggctggtaagagccgcgagcgatccttgaagctgtccc
tgatggtcgtcatctacctgcctggacagcatggcctgcaacgcgggcatcccgatgccgccggaagcgagaagaatcataatggggaa
ggccatccagcctcgcgtcgcgaacgccagcaagacgtagcccagcgcgt

Figure 88C cggccgccatgccggcgataatggcctgcttctcgccgaaacgtttggtggcgggaccagtgacgaaggcttgagcgagggcgtgcaag
attccgaataccgcaagcgacaggccgatcatcgtcgcgctccagcgaaagcggtcctcgccgaaaatgacccagagcgctgccggca
cctgtcctacgagttgcatgataaagaagacagtcataagtgcggcgacgatagtcatgccccgcgcccaccggaaggagctgactggt
tgaaggctctcaagggcatcggtcgagatcccggtgcctaatgagtgagctaacttacattaattgcgttgcgctcactgcccgctttccagtc
gggaaacctgtcgtgccagctgcattaatgaatcggccaacgcgcggggagaggcggtttgcgtattgggcgccaggtggttttctttc
accagtgagacgggcaacagctgattgcccttcaccgcctggccctgagagagttgcagcaagcggtccacgctggtttgccccagcag
gcgaaaatcctgtttgatggtggttaacggcgggatataacatgagctgtcttcggtatcgtcgtatcccactaccgagatatccgcaccaac
gcgcagcccggactcggtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaatttgattgcgagtgagatatttatg
ccagccagccagacgcagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaataacgccggaacatta
gtgcaggcagcttccacagcaatggcatcctggtcatccagcggatagttaatgatcagcccactgacgcgttgcgcgagaagattgtgca
ccgccgctttacaggcttcgacgccgcttcgttctaccatcgacaccaccacgctggcacccagttgatcggcgcgagatttaatcgccgcg
acaatttgcgacggcgcgtgcagggccagactggaggtggcaacgccaatcagcaacgactgtttgcccgccagttgttgtgccacgcgg
ttgggaatgtaattcagctccgccatcgccgcttccacttttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcgctatca
tgccataccgcgaaaggttttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgcca
gcaaccgcacctgtggcgccggtgatgccggccacgatgcgtccggcgtagaggatcgagatctcgatcccgcgaaattaatacgactca
ctatagggaattgtgagcggataacaattcccctctagaaataattttgtttaactttaagaaggagatatacatatgcggggttctcatcatca
tcatcatcatggtatggctagcatgactggtggacagcaaatgggtcgggatctgtacgacgatgacgataaggatcatcccttcaccatggt
atcctgttctgcgccgggtaagatttacctgttcggtgaacacgccgtagtttatggcgaaactgcaattgcgtgtgcggtggaactgcgtacc
cgtgttcgcgcggaactcaatgactctatcactattcagagccagatcggccgcaccggtctggatttcgaaaagcacccttatgtgtctgcg
gtaattgagaaaatgcgcaaatctattcctattaacggtgttttcttgaccgtcgattccgacatcccggtgggctccggtctgggtagcagcg
cagccgttactatcgcgtctattggtgcgctgaacgagctgttcggctttggcctcagcctgcaagaaatcgctaaactgggccacgaaatc
gaaattaaagtacagggtgccgcgtccccaaccgatacgtatgtttctaccttcggcggcgtggttaccatcccggaacgtcgcaaactgaa
aactccggactgcggcattgtgattggcgataccggcgttttctcctccaccaaagagttagtagctaacgtacgtcagctgcgcgaaagcta
cccggatttgatcgaaccgctgatgacctctattggcaaaatctctcgtatcggcgaacaactggttctgtctggcgactacgcatccatcggc
cgcctgatgaacgtcaaccagggtctcctggacgccctgggcgttaacatcttagaactgagccagctgatctattccgctcgtgcggcagg
tgcgtttggcgctaaaatcacgggcgctggcggcggtggctgtatggttgcgctgaccgctccggaaaaatgcaaccaagtggcagaagc
ggtagcaggcgctggcggtaaagtgactatcactaaaccgaccgagcaaggtctgaaagtagattaa
(SEQ ID NO:104)

Figure 90
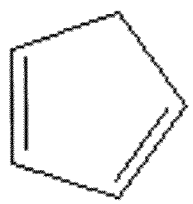
cyclopentadiene
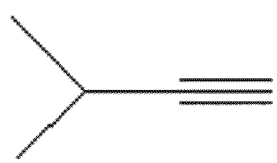
"isopryne" = 3-Me-1-butyne
trans-piperylene
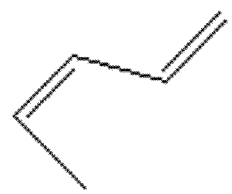
cis-piperylene
1-pentyne
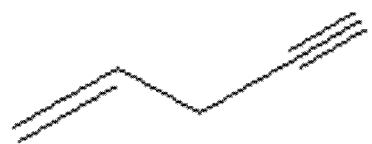
pent-4-ene-1-yne
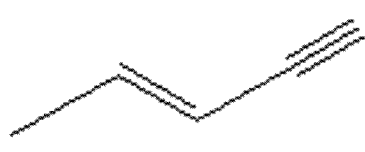
trans-pent-3-ene-1-yne
cis-pent-3-ene-1-yne

Figure 92A 1-
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatggatccgagctcaggaggtaaaaaaacatgaaaacagtagttattattgatgcattac
gaacaccaattggaaaatataaaggcagcttaagtcaagtaagtgccgtagacttaggaacacatgttacaacacaacttttaaaaagacatt
ccactatttctgaagaaattgatcaagtaatctttggaaatgttttacaagctggaaatggccaaaatcccgcacgacaaatagcaataaacag
cggtttgtctcatgaaattcccgcaatgacggttaatgaggtctgcggatcaggaatgaaggccgttattttggcgaaacaattgattcaattag
gagaagcggaagttttaattgctggcgggattgagaatatgtcccaagcacctaaattacaacgttttaattacgaaacagaaagctacgatg
cgccttttctagtatgatgtatgatggattaacggatgcctttagtggtcaggcaatgggcttaactgctgaaaatgtggccgaaaagtatcat
gtaactagagaagagcaagatcaattttctgtacattcacaattaaaagcagctcaagcacaagcagaagggatattcgctgacgaaatagc
cccattagaagtatcaggaacgcttgtggagaaagatgaagggattcgccctaattcgagcgttgagaagctaggaacgcttaaaacagttt
ttaaagaagacggtactgtaacagcagggaatgcatcaaccattaatgatgggcttctgctttgattattgcttcacaagaatatgccgaagc
acacggtcttccttatttagctattattcgagacagtgtggaagtcggtattgatccagcctatatgggaatttcgccgattaaagccattcaaaa
actgttagcgcgcaatcaacttactacggaagaaattgatctgtatgaaatcaacgaagcatttgcagcaacttcaatcgtggtccaaagaga
actggctttaccagaggaaaaggtcaacatttatggtggcggtatttcattaggtcatgcgattggtgccacaggtgctcgtttattaacgagttt
aagttatcaattaaatcaaaaagaaaagaaatatggagtggcttctttatgtatcggcggtggcttaggactcgctatgctactagagagacct
cagcaaaaaaaaaacagccgattttatcaaatgagtcctgaggaacgcctggcttctcttcttaatgaaggccagatttctgctgatacaaaaa
aagaatttgaaaatacggctttatcttcgcagattgccaatcatatgattgaaaatcaaatcagtgaaacagaagtgccgatgggcgttggctt
acatttaacagtggacgaaactgattatttggtaccaatggcgacagaagagccctcagttattgcggctttgagtaatggtgcaaaaatagc
acaaggatttaaaacagtgaatcaacaacgcttaatgcgtggacaaatcgttttttacgatgttgcagatcccgagtcattgattgataaactac
aagtaagagaagcggaagttttcaacaagcagagttaagttatccatctatcgttaaacggggcggcggcttaagagatttgcaatatcgta
cttttgatgaatcatttgtatctgtcgactttttagtagatgttaaggatgcaatgggggcaaatatcgttaacgctatgttggaaggtgtggccga
gttgttccgtgaatggtttgcggagcaaaagattttattcagtattttaagtaattatgccacggagtcggttgttacgatgaaaacggctattcca
gtttcacgtttaagtaaggggagcaatggccgggaaattgctgaaaaaattgttttagcttcacgctatgcttcattagatccttatcgggcagtc
acgcataacaaaggaatcatgaatggcattgaagctgtagttttagctacaggaaatgatacacgcgctgttagcgcttcttgtcatgcttttgc
ggtgaaggaaggtcgctaccaaggcttgactagttggacgctggatggcgaacaactaattggtgaaatttcagttccgcttgctttagccac
ggttggcggtgccacaaaagtcttacctaaatctcaagcagctgctgatttgttagcagtgacggatgcaaaagaactaagtcgagtagtag
cggctgttggtttggcacaaaatttagcggcgttacgggccttagtctctgaaggaattcaaaaaggacacatggctctacaagcacgttcttt
agcgatgacggtcggagctactggtaaagaagttgaggcagtcgctcaacaattaaaacgtcaaaaaacgatgaaccaagaccgagccat
ggctatttaaatgatttaagaaaacaataaggaggtaaaaaaacatgacaattgggattgataaaattagttttttgtgccccttattatattg
atatgacggcactggctgaagccagaaatgtagaccctgaaaatttcatattggtattgggcaagaccaaatggcggtgaacccaatcag
ccaagatattgtgacatttgcagccaatgccgcagaagcgatcttgaccaaagaagataaagaggccattgatatggtgattgtcgggactg
agtccagtatcgatgagtcaaaagcggccgcagttgtcttacatcgtttaatggggattcaacctttcgctcgctctttcgaaatcaaggaagct
tgttacggagcaacagcaggcttacagttagctaagaatcacgtagccttacatccagataaaaaagtcttggtcgtagcggcagatattgca
aaatatggcttaaattctggcggtgagcctacacaaggagctggggcggttgcaatgttagttgctagtgaaccgcgcattttggctttaaaag
aggataatgtgatgctgacgcaagatatctatgacttttggcgtccaacaggccacccgtatcctatggtcgatggtccttgtcaaacgaaac
ctacatccaatcttttgcccaagtctgggatgaacataaaaaacgaaccggtcttgattttgcagattatgatgctttagcgttccatattccttac
acaaaaatgggcaaaaaagccttattagcaaaaatctccgaccaaactgaagcagaacaggaacgaattttagcccgttatgaagaaagtat
cgtctatagtcgtcgcgtaggaaacttgtatacgggttcactttatctgggactcatttcccttttagaaaatgcaacgactttaaccgcaggcaa
tcaaattggtttattcagttatggttctggtgctgtcgctgaattttcactggtgaattag

Figure 92B tagctggttatcaaaatcatttacaaaaagaaactcatttagcactgctggataatcggacagaactttctatcgctgaatatgaagccatgtttg
cagaaactttagacacagacattgatcaaacgttagaagatgaattaaaatatagtatttctgctattaataataccgttcgttcttatcgaaacta
agagatctgcagctggtaccatatgggaattcgaagcttgggcccgaacaaaaactcatctcagaagaggatctgaatagcgccgtcgacc
atcatcatcatcatcattgagtttaaacggtctccagcttggctgttttggcggatgagagaagattttcagcctgatacagattaaatcagaacg
cagaagcggtctgataaaaacagaatttgcctggcggcagtagcgcggtggtcccacctgaccccatgccgaactcagaagtgaaacgcc
gtagcgccgatggtagtgtggggtctccccatgcgagagtagggaactgccaggcatcaaataaaacgaaaggctcagtcgaaagactg
ggcctttcgttttatctgttgtttgtcggtgaacgctctcctgagtaggacaaatccgccgggagcggatttgaacgttgcgaagcaacggccc
ggagggtggcgggcaggacgcccgccataaactgccaggcatcaaattaagcagaaggccatcctgacggatggccttttgcgtttctac
aaactcttttgtttattttctaaatacattcaaatatgtatccgctcatgagacaataaccctgataaatgcttcaataatattgaaaaaggaagag
tatgagtattcaacatttccgtgtcgcccttattcccttttttgcggcattttgccttcctgttttgctcacccagaaacgctggtgaaagtaaaaga
tgctgaagatcagttgggtgcacgagtgggttacatcgaactggatctcaacagcggtaagatccttgagagttttcgccccgaagaacgttt
tccaatgatgagcacttttaaagttctgctatgtggcgcggtattatcccgtgttgacgccgggcaagagcaactcggtcgccgcatacactat
tctcagaatgacttggttgagtactcaccagtcacagaaaagcatcttacggatggcatgacagtaagagaattatgcagtgctgccataacc
atgagtgataacactgcggccaacttacttctgacaacgatcggaggaccgaaggagctaaccgcttttttgcacaacatgggggatcatgt
aactcgccttgatcgttgggaaccggagctgaatgaagccataccaaacgacgagcgtgacaccacgatgcctgtagcaatggcaacaac
gttgcgcaaactattaactggcgaactacttactctagcttcccggcaacaattaatagactggatggaggcggataaagttgcaggaccact
tctgcgctcggcccttccggctggctggtttattgctgataaatctggagccggtgagcgtgggtctcgcggtatcattgcagcactggggcc
agatggtaagccctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcattttaatttaaaaggatctaggtg
aagatcctttttgataatctcatgaccaaaatcccttaacgtgagttttcgttccactgagcgtcagaccccgtagaaaagatcaaaggatcttct
tgagatcctttttttctgcgcgtaatctgctgcttgcaaacaaaaaaaccaccgctaccagcggtggtttgtttgccggatcaagagctaccaac
tcttttccgaaggtaactggcttcagcagagcgcagataccaaatactgtccttctagtgtagccgtagttaggccaccacttcaagaactctg
tagcaccgcctacatacctcgctctgctaatcctgttaccagtggctgctgccagtggcgataagtcgtgtcttaccgggttggactcaagac
gatagttaccggataaggcgcagcggtcgggctgaacggggggttcgtgcacacagcccagcttggagcgaacgacctacaccgaact
gagatacctacagcgtgagctatgagaaagcgccacgcttcccgaagggagaaaggcggacaggtatccggtaagcggcagggtcgg
aacaggagagcgcacgagggagcttccaggggg aaacgcctggtatctttatagtcctgtcgggtttcgccacctctgacttgagcgtcgat
ttttgtgatgctcgtcaggggggcggagcctatggaaaaacgccagcaacgcggcctttttacggttcctggccttttgctggccttttgctca
catgttctttcctgcgttatcccctgattctgtggataaccgtattaccgcctttgagtgagctgataccgctcgccgcagccgaacgaccgag
cgcagcgagtcagtgagcgaggaagcggaagagcgcctgatgcggtattttctccttacgcatctgtgcggtatttcacaccgcatatggtg
cactctcagtacaatctgctctgatgccgcatagttaagccagtatacactccgctatcgctacgtgactgggtcatggctgcgccccgacac
ccgccaacacccgctgacgcgccctgacgggcttgtctgctcccggcatccgcttacagacaagctgtgaccgtctccgggagctgcatgt
gtcagaggttttcaccgtcatcaccgaaacgcgcgaggcagcagatcaattcgcgcgcgaaggcgaagcggcatgcatttacgttgacac
catcgaatggtgcaaaaccttcgcggtatggcatgatagcgcccggaagagagtcaattcaggtggtgaatgtgaaaccagtaacgttat
acgatgtcgcagagtatgccggtgtctcttatcagaccgtttcccgcgtggtgaaccaggccagccacgtttctgcgaaaacgcgggaaaa
agtggaagcggcgatggcggagctgaattacattcccaaccgcgtggcacaacaactggcgggcaaacagtcgttgctgattggcgttgc
cacctccagtctggccctgcacgcgccgtcgcaaattgtcgcggcgattaaatctcgcgccgatcaactgggtgccagcgtggtggtgtcg
atggtagaacgaagcggcgtcgaagcctgtaaagcggcggtgcacaatcttctcgcgcaacgcgtcagtgggctgatcattaactatccgc
tggatgaccaggatgccattgctgtggaagctgcctgcactaatgttccggcgttatttcttgatgtctctgaccagacacccatcaacagtatt
attttctcccatgaagacggtacgcgactgggcgtggagcatctggtcgcattgggtcaccagcaaatcgcgctgttagcgggcccattaag
ttctgtctcggcgcgtctgcgtctggctggctggcataaatatctcactcgcaatcaaattcagccgatagcggaacgggaaggcgactgga
gtgccatgtccggttttcaacaaaccatgcaaatgctgaatgagggcatcg

Figure 92C ttcccactgcgatgctggttgccaacgatcagatggcgctgggcgcaatgcgcgccattaccgagtccgggctgcgcgttggtgcggatat
ctcggtagtgggatacgacgataccgaagacagctcatgttatatcccgccgtcaaccaccatcaaacaggattttcgcctgctggggcaaa
ccagcgtggaccgcttgctgcaactctctcagggccaggcggtgaagggcaatcagctgttgcccgtctcactggtgaaaagaaaaacca
ccctggcgcccaatacgcaaaccgcctctccccgcgcgttggccgattcattaatgcagctggcacgacaggtttcccgactggaaagcg
ggcagtgagcgcaacgcaattaatgtgagttagcgcgaattgatctg (SEQ ID NO:86)

Figure 103A cccgtcttactgtcgggaattcgcgttggccgattcattaatgcagattctgaaatgagctgttgacaattaatcatccggctcgtataatgtgtg
gaattgtgagcggataacaatttcacacaggaaacagcgccgctgagaaaaagcgaagcggcactgctctttaacaatttatcagacaatct
gtgtgggcactcgaccggaattatcgattaactttattattaaaaattaaagaggtatatattaatgtatcgattaaataaggaggaataaaccat
ggatccgagctcaggaggtaaaaaaacatgaaaacagtagttattattgatgcattacgaacaccaattggaaaatataaaggcagcttaagt
caagtaagtgccgtagacttaggaacacatgttacaacacaacttttaaaaagacattccactatttctgaagaaattgatcaagtaatctttgga
aatgttttacaagctggaaatggccaaaatcccgcacgacaaatagcaataaacagcggtttgtctcatgaaattcccgcaatgacggttaat
gaggtctgcggatcaggaatgaaggccgttattttggcgaaacaattgattcaattaggagaagcggaagtttttaattgctggcgggattgag
aatatgtcccaagcacctaaattacaacgttttaattacgaaacagaaagctacgatgcgccttttctagtatgatgtatgatggattaacggat
gcctttagtggtcaggcaatgggcttaactgctgaaaatgtggccgaaaagtatcatgtaactagagaagagcaagatcaattttctgtacatt
cacaattaaaagcagctcaagcacaagcagaagggatattcgctgacgaaatagccccattagaagtatcaggaacgcttgtggagaaag
atgaagggattcgccctaattcgagcgttgagaagctaggaacgcttaaaacagttttaaagaagacggtactgtaacagcagggaatgca
tcaaccattaatgatggggcttctgctttgattattgcttcacaagaatatgccgaagcacacggtcttccttatttagctattattcgagacagtgt
ggaagtcggtattgatccagcctatatgggaatttcgccgattaaagccattcaaaaaactgttagcgcgcaatcaacttactacggaagaaatt
gatctgtatgaaatcaacgaagcatttgcagcaacttcaatcgtggtccaaagagaactggctttaccagaggaaaaggtcaacatttatggt
ggcggtatttcattaggtcatgcgattggtgccacaggtgctcgtttattaacgagtttaagttatcaattaaatcaaaaagaaaagaaatatgg
agtggcttcttatgtatcggcggtggcttaggactcgctatgctactagagagacctcagcaaaaaaaaaacagccgattttatcaaatgagt
cctgaggaacgcctggcttctcttcttaatgaaggccagatttctgctgatacaaaaaaagaatttgaaaatacggctttatcttcgcagattgc
caatcatatgattgaaaatcaaatcagtgaaacagaagtgccgatgggcgttggcttacatttaacagtggacgaaactgattatttggtacca
atggcgacagaagagccctcagttattgcggctttgagtaatggtgcaaaaatagcacaaggatttaaaacagtgaatcaacaacgcttaat
gcgtggacaaatcgtttttacgatgttgcagatcccgagtcattgattgataaactacaagtaagagaagcggaagttttcaacaagcagag
ttaagttatccatctatcgttaaacggggcggcggcttaagagatttgcaatatcgtactttgatgaatcatttgtatctgtcgactttagtagat
gttaaggatgcaatgggggcaaatatcgttaacgctatgttggaaggtgtggccgagttgttccgtgaatggtttgcggagcaaaagatttat
tcagtatttaagtaattatgccacggagtcggttgttacgatgaaaacggctattccagtttcacgttaagtaaggggagcaatggccggga
aattgctgaaaaaattgttttagcttcacgctatgcttcattagatccttatcgggcagtcacgcataacaaaggaatcatgaatggcattgaag
ctgtagtttagctacaggaaatgatacacgcgctgttagcgcttcttgtcatgcttttgcggtgaaggaaggtcgctaccaaggcttgactagt
tggacgctggatggcgaacaactaattggtgaaatttcagttccgcttgctttagccacggttggcggtgccacaaaagtcttacctaaatctc
aagcagctgctgatttgttagcagtgacggatgcaaaagaactaagtcgagtagtagcggctgttggtttggcacaaaatttagcggcgttac
gggccttagtctctgaaggaattcaaaaaggacacatggctctacaagcacgttcttagcgatgacggtcggagctactggtaaagaagtt
gaggcagtcgctcaacaattaaaacgtcaaaaaacgatgaaccaagaccgagccatggctatttaaatgatttaagaaaacaataaagga
ggtaaaaaaacatgacaattgggattgataaaattagttttttttgtgcccccttattatattgatatgacggcactggctgaagccagaaatgtag
accctggaaaatttcatattggtattgggcaagaccaaatggcggtgaacccaatcagccaagatattgtgacatttgcagccaatgccgca
gaagcgatcttgaccaaagaagataaagaggccattgatatggtgattgtcgggactgagtccagtatcgatgagtcaaaagcggccgcag
ttgtcttacatcgtttaatggggattcaacctttcgctcgctctttcgaaatcaaggaagcttgttacggagcaacagcaggcttacagttagcta
agaatcacgtagccttacatccagataaaaaagtcttggtcgtagcggcagatattgcaaaatatggcttaaattctggcggtgagcctacac
aaggagctggggcggttgcaatgttagttgctagtgaaccgcgcatttttggctttaaaagaggataatgtgatgctgacgcaagatatctatg
acttttggcgtccaacaggccaccgtatcctatggtcgatggtcctttgtcaaacgaaacctacatccaatcttttgcccaagtctgggatgaa
cataaaaaacgaaccggtcttgattttgcagattatgatgctttagcgttccatattccttacacaaaaatgggcaaaaaagccttattagcaaaa
atctccgaccaaactgaagcagaacaggaacgaattttagcccgttatgaagaaagtatcgtctatagtcgtcgcgtaggaaacttgtatacg
ggttcactttatctgggactcatttccctttagaaaatgcaacgactttaaccgcaggcaatcaaattggtttattcagttatggttctggtgctgt
cgctgaattttcactggtgaattagtagctggttatcaaaatcatttacaaaaagaaactcatttagcactgctggataatcggacagaactttct
atcgctgaatatgaagccatgtttgcagaaactttagacacagacattgatcaaacgtta

Figure 103B gaagatgaattaaaatatagtatttctgctattaataataccgttcgttcttatcgaaactaaagatctgcatcctgcattcgcccttaggaggtaa
aaaaacatgtgtgcgacctcttctcaatttactcagattaccgagcataattcccgtcgttccgcaaactatcagccaaacctgtggaatttcga
attcctgcaatccctggagaacgacctgaaagtggaaaagctggaggagaaagcgaccaaactggaggaagaagttcgctgcatgatca
accgtgtagacacccagccgctgtccctgctggagctgatcgacgatgtgcagcgcctgggtctgacctacaaatttgaaaaagacatcatt
aaagccctggaaaacatcgtactgctggacgaaaacaaaagaacaaatctgacctgcacgcaaccgctctgtctttccgtctgctgcgtca
gcacggtttcgaggtttctcaggatgtttttgagcgtttcaaggataaagaaggtggtttcagcggtgaactgaaaggtgacgtccaaggcct
gctgagcctgtatgaagcgtcttacctgggtttcgagggtgagaacctgctggaggaggcgcgtaccttttccatcacccacctgaagaaca
acctgaaagaaggcattaataccaaggttgcagaacaagtgagccacgccctggaactgccatatcaccagcgtctgcaccgtctggagg
cacgttggttcctggataaatacgaaccgaaagaaccgcatcaccagctgctgctggagctggcgaagctggatttttaacatggtacagac
cctgcaccagaaagagctgcaagatctgtcccgctggtggaccgagatgggcctggctagcaaactggattttgtacgcgaccgcctgatg
gaagtttatttctgggcactgggtatggcgccagacccgcagtttggtgaatgtcgcaaagctgttactaaaatgtttggtctggtgacgatcat
cgatgacgtgtatgacgtttatggcactctggacgaactgcaactgttcaccgatgctgtagagcgctgggacgttaacgctattaacaccct
gccggactatatgaaactgtgtttcctggcactgtacaacaccgttaacgacacgtcctattctattctgaaagagaaaggtcataacaacctg
tcctatctgacgaaaagctggcgtgaactgtgcaaagcctttctgcaagaggcgaaatggtccaacaacaaaattatcccggctttctccaag
tacctggaaaacgccagcgtttcctcctccggtgtagcgctgctggcgccgtcttacttttccgtatgccagcagcaggaagacatctccgac
cacgcgctgcgttccctgaccgacttccatggtctggtgcgttctagctgcgttatcttccgcctgtgcaacgatctggccacctctgcggcg
gagctggaacgtggcgagactaccaattctatcattagctacatgcacgaaaacgatggtaccagcgaggaacaggcccgcgaagaact
gcgtaaactgatcgacgccgaatggaaaaagatgaatcgtgaacgcgttagcgactccaccctgctgcctaaagcgttcatggaaatcgca
gttaacatggcacgtgtttcccactgcacctaccagtatggcgatggtctgggtcgcccagactacgcgactgaaaaccgcatcaaactgct
gctgattgacccttttcccgattaaccagctgatgtatgtctaactgcagctggtaccatatgggaattcgaagcttgggcccgaacaaaaactc
atctcagaagaggatctgaatagcgccgtcgaccatcatcatcatcatcattgagtttaaacggtctccagcttggctgttttggcggatgaga
gaagattttcagcctgatacagattaaatcagaacgcagaagcggtctgataaaacagaatttgcctggcggcagtagcgcggtggtccca
cctgacccccatgccgaactcagaagtgaaacgccgtagcgccgatggtagtgtggggtctccccatgcgagagtagggaactgccaggc
atcaaataaaacgaaaggctcagtcgaaagactgggcctttcgttttatctgttgtttgtcggtgaacgctctcctgagtaggacaaatccgcc
gggagcggatttgaacgttgcgaagcaacggcccggagggtggcgggcaggacgcccgccataaactgccaggcatcaaattaagca
gaaggccatcctgacggatggcctttttgcgtttctacaaactcttttgtttatttttctaaatacattcaaatatgtatccgctcatgagacaataa
ccctgataaatgcttcaataatctggcgtaatagcgaagaggcccgcaccgatcgcccttcccaacagttgcgcagcctgaatggcgaatg
gcgcctgatgcggtattttctccttacgcatctgtgcggtatttcacaccgcatatggtgcactctcagtacaatctgctctgatgccgcatagtt
aagccagccccgacacccgccaacacccgctgacgagcttagtaaaagccctcgctagattttaatgcggatgttgcgattacttcgccaact
attgcgataacaagaaaaagccagccttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaagcggcgtcggcttgaacgaattgt
tagacattatttgccgactaccttggtgatctcgcctttcacgtagtggacaaattcttccaactgatctgcgcgcgaggccaagcgatcttcttc
ttgtccaagataagcctgtctagcttcaagtatgacgggctgatactgggccggcaggcgctccattgcccagtcggcagcgacatccttcg
gcgcgattttgccggttactgcgctgtaccaaatgcgggacaacgtaagcactacatttcgctcatcgccagcccagtcgggcggcgagttc
catagcgttaaggtttcatttagcgcctcaaatagatcctgttcaggaaccggatcaaagagttcctccgccgctggacctaccaaggcaacg
ctatgttctcttgcttttgtcagcaagatagccagatcaatgtcgatcgtggctggctcgaagatacctgcaagaatgtcattgcgctgccattct
ccaaattgcagttcgcgcttagctggataacgccacggaatgatgtcgtcgtgcacaacaatggtgacttctacagcgcggagaatctcgct
ctctccaggggaagccgaagtttccaaaaggtcgttgatcaaagctcgccgcgttgtttcatcaagccttacggtcaccgtaaccagcaaatc
aatatcactgtgtggcttcaggccgccatccactgcggagccgtacaaatgtacggccagcaacgtcggttcgagatggcgctcgatgacg
ccaactacctctgatagttgagtcgatacttcggcgatcaccgcttccctcatgatgtttaactttgttttagggcgactgccctgctgcgtaaca
tcgttgctgctccataacatcaaacatcgacccacggcgtaacgcgcttgctgcttggat

Figure 103C gcccgaggcatagactgtaccccaaaaaaacagtcataacaagccatgaaaaccgccactgcgccgttaccaccgctgcgttcggtcaag
gttctggaccagttgcgtgagcgcatacgctacttgcattacagcttacgaaccgaacaggcttatgtccactggggttcgtgccttcatccgttt
ccacggtgtgcgtcacccggcaaccttgggcagcagcgaagtcgaggcatttctgtcctggctggcgaacgagcgcaaggtttcggtctc
cacgcatcgtcaggcattggcggccttgctgttcttctacggcaaggtgctgtgcacggatctgccctggcttcaggagatcggaagacctc
ggccgtcgcggcgcttgccggtggtgctgaccccggatgaagtggttcgcatcctcggttttctggaaggcgagcatcgtttgttcgcccag
cttctgtatggaacgggcatgcggatcagtgagggtttgcaactgcgggtcaaggatctggatttcgatcacggcacgatcatcgtgcggga
gggcaagggctccaaggatcgggccttgatgttacccgagagcttggcacccagcctgcgcgagcaggggaattaattcccacgggtttt
gctgcccgcaaacgggctgttctggtgttgctagtttgttatcagaatcgcagatccggcttcagccggtttgccggctgaaagcgctatttctt
ccagaattgccatgatttttcccacgggaggcgtcactggctcccgtgttgtcggcagctttgattcgataagcagcatcgcctgtttcagg
ctgtctatgtgtgactgttgagctgtaacaagttgtctcaggtgttcaatttcatgttctagttgctttgttttactggtttcacctgttctattaggtgtt
acatgctgttcatctgttacattgtcgatctgttcatggtgaacagctttgaatgcaccaaaaactcgtaaaagctctgatgtatctatcttttttaca
ccgttttcatctgtgcatatggacagttttcccttttgatatgtaacggtgaacagttgttctactttgtttgttagtcttgatgcttcactgatagatac
aagagccataagaacctcagatccttccgtatttagccagtatgttctctagtgtggttcgttgttttttgcgtgagccatgagaacgaaccattga
gatcatacttactttgcatgtcactcaaaaatttgcctcaaaactggtgagctgaattttttgcagttaaagcatcgtgtagtgtttttcttagtccgtt
atgtaggtaggaatctgatgtaatggttgttggtattttgtcaccattcattttatctggttgttctcaagttcggttacgagatccatttgtctatcta
gttcaacttggaaaatcaacgtatcagtcgggcggcctcgcttatcaaccaccaatttcatattgctgtaagtgtttaaatctttacttattggtttc
aaaaacccattggttaagccttttaaaactcatggtagttattttcaagcattaacatgaacttaaattcatcaaggctaatctctatatttgccttgtga
gttttcttttgtgttagttcttttaataaccactcataaatcctcatagagtatttgttttcaaaagacttaacatgttccagattatattttatgaatttttt
aactggaaaagataaggcaatatctcttcactaaaaaactaattctaattttcgcttgagaacttggcatagtttgtccactggaaaatctcaaag
cctttaaccaaaggattcctgatttccacagttctcgtcatcagctctctggttgctttagctaatacaccataagcatttttccctactgatgttcatc
atctgagcgtattggttataagtgaacgataccgtccgttctttccttgtagggttttcaatcgtgggggttgagtagtgccacacagcataaaatt
agcttggtttcatgctccgttaagtcatagcgactaatcgctagttcatttgctttgaaaacaactaattcagacatacatctcaattggtctaggt
gattttaatcactataccaattgagatgggctagtcaatgataattactagtcctttcctttgagttgtgggtatctgtaaattctgctagacctttgc
tggaaaacttgtaaattctgctagaccctctgtaaattccgctagacctttgtgtgtttttttgtttatattcaagtggttataatttatagaataaaga
aagaataaaaaagataaaaagaatagatcccagccctgtgtataactcactactttagtcagttccgcagtattacaaaaggatgtcgcaaa
cgctgtttgctcctctacaaaacagaccttaaaaccctaaaggcttaagtagcaccctcgcaagctcgggcaaatcgctgaatattccttttgtc
tccgaccatcaggcacctgagtcgctgtcttttcgtgacattcagttcgctgcgctcacggctctggcagtgaatggggtaaatggcacta
caggcgccttttatggattcatgcaaggaaactacccataatacaagaaaagcccgtcacgggcttctcagggcgttttatggcgggtctgct
atgtggtgctatctgacttttgctgttcagcagttcctgccctctgattttccagtctgaccacttcggattatcccgtgacaggtcattcagactg
gctaatgcacccagtaaggcagcggtatcatcaacaggctta (SEQ ID NO:87)

Figure 108A 1-
caagaaaaatgccccgcttacgcagggcatccatttattactcaaccgtaaccgattttgccaggttacgcggctggtcaacgtcggtgccttt
gatcagcgcgacatggtaagccagcagctgcagcggaacggtgtagaagatcggtgcaatcacctcttccacatgcggcatctcgatgat
gtgcatgttatcgctacttacaaaacccgcatcctgatcggcgaagacatacaactgaccgccacgcgcgcgaacttcttcaatgttggatttc
agtttttccagcaattcgttgttcggtgcaacaacaataaccggcatatcggcatcaattagcgccagcggaccgtgtttcagttcgccagcag
cgtaggcttcagcgtgaatgtaagagatctctttcaacttcaatgcgccttccagcgcgattgggtactgatcgccacggcccaggaacagc
gcgtgatgtttgtcagagaaatcttctgccagcgcttcaatgcgtttgtcctgagacagcatctgctcaatacggctcggcagcgcctgcaga
ccatgcacgatgtcatgttcaatggaggcatccagacctttcaggcgagacagcttcgccaccagcatcaacagcacagttaactgagtggt
gaatgcttagtggatgccacgccgatttctgtaccgcgttggtcattagcgccagatcggattcgcgcaccagagaagaacccggaacgt
tacagattgccagtgaaccaaggtaacccagctctttcgacagacgcaggccagccagggtatccgcggtttcgccagactgtgacacgat
cgcccttcccaacagttgcgcagcctatacgtacggcagtttaaggtttacacctataaagagagagccgttatcgtctgtttgtggatgtac
agagtgatattattgacacgccggggcgacggatggtgatcccctggccagtgcacgtctgctgtcagataaagtctcccgtgaactttac
ccggtggtgcatatcggggatgaaagctggcgcatgatgaccaccgatatggccagtgtgccggtctccgttatcggggaagaagtggct
gatctcagccaccgcgaaaatgacatcaaaaacgccattaacctgatgttctggggaatataaatgtcaggcatgagattatcaaaaaggat
cttcacctagatccttttcacgtagaaagccagtccgcagaaacggtgctgaccccggatgaatgtcagctactgggctatctggacaaggg
aaaacgcaagcgcaaagagaaagcaggtagcttgcagtgggcttacatggcgatagctagactgggcggttttatggacagcaagcgaa
ccggaattgccagctggggcgccctctggtaaggttgggaagccctgcaaagtaaactggatggctttctcgccgccaaggatctgatggc
gcaggggatcaagctctgatcaagagacaggatgaggatcgtttcgcatgattgaacaagatggattgcacgcaggttctccggccgcttg
ggtggagaggctattcggctatgactgggcacaacagacaatcggctgctctgatgccgccgtgttccggctgtcagcgcaggggcgccc
ggttctttttgtcaagaccgacctgtccggtgccctgaatgaactgcaagacgaggcagcgcggctatcgtggctggccacgacgggcgtt
ccttgcgcagctgtgctcgacgttgtcactgaagcgggaagggactggctgctattgggcgaagtgccggggcaggatctcctgtcatctc
accttgctcctgccgagaaagtatccatcatggctgatgcaatgcggcggctgcatacgcttgatccggctacctgcccattcgaccaccaa
gcgaaacatcgcatcgagcgagcacgtactcggatggaagccggtcttgtcgatcaggatgatctggacgaagagcatcaggggctcgc
gccagccgaactgttcgccaggctcaaggcgagcatgcccgacggcgaggatctcgtcgtgacccatggcgatgcctgcttgccgaatat
catggtggaaaatggccgcttttctggattcatcgactgtggccggctgggtgtggcggaccgctatcaggacatagcgttggctacccgtg
atattgctgaagagcttggcggcgaatgggctgaccgcttcctcgtgctttacggtatcgccgctcccgattcgcagcgcatcgccttctatc
gccttcttgacgagttcttctgaattattaacgcttacaatttcctgatgcggtattttctccttacgcatctgtgcggtatttcacaccgcatacagg
tggcacttttcggggaaatgtgcgcggaaccccctatttgtttatttttctaaatacattcaaatatgtatccgctcatgagacaataaccctgataa
atgcttcaataatagcacgtgaggagggccaccatggccaagttgaccagtgccgttccggtgctcaccgcgcgcgacgtcgccggagc
ggtcgagttctggaccgaccggctcgggttctcccctagtaacggccgccagtgtgctggaattcaggcagttcaacctgttgatagtacgt
actaagctctcatgtttcacgtactaagctctcatgtttaacgtactaagctctcatgtttaacgaactaaaccctcatggctaacgtactaagctc
tcatggctaacgtactaagctctcatgtttcacgtactaagctctcatgtttgaacaataaaattaatataaatcagcaacttaaatagcctctaag
gttttaagttttataagaaaaaaagaatatataaggcttttaaagcttttaaggtttaacggttgtggacaacaagccagggatgtaacgcactg
agaagcccttagagcctctcaaagcaattttcagtgacacaggaacacttaaccggctgacagcctgaattctgcagatatctgttttccactct
tcgttcactttcgccaggtagctggtgaagacgaaggaagtcccggagccatctgcgcggcgtactacagcaatgttttgtgaaggcagttt
cagacccggattcagtttggcgatggcttcatcatcccacttcttgattttgcccaggtagatgtcgccgagggttttaccatccagcaccagtt
cgccagacttcagccctggaatgttaaccgccagcaccacgccgccaatcacggtcgggaactggaacagaccttcctgagccagttttc
gtcagacagcggcgcgtcagaggcaccaaaatcaacggtattagcgataatctgttttacgccaccggaagaaccgataccctggtagtta
actttattaccggtttctttctggtaagtgtcagcccatttggcatacaccggcgcagggaaggttgcacctgcacctgtcaggcttgcttctgc
aaacacagagaaagcactcatcgataaggtcgcggcgacaacagttgcgacggtggtacgcataactttcataatgtctcctggggaggatt
cataaagcattgtttgttggctacgagaagcaaaataggacaaacaggtgacagttatatgtaaggaatatgacagttttatgacagagagat
aaagtcttcagtctgatttaaataagcgttgatattcagtcaattacaaacattaataacg

Figure 108B aagagatgacagaaaaattttcattctgtgacagagaaaaagtagccgaagatgacggtttgtcacatggagttggcaggatgtttgattaaa
agcaattaaccctcactaaagggcggccgcgaagttcctattctctagaaagtataggaacttcattctaccgggtaggggaggcgcttttcc
caaggcagtctggagcatgcgctttagcagccccgctgggcacttggcgctacacaagtggcctctggcctcgcacacattccacatccac
cggtaggcgccaaccggctccgttctttggtgccccttcgcgccaccttccactcctcccctagtcaggaagttccccccccgccccgcag
ctcgcgtcgtgcaggacgtgacaaatggaagtagcacgtctcactagtctcgtgcagatggacagcaccgctgagcaatggaagcgggta
ggcctttggggcagcggccaatagcagctttgctccttcgctttctgggctcagaggctgggaagggtgggtccggggcgggctcagg
ggcgggctcagggcggggcgggcgcccgaaggtcctccggaggcccggcattctgcacgcttcaaaagcgcacgtctgccgcgctg
ttctcctcttcctcatctccgggcctttcgacctgcagcagcacgtgttgacaattaatcatcggcatagtatatcggcatagtataatacgacaa
ggtgaggaactaaaccatggagaaaaaaatcactggatataccaccgttgatatatcccaatggcatcgtaaagaacattttgaggcatttca
gtcagttgctcaatgtacctataaccagaccgttcagctggatattacggccttttaaagaccgtaaagaaaaataagcacaagttttatccgg
cctttattcacattcttgcccgcctgatgaatgctcatccggaattccgtatggcaatgaaagacggtgagctggtgatatgggatagtgttcac
ccttgttacaccgttttccatgagcaaactgaaacgtttcatcgctctggagtgaataccacgacgattccggcagtttctacacatatattcg
caagatgtggcgtgttacggtgaaaacctggcctatttccctaaagggtttattgagaatatgttttcgtctcagccaatccctgggtgagtttc
accagttttgatttaaacgtggccaatatggacaacttcttcgcccccgttttcaccatgggcaaatattatacgcaaggcgacaaggtgctgat
gccgctggcgattcaggttcatcatgccgtttgtgatggcttccatgtcggcagaatgcttaatgaattacaacagtactgcgatgagtggcag
ggcggggcgtaagcgggactctggggttcgaataaagaccgaccaagcgacgtctgagagctccctggcgaattcggtaccaataaaag
agctttattttcatgatctgtgtgttggttttgtgtgcggcgcggaagttcctattctctagaaagtataggaacttcctcgagccctatagtgagt
cgtattagcccttgacgatgccacatcctgagcaaataattcaaccactaattgtgagcggataacacaaggaggaaacagctatgtcattac
cgttcttaacttctgcaccgggaaaggttattattttggtgaacactctgctgtgtacaacaagcctgccgtcgctgctagtgtgtctgcgttga
gaacctacctgctaataagcgagtcatctgcaccagatactattgaattggacttcccggacattagctttaatcataagtggtccatcaatgatt
tcaatgccatcaccgaggatcaagtaaactcccaaaaattggccaaggctcaacaagccaccgatggcttgtctcaggaactcgttagtcttt
tggatccgttgttagctcaactatccgaatccttccactaccatgcagcgttttgtttcctgtatatgtttgtttgcctatgccccccatgccaagaat
attaagttttctttaaagtctactttacccatcggtgctggttgggctcaagcgcctctatttctgtatcactggccttagctatggcctacttggg
ggggttaataggatctaatgacttggaaaagctgtcagaaaacgataagcatatagtgaatcaatgggccttcataggtgaaaagtgtattca
cggtacccttcaggaatagataacgctgtggccacttatggtaatgccctgctatttgaaaaagactcacataatggaacaataaacacaaa
caattttaagttcttagatgatttcccagccattccaatgatcctaacctatactagaattccaaggtctacaaaagatcttgttgctcgcgttcgtg
tgttggtcaccgagaaatttcctgaagttatgaagccaattctagatgccatgggtgaatgtgccctacaaggcttagagatcatgactaagtta
agtaaatgtaaaggcaccgatgacgaggctgtagaaactaataatgaactgtatgaacaactattggaattgataagaataaatcatggactg
cttgtctcaatcggtgtttctcatcctggattagaacttattaaaaatctgagcgatgatttgagaattggctccacaaaacttaccggtgctggtg
gcggcggttgctctttgactttgttacgaagagacattactcaagagcaaattgacagcttcaaaaagaaattgcaagatgatttagttacgag
acatttgaaacagacttgggtgggactggctgctgtttgttaagcgcaaaaaatttgaataaagatcttaaaatcaaatccctagtattccaatta
tttgaaaataaaactaccacaaagcaacaaattgacgatctattattgccaggaaacacgaatttaccatggacttcataagctaatttgcgata
ggcctgcacccttaaggaggaaaaaaacatgtcagagttgagagccttcagtgccccagggaaagcgttactagctggtggatatttagtttt
agatacaaaatatgaagcatttgtagtcggattatcggcaagaatgcatgctgtagcccatccttacggttcattgcaagggtctgataagtttg
aagtgcgtgtgaaaagtaaacaatttaaagatggggagtggctgtaccatataagtcctaaaagtggcttcattcctgtttcgataggcggatc
taagaacccttcattgaaaaagttatcgctaacgtatttagctactttaaacctaacatggacgactactgcaatagaaacttgttcgttattgata
ttttctctgatgatgcctaccattctcaggaggatagcgttaccgaacatcgtggcaacagaagattgagttttcattcgcacagaattgaagaa
gttcccaaaacagggctgggctcctcggcaggtttagtcacagttttaactacagctttggcctccttttttgtatcggacctggaaaataatgta
gacaaatatagagaagttattcataatttagcacaagttgctcattgtcaagctcagggtaaaattggaagcgggtttgatgtagcggcggca
gcatatggatctatcagatatagaagattcccacccgcattaatctctaatttgccagatattggaagtgctacttacggcagtaaactggcgca
tttggttgatgaagaagactggaatattacgattaaaagtaaccatttaccttc

Figure 108C gggattaactttatggatgggcgatattaagaatggttcagaaacagtaaaactggtccagaaggtaaaaaattggtatgattcgcatatgcca
gaaagcttgaaaatatatacagaactcgatcatgcaaattctagatttatggatggactatctaaactagatcgcttacacgagactcatgacga
ttacagcgatcagatatttgagtctcttgagaggaatgactgtacctgtcaaaagtatcctgaaatcacagaagttagagatgcagttgccaca
attagacgttcctttagaaaaataactaaagaatctggtgccgatatcgaacctcccgtacaaactagcttattggatgattgccagaccttaaa
aggagttcttacttgcttaatacctggtgctggtggttatgacgccattgcagtgattactaagcaagatgttgatcttagggctcaaaccgctaa
tgacaaaagattttctaaggttcaatggctggatgtaactcaggctgactggggtgttaggaaagaaaaagatccggaaacttatcttgataaa
taacttaaggtagctgcatgcagaattcgcccttaaggaggaaaaaaaaatgaccgtttacacagcatccgttaccgcacccgtcaacatcg
caacccttaagtattgggggaaaagggacacgaagttgaatctgcccaccaattcgtccatatcagtgacttatcgcaagatgacctcagaa
cgttgacctctgcggctactgcacctgagtttgaacgcgacactttgtggttaaatggagaaccacacagcatcgacaatgaaagaactcaa
aattgtctgcgcgacctacgccaattaagaaaggaaatggaatcgaaggacgcctcattgcccacattatctcaatggaaactccacattgtc
tccgaaaataactttcctacagcagctggtttagcttcctccgctgctggctttgctgcattggtctctgcaattgctaagttataccaattaccac
agtcaacttcagaaatatctagaatagcaagaaagggggtctggttcagcttgtagatcgttgtttggcggatacgtggcctgggaaatgggaa
aagctgaagatggtcatgattccatggcagtacaaatcgcagacagctctgactggcctcagatgaaagcttgtgtcctagttgtcagcgata
ttaaaaaggatgtgagttccactcagggtatgcaattgaccgtggcaacctccgaactatttaaagaaagaattgaacatgtcgtaccaaaga
gatttgaagtcatgcgtaaagccattgttgaaaaagatttcgccacctttgcaaaggaaacaatgatggattccaactctttccatgccacatgtt
tggactctttccctccaatattctacatgaatgacacttccaagcgtatcatcagttggtgccacaccattaatcagttttacggagaaacaatcg
ttgcatacacgtttgatgcaggtccaaatgctgtgttgtactacttagctgaaaatgagtcgaaactctttgcatttatctataaattgtttggctctg
ttcctggatgggacaagaaatttactactgagcagcttgaggctttcaaccatcaatttgaatcatctaactttactgcacgtgaattggatcttga
gttgcaaaaggatgttgccagagtgattttaactcaagtcggttcaggcccacaagaaacaaacgaatctttgattgacgcaaagactggtct
accaaaggaataagatcaattcgctgcatcgcccttaggaggtaaaaaaaaatgactgccgacaacaatagtatgccccatggtgcagtatc
tagttacgccaaattagtgcaaaaccaaacacctgaagacattttggaagagtttcctgaaattattccattacaacaaagacctaatacccgat
ctagtgagacgtcaaatgacgaaagcggagaaacatgtttttctggtcatgatgaggagcaaattaagttaatgaatgaaaattgtattgttttg
gattgggacgataatgctattggtgccggtaccaagaaagtttgtcatttaatggaaaatattgaaaagggtttactacatcgtgcattctccgtc
tttattttcaatgaacaaggtgaattacttttacaacaaagagccactgaaaaaataacttccctgatctttggactaacacatgctgctctcatc
cactatgtattgatgacgaattaggtttgaagggtaagctagacgataagattaagggcgctattactgcggcggtgagaaaactagatcatg
aattaggtattccagaagatgaaactaagacaaggggtaagtttcacttttaaacagaatccattacatggcaccaagcaatgaaccatggg
gtgaacatgaaattgattacatcctattttataagatcaacgctaaagaaaacttgactgtcaacccaaacgtcaatgaagttagagacttcaaa
tgggtttcaccaaatgatttgaaaactatgtttgctgacccaagttacaagtttacgccttggtttaagattatttgcgagaattacttattcaactg
gtgggagcaattagatgacctttctgaagtggaaaatgacaggcaaattcatagaatgctataacaacgcgtctacaaataaaaaaggcacg
tcagatgacgtgccttttttcttggggcc (SEQ ID NO:90)

Figure 110A 1-
gtgcggccgcaagcttgtcgacggagctcgaattcggatccctgcagttagacatacatcagctggttaatcgggaaagggtcaatcagca
gcagtttgatgcggttttcagtcgcgtagtctgggcgacccagaccatcgccatactggtaggtgcagtgggaaacacgtgccatgttaact
gcgatttccatgaacgcttaggcagcagggtggagtcgctaacgcgttcacgattcatcttttccattcggcgtcgatcagtttacgcagttct
tcgcgggcctgttcctcgctggtaccatcgttttcgtgcatgtagctaatgatagaattggtagtctcgccacgttccagctccgccgcagagg
tggccagatcgttgcacaggcggaagataacgcagctagaacgcaccagaccatggaagtcggtcagggaacgcagcgcgtggtcgga
gatgtcttcctgctgctggcatacggaaaagtaagacggcgccagcagcgctacaccggaggaggaaacgctggcgttttccaggtactt
ggagaaagccgggataattttgttgttggaccatttcgcctcttgcagaaaggctttgcacagttcacgccagcttttcgtcagataggacagg
ttgttatgaccttctctttcagaatagaataggacgtgtcgttaacggtgttgtacagtgccaggaaacacagtttcatatagtccggcagggt
gttaatagcgttaacgtcccagcgctctacagcatcggtgaacagttgcagttcgtccagagtgccataaacgtcatacacgtcatcgatgat
cgtcaccagaccaaacattttagtaacagctttgcgacattcaccaaactgcgggtctggcgccatacccagtgcccagaaataaacttccat
caggcggtcgcgtacaaaatccagtttgctagccaggcccatctcggtccaccagcgggacagatcttgcagctctttctggtgcagggtct
gtaccatgttaaaatccagcttcgccagctccagcagcagctggtgatgcggttctttcggttcgtatttatccaggaaccaacgtgcctccag
acggtgcagacgctggtgatatggcagttccagggcgtggctcacttgttctgcaaccttggtattaatgccttcttcaggttgttcttcaggtg
ggtgatggaaaaggtacgcgcctcctccagcaggttctcaccctcgaaacccaggtaagacgcttcatacaggctcagcaggccttggac
gtcacctttcagttcaccgctgaaaccaccttctttatccttgaaacgctcaaaaacatcctgagaaacctcgaaaccgtgctgacgcagcag
acggaaagacagagcggttgcgtgcaggtcagatttgttcttttttgttttcgtccagcagtacgatgttttccagggctttaatgatgtcttttcaa
atttgtaggtcagacccaggcgctgcacatcgtcgatcagctccagcagggacagcggctgggtgtctacacggttgatcatgcagcgaac
ttcttcctccagtttggtcgctttctcctccagcttttccactttcaggtcgttctccagggattgcaggaattcgaaattccacaggtttggctgat
agtttgcggaacgacgggaattatgctcggtaatctgagtaaattgagaagaggtcgcacacatggtatatctccttcttaaagttaaacaaaa
ttatttctagagggaattgttatccgctcacaattccctatagtgagtcgtattaatttcgcgggatcgagatctcgatcctctacgccggacg
catcgtggccggcatcaccggcgccacaggtgcggttgctggcgcctatatcgccgacatcaccgatggggaagatcgggctcgccactt
cgggctcatgagcgcttgtttcggcgtgggtatggtggcaggccccgtggccggggggactgttgggcgccatctccttgcatgcaccattc
cttgcggcggcggtgctcaacgcgctcaacctactactgggctgcttcctaatgcaggagtcgcataagggagagcgtcgagatcccgga
caccatcgaatggcgcaaaacctttcgcggtatggcatgatagcgcccggaagagagtcaattcaggtggtgaatgtgaaaccagtaac
gttatacgatgtcgcagagtatgccggtgtctcttatcagaccgtttcccgcgtggtgaaccaggccagccacgtttctgcgaaaacgcggg
aaaaagtggaagcggcgatggcggagctgaattacattcccaaccgcgtggcacaacaactggcgggcaaacagtcgttgctgattggc
gttgccacctccagtctggccctgcacgcgccgtcgcaaattgtcgcggcgattaaatctcgcgccgatcaactgggtgccagcgtggtgg
tgtcgatggtagaacgaagcggcgtcgaagcctgtaaagcggcggtgcacaatcttctcgcgcaacgcgtcagtgggctgatcattaacta
tccgctggatgaccaggatgccattgctgtggaagctgcctgcactaatgttccggcgttatttcttgatgtctctgaccagacacccatcaac
agtattattttctcccatgaagacggtacgcgactgggcgtggagcatctggtcgcattgggtcaccagcaaatcgcgctgttagcgggccc
attaagttctgtctcggcgcgtctgcgtctggctggctggcataaatatctcactcgcaatcaaattcagccgatagcggaacgggaaggcg
actggagtgccatgtccggttttcaacaaaccatgcaaatgctgaatgagggcatcgttcccactgcgatgctggttgccaacgatcagatg
gcgctgggcgcaatgcgcgccattaccgagtccgggctgcgcgttggtgcggatatctcggtagtgggatacgacgataccgaagacag
ctcatgttatatcccgccgttaaccaccatcaaacaggattttcgcctgctggggcaaaccagcgtggaccgcttgctgcaactctctcaggg
ccaggcggtgaagggcaatcagctgttgcccgtctcactggtgaaaagaaaaaccaccctggcgcccaatacgcaaaccgcctctcccc
gcgcgttggccgattcattaatgcagctggcacgacaggtttcccgactggaaagcgggcagtgagcgcaacgcaattaatgtaagttagc
tcactcattaggcaccgggatctcgaccgatgcccttgagagccttcaacccagtcagctccttccggtgggcgcggggcatgactatcgtc
gccgcacttatgactgtcttctttatcatgcaactcgtaggacaggtgccggcagcgctctgggtcatttttcggcgaggaccgctttcgctgga
gcgcgacgatgatcggcctgtcgcttgcggtattcggaatcttgcacgccctcgctcaagccttcgtcactggtcccgccaccaaacgtttcg
gcgagaagcaggccattatcgccggcatggcggccccacgggtgcgcatgatcgtgctcctg

Figure 110B tcgttgaggacccggctaggctggcggggttgccttactggttagcagaatgaatcaccgatacgcgagcgaacgtgaagcgactgctgct
gcaaaacgtctgcgacctgagcaacaacatgaatggtcttcggtttccgtgtttcgtaaagtctggaaacgcggaagtcagcgccctgcacc
attatgttccggatctgcatcgcaggatgctgctggctaccctgtggaacacctacatctgtattaacgaagcgctggcattgaccctgagtga
tttttctctggtcccgccgcatccataccgccagttgtttaccctcacaacgttccagtaaccgggcatgttcatcatcagtaacccgtatcgtga
gcatcctctctcgtttcatcggtatcattaccccatgaacagaaatccccttacacggaggcatcagtgaccaaacaggaaaaaaccgcc
cttaacatggcccgctttatcagaagccagacattaacgcttctggagaaactcaacgagctggacgcggatgaacaggcagacatctgtg
aatcgcttcacgaccacgctgatgagctttaccgcagctgcctcgcgcgtttcggtgatgacggtgaaaacctctgacacatgcagctcccg
gagacggtcacagcttgtctgtaagcggatgccgggagcagacaagcccgtcagggcgcgtcagcgggtgttggcgggtgtcggggcg
cagccatgacccagtcacgtagcgatagcggagtgtatactggcttaactatgcggcatcagagcagattgtactgagagtgcaccatatat
gcggtgtgaaataccgcacagatgcgtaaggagaaaataccgcatcaggcgctcttccgcttcctcgctcactgactcgctgcgctcggtc
gttcggctgcggcgagcggtatcagctcactcaaaggcggtaatacggttatccacagaatcaggggataacgcaggaaagaacatgtga
gcaaaaggccagcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccggtaactatcgtcttgagtc
caacccggtaagacacgacttatcgccactggcagcagccactggtaacaggattagcagagcgaggtatgtaggcggtgctacagagtt
cttgaagtggtggcctaactacggctacactagaaggacagtatttggtatctgcgctctgctgaagccagttaccttcggaaaaagagttgg
tagctcttgatccggcaaacaaaccaccgctggtagcggtggtttttttgtttgcaagcagcagattacgcgcagaaaaaaaggatctcaaga
agatcctttgatcttttctacggggtctgacgctcagtggaacgaaaactcacgttaagggattttggtcatgaacaataaaactgtctgcttaca
taaacagtaatacaagggggtgttatgagccatattcaacgggaaacgtcttgctctaggccgcgattaaattccaacatggatgctgatttatat
gggtataaatgggctcgcgataatgtcgggcaatcaggtgcgacaatctatcgattgtatgggaagcccgatgcgccagagttgtttctgaa
acatggcaaaggtagcgttgccaatgatgttacagatgagatggtcagactaaactggctgacggaatttatgcctcttccgaccatcaagca
ttttatccgtactcctgatgatgcatggttactcaccactgcgatccccgggaaaacagcattccaggtattagaagaatatcctgattcaggtg
aaaatattgttgatgcgctggcagtgttcctgcgccggttgcattcgattcctgtttgtaattgtccttttaacagcgatcgcgtatttcgtctcgct
caggcgcaatcacgaatgaataacggtttggttgatgcgagtgattttgatgacgagcgtaatggctggcctgttgaacaagtctggaaaga
aatgcataaacttttgccattctcaccggattcagtcgtcactcatggtgatttctcacttgataaccttattttttgacgaggggaaattaataggtt
gtattgatgttggacgagtcggaatcgcagaccgataccaggatcttgccatcctatggaactgcctcggtgagttttctccttcattacagaaa
cggcttttcaaaaatatggtattgataatcctgatatgaataaattgcagtttcatttgatgctcgatgagttttctaagaattaattcatgagcgg
atacatatttgaatgtatttagaaaaataaacaaatagggggttccgcgcacatttccccgaaaagtgccacctgaaattgtaaacgttaatattttt
gttaaaattcgcgttaaattttttgttaaatcagctcatttttaaccaataggccgaaatcggcaaaatcccttataaatcaaaagaatagaccga
gatagggttgagtgttgttccagtttggaacaagagtccactattaaagaacgtggactccaacgtcaaagggcgaaaaaccgtctatcagg
gcgatggcccactacgtgaaccatcaccctaatcaagttttttggggtcgaggtgccgtaaagcactaaatcggaacctaaagggagccc
ccgatttagagcttgacggggaaagccggcgaacgtggcgagaaaggaagggaagaaagcgaaaggagcgggcgctagggcgctgg
caagtgtagcggtcacgctgcgcgtaaccaccacacccgccgcgcttaatgcgccgctacagggcgcgtcccattcgccaatccggatat
agttcctcctttcagcaaaaaaccctcaagacccgtttagaggccccaaggggttatgctagttattgctcagcggtggcagcagccaactc
agcttcctttcgggctttgttagcagccggatctcagtggtggtggtggtggtgctcga

SEQUENCE LISTING

<160> NUMBER OF SEQ ID NOS: 109

<210> SEQ ID NO 1
<211> LENGTH: 1692
<212> TYPE: DNA
<213> ORGANISM: Artificial Sequence
<220> FEATURE:
<223> OTHER INFORMATION: Synthetic Construct

<400> SEQUENCE: 1

| | | | | | |
|---|---|---|---|---|---|
| atgtgtgcga | cctcttctca | atttactcag | attaccgagc | ataattcccg | tcgttccgca | 60 |
| aactatcagc | caaacctgtg | gaatttcgaa | ttcctgcaat | ccctggagaa | cgacctgaaa | 120 |
| gtggaaaagc | tggaggagaa | agcgaccaaa | ctggaggaag | aagttcgctg | catgatcaac | 180 |
| cgtgtagaca | cccagccgct | gtccctgctg | gagctgatcg | acgatgtgca | gcgcctgggt | 240 |
| ctgacctaca | aatttgaaaa | agacatcatt | aaagccctgg | aaaacatcgt | actgctggac | 300 |
| gaaaacaaaa | agaacaaatc | tgacctgcac | gcaaccgctc | tgtctttccg | tctgctgcgt | 360 |
| cagcacggtt | tcgaggtttc | tcaggatgtt | tttgagcgtt | tcaaggataa | agaaggtggt | 420 |
| ttcagcggtg | aactgaaagg | tgacgtccaa | ggcctgctga | gcctgtatga | agcgtcttac | 480 |
| ctgggtttcg | agggtgagaa | cctgctggag | gaggcgcgta | cctttccat | cacccacctg | 540 |
| aagaacaacc | tgaaagaagg | cattaatacc | aaggttgcag | aacaagtgag | ccacgccctg | 600 |
| gaactgccat | atcaccagcg | tctgcaccgt | ctggaggcac | gttggttcct | ggataaatac | 660 |
| gaaccgaaag | aaccgcatca | ccagctgctg | ctggagctgg | cgaagctgga | ttttaacatg | 720 |
| gtacagaccc | tgcaccagaa | agagctgcaa | gatctgtccc | gctggtggac | cgagatgggc | 780 |
| ctggctagca | aactggattt | tgtacgcgac | cgcctgatgg | aagtttattt | ctgggcactg | 840 |
| ggtatggcgc | cagacccgca | gtttggtgaa | tgtcgcaaag | ctgttactaa | aatgtttggt | 900 |
| ctggtgacga | tcatcgatga | cgtgtatgac | gtttatggca | ctctggacga | actgcaactg | 960 |
| ttcaccgatg | ctgtagagcg | ctgggacgtt | aacgctatta | acaccctgcc | ggactatatg | 1020 |
| aaactgtgtt | tcctggcact | gtacaacacc | gttaacgaca | cgtcctattc | tattctgaaa | 1080 |
| gagaaaggtc | ataacaacct | gtcctatctg | acgaaaagct | ggcgtgaact | gtgcaaagcc | 1140 |
| tttctgcaag | aggcgaaatg | gtccaacaac | aaaattatcc | cggctttctc | caagtacctg | 1200 |
| gaaaacgcca | gcgtttcctc | ctccggtgta | gcgctgctgg | cgccgtctta | cttttccgta | 1260 |
| tgccagcagc | aggaagacat | ctccgaccac | gcgctgcgtt | ccctgaccga | cttccatggt | 1320 |
| ctggtgcgtt | ctagctgcgt | tatcttccgc | ctgtgcaacg | atctggccac | ctctgcggcg | 1380 |
| gagctggaac | gtggcgagac | taccaattct | atcattagct | acatgcacga | aaacgatggt | 1440 |
| accagcgagg | aacaggcccg | cgaagaactg | cgtaaactga | tcgacgccga | atggaaaaag | 1500 |
| atgaatcgtg | aacgcgttag | cgactccacc | ctgctgccta | aagcgttcat | ggaaatcgca | 1560 |
| gttaacatgg | cacgtgtttc | ccactgcacc | taccagtatg | gcgatggtct | gggtcgccca | 1620 |
| gactacgcga | ctgaaaaccg | catcaaactg | ctgctgattg | accctttccc | gattaaccag | 1680 |
| ctgatgtatg | tc | | | | | 1692 |

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

```
<400> SEQUENCE: 2
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatgtgtgc   420
gacctcttct caatttactc agattaccga gcataattcc cgtcgttccg caaactatca   480
gccaaacctg tggaatttcg aattcctgca atccctggag aacgacctga agtggaaaa    540
gctggaggag aaagcgacca aactggagga agaagttcgc tgcatgatca ccgtgtaga    600
cacccagccg ctgtccctgc tggagctgat cgacgatgtg cagcgcctgg gtctgaccta   660
caaatttgaa aaagacatca ttaaagccct ggaaaacatc gtactgctgg acgaaaacaa   720
aaagaacaaa tctgacctgc acgcaaccgc tctgtctttc cgtctgctgc gtcagcacgg   780
tttcgaggtt tctcaggatg ttttttgagcg tttcaaggat aaagaaggtg gtttcagcgg   840
tgaactgaaa ggtgacgtcc aaggcctgct gagcctgtat gaagcgtctt acctgggttt   900
cgagggtgag aacctgctgg aggaggcgcg taccttttcc atcacccacc tgaagaacaa   960
cctgaaagaa ggcattaata ccaaggttgc agaacaagtg agccacgccc tggaactgcc  1020
atatcaccag cgtctgcacc gtctggaggc acgttggttc ctggataaat acgaaccgaa  1080
agaaccgcat caccagctgc tgctggagct ggcgaagctg gattttaaca tggtacagac  1140
cctgcaccag aaagagctgc aagatctgtc ccgctggtgg accgagatgg gcctggctag  1200
caaactggat tttgtacgcg accgcctgat ggaagtttat ttctgggcac tgggtatggc  1260
gccagacccg cagtttggtg aatgtcgcaa agctgttact aaaatgtttg gtctggtgac  1320
gatcatcgat gacgtgtatg acgtttatgg cactctggac gaactgcaac tgttcaccga  1380
tgctgtagag cgctgggacg ttaacgctat taacaccctg ccggactata tgaaactgtg  1440
tttcctggca ctgtacaaca ccgttaacga cacgtcctat tctattctga agagaaagg    1500
tcataacaac ctgtcctatc tgacgaaaag ctggcgtgaa ctgtgcaaag cctttctgca  1560
agaggcgaaa tggtccaaca acaaaattat cccggctttc tccaagtacc tggaaaacgc  1620
cagcgtttcc tcctccggtg tagcgctgct ggcgccgtct tacttttccg tatgccagca  1680
gcaggaagac atctccgacc acgcgctgcg ttccctgacc gacttccatg tctggtgcg    1740
ttctagctgc gttatcttcc gcctgtgcaa cgatctggcc acctctgcgg cggagctgga  1800
acgtggcgag actaccaatt ctatcattag ctacatgcac gaaaacgatg gtaccagcga  1860
ggaacaggcc cgcgaagaac tgcgtaaact gatcgacgcc gaatgaaaaa agatgaatcg  1920
tgaacgcgtt agcgactcca ccctgctgcc taaagcgttc atggaaatcg cagttaacat  1980
ggcacgtgtt tcccactgca cctaccagta tggcgatggt ctgggtcgcc agactacgc    2040
gactgaaaac cgcatcaaac tgctgctgat tgacccttc ccgattaacc agctgatgta    2100
tgtctaactg cagctggtac catatgggaa ttcgaagctt tctagaacaa aaactcatct  2160
cagaagagga tctgaatagc gccgtcgacc atcatcatca tcatcattga gtttaaacgg  2220
tctccagctt ggctgttttg gcggatgaga agattttc agcctgatac agattaaatc    2280
agaacgcaga agcggtctga taaaacagaa tttgcctggc ggcagtagcg cggtggtccc  2340
```

```
acctgacccc atgccgaact cagaagtgaa acgccgtagc gccgatggta gtgtggggtc    2400
tccccatgcg agagtaggga actgccaggc atcaaataaa acgaaaggct cagtcgaaag    2460
actgggcctt tcgttttatc tgttgtttgt cggtgaacgc tctcctgagt aggacaaatc    2520
cgccgggagc ggatttgaac gttgcgaagc aacggcccgg agggtggcgg gcaggacgcc    2580
cgccataaac tgccaggcat caaattaagc agaaggccat cctgacggat ggccttttttg   2640 cgtttctaca aactctttttt gtttattttt ctaaatacat tcaaatatgt atccgctcat    2700
gagacaataa ccctgataaa tgcttcaata atattgaaaa aggaagagta tgagtattca    2760
acatttccgt gtcgccctta ttcccttttt tgcggcattt tgccttcctg tttttgctca    2820
cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcactttta aagttctgct atgtggcgcg gtattatccc gtgttgacgc    3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gcttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat ccttttttgat aatctcatga ccaaaatccc    3720
ttaacgtgag ttttcgttcc actgagcgtc agacccccgta gaaaagatca aaggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga ttttttgtgat gctcgtcagg gggcggagc ctatgaaaaa acgccagcaa    4380
cgcggccttt ttacggttcc tggccttttg ctggccttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca acacccgctg acgcgccctg acgggcttgt    4740
```

```
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca aatcgcgctg ttagcgggcc    5520
cattaagttc tgtctcggcg cgtctgcgtc tggctggctg gcataaatat ctcactcgca    5580
atcaaattca gccgatagcg gaacgggaag gcgactggag tgccatgtcc ggttttcaac    5640
aaaccatgca aatgctgaat gagggcatcg ttcccactgc gatgctggtt gccaacgatc    5700
agatggcgct gggcgcaatg cgcgccatta ccgagtccgg gctgcgcgtt ggtgcggata    5760
tctcggtagt gggatacgac gataccgaag acagctcatg ttatatcccg ccgtcaacca    5820
ccatcaaaca ggattttcgc ctgctggggc aaaccagcgt ggaccgcttg ctgcaactct    5880
ctcagggcca ggcggtgaag gcaatcagc tgttgcccgt ctcactggtg aaaagaaaaa    5940
ccaccctggc gcccaatacg caaaccgcct ctccccgcgc gttggccgat tcattaatgc    6000
agctggcacg acaggtttcc cgactggaaa gcgggcagtg agcgcaacgc aattaatgtg    6060
agttagcgcg aattgatctg                                                6080

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3
cgtgagatca tatgtgtgcg acctcttctc aatttac                              37

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
cggtcgacgg atccctgcag ttagacatac atcagctg                             38

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5
```

```
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
caccgtcacc ctggatgctg taggcatagg cttggttatg ccggtactgc cgggcctctt   180
gcgggatatc cggatatagt tcctcctttc agcaaaaaac ccctcaagac ccgtttagag   240
gccccaaggg gttatgctag ttattgctca gcggtggcag cagccaactc agcttccttt   300
cgggctttgt tagcagccgg atccctgcag ttagacatac atcagctggt taatcgggaa   360
agggtcaatc agcagcagtt tgatgcggtt tcagtcgcg tagtctgggc gacccagacc    420
atcgccatac tggtaggtgc agtgggaaac acgtgccatg ttaactgcga tttccatgaa   480
cgctttaggc agcagggtgg agtcgctaac gcgttcacga ttcatctttt tccattcggc   540
gtcgatcagt ttacgcagtt cttcgcgggc ctgttcctcg ctggtaccat cgttttcgtg   600
catgtagcta atgatagaat tggtagtctc gccacgttcc agctccgccg cagaggtggc   660
cagatcgttg cacaggcgga agataacgca gctagaacgc accagaccat ggaagtcggt   720
cagggaacgc agcgcgtggt cggagatgtc ttcctgctgc tggcatacgg aaaagtaaga   780
cggcgccagc agcgctacac cggaggagga aacgctggcg ttttccaggt acttggagaa   840
agccgggata attttgttgt tggaccattt cgcctcttgc agaaaggctt tgcacagttc   900
acgccagctt tcgtcagat aggacaggtt gttatgacct ttctctttca gaatagaata    960
ggacgtgtcg ttaacggtgt tgtacagtgc caggaaacac agtttcatat agtccggcag  1020
ggtgttaata gcgttaacgt cccagcgctc tacagcatcg gtgaacagtt gcagttcgtc  1080
cagagtgcca taaacgtcat acacgtcatc gatgatcgtc accagaccaa acattttagt  1140
aacagctttg cgacattcac caaactgcgg gtctggcgcc ataccagtg cccagaaata   1200
aacttccatc aggcggtcgc gtacaaaatc cagtttgcta gccaggccca tctcggtcca  1260
ccagcgggac agatcttgca gctctttctg gtgcagggtc tgtaccatgt taaaatccag  1320
cttcgccagc tccagcagca gctggtgatg cggttctttc ggttcgtatt tatccaggaa  1380
ccaacgtgcc tccagacggt gcagacgctg tgatatggc agttccaggg cgtggctcac   1440
ttgttctgca accttggtat taatgccttc tttcaggttg ttcttcaggt gggtgatgga  1500
aaaggtacgc gcctcctcca gcaggttctc accctcgaaa cccaggtaag acgcttcata  1560
caggctcagc aggccttgga cgtcaccttt cagttcaccg ctgaaaccac cttctttatc  1620
cttgaaacgc tcaaaaacat cctgagaaac ctcgaaaccg tgctgacgca gcagacggaa  1680
agacagagcg gttgcgtgca ggtcagattt gttcttttg ttttcgtcca gcagtacgat   1740
gttttccagg gctttaatga tgtctttttc aaatttgtag gtcagaccca ggcgctgcac  1800
atcgtcgatc agctccagca gggacagcgg ctgggtgtct acacggttga tcatgcagcg  1860
aacttcttcc tccagtttgg tcgctttctc ctccagcttt tccactttca ggtcgttctc  1920
cagggattgc aggaattcga aattccacag gtttggctga tagtttgcgg aacgacggga  1980
attatgctcg gtaatctgag taaattgaga agaggtcgca cacatatgac gaccttcgat  2040
atggccgctg ctgtgatgat gatgatgatg atgatgatga tggcccatgg tatatctcct  2100
tcttaaagtt aaacaaaatt atttctagag gggaattgtt atccgctcac aattccccta  2160
tagtgagtcg tattaatttc gcgggatcga gatctcgatc ctctacgccg gacgcatcgt  2220
ggccggcatc accggcgcca caggtgcggt tgctggcgcc tatatcgccg acatcaccga  2280
tggggaagat cgggctcgcc acttcgggct catgagcgct gtttcggcg tgggtatggt   2340
ggcaggcccc gtggccgggg gactgttggg cgccatctcc ttgcatgcac cattccttgc  2400
```

```
ggcggcggtg ctcaacggcc tcaacctact actgggctgc ttcctaatgc aggagtcgca    2460
taagggagag cgtcgagatc ccggacacca tcgaatggcg caaaaccttt cgcggtatgg    2520
catgatagcg cccggaagag agtcaattca gggtggtgaa tgtgaaacca gtaacgttat    2580
acgatgtcgc agagtatgcc ggtgtctctt atcagaccgt ttcccgcgtg gtgaaccagg    2640
ccagccacgt ttctgcgaaa acgcgggaaa aagtggaagc ggcgatggcg gagctgaatt    2700
acattcccaa ccgcgtggca caacaactgg cgggcaaaca gtcgttgctg attggcgttg    2760
ccacctccag tctggccctg cacgcgccgt cgcaaattgt cgcggcgatt aaatctcgcg    2820
ccgatcaact gggtgccagc gtggtggtgt cgatggtaga acgaagcggc gtcgaagcct    2880
gtaaagcggc ggtgcacaat cttctcgcgc aacgcgtcag tgggctgatc attaactatc    2940
cgctggatga ccaggatgcc attgctgtgg aagctgcctg cactaatgtt ccggcgttat    3000
ttcttgatgt ctctgaccag acacccatca acagtattat tttctcccat gaagacggta    3060
cgcgactggg cgtggagcat ctggtcgcat gggtcacca gcaaatcgcg ctgttagcgg     3120
gcccattaag ttctgtctcg gcgcgtctgc gtctggctgg ctggcataaa tatctcactc    3180
gcaatcaaat tcagccgata gcggaacggg aaggcgactg gagtgccatg tccggttttc    3240
aacaaaccat gcaaatgctg aatgagggca tcgttcccac tgcgatgctg gttgccaacg    3300
atcagatggc gctgggcgca atgcgcgcca ttaccgagtc cgggctgcgc gttggtgcgg    3360
atatctcggt agtgggatac gacgataccg aagacagctc atgttatatc ccgccgttaa    3420
ccaccatcaa acaggatttt cgcctgctgg ggcaaaccag cgtggaccgc ttgctgcaac    3480
tctctcaggg ccaggcggtg aagggcaatc agctgttgcc cgtctcactg gtgaaaagaa    3540
aaaccaccct ggcgcccaat acgcaaaccg cctctccccg cgcgttggcc gattcattaa    3600
tgcagctggc acgacaggtt tcccgactgg aaagcgggca gtgagcgcaa cgcaattaat    3660
gtaagttagc tcactcatta ggcaccggga tctcgaccga tgcccttgag agccttcaac    3720
ccagtcagct ccttccggtg ggcgcggggc atgactatcg tcgccgcact tatgactgtc    3780
ttctttatca tgcaactcgt aggacaggtg ccggcagcgc tctgggtcat tttcggcgag    3840
gaccgctttc gctggagcgc gacgatgatc ggcctgtcgc ttgcggtatt cggaatcttg    3900
cacgccctcg ctcaagcctt cgtcactggt cccgccacca aacgtttcgg cgagaagcag    3960
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
gcgttgcagg ccatgctgtc caggcaggta gatgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacggattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt tccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg atttttctct    4800
```

```
ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatcccccct tacacggagg catcagtgac caaacaggaa aaaaccgccc   4980
ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggg tgttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag gcgctcttcc    5400
gcttcctcgc tcactgactc gctgcgctcg gtcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
ttttctacgg ggtctgacgc tcagtggaac gaaaactcac gttaagggat tttggtcatg    6240
agattatcaa aaaggatctt cacctagatc cttttaaatt aaaaatgaag ttttaaatca    6300
atctaaagta tatatgagta aacttggtct gacagttacc aatgcttaat cagtgaggca    6360
cctatctcag cgatctgtct atttcgttca tccatagttg cctgactccc cgtcgtgtag    6420
ataactacga tacgggaggg cttaccatct ggccccagtg ctgcaatgat accgcgagac    6480
ccacgctcac cggctccaga tttatcagca ataaaccagc cagccggaag ggccgagcgc    6540
agaagtggtc ctgcaacttt atccgcctcc atccagtcta ttaattgttg ccgggaagct    6600
agagtaagta gttcgccagt taatagtttg cgcaacgttg ttgccattgc tgcaggcatc    6660
gtggtgtcac gctcgtcgtt tggtatggct tcattcagct ccggttccca acgatcaagg    6720
cgagttacat gatcccccat gttgtgcaaa aaagcggtta gctccttcgg tcctccgatc    6780
gttgtcagaa gtaagttggc cgcagtgtta tcactcatgg ttatggcagc actgcataat    6840
tctcttactg tcatgccatc cgtaagatgc ttttctgtga ctggtgagta ctcaaccaag    6900
tcattctgag aatagtgtat gcggcgaccg agttgctctt gcccggcgtc aacacgggat    6960
aataccgcgc cacatagcag aactttaaaa gtgctcatca ttggaaaacg ttcttcgggg    7020
cgaaaactct caaggatctt accgctgttg agatccagtt cgatgtaacc cactcgtgca    7080
cccaactgat cttcagcatc ttttactttc accagcgttt ctgggtgagc aaaaacagga    7140
aggcaaaatg ccgcaaaaaa gggaataagg gcgacacgga aatgttgaat actcatactc    7200
```

| | |
|---|---|
| ttccttttc aatattattg aagcatttat cagggttatt gtctcatgag cggatacata | 7260 |
| tttgaatgta tttagaaaaa taaacaaata ggggttccgc gcacatttcc ccgaaaagtg | 7320 |
| ccacctgacg tctaagaaac cattattatc atgacattaa cctataaaaa taggcgtatc | 7380 |
| acgaggccct ttcgtcttca agaa | 7404 |

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6

| | |
|---|---|
| catatgaaag cttgtatcga ttaaataagg aggaataaac c | 41 |

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| cccgtcttac tgtcgggaat tcgcgttggc cgattcatta atgcagctgg cacgacaggt | 60 |
| ttcccgactg gaaagcgggc agtgagcgca acgcaattaa tgtgagttag ctcactcatt | 120 |
| aggcacccca ggctttacac tttatgcttc cggctcgtat gttgtgtgga attgtgagcg | 180 |
| gataacaatt tcacacagga aacagctatg accatgatta cgccaagctt gtatcgatta | 240 |
| aataaggagg aataaaccat gtgtgcgacc tcttctcaat ttactcagat taccgagcat | 300 |
| aattcccgtc gttccgcaaa ctatcagcca aacctgtgga atttcgaatt cctgcaatcc | 360 |
| ctggagaacg acctgaaagt ggaaaagctg gaggagaaag cgaccaaact ggaggaagaa | 420 |
| gttcgctgca tgatcaaccg tgtagacacc cagccgctgt ccctgctgga gctgatcgac | 480 |
| gatgtgcagc gcctgggtct gacctacaaa tttgaaaaag acatcattaa agccctggaa | 540 |
| aacatcgtac tgctggacga aaacaaaaag aacaaatctg acctgcacgc aaccgctctg | 600 |
| tctttccgtc tgctgcgtca gcacggtttc gaggtttctc aggatgtttt tgagcgtttc | 660 |
| aaggataaag aaggtggttt cagcggtgaa ctgaaaggtg acgtccaagg cctgctgagc | 720 |
| ctgtatgaag cgtcttacct gggtttcgag ggtgagaacc tgctggagga ggcgcgtacc | 780 |
| ttttccatca cccaccctgaa gaacaacctg aagaaggca ttaataccaa ggttgcagaa | 840 |
| caagtgagcc acgccctgga actgccatat caccagcgtc tgcaccgtct ggaggcacgt | 900 |
| tggttcctgg ataaatacga accgaaagaa ccgcatcacc agctgctgct ggagctggcg | 960 |
| aagctggatt ttaacatggt acagaccctg caccagaaag agctgcaaga tctgtcccgc | 1020 |
| tggtggaccg agatgggcct ggctagcaaa ctggattttg tacgcgaccg cctgatggaa | 1080 |
| gtttatttct gggcactggg tatggcgcca gacccgcagt ttggtgaatg tcgcaaagct | 1140 |
| gttactaaaa tgtttggtct ggtgacgatc atcgatgacg tgtatgacgt ttatggcact | 1200 |
| ctggacgaac tgcaactgtt caccgatgct gtagagcgct gggacgttaa cgctattaac | 1260 |
| accctgccgg actatatgaa actgtgtttc ctggcactgt acaacaccgt taacgacacg | 1320 |
| tcctattcta ttctgaaaga gaaaggtcat aacaacctgt cctatctgac gaaaagctgg | 1380 |
| cgtgaactgt gcaaagcctt tctgcaagag gcgaaatggt ccaacaacaa aattatcccg | 1440 |
| gctttctcca agtacctgga aaacgccagc gtttcctcct ccggtgtagc gctgctggcg | 1500 |

```
ccgtcttact tttccgtatg ccagcagcag gaagacatct ccgaccacgc gctgcgttcc    1560
ctgaccgact tccatggtct ggtgcgttct agctgcgtta tcttccgcct gtgcaacgat    1620
ctggccacct ctgcggcgga gctggaacgt ggcgagacta ccaattctat cattagctac    1680
atgcacgaaa acgatggtac cagcgaggaa caggcccgcg aagaactgcg taaactgatc    1740
gacgccgaat ggaaaaagat gaatcgtgaa cgcgttagcg actccaccct gctgcctaaa    1800
gcgttcatgg aaatcgcagt taacatggca cgtgtttccc actgcaccta ccagtatggc    1860
gatggtctgg gtcgcccaga ctacgcgact gaaaaccgca tcaaactgct gctgattgac    1920
cctttcccga ttaaccagct gatgtatgtc taactgcagg tcgactctag aggatccccg    1980
ggtaccgagc tcgaattcac tggccgtcgt tttacaacgt cgtgactggg aaaaccctgg    2040
cgttacccaa cttaatcgcc ttgcagcaca tccccctttc gccagctggc gtaatagcga    2100
agaggcccgc accgatcgcc cttcccaaca gttgcgcagc ctgaatggcg aatggcgcct    2160
gatgcggtat tttctcctta cgcatctgtg cggtatttca ccgcatat ggtgcactct     2220 cagtacaatc tgctctgatg ccgcatagtt aagccagccc cgacacccgc caacacccgc    2280
tgacgagctt agtaaagccc tcgctagatt ttaatgcgga gtttgcgatt acttcgccaa    2340
ctattgcgat aacaagaaaa agccagcctt tcatgatata tctcccaatt tgtgtagggc    2400
ttattatgca cgcttaaaaa taataaaagc agacttgacc tgatagtttg gctgtgagca    2460
attatgtgct tagtgcatct aacgcttgag ttaagccgcg ccgcgaagcg cgtcggctt    2520 gaacgaattg ttagacatta tttgccgact accttggtga tctcgccttt cacgtagtgg    2580
acaaattctt ccaactgatc tgcgcgcgag gccaagcgat cttcttcttg tccaagataa    2640
gcctgtctag cttcaagtat gacgggctga tactgggccg gcaggcgctc cattgcccag    2700
tcggcagcga catccttcgg cgcgattttg ccggttactg cgctgtacca aatgcgggac    2760
aacgtaagca ctacatttcg ctcatcgcca gcccagtcgg gcggcgagtt ccatagcgtt    2820
aaggtttcat ttagcgcctc aaatagatcc tgttcaggaa ccggatcaaa gagttcctcc    2880
gccgctggac ctaccaaggc aacgctatgt tctcttgctt ttgtcagcaa gatagccaga    2940
tcaatgtcga tcgtggctgg ctcgaagata cctgcaagaa tgtcattgcg ctgccattct    3000
ccaaattgca gttcgcgctt agctggataa cgccacggaa tgatgtcgtc gtgcacaaca    3060
atggtgactt ctacagcgcg gagaatctcg ctctctccag gggaagccga agtttccaaa    3120
aggtcgttga tcaaagctcg ccgcgttgtt tcatcaagcc ttacggtcac cgtaaccagc    3180
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact tgttttagg gcgactgccc    3360 tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accaccgctg cgttcggtca aggttctgga ccagttgcgt    3540
gagcgcatac gctacttgca ttacagctta cgaaccgaac aggcttatgt ccactgggtt    3600
cgtgccttca tccgtttcca cggtgtgcgt cacccggcaa ccttgggcag cagcgaagtc    3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg gaagacctcg gccgtcgcgg cgcttgccgg tggtgctgac cccggatgaa    3840
gtggttcgca tcctcggttt tctggaaggc gagcatcgtt tgttcgccca gcttctgtat    3900
```

```
ggaacgggca tgcggatcag tgagggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat tcccacgggt tttgctgccc    4080
gcaaacgggc tgttctggtg ttgctagttt gttatcagaa tcgcagatcc ggcttcagcc    4140
ggtttgccgg ctgaaagcgc tatttcttcc agaattgcca tgattttttc cccacgggag    4200
gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag ctttgaatgc accaaaaact cgtaaaagct    4440
ctgatgtatc tatcttttt acaccgtttt catctgtgca tatggacagt tttcccttttg    4500 atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740
agtgtttttc ttagtccgtt atgtaggtag gaatctgatg taatggttgt tggtattttg    4800
tcaccattca tttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaacccattg gttaagcctt    4980
ttaaactcat ggtagttatt ttcaagcatt aacatgaact taaattcatc aaggctaatc    5040
tctatatttg ccttgtgagt tttcttttgt gttagttctt ttaataacca ctcataaatc    5100
ctcatagagt atttgttttc aaaagactta acatgttcca gattatattt tatgaatttt    5160
tttaactgga aaagataagg caatatctct tcactaaaaa ctaattctaa tttttcgctt    5220
gagaacttgg catagtttgt ccactggaaa atctcaaagc ctttaaccaa aggattcctg    5280
atttccacag ttctcgtcat cagctctctg gttgctttag ctaatacacc ataagcatttt    5340 tccctactga tgttcatcat ctgagcgtat tggttataag tgaacgatac cgtccgttct    5400
ttccttgtag ggttttcaat cgtggggttg agtagtgcca cacagcataa aattagcttg    5460
gtttcatgct ccgttaagtc atagcgacta atcgctagtt catttgcttt gaaacaact    5520 aattcagaca tacatctcaa ttggtctagg tgattttaat cactatacca attgagatgg    5580
gctagtcaat gataattact agtccttttc ctttgagttg tgggtatctg taaattctgc    5640
tagacctttg ctggaaaact tgtaaattct gctagaccct ctgtaaattc cgctagacct    5700
ttgtgtgttt tttttgttta tattcaagtg gttataattt atagaataaa gaagaataa    5760 aaaaagataa aagaataga tcccagccct gtgtataact cactacttta gtcagttccg    5820
cagtattaca aaaggatgtc gcaaacgctg tttgctcctc tacaaaacag accttaaaac    5880
cctaaaggct taagtagcac cctcgcaagc tcggcaaat cgctgaatat tccttttgtc    5940
tccgaccatc aggcacctga gtcgctgtct ttttcgtgac attcagttcg ctgcgctcac    6000
ggctctggca gtgaatgggg gtaaatggca ctacaggcgc cttttatgga ttcatgcaag    6060
gaaactaccc ataatacaag aaaagccgt cacgggcttc tcagggcgtt ttatggcggg    6120
tctgctatgt ggtgctatct gactttttgc tgttcagcag ttcctgccct ctgatttttcc    6180 agtctgacca cttcggatta tcccgtgaca ggtcattcag actggctaat gcacccagta    6240
aggcagcggt atcatcaaca ggctta                                          6266
```

```
<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8
atgtgtgcaa cctcctccca gtttactcag attaccgagc ataattctcg acgatctgct      60
aactaccagc cgaacctttg gaactttgag tttctccagt ctctcgaaaa tgacctgaag     120
gtggaaaagc tcgaggagaa ggcgaccaaa ctcgaggagg aggtgcgatg tatgatcaac     180
agagttgaca cccaaccccct gtctttgctg gagctgatcg acgatgtgca gcggttgggt     240
ttgacttata aattcgagaa ggacattatc aaggcactgg agaacattgt gctcctcgac     300
gagaacaaga gaacaagtc tgatcttcac gctaccgctc tctcttccg acttcttcga      360 caacacggct tcgaggtgtc gcaggacgtc ttcgagagat taaggacaa ggagggagga     420 tttagcggcg agctgaaggg agacgttcag ggtcttctct ccttgtacga ggcgtcctac     480
ctgggattcg agggagagaa cctcctggag gaagctcgta catttttccat cactcacctt     540 aagaataacc ttaaggaggg aattaacacc aaggtggccg agcaggtttc tcacgccctg     600
gagctcccct accaccaacg gctccataga ctggaggctc gttggttcct ggacaaaatat     660 gagccaaagg agcctcatca tcagttgctg ttggagttgg ccaagctgga cttcaatatg     720
gttcagacgc tgcaccaaaa ggagttgcag gacctgtctc gatggtggac cgagatggga     780
ttggcctcga agctggattt tgtccgtgac cgacttatgg aggtctattt tgggcccttt     840
ggaatggcgc ctgaccccca gttcggagag tgccggaagg cggtgacgaa gatgttcggt     900
cttgtgacta tcatcgacga cgtctacgat gtctacggca cactcgacga gttgcagctg     960
ttcactgacg ccgtcgagcg atgggatgtg aacgccatta atactctccc tgactatatg    1020
aagctgtgct tcctggctct gtacaacact gtcaacgata cctcgtactc tatcctcaag    1080
gagaagggac acaacaatct ctcctacttg accaaatcct ggcgagaact gtgcaaggct    1140
tttctgcagg aggctaaatg gtccaataac aagatcattc ctgctttttc taaataccctg    1200 gaaaatgcct cggtgtcgag ctctggcgtc gcccttctgg cccccttccta cttctccgtc    1260 tgccagcagc aggaggatat ttccgatcat gctcttagat cgctgaccga ttttcacggc    1320
ctcgtgcgat cttcctgcgt gattttttcgg ttgtgtaatg accttgcgac ctctgctgct    1380
gagctggaac gaggcgagac tacaaattcc attatttctt acatgcacga aaacgatgga    1440
acatctgaag aacaggctag agaggaactg cgaaagttga tcgacgccga gtggaagaag    1500
atgaacagag agcgggtgtc cgactctacc ctgcttccca aggccttcat ggagatcgcc    1560
gtgaacatgg ctcgagtttc ccattgtact taccagtacg gtgacggcct gggtcgtccg    1620
gactacgcta cagagaaccg aatcaagctg ctgctcatcg accccttccc tatcaaccaa    1680
ttgatgtacg tgtaa                                                    1695

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gcttatggat cctctagact attacacgta catcaattgg                            40
```

```
<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac                                        30

<210> SEQ ID NO 11
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 11
tcgaccggtg agaagaacag catcgggaca agggaaggaa gaacaaagac aaagaaaaca        60
aaagaaagca attgaaaaca aaacaaaaca attttcattc cttctcttat cattccttttt     120 cttttcttt ctctcattca acgcactcca tcgtatccgt attcctctta ttttttctct       180
ttctctatat ccatttcttt ctctctaggt gtgtcctctc tctctcttca atttctctac      240
tccgcattcc aacgcatcct tcccccaacc tcccatttcc tccttacggc ccgatagcga      300
tcgtctttcc ctcgctatca ctcgctaccg gccccctcctc tgcaccgtaa cctcctacgt     360
atttaccata tcataaagtt ttttccgacg cttatcgctg accccctgtc gccctcctat     420
tggcttccgg attatcttct tgtccataag gtgatccatg cttcctgaag attcccgaaa     480
tgtgtccact ttggcgggga atcattccat ccacttcttt ctctctcgct ttcctcattc     540
ggcgctcccc ttccgcgtct cattggtctt ccgctccgtt tttgctttgc cgatgttact     600
tggggagagg tgcgataatc ctttcgcaaa aactcggttt gacgcctccc atggtataaa     660
tagtgggtgg tggacaggtg ccttcgcttt tctttaagca agagaatccc attgtcttga     720
ctatcacgaa ttcacataca ttatgaagat caccgctgtc attgccctt tattctcact      780 tgctgctgcc tcacctattc cagttgccga tcctggtgtg gtttcagtta gcaagtcata     840
tgctgatttc cttcgtgttt accaaagttg gaacactttt gctaatcctg atagacccaa     900
ccttaagaag agaaatgata cacctgcaag tggatatcaa gttgaaaaag tcgtaatttt     960
gtcacgtcac ggtgttaggg cccctacaaa aatgactcaa accatgcgtg atgtcactcc    1020
taatacatgg ccagaatggc ccgttaaatt aggatatatt acaccaagag gtgaacactt    1080
gatatcactt atgggcggtt tttaccgtca aaaattccag caacaaggaa tcctttctca    1140
gggctcctgt cctactccta actccatata tgtctgggct gacgtcgatc agcgtacttt    1200
aaaaactggt gaagcattcc ttgctggttt ggcaccacaa tgtggcttga caattcatca    1260
ccaacaaaat cttgagaaag ctgatcctct ttttcatccc gttaaagctg aacctgctc    1320 tatggataaa actcaagttc aacaagctgt tgagaaggag gcacaaactc ctatagataa    1380
tttgaatcaa cattacatcc ccttttagc tttaatgaat acaacattaa attttagtac    1440
ttctgcctgg tgccaaaaac actctgctga taaatcctgt gacctaggtt tatccatgcc    1500
ttctaaattg tccataaaag ataatggtaa caaggtcgca ttggatggag ctattggtct    1560
atcctctact ttggccgaga ttttcttct tgaatatgct caaggcatgc ctcaagctgc    1620
ttggggtaac atccactcag agcaagagtg ggcttccttg ctaaagttgc ataatgttca    1680
attcgatttg atggcccgaa caccttatat tgctcgacat aacggtactc ctttattgca    1740
```

```
agctatatca aatgccctta atcccaacgc cactgaatca aaacttccag atatttcacc   1800
tgataacaaa atattgttca ttgcaggtca tgacacaaat attgctaata tagccggcat   1860
gttaaatatg cgttggacat taccaggtca accagataat actcctccag gtggtgccct   1920
agtatttgaa cgtcttgctg ataaaagtgg aaaacaatat gtttctgtat ctatggttta   1980
tcaaacacta gaacaacttc gatcacagac tccccttttct ctaaatcagc ctgccggatc   2040
tgttcaactt aaaattccag gttgcaatga tcaaacagcc gagggttact gtcctctttc   2100
cacttttaca agagttgttt cccaatctgt tgaacctgga tgccaacttc aataatgagg   2160
atccaagtaa gggaatgaga atgtgatcca ctttttaattc ctaatgaata catgcctata   2220
gttcttttct tttgttcttt atgtcgtttt tcgatggtac ggccgttgtc aatctcagtt   2280
tgtgtgcttg gttgcagctt ggtttcaaat ctgttcatct catgaatctt ttaccatttc   2340
accacacgtt tataccattc tctcatagaa tcttcatcaa accatctcgg ggttagagtg   2400
gaaagaaagt cttgttcttt tatttccttt tttccatctt caaggctttt cttttcttcc   2460
tcctcctcgt tcatcttgag gtttgacgtg tctgtttaga attttgagct gttgcagcat   2520
cttatttttt gttttgcgaa aacgaagcgc tttactctct tcatcagttg gacgattgta   2580
cctttgaaaa ccaactactt ttgcatgttt tgtatagaaa tcaatgatat tagaatccca   2640
tcctttaatt tctttcaaag tagttgagct atagttaagt gtaagggccc tactgcgaaa   2700
gcatttgcca aggatgtttt cattaatcaa gaacgaaagt taggggatcg aagacgatca   2760
gataccgtcg tagtcttaac cataaactat gccgactagg gatcgggcaa tgtttcattt   2820
atcgacttgc tcggcacctt acgagaaatc aaagtctttg ggttccgggg ggagtatggt   2880
cgcaaggctg aaacttaaag gaattgacgg aagggcacca caatggagtg gagcctgcgg   2940
cttaatttga ctcaacacgg ggaaactcac caggtccaga catagtaagg attgacagat   3000
tgagagctct ttcttgattc tatgggtggt ggtgcatggc cgttcttagt tggtggagtg   3060
atttgtctgc ttaattgcga taacgaacga gaccttaacc tgctaaatag ctggatcagc   3120
cattttggct gatcattagc ttcttagagg gactattggc ataaagccaa tggaagtttg   3180
aggcaataac aggtctgtga tgcccttaga tgttctgggc cgcacgcgcg ctacactgac   3240
ggagccaacg agttgaaaaa aatcttttga ttttttatcc ttggccggaa ggtctgggta   3300
atcttgttaa actccgtcgt gctggggata gagcattgca attattgcgg ccgctcctca   3360
attcgatgtt gcagatttta caagttttta aaatgtattt cattattact ttttatatgc   3420
ctaataaaaa agccatagtt taatctatag ataacttttt ttccagtgca ctaacggacg   3480
ttacattccc atacaaaact gcgtagttaa agctaaggaa aagttaatat catgttaatt   3540
aaatacgcta tttacaataa gacattgaac tcatttatat cgttgaatat gaataaccaa   3600
tttcagcgaa tttttaacaa acatcgttca cctcgtttaa ggatatcttg tgtatggggt   3660
gttgacttgc tttatcgaat aattaccgta cctgtaattg gcttgctgga tatagcggta   3720
gtctaatatc tagcaaaaat ctttttgggtg aaaaggcttg caatttcacg acaccgaact   3780
atttgtcatt ttttaataag gaagttttcc ataaattcct gtaattctcg ttgatctaa    3840
ttgaaaagag tagttttgca tcacgatgag gagggctttt gtagaaagaa atacgaacga   3900
aacgaaaatc agcgttgcca tcgctttgga caaagctccc ttacctgaag agtcgaattt   3960
tattgatgaa cttataactt ccaagcatgc aaaccaaaag ggagaacaag taatccaagt   4020
agacacggga attggattct tggatcacat gtatcatgca ctggctaaac atgcaggctg   4080
gagcttacga ctttactcaa gaggtgattt aatcatcgat gatcatcaca ctgcagaaga   4140
```

```
tactgctatt gcacttggta ttgcattcaa gcaggctatg ggtaactttg ccggcgttaa    4200
aagatttgga catgcttatt gtccacttga cgaagctctt tctagaagcg tagttgactt    4260
gtcgggacgg ccctatgctg ttatcgattt gggattaaag cgtgaaaagg ttggggaatt    4320
gtcctgtgaa atgatccctc acttactata ttccttttcg gtagcagctg gaattacttt    4380
gcatgttacc tgcttatatg gtagtaatga ccatcatcgt gctgaaagcg cttttaaatc    4440
tctggctgtt gccatgcgcg cggctactag tcttactgga agttctgaag tcccaagcac    4500
gaagggagtg ttgtaaagat gaattggatt atgtcaggaa aagaacgaca attttgcatc    4560
caaattgtct aaattttaga gttgcttgaa aacaatagaa ccttacttgc tttataatta    4620
cgttaattag aagcgttatc tcgtgaagga atatagtacg tagccgtata aattgaattg    4680
aatgttcagc ttatagaata gagacacttt gctgttcaat gcgtcgtcac ttaccatact    4740
cactttatta tacgacttta agtataaact ccgcggttat ggtaaaatta atgatgcaca    4800
aacgtccgat tccatatggg tacactacaa ttaaatactt ttaagctgat cccccacaca    4860
ccatagcttc aaaatgtttc tactccttt ttactcttcc agattttctc ggactccgcg    4920
catcgccgta ccacttcaaa acacccaagc acagcatact aaattttccc tctttcttcc    4980
tctagggtgt cgttaattac ccgtactaaa ggtttggaaa agaaaaaga gaccgcctcg    5040 tttcttttc ttcgtcgaaa aaggcaataa aaatttttat cacgtttctt tttcttgaaa    5100
tttttttttt tagtttttt ctctttcagt gacctccatt gatatttaag ttaataaacg    5160
gtcttcaatt tctcaagttt cagtttcatt tttcttgttc tattacaact tttttactt    5220 cttgttcatt agaaagaaag catagcaatc taatctaagg gcggtgttga caattaatca    5280
tcggcatagt atatcggcat agtataatac gacaaggtga ggaactaaac catggccaag    5340
ttgaccagtg ccgttccggt gctcaccgcg cgcgacgtcg ccggagcggt cgagttctgg    5400
accgaccggc tcgggttctc ccgggacttc gtggaggacg acttcgccgg tgtggtccgg    5460
gacgacgtga ccctgttcat cagcgcggtc caggaccagg tggtgccgga caacaccctg    5520
gcctgggtgt gggtgcgcgg cctggacgag ctgtacgccg agtggtcgga ggtcgtgtcc    5580
acgaacttcc gggacgcctc cgggccggcc atgaccgaga tcggcgagca gccgtggggg    5640
cgggagttcg ccctgcgcga cccggccggc aactgcgtgc acttcgtggc cgaggagcag    5700
gactgacacg tccgacggcg gcccacgggt cccaggcctc ggagatccgt ccccctttc    5760 ctttgtcgat atcatgtaat tagttatgtc acgcttacat tcacgccctc cccccacatc    5820
cgctctaacc gaaaaggaag gagttagaca acctgaagtc taggtcccta tttatttttt    5880
tatagttatg ttagtattaa gaacgttatt tatatttcaa attttctttt tttttctgta    5940
cagacgcgag cttcccagta aatgtgccat ctcgtaggca gaaaacggtt cccccgtagg    6000
gtctctctct tggcctcctt tctaggtcgg gctgattgct cttgaagctc tctagggggg    6060
ctcacaccat aggcagataa cgttcccac cggctcgcct cgtaagcgca caaggactgc    6120
tcccaaagat cctaggcggg attttgccga tttcggccta aggaaccgg aacacgtaga    6180 aagccagtcc gcagaaacgg tgctgacccc ggatgaatgt cagctactgg gctatctgga    6240
caagggaaaa cgcaagcgca aagagaaagc aggtagcttg cagtgggctt acatggcgat    6300
agctagactg ggcggtttta tggacagcaa gcgaaccgga attgccagct ggggcgccct    6360
ctggtaaggt tgggaagccc tgcaaagtaa actggatggc tttcttgccg ccaaggatct    6420
gatggcgcag gggatcaaga tctgatcaag agacaggatg aggatcgttt cgcatgattg    6480
aacaagatgg attgcacgca ggttctccgg ccgcttgggt ggagaggcta ttcggctatg    6540
```

```
actgggcaca acagacaatc ggctgctctg atgccgccgt gttccggctg tcagcgcagg      6600
ggcgcccggt tcttttttgtc aagaccgacc tgtccggtgc cctgaatgaa ctgcaggacg     6660
aggcagcgcg gctatcgtgg ctggccacga cgggcgttcc ttgcgcagct gtgctcgacg      6720
ttgtcactga agcgggaagg gactggctgc tattgggcga agtgccgggg caggatctcc      6780
tgtcatctcg ccttgctcct gccgagaaag tatccatcat ggctgatgca atgcggcggc      6840
tgcatacgct tgatccggct acctgcccat tcgaccacca agcgaaacat cgcatcgagc      6900
gagcacgtac tcggatggaa gccggtcttg tcgatcagga tgatctggac gaagagcatc      6960
aggggctcgc gccagccgaa ctgttcgcca ggctcaaggc gcgcatgccc gacggcgagg      7020
atctcgtcgt gatccatggc gatgcctgct tgccgaatat catggtggaa aatggccgct      7080
tttctggatt caacgactgt ggccggctgg gtgtggcgga ccgctatcag gacatagcgt      7140
tggatacccg tgatattgct gaagagcttg gcggcgaatg ggctgaccgc ttcctcgtgc      7200
tttacggtat cgccgctccc gattcgcagc gcatcgcctt ctatcgcctt cttgacgagt      7260
tcttctgaat tgaaaaaggt accaagttta ctcatatata ctttagattg atttaaaact      7320
tcatttttaa tttaaaagga tctaggtgaa gatccttttt gataatctca tgaccaaaat      7380
cccttaacgt gagttttcgt tccactgagc gtcagacccc gtagaaaaga tcaaaggatc      7440
ttcttgagat cctttttttc tgcgcgtaat ctgctgcttg caaacaaaaa aaccaccgct      7500
accagcggtg gtttgtttgc cggatcaaga gctaccaact cttttttccga aggtaactgg      7560 cttcagcaga gcgcagatac caaatactgt ccttctagtg tagccgtagt taggccacca      7620
cttcaagaac tctgtagcac cgcctacata cctcgctctg ctaatcctgt taccagtggc      7680
tgctgccagt ggcgataagt cgtgtcttac cgggttggac tcaagacgat agttaccgga      7740
taaggcgcag cggtcgggct gaacggggggg ttcgtgcaca cagcccagct tggagcgaac      7800
gacctacacc gaactgagat acctacagcg tgagcattga gaaagcgcca cgcttcccga      7860
agggagaaag gcggacaggt atccggtaag cggcagggtc ggaacaggag agcgcacgag      7920
ggagcttcca gggggaaacg cctggtatct ttatagtcct gtcgggtttc gccacctctg      7980
acttgagcgt cgatttttgt gatgctcgtc aggggggcgg agcctatgga aaaacgccag      8040
caacgcggcc ttttttacggt tcctggcctt ttgctggcct tttgctcaca tgttctttcc      8100
tgcgttatcc cctgattctg tggataaccg tattaccgcc tttgagtgag ctgataccgc      8160
tcgccgcagc cgaacgaccg agcgcagcga g                                     8191
```

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12

```
gaattcaaaa caaaatgtgt gcaacctcct cccagtttac tcagattacc gagcataatt       60
ctcgacgatc tgctaactac cagccgaacc tttggaactt tgagtttctc cagtctctcg      120
aaaatgacct gaaggtggaa aagctcgagg agaaggcgac caaactcgag gaggaggtgc      180
gatgtatgat caacagagtt gacacccaac ccctgtcttt gctggagctg atcgacgatg      240
tgcagcggtt gggtttgact tataaaattcg agaaggacat tatcaaggca ctggagaaca      300
ttgtgctcct cgacgagaac aagaagaaca agtctgatct tcacgctacc gctctctctt      360
tccgacttct tcgacaacac ggcttcgagg tgtcgcagga cgtcttcgag agatttaagg      420
```

| | |
|---|---|
| acaaggaggg aggatttagc ggcgagctga agggagacgt tcagggtctt ctctccttgt | 480 |
| acgaggcgtc ctacctggga ttcgaggag agaacctcct ggaggaagct cgtacatttt | 540 |
| ccatcactca ccttaagaat aaccttaagg agggaattaa caccaaggtg gccgagcagg | 600 |
| tttctcacgc cctggagctc ccctaccacc aacggctcca tagactggag gctcgttggt | 660 |
| tcctggacaa atatgagcca aggagcctc atcatcagtt gctgttggag ttggccaagc | 720 |
| tggacttcaa tatggttcag acgctgcacc aaaaggagtt gcaggacctg tctcgatggt | 780 |
| ggaccgagat gggattggcc tcgaagctgg attttgtccg tgaccgactt atggaggtct | 840 |
| atttttgggc ccttggaatg gcgcctgacc cccagttcgg agagtgccgg aaggcggtga | 900 |
| cgaagatgtt cggtcttgtg actatcatcg acgacgtcta cgatgtctac ggcacactcg | 960 |
| acgagttgca gctgttcact gacgccgtcg agcgatggga tgtgaacgcc attaatactc | 1020 |
| tccctgacta tatgaagctg tgcttcctgg ctctgtacaa cactgtcaac gatacctcgt | 1080 |
| actctatcct caaggagaag ggacacaaca atctctccta cttgaccaaa tcctggcgag | 1140 |
| aactgtgcaa ggcttttctg caggaggcta aatggtccaa taacaagatc attcctgctt | 1200 |
| tttctaaata cctggaaaat gcctcggtgt cgagctctgg cgtcgccctt ctggcccctt | 1260 |
| cctacttctc cgtctgccag cagcaggagg atatttccga tcatgctctt agatcgctga | 1320 |
| ccgattttca cggcctcgtg cgatcttcct gcgtgatttt tcggttgtgt aatgaccttg | 1380 |
| cgacctctgc tgctgagctg gaacgaggcg agactacaaa ttccattatt cttacatgc | 1440 |
| acgaaaacga tggaacatct gaagaacagg ctagagagga actgcgaaag ttgatcgacg | 1500 |
| ccgagtggaa gaagatgaac agagagcggg tgtccgactc taccctgctt cccaaggcct | 1560 |
| tcatggagat cgccgtgaac atggctcgag tttcccattg tacttaccag tacggtgacg | 1620 |
| gcctgggtcg tccggactac gctacagaga accgaatcaa gctgctgctc atcgacccct | 1680 |
| tccctatcaa ccaattgatg tacgtgtaat agtctagagg atcc | 1724 |

<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

| | |
|---|---|
| gaattcaaca aaaatgtgct ctgtttccac tgagaacgtg tcctttactg agactgagac | 60 |
| tgaagcacgt agaagcgcca actacgaacc caactcctgg gattatgact ttctgctgtc | 120 |
| ttctgacacc gacgagtcga tcgaggttta aaggataag gccaagaaac ttgaggccga | 180 |
| ggtcagacga gagattaaca acgagaaggc cgagttcctg acccttcttg agctgatcga | 240 |
| caacgttcaa cgacttggtc ttggttaccg tttcgaatcc gatatccgac gtgcattgga | 300 |
| tcgatttgtc tcgtccggag gtttcgatgg tgtgactaag acgtcgctgc acgccacagc | 360 |
| tcttccttc agactgttgc ggcagcatgg atttgaggtt tcccaggaag ccttttctgg | 420 |
| tttcaaggat cagaacggaa acttttggga gaatctcaag gaggacacca aggccatcct | 480 |
| gtcgttgtat gaggcctcgt tcctggctct tgagggcgag aatattctgg atgaggctcg | 540 |
| ggttttcgct atttcgcacc tgaaggagtt gtcggaggaa aagatcggaa aggaactggc | 600 |
| cgagcaggtc aaccatgcac ttgaacttcc cctgcatcga cgtacccagc gactggaggc | 660 |
| cgtgtgggagc atcgaggcgt acagaaaaaa ggaggatgct aatcaggttc tgctcgaact | 720 |
| cgctatcctc gactataaca tgattcagag cgtgtaccag cgtgacttgc gagagacaag | 780 |

```
ccggtggtgg cgacgggtgg gactggccac gaagctccac tttgctaaag atcgattgat    840
tgagtcgttc tactgggcag tgggtgtggc ctttgagcct cagtactccg actgccgaaa    900
ctccgttgca aagatgtttt cttttgtcac tatcatcgac gacatctacg atgtttacgg    960
cactctcgat gaactcgaac tcttcacgga cgctgtcgag cgatgggatg tgaatgccat   1020
taatgatctg ccagattata tgaagttgtg tttcttggcg ctctacaaca caattaatga   1080
aattgcctac gacaacctca aggacaaggg agagaacatt ctgccctacc ttactaaagc   1140
ctgggccgac ctgtgtaacg ccttttttgca ggaagccaag tggctctata acaaatctac   1200
tcctacattt gatgactact tcggcaacgc ttggaagtct tccagcggcc ctctccagtt   1260
gatcttcgct tactttgcag tggtccagaa catcaagaaa gaggagattg agaacctcca   1320
gaagtatcac gacatcatct cccgaccttc gcacatcttt cgactgtgca atgaccttgc   1380
ctccgcatcc gctgagattg cccgaggaga aacagccaat tctgtgtcgt gttacatgcg   1440
tacaaagggc atctccgagg agctggctac cgagtctgtg atgaacctga tcgatgaaac   1500
ctgtaagaag atgaacaaag agaaactggg cggttctctg ttcgccaaac catttgttga   1560
aaccgcgatc aatctggctc gtcagtctca ttgtacttac cataacggtg acgcgcacac   1620
ttcgccggac gaattgaccc gtaagcgtgt gctttcggtg attaccgagc cgatcctgcc   1680
gttcgaaaga taataggatc c                                             1701
```

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gatcaagctt aaccggaatt gccagctg                                        28

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc                                  33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac                             38

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
ccttctgcag gacgcgttgt tatagc                                          26

```
<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg    60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t                                   31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc    60
tgaatagcgc cgtcgaccat catcatcatc atcattgagt ttaaacggtc tccagcttgg   120
ctgttttggc ggatgagaga agattttcag cctgatacag attaaatcag aacgcagaag   180
cggtctgata aaacagaatt tgcctggcgg cagtagcgcg gtggtcccac ctgaccccat   240
gccgaactca gaagtgaaac gccgtagcgc cgatggtagt gtggggtctc cccatgcgag   300
agtagggaac tgccaggcat caaataaaac gaaaggctca gtcgaaagac tgggcctttc   360
gttttatctg ttgtttgtcg gtgaacgctc tcctgagtag acaaatccgc cgggagcgg    420 atttgaacgt tgcgaagcaa cggcccggag ggtggcgggc aggacgcccg ccataaactg   480
ccaggcatca aattaagcag aaggccatcc tgacggatgg cctttttgcg tttctacaaa   540 ctcttttttgt ttatttttct aaatacattc aaatatgtat ccgcttaacc ggaattgcca   600 gctgggcgc cctctggtaa ggttgggaag ccctgcaaag taaactggat ggctttctcg    660
ccgccaagga tctgatggcg caggggatca agctctgatc aagagacagg atgaggatcg    720
tttcgcatga ttgaacaaga tggattgcac gcaggttctc cggccgcttg ggtggagagg    780
ctattcggct atgactgggc acaacagaca atcggctgct ctgatgccgc cgtgttccgg    840
ctgtcagcgc aggggcgccc ggttctttttt gtcaagaccg acctgtccgg tgccctgaat    900
gaactgcaag acgaggcagc gcggctatcg tggctggcca cgacgggcgt tccttgcgca    960
gctgtgctcg acgttgtcac tgaagcggga agggactggc tgctattggg cgaagtgccg   1020
gggcaggatc tcctgtcatc tcaccttgct cctgccgaga agtatccat catgctgat    1080 gcaatgcggc ggctgcatac gcttgatccg gctacctgcc cattcgacca ccaagcgaaa   1140
catcgcatcg agcgagcacg tactcggatg aagccggtc ttgtcgatca ggatgatctg    1200
gacgaagagc atcagggct cgcgccagcc gaactgttcg ccaggctcaa ggcgagcatg    1260
cccgacggcg aggatctcgt cgtgacccat ggcgatgcct gcttgccgaa tatcatggtg    1320
gaaaatggcc gcttttctgg attcatcgac tgtggccggc tgggtgtggc ggaccgctat    1380
```

| | | | | |
|---|---|---|---|---|
| caggacatag | cgttggctac | ccgtgatatt | gctgaagagc | ttggcggcga atgggctgac | 1440 |
| cgcttcctcg | tgctttacgg | tatcgccgct | cccgattcgc | agcgcatcgc cttctatcgc | 1500 |
| cttcttgacg | agttcttctg | acatgaccaa | aatcccttaa | cgtgagtttt cgttccactg | 1560 |
| agcgtcagac | cccgtagaaa | agatcaaagg | atcttcttga | gatccttttt ttctgcgcgt | 1620 |
| aatctgctgc | ttgcaaacaa | aaaaaccacc | gctaccagcg | gtggtttgtt tgccggatca | 1680 |
| agagctacca | actcttttc | cgaaggtaac | tggcttcagc | agagcgcaga taccaaatac | 1740 |
| tgtccttcta | gtgtagccgt | agttaggcca | ccacttcaag | aactctgtag caccgcctac | 1800 |
| atacctcgct | ctgctaatcc | tgttaccagt | ggctgctgcc | agtggcgata agtcgtgtct | 1860 |
| taccgggttg | gactcaagac | gatagttacc | ggataaggcg | cagcggtcgg gctgaacggg | 1920 |
| gggttcgtgc | acacagccca | gcttggagcg | aacgacctac | accgaactga gatacctaca | 1980 |
| gcgtgagcta | tgagaaagcg | ccacgcttcc | cgaagggaga | aaggcggaca ggtatccggt | 2040 |
| aagcggcagg | gtcggaacag | gagagcgcac | gagggagctt | ccagggggaa acgcctggta | 2100 |
| tctttatagt | cctgtcgggt | ttcgccacct | ctgacttgag | cgtcgatttt tgtgatgctc | 2160 |
| gtcaggggg | cggagcctat | ggaaaaacgc | cagcaacgcg | gccttttac ggttcctggc | 2220 |
| cttttgctgg | ccttttgctc | acatgttctt | tcctgcgtta | tcccctgatt ctgtggataa | 2280 |
| ccgtattacc | gcctttgagt | gagctgatac | cgctcgccgc | agccaacga ccagcgcag | 2340 |
| cgagtcagtg | agcgaggaag | cggaagagcg | cctgatgcgg | tattttctcc ttacgcatct | 2400 |
| gtgcggtatt | tcacaccgca | tatggtgcac | tctcagtaca | atctgctctg atgccgcata | 2460 |
| gttaagccag | tatacactcc | gctatcgcta | cgtgactggg | tcatggctgc gccccgacac | 2520 |
| ccgccaacac | ccgctgacgc | gccctgacgg | gcttgtctgc | tcccggcatc cgcttacaga | 2580 |
| caagctgtga | ccgtctccgg | gagctgcatg | tgtcagaggt | tttcaccgtc atcaccgaaa | 2640 |
| cgcgcgaggc | agcagatcaa | ttcgcgcgcg | aaggcgaagc | ggcatgcatt tacgttgaca | 2700 |
| ccatcgaatg | gtgcaaaacc | tttcgcggta | tggcatgata | gcgcccggaa gagagtcaat | 2760 |
| tcagggtggt | gaatgtgaaa | ccagtaacgt | tatacgatgt | cgcagagtat gccggtgtct | 2820 |
| cttatcagac | cgtttcccgc | gtggtgaacc | aggccagcca | cgtttctgcg aaaacgcggg | 2880 |
| aaaaagtgga | agcggcgatg | gcggagctga | attacattcc | caaccgcgtg gcacaacaac | 2940 |
| tggcgggcaa | acagtcgttg | ctgattggcg | ttgccacctc | cagtctggcc ctgcacgcgc | 3000 |
| cgtcgcaaat | tgtcgcggcg | attaaatctc | gcgccgatca | actgggtgcc agcgtggtgg | 3060 |
| tgtcgatggt | agaacgaagc | ggcgtcgaag | cctgtaaagc | ggcggtgcac aatcttctcg | 3120 |
| cgcaacgcgt | cagtgggctg | atcattaact | atccgctgga | tgaccaggat gccattgctg | 3180 |
| tggaagctgc | ctgcactaat | gttccggcgt | tatttcttga | tgtctctgac cagacaccca | 3240 |
| tcaacagtat | tattttctcc | catgaagacg | gtacgcgact | gggcgtggag catctggtcg | 3300 |
| cattgggtca | ccagcaaatc | gcgctgttag | cgggcccatt | aagttctgtc tcggcgcgtc | 3360 |
| tgcgtctggc | tggctggcat | aaatatctca | ctcgcaatca | aattcagccg atagcggaac | 3420 |
| gggaaggcga | ctggagtgcc | atgtccggtt | ttcaacaaac | catgcaaatg ctgaatgagg | 3480 |
| gcatcgttcc | cactgcgatg | ctggttgcca | acgatcagat | ggcgctgggc gcaatgcgcg | 3540 |
| ccattaccga | gtccgggctg | cgcgttgtg | cggatatctc | ggtagtggga tacgacgata | 3600 |
| ccgaagacag | ctcatgttat | atcccgccgt | caaccaccat | caaacaggat tttcgcctgc | 3660 |
| tggggcaaac | cagcgtggac | cgcttgctgc | aactctctca | gggccaggcg gtgaagggca | 3720 |
| atcagctgtt | gcccgtctca | ctggtgaaaa | gaaaaaccac | cctggcgccc aatacgcaaa | 3780 |

```
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
ttatcagaca atctgtgtgg gcactcgacc ggaattatcg attaacttta ttattaaaaa   4260
ttaaagaggt atatattaat gtatcgatta ataaggagg aataaaccat gtgtgcgacc   4320
tcttctcaat ttactcagat taccgagcat aattcccgtc gttccgcaaa ctatcagcca   4380
aacctgtgga atttcgaatt cctgcaatcc ctggagaacg acctgaaagt ggaaaagctg   4440
gaggagaaag cgaccaaact ggaggaagaa gttcgctgca tgatcaaccg tgtagacacc   4500
cagccgctgt ccctgctgga gctgatcgac gatgtgcagc gcctgggtct gacctacaaa   4560
tttgaaaaag acatcattaa agccctggaa aacatcgtac tgctggacga aaacaaaaag   4620
aacaaatctg acctgcacgc aaccgctctg tctttccgtc tgctgcgtca gcacggtttc   4680
gaggtttctc aggatgtttt tgagcgtttc aaggataaag aaggtggttt cagcggtgaa   4740
ctgaaaggtg acgtccaagg cctgctgagc ctgtatgaag cgtcttacct gggtttcgag   4800
ggtgagaacc tgctgagga ggcgcgtacc ttttccatca cccacctgaa gaacaacctg   4860
aaagaaggca ttaataccaa ggttgcagaa caagtgagcc acgccctgga actgccatat   4920
caccagcgtc tgcaccgtct ggaggcacgt tggttcctgg ataaatacga accgaaagaa   4980
ccgcatcacc agctgctgct ggagctggcg aagctggatt ttaacatggt acagaccctg   5040
caccagaaag agctgcaaga tctgtcccgc tggtggaccg agatgggcct ggctagcaaa   5100
ctggatttg tacgcgaccg cctgatggaa gtttatttct gggcactggg tatggcgcca   5160
gacccgcagt ttggtgaatg tcgcaaagct gttactaaaa tgtttggtct ggtgacgatc   5220
atcgatacg tgtatgacgt ttatggcact ctggacgaac tgcaactgtt caccgatgct   5280
gtagagcgct gggacgttaa cgctattaac accctgccgg actatatgaa actgtgtttc   5340
ctggcactgt acaacaccgt taacgacacg tcctattcta ttctgaaaga gaaaggtcat   5400
aacaacctgt cctatctgac gaaaagctgg cgtgaactgt gcaaagcctt tctgcaagag   5460
gcgaaatggt ccaacaacaa aattatcccg gctttctcca gtacctgga aaacgccagc   5520
gtttcctcct ccggtgtagc gctgctggcg ccgtcttact tttccgtatg ccagcagcag   5580
gaagacatct ccgaccacgc gctgcgttcc ctgaccgact ccatggtct ggtgcgttct   5640
agctgcgtta tcttccgcct gtgcaacgat ctggccacct ctgcggcgga gctggaacgt   5700
ggcgagacta ccaattctat cattagctac atgcacgaaa acgatggtac cagcgaggaa   5760
caggcccgcg aagaactgcg taaactgatc gacgccgaat ggaaaagat gaatcgtgaa   5820
cgcgttagcg actccaccct gctgcctaaa gcgttcatgg aaatcgcagt taacatggca   5880
cgtgtttccc actgcaccta ccagtatggc gatggtctgg tcgcccaga ctacgcgact   5940
gaaaaccgca tcaaactgct gctgattgac ccttttcccga ttaaccagct gatgtatgtc   6000
taactgcatc gcccttagga ggtaaaaaaa aatgactgcc gacaacaata gtatgcccca   6060
tggtgcagta tctagttacg ccaaattagt gcaaaaccaa acacctgaag acattttgga   6120
agagtttcct gaaattattc cattacaaca aagacctaat acccgatcta gtgagacgtc   6180
```

```
aaatgacgaa agcggagaaa catgtttttc tggtcatgat gaggagcaaa ttaagttaat    6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattactttt acaacaaaga gccactgaaa aaataacttt    6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcactttt    6600 aaacagaatc cattacatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttcaccaaa tgatttgaaa actatgtttg ctgacccaag    6780
ttacaagttt acgccttggt ttaagattat ttgcgagaat tacttattca actggtggga    6840
gcaattagat gaccttttctg aagtggaaaa tgacaggcaa attcatagaa tgctataaca    6900
acgcgtcctg cattcgccct taggaggtaa aaaaacatga gttttgatat tgccaaatac    6960
ccgaccctgg cactggtcga ctccacccag gagttacgac tgttgccgaa agagagttta    7020
ccgaaactct gcgacgaact gcgccgctat ttactcgaca gcgtgagccg ttccagcggg    7080
cacttcgcct ccgggctggg cacggtcgaa ctgaccgtgg cgctgcacta tgtctacaac    7140
accccgtttg accaattgat ttgggatgtg gggcatcagg cttatccgca taaaattttg    7200 accgacgcc gcgacaaaat cggcaccatc cgtcagaaag gcggtctgca cccgttcccg    7260
tggcgcggcg aaagcgaata tgacgtatta agcgtcgggc attcatcaac ctccatcagt    7320
gccggaattg gtattgcggt tgctgccgaa aaagaaggca aaaatcgccg caccgtctgt    7380
gtcattggcg atggcgcgat taccgcaggc atggcgtttg aagcgatgaa tcacgcgggc    7440
gatatccgtc ctgatatgct ggtgattctc aacgacaatg aaatgtcgat ttccgaaaat    7500
gtcggcgcgc tcaacaacca tctggcacag ctgctttccg gtaagcttta ctcttcactg    7560
cgcgaaggcg ggaaaaaagt tttctctggc gtgccgccaa ttaaagagct gctcaaacgc    7620
accgaagaac atattaaagg catggtagtg cctggcacgt tgtttgaaga gctgggcttt    7680
aactacatcg gcccggtgga cggtcacgat gtgctggggc ttatcaccac gctaagaac     7740 atgcgcgacc tgaaagggccc gcagttcctg catatcatga ccaaaaaagg tcgtggttat    7800
gaaccggcag aaaaagaccc gatcacttc cacgccgtgc ctaaatttga tccctccagc    7860
ggttgtttgc cgaaaagtag cggcggtttg ccgagctatt caaaaatctt tggcgactgg    7920
ttgtgcgaaa cggcagcgaa agacaacaag ctgatggcga ttactccggc gatgcgtgaa    7980
ggttccggca tggtcgagtt ttcacgtaaa tccccggatc gctacttcga cgtgcaatt    8040 gccgagcaac acgcggtgac ctttgctgcg gtctggcga ttggtgggta caaacccatt    8100
gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220 caaaccccatc agggtgcttt tgatctctct tacctgcgct gcataccgga aatggtcatt    8280 atgacccga gcgatgaaaa cgaatgtcgc cagatgctct ataccggcta tcactataac    8340
gatgccccgt cagcggtgcg ctacccgcgt ggcaacgcgg tcggcgtgga actgacgccg    8400
ctggaaaaac taccaattgg caaaggcatt gtgaagcgtc gtggcgagaa actggcgatc    8460
cttaactttg gtacgctgat gccagaagcg gcgaaagtcg ccgaatcgct gaacgccacg    8520
ctggtcgata tgcgttttgt gaaaccgctt gatgaagcgt taattctgga aatggccgcc    8580
```

```
agccatgaag cgctggtcac cgtagaagaa aacgccatta tgggcggcgc aggcagcggc    8640
gtgaacgaag tgctgatggc ccatcgtaaa ccagtacccg tgctgaacat tggcctgccg    8700
gacttcttta ttccgcaagg aactcaggaa gaaatgcgcg ccgaactcgg cctcgatgcc    8760
gctggtatgg aagccaaaat caaggcctgg ctggcataac tgca                     8804
```

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct

<400> SEQUENCE: 21

```
aggaggtaaa aaacatgtc attaccgttc ttaacttctg c                          41
```

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22

```
atggctgcag gcctatcgca aattagctta tgaagtccat ggtaaattcg tg             52
```

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23

```
gaattcgccc ttctgcagct acc                                             23
```

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24

```
cgactggtgc acccttaagg aggaaaaaaa catgtcag                             38
```

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25

```
gtgctggaat tcgcccttct gcagc                                           25
```

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26

```
gtagatgcat gcagaattcg cccttaagga gg                                   32
```

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc 26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac 38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg 25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg 36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact 60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg 38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33

```
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggatcc   420
gagctcggat ccactagtaa cggccgccag tgtgctggaa ttcgccctta ggaggtaaaa   480
aaacatgtca ttaccgttct taacttctgc accgggaaag gttattattt ttggtgaaca   540
ctctgctgtg tacaacaagc ctgccgtcgc tgctagtgtg tctgcgttga aacctacct   600
gctaataagc gagtcatctg caccagatac tattgaattg acttcccgg acattagctt   660
taatcataag tggtccatca atgatttcaa tgccatcacc gaggatcaag taaactccca   720
aaaattggcc aaggctcaac aagccaccga tggcttgtct caggaactcg ttagtctttt   780
ggatccgttg ttagctcaac tatccgaatc cttccactac catgcagcgt tttgtttcct   840
gtatatgttt gtttgcctat gcccccatgc caagaatatt aagttttctt taaagtctac   900
tttacccatc ggtgctgggt tgggctcaag cgcctctatt tctgtatcac tggccttagc   960
tatggcctac ttgggggggt taataggatc taatgacttg gaaaagctgt cagaaaacga  1020
taagcatata gtgaatcaat gggccttcat aggtgaaaag tgtattcacg gtaccccttc  1080
aggaatagat aacgctgtgg ccacttatgg taatgccctg ctatttgaaa agactcaca   1140
taatggaaca ataaacacaa acaattttaa gttcttagat gatttcccag ccattccaat  1200
gatcctaacc tatactagaa ttccaaggtc tacaaaagat cttgttgctc gcgttcgtgt  1260
gttggtcacc gagaaatttc ctgaagttat gaagccaatt ctagatgcca tgggtgaatg  1320
tgccctacaa ggcttagaga tcatgactaa gttaagtaaa tgtaaaggca ccgatgacga  1380
ggctgtagaa actaataatg aactgtatga acaactattg gaattgataa gaataaatca  1440
tggactgctt gtctcaatcg gtgtttctca tcctggatta gaacttatta aaaatctgag  1500
cgatgatttg agaattggct ccacaaaact taccggtgct ggtggcggcg ttgctctttt  1560
gactttgtta cgaagagaca ttactcaaga gcaaattgac agcttcaaaa agaaattgca  1620
agatgatttt agttacgaga catttgaaac agacttgggt gggactggct gctgtttgtt  1680
aagcgcaaaa aatttgaata agatcttaa aatcaaatcc ctagtattcc aattatttga  1740
aaataaaact accacaaagc aacaaattga cgatctatta ttgccaggaa acacgaattt  1800
accatggact tcataagcta atttgcgata ggcctgcacc cttaaggagg aaaaaaacat  1860
gtcagagttg agagccttca gtgccccagg gaaagcgtta ctagctggtg gatatttagt  1920
tttagataca aaatatgaag catttgtagt cggattatcg gcaagaatgc atgctgtagc  1980
ccatccttac ggttcattgc aagggtctga taagtttgaa gtgcgtgtga aaagtaaaca  2040
atttaaagat ggggagtggc tgtaccatat aagtcctaaa agtggcttca ttcctgtttc  2100
gataggcgga tctaagaacc cttttcattga aaaagttatc gctaacgtat ttagctactt  2160
taaacctaac atggacgact actgcaatag aaacttgttc gttattgata ttttctctga  2220
tgatgcctac cattctcagg aggatagcgt taccgaacat cgtggcaaca gaagattgag  2280
ttttcattcg cacagaattg aagaagttcc caaaacaggg ctgggctcct cggcaggttt  2340
```

```
agtcacagtt taactacag ctttggcctc ctttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaacccct taagtattgg gggaaaaggg acacgaagtt gaatctgccc accaattcgt    3360
ccatatcagt gactttatcg caagatgacc tcagaacgtt gacctctgcg gctactgcac    3420
ctgagtttga acgcgacact ttgtggttaa atggagaacc acacagcatc gacaatgaaa    3480
gaactcaaaa ttgtctgcgc gacctacgcc aattaagaaa ggaaatggaa tcgaaggacg    3540
cctcattgcc cacattatct caatggaaac tccacattgt ctccgaaaat aactttccta    3600
cagcagctgg tttagcttcc tccgctgctg gctttgctgc attggtctct gcaattgcta    3660
agttatacca attaccacag tcaacttcag aaatatctag aatagcaaga aagggtctg    3720
gttcagcttg tagatcgttg ttttggcggat acgtggcctg ggaaatggga aaagctgaag    3780
atggtcatga ttccatggca gtacaaatcg cagacagctc tgactggcct cagatgaaag    3840
cttgtgtcct agttgtcagc gatattaaaa aggatgtgag ttccactcag ggtatgcaat    3900
tgaccgtggc aacctccgaa ctatttaaag aaagaattga acatgtcgta ccaaagagat    3960
ttgaagtcat gcgtaaagcc attgttgaaa aagatttcgc cacctttgca aaggaaacaa    4020
tgatggattc caactctttc catgccacat gtttggactc tttccctcca atattctaca    4080
tgaatgacac ttccaagcgt atcatcagtt ggtgccacac cattaatcag ttttacggag    4140
aaacaatcgt tgcatacacg tttgatgcag gtccaaatgc tgtgttgtac tacttagctg    4200
aaaatgagtc gaaactcttt gcatttatct ataaaattgtt tggctctgtt cctggatggg    4260
acaagaaatt tactactgag cagcttgagg ctttcaacca tcaatttgaa tcatctaact    4320
ttactgcacg tgaattggat cttgagttgc aaaaggatgt tgccagagtg attttaactc    4380
aagtcggttc aggcccacaa gaaacaaacg aatctttgat tgacgcaaag actggtctac    4440
caaaggaata agatcaattc gctgcatcgc ccttaggagg taaaaaaaaa tgactgccga    4500
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttttctg gtcatgatga    4680
ggagcaaatt aagttaatga atgaaaattg tattgttttg gattgggacg ataatgctat    4740
```

```
tggtgccggt accaagaaag tttgtcattt aatggaaaat attgaaaagg gtttactaca    4800
tcgtgcattc tccgtctttt ttttcaatga acaaggtgaa ttacttttac aacaaagagc    4860
cactgaaaaa ataactttcc ctgatctttg gactaacaca tgctgctctc atccactatg    4920
tattgatgac gaattaggtt tgaagggtaa gctagacgat aagattaagg gcgctattac    4980
tgcggcggtg agaaaactag atcatgaatt aggtattcca gaagatgaaa ctaagacaag    5040
gggtaagttt cacttttttaa acagaatcca ttacatggca ccaagcaatg aaccatgggg    5100
tgaacatgaa attgattaca tcctatttta taagatcaac gctaaagaaa acttgactgt    5160
caacccaaac gtcaatgaag ttagagactt caaatgggtt tcaccaaatg atttgaaaac    5220
tatgtttgct gacccaagtt acaagtttac gccttggttt aagattattt gcgagaatta    5280
cttattcaac tggtgggagc aattagatga ccttctgaa gtggaaaatg acaggcaaat     5340
tcatagaatg ctataacaac gcgtcctgca ttcgcccta ggaggtaaaa aacatgtgt      5400 gcgacctctt ctcaatttac tcagattacc gagcataatt cccgtcgttc cgcaaactat    5460
cagccaaacc tgtggaattt cgaattcctg caatccctgg agaacgacct gaaagtggaa    5520
aagctggagg agaaagcgac caaactggag gaagaagttc gctgcatgat caaccgtgta    5580
gacacccagc cgctgtccct gctggagctg atcgacgatg tgcagcgcct gggtctgacc    5640
tacaaatttg aaaagacat cattaaagcc ctggaaaaca tcgtactgct ggacgaaaac    5700
aaaaagaaca atctgacct gcacgcaacc gctctgtctt ccgtctgct gcgtcagcac    5760 ggtttcgagg tttctcagga tgtttttgag cgtttcaagg ataaagaagg tggtttcagc    5820
ggtgaactga aggtgacgt ccaaggcctg ctgagcctgt atgaagcgtc ttacctgggt     5880 ttcgaggtg agaacctgct ggaggaggcg cgtaccttt ccatcaccca cctgaagaac      5940
aacctgaaag aaggcattaa taccaaggtt gcagaacaag tgagccacgc cctggaactg    6000
ccatatcacc agcgtctgca ccgtctggag gcacgttggt tcctggataa atacgaaccg    6060
aaagaaccgc atcaccagct gctgctggag ctggcgaagc tggattttaa catggtacag    6120
accctgcacc agaaagagct gcaagatctg tcccgctggt ggaccgagat gggcctggct    6180
agcaaactgg attttgtacg cgaccgcctg atggaagttt atttctgggc actgggtatg    6240
gcgccagacc cgcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga atggtccaa caacaaaatt atcccggctt tctccaagta cctggaaaac    6600
gccagcgttt cctcctccgg tgtagcgctg ctggcgccgt cttactttc cgtatgccag    6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccct tcccgattaa ccagctgatg    7080
tatgtctaac tgcagctggt accatatggg aattcgaagc tttctagaac aaaaactcat    7140
```

```
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggcctttt    7620
tgcgtttcta caaactcttt ttgtttattt ttctaaatac attcaaatat gtatccgctt    7680
aaccggaatt gccagctggg gcgccctctg gtaaggttgg gaagccctgc aaagtaaact    7740
ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccggctgtca gcgcaggggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
tcgccttcta tcgccttctt gacgagttct tctgacgcat gaccaaaatc ccttaacgtg    8640
agttttcgtt ccactgagcg tcagaccccg tagaaaagat caaaggatct tcttgagatc    8700
ctttttttct gcgcgtaatc tgctgcttgc aaacaaaaaa accaccgcta ccagcggtgg    8760
tttgtttgcc ggatcaagag ctaccaactc tttttccgaa ggtaactggc ttcagcagag    8820
cgcagatacc aaatactgtc cttctagtgt agccgtagtt aggccaccac ttcaagaact    8880
ctgtagcacc gcctacatac ctcgctctgc taatcctgtt accagtggct gctgccagtg    8940
gcgataagtc gtgtcttacc gggttggact caagacgata gttaccggat aaggcgcagc    9000
ggtcgggctg aacggggggt tcgtgcacac agcccagctt ggagcgaacg acctacaccg    9060
aactgagata cctacagcgt gagctatgag aaagcgccac gcttcccgaa gggagaaagg    9120
cggacaggta tccggtaagc ggcagggtcg gaacaggaga gcgcacgagg gagcttccag    9180
ggggaaacgc ctggtatctt tatagtcctg tcgggtttcg ccacctctga cttgagcgtc    9240
gatttttgtg atgctcgtca ggggggcgga gcctatggaa aaacgccagc aacgcggcct    9300
ttttacggtt cctggccttt tgctggcctt ttgctcacat gttctttcct gcgttatccc    9360
ctgattctgt ggataaccgt attaccgcct ttgagtgagc tgataccgct cgccgcagcc    9420
gaacgaccga gcgcagcgag tcagtgagcg aggaagcgga agagcgcctg atgcggtatt    9480
ttctccttac gcatctgtgc ggtatttcac accgcatatg gtgcactctc agtacaatct    9540
```

-continued

```
gctctgatgc cgcatagtta agccagtata cactccgcta tcgctacgtg actgggtcat   9600
ggctgcgccc cgacacccgc caacacccgc tgacgcgccc tgacgggctt gtctgctccc   9660
ggcatccgct tacagacaag ctgtgaccgt ctccgggagc tgcatgtgtc agaggttttc   9720
accgtcatca ccgaaacgcg cgaggcagca gatcaattcg cgcgcgaagg cgaagcggca   9780
tgcatttacg ttgacaccat cgaatggtgc aaaacctttc gcggtatggc atgatagcgc   9840
ccggaagaga gtcaattcag ggtggtgaat gtgaaaccag taacgttata cgatgtcgca   9900
gagtatgccg gtgtctctta tcagaccgtt tccgcgtgg tgaaccaggc cagccacgtt    9960
tctgcgaaaa cgcgggaaaa agtggaagcg gcgatggcgg agctgaatta cattcccaac  10020
cgcgtggcac aacaactggc gggcaaacag tcgttgctga ttggcgttgc cacctccagt  10080
ctggccctgc acgcgccgtc gcaaattgtc gcggcgatta atctcgcgc cgatcaactg   10140 ggtgccagcg tggtggtgtc gatggtagaa cgaagcggcg tcgaagcctg taaagcggcg  10200
gtgcacaatc ttctcgcgca acgcgtcagt gggctgatca ttaactatcc gctggatgac  10260
caggatgcca ttgctgtgga agctgcctgc actaatgttc cggcgttatt tcttgatgtc  10320
tctgaccaga cacccatcaa cagtattatt ttctcccatg aagacggtac gcgactgggc  10380
gtggagcatc tggtcgcatt gggtcaccag caaatcgcgc tgttagcggg cccattaagt  10440
tctgtctcgg cgcgtctgcg tctggctggc tggcataaat atctcactcg caatcaaatt  10500
cagccgatag cggaacggga aggcgactgg agtgccatgt ccggttttca acaaaccatg  10560
caaatgctga atgagggcat cgttcccact gcgatgctgg ttgccaacga tcagatggcg  10620
ctgggcgcaa tgcgcgccat taccgagtcc gggctgcgcg ttggtgcgga tatctcggta  10680
gtgggatacg acgataccga agacagctca tgttatatcc cgccgtcaac caccatcaaa  10740
caggattttc gcctgctggg gcaaaccagc gtggaccgct tgctgcaact ctctcagggc  10800
caggcggtga agggcaatca gctgttgccc gtctcactgg tgaaaagaaa aaccaccctg  10860
gcgcccaata cgcaaaccgc ctctccccgc gcgttggccg attcattaat gcagctggca  10920
cgacaggttt cccgactgga aagcgggcag tgagcgcaac gcaattaatg tgagttagcg  10980
cgaattgatc tg                                                      10992
```

```
<210> SEQ ID NO 34
<211> LENGTH: 50
<212> TYPE: DNA
<213> ORGANISM: Artificial Sequence
<220> FEATURE:
<223> OTHER INFORMATION: Synthetic Construct

<400> SEQUENCE: 34
gagacatgag ctcaggaggt aaaaaaacat gaaaacagta gttattattg              50

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
tttatcaatc ccaattgtca tgttttttta cctcctttat tgttttctta aatc         54

<210> SEQ ID NO 36
<211> LENGTH: 54
<212> TYPE: DNA
<213> ORGANISM: Artificial Sequence
<220> FEATURE:
```

<223> OTHER INFORMATION: Synthetic Construct

<400> SEQUENCE: 36
gatttaagaa aacaataaag gaggtaaaaa aacatgacaa ttgggattga taaa        54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt        40

<210> SEQ ID NO 38
<211> LENGTH: 26
<212> TYPE: DNA
<213> ORGANISM: Artificial Sequence
<220> FEATURE:
<223> OTHER INFORMATION: Synthetic Construct

<400> SEQUENCE: 38
atgaaaacag tagttattat tgatgc        26

<210> SEQ ID NO 39
<211> LENGTH: 33
<212> TYPE: DNA
<213> ORGANISM: Artificial Sequence
<220> FEATURE:
<223> OTHER INFORMATION: Synthetic Construct

<400> SEQUENCE: 39
atgttattgt tttcttaaat catttaaaat agc        33

<210> SEQ ID NO 40
<211> LENGTH: 26
<212> TYPE: DNA
<213> ORGANISM: Artificial Sequence
<220> FEATURE:
<223> OTHER INFORMATION: Synthetic Construct

<400> SEQUENCE: 40
atgacaattg ggattgataa aattag        26

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ttagtttcga taagaacgaa cggt        24

<210> SEQ ID NO 42
<211> LENGTH: 23
<212> TYPE: DNA
<213> ORGANISM: Artificial Sequence
<220> FEATURE:
<223> OTHER INFORMATION: Synthetic Construct

<400> SEQUENCE: 42
gaaatagccc cattagaagt atc        23

<210> SEQ ID NO 43

| | |
|---|---|
| <211> LENGTH: 24 | |
| <212> TYPE: DNA | |
| <213> ORGANISM: Artificial Sequence | |
| <220> FEATURE: | |
| <223> OTHER INFORMATION: Synthetic Construct | |

<400> SEQUENCE: 43
ttgccaatca tatgattgaa aatc 24

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
gctatgcttc attagatcct tatcg 25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
gaaacctaca tccaatcttt tgccc 25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46

| | |
|---|---|
| cccgtcttac tgtcgggaat tcgcgttggc cgattcatta atgcagattc tgaaatgagc | 60 |
| tgttgacaat taatcatccg gctcgtataa tgtgtggaat tgtgagcgga taacaatttc | 120 |
| acacaggaaa cagcgccgct gagaaaaagc gaagcggcac tgctctttaa caatttatca | 180 |
| gacaatctgt gtgggcactc gaccggaatt atcgattaac tttattatta aaaattaaag | 240 |
| aggtatatat taatgtatcg attaaataag gaggaataaa ccatggatcc gagctcagga | 300 |
| ggtaaaaaaa catgaaaaca gtagttatta ttgatgcatt acgaacacca attggaaaat | 360 |
| ataaaggcag cttaagtcaa gtaagtgccg tagacttagg aacacatgtt acaacacaac | 420 |
| ttttaaaaag acattccact atttctgaag aaattgatca agtaatcttt ggaaatgttt | 480 |
| tacaagctgg aaatggccaa atcccgcac gacaaatagc aataaacagc ggtttgtctc | 540 |
| atgaaattcc cgcaatgacg gttaatgagg tctgcggatc aggaatgaag gccgttattt | 600 |
| tggcgaaaca attgattcaa ttaggagaag cggaagtttt aattgctggc gggattgaga | 660 |
| atatgtccca agcacctaaa ttacaacgtt ttaattacga acagaaagc tacgatgcgc | 720 |
| cttttttctag tatgatgtat gatggattaa cggatgcctt tagtggtcag gcaatgggct | 780 |
| taactgctga aaatgtggcc gaaaagtatc atgtaactag agaagagcaa gatcaatttt | 840 |
| ctgtacattc acaattaaaa gcagctcaag cacaagcaga agggatattc gctgacgaaa | 900 |
| tagcccccatt agaagtatca ggaacgcttg tggagaaaga tgaagggatt cgccctaatt | 960 |
| cgagcgttga agctagga acgcttaaaa cagttttaa agaagacggt actgtaacag | 1020 |
| cagggaatgc atcaaccatt aatgatgggg cttctgcttt gattattgct tcacaagaat | 1080 |

-continued

```
atgccgaagc acacggtctt ccttatttag ctattattcg agacagtgtg aagtcggta    1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaagaa aagaaatatg gagtggcttc tttatgtatc ggcggtggct    1440
taggactcgc tatgctacta gagagacctc agcaaaaaaa aaacagccga tttttatcaaa  1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga acagaagtg ccgatgggcg ttggcttaca tttaacagtg gacgaaactg    1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagttttca acaagcagag ttaagttatc catctatcgt taaacggggc ggcggcttaa    1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
cagtcgctca acaattaaaa cgtcaaaaaa cgatgaacca agaccgagcc atggctattt   2700
taaatgattt aagaaaacaa taaggaggt aaaaaaacat gacaattggg attgataaaa    2760
ttagtttttt tgtgccccct tattatattg atatgacggc actggctgaa gccagaaatg   2820
tagaccctgg aaaatttcat attggtattg ggcaagacca aatggcggtg aacccaatca   2880
gccaagatat tgtgacattt gcagccaatg ccgcagaagc gatcttgacc aaagaagata   2940
agaggccat tgatatggtg attgtcggga ctgagtccag tatcgatgag tcaaaagcgg    3000
ccgcagttgt cttacatcgt ttaatgggga ttcaacctt cgctcgctct ttcgaaatca    3060
aggaagcttg ttacggagca acagcaggct tacagttagc taagaatcac gtagccttac   3120
atccagataa aaagtcttg gtcgtagcgg cagatattgc aaaatatggc ttaaattctg    3180
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtccttttgtc aaacgaaacc tacatccaat   3360
cttttgccca gtctgggat gaacataaaa acgaaccgg tcttgatttt gcagattatg     3420
atgctttagc gttccatatt ccttacacaa aaatgggcaa aaaagcctta ttagcaaaaa   3480
```

```
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa aatcatttac   3720
aaaagaaac tcatttagca ctgctggata tcggacaga actttctatc gctgaatatg     3780
aagccatgtt tgcagaaact ttagacacag acattgatca aacgttagaa gatgaattaa   3840
aatatagtat ttctgctatt aataataccg ttcgttctta tcgaaactaa gagatctgca   3900
gctggtacca tatgggaatt cgaagcttgg gcccgaacaa aaactcatct cagaagagga   3960
tctgaatagc gccgtcgacc atcatcatca tcatcattga gtttaaacgg tctccagctt   4020
ggctgttttg gcggatgaga gaagattttc agcctgatac agattaaatc agaacgcaga   4080
agcggtctga taaaacagaa tttgcctggc ggcagtagcg cggtggtccc acctgacccc   4140
atgccgaact cagaagtgaa acgccgtagc gccgatggta gtgtggggtc tccccatgcg   4200
agagtaggga actgccaggc atcaaataaa acgaaaggct cagtcgaaag actgggcctt   4260
tcgttttatc tgttgtttgt cggtgaacgc tctcctgagt aggacaaatc cgccgggagc   4320
ggatttgaac gttgcgaagc aacggcccgg agggtggcgg gcaggacgcc cgccataaac   4380
tgccaggcat caaattaagc agaaggccat cctgacggat ggccttttg cgtttctaca    4440
aactctttt gtttatttt ctaaatacat tcaaatatgt atccgctcat gagacaataa      4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagatttta atgcggatgt tgcgattact tcgccaacta ttgcgataac aagaaaaagc   4800
cagcctttca tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat gcccagtcg gcagcgacat ccttcggcgc    5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
gctatgttct cttgcttttg tcagcaagat agccagatca atgtcgatcg tggctggctc   5400
gaagatacct gcaagaatgt cattgcgctg ccattctcca aattgcagtt cgcgcttagc   5460
tggataacgc cacggaatga tgtcgtcgtg cacaacaatg gtgacttcta cagcgcggag   5520
aatctcgctc tctccagggg aagccgaagt ttccaaaagg tcgttgatca agctcgccg    5580
cgttgtttca tcaagcctta cggtcaccgt aaccagcaaa tcaatatcac tgtgtggctt   5640
caggccgcca tccactgcgg agccgtacaa atgtacggcc agcaacgtcg gttcgagatg   5700
gcgctcgatg acgccaacta cctctgatag ttgagtcgat acttcggcga tcaccgcttc   5760
cctcatgatg tttaactttg ttttagggcg actgccctgc tgcgtaacat cgttgctgct   5820
ccataacatc aaacatcgac ccacggcgta acgcgcttgc tgcttggatg cccgaggcat   5880
```

```
agactgtacc ccaaaaaaac agtcataaca agccatgaaa accgccactg cgccgttacc   5940
accgctgcgt tcggtcaagg ttctggacca gttgcgtgag cgcatacgct acttgcatta   6000
cagcttacga accgaacagg cttatgtcca ctgggttcgt gccttcatcc gtttccacgg   6060
tgtgcgtcac ccggcaacct tgggcagcag cgaagtcgag gcatttctgt cctggctggc   6120
gaacgagcgc aaggtttcgg tctccacgca tcgtcaggca ttggcggcct tgctgttctt   6180
ctacggcaag gtgctgtgca cggatctgcc ctggcttcag gagatcggaa gacctcggcc   6240
gtcgcggcgc ttgccggtgg tgctgacccc ggatgaagtg gttcgcatcc tcggttttct   6300
ggaaggcgag catcgtttgt tcgcccagct tctgtatgga acgggcatgc ggatcagtga   6360
gggtttgcaa ctgcgggtca aggatctgga tttcgatcac ggcacgatca tcgtgcggga   6420
gggcaagggc tccaaggatc gggccttgat gttacccgag agcttggcac ccagcctgcg   6480
cgagcagggg aattaattcc cacgggtttt gctgcccgca acgggctgt tctggtgttg   6540
ctagtttgtt atcagaatcg cagatccggc ttcagccggt ttgccggctg aaagcgctat   6600
ttcttccaga attgccatga ttttttcccc acgggaggcg tcactggctc ccgtgttgtc   6660
ggcagctttg attcgataag cagcatcgcc tgtttcaggc tgtctatgtg tgactgttga   6720
gctgtaacaa gttgtctcag gtgttcaatt tcatgttcta gttgctttgt tttactggtt   6780
tcacctgttc tattaggtgt tacatgctgt tcatctgtta cattgtcgat ctgttcatgg   6840
tgaacagctt tgaatgcacc aaaaactcgt aaaagctctg atgtatctat cttttttaca   6900
ccgttttcat ctgtgcatat ggacagtttt ccctttgata tgtaacggtg aacagttgtt   6960
ctacttttgt ttgttagtct tgatgcttca ctgatagata caagagccat aagaacctca   7020
gatccttccg tatttagcca gtatgttctc tagtgtggtt cgttgttttt gcgtgagcca   7080
tgagaacgaa ccattgagat catacttact ttgcatgtca ctcaaaaatt ttgcctcaaa   7140
actggtgagc tgaattttg cagttaaagc atcgtgtagt gtttttctta gtccgttatg   7200
taggtaggaa tctgatgtaa tggttgttgg tattttgtca ccattcattt ttatctggtt   7260
gttctcaagt tcggttacga gatccatttg tctatctagt tcaacttgga aaatcaacgt   7320
atcagtcggg cggcctcgct tatcaaccac caatttcata ttgctgtaag tgtttaaatc   7380
tttacttatt ggtttcaaaa cccattggtt aagccttta aactcatggt agttattttc   7440
aagcattaac atgaacttaa attcatcaag gctaatctct atatttgcct tgtgagtttt   7500
cttttgtgtt agttctttta ataaccactc ataaatcctc atagagtatt tgttttcaaa   7560
agacttaaca tgttccagat tatattttat gaattttttt aactggaaaa gataaggcaa   7620
tatctcttca ctaaaaacta attctaattt ttcgcttgag aacttggcat agtttgtcca   7680
ctggaaaatc tcaaagcctt taaccaaagg attcctgatt tccacagttc tcgtcatcag   7740
ctctctggtt gctttagcta atacaccata agcattttcc ctactgatgt tcatcatctg   7800
agcgtattgg ttataagtga acgataccgt ccgttctttc cttgtagggt tttcaatcgt   7860
ggggttgagt agtgccacac agcataaaat tagcttggtt tcatgctccg ttaagtcata   7920
gcgactaatc gctagttcat ttgctttgaa acaactaat tcagacatac atctcaattg   7980
gtctaggtga tttttaatcac tataccaatt gagatgggct agtcaatgat aattactagt   8040
ccttttcctt tgagttgtgg gtatctgtaa attctgctag acctttgctg gaaaacttgt   8100
aaattctgct agaccctctg taaattccgc tagaccttg tgtgtttttt ttgtttatat   8160
tcaagtggtt ataatttata gaataaagaa agaataaaaa aagataaaaa gaatagatcc   8220
cagccctgtg tataactcac tactttagtc agttccgcag tattacaaaa ggatgtcgca   8280
```

```
aacgctgttt gctcctctac aaaacagacc ttaaaaccct aaaggcttaa gtagcaccct    8340
cgcaagctcg ggcaaatcgc tgaatattcc ttttgtctcc gaccatcagg cacctgagtc    8400
gctgtctttt tcgtgacatt cagttcgctg cgctcacggc tctggcagtg aatggggggta   8460 aatggcacta caggcgcctt ttatggattc atgcaaggaa actacccata atacaagaaa    8520
agcccgtcac gggcttctca gggcgtttta tggcgggtct gctatgtggt gctatctgac    8580
tttttgctgt tcagcagttc ctgccctctg attttccagt ctgaccactt cggattatcc    8640
cgtgacaggt cattcagact ggctaatgca cccagtaagg cagcggtatc atcaacaggc    8700
tta                                                                  8703

<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47
tgtaaccttt gctttcaaat gagtagaaat aatgcacatc catgtttgta tcgtgcaaat      60
aaagtgtttc atccgtagga aaaatgact ttagtatctg ttccgctttt tctgatgaaa     120
tgtgctcccc gacaaaattg aatgaatcat ggacatttgc tggctttgat acagcgaaag    180
cagccgttcc tatgttatat atcggattta acagcaggac aaaaaacacc atgacagcca    240
tcgtcaccca cttattcaca cgcacataaa ccttttcctga cttttggaac agatgatagc    300
tcatcaaaaa tcccgccatt gccaaataaa tcgtatatgg cattactgca ccataatctt    360
ttgagatttg attgggatat ggcgcaagca gcaagacaag cagtccgata atcagcgtat    420
aaaataagcc tagtaagatc ttatccgttc tccaatacag cttgaaaaac actacattca    480
acgcaatggg aagagtgatg atgaaaaaca gaaacacgaa tgcaatcggc tccatcccat    540
ccgggtattc cttccaatac gaaaagaaac taaaaatcat ttgtacgatc ggcaaactga    600
caacagcaag gtcgaacgta taaaacttac cctttccgcc atgatcacgc ggcatcagca    660
tatagtgaaa agccgtcagc agcacatatc cgtataacaa aaaatgcagc agcggcagca    720 gttctttttcc gtcctctctt aagtaagcgc tggtgaagtt tgttgattgc acctggtgaa    780
taagttcaac agacactccc gccagcagca caatccgcaa tataacaccc gccaagaaca    840
ttgtgcgctg ccggtttatt tgggatgat gcaccaaaag atataagccc gccagaacaa    900
caattgacca ttgaatcagc agggtgcttt gtctgcttaa tataaaataa cgttcgaaat    960
gcaatacata atgactgaat aactccaaca cgaacaacaa ctccattttc ttctgctatc   1020
aaaataacag actcgtgatt ttccaaacga gctttcaaaa aagcctctgc cccttgcaaa   1080
tcggatgcct gtctataaaa ttcccgatat tggttaaaca gcggcgcaat ggcggccgca   1140
tctgatgtct ttgcttggcg aatgttcatc ttatttcttc ctccctctca ataattttt    1200 cattctatcc cttttctgta aagtttattt ttcagaatac tttatcatc atgctttgaa    1260 aaaatatcac gataatatcc attgttctca cggaagcaca cgcaggtcat ttgaacgaat   1320 ttttcgaca ggaatttgcc gggactcagg agcatttaac ctaaaaaagc atgacatttc    1380
agcataatga acatttactc atgtctattt tcgttctttt ctgtatgaaa atagttattt   1440
cgagtctcta cggaaatagc gagagatgat atacctaaat agagataaaa tcatctcaaa   1500
aaaatgggtc tactaaaata ttattccatc tattacaata aattcacaga atagtctttt    1560
aagtaagtct actctgaatt tttttaaaag gagagggtaa agagtgtcat taccgttctt   1620
```

-continued

```
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980
cccccatgcc aagaatatta agttttcttt aaagtctact ttacccatcg gtgctgggtt   2040
gggctcaagc gcctctattt ctgtatcact ggccttagct atggcctact ggggggggtt   2100
aataggatct aatgacttgg aaaagctgtc agaaaacgat aagcatatag tgaatcaatg   2160
ggccttcata ggtgaaaagt gtattcacgg taccccttca ggaatagata acgctgtggc   2220
cacttatggt aatgccctgc tatttgaaaa agactcacat aatggaacaa taaacacaaa   2280
caattttaag ttcttagatg atttcccagc cattccaatg atcctaacct atactagaat   2340
tccaaggtct acaaaagatc ttgttgctcg cgttcgtgtg ttggtcaccg agaaatttcc   2400
tgaagttatg aagccaattc tagatgccat gggtgaatgt gccctacaag cttagagat   2460
catgactaag ttaagtaaat gtaaaggcac cgatgacgag gctgtagaaa ctaataatga   2520
actgtatgaa caactattgg aattgataag aataaatcat ggactgcttg tctcaatcgg   2580
tgtttctcat cctggattag aacttattaa aaatctgagc gatgatttga gaattggctc   2640
cacaaaactt accggtgctg gtggcggcgg ttgctctttg actttgttac gaagagacat   2700
tactcaagag caaattgaca gcttcaaaaa gaaattgcaa gatgatttta gttacgagac   2760
atttgaaaca gacttgggtg ggactggctg ctgtttgtta agcgcaaaaa atttgaataa   2820
agatcttaaa atcaaatccc tagtattcca attatttgaa aataaaacta ccacaaagca   2880
acaaattgac gatctattat tgccaggaaa cacgaattta ccatggactt cataaaagga   2940
gagggtgtca gagttgagag ccttcagtgc cccagggaaa gcgttactag ctggtggata   3000
tttagtttta gatacaaaat atgaagcatt tgtagtcgga ttatcggcaa gaatgcatgc   3060
tgtagcccat ccttacggtt cattgcaagg gtctgataag tttgaagtgc gtgtgaaaag   3120
taaacaattt aaagatgggg agtggctgta ccatataagt cctaaaagtg gcttcattcc   3180
tgtttcgata ggcggatcta agaaccctt cattgaaaaa gttatcgcta acgtatttag   3240
ctactttaaa cctaacatgg acgactactg caatagaaac ttgttcgtta ttgatatttt   3300
ctctgatgat gcctaccatt ctcaggagga tagcgttacc gaacatcgtg gcaacagaag   3360
attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
taatgtagac aaatatagag aagttattca taatttagca caagttgctc attgtcaagc   3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaacca   3720
tttaccttcg ggattaactt tatggatggg cgatattaag aatggttcag aaacagtaaa   3780
actggtccag aagtaaaaaa attggtatga ttcgcatatg ccagaaagct tgaaaatata   3840
tacagaactc gatcatgcaa attctagatt tatggatgga ctatctaaac tagatcgctt   3900
acacgagact catgacgatt acagcgatca gatatttgag tctcttgaga ggaatgactg   3960
tacctgtcaa aagtatcctg aaatcacaga agttagagat gcagttgcca caattagacg   4020
```

```
ttcctttaga aaaataacta aagaatctgg tgccgatatc gaacctcccg tacaaactag    4080
cttattggat gattgccaga ccttaaaagg agttcttact tgcttaatac ctggtgctgg    4140
tggttatgac gccattgcag tgattactaa gcaagatgtt gatcttaggg ctcaaaccgc    4200
taatgacaaa agattttcta aggttcaatg gctggatgta actcaggctg actggggtgt    4260
taggaaagaa aaagatccgg aaacttatct tgataaataa aaggagaggg tgaccgttta    4320
cacagcatcc gttaccgcac ccgtcaacat cgcaacccct aagtattggg ggaaaaggga    4380
cacgaagttg aatctgccca ccaattcgtc catatcagtg actttatcgc aagatgacct    4440
cagaacgttg acctctgcgg ctactgcacc tgagtttgaa cgcgacactt tgtggttaaa    4500
tggagaacca cacagcatcg acaatgaaag aactcaaaat tgtctgcgcg acctacgcca    4560
attaagaaag gaaatggaat cgaaggacgc ctcattgccc acattatctc aatgaaaact    4620
ccacattgtc tccgaaaata actttcctac agcagctggt ttagcttcct ccgctgctgg    4680
ctttgctgca ttggtctctg caattgctaa gttataccaa ttccacagt  caacttcaga    4740
aatatctaga atagcaagaa aggggtctgg ttcagcttgt agatcgttgt ttggcggata    4800
cgtggcctgg gaaatgggaa aagctgaaga tggtcatgat ccatggcag  tacaaatcgc    4860
agacagctct gactggcctc agatgaaagc ttgtgtccta gttgtcagcg atattaaaaa    4920
ggatgtgagt tccactcagg gtatgcaatt gaccgtggca acctccgaac tatttaaaga    4980
aagaattgaa catgtcgtac caaagagatt tgaagtcatg cgtaaagcca ttgttgaaaa    5040
agatttcgcc acctttgcaa aggaaacaat gatggattcc aactctttcc atgccacatg    5100
tttggactct ttccctccaa tattctacat gaatgacact tccaagcgta tcatcagttg    5160
gtgccacacc attaatcagt tttacggaga acaatcgtt  gcatacacgt ttgatgcagg    5220
tccaaatgct gtgttgtact acttagctga aaatgagtcg aaactctttg catttatcta    5280
taaattgttt ggctctgttc ctggatggga caagaaattt actactgagc agcttgaggc    5340
tttcaaccat caatttgaat catctaactt tactgcacgt gaattggatc ttgagttgca    5400
aaaggatgtt gccagagtga ttttaactca agtcggttca ggcccacaag aaacaaacga    5460
atctttgatt gacgcaaaga ctggtctacc aaaggaataa aaggagaggg tgactgccga    5520
caacaatagt atgccccatg gtgcagtatc tagttacgcc aaattagtgc aaaaccaaac    5580
acctgaagac attttggaag agtttcctga aattattcca ttacaacaaa gacctaatac    5640
ccgatctagt gagacgtcaa atgacgaaag cggagaaaca tgttttttctg gtcatgatga    5700
ggagcaaatt aagttaatga atgaaaattg tattgttttg gattgggacg ataatgctat    5760
tggtgccggt accaagaaag tttgtcattt aatggaaaat attgaaaagg gtttactaca    5820
tcgtgcattc tccgtctta  ttttcaatga acaaggtgaa ttacttttac aacaaagagc    5880
cactgaaaaa ataactttcc ctgatctttg gactaacaca tgctgctctc atccactatg    5940
tattgatgac gaattaggtt tgaagggtaa gctagcgat  aagattaagg gcgctattac    6000
tgcggcggtg agaaaactag atcatgaatt aggtattcca gaagatgaaa ctaagacaag    6060
gggtaagttt cacttttaa  acagaatcca ttacatggca ccaagcaatg aaccatgggg    6120
tgaacatgaa attgattaca tcctatttta taagatcaac gctaaagaaa acttgactgt    6180
caacccaaac gtcaatgaag ttagagactt caaatgggtt tcaccaaatg atttgaaaac    6240
tatgtttgct gacccaagtt acaagtttac gccttggttt aagattattt gcgagaatta    6300
cttattcaac tggtgggagc aattagatga ccttttctgaa gtggaaaatg acaggcaaat    6360
tcatagaatg ctataaaaaa aaccggcctt ggccccgccg gttttttatt attttcttc    6420
```

```
ctccgcatgt tcaatccgct ccataatcga cggatggctc cctctgaaaa ttttaacgag    6480
aaacggcggg ttgacccggc tcagtccgt aacggccaag tcctgaaacg tctcaatcgc    6540
cgcttcccgg tttccggtca gctcaatgcc gtaacggtcg gcggcgtttt cctgataccg    6600
ggagacggca ttcgtaattt gaatacatac gaacaaatta ataaagtgaa aaaatactt    6660 cggaaacatt taaaaaataa ccttattggt acttacatgt ttggatcagg agttgagagt    6720
ggactaaaac caaatagtga tcttgacttt ttagtcgtcg tatctgaacc attgacagat    6780
caaagtaaag aaatacttat acaaaaaatt agacctattt caaaaaaaat aggagataaa    6840
agcaacttac gatatattga attaacaatt attattcagc aagaaatggt accgtggaat    6900
catcctccca aacaagaatt tatttatgga gaatggttac aagagcttta tgaacaagga    6960
tacattcctc agaaggaatt aaattcagat ttaaccataa tgctttacca agcaaaacga    7020
aaaaataaaa gaatatacgg aaattatgac ttagaggaat tactacctga tattccattt    7080
tctgatgtga aagagccat tatggattcg tcagaggaat aatagataaa ttatcaggat    7140
gatgaaacca actctatatt aactttatgc cgtatgattt taactatgga cacgggtaaa    7200
atcataccaa aagatattgc gggaaatgca gtggctgaat cttctccatt agaacatagg    7260
gagagaattt tgttagcagt tcgtagttat cttggagaga atattgaatg gactaatgaa    7320
aatgtaaatt taactataaa ctatttaaat aacagattaa aaaaattata atgtaaacctt    7380 tgctttcaaa tgagtagaaa taatgcacat ccatgtttgt atcgtgcaaa taaagtgttt    7440
catccgtagg aaaaaatgac tttagtatct gttccgcttt ttctgatgaa atgtgctccc    7500
cgacaaaatt gaatgaatca tggacatttg ctggctttga tacagcgaaa gcagccgttc    7560
ctatgttata tatcggattt aacagcagga caaaaaacac catgcagcc atcgtcaccc    7620 acttattcac acgcacataa acctttcctg acttttggaa cagatgatag ctcatcaaaa    7680
atcccgccat tgccaaataa atcgtatatg gcattactgc accataatct tttgagattt    7740
gattgggata tggcgcaagc agcaagacaa gcagtccgat aatcagcgta taaaataagc    7800
ctagtaagat cttatccgtt ctccaataca gcttgaaaaa cactcattc aacgcaatgg    7860 gaagagtgat gatgaaaaac agaaacacga atgcaatcgg ctccatccca tccgggtatt    7920
ccttccaata cgaaaagaaa ctaaaaatca tttgtacgat cggcaaactg acaacagcaa    7980
ggtcgaacgt ataaaactta ccctttccgc catgatcacg cggcatcagc atatagtgaa    8040
aagccgtcag cagcacatat ccgtataaca aaaaatgcag cagcggcagc agttctttc    8100 cgtcctctct taagtaagcg ctggtgaagt ttgttgattg cacctggtga ataagttcaa    8160
cagacactcc cgccagcagc acaatccgca atataacacc cgccaagaac attgtgcgct    8220
gccggtttat tttgggatga tgcaccaaaa gatataagcc cgccagaaca caattgacc    8280 attgaatcag cagggtgctt tgtctgctta atataaaata acgttcgaaa tgcaatacat    8340
aatgactgaa taactccaac acgaacaaca aaagtgcgca ttttataaaa gctaatgatt    8400
cagtccacat aattgataga cgaattctgc tacaggtcac gtggctatgt gaaggatcgc    8460
gcgtccagtt aagagcaaaa acattgacaa aaaaattat ttatgctaaa atttactatt    8520
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgttttttca    8760 acaaagagat cgccgaacgt cttcaaaatg atcctgaaaa aatattaaaa tgggttgcac    8820
```

```
aaatccagct gtctccaacg cccctagcac gtgcttctta ttgtgaaaaa gtcttgcaca      8880
acgaattaat cctgggggca aaacagtatg tcattcttgg agcgggactg gatactttct      8940
gctttcggca tccagaatta gaaaacagct tacaggtttt cgaggttgat catccggcca      9000
cacagcaatt gaaaaaaaat aagctgaagg atgcaaatct gacaattccg ggtcatcttc      9060
attttgttcc tatggatttc accaaaacgt tttcgtatga tcctctctta gatgaaggat      9120
ttaaaaacac aaaaacattc ttcagccttc tcggagtgtc ttattatgta acacgggaag      9180
aaaatgcaag cttgatcagc aatttatttt ctcatgtccc gcctggaagc tctattgttt      9240
ttgattatgc ggacgaaaca cttttttacag caaaagggac gtcgaatcga gttgaacata      9300
tggtgaagat ggctgccgca agcggggaac cgatgaaatc atgtttcact tatcaagaga      9360
ttgaacatct g                                                            9371

<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48
tagaaaaact catcgagcat caaatgaaac tgcaatttat tcatatcagg attatcaata        60
ccatattttt gaaaaagccg tttctgtaat gaaggagaaa actcaccgag gcagttccat       120
aggatggcaa gatcctggta tcggtctgcg attccgactc gtccaacatc aatcaaacct       180
attaatttcc cctcgtcaaa aataaggtta tcaagtgaga atcaccatg agtgacgact        240 gaatccggtg agaatggcaa aagtttatgc atttctttcc agacttgttc aacaggccag       300
ccattacgct cgtcatcaaa atcactcgca tcaaccaaac cgttattcat tcgtgattgc       360
gcctgagcga ggcgaaatac gcgatcgctg ttaaaaggac aattacaaac aggaatcgag       420
tgcaaccggc gcaggaacac tgccagcgca tcaacaatat tttcacctga atcaggatat       480
tcttctaata cctggaacgc tgttttttccg gggatcgcag tggtgagtaa ccatgcatca       540
tcaggagtac ggataaaatg cttgatggtc ggaagtggca taaattccgt cagccagttt       600
agtctgacca tctcatctgt aacatcattg gcaacgctac ctttgccatg tttcagaaac       660
aactctggcg catcgggctt cccatacaag cgatagattg tcgcacctga ttgcccgaca       720
ttatcgcgag cccatttata cccatataaa tcagcatcca tgttggaatt taatcgcggc       780
ctcgacgttt cccgttgaat atggctcata ttcttccttt ttcaatatta ttgaagcatt       840
tatcagggtt attgtctcat gagcggatac atatttgaat gtatttagaa aaataaacaa       900
ataggggtca gtgttacaac caattaacca attctgaaca ttatcgcgag cccatttata       960
cctgaatatg gctcataaca ccccttgttt gcctggcggc agtagcgcgg tggtcccacc      1020
tgaccccatg ccgaactcag aagtgaaacg ccgtagcgcc gatggtagtg tggggactcc      1080
ccatgcgaga gtagggaact gccaggcatc aaataaaacg aaaggctcag tcgaaagact      1140
gggcctttcg cccgggctaa ttaggggggt tcgcccttta gtcgctgaac atgtgctctg      1200
tttctaccga gaacgtttcc ttcactgaga cggaaaccga ggcacgtcgt agcgcgaact      1260
acgagccgaa tagctgggac tacgattccc tgctgtcttc cgatactgac gaatctattg      1320
aggtgtacaa agacaaagca aagaaactgg aggctgaagt gcgccgcgaa attaacaacg      1380
agaaagctga attcctgact ctgctggagc tgatcgataa cgtacagcgc ctgggtctgg      1440
gttaccgctt cgaatctgat atccgtcgcg cactggatcg tttcgtaagc agcggcggtt      1500
```

-continued

```
tcgatggcgt gaccaaaacg agcctgcacg ctaccgcgct gtccttccgt ctgctgcgtc    1560
agcacggctt cgaagtttct caggaagcat tctccggttt caaagatcaa aacggtaact    1620
tcctggaaaa cctgaaagaa gacactaagg cgatcctgag cctgtatgag gcaagctttc    1680 tggcccctgga gggtgagaac atcctggatg aggcgcgcgt attcgccatc tcccatctga    1740
aagagctgtc tgaagagaaa atcggtaagg aactggcaga gcaggttaat cacgcactgg    1800
aactgccgct gcatcgtcgt acccagcgtc tggaggcggt ttggtccatc gaagcgtacc    1860
gcaaaaagga ggatgctaac caggttctgc tggaactggc catcctggac tacaacatga    1920
tccagtccgt ttaccagcgt gatctgcgtg aaacctcccg ttggtggcgc cgtgtgggcc    1980
tggcgaccaa actgcacttc gctaaggacc gcctgattga gtctttttac tgggcagtcg    2040
gcgttgcgtt cgaacctcag tattctgact gccgtaacag cgttgcgaaa atgttcagct    2100
tcgttactat tatcgacgac atctacgacg tttacggtac tctggacgag ctggaactgt    2160
ttaccgacgc tgtcgaacgt tgggatgtta acgccatcaa cgatctgcct gactacatga    2220
aactgtgctt cctggcactg tataacacga tcaacgaaat tgcatacgac aacctgaaag    2280
acaaaggtga aacatcctg ccgtacctga ctaaagcgtg gcggatctg tgtaacgctt    2340 ttctgcaaga agcgaaatgg ctgtataaca aatccactcc gacctttgac gattatttcg    2400
gcaatgcctg gaaatccagc tctggcccgc tgcaactgat cttcgcttat tttgcggttg    2460
tccaaaacat caaaaggag gaaattgaaa acctgcaaaa ataccacgat atcattagcc    2520
gtccttctca tatctttcgc ctgtgcaacg acctggcaag cgcgtccgca gagatcgcac    2580
gtggcgaaac cgctaactct gtttcctgct acatgcgcac caagggcatt tccgaagagc    2640
tggcaaccga gagcgtaatg aatctgatcg acgaaacctg taagaaaatg aacaaagaaa    2700
aactgggtgg ctccctgttc gctaaaccgt tcgtagagac tgctattaac ctggcacgtc    2760
agagccactg cacctaccac aatggtgacg cacatactag cccggatgaa ctgactcgta    2820
aacgtgtact gtctgttatc accgaaccga ttctgccgtt cgaacgttaa ctgcagcgtc    2880
aatcgaaagg gcgacacaaa atttattcta aatgcataat aaatactgat aacatcttat    2940
agtttgtatt atattttgta ttatcgttga catgtataat tttgatatca aaaactgatt    3000
ttccctttat tattttcgag attatttttc ttaattctct ttaacaaact agaaatattg    3060
tatatacaaa aaatcataaa taatagatga atagttaat tataggtgtt catcaatcga    3120
aaaagcaacg tatcttattt aaagtgcgtt gcttttttct catttataag gttaaataat    3180
tctcatatat caagcaaagt gacaggcgcc cttaaatatt ctgacaaatg ctctttccct    3240 aaactcccc cataaaaaaa cccgccgaag cgggttttta cgttatttgc ggattaacga    3300
ttactcgtta tcagaaccgc ccaggggggcc cgagcttaag actggccgtc gttttacaac    3360
acagaaagag tttgtagaaa cgcaaaaagg ccatccgtca ggggccttct gcttagtttg    3420
atgcctggca gttccctact ctcgccttcc gcttcctcgc tcactgactc gctgcgctcg    3480
gtcgttcggc tgcggcgagc ggtatcagct cactcaaagg cggtaatacg ttatccaca    3540 gaatcagggg ataacgcagg aaagaacatg tgagcaaaag gccagcaaaa ggccaggaac    3600
cgtaaaaagg ccgcgttgct ggcgtttttc cataggctcc gcccccctga cgagcatcac    3660
aaaaatcgac gctcaagtca gaggtggcga aacccgacag gactataaag ataccaggcg    3720
tttccccctg gaagctccct cgtgcgctct cctgttccga ccctgccgct taccggatac    3780
ctgtccgcct ttctcccttc gggaagcgtg gcgctttctc atagctcacg ctgtaggtat    3840
ctcagttcgg tgtaggtcgt tcgctccaag ctgggctgtg tgcacgaacc ccccgttcag    3900
```

```
cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtgggctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tcctttgatc ttttctacgg ggtctgacgc tcagtggaac    4260
gacgcgcgcg taactcacgt taagggattt tggtcatgag cttgcgccgt cccgtcaagt    4320
cagcgtaatg ctctgctttt                                               4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgctc     420
tgtttctacc gagaacgttt ccttcactga gacggaaacc gaggcacgtc gtagcgcgaa     480
ctacgagccg aatagctggg actacgattt cctgctgtct tccgatactg acgaatctat     540
tgaggtgtac aaagacaaag caaagaaact ggaggctgaa gtgcgccgcg aaattaacaa     600
cgagaaagct gaattcctga ctctgctgga gctgatcgat aacgtacagc gcctgggtct     660
gggttaccgc ttcgaatctg atatccgtcg cgcactggat cgtttcgtaa gcagcggcgg     720
tttcgatggc gtgaccaaaa cgagcctgca cgctaccgcg ctgtccttcc gtctgctgcg     780
tcagcacggc ttcgaagttt ctcaggaagc attctccggt ttcaaagatc aaaacgttaa     840
cttcctggaa aacctgaaag aagacactaa ggcgatcctg agcctgtatg aggcaagctt     900
tctggccctg gaggtgaga acatcctgga tgaggcgcgc gtattcgcca tctcccatct     960
gaaagagctg tctgaagaga aaatcggtaa ggaactggca gagcaggtta atcacgcact    1020
ggaactgccg ctgcatcgtc gtacccagcg tctggaggcg gtttggtcca tcgaagcgta    1080
ccgcaaaaag gaggatgcta accaggttct gctggaactg gccatcctgg actacaacat    1140
gatccagtcc gttaccagcc gtgatctgcg tgaaacctcc cgttggtggc gccgtgtggg    1200
cctggcgacc aaactgcact tcgctaagga ccgcctgatt gagtcttttt actgggcagt    1260
cggcgttgcg ttcgaacctc agtattctga ctgccgtaac agcgttgcga aaatgttcag    1320
cttcgttact attatcgacg acatctacga cgtttacggt actctggacg agctggaact    1380
gtttaccgac gctgtcgaac gttgggatgt taacgccatc aacgatcgc ctgactacat    1440 gaaactgtgc ttcctggcac tgtataacac gatcaacgaa attgcatacg acaacctgaa    1500
agacaaaggt gaaacatcc tgccgtacct gactaaagcg tgggcggatc tgtgtaacgc    1560 tttttctgcaa gaagcgaaat ggctgtataa caatccact ccgaccttg acgattattt    1620
```

```
cggcaatgcc tggaaatcca gctctggccc gctgcaactg atcttcgctt attttgcggt   1680
tgtccaaaac atcaaaaagg aggaaattga aaacctgcaa aaataccacg atatcattag   1740
ccgtccttct catatctttc gcctgtgcaa cgacctggca agcgcgtccg cagagatcgc   1800
acgtggcgaa accgctaact ctgtttcctg ctacatgcgc accaagggca tttccgaaga   1860
gctggcaacc gagagcgtaa tgaatctgat cgacgaaacc tgtaagaaaa tgaacaaaga   1920
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agctttctag aacaaaaact catctcagaa gaggatctga   2160
atagcgccgt cgaccatcat catcatcatc attgagttta acggtctcca gcttggctg   2220 ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg cctttcgtt   2460 ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640 ttttgttta tttttctaaa tacattcaaa tatgtatccg ctcatgagac aataaccctg   2700
ataaatgctt caataatatt gaaaaggaa gagtatgagt attcaacatt tccgtgtcgc   2760
ccttattccc ttttttgcgg catttttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
tttgcacaac atgggggatc atgtaactcg ccttgatcgt tgggaaccgg agctgaatga   3240
agccatacca aacgacgagc gtgacaccac gatgcctgta gcaatggcaa caacgttgcg   3300
caaactatta actggcgaac tacttactct agcttcccgg caacaattaa tagactggat   3360
ggaggcggat aaagttgcag gaccacttct gcgctcggcc cttccggctg gctggtttat   3420
tgctgataaa tctggagccg gtgagcgtgg gtctcgcggt atcattgcag cactgggcc   3480 agatggtaag ccctcccgta tcgtagttat ctacacgacg gggagtcagg caactatgga   3540
tgaacgaaat agacagatcg ctgagatagg tgcctcactg attaagcatt ggtaactgtc   3600
agaccaagtt tactcatata ctttagat tgatttaaaa cttcattttt aatttaaaag   3660
gatctaggtg aagatccttt ttgataatct catgaccaaa atcccttaac gtgagttttc   3720
gttccactga gcgtcagacc ccgtagaaaa gatcaaagga tcttcttgag atcctttttt   3780
tctgcgcgta atctgctgct tgcaaacaaa aaaaccaccg ctaccagcgg tggtttgttt   3840
gccggatcaa gagctaccaa ctctttttcc gaaggtaact ggcttcagca gagcgcagat   3900
accaaatact gtccttctag tgtagccgta gttaggccac cacttcaaga actctgtagc   3960
accgcctaca tacctcgctc tgctaatcct gttaccagtg gctgctgcca gtggcgataa   4020
```

| | | | |
|---|---|---|---|
| gtcgtgtctt | accgggttgg actcaagacg atagttaccg gataaggcgc agcggtcggg | 4080 |
| ctgaacgggg | ggttcgtgca cacagcccag cttggagcga acgacctaca ccgaactgag | 4140 |
| atacctacag | cgtgagctat gagaaagcgc cacgcttccc gaagggagaa aggcggacag | 4200 |
| gtatccggta | agcggcaggg tcggaacagg agagcgcacg agggagcttc caggggggaaa | 4260 |
| cgcctggtat | ctttatagtc ctgtcgggtt tcgccacctc tgacttgagc gtcgattttt | 4320 |
| gtgatgctcg | tcaggggggc ggagcctatg gaaaaacgcc agcaacgcgg ccttttttacg | 4380 |
| gttcctggcc | ttttgctggc cttttgctca catgttcttt cctgcgttat cccctgattc | 4440 |
| tgtggataac | cgtattaccg cctttgagtg agctgatacc gctcgccgca gccgaacgac | 4500 |
| cgagcgcagc | gagtcagtga gcgaggaagc ggaagagcgc ctgatgcggt attttctcct | 4560 |
| tacgcatctg | tgcggtattt cacaccgcat atggtgcact ctcagtacaa tctgctctga | 4620 |
| tgccgcatag | ttaagccagt atacactccg ctatcgctac gtgactgggt catggctgcg | 4680 |
| ccccgacacc | cgccaacacc cgctgacgcg ccctgacggg cttgtctgct cccggcatcc | 4740 |
| gcttacagac | aagctgtgac cgtctccggg agctgcatgt gtcagaggtt ttcaccgtca | 4800 |
| tcaccgaaac | gcgcgaggca gcagatcaat tcgcgcgcga aggcgaagcg gcatgcattt | 4860 |
| acgttgacac | catcgaatgg tgcaaaacct ttcgcggtat ggcatgatag cgcccggaag | 4920 |
| agagtcaatt | cagggtggtg aatgtgaaac cagtaacgtt atacgatgtc gcagagtatg | 4980 |
| ccggtgtctc | ttatcagacc gtttcccgcg tggtgaacca ggccagccac gtttctgcga | 5040 |
| aaacgcggga | aaaagtggaa gcggcgatgg cggagctgaa ttacattccc aaccgcgtgg | 5100 |
| cacaacaact | ggcgggcaaa cagtcgttgc tgattggcgt tgccacctcc agtctggccc | 5160 |
| tgcacgcgcc | gtcgcaaatt gtcgcggcga ttaaatctcg cgccgatcaa ctgggtgcca | 5220 |
| gcgtggtggt | gtcgatggta gaacgaagcg gcgtcgaagc ctgtaaagcg gcggtgcaca | 5280 |
| atcttctcgc | gcaacgcgtc agtgggctga tcattaacta tccgctggat gaccaggatg | 5340 |
| ccattgctgt | ggaagctgcc tgcactaatg ttccggcgtt atttcttgat gtctctgacc | 5400 |
| agacacccat | caacagtatt attttctccc atgaagacgg tacgcgactg ggcgtggagc | 5460 |
| atctggtcgc | attgggtcac cagcaaatcg cgctgttagc gggcccatta agttctgtct | 5520 |
| cggcgcgtct | gcgtctggct ggctggcata aatatctcac tcgcaatcaa attcagccga | 5580 |
| tagcggaacg | ggaaggcgac tggagtgcca tgtccggttt tcaacaaacc atgcaaatgc | 5640 |
| tgaatgaggg | catcgttccc actgcgatgc tggttgccaa cgatcagatg gcgctgggcg | 5700 |
| caatgcgcgc | cattaccgag tccgggctgc gcgttggtgc ggatatctcg gtagtgggat | 5760 |
| acgacgatac | cgaagacagc tcatgttata tcccgccgtc aaccaccatc aaacaggatt | 5820 |
| ttcgcctgct | ggggcaaacc agcgtggacc gcttgctgca actctctcag gccaggcgg | 5880 |
| tgaagggcaa | tcagctgttg cccgtctcac tggtgaaaag aaaaaccacc ctggcgccca | 5940 |
| atacgcaaac | cgcctctccc cgcgcgttgg ccgattcatt aatgcagctg gcacgacagg | 6000 |
| tttcccgact | ggaaagcggg cagtgagcgc aacgcaatta atgtgagtta gcgcgaattg | 6060 |
| atctg | | 6065 |

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50

```
ttgtctgctc ccggcatccg cttacagaca agctgtgacc gtctccggga gctgcatgtg    60
tcagaggttt tcaccgtcat caccgaaacg cgcgaggcag cagatcaatt cgcgcgcgaa   120
ggcgaagcgg catgcattta cgttgacacc atcgaatggt gcaaaacctt tcgcggtatg   180
gcatgatagc gcccggaaga gagtcaattc agggtggtga atgtgaaacc agtaacgtta   240
tacgatgtcg cagagtatgc cggtgtctct tatcagaccg tttccgcgt ggtgaaccag    300 gccagccacg tttctgcgaa aacgcgggaa aaagtggaag cggcgatggc ggagctgaat   360
tacattccca accgcgtggc acaacaactg gcgggcaaac agtcgttgct gattggcgtt   420
gccacctcca gtctggccct gcacgcgccg tcgcaaattg tcgcggcgat taaatctcgc   480
gccgatcaac tgggtgccag cgtggtggtg tcgatggtag aacgaagcgg cgtcgaagcc   540
tgtaaagcgg cggtgcacaa tcttctcgcg caacgcgtca gtgggctgat cattaactat   600
ccgctggatg accaggatgc cattgctgtg gaagctgcct gcactaatgt tccggcgtta   660
tttcttgatg tctctgacca gacacccatc aacagtatta ttttctccca tgaagacggt   720
acgcgactgg gcgtggagca tctggtcgca ttgggtcacc agcaaatcgc gctgttagcg   780
ggcccattaa gttctgtctc ggcgcgtctg cgtctggctg gctggcataa atatctcact   840
cgcaatcaaa ttcagccgat agcggaacgg gaaggcgact ggagtgccat gtccggtttt   900
caacaaacca tgcaaatgct gaatgagggc atcgttccca ctgcgatgct ggttgccaac   960
gatcagatgg cgctgggcgc aatgcgcgcc attaccgagt ccgggctgcg cgttggtgcg  1020
gatatctcgg tagtgggata cgacgatacc gaagacagct catgttatat cccgccgtca  1080
accaccatca acaggatttt cgcctgctg gggcaaacca gcgtggaccg cttgctgcaa   1140
ctctctcagg gccaggcggt gaagggcaat cagctgttgc ccgtctcact ggtgaaaaga  1200
aaaaccaccc tggcgcccaa tacgcaaacc gcctctcccc gcgcgttggc cgattcatta  1260
atgcagctgg cacgacaggt ttcccgactg gaaagcgggc agtgagcgca acgcaattaa  1320
tgtgagttag cgcgaattga tctggtttga cagcttatca tcgactgcac ggtgcaccaa  1380
tgcttctggc gtcaggcagc catcggaagc tgtggtatgg ctgtgcaggt cgtaaatcac  1440
tgcataattc gtgtcgctca aggcgcactc ccgttctgga taatgttttt tgcgccgaca  1500
tcataacggt tctggcaaat attctgaaat gagctgttga caattaatca tccggctcgt  1560
ataatgtgtg gaattgtgag cggataacaa tttcacacag gaaacagcgc cgctgagaaa  1620
aagcgaagcg gcactgctct ttaacaattt atcagacaat ctgtgtgggc actcgaccgg  1680
aattatcgat taactttatt attaaaaatt aaagaggtat atattaatgt atcgattaaa  1740
taaggaggaa taaaccatgt gtgcgacctc ttctcaattt actcagatta ccgagcataa  1800
ttcccgtcgt tccgcaaact atcagccaaa cctgtggaat ttcgaattcc tgcaatccct  1860
ggagaacgac ctgaaagtgg aaaagctgga ggagaaagcg accaaactgg aggaagaagt  1920
tcgctgcatg atcaaccgtg tagacaccca gccgctgtcc ctgctggagc tgatcgacga  1980
tgtgcagcgc ctgggtctga cctacaaatt tgaaaaagac atcattaaag ccctggaaaa  2040
catcgtactg ctggacgaaa acaaaaagaa caaatctgac ctgcacgcaa ccgctctgtc  2100
tttccgtctg ctgcgtcagc acggtttcga ggtttctcag gatgttttg agcgtttcaa   2160 ggataaagaa ggtggtttca gcggtgaact gaaaggtgac gtccaaggcc tgctgagcct  2220
gtatgaagcg tcttacctgg gtttcgaggg tgagaacctg ctggaggagg cgcgtacctt  2280
ttccatcacc cacctgaaga caacctgaaa agaaggcatt aataccaagg ttgcagaaca  2340
agtgagccac gccctggaac tgccatatca ccagcgtctg caccgtctgg aggcacgttg  2400
```

```
gttcctggat aaatacgaac cgaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggatttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgacgttt atggcactct    2700
ggacgaactg caactgttca ccgatgctgt agagcgctgg gacgttaacg ctattaacac    2760
cctgccggac tatatgaaac tgtgtttcct ggcactgtac aacaccgtta cgacacgtc    2820 ctattctatt ctgaaagaga aaggtcataa caacctgtcc tatctgacga aaagctggcg    2880
tgaactgtgc aaagccttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcatcgc ccttaggagg taaaaaaaaa    3480
tgactgccga caacaatagt atgccccatg gtgcagtatc tagttacgcc aaattagtgc    3540
aaaaccaaac acctgaagac attttggaag agtttcctga aattattcca ttacaacaaa    3600
gacctaatac ccgatctagt gagacgtcaa atgacgaaag cggagaaaca tgttttctg    3660 gtcatgatga ggagcaaatt aagttaatga atgaaaattg tatttgtttg gattgggacg    3720
ataatgctat tggtgccggt accaagaaag tttgtcattt aatggaaaat attgaaaagg    3780
gtttactaca tcgtgcattc tccgtcttta ttttcaatga acaaggtgaa ttacttttac    3840
aacaaagagc cactgaaaaa ataactttcc ctgatctttg gactaacaca tgctgctctc    3900
atccactatg tattgatgac gaattaggtt tgaagggtaa gctagacgat aagattaagg    3960
gcgctattac tgcggcggtg agaaaactag atcatgaatt aggtattcca gaagatgaaa    4020
ctaagacaag gggtaagttt cacttttaa acagaatcca ttacatggca ccaagcaatg    4080
aaccatgggg tgaacatgaa attgattaca tcctatttta taagatcaac gctaaagaaa    4140
acttgactgt caaccccaaa cgtcaatgaa gttagagactt caaatgggtt tcaccaaatg    4200
atttgaaaac tatgtttgct gacccaagtt acaagtttac gccttggttt aagattattt    4260
gcgagaatta cttattcaac tggtgggagc aattagatga cctttctgaa gtggaaaatg    4320
acaggcaaat tcatagaatg ctataacaac gcgtcctgca gctggtacca tatgggaatt    4380
cgaagctttc tagaacaaaa actcatctca gaagaggatc tgaatagcgc cgtcgaccat    4440
catcatcatc atcattgagt ttaaacggtc tccagcttgg ctgttttggc ggatgagaga    4500
agattttcag cctgatacag attaaatcag aacgcagaag cggtctgata aaacagaatt    4560
tgcctggcgg cagtagcgcg gtggtcccac ctgaccccat gccgaactca gaagtgaaac    4620
gccgtagcgc cgatggtagt gtggggtctc cccatgcgag agtagggaac tgccaggcat    4680
caaataaaac gaaaggctca gtcgaaagac tgggcctttc gttttatctg ttgtttgtcg    4740
gtgaacgctc tcctgagtag gacaaatccg ccgggagcgg atttgaacgt tgcgaagcaa    4800
```

```
cggcccggag ggtggcgggc aggacgcccg ccataaactg ccaggcatca aattaagcag    4860
aaggccatcc tgacggatgg ccttttttgcg tttctacaaa ctcttttttgt ttattttttct  4920 aaatacattc aaatatgtat ccgcttaacc ggaattgcca gctggggcgc cctctggtaa    4980
ggttgggaag ccctgcaaag taaactggat ggctttctcg ccgccaagga tctgatggcg    5040
caggggatca agctctgatc aagagacagg atgaggatcg tttcgcatga ttgaacaaga    5100
tggattgcac gcaggttctc cggccgcttg ggtggagagg ctattcggct atgactgggc    5160
acaacagaca atcggctgct ctgatgccgc cgtgttccgg ctgtcagcgc aggggcgccc    5220
ggttcttttt gtcaagaccg acctgtccgg tgccctgaat gaactgcaag acgaggcagc    5280
gcggctatcg tggctggcca cgacgggcgt tccttgcgca gctgtgctcg acgttgtcac    5340
tgaagcggga agggactggc tgctattggg cgaagtgccg gggcaggatc tcctgtcatc    5400
tcaccttgct cctgccgaga agtatccat catggctgat gcaatgcggc ggctgcatac    5460
gcttgatccg gctacctgcc cattcgacca ccaagcgaaa catcgcatcg agcgagcacg    5520
tactcggatg gaagccggtc ttgtcgatca ggatgatctg gacgaagagc atcaggggct    5580
cgcgccagcc gaactgttcg ccaggctcaa ggcgagcatg cccgacggcg aggatctcgt    5640
cgtgacccat ggcgatgcct gcttgccgaa tatcatggtg gaaaatggcc gcttttctgg    5700
attcatcgac tgtggccggc tgggtgtggc ggaccgctat caggacatag cgttggctac    5760
ccgtgatatt gctgaagagc ttggcggcga atgggctgac cgcttcctcg tgctttacgg    5820
tatcgccgct cccgattcgc agcgcatcgc cttctatcgc cttcttgacg agttcttctg    5880
acatgaccaa aatcccttaa cgtgagtttt cgttccactg agcgtcagac cccgtagaaa    5940
agatcaaagg atcttcttga gatccttttt ttctgcgcgt aatctgctgc ttgcaaacaa    6000
aaaaaccacc gctaccagcg gtggtttgtt tgccggatca agagctacca actctttttc    6060
cgaaggtaac tggcttcagc agagcgcaga taccaaatac tgtccttcta gtgtagccgt    6120
agttaggcca ccacttcaag aactctgtag caccgcctac atacctcgct ctgctaatcc    6180
tgttaccagt ggctgctgcc agtggcgata agtcgtgtct taccgggttg gactcaagac    6240
gatagttacc ggataaggcg cagcggtcgg gctgaacggg gggttcgtgc acacagccca    6300
gcttggagcg aacgacctac accgaactga gatacctaca gcgtgagcta tgagaaagcg    6360
ccacgcttcc cgaagggaga aaggcggaca ggtatccggt aagcggcagg gtcggaacag    6420
gagagcgcac gagggagctt ccagggggaa acgcctggta tctttatagt cctgtcgggt    6480
ttcgccacct ctgacttgag cgtcgatttt tgtgatgctc gtcagggggg cggagcctat    6540
ggaaaaacgc cagcaacgcg gcctttttac ggttcctggc cttttgctgg ccttttgctc    6600
acatgttctt tcctgcgtta tcccctgatt ctgtggataa ccgtattacc gcctttgagt    6660
gagctgatac cgctcgccgc agccgaacga ccgagcgcag cgagtcagtg agcgaggaag    6720
cggaagagcg cctgatgcgg tattttctcc ttacgcatct gtgcggtatt tcacaccgca    6780
tatggtgcac tctcagtaca atctgctctg atgccgcata gttaagccag tatacactcc    6840
gctatcgcta cgtgactggg tcatggctgc gccccgacac ccgccaacac ccgctgacgc    6900
gccctgacgg gc                                                        6912
```

<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

```
<400> SEQUENCE: 51
ttgtctgctc ccggcatccg cttacagaca agctgtgacc gtctccggga gctgcatgtg    60
tcagaggttt tcaccgtcat caccgaaacg cgcgaggcag cagatcaatt cgcgcgcgaa   120
ggcgaagcgg catgcattta cgttgacacc atcgaatggt gcaaaacctt tcgcggtatg   180
gcatgatagc gcccggaaga gagtcaattc agggtggtga atgtgaaacc agtaacgtta   240
tacgatgtcg cagagtatgc cggtgtctct tatcagaccg tttccgcgt ggtgaaccag    300
gccagccacg tttctgcgaa aacgcgggaa aaagtggaag cggcgatggc ggagctgaat   360
tacattccca accgcgtggc acaacaactg gcgggcaaac agtcgttgct gattggcgtt   420
gccacctcca gtctggccct gcacgcgccg tcgcaaattg tcgcggcgat taaatctcgc   480
gccgatcaac tgggtgccag cgtggtggtg tcgatggtag aacgaagcgg cgtcgaagcc   540
tgtaaagcgg cggtgcacaa tcttctcgcg caacgcgtca gtgggctgat cattaactat   600
ccgctggatg accaggatgc cattgctgtg gaagctgcct gcactaatgt tccggcgtta   660
tttcttgatg tctctgacca gacacccatc aacagtatta ttttctccca tgaagacggt   720
acgcgactgg gcgtggagca tctggtcgca ttgggtcacc agcaaatcgc gctgttagcg   780
ggcccattaa gttctgtctc ggcgcgtctg cgtctggctg gctggcataa atatctcact   840
cgcaatcaaa ttcagccgat agcggaacgg gaaggcgact ggagtgccat gtccggtttt   900
caacaaacca tgcaaatgct gaatgagggc atcgttccca ctgcgatgct ggttgccaac   960
gatcagatgg cgctgggcgc aatgcgcgcc attaccgagt ccgggctgcg cgttggtgcg  1020
gatatctcgg tagtgggata cgacgatacc gaagacagct catgttatat cccgccgtca  1080
accaccatca acaggatttt cgcctgctg gggcaaacca gcgtggaccg cttgctgcaa   1140
ctctctcagg gccaggcggt gaagggcaat cagctgttgc ccgtctcact ggtgaaaaga  1200
aaaaccaccc tggcgcccaa tacgcaaacc gcctctcccc gcgcgttggc cgattcatta  1260
atgcagctgg cacgacaggt ttcccgactg gaaagcgggc agtgagcgca acgcaattaa  1320
tgtgagttag cgcgaattga tctggtttga cagcttatca tcgactgcac ggtgcaccaa  1380
tgcttctggc gtcaggcagc catcggaagc tgtggtatgg ctgtgcaggt cgtaaatcac  1440
tgcataattc gtgtcgctca aggcgcactc ccgttctgga taatgttttt tgcgccgaca  1500
tcataacggt tctggcaaat attctgaaat gagctgttga caattaatca tccggctcgt  1560
ataatgtgtg gaattgtgag cggataacaa tttcacacag gaaacagcgc cgctgagaaa  1620
aagcgaagcg gcactgctct ttaacaattt atcagacaat ctgtgtgggc actcgaccgg  1680
aattatcgat taactttatt attaaaaatt aaagaggtat atattaatgt atcgattaaa  1740
taaggaggaa taaccatgt gtgcgacctc ttctcaattt actcagatta ccgagcataa   1800
ttcccgtcgt tccgcaaact atcagccaaa cctgtggaat ttcgaattcc tgcaatccct  1860
ggagaacgac ctgaaagtgg aaaagctgga ggagaaagcg accaaactgg aggaagaagt  1920
tcgctgcatg atcaaccgtg tagacaccca gccgctgtcc ctgctggagc tgatcgacga  1980
tgtgcagcgc ctgggtctga cctacaaatt tgaaaaagac atcattaaag ccctggaaa   2040
catcgtactg ctggacgaaa acaaaaagaa caaatctgac ctgcacgcaa ccgctctgtc  2100
tttccgtctg ctgcgtcagc acggtttcga ggtttctcag gatgttttg agcgtttcaa   2160
ggataaagaa ggtggtttca gcggtgaact gaaaggtgac gtccaaggcc tgctgagcct  2220
gtatgaagcg tcttacctgg gtttcgaggg tgagaacctg ctggaggagg cgcgtacctt  2280
ttccatcacc cacctgaaga caacctgaa agaaggcatt aataccaagg ttgcagaaca   2340
```

-continued

```
agtgagccac gccctggaac tgccatatca ccagcgtctg caccgtctgg aggcacgttg    2400
gttcctggat aaatacgaac cgaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggattttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgacgttt atggcactct    2700
ggacgaactg caactgttca ccgatgctgt agagcgctgg gacgttaacg ctattaacac    2760
cctgccggac tatatgaaac tgtgtttcct ggcactgtac aacaccgtta acgacacgtc    2820
ctattctatt ctgaaagaga aggtcataa caacctgtcc tatctgacga aaagctggcg    2880
tgaactgtgc aaagcctttc tgcaagaggc gaaatggtcc aacaacaaaa ttatcccggc    2940
tttctccaag tacctggaaa cgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcattcg cccttaggag gtaaaaaaac    3480
atgagttttg atattgccaa ataccccgacc ctggcactgg tcgactccac ccaggagtta    3540
cgactgttgc cgaaagagag tttaccgaaa ctctgcgacg aactgcgccg ctatttactc    3600
gacagcgtga gccgttccag cgggcacttc gcctccgggc tgggcacggt cgaactgacc    3660
gtggcgctgc actatgtcta caacaccccg tttgaccaat tgatttggga tgtggggcat    3720
caggcttatc cgcataaaat tttgaccgga cgccgcgaca aaatcggcac catccgtcag    3780
aaaggcggtc tgcacccgtt cccgtggcgc ggcgaaagcg aatatgacgt attaagcgtc    3840
gggcattcat caacctccat cagtgccgga attggtattg cggttgctgc cgaaaaagaa    3900
ggcaaaaatc gccgcaccgt ctgtgtcatt ggcgatggcg cgattaccgc aggcatggcg    3960
tttgaagcga tgaatcacgc gggcgatatc cgtcctgata tgctggtgat tctcaacgac    4020
aatgaaatgt cgatttccga aaatgtcggc gcgctcaaca accatctggc acagctgctt    4080
tccggtaagc tttactcttc actgcgcgaa ggcgggaaaa agttttctc tggcgtgccg    4140 ccaattaaag agctgctcaa acgcaccgaa gaacatatta aaggcatggt agtgcctggc    4200
acgttgtttg aagagctggg ctttaactac atcggcccgg tggacggtca cgatgtgctg    4260
gggcttatca ccacgctaaa gaacatgcgc gacctgaaag gcccgcagtt cctgcatatc    4320
atgaccaaaa aaggtcgtgg ttatgaaccg gcagaaaaag acccgatcac tttccacgcc    4380
gtgcctaaat ttgatccctc cagcggttgt ttgccgaaaa gtagcggcgg tttgccgagc    4440
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtgcgc atttactcca cttttcctgca acgcgcctat    4680 gatcaggtgc tgcatgacgt ggcgattcaa aagcttccgg tcctgttcgc catcgaccgc    4740
```

```
gcgggcattg ttggtgctga cggtcaaacc catcagggtg cttttgatct ctcttacctg   4800
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aaggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc tttttgcgtt   5880
tctacaaact cttttttgttt attttttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
tggagaggct attcggctat gactgggcac aacagacaat cggctgctct gatgccgccg   6180
tgttccggct gtcagcgcag gggcgcccgg ttcttttttgt caagaccgac ctgtccggtg   6240
ccctgaatga actgcaagac gaggcagcgc ggctatcgtg gctggccacg acgggcgttc   6300
cttgcgcagc tgtgctcgac gttgtcactg aagcgggaag ggactggctg ctattgggcg   6360
aagtgccggg gcaggatctc ctgtcatctc accttgctcc tgccgagaaa gtatccatca   6420
tggctgatgc aatgcggcgg ctgcatacgc ttgatccggc tacctgccca ttcgaccacc   6480
aagcgaaaca tcgcatcgag cgagcacgta ctcggatgga agccggtctt gtcgatcagg   6540
atgatctgga cgaagagcat caggggctcg cgccagccga actgttcgcc aggctcaagg   6600
cgagcatgcc cgacggcgag gatctcgtcg tgacccatgg cgatgcctgc ttgccgaata   6660
tcatggtgga aaatggccgc ttttctggat tcatcgactg tggccggctg ggtgtggcgg   6720
accgctatca ggacatagcg ttggctaccc gtgatattgc tgaagagctt ggcggcgaat   6780
gggctgaccg cttcctcgtg ctttacggta tcgccgctcc cgattcgcag cgcatcgcct   6840
tctatcgcct tcttgacgag ttcttctgac gcatgaccaa aatcccttaa cgtgagtttt   6900
cgttccactg agcgtcagac cccgtagaaa agatcaaagg atcttcttga tccttttttt   6960
ttctgcgcgt aatctgctgc ttgcaaacaa aaaaaccacc gctaccagcg gtggtttgtt   7020
tgccggatca agagctacca actcttttttc cgaaggtaac tggcttcagc agagcgcaga   7080
taccaaatac tgtccttcta gtgtagccgt agttaggcca ccacttcaag aactctgtag   7140
```

-continued

| | |
|---|---|
| caccgcctac ataccctcgct ctgctaatcc tgttaccagt ggctgctgcc agtggcgata | 7200 |
| agtcgtgtct taccgggttg gactcaagac gatagttacc ggataaggcg cagcggtcgg | 7260 |
| gctgaacggg gggttcgtgc acacagccca gcttggagcg aacgacctac accgaactga | 7320 |
| gatacctaca gcgtgagcta tgagaaagcg ccacgcttcc cgaagggaga aaggcggaca | 7380 |
| ggtatccggt aagcggcagg gtcggaacag gagagcgcac gagggagctt ccaggggaa | 7440 |
| acgcctggta tctttatagt cctgtcgggt ttcgccacct ctgacttgag cgtcgatttt | 7500 |
| tgtgatgctc gtcaggggg cggagcctat ggaaaaacgc cagcaacgcg cctttttac | 7560 |
| ggttcctggc cttttgctgg cctttgctc acatgttctt tcctgcgtta tcccctgatt | 7620 |
| ctgtggataa ccgtattacc gcctttgagt gagctgatac cgctcgccgc agccgaacga | 7680 |
| ccgagcgcag cgagtcagtg agcgaggaag cggaagagcg cctgatgcgg tattttctcc | 7740 |
| ttacgcatct gtgcggtatt tcacaccgca tatggtgcac tctcagtaca atctgctctg | 7800 |
| atgccgcata gttaagccag tatacactcc gctatcgcta cgtgactggg tcatggctgc | 7860 |
| gccccgacac ccgccaacac ccgctgacgc gccctgacgg gc | 7902 |

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52

| | |
|---|---|
| ctggcgtaat agcgaagagg cccgcaccga tcgcccttcc caacagttgc gcagcctgaa | 60 |
| tggcgaatgg cgcctgatgc ggtatttttct ccttacgcat ctgtgcggta tttcacaccg | 120 |
| catatggtgc actctcagta caatctgctc tgatgccgca tagttaagcc agccccgaca | 180 |
| cccgccaaca cccgctgacg agcttagtaa agccctcgct agattttaat gcggatgttg | 240 |
| cgattacttc gccaactatt gcgataacaa gaaaaagcca gcctttcatg atatatctcc | 300 |
| caatttgtgt agggcttatt atgcacgctt aaaaataata aaagcagact tgacctgata | 360 |
| gtttggctgt gagcaattat gtgcttagtg catctaacgc ttgagttaag ccgcgccgcg | 420 |
| aagcggcgtc ggcttgaacg aattgttaga cattatttgc cgactacctt ggtgatctcg | 480 |
| cctttcacgt agtggacaaa ttcttccaac tgatctgcgc gcgaggccaa gcgatcttct | 540 |
| tcttgtccaa gataagcctg tctagcttca agtatgacgg gctgatactg ggccggcagg | 600 |
| cgctccattg cccagtcggc agcgacatcc ttcggcgcga ttttgccggt tactgcgctg | 660 |
| taccaaatgc gggacaacgt aagcactaca tttcgctcat cgccagccca gtcgggcggc | 720 |
| gagttccata gcgttaaggt ttcatttagc gcctcaaata gatcctgttc aggaaccgga | 780 |
| tcaaagagtt cctccgccgc tggacctacc aaggcaacgc tatgttctct tgcttttgtc | 840 |
| agcaagatag ccagatcaat gtcgatcgtg gctggctcga agatacctgc aagaatgtca | 900 |
| ttgcgctgcc attctccaaa ttgcagttcg cgcttagctg gataacgcca cggaatgatg | 960 |
| tcgtcgtgca caacaatggt gacttctaca gcgcggagaa tctcgctctc tccagggga | 1020 |
| gccgaagttt ccaaaaggtc gttgatcaaa gctcgccgcg ttgtttcatc aagccttacg | 1080 |
| gtcaccgtaa ccagcaaatc aatatcactg tgtggcttca ggccgccatc cactgcggag | 1140 |
| ccgtacaaat gtacggccag caacgtcggt tcgagatggc gctcgatgac gccaactacc | 1200 |
| tctgatagtt gagtcgatac ttcggcgatc accgcttccc tcatgatgtt taactttgtt | 1260 |
| ttagggcgac tgccctgctg cgtaacatcg ttgctgctcc ataacatcaa acatcgaccc | 1320 |

```
acggcgtaac gcgcttgctg cttggatgcc cgaggcatag actgtacccc aaaaaaacag    1380
tcataacaag ccatgaaaac cgccactgcg ccgttaccac cgctgcgttc ggtcaaggtt    1440
ctggaccagt tgcgtgagcg catacgctac ttgcattaca gcttacgaac cgaacaggct    1500
tatgtccact gggttcgtgc cttcatccgt ttccacggtg tgcgtcaccc ggcaaccttg    1560
ggcagcagcg aagtcgaggc atttctgtcc tggctggcga acgagcgcaa ggtttcggtc    1620
tccacgcatc gtcaggcatt ggcggccttg ctgttcttct acggcaaggt gctgtgcacg    1680
gatctgccct ggcttcagga gatcggaaga cctcggccgt cgcggcgctt gccggtggtg    1740
ctgaccccgg atgaagtggt tcgcatcctc ggttttctgg aaggcgagca tcgtttgttc    1800
gcccagcttc tgtatggaac gggcatgcgg atcagtgagg gtttgcaact gcgggtcaag    1860
gatctggatt tcgatcacgg cacgatcatc gtgcgggagg gcaagggctc caaggatcgg    1920
gccttgatgt tacccgagag cttggcaccc agcctgcgcg agcaggggaa ttaattccca    1980
cgggttttgc tgcccgcaaa cgggctgttc tggtgttgct agtttgttat cagaatcgca    2040
gatccggctt cagccggttt gccggctgaa agcgctattt cttccagaat tgccatgatt    2100
ttttccccac gggaggcgtc actggctccc gtgttgtcgg cagctttgat tcgataagca    2160
gcatcgcctg tttcaggctg tctatgtgtg actgttgagc tgtaacaagt tgtctcaggt    2220
gttcaatttc atgttctagt tgctttgttt tactggtttc acctgttcta ttaggtgtta    2280
catgctgttc atctgttaca ttgtcgatct gttcatggtg aacagctttg aatgcaccaa    2340
aaactcgtaa aagctctgat gtatctatct tttttacacc gttttcatct gtgcatatgg    2400
acagttttcc ctttgatatg taacggtgaa cagttgttct acttttgttt gttagtcttg    2460
atgcttcact gatagataca agagccataa gaacctcaga tccttccgta tttagccagt    2520
atgttctcta gtgtggttcg ttgttttttgc gtgagccatg agaacgaacc attgagatca    2580
tacttacttt gcatgtcact caaaaatttt gcctcaaaac tggtgagctg aatttttgca    2640
gttaaagcat cgtgtagtgt ttttcttagt ccgttatgta ggtaggaatc tgatgtaatg    2700
gttgttggta ttttgtcacc attcatttttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gcctttaaa ctcatggtag ttattttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga atttttttaa ctggaaaaga taaggcaata tctcttcact aaaaactaat    3120 tctaatttt cgcttgagaa cttggcatag tttgtccact ggaaaatctc aaagccttta    3180
accaaaggat tcctgatttc cacagttctc gtcatcagct ctctggttgc tttagctaat    3240
acaccataag catttttccct actgatgttc atcatctgag cgtattggtt ataagtgaac    3300
gataccgtcc gttctttcct tgtagggttt tcaatcgtgg ggttgagtag tgccacacag    3360
cataaaatta gcttggtttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc ttttcctttg agttgtgggt    3540
atctgtaaat tctgctagac ctttgctgga aaacttgtaa attctgctag accctctgta    3600
aattccgcta gacctttgtg tgttttttttt gtttatattc aagtggttat aatttataga    3660 ataagaaag aataaaaaaa gataaaaaga atagatccca gccctgtgta taactcacta    3720
```

```
ctttagtcag ttccgcagta ttacaaaagg atgtcgcaaa cgctgtttgc tcctctacaa    3780
aacagacctt aaaaccctaa aggcttaagt agcaccctcg caagctcggg caaatcgctg    3840
aatattcctt ttgtctccga ccatcaggca cctgagtcgc tgtctttttc gtgacattca    3900
gttcgctgcg ctcacggctc tggcagtgaa tgggggtaaa tggcactaca ggcgcctttt    3960
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag acacccagcc gctgtccctg ctggagctga    4680
tcgacgatgt gcagcgcctg ggtctgacct acaaatttga aaagacatc attaaagccc    4740 tggaaaacat cgtactgctg gacgaaaaca aaagaacaa atctgacctg cacgcaaccg    4800
ctctgtcttt ccgtctgctg cgtcagcacg gtttcgaggt ttctcaggat gtttttgagc    4860
gtttcaagga taagaaggt ggtttcagcg gtgaactgaa aggtgacgtc caaggcctgc    4920
tgagcctgta tgaagcgtct tacctgggtt tcgagggtga aacctgctg gaggaggcgc    4980 gtaccttttc catcacccac ctgaagaaca acctgaaaga aggcattaat accaaggttg    5040
cagaacaagt gagccacgcc ctggaactgc catatcacca gcgtctgcac cgtctggagg    5100
cacgttggtt cctggataaa tacgaaccga agaaccgca tcaccagctg ctgctggagc    5160
tggcgaagct ggatttttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt ttcccactgc acctaccagt    6060
atggcgatgg tctgggtcgc ccagactacg cgactgaaaa ccgcatcaaa ctgctgctga    6120
```

```
ttgaccctttt cccgattaac cagctgatgt atgtctaact gcagctggta ccatatggga    6180
attcgaagct ttctagaaca aaaactcatc tcagaagagg atctgaatag cgccgtcgac    6240
catcatcatc atcatcattg agtttaaacg gtctccagct tggctgtttt ggcggatgag    6300
agaagatttt cagcctgata cagattaaat cagaacgcag aagcggtctg ataaaacaga    6360
atttgcctgg cggcagtagc gcggtggtcc cacctgaccc catgccgaac tcagaagtga    6420
aacgccgtag cgccgatggt agtgtggggt ctccccatgc gagagtaggg aactgccagg    6480
catcaaataa aacgaaaggc tcagtcgaaa gactgggcct ttcgttttat ctgttgtttg    6540
tcggtgaacg ctctcctgag taggacaaat ccgccgggag cggatttgaa cgttgcgaag    6600
caacggcccg gagggtggcg ggcaggacgc ccgccataaa ctgccaggca tcaaattaag    6660
cagaaggcca tcctgacgga tggcctttt gcgtttctac aaactctttt tgtttatttt    6720
tctaaataca ttcaaatatg tatccgctca tgagacaata accctgataa atgcttcaat    6780
aat                                                                  6783

<210> SEQ ID NO 53
<211> LENGTH: 6784
<212> TYPE: DNA
<213> ORGANISM: Artificial Sequence
<220> FEATURE:
<223> OTHER INFORMATION: Synthetic Construct

<400> SEQUENCE: 53
acccgtctta ctgtcgggaa ttcgcgttgg ccgattcatt aatgcagatt attgaagcat      60
ttatcagggt tattgtctca tgagcggata catatttgaa tgtatttaga aaataaaaca     120
aaaagagttt gtagaaacgc aaaaaggcca tccgtcagga tggccttctg cttaatttga     180
tgcctggcag tttatggcgg gcgtcctgcc cgccaccctc cgggccgttg cttcgcaacg     240
ttcaaatccg ctcccggcgg atttgtccta ctcaggagag cgttcaccga caaacaacag     300
ataaaacgaa aggcccagtc tttcgactga gcctttcgtt ttatttgatg cctggcagtt     360
ccctactctc gcatggggag accccacact accatcggcg ctacggcgtt tcacttctga     420
gttcggcatg gggtcaggtg ggaccaccgc gctactgccg ccaggcaaat tctgttttat     480
cagaccgctt ctgcgttctg atttaatctg tatcaggctg aaaatcttct ctcatccgcc     540
aaaacagcca agctggagac cgtttaaact caatgatgat gatgatgatg gtcgacggcg     600
ctattcagat cctcttctga gatgagtttt tgttctagaa agcttcgaat tcccatatgg     660
taccagctgc agttagacat acatcagctg gttaatcggg aaagggtcaa tcagcagcag     720
tttgatgcgg ttttcagtcg cgtagtctgg gcgacccaga ccatcgccat actggtaggt     780
gcagtgggaa acacgtgcca tgttaactgc gatttccatg aacgctttag gcagcagggt     840
ggagtcgcta acgcgttcac gattcatctt tttccattcg gcgtcgatca gtttacgcag     900
ttcttcgcgg gcctgttcct cgctggtacc atcgttttcg tgcatgtagc taatgataga     960
attggtagtc tcgccacgtt ccagctccgc cgcagaggtg gccagatcgt tgcacaggcg    1020
gaagataacg cagctagaac gcaccagacc atggaagtcg gtcagggaac gcagcgcgtg    1080
gtcggagatg tcttcctgct gctggcatac ggaaaagtaa gacggcgcca gcagcgctac    1140 accgaggag gaaacgctgg cgttttccag gtacttggag aaagccggga taattttgtt    1200
gttggaccat ttcgcctctt gcagaaaggc tttgcacagt tcacgccagc ttttcgtcag    1260
ataggacagg ttgttatgac ctttctcttt cagaatagaa taggacgtgt cgttaacggt    1320
gttgtacagt gccaggaaac acagtttcat atagtccggc agggtgttaa tagcgttaac    1380
```

```
gtcccagcgc tctacagcat cggtgaacag ttgcagttcg tccagagtgc cataaacgtc    1440
atacacgtca tcgatgatcg tcaccagacc aaacatttta gtaacagctt tgcgacattc    1500
accaaactgc gggtctggcg ccatacccag tgcccagaaa taaacttcca tcaggcggtc    1560
gcgtacaaaa tccagtttgc tagccaggcc catctcggtc caccagcggg acagatcttg    1620
cagctctttc tggtgcaggg tctgtaccat gttaaaatcc agcttcgcca gctccagcag    1680
cagctggtga tgcggttctt tcggttcgta tttatccagg aaccaacgtg cctccagacg    1740
gtgcagacgc tggtgatatg cagttccag gcgtggctc acttgttctg caaccttggt     1800
attaatgcct tctttcaggt tgttcttcag gtgggtgatg aaaaggtac gcgcctcctc     1860
cagcaggttc tcaccctcga acccaggta agacgcttca tacaggctca gcaggccttg     1920
gacgtcacct ttcagttcac cgctgaaacc accttcttta tccttgaaac gctcaaaaac    1980
atcctgagaa acctcgaaac cgtgctgacg cagcagacgg aaagacagag cggttgcgtg    2040
caggtcagat ttgttctttt tgttttcgtc cagcagtacg atgttttcca gggctttaat    2100
gatgtctttt tcaaatttgt aggtcagacc caggcgctgc acatcgtcga tcagctccag    2160
cagggacagc ggctgggtgt ctacacggtt gatcatgcag cgaacttctt cctccagttt    2220
ggtcgctttc tcctccagct tttccacttt caggtcgttc tccagggatt gcaggaattc    2280
gaaattccac aggtttggct gatagtttgc ggaacgacgg gaattatgct cggtaatctg    2340
agtaaattga gaagaggtcg cacacatggt ttattcctcc ttatttaatc gatacattaa    2400
tatatacctc tttaattttt aataataaag ttaatcgata attccggtcg agtgcccaca    2460
cagattgtct gataaattgt taaagagcag tgccgcttcg cttttctca gcggcgctgt     2520
ttcctgtgtg aaattgttat ccgctcacaa ttccacacat tatacgagcc ggatgattaa    2580
ttgtcaacag ctcatttcag aatctggcgt aatagcgaag aggcccgcac cgatcgccct    2640
tcccaacagt tgcgcagcct gaatggcgaa tggcgcctga tgcggtattt tctccttacg    2700
catctgtgcg gtatttcaca ccgcatatgg tgcactctca gtacaatctg ctctgatgcc    2760
gcatagttaa gccagccccg acacccgcca cacccgctg acgagcttag taaagccctc     2820
gctagatttt aatgcggatg ttgcgattac ttcgccaact attgcgataa caagaaaaag    2880
ccagcctttc atgatatatc tcccaatttg tgtagggctt attatgcacg cttaaaaata    2940
ataaaagcag acttgacctg atagtttggc tgtgagcaat tatgtgctta gtgcatctaa    3000
cgcttgagtt aagccgcgcc gcgaagcggc gtcggcttga acgaattgtt agacattatt    3060
tgccgactac cttggtgatc tcgcctttca cgtagtggac aaattcttcc aactgatctg    3120
cgcgcgaggc caagcgatct tcttcttgtc aagataagc ctgtctagct tcaagtatga     3180
cgggctgata ctgggccggc aggcgctcca ttgcccagtc ggcagcgaca tccttcggcg    3240
cgattttgcc ggttactgcg ctgtaccaaa tgcgggacaa cgtaagcact acatttcgct    3300
catcgccagc ccagtcgggc ggcgagttcc atagcgttaa ggtttcattt agcgcctcaa    3360
atagatcctg ttcaggaacc ggatcaaaga gttcctccgc cgctggacct accaaggcaa    3420
cgctatgttc tcttgctttt gtcagcaaga tagccagatc aatgtcgatc gtggctggct    3480
cgaagatacc tgcaagaatg tcattgcgct gccattctcc aaattgcagt tcgcgcttag    3540
ctggataacg ccacggaatg atgtcgtcgt gcacaacaat ggtgacttct acagcgcgga    3600
gaatctcgct ctctccaggg gaagccgaag tttccaaaag gtcgttgatc aaagctcgcc    3660
gcgttgtttc atcaagcctt acggtcaccg taaccagcaa atcaatatca ctgtgtggct    3720
tcaggccgcc atccactgcg gagccgtaca aatgtacggc cagcaacgtc ggttcgagat    3780
```

```
ggcgctcgat gacgccaact acctctgata gttgagtcga tacttcggcg atcaccgctt    3840
ccctcatgat gtttaactt tgttttaggc gactgccctg ctgcgtaaca tcgttgctgc    3900
tccataacat caaacatcga cccacggcgt aacgcgcttg ctgcttggat gcccgaggca    3960
tagactgtac cccaaaaaaa cagtcataac aagccatgaa aaccgccact cgccgttac     4020 caccgctgcg ttcggtcaag gttctggacc agttgcgtga gcgcatacgc tacttgcatt    4080
acagcttacg aaccgaacag gcttatgtcc actgggttcg tgccttcatc cgttccacg     4140 gtgtgcgtca cccggcaacc ttgggcagca gcgaagtcga ggcatttctg tcctggctgg    4200
cgaacgagcg caaggtttcg gtctccacgc atcgtcaggc attggcggcc ttgctgttct    4260
tctacggcaa ggtgctgtgc acggatctgc cctggcttca ggagatcgga agacctcggc    4320
cgtcgcggcg cttgccggtg gtgctgaccc cggatgaagt ggttcgcatc ctcggttttc    4380
tggaaggcga gcatcgtttg ttcgcccagc ttctgtatgg aacgggcatg cggatcagtg    4440
agggtttgca actgcgggtc aaggatctgg atttcgatca cggcacgatc atcgtgcggg    4500
agggcaaggg ctccaaggat cgggccttga tgttacccga gagcttggca cccagcctgc    4560
gcgagcaggg gaattaattc ccacgggttt gctgcccgc aaacgggctg ttctggtgtt     4620
gctagtttgt tatcagaatc gcagatccgg cttcagccgg tttgccggct gaaagcgcta    4680
tttcttccag aattgccatg atttttttccc cacgggaggc gtcactggct cccgtgttgt    4740
cggcagcttt gattcgataa gcagcatcgc ctgtttcagg ctgtctatgt gtgactgttg    4800
agctgtaaca agttgtctca ggtgttcaat ttcatgttct agttgctttg ttttactggt    4860
ttcacctgtt ctattaggtg ttacatgctg ttcatctgtt acattgtcga tctgttcatg    4920
gtgaacagct ttgaatgcac caaaaactcg taaaagctct gatgtatcta tctttttac     4980 accgttttca tctgtgcata tggacagttt tcccttgat atgtaacggt gaacagttgt     5040
tctacttttg tttgttagtc ttgatgcttc actgatagat acaagagcca taagaacctc    5100
agatccttcc gtatttagcc agtatgttct ctagtgtggt tcgttgtttt tgcgtgagcc    5160
atgagaacga accattgaga tcatacttac tttgcatgtc actcaaaaat tttgcctcaa    5220
aactggtgag ctgaattttt gcagttaaag catcgtgtag tgtttttctt agtccgttat    5280
gtaggtagga atctgatgta atggttgttg gtattttgtc accattcatt tttatctggt    5340
tgttctcaag ttcggttacg agatccattt gtctatctag ttcaacttgg aaaatcaacg    5400
tatcagtcgg gcggcctcgc ttatcaacca ccaatttcat attgctgtaa gtgtttaaat    5460
ctttacttat tggtttcaaa acccattggt taagcctttt aaactcatgg tagttatttt    5520
caagcattaa catgaactta aattcatcaa ggctaatctc tatatttgcc ttgtgagttt    5580
tcttttgtgt tagttctttt aataaccact cataaatcct catagagtat tgttttcaa     5640 aagacttaac atgttccaga ttatatttta tgaattttt taactggaaa agataaggca    5700
atatctcttc actaaaaact aattctaatt tttcgcttga gaacttggca tagtttgtcc    5760
actggaaaat ctcaaagcct ttaaccaaag gattcctgat ttccacagtt ctcgtcatca    5820
gctctctggt tgctttagct aatacaccat aagcattttc cctactgatg ttcatcatct    5880
gagcgtattg gttataagtg aacgataccg tccgttcttt ccttgtaggg ttttcaatcg    5940
tggggttgag tagtgccaca cagcataaaa ttagcttggt ttcatgctcc gttaagtcat    6000
agcgactaat cgctagttca tttgctttga aaacaactaa ttcagacata catctcaatt    6060
ggtctaggtg attttaatca ctataccaat tgagatgggc tagtcaatga taattactag    6120
tccttttcct ttgagttgtg ggtatctgta aattctgcta gacctttgct ggaaaacttg    6180
```

```
taaattctgc tagaccctct gtaaattccg ctagaccttt gtgtgttttt tttgtttata   6240
ttcaagtggt tataatttat agaataaaga aagaataaaa aaagataaaa agaatagatc   6300
ccagccctgt gtataactca ctactttagt cagttccgca gtattacaaa aggatgtcgc   6360
aaacgctgtt tgctcctcta caaaacagac cttaaaaccc taaaggctta agtagcaccc   6420
tcgcaagctc gggcaaatcg ctgaatattc cttttgtctc cgaccatcag gcacctgagt   6480
cgctgtcttt ttcgtgacat tcagttcgct gcgctcacgg ctctggcagt gaatgggggt   6540
aaatggcact acaggcgcct tttatggatt catgcaagga aactacccat aatacaagaa   6600
aagcccgtca cgggcttctc agggcgtttt atggcgggtc tgctatgtgg tgctatctga   6660 cttttttgctg ttcagcagtt cctgccctct gattttccag tctgaccact tcggattatc   6720
ccgtgacagg tcattcagac tggctaatgc acccagtaag gcagcggtat catcaacagg   6780
ctta                                                                6784

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54
ctggcgtaat agcgaagagg cccgcaccga tcgcccttcc caacagttgc gcagcctgaa     60
tggcgaatgg cgcctgatgc ggtatttttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccagggggaa   1020 gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
```

-continued

```
ctggaccagt tgcgtgagcg catacgctac ttgcattaca gcttacgaac cgaacaggct    1500
tatgtccact gggttcgtgc cttcatccgt ttccacggtg tgcgtcaccc ggcaaccttg    1560
ggcagcagcg aagtcgaggc atttctgtcc tggctggcga acgagcgcaa ggtttcggtc    1620
tccacgcatc gtcaggcatt ggcggccttg ctgttcttct acggcaaggt gctgtgcacg    1680
gatctgccct ggcttcagga gatcggaaga cctcggccgt cgcggcgctt gccggtggtg    1740
ctgaccccgg atgaagtggt tcgcatcctc ggttttctgg aaggcgagca tcgtttgttc    1800
gcccagcttc tgtatggaac gggcatgcgg atcagtgagg gtttgcaact gcgggtcaag    1860
gatctggatt tcgatcacgg cacgatcatc gtgcgggagg gcaagggctc caaggatcgg    1920
gccttgatgt tacccgagag cttggcaccc agcctgcgcg agcaggggaa ttaattccca    1980 cggggttttgc tgcccgcaaa cgggctgttc tggtgttgct agtttgttat cagaatcgca    2040
gatccggctt cagccggttt gccggctgaa agcgctattt cttccagaat tgccatgatt    2100 tttttccccac gggaggcgtc actggctccc gtgttgtcgg cagctttgat tcgataagca    2160
gcatcgcctg tttcaggctg tctatgtgtg actgttgagc tgtaacaagt tgtctcaggt    2220 gttcaattte atgttctagt tgctttgttt tactggtttc acctgttcta ttaggtgtta    2280
catgctgttc atctgttaca ttgtcgatct gttcatggtg aacagctttg aatgcaccaa    2340
aaactcgtaa aagctctgat gtatctatct tttttacacc gttttcatct gtgcatatgg    2400
acagttttcc ctttgatatg taacggtgaa cagttgttct acttttgttt gttagtcttg    2460
atgcttcact gatagataca agagccataa gaacctcaga tccttccgta tttagccagt    2520
atgttctcta gtgtggttcg ttgttttgc gtgagccatg agaacgaacc attgagatca    2580
tacttacttt gcatgtcact caaaaattt gcctcaaaac tggtgagctg aattttgca    2640 gttaaagcat cgtgtagtgt ttttcttagt ccgttatgta ggtaggaatc tgatgtaatg    2700
gttgttggta ttttgtcacc attcatttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gccttttaaa ctcatggtag ttatttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga atttttttaa ctggaaaaga taaggcaata tctcttcact aaaaactaat    3120
tctaattttt cgcttgagaa cttggcatag tttgtccact ggaaaatctc aaagcccttta    3180 accaaaggat tcctgatttc cacagttctc gtcatcagct ctctggttgc tttagctaat    3240
acaccataag cattttccct actgatgttc atcatctgag cgtattggtt ataagtgaac    3300
gataccgtcc gttctttcct tgtagggttt tcaatcgtgg ggttgagtag tgccacacag    3360
cataaaatta gcttggtttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc tttcctttg agttgtgggt    3540 atctgtaaat tctgctagac cttgctgga aaacttgtaa attctgctag accctctgta    3600
aattccgcta gaccttgtg tgttttttt gtttatattc aagtggttat aatttatga    3660 ataagaaag aataaaaaa gataaaaga atagatccca gccctgtgta taactcacta    3720
ctttagtcag ttccgcagta ttacaaaagg atgtcgcaaa cgctgttttgc tcctctacaa    3780 aacagacctt aaaaccctaa aggcttaagt agcaccctcg caagctcggg caaatcgctg    3840
```

```
aatattcctt ttgtctccga ccatcaggca cctgagtcgc tgtcttttc gtgacattca    3900
gttcgctgcg ctcacggctc tggcagtgaa tgggggtaaa tggcactaca ggcgcctttt    3960
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag acacccagcc gctgtccctg ctggagctga    4680
tcgacgatgt gcagcgcctg ggtctgacct acaaatttga aaagacatc attaaagccc    4740
tggaaaacat cgtactgctg gacgaaaaca aaaagaacaa atctgacctg cacgcaaccg    4800
ctctgtcttt ccgtctgctg cgtcagcacg gtttcgaggt ttctcaggat gttttgagc    4860
gtttcaagga taagaaggt ggtttcagcg gtgaactgaa aggtgacgtc caaggcctgc    4920
tgagcctgta tgaagcgtct tacctgggtt tcgagggtga gaacctgctg gaggaggcgc    4980
gtaccttttc catcacccac ctgaagaaca acctgaaaga aggcattaat accaaggttg    5040
cagaacaagt gagccacgcc ctggaactgc catatcacca gcgtctgcac cgtctggagg    5100
cacgttggtt cctggataaa tacgaaccga agaaccgca tcaccagctg ctgctggagc    5160
tggcgaagct ggatttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacacccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccgcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt ttcccactgc acctaccagt    6060
atggcgatgg tctgggtcgc ccagactacg cgactgaaaa ccgcatcaaa ctgctgctga    6120
ttgacccttt cccgattaac cagctgatgt atgtctaact gcatcgccct taggaggtaa    6180
aaaaaaatga ctgccgacaa caatagtatg ccccatggtg cagtatctag ttacgccaaa    6240
```

| | |
|---|---|
| ttagtgcaaa accaaacacc tgaagacatt ttggaagagt ttcctgaaat tattccatta | 6300 |
| caacaaagac ctaatacccg atctagtgag acgtcaaatg acgaaagcgg agaaacatgt | 6360 |
| ttttctggtc atgatgagga gcaaattaag ttaatgaatg aaaattgtat tgtttttggat | 6420 |
| tgggacgata atgctattgg tgccggtacc aagaaagttt gtcatttaat ggaaaatatt | 6480 |
| gaaaagggtt tactacatcg tgcattctcc gtctttattt tcaatgaaca aggtgaatta | 6540 |
| cttttacaac aaagagccac tgaaaaaata actttccctg atctttggac taacacatgc | 6600 |
| tgctctcatc cactatgtat tgatgacgaa ttaggtttga agggtaagct agacgataag | 6660 |
| attaagggcg ctattactgc ggcggtgaga aaactagatc atgaattagg tattccagaa | 6720 |
| gatgaaacta agacaagggg taagtttcac tttttaaaca gaatccatta catggcacca | 6780 |
| agcaatgaac catgggggtga acatgaaatt gattacatcc tattttataa gatcaacgct | 6840 |
| aaagaaaact tgactgtcaa cccaaacgtc aatgaagtta gagacttcaa atgggtttca | 6900 |
| ccaaatgatt tgaaaactat gtttgctgac ccaagttaca agtttacgcc ttggtttaag | 6960 |
| attatttgcg agaattactt attcaactgg tgggagcaat tagatgacct ttctgaagtg | 7020 |
| gaaaatgaca ggcaaattca tagaatgcta taacgacgcg tcctgcagct ggtaccatat | 7080 |
| gggaattcga agctttctag aacgaaaact catctcagaa gaggatctga atagcgccgt | 7140 |
| cgaccatcat catcatcatc attgagttta acggtctcc agcttggctg ttttggcgga | 7200 |
| tgagagaaga tttcagcct gatacagatt aaatcagaac gcagaagcgg tctgataaaa | 7260 |
| cagaatttgc ctggcggcag tagcgcggtg gtcccacctg accccatgcc gaactcagaa | 7320 |
| gtgaaacgcc gtagcgccga tggtagtgtg gggtctcccc atgcgagagt agggaactgc | 7380 |
| caggcatcaa ataaaacgaa aggctcagtc gaaagactgg gcctttcgtt ttatctgttg | 7440 |
| tttgtcggtg aacgctctcc tgagtaggac aaatccgccg ggagcggatt tgaacgttgc | 7500 |
| gaagcaacgg cccggagggt ggcgggcagg acgcccgcca taaactgcca ggcatcaaat | 7560 |
| taagcagaag gccatcctga cggatggcct ttttgcgttt ctacaaactc tttttgttta | 7620 |
| tttttctaaa tacattcaaa tatgtatccg ctcatgagac aataaccctg ataaatgctt | 7680 |
| caataat | 7687 |

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55

| | |
|---|---|
| cccgtcttac tgtcgggaat tcgcgttggc cgattcatta atgcagatta ttgaagcatt | 60 |
| tatcagggtt attgtctcat gagcggatac atatttgaat gtatttagaa aaataaacaa | 120 |
| aaagagtttg tagaaacgca aaaaggccat ccgtcaggat ggccttctgc ttaatttgat | 180 |
| gcctggcagt ttatggcggg cgtcctgccc gccacccctcc gggccgttgc ttcgcaacgt | 240 |
| tcaaatccgc tcccggcgga tttgtcctac tcaggagagc gttcaccgac aaacaacaga | 300 |
| taaaacgaaa ggcccagtct ttcgactgag cctttcgttt tatttgatgc ctggcagttc | 360 |
| cctactctcg catggggaga ccccacacta ccatcggcgc tacggcgttt cacttctgag | 420 |
| ttcggcatgg ggtcaggtgg gaccaccgcg ctactgccgc caggcaaatt ctgttttatc | 480 |
| agaccgcttc tgcgttctga tttaatctgt atcaggctga aaatcttctc tcatccgcca | 540 |
| aaacagccaa gctggagacc gtttaaactc aatgatgatg atgatgatgg tcgacggcgc | 600 |

```
tattcagatc ctcttctgag atgagttttt gttctagaaa gcttcgaatt cccatatggt    660
accagctgca gttatgccag ccaggccttg attttggctt ccataccagc ggcatcgagg    720
ccgagttcgg cgcgcatttc ttcctgagtt ccttgcggaa taaagaagtc cggcaggcca    780
atgttcagca cgggtactgg tttacgatgg ccatcagca cttcgttcac gccgctgcct    840
gcgccgccca taatggcgtt ttcttctacg gtgaccagcg cttcatggct ggcggccatt    900
tccagaatta acgcttcatc aagcggtttc acaaaacgca tatcgaccag cgtggcgttc    960
agcgattcgg cgactttcgc cgcttctggc atcagcgtac caaagttaag gatcgccagt   1020
ttctcgccac gacgcttcac aatgcctttg ccaattggta gttttccag cggcgtcagt   1080 tccacgccga ccgcgttgcc acgcgggtag cgcaccgctg acgggccatc gttatagtga   1140
tagccggtat agagcatctg gcgacattcg ttttcatcgc tcggggtcat aatgaccatt   1200
tccggtatgc agcgcaggta agagagatca aaagcaccct gatgggtttg accgtcagca   1260
ccaacaatgc ccgcgcggtc gatggcgaac aggaccggaa gcttttgaat cgccacgtca   1320
tgcagcacct gatcataggc gcgttgcagg aaagtggagt aaatcgcgac aatgggtttg   1380
tacccaccaa tcgccagacc cgcagcaaag gtcaccgcgt gttgctcggc aattgccacg   1440
tcgaagtagc gatccgggaa tttacgtgaa aactcgacca tgccggaacc ttcacgcatc   1500 gccgagtaa tcgccatcag cttgttgtct ttcgctgccg tttcgcacaa ccagtcgcca   1560
aagatttttg aatagctcgg caaaccgccg ctacttttcg gcaaacaacc gctggaggga   1620
tcaaatttag gcacgcgtg gaaagtgatc gggtcttttt ctgccggttc ataaccacga   1680
ccttttttgg tcatgatatg caggaactgc gggcctttca ggtcgcgcat gttctttagc   1740
gtggtgataa gccccagcac atcgtgaccg tccaccgggc cgatgtagtt aaagcccagc   1800
tcttcaaaca acgtgccagg cactaccatg cctttaatat gttcttcggt gcgtttgagc   1860
agctctttaa ttggcggcac gccagagaaa acttttttcc cgccttcgcg cagtgaagag   1920
taaagcttac cggaaagcag ctgtgccaga tggttgttga gcgcgccgac attttcggaa   1980
atcgacattt cattgtcgtt gagaatcacc agcatatcag gacggatatc gcccgcgtga   2040
ttcatcgctt caaacgccat gcctgcgta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaatttta   2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400 cggctcacg tgtcgagtaa atagcggcgc agttcgtcgc agagtttcgg taaactctct   2460
ttcggcaaca gtcgtaactc ctgggtggag tcgaccagtg ccagggtcgg gtatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga acacgtgcc atgttaactg   2700 cgatttccat gaacgcttta ggcagcaggg tggagtcgct aacgcgttca cgattcatct   2760 tttccattc ggcgtcgatc agtttacgca gttcttcgcg ggcctgttcc tcgctggtac   2820
catcgttttc gtgcatgtag ctaatgatag aattggtagt ctcgccacgt ccagctccg    2880 ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
```

```
cggaaaagta agacggcgcc agcagcgcta caccggagga ggaaacgctg gcgttttcca   3060
ggtacttgga gaaagccggg ataattttgt tgttggacca tttcgcctct tgcagaaagg   3120
ctttgcacag ttcacgccag cttttcgtca gataggacag gttgttatga cctttctctt   3180
tcagaataga ataggacgtg tcgttaacgg tgttgtacag tgccaggaaa cacagtttca   3240
tatagtccgg cagggtgtta atagcgttaa cgtcccagcg ctctacagca tcggtgaaca   3300
gttgcagttc gtccagagtg ccataaacgt catacacgtc atcgatgatc gtcaccagac   3360
caaacatttt agtaacagct ttgcgacatt caccaaactg cgggtctggc gccataccca   3420
gtgcccagaa ataaacttcc atcaggcggt cgcgtacaaa atccagtttg ctagccaggc   3480
ccatctcggt ccaccagcgg gacagatctt gcagctcttt ctggtgcagg gtctgtacca   3540
tgttaaaatc cagcttcgcc agctccagca gcagctggtg atgcgttct ttcggttcgt   3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca   3720
ggtgggtgat ggaaaaggta cgcgcctcct ccagcaggtt ctcaccctcg aaacccaggt   3780
aagacgcttc atacaggctc agcaggcctt ggacgtcacc tttcagttca ccgctgaaac   3840
caccttcttt atccttgaaa cgctcaaaaa catcctgaga aacctcgaaa ccgtgctgac   3900
gcagcagacg gaaagacaga gcggttgcgt gcaggtcaga tttgttcttt ttgttttcgt   3960
ccagcagtac gatgtttcc agggctttaa tgatgtcttt ttcaaatttg taggtcagac   4020
ccaggcgctg cacatcgtcg atcagctcca gcagggacag cggctgggtg tctacacggt   4080
tgatcatgca gcgaacttct tcctccagtt tggtcgcttt ctcctccagc ttttccactt   4140
tcaggtcgtt ctccagggat tgcaggaatt cgaaattcca caggtttggc tgatagtttg   4200
cggaacgacg ggaattatgc tcggtaatct gagtaaattg agaagaggtc gcacacatgg   4260
tttattcctc cttatttaat cgatacatta atatatacct cttaattttt taataataaa   4320
gttaatcgat aattccggtc gagtgcccac acagattgtc tgataaattg ttaaagagca   4380
gtgccgcttc gcttttctc agcggcgctg tttcctgtgt gaaattgtta ccgctcaca   4440
attccacaca ttatacgagc cggatgatta attgtcaaca gctcatttca gaatctggcg   4500
taatagcgaa gaggcccgca ccgatcgccc ttcccaacag ttgcgcagcc tgaatggcga   4560
atggcgcctg atgcggtatt ttctccttac gcatctgtgc ggtatttcac accgcatatg   4620
gtgcactctc agtacaatct gctctgatgc cgcatagtta agccagcccc gacacccgcc   4680
aacacccgct gacgagctta gtaaagccct cgctagattt taatgcggat gttgcgatta   4740
cttcgccaac tattgcgata caagaaaaa gccagccttt catgatatat ctcccaattt   4800
gtgtagggct tattatgcac gcttaaaaat aataaaagca gacttgacct gatagtttgg   4860
ctgtgagcaa ttatgtgctt agtgcatcta acgcttgagt taagccgcgc cgcgaagcgg   4920
cgtcggcttg aacgaattgt tagacattat ttgccgacta ccttggtgat ctcgcctttc   4980
acgtagtgga caaattcttc caactgatct gcgcgcgagg ccaagcgatc ttcttcttgt   5040
ccaagataag cctgtctagc ttcaagtatg acgggctgat actgggccgg caggcgctcc   5100
attgcccagt cggcagcgac atccttcggc gcgattttgc cggttactgc gctgtaccaa   5160
atgcgggaca acgtaagcac tacatttcgc tcatcgccag cccagtcggg cggcgagttc   5220
catagcgtta aggtttcatt tagcgcctca aatagatcct gttcaggaac cggatcaaag   5280
agttcctccg ccgctggacc taccaaggca acgctatgtt ctcttgcttt tgtcagcaag   5340
atagccagat caatgtcgat cgtggctggc tcgaagatac ctgcaagaat gtcattgcgc   5400
```

-continued

```
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca aatcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct tccctcatga tgtttaactt tgttttaggg    5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg gaacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atctttttta caccgttttc atctgtgcat atggacagtt    6900 ttcccttga tatgtaacgg tgaacagttg ttctacttt gtttgttagt cttgatgctt    6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgtttaaa tctttactta ttggtttcaa acccattgg    7380 ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgttttca aaagacttaa catgttccag attatatttt    7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
```

```
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaagataaa aagaatagat cccagccctg tgtataactc actactttag    8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340
cctttttgtct ccgaccatca ggcacctgag tcgctgtctt tttcgtgaca ttcagttcgc    8400
tgcgctcacg gctctggcag tgaatggggg taaatggcac tacaggcgcc ttttatggat    8460
tcatgcaagg aaactaccca taatacaaga aaagcccgtc acgggcttct cagggcgttt    8520
tatgcgggt ctgctatgtg gtgctatctg acttttttgct gttcagcagt tcctgccctc    8580
tgattttcca gtctgaccac ttcggattat cccgtgacag gtcattcaga ctggctaatg    8640
cacccagtaa ggcagcggta tcatcaacag gctta    8675
```

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56

```
tcgctgcgct cggtcgttcg gctgcggcga gcggtatcag ctcactcaaa ggcggtaata      60
cggttatcca cagaatcagg ggataacgca ggaaagaaca tgtgagcaaa aggccagcaa     120
aaggccagga accgtaaaaa ggccgcgttg ctggcgtttt tccataggct ccgcccccct     180
gacgagcatc acaaaaatcg acgctcaagt cagaggtggc gaaacccgac aggactataa     240
agataccagg cgtttccccc tggaagctcc ctcgtgcgct ctcctgttcc gaccctgccg     300
cttaccggat acctgtccgc ctttctccct tcgggaagcg tggcgctttc tcatagctca     360
cgctgtaggt atctcagttc ggtgtaggtc gttcgctcca agctgggctg tgtgcacgaa     420
ccccccgttc agcccgaccg ctgcgcctta tccggtaact atcgtcttga gtccaacccg     480
gtaagacacg acttatcgcc actggcagca gccactggta acaggattag cagagcgagg     540
tatgtaggcg gtgctacaga gttcttgaag tggtggccta actacggcta cactagaaga     600
acagtatttg gtatctgcgc tctgctgaag ccagttacct tcggaaaaag agttggtagc     660
tcttgatccg gcaaacaaac caccgctggt agcggtggtt tttttgtttg caagcagcag     720
attacgcgca gaaaaaaagg atctcaagaa gatcctttga tcttttctac ggggtctgac     780
gctcagtgga acgaaaactc acgttaaggg attttggtca tgagattatc aaaaaggatc     840
ttcacctaga tccttttaaa ttaaaaatga agttttaaat caatctaaag tatatatgag     900
taaacttggt ctgacagtta ccaatgctta atcagtgagg cacctatctc agcgatctgt     960
ctatttcgtt catccatagt tgcctgactc ccgtcgtgt agataactac gatacgggag    1020
ggcttaccat ctggccccag tgctgcaatg ataccgcgag acccacgctc accggctcca    1080
gatttatcag caataaacca gccagccgga agggccgagc gcagaagtgg tcctgcaact    1140
ttatccgcct ccatccagtc tattaattgt tgccgggaag ctagagtaag tagttcgcca    1200
```

```
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaaagcggt tagctccttc ggtcctccga tcgttgtcag aagtaagttg   1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga gacggtcaca   2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta aagatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg gctctaactt atcccaataa cctaactctc cgtcgctatt   2700
gtaaccagtt ctaaaagctg tatttgagtt tatcacccctt gtcactaaga aaataaatgc   2760
agggtaaaat ttatatcctt cttgttttat gtttcggtat aaaacactaa tatcaatttc   2820
tgtggttata ctaaaagtcg tttgttggtt caaataatga ttaaatatct cttttctctt   2880
ccaattgtct aaatcaattt tattaaagtt catttgatat gcctcctaaa tttttatcta   2940
aagtgaattt aggaggctta cttgtctgct ttcttcatta gaatcaatcc ttttttaaaa   3000
gtcaatatta ctgtaacata aatatatatt ttaaaaatat cccactttat ccaattttcg   3060
tttgttgaac taatgggtgc tttagttgaa gaataaaaga cctatgcggt gtgaaatacc   3120
gcacagatgc gtaaggagaa aataccgcat caggcgccat cgccattcca ggctgcgcaa   3180
ctgttgggaa gggcgatcgg tgcgggcctc ttcgctatta cgccagctgg cgaaaggggg   3240
atgtgctgca aggcgattaa gttgggtaac gccaggggttt tcccagtcac gacgttgtaa   3300
aacgacggcc agtgccaagc ttgcatgcct gcactccatt ttcttctgct atcaaaataa   3360
cagactcgtg attttccaaa cgagctttca aaaaagcctc tgcccttgc aaatcggatg   3420 cctgtctata aaattcccga tattggttaa acagcggcgc aatggcggcc gcatctgatg   3480
tctttgcttg gcgaatgttc atcttatttc ttcctccctc tcaataattt tttcattcta   3540
tcccttttct gtaaagttta ttttttcagaa tacttttatc atcatgcttt gaaaaaatat   3600
```

```
cacgataata tccattgttc tcacggaagc acacgcaggt catttgaacg aattttttcg    3660
acaggaattt gccggactc aggagcattt aacctaaaaa agcatgacat ttcagcataa     3720
tgaacattta ctcatgtcta ttttcgttct tttctgtatg aaaatagtta tttcgagtct    3780
ctacggaaat agcgagagat gatataccta aatagagata aaatcatctc aaaaaaatgg    3840
gtctactaaa atattattcc atctattaca ataaattcac agaatagtct tttaagtaag    3900
tctactctga atttttttaa aaggagaggg taaagagtga aaacagtagt tattattgat    3960
gcattacgaa caccaattgg aaaatataaa ggcagcttaa gtcaagtaag tgccgtagac    4020
ttaggaacac atgttacaac acaactttta aaaagacatt ccactatttc tgaagaaatt    4080
gatcaagtaa tctttggaaa tgttttacaa gctggaaatg gccaaaatcc cgcacgacaa    4140
atagcaataa acagcggttt gtctcatgaa attcccgcaa tgacggttaa tgaggtctgc    4200
ggatcaggaa tgaaggccgt tattttggcg aaacaattga ttcaattagg agaagcggaa    4260
gttttaattg ctggcgggat tgagaatatg tcccaagcac ctaaattaca acgttttaat    4320
tacgaaacag aaagctacga tgcgcctttt tctagtatga tgtatgatgg attaacggat    4380
gcctttagtg gtcaggcaat gggcttaact gctgaaaatg tggccgaaaa gtatcatgta    4440
actagagaag agcaagatca attttctgta cattcacaat aaaagcagc tcaagcacaa     4500 gcagaaggga tattcgctga cgaaatagcc ccattagaag tatcaggaac gcttgtggag    4560
aaagatgaag ggattcgccc taattcgagc gttgagaagc taggaacgct taaaacagtt    4620 tttaagaag acggtactgt aacagcaggg aatgcatcaa ccattaatga tggggcttct     4680
gctttgatta ttgcttcaca agaatatgcc gaagcacacg gtcttcctta tttagctatt    4740
attcgagaca gtgtggaagt cggtattgat ccagcctata tgggaatttc gccgattaaa    4800
gccattcaaa aactgttagc gcgcaatcaa cttactacgg aagaaattga tctgtatgaa    4860
atcaacgaag catttgcagc aacttcaatc gtggtccaaa gagaactggc tttaccagag    4920
gaaaaggtca acatttatgg tggcggtatt tcattaggtc atgcgattgg tgccacaggt    4980
gctcgtttat taacgagttt aagttatcaa ttaaatcaaa aagaaaagaa atatggagtg    5040
gcttctttat gtatcggcgg tggcttagga ctcgctatgc tactagagag acctcagcaa    5100
aaaaaaaaca gccgattta tcaaatgagt cctgaggaac gcctggcttc tcttcttaat     5160
gaaggccaga tttctgctga tacaaaaaaa gaatttgaaa atacggcttt atcttcgcag    5220
attgccaatc atatgattga aaatcaaatc agtgaaacag aagtgccgat gggcgttggc    5280
ttacatttaa cagtggacga aactgattat ttggtaccaa tggcgacaga agagccctca    5340
gttattgcgg ctttgagtaa tggtgcaaaa atagcacaag gatttaaaac agtgaatcaa    5400
caacgcttaa tgcgtggaca aatcgttttt tacgatgttg cagatcccga gtcattgatt    5460
gataaactac aagtaagaga agcggaagtt tttcaacaag cagagttaag ttatccatct    5520
atcgttaaac ggggcggcgg cttaagagat ttgcaatatc gtacttttga tgaatcattt    5580
gtatctgtcg acttttagt agatgttaag gatgcaatgg gggcaaatat cgttaacgct     5640 atgtggaag gtgtggccga gttgttccgt gaatggtttg cggagcaaaa gattttattc    5700
agtattttaa gtaattatgc cacggagtcg gttgttacga tgaaaacggc tattccagtt    5760
tcacgtttaa gtaaggggag caatggccgg gaaattgctg aaaaaattgt tttagcttca    5820
cgctatgctt cattagatcc ttatcgggca gtcacgcata caaaggaat catgaatggc      5880 attgaagctg tagttttagc tacaggaaat gatacacgcg ctgttagcgc ttcttgtcat    5940
gcttttgcgg tgaaggaagg tcgctaccaa ggcttgacta gttggacgct ggatggcgaa    6000
```

| | |
|---|---|
| caactaattg gtgaaatttc agttccgctt gctttagcca cggttggcgg tgccacaaaa | 6060 |
| gtcttaccta aatctcaagc agctgctgat ttgttagcag tgacggatgc aaaagaacta | 6120 |
| agtcgagtag tagcggctgt tggtttggca caaaatttag cggcgttacg ggccttagtc | 6180 |
| tctgaaggaa ttcaaaaagg acacatggct ctacaagcac gttctttagc gatgacggtc | 6240 |
| ggagctactg gtaaagaagt tgaggcagtc gctcaacaat taaaacgtca aaaaacgatg | 6300 |
| aaccaagacc gagccatggc tattttaaat gatttaagaa acaataaaa ggagagggtg | 6360 |
| acaattggga ttgataaaat tagtttttt gtgcccctt attatattga tatgacggca | 6420 |
| ctggctgaag ccagaaatgt agaccctgga aaatttcata ttggtattgg gcaagaccaa | 6480 |
| atggcggtga acccaatcag ccaagatatt gtgacatttg cagccaatgc cgcagaagcg | 6540 |
| atcttgacca agaagataa agaggccatt gatatggtga ttgtcgggac tgagtccagt | 6600 |
| atcgatgagt caaaagcggc cgcagttgtc ttacatcgtt taatggggat tcaacctttc | 6660 |
| gctcgctctt tcgaaatcaa ggaagcttgt tacggagcaa cagcaggctt acagttagct | 6720 |
| aagaatcacg tagccttaca tccagataaa aaagtcttgg tcgtagcggc agatattgca | 6780 |
| aaatatggct taaattctgg cggtgagcct acacaaggag ctggggcggt tgcaatgtta | 6840 |
| gttgctagtg aaccgcgcat tttggcttta aaagaggata atgtgatgct gacgcaagat | 6900 |
| atctatgact tttggcgtcc aacaggccac ccgtatccta tggtcgatgg tcctttgtca | 6960 |
| aacgaaacct acatccaatc ttttgcccaa gtctgggatg aacataaaaa acgaaccggt | 7020 |
| cttgattttg cagattatga tgctttagcg ttccatattc cttacacaaa aatgggcaaa | 7080 |
| aaagccttat tagcaaaaat ctccgaccaa actgaagcag aacaggaacg aatttttagcc | 7140 |
| cgttatgaag aaagtatcgt ctatagtcgt cgcgtaggaa acttgtatac gggttcactt | 7200 |
| tatctgggac tcatttccct tttagaaaat gcaacgactt taaccgcagg caatcaaatt | 7260 |
| ggtttattca gttatggttc tggtgctgtc gctgaatttt tcactggtga attagtagct | 7320 |
| ggttatcaaa atcatttaca aaagaaact catttagcac tgctggataa tcggacagaa | 7380 |
| ctttctatcg ctgaatatga agccatgttt gcagaaactt tagacacaga cattgatcaa | 7440 |
| acgttagaag atgaattaaa atatagtatt tctgctatta ataataccgt tcgttcttat | 7500 |
| cgaaactaaa aaaaccggc cttggccccg ccggttttt attatttttc ttcctccgca | 7560 |
| tgttcaatcc gctccataat cgacggatgg ctccctctga aaattttaac gagaaacggc | 7620 |
| gggttgaccc ggctcagtcc cgtaacggcc aagtcctgaa acgtctcaat cgccgcttcc | 7680 |
| cggtttccgg tcagctcaat gccgtaacgg tcggcggcgt tttcctgata ccgggagacg | 7740 |
| gcattcgtaa tcgggatccc cgggtaccga gctcgaattc gtaatcatgt catagctgtt | 7800 |
| tcctgtgtga aattgttatc cgctcacaat tccacacaac atacgagccg gaagcataaa | 7860 |
| gtgtaaagcc tggggtgcct aatgagtgag ctaactcaca ttaattgcgt tgcgctcact | 7920 |
| gcccgctttc cagtcgggaa acctgtcgtg ccagctgcat taatgaatcg gccaacgcgc | 7980 |
| ggggagaggc ggtttgcgta ttgggcgctc ttccgcttcc tcgctcactg ac | 8032 |

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57

| | |
|---|---|
| gaattgctcc attttcttct gctatcaaaa taacagactc gtgattttcc aaacgagctt | 60 |

```
tcaaaaaagc ctctgcccct tgcaaatcgg atgcctgtct ataaaattcc cgatattggt    120
taaacagcgg cgcaatggcg gccgcatctg atgtctttgc ttggcgaatg ttcatcttat    180
ttcttcctcc ctctcaataa tttttcatt ctatcccttt tctgtaaagt ttattttca     240 gaatactttt atcatcatgc tttgaaaaaa tatcacgata atatccattg ttctcacgga    300
agcacacgca ggtcatttga acgaattttt tcgacaggaa tttgccggga ctcaggagca    360
tttaacctaa aaaagcatga catttcagca taatgaacat ttactcatgt ctattttcgt    420
tcttttctgt atgaaaatag ttatttcgag tctctacgga aatagcgaga gatgatatac    480
ctaaatagag ataaaatcat ctcaaaaaaa tgggtctact aaaatattat tccatctatt    540
acaataaatt cacagaatag tcttttaagt aagtctactc tgaattttt taaaaggaga    600 gggtaaagag tgtgtgcgac ctcttctcaa tttactcaga ttaccgagca taattcccgt    660
cgttccgcaa actatcagcc aaacctgtgg aatttcgaat tcctgcaatc cctggagaac    720
gacctgaaag tggaaaagct ggaggagaaa gcgaccaaac tggaggaaga agttcgctgc    780
atgatcaacc gtgtagacac ccagccgctg tccctgctgg agctgatcga cgatgtgcag    840
cgcctgggtc tgacctacaa atttgaaaaa gacatcatta aagccctgga aaacatcgta    900
ctgctggacg aaaacaaaaa gaacaaatct gacctgcacg caaccgctct gtctttccgt    960
ctgctgcgtc agcacggttt cgaggtttct caggatgttt ttgagcgttt caaggataaa   1020
gaaggtggtt tcagcggtga actgaaaggt gacgtccaag gcctgctgag cctgtatgaa   1080
gcgtcttacc tgggttttcga gggtgagaac ctgctggagg aggcgcgtac cttttccatc   1140
acccacctga agaacaacct gaaagaaggc attaatacca aggttgcaga acaagtgagc   1200
cacgccctgg aactgccata tcaccagcgt ctgcaccgtc tggaggcacg ttggttcctg   1260
gataaatacg aaccgaaaga accgcatcac cagctgctgc tggagctggc gaagctggat   1320
tttaacatgg tacagaccct gcaccagaaa gagctgcaag atctgtcccg ctggtggacc   1380
gagatgggcc tggctagcaa actggatttt gtacgcgacc gcctgatgga agtttatttc   1440
tgggcactgg gtatggcgcc agacccgcag tttggtgaat gtcgcaaagc tgttactaaa   1500
atgtttggtc tggtgacgat catcgatgac gtgtatgacg tttatggcac tctgacgaa    1560 ctgcaactgt tcaccgatgc tgtagagcgc tgggacgtta acgctattaa caccctgccg   1620
gactatatga aactgtgttt cctggcactg tacaacaccg ttaacgacac gtcctattct   1680
attctgaaag agaaaggtca taacaacctg tcctatctga cgaaaagctg gcgtgaactg   1740
tgcaaagcct ttctgcaaga ggcgaaatgg tccaacaaca aaattatccc ggctttctcc   1800
aagtacctgg aaaacgccag cgtttcctcc tccggtgtag cgctgctggc gccgtcttac   1860
ttttccgtat gccagcagca ggaagacatc tccgaccacg cgctgcgttc cctgaccgac   1920
ttccatggtc tggtgcgttc tagctgcgtt atcttccgcc tgtgcaacga tctggccacc   1980
tctgcggcgg agctggaacg tggcgagact accaattcta tcattagcta catgcacgaa   2040
aacgatggta ccagcgagga acaggcccgc gaagaactgc gtaaactgat cgacgccgaa   2100
tggaaaaaga tgaatcgtga acgcgttagc gactccaccc tgctgcctaa gcgttcatg    2160 gaaatcgcag ttaacatggc acgtgtttcc cactgcacct accagtatgg cgatggtctg   2220
ggtcgcccag actacgcgac tgaaaaccgc atcaaactgc tgctgattga ccctttcccg   2280
attaaccagc tgatgtatgt ctaaaaaaaa ccggccttgg ccccgccggt ttttttattat   2340 ttttcttcct ccgcatgttc aatccgctcc ataatcgacg gatggctccc tctgaaaatt   2400
ttaacgagaa acggcgggtt gacccggctc agtcccgtaa cggccaagtc ctgaaacgtc   2460
```

```
tcaatcgccg cttcccggtt tccggtcagc tcaatgccgt aacggtcggc ggcgttttcc   2520
tgataccggg agacggcatt cgtaatcgga tcctctagag tcgacctgca ggcatgcaag   2580
ctttgcctcg cgcgtttcgg tgatgacggt gaaaacctct gacacatgca gctcccggag   2640
acggtcacag cttgtctgta agcggatgcc gggagcagac aagcccgtca gggcgcgtca   2700
gcgggtgttg gcgggtgtcg gggcgcagcc atgacccagt cacgtagcga tagcggagtg   2760
tatactggct taactatgcg gcatcagagc agattgtact gagagtgcac catatgcggt   2820
gtgaaatacc gcacagatgc gtaaggagaa ataccgcat caggcgctct ccgcttcct    2880 cgctcactga ctcgctgcgc tcggtcgttc ggctgcggcg agcggtatca gctcactcaa   2940
aggcggtaat acggttatcc acagaatcag gggataacgc aggaaagaac atgtgagcaa   3000
aaggccagca aaaggccagg aaccgtaaaa aggccgcgtt gctggcgttt ttccataggc   3060
tccgcccccc tgacgagcat cacaaaaatc gacgctcaag tcagaggtgg cgaaacccga   3120
caggactata aagataccag gcgtttcccc ctggaagctc cctcgtgcgc tctcctgttc   3180
cgaccctgcc gcttaccgga tacctgtccg cctttctccc ttcgggaagc gtggcgcttt   3240
ctcaatgctc acgctgtagg tatctcagtt cggtgtaggt cgttcgctcc aagctgggct   3300
gtgtgcacga accccccgtt cagcccgacc gctgcgcctt atccggtaac tatcgtcttg   3360
agtccaaccc ggtaagacac gacttatcgc cactggcagc agccactggt aacaggatta   3420
gcagagcgag gtatgtaggc ggtgctacag agttcttgaa gtggtggcct aactacggct   3480
acactagaag gacagtattt ggtatctgcg ctctgctgaa gccagttacc ttcggaaaaa   3540
gagttggtag ctcttgatcc ggcaaacaaa ccaccgctgg tagcggtggt ttttttgttt   3600
gcaagcagca gattacgcgc agaaaaaaag gatctcaaga agatcctttg atcttttcta   3660
cggggtctga cgctcagtgg aacgaaaact cacgttaagg gattttggtc atgagattat   3720
caaaaaggat cgaagtcggt tcagaaaaag aaggatatgg atctgagct gtaatataaa    3780 aaccttcttc aactaacggg gcaggttagt gacattagaa aaccgactgt aaaaagtaca   3840
gtcggcatta tctcatatta taaaagccag tcattaggcc tatctgacaa ttcctgaata   3900
gagttcataa acaatcctgc atgataacca tcacaaacag aatgatgtac ctgtaaagat   3960
agcggtaaat atattgaatt acctttatta atgaattttc ctgctgtaat aatgggtaga   4020
aggtaattac tattattatt gatatttaag ttaaacccag taaatgaagt ccatggaata   4080
atagaaagag aaaaagcatt ttcaggtata ggtgttttgg gaaacaattt aaaagaacca   4140
ttatatttct ctacatcaga aaggtataaa tcataaaact ctttgaagtc attctttaca   4200
ggagtccaaa taccagagaa tgttttagat acaccatcaa aaattgtata agtggctct    4260 aacttatccc aataacctaa ctctccgtcg ctattgtaac cagttctaaa agctgtattt   4320
gagtttatca cccttgtcac taagaaaata aatgcagggt aaaatttata tccttcttgt   4380
tttatgtttc ggtataaaac actaatatca atttctgtgg ttatactaaa agtcgtttgt   4440
tggttcaaat aatgattaaa tatctctttt ctcttccaat tgtctaaatc aattttatta   4500
aagttcattt gatatgcctc ctaaatttt atctaaagtg aatttaggag cttacttgt     4560 ctgctttctt cattagaatc aatccttttt taaagtcaat attactgtaa cataaatata   4620
tattttaaaa atatcccact ttatccaatt ttcgtttgtt gaactaatgg gtgctttagt   4680
tgaagaataa agaccacatt aaaaaatgtg gtcttttgtg ttttttttaaa ggatttgagc   4740 gtacgcgaaa aatccttttc tttctttctt atcttgataa taagggtaac tattgccggt   4800
tgtccattca tggctgaact ctgcttcctc tgttgacatg acacacatca tctcaatatc   4860
```

-continued

```
cgaatagggc ccatcagtct gacgaccaag agagccataa acaccaatag ccttaacatc    4920
atccccatat ttatccaata ttcgttcctt aatttcatga acaatcttca ttctttcttc    4980
tctagtcatt attattggtc cattcactat tctcattccc ttttcagata attttagatt    5040
tgcttttcta aataagaata tttggagagc accgttctta ttcagctatt aataactcgt    5100
cttcctaagc atccttcaat ccttttaata acaattatag catctaatct tcaacaaact    5160
ggcccgtttg ttgaactact cttaataaa ataattttc cgttcccaat tccacattgc      5220
aataatagaa aatccatctt catcggcttt tcgtcatca tctgtatgaa tcaaatcgcc     5280
ttcttctgtg tcatcaaggt ttaatttttt atgtatttct tttaacaaac caccatagga   5340
gattaacctt ttacggtgta aaccttcctc caaatcagac aaacgtttca aattcttttc   5400
ttcatcatcg gtcataaaat ccgtatcctt acaggatat tttgcagttt cgtcaattgc    5460
cgattgtata tccgatttat atttattttt cggtcgaatc atttgaactt ttacatttgg   5520
atcatagtct aatttcattg cctttttcca aaattgaatc cattgttttt gattcacgta   5580
gttttctgtt attctaaaat aagttggttc cacacatacc attacatgca tgtgctgatt   5640
ataagaatta tctttattat ttattgtcac atccgttgca cgcataaaac caacaagatt   5700
tttattaatt tttttatatt gcatcattcg gcgaaatcct tgagccatat ctgtcaaact   5760
cttatttaat tcttcgccat cataaacatt tttaactgtt aatgtgagaa acaaccaacg   5820
aactgttggc ttttgtttaa taacttcagc aacaaccttt tgtgactgaa tgccatgttt   5880
cattgctctc ctccagttgc acattggaca aagcctggat ttgcaaaacc acactcgata   5940
ccactttctt tcgcctgttt cacgattttg tttatactct aatatttcag cacaatcttt   6000 tactcttca gccttttaa attcaagaat atgcagaagt tcaaagtaat caacattagc      6060
gattttcttt tctctccatg gtctcacttt tccactttt gtcttgtcca ctaaaaccct    6120 tgattttca tctgaataaa tgctactatt aggacacata atattaaaag aaaccccccat   6180 ctatttagtt atttgtttag tcacttataa ctttaacaga tggggttttt ctgtgcaacc    6240
aattttaagg gtttttcaata ctttaaaaca catacatacc aacacttcaa cgcacctttc   6300
agcaactaaa ataaaatga cgttattct atatgtatca agataagaaa gaacaagttc       6360
aaaaccatca aaaaagaca ccttttcagg tgcttttttt atttatataaa ctcattccct    6420 gatctcgact tcgttctttt tttacctctc ggttatgagt tagttcaaat tcgttctttt    6480
taggttctaa atcgtgtttt tcttggaatt gtgctgtttt atcctttacc ttgtctacaa    6540
accccttaaa aacgttttta aaggcttta agccgtctgt acgttcctta ag             6592
```

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
gacatcaatt gctccatttt cttctgctat c          31

<210> SEQ ID NO 59
<211> LENGTH: 41
<212> TYPE: DNA
<213> ORGANISM: Artificial Sequence
<220> FEATURE:
<223> OTHER INFORMATION: Synthetic Construct

<400> SEQUENCE: 59

```
attgagaaga ggtcgcacac actctttacc ctctcctttt a                           41

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t                           41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
ccaaggccgg ttttttttag acatacatca gctggttaat c                           41

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g                           41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc                                     32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c                                      31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc                                           27

<210> SEQ ID NO 66
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 66
aggagagggt aaagagtgag                                                  20

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cttttccatc acccacctga ag                                               22

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
ggcgaaatgg tccaacaaca aaattatc                                         28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c               51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70
gcaggtggga aactatgcac tcc                                              23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg                                36

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc                                       30

<210> SEQ ID NO 73

```
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag                           32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg                   40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg                       36

<210> SEQ ID NO 76
<211> LENGTH: 37
<212> TYPE: DNA
<213> ORGANISM: Artificial Sequence
<220> FEATURE:
<223> OTHER INFORMATION: Synthetic Construct

<400> SEQUENCE: 76
ggtgggccca ttaaatcagt tatcgtttat ttgatag                      37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg                        35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg                        35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
```

```
gcggccgcag actaaattta tttcagtctc c                                    31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt                                                                7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg                                                                7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc                                         27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa                        42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84 ttaaaggag agggtaaaga gtgaaaacag tagttattat tg                         42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt                     45

<210> SEQ ID NO 86
<211> LENGTH: 8000
<212> TYPE: DNA
<213> ORGANISM: Artificial Sequence
<220> FEATURE:
```

<223> OTHER INFORMATION: Synthetic Construct

<400> SEQUENCE: 86

```
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggatcc   420
gagctcagga ggtaaaaaaa catgaaaaca gtagttatta ttgatgcatt acgaacacca   480
attggaaaat ataaaggcag cttaagtcaa gtaagtgccg tagacttagg aacacatgtt   540
acaacacaac ttttaaaaag acattccact atttctgaag aaattgatca agtaatcttt   600
ggaaatgttt tacaagctgg aaatggccaa atcccgcac gacaaatagc aataaacagc   660
ggtttgtctc atgaaattcc cgcaatgacg gttaatgagg tctgcggatc aggaatgaag   720
gccgttattt tggcgaaaca attgattcaa ttaggagaag cggaagtttt aattgctggc   780
gggattgaga atatgtccca agcacctaaa ttacaacgtt ttaattacga aacagaaagc   840
tacgatgcgc cttttttctag tatgatgtat gatggattaa cggatgcctt tagtggtcag   900
gcaatgggct taactgctga aaatgtggcc gaaaagtatc atgtaactag agaagagcaa   960
gatcaatttt ctgtacattc acaattaaaa gcagctcaag cacaagcaga agggatattc  1020
gctgacgaaa tagccccatt agaagtatca ggaacgcttg tggagaaaga tgaagggatt  1080
cgccctaatt cgagcgttga agctagga acgcttaaaa cagttttaa agaagacggt  1140
actgtaacag cagggaatgc atcaaccatt aatgatgggg cttctgcttt gattattgct  1200
tcacaagaat atgccgaagc acacggtctt ccttatttag ctattattcg agacagtgtg  1260
gaagtcggta ttgatccagc ctatatggga atttcgccga ttaaagccat tcaaaaactg  1320
ttagcgcgca atcaacttac tacggaagaa attgatctgt atgaaatcaa cgaagctttt  1380
gcagcaactt caatcgtggt ccaaagagaa ctggctttac cagaggaaaa ggtcaacatt  1440
tatggtggcg gtatttcatt aggtcatgcg attggtgcca caggtgctcg tttattaacg  1500
agtttaagtt atcaattaaa tcaaaagaa aagaaatatg gagtggcttc tttatgtatc  1560
ggcggtggct taggactcgc tatgctacta gagagacctc agcaaaaaaa aaacagccga  1620
ttttatcaaa tgagtcctga ggaacgcctg gcttctcttc ttaatgaagg ccagatttct  1680
gctgatacaa aaaagaatt tgaaaatacg gctttatctt cgcagattgc caatcatatg  1740
attgaaaatc aaatcagtga acagaagtg ccgatgggcg ttggcttaca tttaacagtg  1800
gacgaaactg ttatttggt accaatggcg acagaagagc cctcagttat tgcggctttg  1860
agtaatggtg caaaaatagc acaaggattt aaaacagtga atcaacaacg cttaatgcgt  1920
ggacaaatcg ttttttacga tgttgcagat cccgagtcat tgattgataa actacaagta  1980
agagaagcgg aagttttttca acaagcagag ttaagttatc catctatcgt taaacggggc  2040
ggcggcttaa gagatttgca atatcgtact tttgatgaat catttgtatc tgtcgacttt  2100
ttagtagatg ttaaggatgc aatgggggca aatatcgtta acgctatgtt ggaaggtgtg  2160
gccgagttgt tccgtgaatg gtttgcggag caaaagattt tattcagtat tttaagtaat  2220
tatgccacgg agtcggttgt tacgatgaaa acggctattc cagtttcacg tttaagtaag  2280
```

```
gggagcaatg gccgggaaat tgctgaaaaa attgttttag cttcacgcta tgcttcatta    2340
gatccttatc gggcagtcac gcataacaaa ggaatcatga atggcattga agctgtagtt    2400
ttagctacag gaaatgatac acgcgctgtt agcgcttctt gtcatgcttt tgcggtgaag    2460
gaaggtcgct accaaggctt gactagttgg acgctggatg gcgaacaact aattggtgaa    2520
atttcagttc cgcttgcttt agccacggtt ggcggtgcca caaaagtctt acctaaatct    2580
caagcagctg ctgatttgtt agcagtgacg gatgcaaaag aactaagtcg agtagtagcg    2640
gctgttggtt tggcacaaaa tttagcggcg ttacgggcct tagtctctga aggaattcaa    2700
aaaggacaca tggctctaca agcacgttct ttagcgatga cggtcggagc tactggtaaa    2760
gaagttgagg cagtcgctca acaattaaaa cgtcaaaaaa cgatgaacca agaccgagcc    2820
atggctattt taaatgattt aagaaaacaa taaaggaggt aaaaaaacat gacaattggg    2880
attgataaaa ttagtttttt tgtgcccccct tattatattg atatgacggc actggctgaa    2940
gccagaaatg tagaccctgg aaaatttcat attggtattg ggcaagacca aatggcggtg    3000
aacccaatca gccaagatat tgtgacattt gcagccaatg ccgcagaagc gatcttgacc    3060
aaagaagata agaggccat tgatatggtg attgtcggga ctgagtccag tatcgatgag    3120
tcaaaagcgg ccgcagttgt cttacatcgt ttaatgggga ttcaacctttt cgctcgctct    3180 ttcgaaatca aggaagcttg ttacggagca acagcaggct tacagttagc taagaatcac    3240
gtagccttac atccagataa aaaagtcttg gtcgtagcgg cagatattgc aaaatatggc    3300
ttaaattctg gcggtgagcc tacacaagga gctggggcgg ttgcaatgtt agttgctagt    3360
gaaccgcgca ttttggcttt aaaagaggat aatgtgatgc tgacgcaaga tatctatgac    3420
ttttggcgtc caacaggcca cccgtatcct atggtcgatg gtcctttgtc aaacgaaacc    3480
tacatccaat cttttgccca gtctgggat gaacataaaa aacgaaccgg tcttgatttt    3540
gcagattatg atgctttagc gttccatatt ccttacacaa aaatgggcaa aaaagcctta    3600
ttagcaaaaa tctccgacca aactgaagca gaacaggaac gaattttagc ccgttatgaa    3660
gaaagtatcg tctatagtcg tcgcgtagga aacttgtata cggggttcact ttatctggga    3720 ctcatttccc ttttagaaaa tgcaacgact ttaaccgcag gcaatcaaat tggtttattc    3780
agttatggtt ctggtgctgt cgctgaattt ttcactggtg aattagtagc tggttatcaa    3840
aatcatttac aaaagaaac tcatttagca ctgctggata atcggacaga actttctatc    3900
gctgaatatg aagccatgtt tgcagaaact ttagacacag acattgatca aacgttagaa    3960
gatgaattaa aatatagtat ttctgctatt aataataccg ttcgttctta tcgaaactaa    4020
gagatctgca gctggtacca tatgggaatt cgaagcttgg gcccgaacaa aaactcatct    4080
cagaagagga tctgaatagc gccgtcgacc atcatcatca tcatcattga gtttaaacgg    4140
tctccagctt ggctgttttg gcggatgaga aagattttc agcctgatac agattaaatc    4200
agaacgcaga gcggtctga taaaacagaa tttgcctggc ggcagtagcg cggtggtccc    4260
acctgacccc atgccgaact cagaagtgaa acgccgtagc gccgatggta gtgtggggtc    4320
tccccatgcg agagtaggga actgccaggc atcaaataaa acgaaaggct cagtcgaaag    4380
actgggcctt tcgttttatc tgttgtttgt cggtgaacgc tctcctgagt aggacaaatc    4440
cgccgggagc ggatttgaac gttgcgaagc aacggcccgg agggtggcgg gcaggacgcc    4500
cgccataaac tgccaggcat caaattaagc agaaggccat cctgacggat ggcctttttg    4560
cgtttctaca aactctttt gtttattttt ctaaatacat tcaaatatgt atccgctcat    4620
gagacaataa ccctgataaa tgcttcaata atattgaaaa aggaagagta tgagtattca    4680
```

```
acatttccgt gtcgcccttc ttcccttttt tgcggcattt tgccttcctg ttttttgctca    4740
cccagaaacg ctggtgaaag taaaagatgc tgaagatcag ttgggtgcac gagtgggtta    4800
catcgaactg gatctcaaca gcggtaagat ccttgagagt tttcgccccg aagaacgttt    4860
tccaatgatg agcacttttta aagttctgct atgtggcgcg gtattatccc gtgttgacgc    4920
cgggcaagag caactcggtc gccgcataca ctattctcag aatgacttgg ttgagtactc    4980
accagtcaca gaaaagcatc ttacggatgg catgacagta agagaattat gcagtgctgc    5040
cataaccatg agtgataaca ctgcggccaa cttacttctg acaacgatcg gaggaccgaa    5100
ggagctaacc gcttttttgc acaacatggg ggatcatgta actcgccttg atcgttggga    5160
accggagctg aatgaagcca taccaaacga cgagcgtgac accacgatgc ctgtagcaat    5220
ggcaacaacg ttgcgcaaac tattaactgg cgaactactt actctagctt cccggcaaca    5280
attaatagac tggatggagg cggataaagt tgcaggacca cttctgcgct cggcccttcc    5340
ggctggctgg tttattgctg ataaatctgg agccggtgag cgtgggtctc gcggtatcat    5400
tgcagcactg gggccagatg gtaagccctc ccgtatcgta gttatctaca cgacggggag    5460
tcaggcaact atggatgaac gaaatagaca gatcgctgag ataggtgcct cactgattaa    5520
gcattggtaa ctgtcagacc aagtttactc atatatactt tagattgatt taaaacttca    5580
ttttttaattt aaaaggatct aggtgaagat cctttttgat aatctcatga ccaaaatccc    5640
ttaacgtgag ttttcgttcc actgagcgtc agaccccgta gaaaagatca aaggatcttc    5700
ttgagatcct ttttttctgc gcgtaatctg ctgcttgcaa acaaaaaaac caccgctacc    5760
agcggtggtt tgtttgccgg atcaagagct accaactctt tttccgaagg taactggctt    5820
cagcagagcg cagataccaa atactgtcct tctagtgtag ccgtagttag gccaccactt    5880
caagaactct gtagcaccgc ctacatacct cgctctgcta atcctgttac cagtggctgc    5940
tgccagtggc gataagtcgt gtcttaccgg gttggactca agacgatagt taccggataa    6000
ggcgcagcgg tcgggctgaa cggggggttc gtgcacacag cccagcttgg agcgaacgac    6060
ctacaccgaa ctgagatacc tacagcgtga gctatgagaa agcgccacgc ttcccgaagg    6120
gagaaaggcg gacaggtatc cggtaagcgg cagggtcgga acaggagagc gcacgaggga    6180
gcttccaggg ggaaacgcct ggtatcttta tagtcctgtc gggtttcgcc acctctgact    6240
tgagcgtcga tttttgtgat gctcgtcagg ggggcggagc ctatggaaaa acgccagcaa    6300
cgcggccttt ttacggttcc tggccttttg ctggccttttt gctcacatgt tctttcctgc    6360
gttatcccct gattctgtgg ataaccgtat taccgccttt gagtgagctg ataccgctcg    6420
ccgcagccga acgaccgagc gcagcgagtc agtgagcgag gaagcggaag agcgcctgat    6480
gcggtattttt ctccttacgc atctgtgcgg tatttcacac cgcatatggt gcactctcag    6540
tacaatctgc tctgatgccg catagttaag ccagtataca ctccgctatc gctacgtgac    6600
tgggtcatgg ctgcgcccg acacccgcca cacccgctg acgcgccctg acgggcttgt    6660
ctgctcccgg catccgctta cagacaagct gtgaccgtct ccgggagctg catgtgtcag    6720
aggttttcac cgtcatcacc gaaacgcgcg aggcagcaga tcaattcgcg cgcgaaggcg    6780
aagcggcatg catttacgtt gacaccatcg aatggtgcaa aacctttcgc ggtatggcat    6840
gatagcgccc ggaagagagt caattcaggg tggtgaatgt gaaaccagta acgttatacg    6900
atgtcgcaga gtatgccggt gtctcttatc agaccgtttc ccgcgtggtg aaccaggcca    6960
gccacgtttc tgcgaaaacg cgggaaaaag tggaagcggc gatggcggag ctgaattaca    7020
ttcccaaccg cgtggcacaa caactggcgg gcaaacagtc gttgctgatt ggcgttgcca    7080
```

```
cctccagtct ggccctgcac gcgccgtcgc aaattgtcgc ggcgattaaa tctcgcgccg    7140
atcaactggg tgccagcgtg gtggtgtcga tggtagaacg aagcggcgtc gaagcctgta    7200
aagcggcggt gcacaatctt ctcgcgcaac gcgtcagtgg gctgatcatt aactatccgc    7260
tggatgacca ggatgccatt gctgtggaag ctgcctgcac taatgttccg gcgttatttc    7320
ttgatgtctc tgaccagaca cccatcaaca gtattatttt ctcccatgaa gacggtacgc    7380
gactgggcgt ggagcatctg gtcgcattgg gtcaccagca atcgcgctg ttagcgggcc     7440 cattaagttc tgtctcggcg cgtctgcgtc tggctggctg gcataaatat ctcactcgca    7500
atcaaattca gccgatagcg gaacgggaag gcgactggag tgccatgtcc ggttttcaac    7560
aaaccatgca aatgctgaat gagggcatcg ttcccactgc gatgctggtt gccaacgatc    7620
agatggcgct gggcgcaatg cgcgccatta ccgagtccgg gctgcgcgtt ggtgcggata    7680
tctcggtagt gggatacgac gataccgaag acagctcatg ttatatcccg ccgtcaacca    7740
ccatcaaaca ggattttcgc ctgctggggc aaaccagcgt ggaccgcttg ctgcaactct    7800
ctcagggcca ggcggtgaag ggcaatcagc tgttgcccgt ctcactggtg aaaagaaaaa    7860
ccaccctggc gcccaatacg caaaccgcct ctccccgcgc gttggccgat tcattaatgc    7920
agctggcacg acaggtttcc cgactggaaa gcgggcagtg agcgcaacgc aattaatgtg    7980
agttagcgcg aattgatctg                                                 8000

<210> SEQ ID NO 87
<211> LENGTH: 10433
<212> TYPE: DNA
<213> ORGANISM: Artificial Sequence
<220> FEATURE:
<223> OTHER INFORMATION: Synthetic Construct

<400> SEQUENCE: 87
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca    180
gacaatctgt gtgggcactc gaccggaatt atcgattaac tttattatta aaattaaag     240 aggtatatat taatgtatcg attaaataag gaggaataaa ccatggatcc gagctcagga    300
ggtaaaaaaa catgaaaaca gtagttatta ttgatgcatt acgaacacca attggaaaat    360
ataaaggcag cttaagtcaa gtaagtgccg tagacttagg aacacatgtt acaacacaac    420
ttttaaaaag acattccact atttctgaag aaattgatca gtaatctttt ggaaatgttt    480
tacaagctgg aaatggccaa atcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga aacagaaagc tacgatgcgc    720 cttttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga agctagga acgcttaaaa cagttttaa agaagacggt actgtaacag       1020
cagggaatgc atcaaccatt aatgatgggg cttctgcttt gattattgct tcacaagaat    1080
atgccgaagc acacggtctt ccttatttag ctattattcg agacagtgtg gaagtcggta    1140
```

```
ttgatccagc ctatatggga atttcgccga ttaaagccat tcaaaaactg ttagcgcgca    1200
atcaacttac tacggaagaa attgatctgt atgaaatcaa cgaagcattt gcagcaactt    1260
caatcgtggt ccaaagagaa ctggctttac cagaggaaaa ggtcaacatt tatggtggcg    1320
gtatttcatt aggtcatgcg attggtgcca caggtgctcg tttattaacg agtttaagtt    1380
atcaattaaa tcaaaagaa aagaaatatg gagtggcttc tttatgtatc ggcggtggct    1440
taggactcgc tatgctacta gagagacctc agcaaaaaaa aaacagccga ttttatcaaa    1500
tgagtcctga ggaacgcctg gcttctcttc ttaatgaagg ccagatttct gctgatacaa    1560
aaaaagaatt tgaaaatacg gctttatctt cgcagattgc caatcatatg attgaaaatc    1620
aaatcagtga acagaagtg ccgatgggcg ttggcttaca tttaacagtg gacgaaactg    1680
attatttggt accaatggcg acagaagagc cctcagttat tgcggctttg agtaatggtg    1740
caaaaatagc acaaggattt aaaacagtga atcaacaacg cttaatgcgt ggacaaatcg    1800
ttttttacga tgttgcagat cccgagtcat tgattgataa actacaagta agagaagcgg    1860
aagtttttca acaagcagag ttaagttatc catctatcgt taaacggggc ggcggcttaa    1920
gagatttgca atatcgtact tttgatgaat catttgtatc tgtcgacttt ttagtagatg    1980
ttaaggatgc aatgggggca aatatcgtta acgctatgtt ggaaggtgtg gccgagttgt    2040
tccgtgaatg gtttgcggag caaaagattt tattcagtat tttaagtaat tatgccacgg    2100
agtcggttgt tacgatgaaa acggctattc cagtttcacg tttaagtaag gggagcaatg    2160
gccgggaaat tgctgaaaaa attgttttag cttcacgcta tgcttcatta gatccttatc    2220
gggcagtcac gcataacaaa ggaatcatga atggcattga agctgtagtt ttagctacag    2280
gaaatgatac acgcgctgtt agcgcttctt gtcatgcttt tgcggtgaag gaaggtcgct    2340
accaaggctt gactagttgg acgctggatg gcgaacaact aattggtgaa atttcagttc    2400
cgcttgcttt agccacggtt ggcggtgcca caaaagtctt acctaaatct caagcagctg    2460
ctgatttgtt agcagtgacg gatgcaaaag aactaagtcg agtagtagcg gctgttggtt    2520
tggcacaaaa tttagcggcg ttacgggcct tagtctctga aggaattcaa aaaggacaca    2580
tggctctaca agcacgttct ttagcgatga cggtcggagc tactggtaaa gaagttgagg    2640
cagtcgctca acaattaaaa cgtcaaaaaa cgatgaacca agaccgagcc atggctattt    2700
taaatgattt aagaaaacaa taaggaggt aaaaaaacat gacaattggg attgataaaa    2760
ttagtttttt tgtgccccct tattatattg atatgacggc actggctgaa gccagaaatg    2820
tagaccctgg aaaatttcat attggtattg ggcaagacca aatggcggtg aacccaatca    2880
gccaagatat tgtgacattt gcagccaatg ccgcagaagc gatcttgacc aaagaagata    2940
aagaggccat tgatatggtg attgtcggga ctgagtccag tatcgatgag tcaaaagcgg    3000
ccgcagttgt cttacatcgt ttaatgggga ttcaacctt cgctcgctct ttcgaaatca    3060
aggaagcttg ttacggagca acagcaggct tacagttagc taagaatcac gtagccttac    3120
atccagataa aaaagtcttg gtcgtagcgg cagatattgc aaaatatggc ttaaattctg    3180
gcggtgagcc tacacaagga gctggggcgg ttgcaatgtt agttgctagt gaaccgcgca    3240
ttttggcttt aaaagaggat aatgtgatgc tgacgcaaga tatctatgac ttttggcgtc    3300
caacaggcca cccgtatcct atggtcgatg gtccttttgtc aaacgaaacc tacatccaat    3360
cttttgccca agtctgggat gaacataaaa aacgaaccgg tcttgatttt gcagattatg    3420 atgcttagc gttccatatt ccttacacaa aaatgggcaa aaaagcctta ttagcaaaaa    3480
tctccgacca aactgaagca gaacaggaac gaattttagc ccgttatgaa gaaagtatcg    3540
```

```
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa aatcatttac    3720
aaaaagaaac tcatttagca ctgctggata atcggacaga actttctatc gctgaatatg    3780
aagccatgtt tgcagaaact ttagacacag acattgatca aacgttagaa gatgaattaa    3840
aatatagtat ttctgctatt aataataccg ttcgttctta tcgaaactaa agatctgcat    3900
cctgcattcg cccttaggag gtaaaaaaac atgtgtgcga cctcttctca atttactcag    3960
attaccgagc ataattcccg tcgttccgca aactatcagc caaacctgtg gaatttcgaa    4020
ttcctgcaat ccctggagaa cgacctgaaa gtggaaaagc tggaggagaa agcgaccaaa    4080
ctggaggaag aagttcgctg catgatcaac cgtgtagaca cccagccgct gtccctgctg    4140
gagctgatcg acgatgtgca gcgcctgggt ctgacctaca aatttgaaaa agacatcatt    4200
aaagccctgg aaaacatcgt actgctggac gaaaacaaaa agaacaaatc tgacctgcac    4260
gcaaccgctc tgtctttccg tctgctgcgt cagcacggtt tcgaggtttc tcaggatgtt    4320
tttgagcgtt tcaaggataa agaaggtggt ttcagcggtg aactgaaagg tgacgtccaa    4380
ggcctgctga gcctgtatga agcgtcttac ctgggtttcg agggtgagaa cctgctggag    4440
gaggcgcgta ccttttccat cacccacctg aagaacaacc tgaaagaagg cattaatacc    4500
aaggttgcag aacaagtgag ccacgccctg gaactgccat atcaccagcg tctgcaccgt    4560
ctggaggcac gttggttcct ggataaatac gaaccgaaag aaccgcatca ccagctgctg    4620
ctggagctgg cgaagctgga ttttaacatg gtacagaccc tgcaccagaa agagctgcaa    4680
gatctgtccc gctggtggac cgagatgggc ctggctagca aactggattt tgtacgcgac    4740
cgcctgatgg aagtttattt ctgggcactg ggtatggcgc cagacccgca gtttggtgaa    4800
tgtcgcaaag ctgttactaa aatgtttggt ctggtgacga tcatcgatga cgtgtatgac    4860
gtttatggca ctctggacga actgcaactg ttcaccgatg ctgtagagcg ctgggacgtt    4920
aacgctatta acaccctgcc ggactatatg aaactgtgtt tcctggcact gtacaacacc    4980
gttaacgaca cgtcctattc tattctgaaa gagaaaggtc ataacaacct gtcctatctg    5040
acgaaaagct ggcgtgaact gtgcaaagcc tttctgcaag aggcgaaatg gtccaacaac    5100
aaaattatcc cggctttctc caagtacctg gaaaacgcca cgtttcctc ctccggtgta    5160
gcgctgctgg cgccgtctta cttttccgta tgccagcagc aggaagacat ctccgaccac    5220
gcgctgcgtt ccctgaccga cttccatggt ctggtgcgtt ctagctgcgt tatcttccgc    5280
ctgtgcaacg atctggccac ctctgcggcg gagctggaac gtggcgagac taccaattct    5340
atcattagct acatgcacga aaacgatggt accagcgagg aacaggcccg cgaagaactg    5400
cgtaaactga tcgacgccga atggaaaaag atgaatcgtg aacgcgttag cgactccacc    5460
ctgctgccta aagcgttcat ggaaatcgca gttaacatgg cacgtgtttc ccactgcacc    5520
taccagtatg gcgatggtct gggtcgccca gactacgcga ctgaaaaccg catcaaactg    5580
ctgctgattg acccttttccc gattaaccag ctgatgtatg tctaactgca gctggtacca    5640
tatgggaatt cgaagcttgg gcccgaacaa aaactcatct cagaagagga tctgaatagc    5700
gccgtcgacc atcatcatca tcatcattga gtttaaacgg tctccagctt ggctgttttg    5760
gcggatgaga gaagattttc agcctgatac agattaaatc agaacgcaga gcggtctga    5820
taaaacagaa tttgcctggc ggcagtagcg cggtggtccc acctgacccc atgccgaact    5880
cagaagtgaa acgccgtagc gccgatggta gtgtggggtc tccccatgcg agagtaggga    5940
```

```
actgccaggc atcaaataaa acgaaaggct cagtcgaaag actgggcctt tcgttttatc    6000
tgttgtttgt cggtgaacgc tctcctgagt aggacaaatc cgccgggagc ggatttgaac    6060
gttgcgaagc aacggcccgg agggtggcgg gcaggacgcc cgccataaac tgccaggcat    6120
caaattaagc agaaggccat cctgacggat ggccttttg cgtttctaca aactcttttt     6180
gtttattttt ctaaatacat tcaaatatgt atccgctcat gagacaataa ccctgataaa    6240
tgcttcaata atctggcgta atagcgaaga ggcccgcacc gatcgccctt cccaacagtt    6300
gcgcagcctg aatggcgaat ggcgcctgat gcggtatttt ctccttacgc atctgtgcgg    6360
tatttcacac cgcatatggt gcactctcag tacaatctgc tctgatgccg catagttaag    6420
ccagccccga cacccgccaa cacccgctga cgagcttagt aaagccctcg ctagatttta    6480
atgcggatgt tgcgattact tcgccaacta ttgcgataac aagaaaaagc cagccttca    6540 tgatatatct cccaatttgt gtagggctta ttatgcacgc ttaaaaataa taaaagcaga    6600
cttgacctga tagtttggct gtgagcaatt atgtgcttag tgcatctaac gcttgagtta    6660
agccgcgccg cgaagcggcg tcggcttgaa cgaattgtta gacattattt gccgactacc    6720
ttggtgatct cgcctttcac gtagtggaca aattcttcca actgatctgc gcgcgaggcc    6780
aagcgatctt cttcttgtcc aagataagcc tgtctagctt caagtatgac gggctgatac    6840
tgggccggca ggcgctccat tgcccagtcg gcagcgacat ccttcggcgc gattttgccg    6900
gttactgcgc tgtaccaaat gcgggacaac gtaagcacta catttcgctc atcgccagcc    6960
cagtcgggcg gcgagttcca tagcgttaag gtttcattta gcgcctcaaa tagatcctgt    7020
tcaggaaccg gatcaaagag ttcctccgcc gctggaccta ccaaggcaac gctatgttct    7080
cttgcttttg tcagcaagat agccagatca atgtcgatcg tggctggctc gaagatacct    7140
gcaagaatgt cattgcgctg ccattctcca aattgcagtt cgcgcttagc tggataacgc    7200
cacggaatga tgtcgtcgtg cacaacaatg gtgacttcta cagcgcggag aatctcgctc    7260
tctccagggg aagccgaagt ttccaaaagg tcgttgatca aagctcgccg cgttgtttca    7320
tcaagcctta cggtcaccgt aaccagcaaa tcaatatcac tgtgtggctt caggccgcca    7380
tccactgcgg agccgtacaa atgtacggcc agcaacgtcg gttcgagatg gcgctcgatg    7440
acgccaacta cctctgatag ttgagtcgat acttcggcga tcaccgcttc cctcatgatg    7500
tttaactttg ttttagggcg actgccctgc tgcgtaacat cgttgctgct ccataacatc    7560
aaacatcgac ccacggcgta acgcgcttgc tgcttggatg cccgaggcat agactgtacc    7620
ccaaaaaaac agtcataaca agccatgaaa accgccactg cgccgttacc accgctgcgt    7680
tcggtcaagg ttctggacca gttgcgtgag cgcatacgct acttgcatta cagcttacga    7740
accgaacagg cttatgtcca ctgggttcgt gccttcatcc gtttccacgg tgtgcgtcac    7800
ccggcaacct tgggcagcag cgaagtcgag gcatttctgt cctggctggc gaacgagcgc    7860
aaggtttcgg tctccacgca tcgtcaggca ttggcggcct tgctgttctt ctacggcaag    7920
gtgctgtgca cggatctgcc ctggcttcag gagatcggaa gacctcggcc gtcgcggcgc    7980
ttgccggtgg tgctgacccc ggatgaagtg gttcgcatcc tcggttttct ggaaggcgag    8040
catcgtttgt tcgcccagct tctgtatgga acgggcatgc ggatcagtga gggtttgcaa    8100
ctgcgggtca aggatctgga tttcgatcac ggcacgatca tcgtgcggga gggcaagggc    8160
tccaaggatc gggccttgat gttacccgag agcttggcac ccagcctgcg cgagcagggg    8220
aattaattcc cacgggtttt gctgcccgca aacgggctgt tctggtgttg ctagtttgtt    8280
atcagaatcg cagatccggc ttcagccggt ttgccggctg aaagcgctat ttcttccaga    8340
```

```
attgccatga ttttttcccc acgggaggcg tcactggctc ccgtgttgtc ggcagctttg   8400
attcgataag cagcatcgcc tgtttcaggc tgtctatgtg tgactgttga gctgtaacaa   8460
gttgtctcag gtgttcaatt tcatgttcta gttgctttgt tttactggtt tcacctgttc   8520
tattaggtgt tacatgctgt tcatctgtta cattgtcgat ctgttcatgg tgaacagctt   8580
tgaatgcacc aaaaactcgt aaaagctctg atgtatctat cttttttaca ccgttttcat   8640
ctgtgcatat ggacagtttt ccctttgata tgtaacggtg aacagttgtt ctacttttgt   8700
ttgttagtct tgatgcttca ctgatagata caagagccat aagaacctca gatccttccg   8760
tatttagcca gtatgttctc tagtgtggtt cgttgttttt gcgtgagcca tgagaacgaa   8820
ccattgagat catacttact ttgcatgtca ctcaaaaatt ttgcctcaaa actggtgagc   8880
tgaattttg cagttaaagc atcgtgtagt gttttttctta gtccgttatg taggtaggaa   8940
tctgatgtaa tggttgttgg tattttgtca ccattcattt ttatctggtt gttctcaagt   9000
tcggttacga gatccatttg tctatctagt tcaacttgga aaatcaacgt atcagtcggg   9060
cggcctcgct tatcaaccac caatttcata ttgctgtaag tgtttaaatc tttacttatt   9120
ggtttcaaaa cccattggtt aagccttttta aactcatggt agttattttc aagcattaac   9180
atgaacttaa attcatcaag gctaatctct atatttgcct tgtgagtttt cttttgtgtt   9240
agttctttta ataaccactc ataaatcctc atagagtatt tgttttcaaa agacttaaca   9300
tgttccagat tatattttat gaatttttt aactggaaaa gataaggcaa tatctcttca   9360
ctaaaaacta attctaattt ttcgcttgag aacttggcat agtttgtcca ctggaaaatc   9420
tcaaagcctt taaccaaagg attcctgatt tccacagttc tcgtcatcag ctctctggtt   9480
gctttagcta atacaccata agcatttttcc ctactgatgt tcatcatctg agcgtattgg   9540
ttataagtga acgataccgt ccgttctttc cttgtagggt tttcaatcgt ggggttgagt   9600
agtgccacac agcataaaat tagcttggtt tcatgctccg ttaagtcata gcgactaatc   9660
gctagttcat ttgctttgaa aacaactaat tcagacatac atctcaattg gtctaggtga   9720
ttttaatcac tataccaatt gagatgggct agtcaatgat aattactagt ccttttcctt   9780
tgagttgtgg gtatctgtaa attctgctag acctttgctg gaaaacttgt aaattctgct   9840
agaccctctg taaattccgc tagacctttg tgtgtttttt ttgtttatat tcaagtggtt   9900
ataatttata gaataaagaa agaataaaaa aagataaaaa gaatagatcc cagccctgtg   9960
tataactcac tactttagtc agttccgcag tattacaaaa ggatgtcgca aacgctgttt  10020
gctcctctac aaaacagacc ttaaaaccct aaaggcttaa gtagcaccct cgcaagctcg  10080
ggcaaatcgc tgaatattcc ttttgtctcc gaccatcagg cacctgagtc gctgtctttt  10140
tcgtgacatt cagttcgctg cgctcacggc tctggcagtg aatgggggta aatggcacta  10200
caggcgcctt ttatggattc atgcaaggaa actacccata atacaagaaa agcccgtcac  10260
gggcttctca gggcgtttta tggcgggtct gctatgtggt gctatctgac ttttttgctgt  10320
tcagcagttc ctgccctctg attttccagt ctgaccactt cggattatcc cgtgacaggt  10380
cattcagact ggctaatgca cccagtaagg cagcggtatc atcaacaggc tta          10433
```

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88

-continued

| cttgatgcat cctgcattcg cccttaggag g | 31 |

<210> SEQ ID NO 89
<211> LENGTH: 23
<212> TYPE: DNA
<213> ORGANISM: Artificial Sequence
<220> FEATURE:
<223> OTHER INFORMATION: Synthetic Construct

<400> SEQUENCE: 89

| ccaggcaaat tctgttttat cag | 23 |

<210> SEQ ID NO 90
<211> LENGTH: 10356
<212> TYPE: DNA
<213> ORGANISM: Artificial Sequence
<220> FEATURE:
<223> OTHER INFORMATION: Synthetic Construct

<400> SEQUENCE: 90

| caagaaaaat gccccgctta cgcagggcat ccatttatta ctcaaccgta accgattttg | 60 |
| ccaggttacg cggctggtca acgtcggtgc ctttgatcag cgcgacatgg taagccagca | 120 |
| gctgcagcgg aacggtgtag aagatcggtg caatcacctc ttccacatgc ggcatctcga | 180 |
| tgatgtgcat gttatcgcta cttacaaaac ccgcatcctg atcggcgaag acatacaact | 240 |
| gaccgccacg cgcgcgaact tcttcaatgt tggatttcag ttttccagc aattcgttgt | 300 |
| tcggtgcaac aacaataacc ggcatatcgg catcaattag cgccagcgga ccgtgtttca | 360 |
| gttcgccagc agcgtaggct tcagcgtgaa tgtaagagat ctctttcaac ttcaatgcgc | 420 |
| cttccagcgc gattgggtac tgatcgccac ggcccaggaa cagcgcgtga tgtttgtcag | 480 |
| agaaatcttc tgccagcgct tcaatgcgtt tgtcctgaga cagcatctgc tcaatacggc | 540 |
| tcggcagcgc ctgcagacca tgcacgatgt catgttcaat ggaggcatcc agaccttctca | 600 |
| ggcgagacag cttcgccacc agcatcaaca gcacagttaa ctgagtggtg aatgctttag | 660 |
| tggatgccac gccgatttct gtacccgcgt tggtcattag cgccagatcg gattcgcgca | 720 |
| ccagagaaga acccggaacg ttacagattg ccagtgaacc aaggtaaccc agctctttcg | 780 |
| acagacgcag gccagccagg gtatccgcgg tttcgccaga ctgtgacacg atcgcccttc | 840 |
| ccaacagttg cgcagcctat acgtacggca gtttaaggtt tacacctata aagagagag | 900 |
| ccgttatcgt ctgtttgtgg atgtacagag tgatattatt gacacgccgg ggcgacggat | 960 |
| ggtgatcccc ctggccagtg cacgtctgct gtcagataaa gtctcccgtg aactttaccc | 1020 |
| ggtggtgcat atcggggatg aaagctggcg catgatgacc accgatatgg ccagtgtgcc | 1080 |
| ggtctccgtt atcggggaag aagtggctga tctcagccac cgcgaaaatg acatcaaaaa | 1140 |
| cgccattaac ctgatgttct ggggaatata aatgtcaggc atgagattat caaaaaggat | 1200 |
| cttcacctag atccttttca cgtagaaagc cagtccgcag aaacggtgct gaccccggat | 1260 |
| gaatgtcagc tactgggcta tctggacaag ggaaaacgca agcgcaaaga gaaagcaggt | 1320 |
| agcttgcagt gggcttacat ggcgatagct agactgggcg gttttatgga cagcaagcga | 1380 |
| accggaattg ccagctgggg cgccctctgg taaggttggg aagccctgca agtaaactg | 1440 |
| gatggctttc tcgccgccaa ggatctgatg gcgcagggga tcaagctctg atcaagagac | 1500 |
| aggatgagga tcgtttcgca tgattgaaca agatggattg cacgcaggtt ctccggccgc | 1560 |
| ttgggtggag aggctattcg gctatgactg ggcacaacag acaatcggct gctctgatgc | 1620 |
| cgccgtgttc cggctgtcag cgcaggggcg cccggttctt tttgtcaaga ccgacctgtc | 1680 |

```
cggtgccctg aatgaactgc aagacgaggc agcgcggcta tcgtggctgg ccacgacggg   1740
cgttccttgc gcagctgtgc tcgacgttgt cactgaagcg ggaagggact ggctgctatt   1800
gggcgaagtg ccggggcagg atctcctgtc atctcacctt gctcctgccg agaaagtatc   1860
catcatggct gatgcaatgc ggcggctgca tacgcttgat ccggctacct gcccattcga   1920
ccaccaagcg aaacatcgca tcgagcgagc acgtactcgg atggaagccg gtcttgtcga   1980
tcaggatgat ctggacgaag agcatcaggg gctcgcgcca gccgaactgt tcgccaggct   2040
caaggcgagc atgcccgacg gcgaggatct cgtcgtgacc catggcgatg cctgcttgcc   2100
gaatatcatg gtggaaaatg gccgcttttc tggattcatc gactgtggcc ggctgggtgt   2160
ggcggaccgc tatcaggaca tagcgttggc tacccgtgat attgctgaag agcttggcgg   2220
cgaatgggct gaccgcttcc tcgtgcttta cggtatcgcc gctcccgatt cgcagcgcat   2280
cgccttctat cgccttcttg acgagttctt ctgaattatt aacgcttaca atttcctgat   2340
gcggtatttt ctccttacgc atctgtgcgg tatttcacac cgcatacagg tggcactttt   2400
cggggaaatg tgcgcggaac ccctatttgt ttattttttct aaatacattc aaatatgtat   2460
ccgctcatga caataaacc ctgataaatg cttcaataat agcacgtgag gagggccacc   2520
atggccaagt tgaccagtgc cgttccggtg ctcaccgcgc gcgacgtcgc cggagcggtc   2580
gagttctgga ccgaccggct cgggttctcc cctagtaacg gccgccagtg tgctggaatt   2640
caggcagttc aacctgttga tagtacgtac taagctctca tgtttcacgt actaagctct   2700
catgtttaac gtactaagct ctcatgttta cgaactaaaa ccctcatggc taacgtacta   2760
agctctcatg gctaacgtac taagctctca tgtttcacgt actaagctct catgtttgaa   2820
caataaaatt aatataaatc agcaacttaa atagcctcta aggttttaag ttttataaga   2880 aaaaaagaa tatataaggc ttttaaagct tttaaggttt aacggttgtg gacaacaagc   2940
cagggatgta acgcactgag aagcccttag agcctctcaa agcaattttc agtgacacag   3000
gaacacttaa cggctgacag cctgaattct gcagatatct gttttttccac tcttcgttca   3060 ctttcgccag gtagctggtg aagacgaagg aagtcccgga gccatctgcg cggcgtacta   3120
cagcaatgtt ttgtgaaggc agtttcagac ccggattcag tttggcgatg gcttcatcat   3180
cccacttctt gattttgccc aggtagatgt cgccgagggt tttaccatcc agcaccagtt   3240
cgccagactt cagccctgga atgttaaccg ccagcaccac gccgcaatc acggtcggga   3300 actggaacag accttcctga gccagttttt cgtcagacag cggcgcgtca gaggcaccaa   3360
aatcaacggt attagcgata atctgtttta cgccaccgga agaaccgata ccctggtagt   3420
taactttatt accggtttct ttctggtaag tgtcagccca tttggcatac accggcgcag   3480
ggaaggttgc acctgcacct gtcaggcttg cttctgcaaa cacagagaaa gcactcatcg   3540
ataaggtcgc ggcgacaaca gttgcgacgg tggtacgcat aactttcata atgtctcctg   3600
ggaggattca taaagcattg tttgttggct acgagaagca aaataggaca aacaggtgac   3660
agttatatgt aaggaatatg acagttttat gacagagaga taaagtcttc agtctgattt   3720
aaataagcgt tgatattcag tcaattacaa acattaataa cgaagagatg acagaaaaat   3780
tttcattctg tgacagagaa aaagtagccg aagatgacgg tttgtcacat ggagttggca   3840
ggatgtttga ttaaaagcaa ttaaccctca ctaaagggcg gccgcgaagt tcctattctc   3900
tagaaagtat aggaacttca ttctaccggg tagggaggc gcttttccca aggcagtctg   3960
gagcatgcgc tttagcagcc ccgctgggca cttggcgcta cacaagtggc ctctggcctc   4020
gcacacattc cacatccacc ggtaggcgcc aaccggctcc gttctttggt ggcccctttcg   4080
```

```
cgccaccttc cactcctccc ctagtcagga agttcccccc cgccccgcag ctcgcgtcgt    4140
gcaggacgtg acaaatggaa gtagcacgtc tcactagtct cgtgcagatg acagcaccg     4200 ctgagcaatg gaagcgggta ggcctttggg gcagcggcca atagcagctt tgctccttcg    4260
ctttctgggc tcagaggctg ggaagggtgt ggtccggggg cgggctcagg ggcgggctca    4320
ggggcggggc gggcgcccga aggtcctccg gaggcccggc attctgcacg cttcaaaagc    4380
gcacgtctgc cgcgctgttc tcctcttcct catctccggg cctttcgacc tgcagcagca    4440
cgtgttgaca attaatcatc ggcatagtat atcggcatag tataatacga caaggtgagg    4500
aactaaacca tggagaaaaa aatcactgga tataccaccg ttgatatatc ccaatggcat    4560
cgtaaagaac attttgaggc atttcagtca gttgctcaat gtacctataa ccagaccgtt    4620
cagctggata ttacggcctt tttaaagacc gtaaagaaaa ataagcacaa gttttatccg    4680
gcctttattc acattcttgc ccgcctgatg aatgctcatc cggaattccg tatggcaatg    4740
aaagacggtg agctggtgat atgggatagt gttcacccct tgttacaccgt tttccatgag    4800 caaactgaaa cgttttcatc gctctggagt gaataccacg acgatttccg gcagtttcta    4860
cacatatatt cgcaagatgt ggcgtgttac ggtgaaaacc tggcctattt ccctaaaggg    4920
tttattgaga atatgttttt cgtctcagcc aatccctggg tgagtttcac cagttttgat    4980
ttaaacgtgg ccaatatgga caacttcttc gcccccgttt tcaccatggg caaatattat    5040
acgcaaggcg acaaggtgct gatgccgctg gcgattcagg ttcatcatgc cgtttgtgat    5100
ggcttccatg tcggcagaat gcttaatgaa ttacaacagt actgcgatga gtggcagggc    5160
ggggcgtaag cgggactctg gggttcgaat aaagaccgac caagcgacgt ctgagagctc    5220
cctggcgaat tcggtaccaa taaaagagct ttattttcat gatctgtgtg ttggttttg     5280 tgtgcggcgc ggaagttcct attctctaga aagtatagga acttcctcga gcctatagt    5340 gagtcgtatt agcccttgac gatgccacat cctgagcaaa taattcaacc actaattgtg    5400
agcggataac acaaggagga aacagctatg tcattaccgt tcttaacttc tgcaccggga    5460
aaggttatta ttttggtga acactctgct gtgtacaaca gcctgccgt cgctgctagt     5520 gtgtctgcgt tgagaaccta cctgctaata agcgagtcat ctgcaccaga tactattgaa    5580
ttggacttcc cggacattag ctttaatcat aagtggtcca tcaatgattt caatgccatc    5640
accgaggatc aagtaaactc ccaaaaattg gccaaggctc aacaagccac cgatggcttg    5700
tctcaggaac tcgttagtct tttggatccg ttgttagctc aactatccga atccttccac    5760
taccatgcag cgttttgttt cctgtatatg tttgtttgcc tatgccccca tgccaagaat    5820
attaagtttt ctttaaagtc tactttaccc atcggtgctg ggttgggctc aagcgcctct    5880
atttctgtat cactggcctt agctatggcc tacttggggg ggttaatagg atctaatgac    5940
ttggaaaagc tgtcagaaaa cgataagcat atagtgaatc aatgggcctt cataggtgaa    6000
aagtgtattc acggtacccc ttcaggaata gataacgctg tggccactta tggtaatgcc    6060
ctgctatttg aaaaagactc acataatgga acaataaaca caaacaattt taagttctta    6120
gatgatttcc cagccattcc aatgatccta acctatacta gaattccaag gtctacaaaa    6180
gatcttgttg ctcgcgttcg tgtgttggtc accgagaaat ttcctgaagt tatgaagcca    6240
attctagatg ccatgggtga atgtgcccta caaggcttag agatcatgac taagttaagt    6300
aaatgtaaag gcaccgatga cgaggctgta gaaactaata tgaactgta tgaacaacta    6360 ttggaattga taagaataaa tcatggactg cttgtctcaa tcggtgtttc tcatcctgga    6420
ttagaactta tttaaaatct gagcgatgat ttgagaattg gctccacaaa acttaccggt    6480
```

```
gctggtggcg gcggttgctc tttgactttg ttacgaagag acattactca agagcaaatt    6540
gacagcttca aaaagaaatt gcaagatgat tttagttacg agacatttga aacagacttg    6600
ggtgggactg gctgctgttt gttaagcgca aaaatttga ataaagatct taaaatcaaa    6660
tccctagtat tccaattatt tgaaaataaa actaccacaa agcaacaaat tgacgatcta    6720
ttattgccag gaaacacgaa tttaccatgg acttcataag ctaatttgcg ataggcctgc    6780
acccttaagg aggaaaaaaa catgtcagag ttgagagcct tcagtgcccc agggaaagcg    6840
ttactagctg gtggatattt agttttagat acaaatatg aagcatttgt agtcggatta    6900
tcggcaagaa tgcatgctgt agcccatcct tacggttcat gcaagggtc tgataagttt    6960 gaagtgcgtg tgaaaagtaa acaatttaaa gatggggagt ggctgtacca tataagtcct    7020
aaaagtggct tcattcctgt ttcgataggc ggatctaaga acccttcat tgaaaaagtt    7080 atcgctaacg tatttagcta ctttaaacct aacatggacg actactgcaa tagaaacttg    7140
ttcgttattg atattttctc tgatgatgcc taccattctc aggaggatag cgttaccgaa    7200
catcgtggca acagaagatt gagttttcat tcgcacagaa ttgaagaagt tcccaaaaca    7260
gggctgggct cctcggcagg tttagtcaca gttttaacta cagctttggc ctcctttttt    7320
gtatcggacc tggaaaataa tgtagacaaa tatagagaag ttattcataa tttagcacaa    7380
gttgctcatt gtcaagctca gggtaaaatt ggaagcgggt ttgatgtagc ggcggcagca    7440
tatggatcta tcagatatag aagattccca cccgcattaa tctctaattt gccagatatt    7500
ggaagtgcta cttacggcag taaactggcg catttggttg atgaagaaga ctggaatatt    7560
acgattaaaa gtaaccattt accttcggga ttaactttat ggatgggcga tattaagaat    7620
ggttcagaaa cagtaaaact ggtccagaag gtaaaaaatt ggtatgattc gcatatgcca    7680
gaaagcttga aaatatatac agaactcgat catgcaaatt ctagatttat ggatggacta    7740
tctaaactag atcgcttaca cgagactcat gacgattaca gcgatcagat atttgagtct    7800
cttgagagga atgactgtac ctgtcaaaag tatcctgaaa tcacagaagt tagagatgca    7860
gttgccacaa ttgacgttc ctttagaaaa ataactaaag aatctggtgc cgatatcgaa    7920
cctcccgtac aaactagctt attggatgat tgccagacct taaaggagt tcttacttgc    7980 ttaatacctg gtgctggtgg ttatgacgcc attgcagtga ttactaagca agatgttgat    8040
cttagggctc aaaccgctaa tgacaaaaga ttttctaagg ttcaatggct ggatgtaact    8100
caggctgact ggggtgttag gaaagaaaaa gatccggaaa cttatcttga taaataactt    8160
aaggtagctg catgcagaat tcgcccttaa ggaggaaaaa aaaatgaccg tttacacagc    8220
atccgttacc gcacccgtca acatcgcaac ccttaagtat tgggggaaaa gggacacgaa    8280
gttgaatctg cccaccaatt cgtccatatc agtgacttta tcgcaagatg acctcagaac    8340
gttgacctct gcggctactg cacctgagtt tgaacgcgac actttgtggt taaatggaga    8400
accacacagc atcgacaatg aaagaactca aaattgtctg cgcgacctac gccaattaag    8460
aaaggaaatg gaatcgaagg acgcctcatt gcccacatta tctcaatgga aactccacat    8520
tgtctccgaa aataactttc ctacagcagc tggtttagct tcctccgctg ctggctttgc    8580
tgcattggtc tctgcaattg ctaagttata ccaattacca cagtcaactt cagaaatatc    8640
tagaatagca agaaagggt ctggttcagc ttgtagatcg ttgtttggcg gatacgtggc    8700
ctgggaaatg gaaaagctg aagatggtca tgattccatg gcagtacaaa tcgcagacag    8760
ctctgactgg cctcagatga aagcttgtgt cctagttgtc agcgatatta aaaggatgt    8820 gagttccact cagggtatgc aattgaccgt ggcaacctcc gaactattta agaaagaat    8880
```

-continued

```
tgaacatgtc gtaccaaaga gatttgaagt catgcgtaaa gccattgttg aaaaagattt    8940
cgccaccttt gcaaaggaaa caatgatgga ttccaactct ttccatgcca catgtttgga    9000
ctctttccct ccaatattct acatgaatga cacttccaag cgtatcatca gttggtgcca    9060
caccattaat cagttttacg gagaaacaat cgttgcatac acgtttgatg caggtccaaa    9120
tgctgtgttg tactacttag ctgaaaatga gtcgaaactc tttgcattta tctataaatt    9180
gtttggctct gttcctggat gggacaagaa atttactact gagcagcttg aggctttcaa    9240
ccatcaattt gaatcatcta actttactgc acgtgaattg gatcttgagt tgcaaaagga    9300
tgttgccaga gtgattttaa ctcaagtcgg ttcaggccca caagaaacaa acgaatcttt    9360
gattgacgca aagactggtc taccaaagga ataagatcaa ttcgctgcat cgcccttagg    9420
aggtaaaaaa aaatgactgc cgacaacaat agtatgcccc atggtgcagt atctagttac    9480
gccaaattag tgcaaaacca acacctgaaa gacattttgg aagagtttcc tgaaattatt    9540
ccattacaac aaagacctaa tacccgatct agtgagacgt caaatgacga agcggagaa     9600 acatgttttt ctggtcatga tgaggagcaa attaagttaa tgaatgaaaa ttgtattgtt    9660
ttggattggg acgataatgc tattggtgcc ggtaccaaga agtttgtca tttaatggaa     9720 aatattgaaa agggtttact acatcgtgca ttctccgtct ttattttcaa tgaacaaggt    9780
gaattacttt tacaacaaag agccactgaa aaaataactt tccctgatct ttggactaac    9840
acatgctgct ctcatccact atgtattgat gacgaattag gtttgaaggg taagctagac    9900
gataagatta agggcgctat tactgcggcg gtgagaaaac tagatcatga attaggtatt    9960
ccagaagatg aaactaagac aaggggtaag tttcactttt taaacagaat ccattacatg    10020
gcaccaagca atgaaccatg gggtgaacat gaaattgatt acatcctatt ttataagatc    10080
aacgctaaag aaaacttgac tgtcaaccca aacgtcaatg aagttagaga cttcaaatgg    10140
gtttcaccaa atgatttgaa aactatgttt gctgacccaa gttacaagtt tacgccttgg    10200
tttaagatta tttgcgagaa ttacttattc aactggtggg agcaattaga tgaccttcct    10260
gaagtggaaa atgacaggca aattcataga atgctataac aacgcgtcta caaataaaaa    10320
aggcacgtca gatgacgtgc ctttttcctt ggggcc                              10356
```

<210> SEQ ID NO 91
<211> LENGTH: 43
<212> TYPE: DNA
<213> ORGANISM: Artificial Sequence
<220> FEATURE:
<223> OTHER INFORMATION: Synthetic Construct

<400> SEQUENCE: 91

```
gcatgctcga gcggccgctt ttaatcaaac atcctgccaa ctc                       43
```

<210> SEQ ID NO 92
<211> LENGTH: 37
<212> TYPE: DNA
<213> ORGANISM: Artificial Sequence
<220> FEATURE:
<223> OTHER INFORMATION: Synthetic Construct

<400> SEQUENCE: 92

```
gatcgaaggg cgatcgtgtc acagtctggc gaaaccg                              37
```

<210> SEQ ID NO 93
<211> LENGTH: 43
<212> TYPE: DNA
<213> ORGANISM: Artificial Sequence
<220> FEATURE:

<223> OTHER INFORMATION: Synthetic Construct

<400> SEQUENCE: 93
ctgaattctg cagatatctg tttttccact cttcgttcac ttt                43

<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94
tctagagggc ccaagaaaaa tgccccgctt acg                           33

<210> SEQ ID NO 95
<211> LENGTH: 111
<212> TYPE: DNA
<213> ORGANISM: Artificial Sequence
<220> FEATURE:
<223> OTHER INFORMATION: Synthetic Construct

<400> SEQUENCE: 95
gatcgcggcc gcgcccttga cgatgccaca tcctgagcaa ataattcaac cactaattgt    60
gagcggataa cacaaggagg aaacagctat gtcattaccg ttcttaactt c             111

<210> SEQ ID NO 96
<211> LENGTH: 75
<212> TYPE: DNA
<213> ORGANISM: Artificial Sequence
<220> FEATURE:
<223> OTHER INFORMATION: Synthetic Construct

<400> SEQUENCE: 96
gatcgggccc caagaaaaaa ggcacgtcat ctgacgtgcc ttttttattt gtagacgcgt    60
tgttatagca ttcta                                                     75

<210> SEQ ID NO 97
<211> LENGTH: 81
<212> TYPE: DNA
<213> ORGANISM: Artificial Sequence
<220> FEATURE:
<223> OTHER INFORMATION: Synthetic Construct

<400> SEQUENCE: 97
aaagtagccg aagatgacgg tttgtcacat ggagttggca ggatgtttga ttaaaagcaa    60
ttaaccctca ctaaagggcg g                                              81

<210> SEQ ID NO 98
<211> LENGTH: 160
<212> TYPE: DNA
<213> ORGANISM: Artificial Sequence
<220> FEATURE:
<223> OTHER INFORMATION: Synthetic Construct

<400> SEQUENCE: 98
agagtgttca ccaaaaataa taacctttcc cggtgcagaa gttaagaacg gtaatgacat    60 agctgttttcc tccttgtgtt atccgctcac aattagtggt tgaattattt gctcaggatg    120
tggcatcgtc aagggctaat acgactcact atagggctcg                          160

<210> SEQ ID NO 99
<211> LENGTH: 60
<212> TYPE: DNA

```
<213> ORGANISM: Artificial Sequence
<220> FEATURE:
<223> OTHER INFORMATION: Synthetic Construct

<400> SEQUENCE: 99
gatcatgcat tcgcccttag gaggtaaaaa aacatgtgtg cgacctcttc tcaatttact    60

<210> SEQ ID NO 100
<211> LENGTH: 38
<212> TYPE: DNA
<213> ORGANISM: Artificial Sequence
<220> FEATURE:
<223> OTHER INFORMATION: Synthetic Construct

<400> SEQUENCE: 100
cggtcgacgg atccctgcag ttagacatac atcagctg                            38

<210> SEQ ID NO 101
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 101
gtgcggccgc aagcttgtcg acggagctcg aattcggatc cctgcagtta gacatacatc    60
agctggttaa tcgggaaagg gtcaatcagc agcagtttga tgcggttttc agtcgcgtag   120
tctgggcgac ccagaccatc gccatactgg taggtgcagt gggaaacacg tgccatgtta   180
actgcgattt ccatgaacgc tttaggcagc agggtggagt cgctaacgcg ttcacgattc   240
atctttttcc attcggcgtc gatcagttta cgcagttctt cgcgggcctg ttcctcgctg   300
gtaccatcgt tttcgtgcat gtagctaatg atagaattgg tagtctcgcc acgttccagc   360
tccgccgcag aggtggccag atcgttgcac aggcggaaga taacgcagct agaacgcacc   420
agaccatgga agtcggtcag ggaacgcagc gcgtggtcgg agatgtcttc ctgctgctgg   480
catacggaaa agtaagacgg cgccagcagc gctacaccgg aggaggaaac gctggcgttt   540
tccaggtact tggagaaagc cgggataatt ttgttgttgg accatttcgc ctcttgcaga   600
aaggctttgc acagttcacg ccagcttttc gtcagatagg acaggttgtt atgacctttc   660
tctttcagaa tagaatagga cgtgtcgtta acgtgttgt acagtgccag gaaacacagt   720
ttcatatagt ccggcagggt gttaatagcg ttaacgtccc agcgctctac agcatcggtg   780
aacagttgca gttcgtccag agtgccataa acgtcataca cgtcatcgat gatcgtcacc   840
agaccaaaca tttagtaac agctttgcga cattcaccaa actgcgggtc tggcgccata   900
cccagtgccc agaaataaac ttccatcagg cggtcgcgta caaaatccag tttgctagcc   960
aggcccatct cggtccacca gcgggacaga tcttgcagct cttctggtg cagggtctgt   1020 accatgttaa aatccagctt cgccagctcc agcagcagct ggtgatgcgg ttcttcggt    1080 tcgtatttat ccaggaacca acgtgcctcc agacggtgca gacgctggtg atatggcagt   1140
tccagggcgt ggctcacttg ttctgcaacc ttggtattaa tgccttcttt caggttgttc   1200
ttcaggtggg tgatggaaaa ggtacgcgcc tcctccagca ggttctcacc ctcgaaaccc   1260
aggtaagacg cttcatacag gctcagcagg ccttggacgt caccttcag ttcaccgctg    1320 aaaccacctt ctttatcctt gaaacgctca aaaacatcct gagaaacctc gaaaccgtgc   1380
tgacgcagca gacggaaaga cagagcggtt gcgtgcaggt cagatttgtt ctttttgttt   1440
tcgtccagca gtacgatgtt ttccagggct ttaatgatgt cttttttcaaa tttgtaggtc   1500
```

-continued

| | | | | |
|---|---|---|---|---|
| agacccaggc | gctgcacatc | gtcgatcagc | tccagcaggg | acagcggctg ggtgtctaca | 1560 |
| cggttgatca | tgcagcgaac | ttcttcctcc | agtttggtcg | ctttctcctc cagcttttcc | 1620 |
| actttcaggt | cgttctccag | ggattgcagg | aattcgaaat | tccacaggtt tggctgatag | 1680 |
| tttgcggaac | gacgggaatt | atgctcggta | atctgagtaa | attgagaaga ggtcgcacac | 1740 |
| atggtatatc | tccttcttaa | agttaaacaa | aattatttct | agaggggaat tgttatccgc | 1800 |
| tcacaattcc | cctatagtga | gtcgtattaa | tttcgcggga | tcgagatctc gatcctctac | 1860 |
| gccggacgca | tcgtggccgg | catcaccggc | gccacaggtg | cggttgctgg cgcctatatc | 1920 |
| gccgacatca | ccgatgggga | agatcgggct | cgccacttcg | gctcatgagc gcttgtttc | 1980 |
| ggcgtgggta | tggtggcagg | ccccgtggcc | ggggactgt  | tgggcgccat ctccttgcat | 2040 |
| gcaccattcc | ttgcggcggc | ggtgctcaac | ggcctcaacc | tactactggg ctgcttccta | 2100 |
| atgcaggagt | cgcataaggg | agagcgtcga | gatcccggac | accatcgaat ggcgcaaaac | 2160 |
| ctttcgcggt | atggcatgat | agcgcccgga | agagagtcaa | ttcagggtgg tgaatgtgaa | 2220 |
| accagtaacg | ttatacgatg | tcgcagagta | tgccggtgtc | tcttatcaga ccgtttcccg | 2280 |
| cgtggtgaac | caggccagcc | acgtttctgc | gaaaacgcgg | gaaaaagtgg aagcggcgat | 2340 |
| ggcggagctg | aattacattc | ccaaccgcgt | ggcacaacaa | ctggcgggca acagtcgtt  | 2400 |
| gctgattggc | gttgccacct | ccagtctggc | cctgcacgcg | ccgtcgcaaa ttgtcgcggc | 2460 |
| gattaaatct | cgcgccgatc | aactgggtgc | cagcgtggtg | gtgtcgatgg tagaacgaag | 2520 |
| cggcgtcgaa | gcctgtaaag | cggcggtgca | caatcttctc | gcgcaacgcg tcagtgggct | 2580 |
| gatcattaac | tatccgctgg | atgaccagga | tgccattgct | gtggaagctg cctgcactaa | 2640 |
| tgttccggcg | ttatttcttg | atgtctctga | ccagacaccc | atcaacagta ttattttctc | 2700 |
| ccatgaagac | ggtacgcgac | tgggcgtgga | gcatctggtc | gcattgggtc accagcaaat | 2760 |
| cgcgctgtta | gcgggcccat | taagttctgt | ctcggcgcgt | ctgcgtctgg ctggctggca | 2820 |
| taaatatctc | actcgcaatc | aaattcagcc | gatagcggaa | cgggaaggcg actgagtgc  | 2880 |
| catgtccggt | tttcaacaaa | ccatgcaaat | gctgaatgag | ggcatcgttc ccactgcgat | 2940 |
| gctggttgcc | aacgatcaga | tggcgctggg | cgcaatgcgc | gccattaccg agtccgggct | 3000 |
| gcgcgttggt | gcggatatct | cggtagtggg | atacgacgat | accgaagaca gctcatgtta | 3060 |
| tatcccgccg | ttaaccacca | tcaaacagga | ttttcgcctg | ctggggcaaa ccagcgtgga | 3120 |
| ccgcttgctg | caactctctc | agggccaggc | ggtgaagggc | aatcagctgt tgcccgtctc | 3180 |
| actggtgaaa | agaaaaacca | ccctggcgcc | caatacgcaa | accgcctctc ccgcgcgtt  | 3240 |
| ggccgattca | ttaatgcagc | tggcacgaca | ggtttcccga | ctggaaagcg gcagtgagc  | 3300 |
| gcaacgcaat | taatgtaagt | tagctcactc | attaggcacc | gggatctcga ccgatgccct | 3360 |
| tgagagcctt | caacccagtc | agctccttcc | ggtgggcgcg | gggcatgact atcgtcgccg | 3420 |
| cacttatgac | tgtcttcttt | atcatgcaac | tcgtaggaca | ggtgccggca gcgctctggg | 3480 |
| tcatttcgg  | cgaggaccgc | tttcgctgga | gcgcgacgat | gatcggcctg tcgcttgcgg | 3540 |
| tattcggaat | cttgcacgcc | ctcgctcaag | ccttcgtcac | tggtcccgcc accaaacgtt | 3600 |
| tcggcgagaa | gcaggccatt | atcgccggca | tggcggcccc | acgggtgcgc atgatcgtgc | 3660 |
| tcctgtcgtt | gaggacccgg | ctaggctggc | ggggttgcct | tactggttag cagaatgaat | 3720 |
| caccgatacg | cgagcgaacg | tgaagcgact | gctgctgcaa | aacgtctgcg acctgagcaa | 3780 |
| caacatgaat | ggtcttcggt | ttccgtgttt | cgtaaagtct | ggaaacgcgg aagtcagcgc | 3840 |
| cctgcaccat | tatgttccgg | atctgcatcg | caggatgctg | ctggctaccc tgtggaacac | 3900 |

```
ctacatctgt attaacgaag cgctggcatt gaccctgagt gattttctc tggtcccgcc    3960
gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacggag gcatcagtga ccaaacagga aaaaaccgcc cttaacatgg    4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcggggc gcagccatga cccagtcacg tagcgatagc ggagtgtata    4440
ctggcttaac tatgcggcat cagagcagat tgtactgaga gtgcaccata tgcggtgt    4500
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gctgtaggta tctcagttcg gtgtaggtcg ttcgctccaa gctgggctgt    4980
gtgcacgaac ccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gaacaataaa    5400
actgtctgct tacataaaca gtaatacaag gggtgttatg agccatattc aacgggaaac    5460
gtcttgctct aggccgcgat taaattccaa catggatgct gatttatatg ggtataaatg    5520
ggctcgcgat aatgtcgggc aatcaggtgc gacaatctat cgattgtatg ggaagcccga    5580
tgcgccagag ttgtttctga acatggcaa aggtagcgtt gccaatgatg ttacagatga    5640
gatggtcaga ctaaactggc tgacggaatt tatgcctctt ccgaccatca agcattttat    5700
ccgtactcct gatgatgcat ggttactcac cactgcgatc cccgggaaaa cagcattcca    5760
ggtattagaa gaatatcctg attcaggtga aaatattgtt gatgcgctgg cagtgttcct    5820
gcgccggttg cattcgattc ctgtttgtaa ttgtcctttt aacagcgatc gcgtatttcg    5880
tctcgctcag gcgcaatcac gaatgaataa cggtttggtt gatgcgagtg attttgatga    5940
cgagcgtaat ggctggcctg ttgaacaagt ctggaaagaa atgcataaac ttttgccatt    6000
ctcaccggat tcagtcgtca ctcatggtga tttctcactt gataaccttt ttttgacga    6060
ggggaaatta ataggttgta ttgatgttgg acgagtcgga atcgcagacc gataccagga    6120
tcttgccatc ctatggaact gcctcggtga gttttctcct tcattacaga aacggctttt    6180
tcaaaaatat ggtattgata atcctgtat gaataaattg cagtttcatt tgatgctcga    6240
tgagttttc taagaattaa ttcatgagcg gatacatatt tgaatgtatt tagaaaaata    6300
```

-continued

| | |
|---|---|
| aacaaatagg ggttccgcgc acatttcccc gaaaagtgcc acctgaaatt gtaaacgtta | 6360 |
| atattttgtt aaaattcgcg ttaaattttt gttaaatcag ctcattttt aaccaatagg | 6420 |
| ccgaaatcgg caaaatccct tataaatcaa agaatagac cgagataggg ttgagtgttg | 6480 |
| ttccagtttg gaacaagagt ccactattaa agaacgtgga ctccaacgtc aaagggcgaa | 6540 |
| aaaccgtcta tcagggcgat ggcccactac gtgaaccatc accctaatca gttttttgg | 6600 |
| ggtcgaggtg ccgtaaagca ctaaatcgga accctaaagg gagcccccga tttagagctt | 6660 |
| gacggggaaa gccggcgaac gtggcgagaa aggaagggaa gaaagcgaaa ggagcgggcg | 6720 |
| ctagggcgct ggcaagtgta gcggtcacgc tgcgcgtaac caccaccc gccgcgctta | 6780 |
| atgcgccgct acagggcgcg tcccattcgc caatccggat atagttcctc ctttcagcaa | 6840 |
| aaaacccctc aagacccgtt tagaggcccc aaggggttat gctagttatt gctcagcggt | 6900 |
| ggcagcagcc aactcagctt cctttcgggc tttgttagca gccggatctc agtggtggtg | 6960 |
| gtggtggtgc tcga | 6974 |

<210> SEQ ID NO 102
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 102

| | |
|---|---|
| gcggccgcgc ccttgacgat gccacatcct gagcaaataa ttcaaccact aattgtgagc | 60 |
| ggataacaca aggaggaaac agccatggta tcctgttctg cgccgggtaa gatttacctg | 120 |
| ttcggtgaac acgccgtagt ttatggcgaa actgcaattg cgtgtgcggt ggaactgcgt | 180 |
| acccgtgttc gcgcggaact caatgactct atcactattc agagccagat cggccgcacc | 240 |
| ggtctggatt cgaaaagca cccttatgtg tctgcggtaa ttgagaaaat gcgcaaatct | 300 |
| attcctatta acggtgtttt cttgaccgtc gattccgaca tcccggtggg ctccggtctg | 360 |
| ggtagcagcg cagccgttac tatcgcgtct attggtgcgc tgaacgagct gttcggcttt | 420 |
| ggcctcagcc tgcaagaaat cgctaaactg gccacgaaa tcgaaattaa agtacagggt | 480 |
| gccgcgtccc caaccgatac gtatgttct accttcggcg gcgtggttac catcccggaa | 540 |
| cgtcgcaaac tgaaaactcc ggactgcggc attgtgattg gcgataccgg cgttttctcc | 600 |
| tccaccaaag agttagtagc taacgtacgt cagctgcgcg aaagctaccc ggatttgatc | 660 |
| gaaccgctga tgacctctat tggcaaaatc tctcgtatcg gcgaacaact ggttctgtct | 720 |
| ggcgactacg catccatcgg ccgcctgatg aacgtcaacc agggtctcct ggacgccctg | 780 |
| ggcgttaaca tcttagaact gagccagctg atctattccg ctcgtgcggc aggtgcgttt | 840 |
| ggcgctaaaa tcacgggcgc tggcggcggt ggctgtatgg ttgcgctgac cgctccggaa | 900 |
| aaatgcaacc aagtggcaga gcggtagca ggcgctggcg gtaaagtgac tatcactaaa | 960 |
| ccgaccgagc aaggtctgaa agtagattaa gccttgactt aatagctgct tatttcgccc | 1020 |
| ttatggtacc tagtaggagg aaaaaaacat ggaaatgcgt caaccggctg tcgcaggtca | 1080 |
| attctaccca ctgcgttgcg agaacctgga aaacgaactg aaacgctgct cgaaggcct | 1140 |
| ggagatccgc gaacaagaag tgctgggcgc agtctgtccg cacgccggtt atatgtactc | 1200 |
| tggcaaagtt gcggcgcacg tctatgccac tctgccggaa gctgatacct acgtaatctt | 1260 |
| cggcccgaac cacaccggct acggtagccc tgtctctgtg agccgtgaaa cttgaagac | 1320 |
| cccgttgggc aatatcgatg ttgacctgga actggcggac ggcttcctgg gttccatcgt | 1380 |

| | |
|---|---|
| agatgcggat gaactcggtc acaaatacga acactctatc gaagttcagc tgccgtttct | 1440 |
| gcaataccgt tttgaacgcg atttcaaaat tctgccaatc tgcatgggta tgcaagacga | 1500 |
| agaaaccgcg gtcgaagtag gtaacctgct ggcggatctg atcagcgagt ccggtaaacg | 1560 |
| tgctgtgatc atcgcaagct ctgatttcac ccactatgag acggctgaac gtgccaaaga | 1620 |
| aatcgattcc gaagttattg attctatcct gaactttgac atctctggca tgtacgatcg | 1680 |
| cctgtatcgc cgtaacgcct ctgtttgcgg ttacggcccg atcaccgcta tgctgacggc | 1740 |
| aagcaaaaag ctgggcggct ctcgtgcgac tttgctgaaa tacgcaaaca gcggtgacgt | 1800 |
| gtccggtgat aaagacgctg tggtgggcta cgccgccatc atcgttgagt aagctgatta | 1860 |
| aaggttgaac agataggatt tcgtcatgga tcctacaagg aggaaaaaaa catgaatgct | 1920 |
| tctaatgaac cggtgattct gaaactgggt ggctctgcta ttaccgacaa aggtgcctac | 1980 |
| gaaggcgtag ttaaggaagc tgatttgctg cgcatcgcac aggaagttag cggtttccgt | 2040 |
| ggcaagatga tcgtggttca tggtgctggt agcttcggcc atacgtacgc gaagaaatac | 2100 |
| ggcctggacc gtaccttcga cccagagggc gcaattgtta ctcatgaatc tgttaaaaag | 2160 |
| ctcgcctcca aagttgtagg tgctctgaat agcttcggcg tgcgtgctat cgcggtgcat | 2220 |
| cctatggact gcgcagtatg ccgtaacggt cgtatcgaaa cgatgtatct ggactccatc | 2280 |
| aagttaatgc tggaaaaagg tctggtgccg gttctgcacg gcgacgtcgc aatggatatt | 2340 |
| gaactgggca cttgtatcct gtccggtgat caaatcgttc cttacctggc caaagaactg | 2400 |
| ggtatctccc gcctcggcct gggcagcgca gaggatggtg tgctggatat ggagggcaaa | 2460 |
| cctgtaccgg aaatcacccc agaaactttc gaagagttcc gccactgcat cggtggttct | 2520 |
| ggttctactg atgtaaccgg tggcatgctg ggcaaagtgc tggaacttct ggaattgagc | 2580 |
| aaaaattctt ccattactag ctacattttc aacgctggta aagcagacaa catctaccgc | 2640 |
| tttctgaatg gtgagtccat cggcactcgc atcagcccgg acaagcgtgt ttaagctagt | 2700 |
| tattaaccta aatgctctaa accagttatg agctctacaa ggaggaaaaa aacatgatta | 2760 |
| acactaccag ccgccgcaaa attgaacacc tgaaactctg cgcagaatcc ccggttgaag | 2820 |
| cgcgtcaggt atctgccggc tttgaagacg ttactctgat ccaccgcgct ttaccggagc | 2880 |
| tgaacatgga tgaactggac ctcagcgttg atttcctggg taaacgcatc aaagcgccgt | 2940 |
| tcctgattgc gtctatcacg ggtggtcacc cagataccat cccggttaac gctgcgctgg | 3000 |
| cagctgctgc tgaggagctg ggtgttggca tcggcgttgg ctctcagcgc gcggccattg | 3060 |
| atgatccgag ccaggaagac agcttccgtg tagtgcgtga tgaagcccca gatgcgtttg | 3120 |
| tttatggcaa cgtcggcgca gcacagatcc gtcagtatgg tgttgaaggt gttgaaaaac | 3180 |
| tgatcgaaat gattgacgca gatgccttgg caatccacct gaactttctg caagaagcgg | 3240 |
| tccaaccgga aggtgaccgc gacgcgaccg gttgcctgga catgattacc gaaatttgct | 3300 |
| ctcagattaa aactccggta atcgtgaaag aaaccggtgc aggcattagc cgtgaagatg | 3360 |
| cgattctgtt ccagaaagct ggcgtgagcg caatcgacgt tggcggcgcg ggcggcacct | 3420 |
| cctgggctgg cgtcgaggtc taccgtgcta agaaagccg tgactctgtt agcgagcgtt | 3480 |
| taggtgagct gttttgggat tcggcattc cgacggtagc ttctctgatt gaatcccgcg | 3540 |
| tttccttgcc gctgatcgca accggcgta tccgtaacgg tctggacatt gctaaaagca | 3600 |
| ttgctctcgg cgcaagcgct gccagcgccg ctctgccgtt cgttggtccg tccctggagg | 3660 |
| gcaaagaatc cgttgtacgt gtgctgagct gcatgctgga agaatttaaa gcagcaatgt | 3720 |
| ttttgtgcgg ttgcggcaac atcaaagacc tgcacaactc tccagtagtg gtaactggtt | 3780 |

```
ggacccgcga ataccggag cagcgcggtt ttaacgttaa ggacctctcc ctgccgggca    3840
acgctctgta agcttcaacg cgtctacaaa taaaaaaggc acgtcagatg acgtgccttt    3900
tttcttgtct aga                                                       3913
```

<210> SEQ ID NO 103
<211> LENGTH: 6848
<212> TYPE: DNA
<213> ORGANISM: Artificial Sequence
<220> FEATURE:
<223> OTHER INFORMATION: Synthetic Construct

<400> SEQUENCE: 103

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgtgc     420
gacctcttct caattactc agattaccga gcataattcc cgtcgttccg caaactatca     480
gccaaacctg tggaatttcg aattcctgca atccctggag aacgacctga agtggaaaa     540 gctggaggag aaagcgacca aactggagga agaagttcgc tgcatgatca accgtgtaga     600
cacccagccg ctgtccctgc tggagctgat cgacgatgtg cagcgcctgg gtctgaccta     660
caaatttgaa aaagacatca ttaaagcccct ggaaaacatc gtactgctgg acgaaaacaa     720
aaagaacaaa tctgacctgc acgcaaccgc tctgtctttc cgtctgctgc gtcagcacgg     780
tttcgaggtt tctcaggatg ttttttgagcg tttcaaggat aaagaaggtg gtttcagcgg     840
tgaactgaaa ggtgacgtcc aaggcctgct gagcctgtat gaagcgtctt acctgggttt     900
cgagggtgag aacctgctgg aggagcgcg taccttttcc atcacccacc tgaagaacaa     960
cctgaaagaa ggcattaata ccaaggttgc agaacaagtg agccacgccc tggaactgcc    1020
atatcaccag cgtctgcacc gtctggaggc acgttggttc ctggataaat acgaaccgaa    1080
agaaccgcat caccagctgc tgctggagct ggcgaagctg gattttaaca tggtacagac    1140
cctgcaccag aaagagctgc aagatctgtc ccgctggtgg accgagatgg gcctggctag    1200
caaactggat tttgtacgcg accgcctgat ggaagtttat ttctgggcac tgggtatggc    1260
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga agagaaaagg    1500
tcataacaac ctgtcctatc tgacgaaaag ctggcgtgaa ctgtgcaaag cctttctgca    1560
agaggcgaaa tggtccaaca caaaaattat cccggctttc tccaagtacc tggaaaacgc    1620
cagcgtttcc tcctccggtg tagcgctgct ggcgccgtct acttttccg tatgccagca    1680 gcaggaagac atccccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
```

```
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgaccctttc ccgattaacc agctgatgta    2100
tgtctaactg cataaaggag gtaaaaaaac atggtatcct gttctgcgcc gggtaagatt    2160
tacctgttcg gtgaacacgc cgtagtttat ggcgaaactg caattgcgtg tgcggtggaa    2220
ctgcgtaccc gtgttcgcgc ggaactcaat gactctatca ctattcagag ccagatcggc    2280
cgcaccggtc tggatttcga aaagcaccct tatgtgtctg cggtaattga gaaaatgcgc    2340
aaatctattc ctattaacgg tgttttcttg accgtcgatt ccgacatccc ggtgggctcc    2400
ggtctgggta gcagcgcagc cgttactatc gcgtctattg gtgcgctgaa cgagctgttc    2460
ggctttggcc tcagcctgca agaaatcgct aaactgggcc acgaaatcga attaaagta    2520 cagggtgccg cgtccccaac cgatacgtat gtttctacct tcggcggcgt ggttaccatc    2580
ccggaacgtc gcaaactgaa aactccggac tgcggcattg tgattggcga taccggcgtt    2640
ttctcctcca ccaaagagtt agtagctaac gtacgtcagc tgcgcgaaag ctacccggat    2700
ttgatcgaac cgctgatgac ctctattggc aaaatctctc gtatcggcga caactggtt    2760 ctgtctggcg actacgcatc catcggccgc ctgatgaacg tcaaccaggg tctcctggac    2820
gccctgggcg ttaacatctt agaactgagc cagctgatct attccgctcg tgcggcaggt    2880
gcgtttggcg ctaaaatcac gggcgctggc ggcggtggct gtatggttgc gctgaccgct    2940
ccggaaaaat gcaaccaagt ggcagaagcg gtagcaggcg ctggcggtaa agtgactatc    3000
actaaaccga ccgagcaagg tctgaaagta gattaaagtc tagttaaagt ttaaacggtc    3060
tccagcttgg ctgttttggc ggatgagaga agattttcag cctgatacag attaaatcag    3120
aacgcagaag cggtctgata aaacagaatt tgcctggcgg cagtagcgcg gtggtcccac    3180
ctgaccccat gccgaactca gaagtgaaac gccgtagcgc cgatggtagt gtggggtctc    3240
cccatgcgag agtagggaac tgccaggcat caaataaaac gaaaggctca gtcgaaagac    3300
tgggcctttc gttttatctg ttgtttgtcg gtgaacgctc tcctgagtag gacaaatccg    3360
ccgggagcgg atttgaacgt tgcgaagcaa cggcccggag ggtggcgggc aggacgcccg    3420
ccataaactg ccaggcatca aattaagcag aaggccatcc tgacggatgg ccttttttgcg    3480 tttctacaaa ctcttttttgt ttattttttct aaatacattc aaatatgtat ccgcttaacc    3540
ggaattgcca gctggggcgc cctctggtaa ggttgggaag ccctgcaaag taaactggat    3600
ggctttctcg ccgccaagga tctgatgcg caggggatca agctctgatc aagagacagg    3660
atgaggatcg tttcgcatga ttgaacaaga tggattgcac gcaggttctc cggccgcttg    3720
ggtggagagg ctattcggct atgactgggc acaacagaca atcggctgct ctgatgccgc    3780
cgtgttccgg ctgtcagcgc aggggcgccc ggttcttttt gtcaagaccg acctgtccgg    3840
tgccctgaat gaactgcaag acgaggcagc gcggctatcg tggctggcca cgacgggcgt    3900
tccttgcgca gctgtgctcg acgttgtcac tgaagcggga agggactggc tgctattggg    3960
cgaagtgccg gggcaggatc tcctgtcatc tcaccttgct cctgccgaga agtatccat    4020 catggctgat gcaatgcggc ggctgcatac gcttgatccg gctacctgcc cattcgacca    4080
ccaagcgaaa catcgcatcg agcgagcacg tactcggatg gaagccggtc ttgtcgatca    4140
ggatgatctg gacgaagagc atcaggggct cgcgccagcc gaactgttcg ccaggctcaa    4200
ggcgagcatg cccgacggcg aggatctcgt cgtgacccat ggcgatgcct gcttgccgaa    4260
tatcatggtg gaaaatggcc gcttttctgg attcatcgac tgtggccggc tgggtgtggc    4320
```

```
ggaccgctat caggacatag cgttggctac ccgtgatatt gctgaagagc ttggcggcga   4380
atgggctgac cgcttcctcg tgctttacgg tatcgccgct cccgattcgc agcgcatcgc   4440
cttctatcgc cttcttgacg agttcttctg acgcatgacc aaaatcccctt aacgtgagtt   4500
ttcgttccac tgagcgtcag accccgtaga aagatcaaa ggatcttctt gagatccttt    4560
ttttctgcgc gtaatctgct gcttgcaaac aaaaaaacca ccgctaccag cggtggtttg   4620
tttgccggat caagagctac caactctttt tccgaaggta actggcttca gcagagcgca   4680
gataccaaat actgtccttc tagtgtagcc gtagttaggc caccacttca agaactctgt   4740
agcaccgcct acatacctcg ctctgctaat cctgttacca gtggctgctg ccagtggcga   4800
taagtcgtgt cttaccgggt tggactcaag acgatagtta ccggataagg cgcagcggtc   4860
gggctgaacg gggggttcgt gcacacagcc cagcttggag cgaacgacct acaccgaact   4920
gagataccta cagcgtgagc tatgagaaag cgccacgctt cccgaaggga gaaaggcgga   4980
caggtatccg gtaagcggca gggtcggaac aggagagcgc acgagggagc ttccagggggg  5040
aaacgcctgg tatctttata gtcctgtcgg gtttcgccac ctctgacttg agcgtcgatt   5100
tttgtgatgc tcgtcagggg ggcggagcct atggaaaaac gccagcaacg cggccttttt   5160
acggttcctg gccttttgct ggccttttgc tcacatgttc tttcctgcgt tatcccctga   5220
ttctgtggat aaccgtatta ccgcctttga gtgagctgat accgctcgcc gcagccgaac   5280
gaccgagcgc agcgagtcag tgagcgagga agcggaagag cgcctgatgc ggtattttct   5340
ccttacgcat ctgtgcggta tttcacaccg catatggtgc actctcagta caatctgctc   5400
tgatgccgca tagttaagcc agtatacact ccgctatcgc tacgtgactg ggtcatggct   5460
gcgccccgac acccgccaac acccgctgac gcgccctgac gggcttgtct gctcccggca   5520
tccgcttaca gacaagctgt gaccgtctcc gggagctgca tgtgtcagag gttttcaccg   5580
tcatcaccga aacgcgcgag gcagcagatc aattcgcgcg cgaaggcgaa gcggcatgca   5640
tttacgttga caccatcgaa tggtgcaaaa cctttcgcgg tatggcatga tagcgcccgg   5700
aagagagtca attcagggtg gtgaatgtga accagtaac gttatacgat gtcgcagagt    5760
atgccggtgt ctcttatcag accgtttccc gcgtggtgaa ccaggccagc cacgtttctg   5820
cgaaaacgcg ggaaaaagtg gaagcggcga tggcggagct gaattacatt cccaaccgcg   5880
tggcacaaca actggcgggc aaacagtcgt tgctgattgg cgttgccacc tccagtctgg   5940
ccctgcacgc gccgtcgcaa attgtcgcgg cgattaaatc tcgcgccgat caactgggtg   6000
ccagcgtggt ggtgtcgatg gtagaacgaa gcggcgtcga agcctgtaaa gcggcggtgc   6060
acaatcttct cgcgcaacgc gtcagtgggc tgatcattaa ctatccgctg gatgaccagg   6120
atgccattgc tgtggaagct gcctgcacta atgttccggc gttatttctt gatgtctctg   6180
accagacacc catcaacagt attatttttct cccatgaaga cggtacgcga ctgggcgtgg   6240
agcatctggt cgcattgggt caccagcaaa tcgcgctgtt agcgggccca ttaagttctg   6300
tctcggcgcg tctgcgtctg gctggctggc ataaatatct cactcgcaat caaattcagc   6360
cgatagcgga acgggaaggc gactggagtg ccatgtccgg ttttcaacaa accatgcaaa   6420
tgctgaatga gggcatcgtt cccactgcga tgctggttgc caacgatcag atggcgctgg   6480
gcgcaatgcg cgccattacc gagtccggc tgcgcgttgg tgcggatatc tcggtagtgg    6540
gatacgacga taccgaagac agctcatgtt atatcccgcc gtcaaccacc atcaaacagg   6600
attttcgcct gctggggcaa accagcgtgg accgcttgct gcaactctct cagggccagg   6660
cggtgaaggg caatcagctg ttgcccgtct cactggtgaa aagaaaaacc accctggcgc   6720
```

```
ccaatacgca aaccgcctct ccccgcgcgt tggccgattc attaatgcag ctggcacgac    6780
aggtttcccg actggaaagc gggcagtgag cgcaacgcaa ttaatgtgag ttagcgcgaa    6840
ttgatctg                                                            6848
```

<210> SEQ ID NO 104
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 104

```
aagggcgagc tcaacgatcc ggctgctaac aaagcccgaa aggaagctga gttggctgct      60
gccaccgctg agcaataact agcataaccc cttggggcct ctaaacgggt cttgaggagt     120
tttttgctga aaggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aaccccctatt tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcagggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat tgggcgaagt     840
gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080
catgcccgac ggcgaggatc tcgtcgtgac acatggcgat gcctgcttgc cgaatatcat    1140
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctggggt tcgaaatgac cgaccaagcg    1380
acgcctaact gtcagaccaa gtttactcat atatacttta gattgattta aacttcatt    1440 tttaatttaa aaggatctag gtgaagatcc ttttttgataa tctcatgacc aaaatccctt    1500
aacgtgagtt ttcgttccac tgagcgtcag accccgtaga aaagatcaaa ggatcttctt    1560
gagatccttt tttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
```

-continued

```
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg ggcggagcct atggaaaaac gccagcaacg    2160
cggccttttt acggttcctg gccttttgct ggccttttgc tcacatgttc tttcctgcgt    2220
tatcccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt ttcctgtttg    2760
gtcactgatg cctccgtgta aggggggattt ctgttcatgg gggtaatgat accgatgaaa    2820
cgagagagga tgctcacgat acgggttact gatgatgaac atgcccggtt actggaacgt    2880
tgtgagggta acaactggc ggtatggatg cggcggacc agagaaaaat cactcagggt    2940
caatgccagc gcttcgttaa tacagatgta ggtgttccac agggtagcca gcagcatcct    3000
gcgatgcaga tccggaacat aatggtgcag gcgctgact tccgcgtttc cagactttac    3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480
tccatgccaa cccgttccat gtgctcgccg aggcggcata atcgccgtg acgatcagcg    3540
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa atgacccaga    3900
gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
```

```
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctc ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct cgcatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctcccta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580
aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
gccagatcgg ccgcaccggt ctggatttcg aaaagcaccc ttatgtgtct gcggtaattg    5940
agaaaatgcg caaatctatt cctattaacg gtgttttctt gaccgtcgat tccgacatcc    6000
cggtgggctc cggtctgggt agcagcgcag ccgttactat cgcgtctatt ggtgcgctga    6060
acgagctgtt cggctttggc ctcagcctgc aagaaatcgc taaactgggc cacgaaatcg    6120
aaattaaagt acagggtgcc gcgtcccaa ccgatacgta tgtttctacc ttcggcggcg    6180
tggttaccat cccggaacgt cgcaaactga aaactccgga ctgcggcatt gtgattggcg    6240
ataccggcgt tttctcctcc accaaagagt tagtagctaa cgtacgtcag ctgcgcgaaa    6300
gctacccgga tttgatcgaa ccgctgatga cctctattgg caaaatctct cgtatcggcg    6360
aacaactggt tctgtctggc gactacgcat ccatcggccg cctgatgaac gtcaaccagg    6420
gtctcctgga cgccctgggc gttaacatct agaactgag ccagctgatc tattccgctc    6480
gtgcggcagg tgcgtttggc gctaaaatca cgggcgctgg cggcggtggc tgtatggttg    6540
cgctgaccgc tccggaaaaa tgcaaccaag tggcagaagc ggtagcaggc gctggcggta    6600
aagtgactat cactaaaccg accgagcaag gtctgaaagt agattaa                  6647
```

<210> SEQ ID NO 105

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 105
caccatggta tcctgttctg cg                                              22

<210> SEQ ID NO 106
<211> LENGTH: 22
<212> TYPE: DNA
<213> ORGANISM: Artificial Sequence
<220> FEATURE:
<223> OTHER INFORMATION: Synthetic Construct

<400> SEQUENCE: 106
ttaatctact ttcagacctt gc                                              22

<210> SEQ ID NO 107
<211> LENGTH: 66
<212> TYPE: DNA
<213> ORGANISM: Artificial Sequence
<220> FEATURE:
<223> OTHER INFORMATION: Synthetic Construct

<400> SEQUENCE: 107
gcgaacgatg cataaaggag gtaaaaaaac atggtatcct gttctgcgcc gggtaagatt     60
tacctg                                                                66

<210> SEQ ID NO 108
<211> LENGTH: 48
<212> TYPE: DNA
<213> ORGANISM: Artificial Sequence
<220> FEATURE:
<223> OTHER INFORMATION: Synthetic Construct

<400> SEQUENCE: 108
gggcccgttt aaactttaac tagactttaa tctactttca gaccttgc                  48

<210> SEQ ID NO 109
<211> LENGTH: 45
<212> TYPE: DNA
<213> ORGANISM: Artificial Sequence
<220> FEATURE:
<223> OTHER INFORMATION: Synthetic Construct

<400> SEQUENCE: 109
accgttcgtt cttatcgaaa ctaaaaaaaa ccggccttgg ccccg                     45
```

REDUCTION OF CARBON DIOXIDE EMISSION DURING ISOPRENE PRODUCTION BY FERMENTATION

CROSS-REFERENCE TO RELATED APPLICATIONS

This application claims benefit to U.S. Provisional patent application 61/097,200, filed on Sep. 15, 2008, the contents of which are hereby incorporated by reference in its entirety.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

The invention provides compositions and methods for isoprene and production of isoprene. In one aspect, the invention provides cells comprising a heterologous nucleic acid that encodes an isoprene synthase polypeptide in operable combination with a promoter wherein the cells are in culture medium comprising one or more uncommon carbon sources and wherein the ratio of carbon dioxide emitted per isoprene produced in off gas from the cultured cells is less than 500. In one embodiment, the culture medium comprises one or more carbon sources selected from the group consisting of carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, microbial polypeptide, plant protein polypeptide, yeast extract, one or more components from a yeast extract, algae, and algae components.

In another aspect, the invention features cells in culture that produce isoprene. In some embodiments, the invention provides cells in culture that produce greater than about 400 nmole of isoprene/gram wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the carbon source is synthesized from carbon dioxide. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1). Thus the present invention provides methods for one or both of recycling carbon dioxide and reducing carbon dioxide emission during biological production of isoprene.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1).

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1). In some embodiments, the invention provides for compositions comprising any of the cells disclosed herein.

In one aspect, the invention features methods of producing isoprene, such as methods of using any of the cells described herein to produce isoprene. In one aspect, the invention features methods of producing isoprene (a) culturing cells comprising a heterologous nucleic acid that encodes an isoprene synthase polypeptide in operable combination with a promoter wherein the cells are in culture medium comprising one or more uncommon carbon sources and wherein the ratio of carbon dioxide emitted per isoprene produced in off gas from the cultured cells is less than 500 in culture medium under conditions suitable for the production of isoprene, wherein the culture medium comprises one or more uncommon carbon sources and the cells comprise a heterologous nucleic acid that encodes an isoprene synthase polypeptide in operable combination with a promoter; and (b) producing isoprene, wherein the ratio of carbon dioxide emitted per isoprene produced in off gas from the cultured cells is less than 500.

In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1). In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, the method includes culturing cells under conditions sufficient to convert more than about 0.002% of the carbon (mol/mol) in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1).

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol(trans-3,7-dimethyl-2,6-octadien-1-ol) and citronellol(3,7-dimethyl-6-octen-1-ol)) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments the composition also has greater than about 2 mg of isoprene.

In some embodiments, the composition has one or more compounds selected from the group consisting of ethanol, acetone, C5 prenyl alcohols, and isoprenoid compounds with 10 or more carbon atoms. In some embodiments, the composition has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the composition has greater than about 2 mg of isoprene and has one or more compounds selected from the group consisting of ethanol, acetone, C5 prenyl alcohols, and isoprenoid compounds with 10 or more carbon atoms.

In some embodiments, the composition includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to the amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w).

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5, 10, 20, 30, 40, 50, 60, 70, 80, 90, 100 ug/L of isoprene when normalized to 1 mL of 1 $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol(trans-3,7-dimethyl-2,6-octadien-1-ol) and citronellol(3,7-dimethyl-6-octen-1-ol)) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol(trans-3,7-dimethyl-2,6-octadien-1-ol) and citronellol (3,7-dimethyl-6-octen-1-ol) by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments the volatile organic fraction of the gas phase also has greater than about 2 mg of isoprene.

In some embodiments, the volatile organic fraction of the gas phase has one or more compounds selected from the group consisting of ethanol, acetone, C5 prenyl alcohols, and isoprenoid compounds with 10 or more carbon atoms. In some embodiments, the volatile organic fraction of the gas phase has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the volatile organic fraction of the gas phase has greater than about 2 mg of isoprene and has one or more compounds selected from the group consisting of ethanol, acetone, C5 prenyl alcohols, and isoprenoid compounds with 10 or more carbon atoms.

In some embodiments, the volatile organic fraction of the gas phase has includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w) in the volatile organic fraction of the gas phase.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene. In another aspect, the invention provides methods of manufacturing a tire wherein the improvement comprises using any one or more the compositions, cells, systems and/or methods described herein to produce isoprene for the manufacture of the tire.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid). In any of the embodiments, the MVA pathway nucleic acid encodes for mevalonate kinase.

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides, Populus alba, Populus nigra, Populus trichocarpa*, or the hybrid, *Populus alba×Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIG. 3 is the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIG. 5 is the nucleotide sequence of pETNHisKudzu (SEQ ID NO:5).

FIG. 7 is the nucleotide sequence of pCL-lac-Kudzu (SEQ ID NO:7).

FIG. 9A is a graph showing OD over time of fermentation of *E. coli* BL21/pTrcKudzu in a 14 liter fed batch fermentation.

FIG. 9B is a graph showing isoprene production over time of fermentation of *E. coli* BL21/pTrcKudzu in a 14 liter fed batch fermentation.

FIG. 12 is the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIG. 15 is the nucleotide sequence of vector pSPZ1 (MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba×Populus tremula*) isoprene synthase gene (SEQ ID NO:13). The ATG start codon is in bold and the stop codon is underlined.

FIGS. 18A1 and 18A2 show a schematic outlining construction of vectors pYLA 1, pYL1 and pYL2 (SEQ ID NO: 79, 77, 76, 75) and (SEQ ID NO: 74, 73), respectively.

FIG. 22 is the nucleotide sequence of pTrcKudzu yIDI DXS Kan (SEQ ID NO:20).

FIG. 23C is a graph showing production of isoprene from glucose in BL21/pTrcKudzu DXS kan. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).

FIG. 25 is a nucleotide sequence of pTrcKKDyIkIS kan (SEQ ID NO:33).

FIGS. 27A-27D is a nucleotide sequence of pCL PtrcUpperPathway (SEQ ID NO:46).

FIG. 29 is a nucleotide sequence of cassette containing the lower MVA pathway and yeast idi for integration into the *B. subtilis* chromosome at the nprE locus (SEQ ID NO:47).

FIG. 31 is a nucleotide sequence of p9796-poplar (SEQ ID NO:48).

FIG. 33 is a nucleotide sequence of pTrcPoplar (SEQ ID NO:49).

FIG. 35 is a nucleotide sequence of pTrcKudzu yIDI Kan (SEQ ID NO:50).

FIG. 37 is a nucleotide sequence of pTrcKudzuDXS Kan (SEQ ID NO:51).

FIG. 39 is a nucleotide sequence of pCL PtrcKudzu (SEQ ID NO:52).

FIG. 41 is a nucleotide sequence of pCL PtrcKudzu A3 (SEQ ID NO:53).

FIG. 43 is a nucleotide sequence of pCL PtrcKudzu yIDI (SEQ ID NO:54).

FIG. 45 is a nucleotide sequence of pCL PtrcKudzu DXS (SEQ ID NO:55).

FIG. 51 is the nucleotide sequence of pJMupperpathway2 (SEQ ID NO:56).

FIGS. 62A-62C are the time courses of optical density, mevalonic acid titer, and specific productivity within the 15-L bioreactor fed with glucose.

FIGS. 65A-65C are the time courses of optical density, isoprene titer, and specific productivity within the 15-L bioreactor fed with glucose.

FIGS. 66A-66C are the time courses of optical density, isoprene titer, and specific productivity within the 15-L bioreactor fed with glucose.

FIG. 75A is a table of the conversion of the CAFT Model results from weight percent to volume percent for series A.

FIG. 76A is a table of the conversion of the CAFT Model results from weight percent to volume percent for series B.

FIG. 78A is a graph of the flammability Curve for Test Series 1: 0% Steam, 0 psig, and 40° C.

FIG. 78B is a table summarizing the explosion and non-explosion data points for Test Series 1.

FIG. 78C is a graph of the flammability curve for Test Series 1 compared with the CAFT Model.

FIG. 79B is a table summarizing the explosion and non-explosion data points for Test Series 2.

FIGS. 80A and 80B are a table of the detailed experimental conditions and results for Test Series 1.

FIG. 81 is a table of the detailed experimental conditions and results for Test Series 2.

FIGS. 86B and 86C provide the nucleotide sequence of the *M. mazei* archeal lower pathway operon (SEQ ID NO:102).

FIGS. 87B and 87C provide the nucleotide sequence of MCM382-pTrcKudzuMVK(mazei) (SEQ ID NO:103).

FIGS. 88B and 88C provide the nucleotide sequence of MCM376-MVK from *M. mazei* archeal Lowerin pET200D (SEQ ID NO:104).

FIG. 90 shows the structures of several impurities that are structurally similar to isoprene and may also act as polymerization catalyst poisons.

FIGS. 92A-92C are the nucleotide sequence of pTrcHis2AUpperPathway (also called pTrcUpperMVA) (SEQ ID NO:86).

FIG. 93 is a time course of optical density within the 15-L bioreactor fed with glucose.

FIG. 94 is a time course of isoprene titer within the 15-L bioreactor fed with glucose. The titer is defined as the amount of isoprene produced per liter of fermentation broth.

FIG. 95 is a time course of total isoprene produced from the 15-L bioreactor fed with glucose.

FIG. 96 is a time course of optical density within the 15-L bioreactor fed with invert sugar.

FIG. 97 is a time course of isoprene titer within the 15-L bioreactor fed with invert sugar. The titer is defined as the amount of isoprene produced per liter of fermentation broth.

FIG. 98 is a time course of total isoprene produced from the 15-L bioreactor fed with invert sugar.

FIG. 99 is a time course of optical density within the 15-L bioreactor fed with glucose.

FIG. 100 is a time course of isoprene titer within the 15-L bioreactor fed with glucose. The titer is defined as the amount of isoprene produced per liter of fermentation broth.

FIG. 101 is a time course of isoprene specific activity from the 15-L bioreactor fed with glucose.

FIG. 102 is a map of pCLPtrcUpperPathwayHGS2 (also referred to as pCL UpperHGS2).

FIGS. 103A-103C are the nucleotide sequence of pCLPtrcUpperPathwayHGS2 (SEQ ID NO:87).

Figure 104:
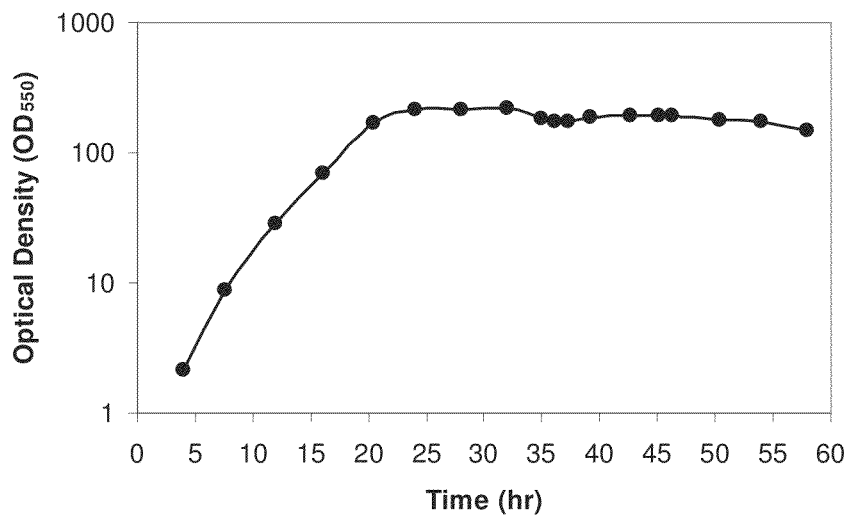

FIG. 104 is a time course of optical density within the 15-L bioreactor fed with glucose.

Figure 105:
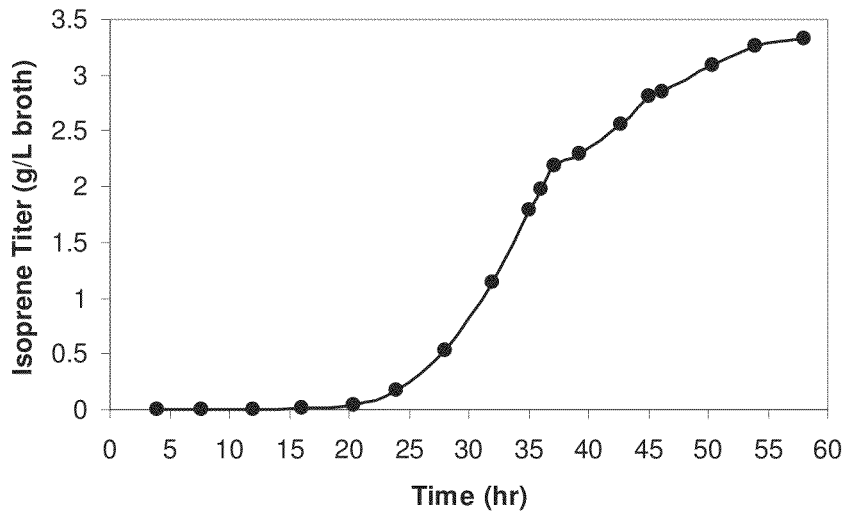

FIG. 105 is a time course of isoprene titer within the 15-L bioreactor fed with glucose. The titer is defined as the amount of isoprene produced per liter of fermentation broth.

Figure 106:
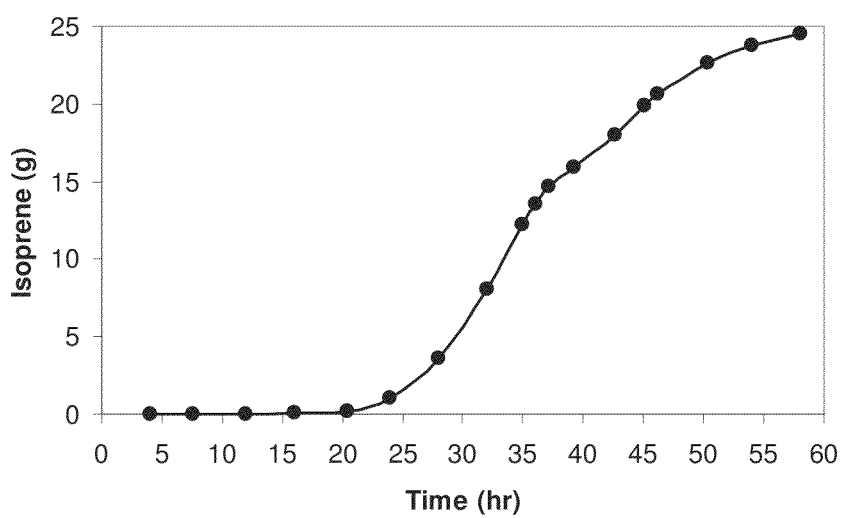

FIG. 106 is a time course of total isoprene produced from the 15-L bioreactor fed with glucose.

Figure 107:
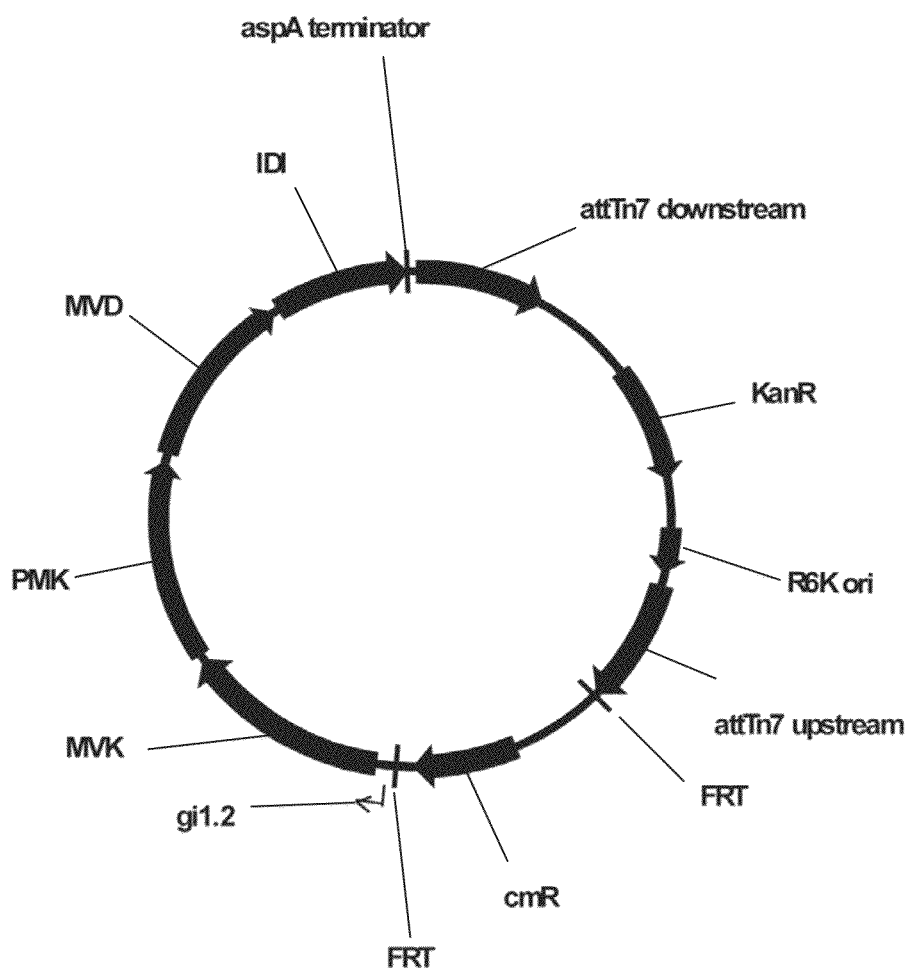

FIG. 107 is a map of plasmid MCM330.

FIGS. 108A-108C are the nucleotide sequence of plasmid MCM330 (SEQ ID NO:90).

Figure 109:
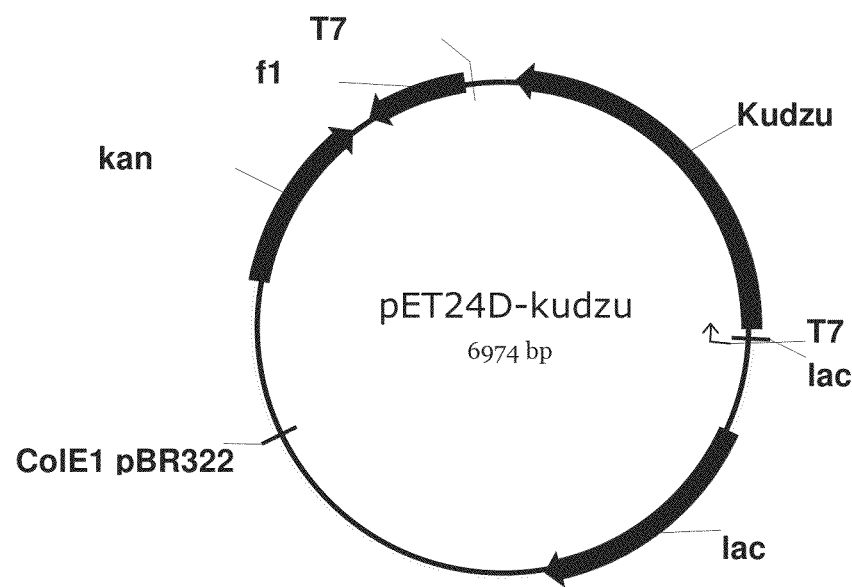

FIG. 109 is a map of pET24D-Kudzu.

FIGS. 110A and 110B are the nucleotide sequence of pET24D-Kudzu (SEQ ID NO:101).

Figure 111A:
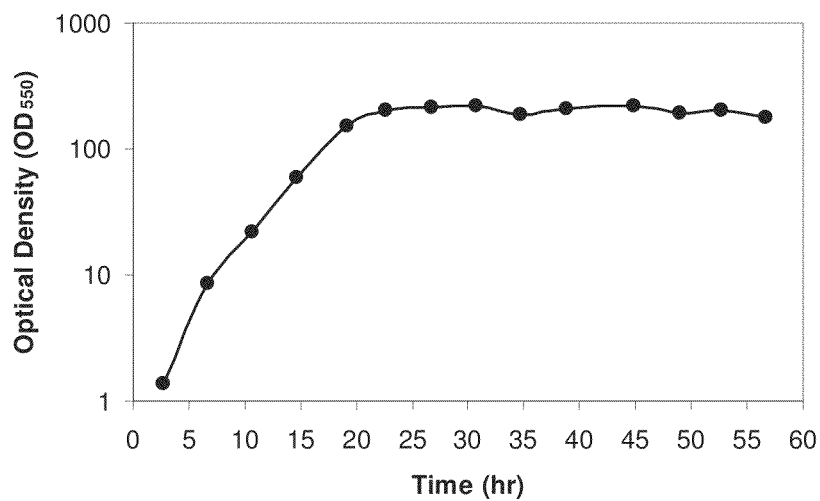

FIG. 111A is a time course of optical density within the 15-L bioreactor fed with glucose.

Figure 111B:
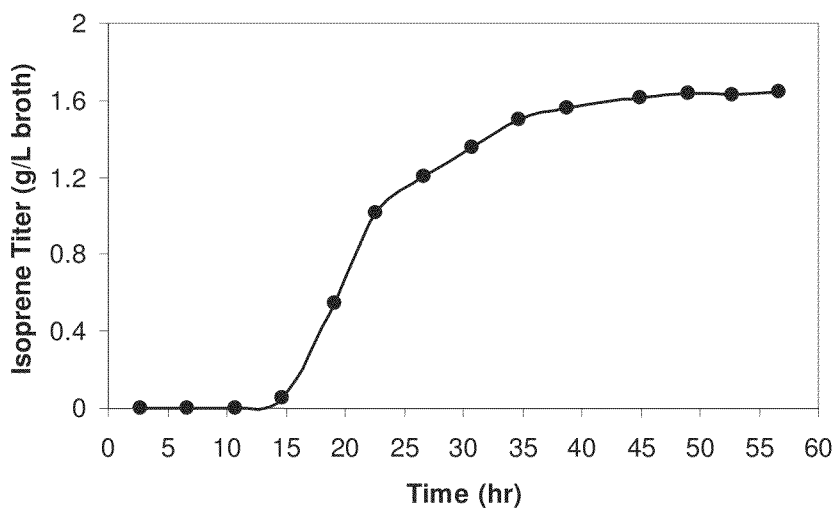

FIG. 111B is a time course of isoprene titer within the 15-L bioreactor fed with glucose. The titer is defined as the amount of isoprene produced per liter of fermentation broth.

Figure 111C:
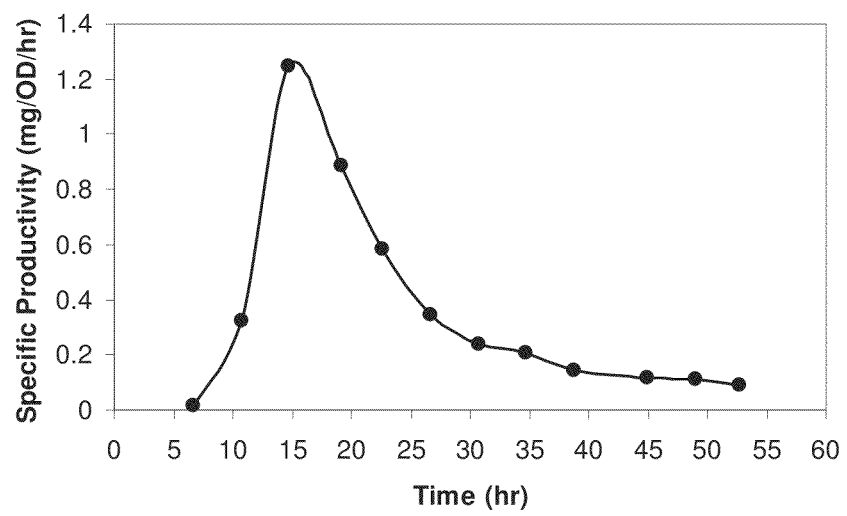

FIG. 111C is a time course of specific productivity of isoprene in the 15-L bioreactor fed with glucose.

Figure 112A:
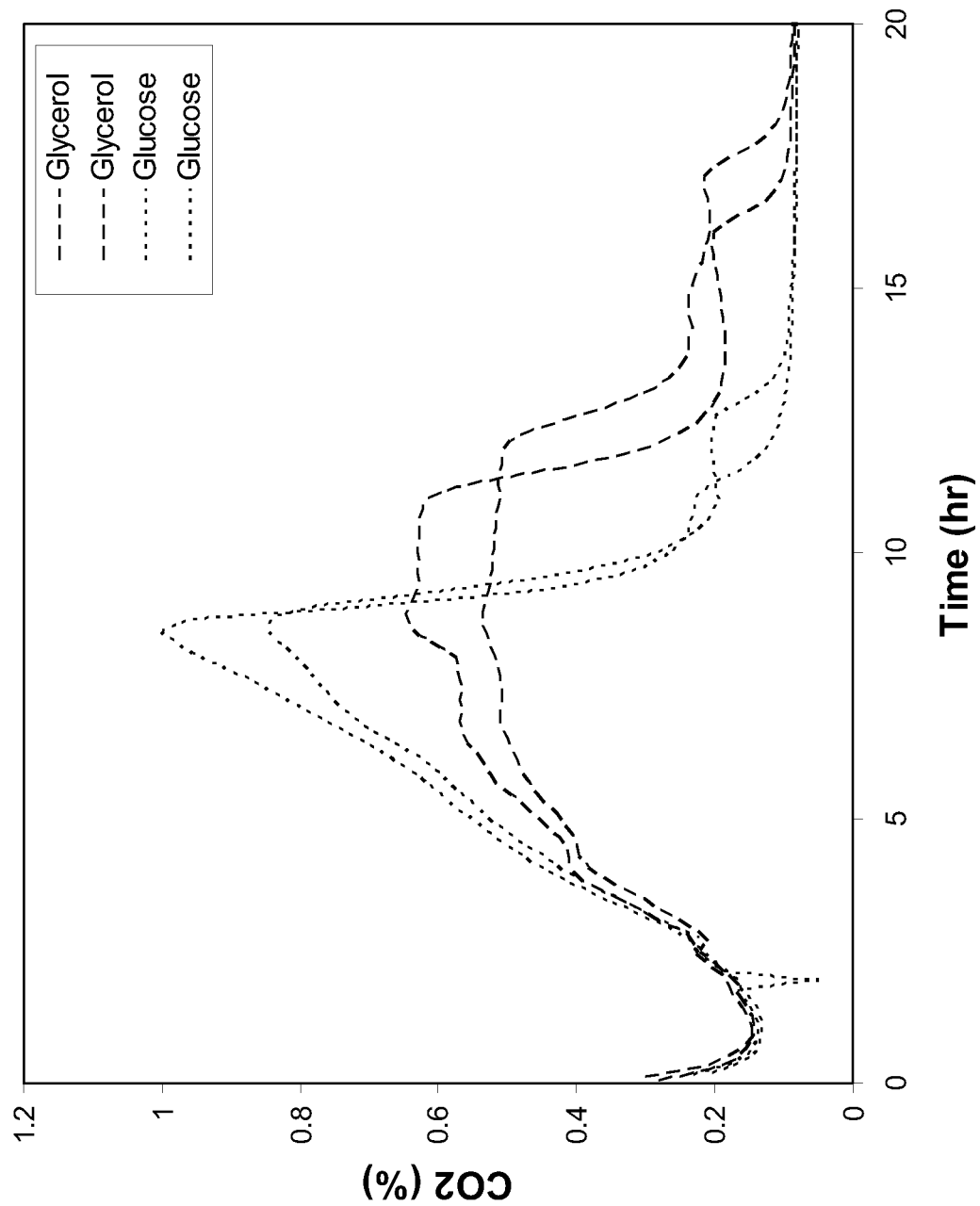
Figure 112B:
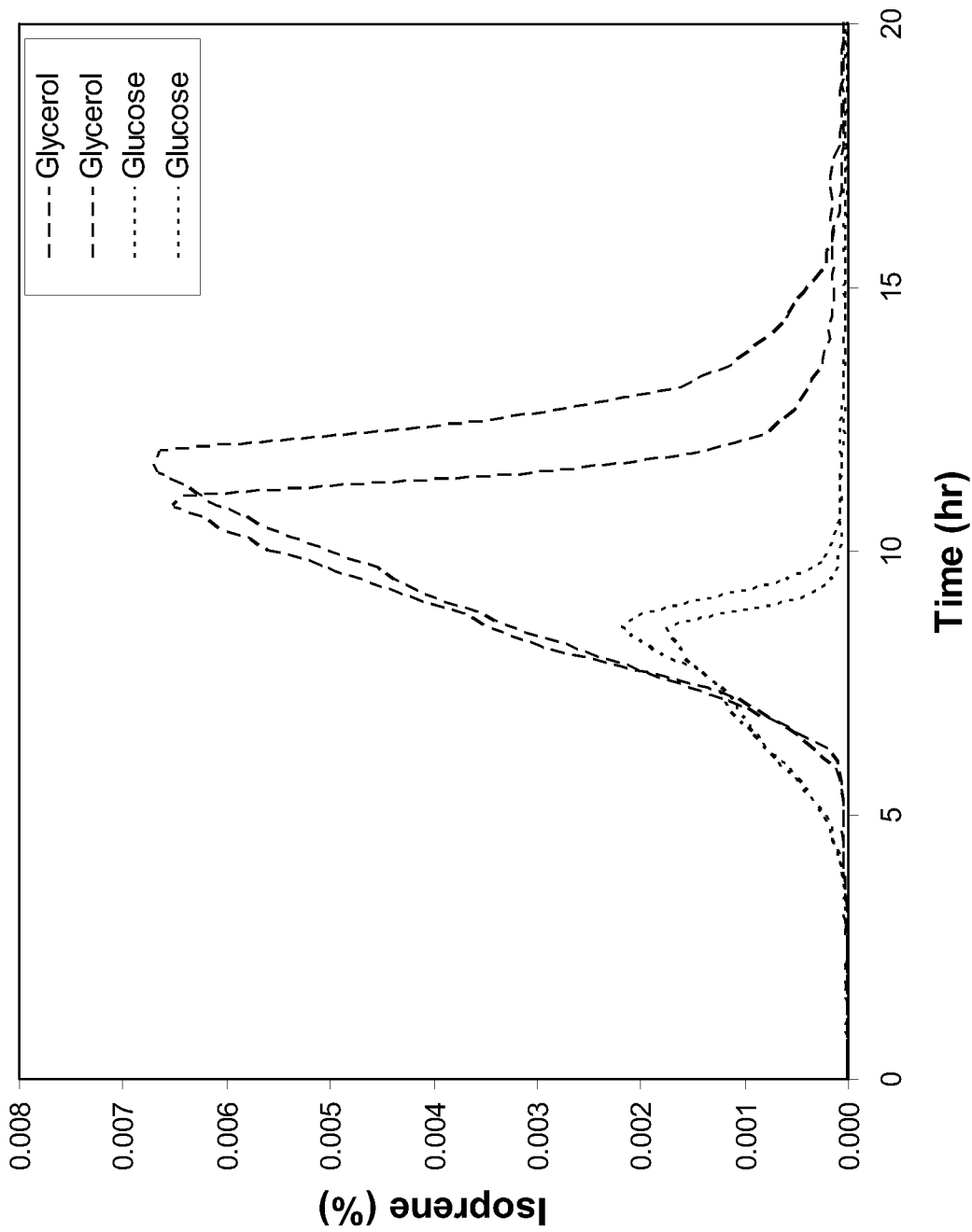

FIGS. 112A and 112B provide graphs showing carbon dioxide emission and isoprene production, respectively, during growth of MCM127 cells in culture medium containing either glycerol or glucose as a carbon source.

DETAILED DESCRIPTION OF THE INVENTION

In one aspect, the invention features compositions and methods for the production of isoprene in increased amounts and/or purity. As used herein, the term "isoprene" or "2-methyl-1,3-butadiene" (CAS #78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol(trans-3,7-dimethyl-2,6-octadien-1-ol) and citronellol(3,7-dimethyl-6-octen-1-ol) (FIG. 90). In some embodiments, the isoprene composition of the invention is substantially free of any contaminating unsaturated C5 hydrocarbons. No detectable amount of unsaturated C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol(trans-3,7-dimethyl-2,6-octadien-1-ol) and citronellol(3,7-dimethyl-6-octen-1-ol)) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

In one aspect, compositions and methods of the invention increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Panteoa citrea, Bacillus subtilis, Yarrowia lipolytica,* and *Trichoderma reesei.* All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| Strain | Isoprene Production in a Headspace vial* | |
|---|---|---|
| | Headspace concentration $\mu g/L_{gas}$ | Specific Rate $\mu g/L_{broth}/hr/OD$ ($nmol/g_{wcm}/hr$) |
| E. coli BL21/pTrcKudzu IS | 1.40 | 53.2 (781.2) |
| E. coli BL21/pCL DXS yidi Kudzu IS | 7.61 | 289.1 ($4.25 \times 10^3$) |
| E. coli BL21/MCM127 with kudzu IS and entire MVA pathway | 23.0 | 874.1 ($12.8 \times 10^3$) |
| E. coli BL21/pET N-HisKudzu IS | 1.49 | 56.6 (831.1) |
| Pantoea citrea/pTrcKudzu IS | 0.66 | 25.1 (368.6) |
| E. coli w/Poplar IS [Miller (2001)] | — | 5.6 (82.2) |
| Bacillis licheniformis Fall U.S. Pat. No. 5,849,970 | — | 4.2 (61.4) |
| Yarrowia lipolytica with kudzu isoprene synthase | ~0.05 µg/L | ~2 (~30) |
| Trichoderma reesei with kudzu isoprene synthase | ~0.05 µg/L | ~2 (~30) |
| E. coli BL21/pTrcKKD$_y$I$_k$IS with kudzu IS and lower MVA pathway | 85.9 | $3.2 \times 10^3$ ($4.8 \times 10^4$) |

*Normalized to 1 mL of 1 $OD_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| Strain | Isoprene Production in Fermentors | | |
|---|---|---|---|
| | Peak Headspace concentration** ($ug/L_{gas}$) | Titer ($mg/L_{broth}$) | Peak Specific rate $\mu g/L_{broth}/hr/OD$ ($nmol/g_{wcm}/hr$) |
| E. coli BL21/pTrcKudzu with Kudzu IS | 52 | 41.2 | 37 (543.3) |
| E. coli FM5/pTrcKudzu IS | 3 | 3.5 | 21.4 (308.1) |
| E. coli BL21/triple strain (DXS, yidi, IS) | 285 | 300 | 240 ($3.52 \times 10^3$) |
| E. coli FM5/triple strain (DXS, yidi, IS) | 50.8 | 29 | 180.8 ($2.65 \times 10^3$) |
| E. coli/MCM127 with Kudzu IS and entire MVA pathway | 3815 | 3044 | 992.5 ($1.46 \times 10^4$) |
| E. coli BL21/pCLPtrc UpperPathway gi1.2 integrated lower pathway pTrcKudzu | 2418 | 1640 | 1248 ($1.83 \times 10^4$) |
| E. coli BL21/MCM401 with 4 × 50 µM IPTG | 13991 | 23805 | 3733 ($5.49 \times 10^4$) |
| E. coli BL21/MCM401 with 2 × 100 µM IPTG | 22375 | 19541 | 5839.5 ($8.59 \times 10^4$) |
| E. coli BL21/pCLPtrc UpperPathwayHGS2-pTrcKKDyIkIS | 3500 | 3300 | 1088 ($1.60 \times 10^4$) |
| Bacillus subtilis wild-type | 1.5 | 2.5 | 0.8 (11.7) |
| Bacillus pBS Kudzu IS | 16.6 | ~30 (over 100 hrs) | 5 (73.4) |
| Bacillus Marburg 6051 [Wagner and Fall (1999)] | 2.04 | 0.61 | 24.5 (359.8) |

TABLE 2-continued

Exemplary yields of isoprene in a fermentor using the cell cultures and methods of the invention. The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| Strain | Isoprene Production in Fermentors | | |
|---|---|---|---|
| | Peak Headspace concentration** (ug/$L_{gas}$) | Titer (mg/$L_{broth}$) | Peak Specific rate µg/$L_{broth}$/hr/OD (nmol/$g_{wcm}$/hr) |
| *Bacillus Marburg* 6051 Fall U.S. Pat. No. 5,849,970 | 0.7 | 0.15 | 6.8 (100) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
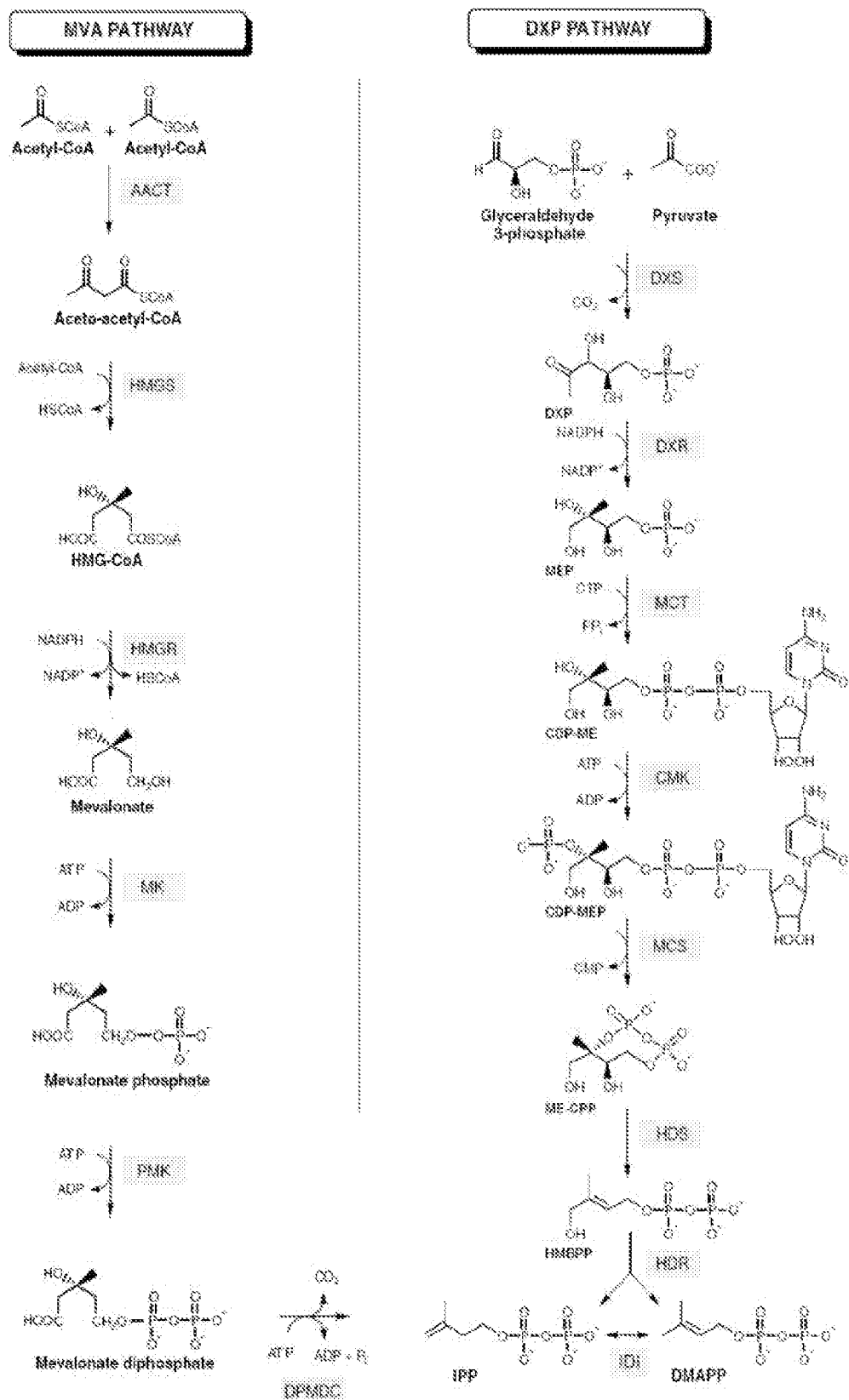
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of *E. coli* cells with a kudzu isoprene synthase, *S. cerevisia* IDI, and *E. coli* DXS nucleic acids was used to produce isoprene. The levels of isoprene varied from 50 to 300 µg/L over a time period of 15 hours (Example 7, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by *E. coli* cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
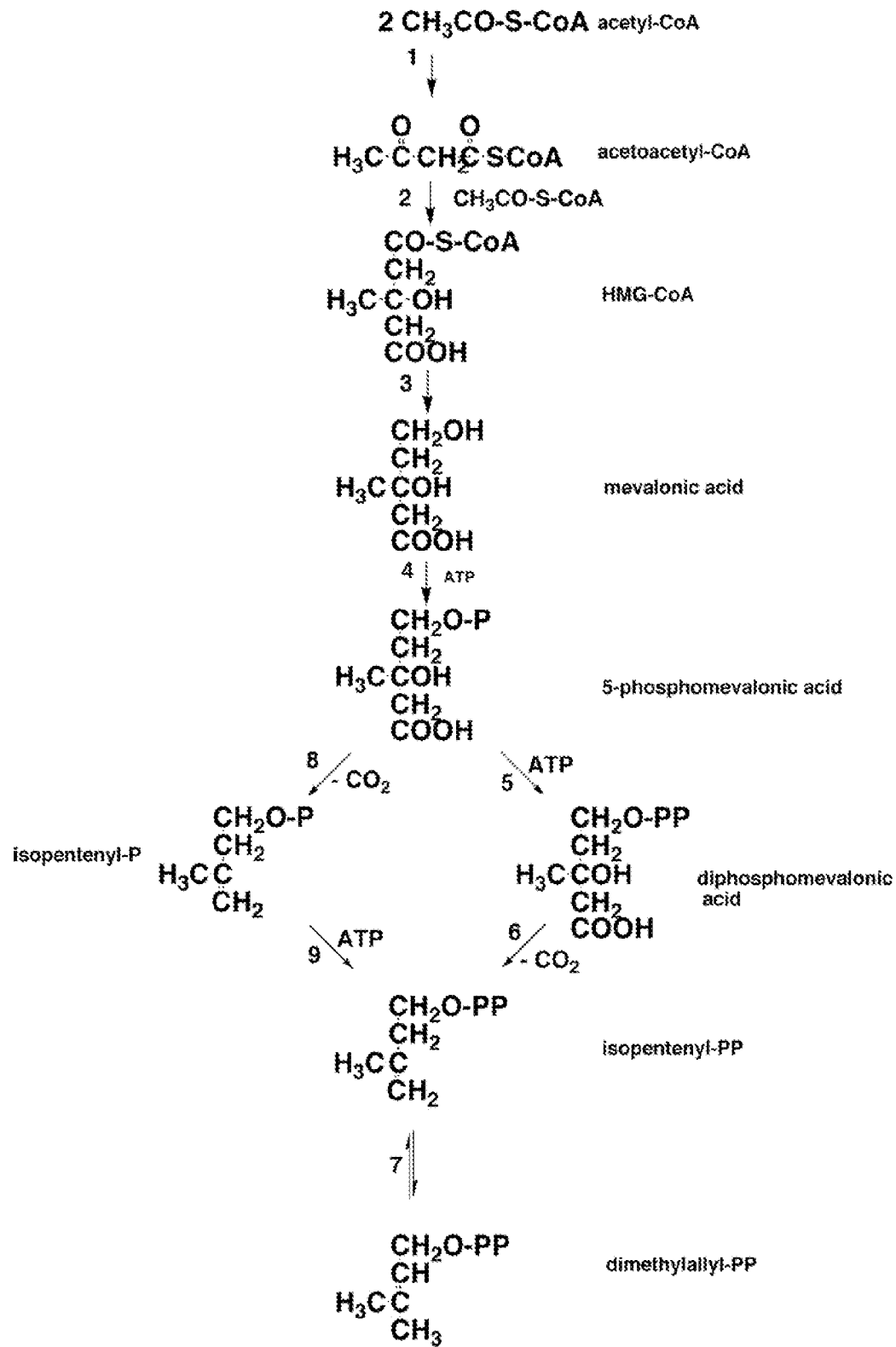
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews*, 71:97-120, 2007, which is incorporated by reference in its entirety, particular with respect to nucleic acids and polypetides fo the modified MVA pathway. The modified MVA pathway is present, for example, in some archaeal organisms, such as *Methanosarcina mazei*.

In some embodiments, the production of isoprene by cells by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonte decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain an entire MVA pathway that includes AA-CoA thiolase, HMG-CoA synthase, HMG-CoA reductase, MVK, PMK, MVD, and IDI nucleic acids. In some embodiments, the cells contain an entire modified MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, E. coli cells containing a nucleic acid encoding a kudzu isoprene synthase polypeptide and nucleic acids encoding Saccharomyces cerevisia MVK, PMK, MVD, and IDI polypeptides generated isoprene at a rate of $6.67 \times 10^{-4}$ mol/$L_{broth}$/$OD_{600}$/hr (see Example 8). Additionally, a 14 liter fermentation of E. coli cells with nucleic acids encoding Enterococcus faecalis AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in E. coli. E. coli cells that contain nucleic acids for both the upper MVA pathway and the lower MVA pathway as well as a kudzu isoprene synthase (strain MCM 127) produced significantly more isoprene (874 ug/L) compared to E. coli cells with nucleic acids for only the lower MVA pathway and the kudzu isoprene synthase (strain MCM 131) (see Table 3 and Example 8, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
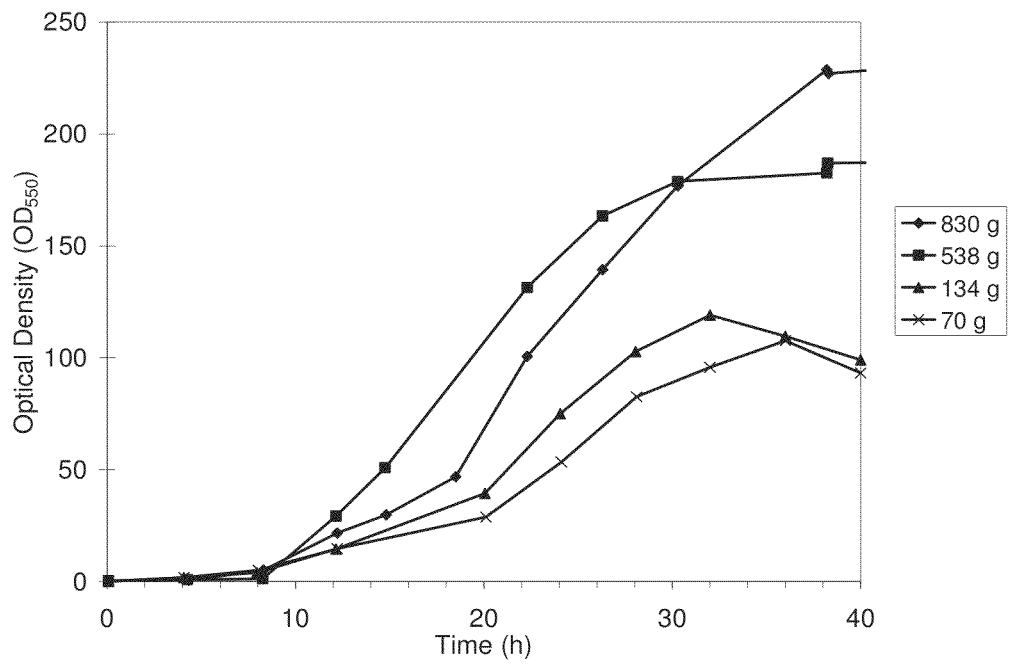
FIG. 48 shows graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 48B:
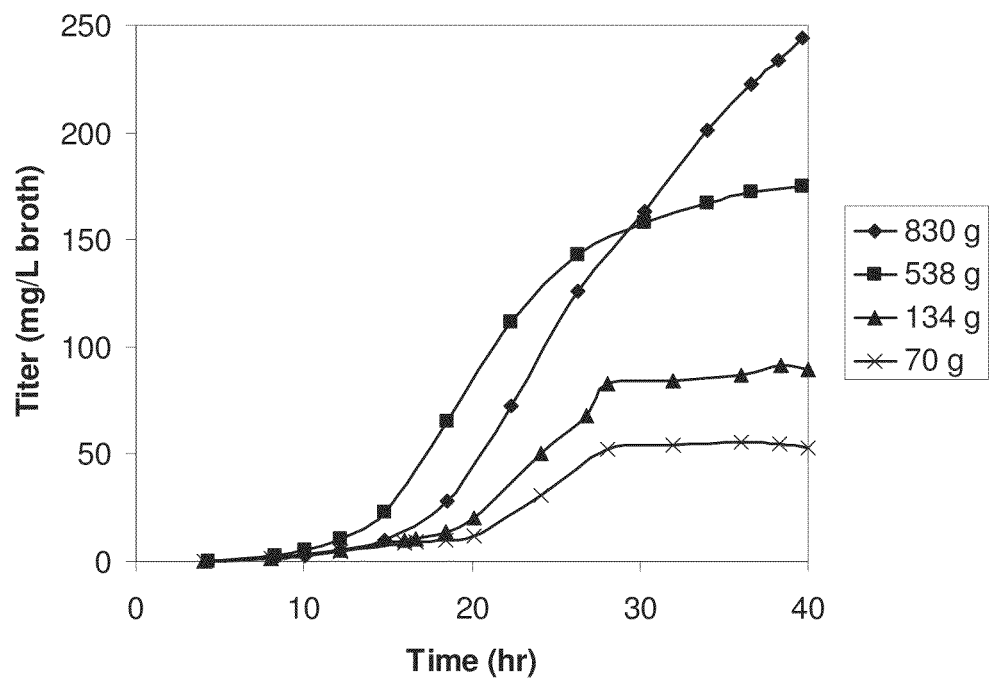
Figure 48C:
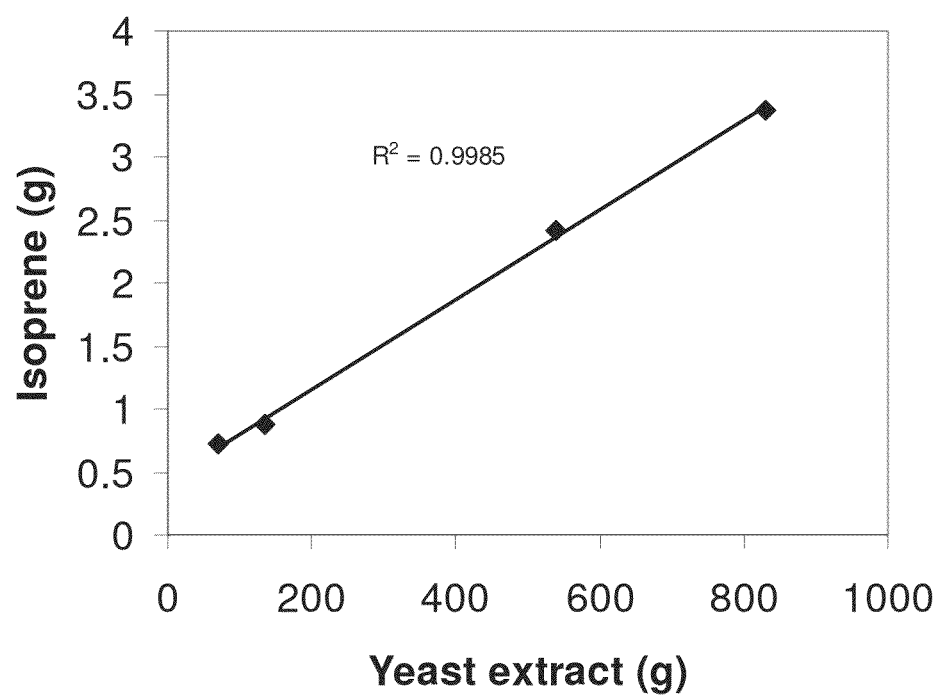

As indicated in Example 7, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Both of these experiments used E. coli cells with kudzu isoprene synthase, S. cerevisia IDI, and E. coli DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 46A:
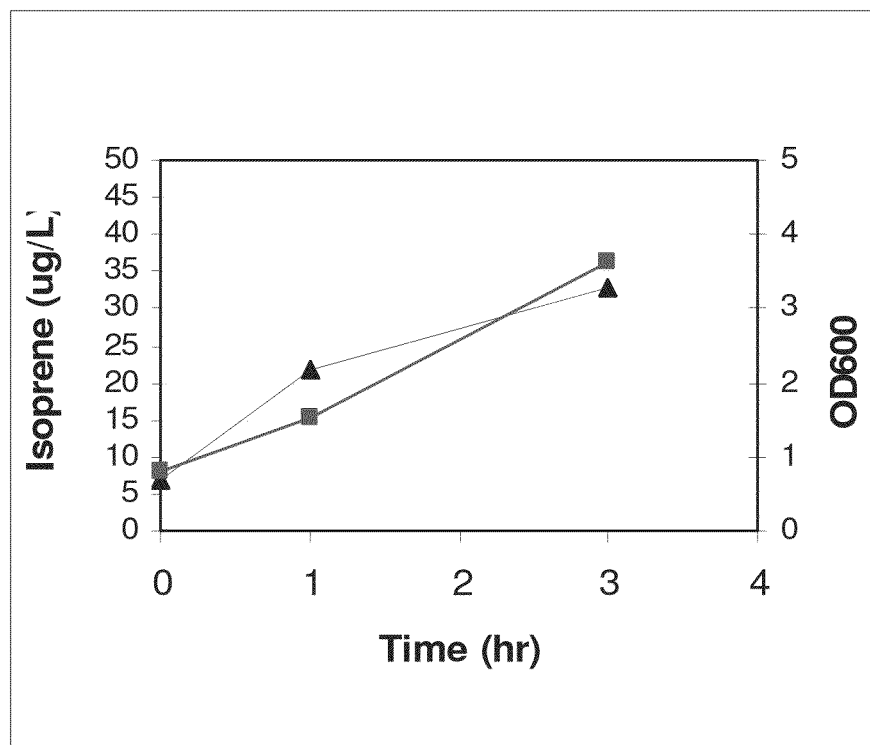
FIG. 46 shows graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.
Figure 46B:
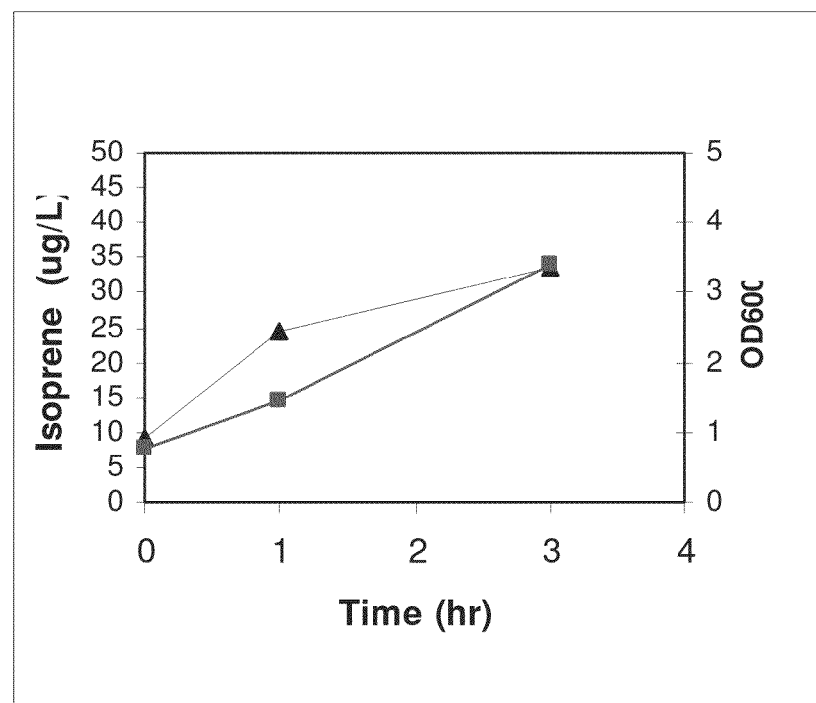
Figure 46C:
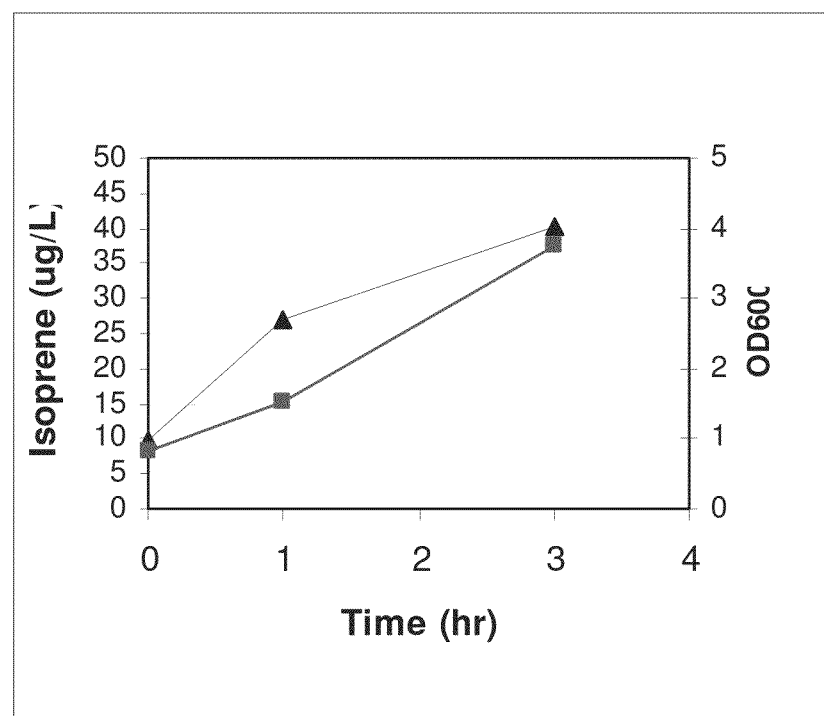
Figure 46D:
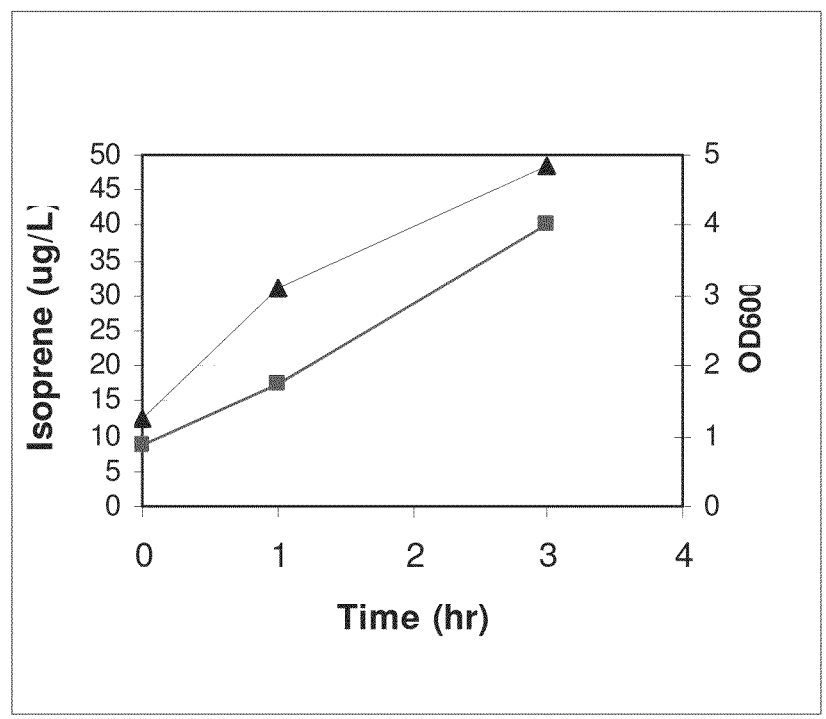
Figure 46E:
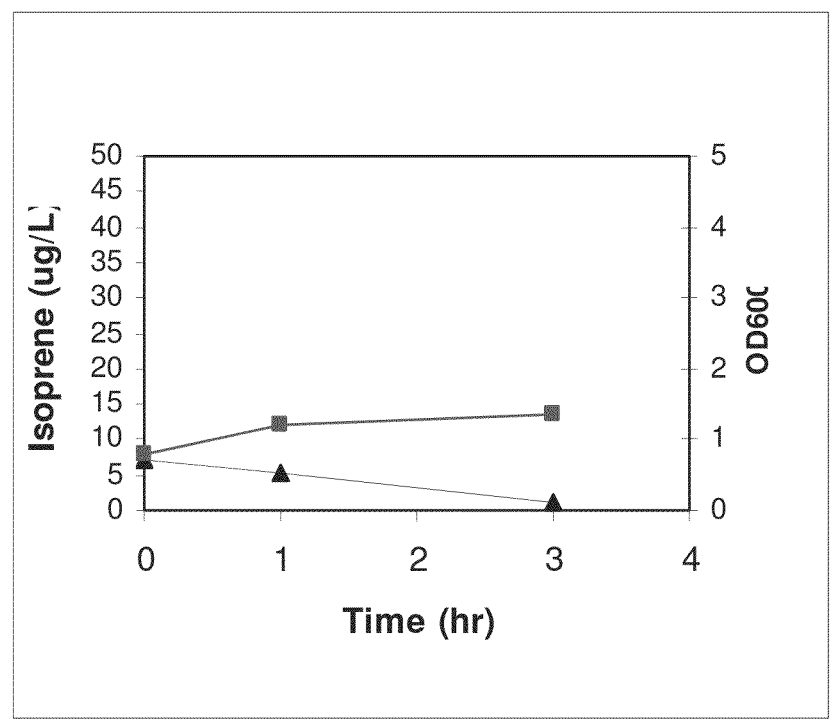
Figure 47A:
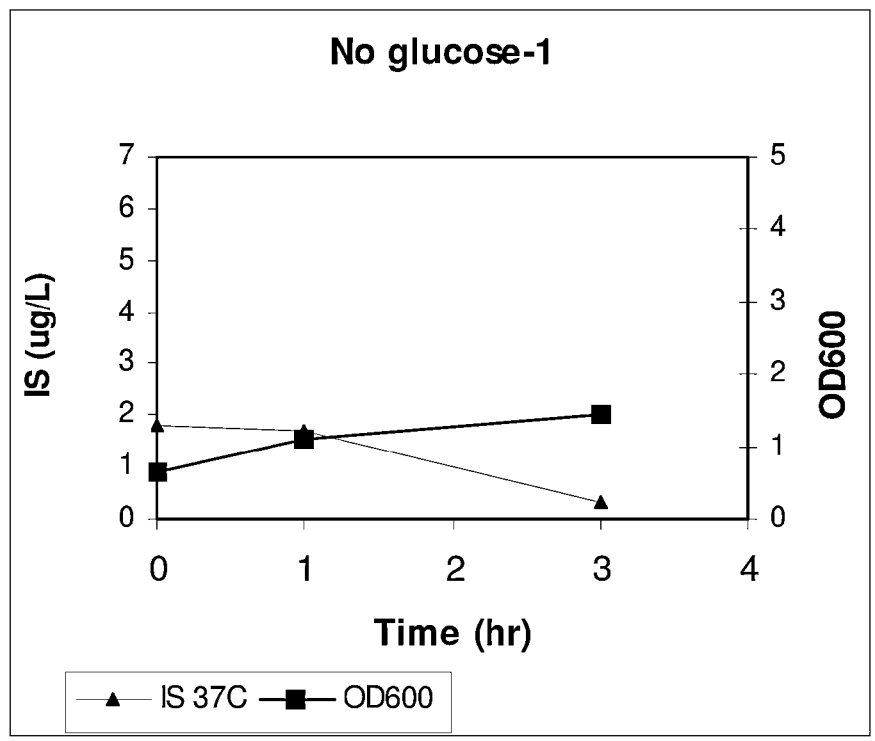
FIG. 47A shows a graph representing isoprene production by BL21 (λDE3) pTrcKudzu yIDI DXS (kan) in a culture with no glucose added. Squares represent $OD_{600}$, and triangles represent isoprene produced (µg/ml).
Figure 47B:
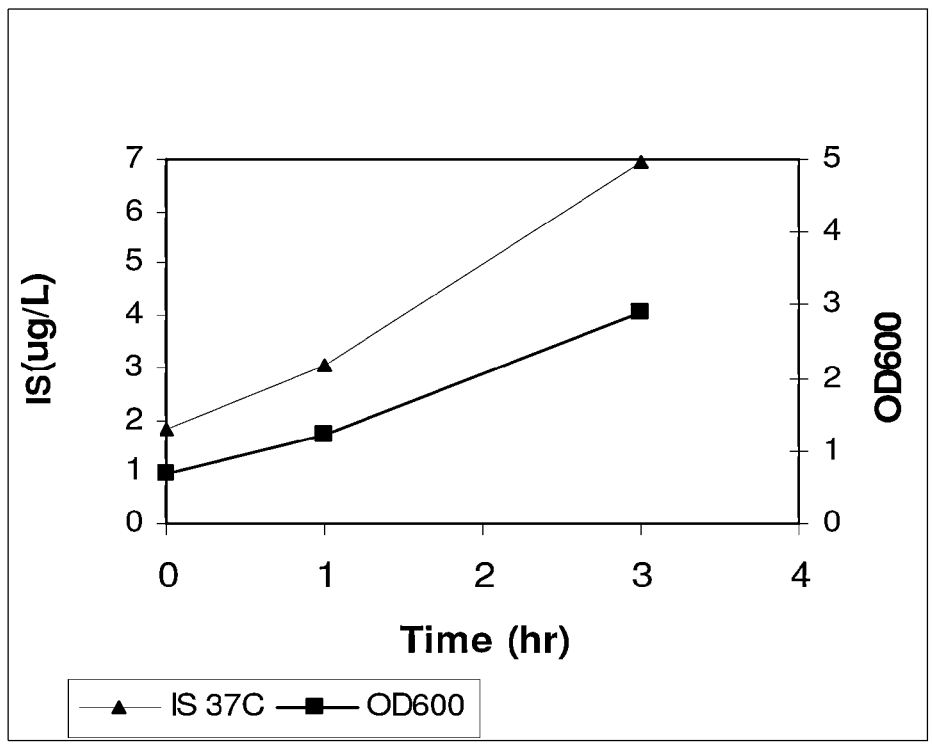
FIG. 47B shows a graph representing isoprene production from 1% glucose feedstock invert sugar by BL21 (λDE3) pTrcKudzu yIDI DXS (kan). Squares represent $OD_{600}$, and triangles represent isoprene produced (µg/ml).
Figure 47C:
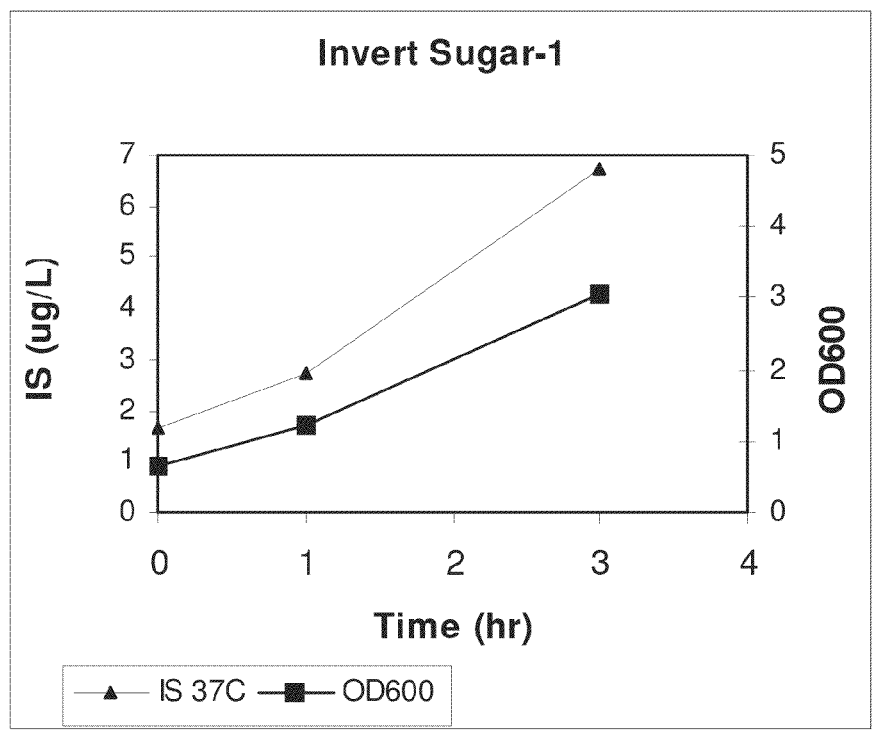
FIG. 47C shows a graph representing isoprene production from 1% invert sugar feedstock by BL21 (λDE3) pTrcKudzu yIDI DXS (kan). Squares represent $OD_{600}$, and triangles represent isoprene produced (µg/ml).
Figure 47D:
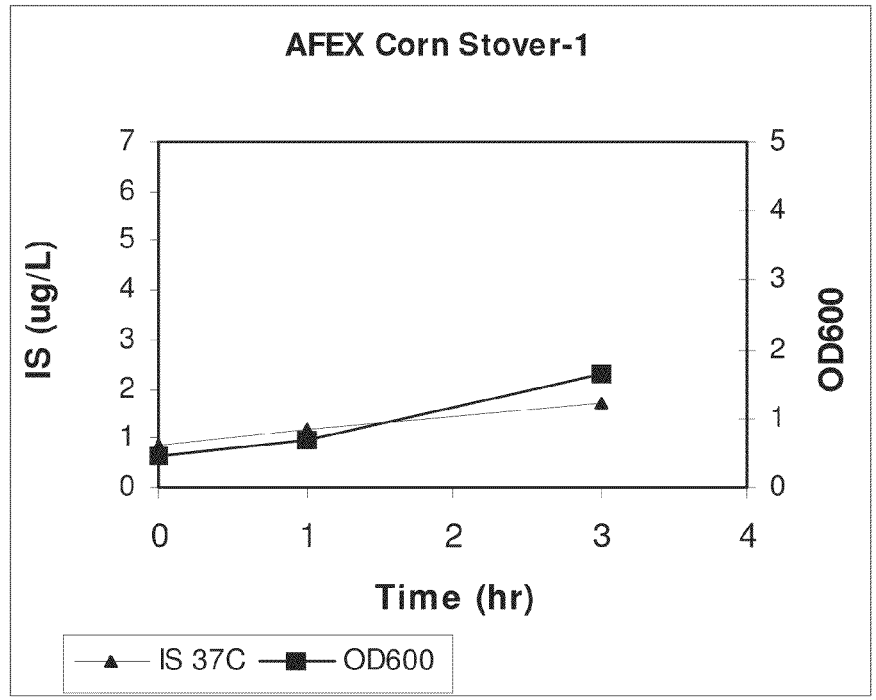
FIG. 47D shows a graph representing isoprene production from 1% AFEX corn stover feedstock by BL21 (λDE3) pTrcKudzu yIDI DXS (kan). Squares represent $OD_{600}$, and triangles represent isoprene produced (µg/ml).

Isoprene production was also demonstrated using three types of hydrolyzed biomass (bagasse, corn stover, and soft wood pulp) as the carbon source (FIGS. 46A-C). E. coli cells with kudzu isoprene synthase, S. cerevisia IDI, and E. coli DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene (FIGS. 47C and 96-98). For example, 2.4 g/L of isoprene was produced from cells expressing MVA pathway polypeptides and a Kudzu isoprene synthase (Example 8, part XV). Glycerol was as also used as a carbon source for the generation of 2.2 mg/L of isoprene from cells expressing a Kudzu isoprene synthase (Example 8, part XIV). Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, B. subtilis cells containing a kudzu isoprene synthase nucleic acid produced isoprene when cultured in a cell medium containing an oil and a source of glucose (Example 4, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 10, E. coli cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from Enterococcus faecalis. Isoprene was formed from cells expressing the upper MVA pathway from Enterococcus faecalis, the lower MVA pathway from Saccharomyces cerevisiae, and the isoprene synthase from Pueraria montana (Kudzu). This decoupling of isoprene or mevalonic acid production from growth was demonstrated in four different strains of E. coli: BL21(LDE3), BL21(LDE3) Tuner, FM5, and MG1655. The first two E. coli strains are B strains, and the latter two are K12 strains. Decoupling of production from growth was also demonstrated in a variant of MG1655 with ack and pta genes deleted. This variant also demonstrated less production of acetate.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an isoprene synthase, DXS, IDI, or MVA pathway polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. It is to be understood that mutations, including single nucleotide mutations, can occur within a nucleic acid as defined herein.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the worldwide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Sep. 14, 2008 such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) is added to 25 µL of cell extract in a 20 ml Headspace vial with a metal screw cap and teflon coated silicon septum (Agilent Technologies) and cultured at 37° C. for 15 minutes with shaking. The reaction is quenched by adding 200 µL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba×tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide.

Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentenyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as E. coli, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as E. coli. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., *EMBO J.* 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132, 527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous Escherichia, Panteoa, Bacillus, Yarrowia, Streptomyces, or Trichoderma promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a Trichoderma host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when T. reesei is the host, the promoter is a native T. reesei promoter. In some embodiments, the promoter is T. reesei cbh1, which is an inducible promoter and has been deposited in GenBank under Accession No. D86235, which is incorporated by reference in its entirety, particularly with respect to promoters. In some embodiments, the promoter is one that is heterologous to the fungal host cell.

Other examples of useful promoters include promoters from the genes of A. awamori and A. niger glucoamylase (glaA) (Nunberg et al., Mol. Cell Biol. 4:2306-2315, 1984 and Boel et al., EMBO J. 3:1581-1585, 1984, which are each hereby incorporated by reference in their entireties, particularly with respect to promoters); Aspergillus niger alpha amylases, Aspergillus oryzae TAKA amylase, T. reesei xln1, and the T. reesei cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a Trichoderma strain (such as T. reesei). Other useful fungal terminators include the terminator from an A. niger or A. awamori glucoamylase nucleic acid (Nunberg et al., Mol. Cell Biol. 4:2306-2315, 1984 and Boel et al., EMBO J. 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 19A and 19B). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae, A. aculeatus, A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, or strains of *Escherichia* such as *E. coli*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some embodiments, the source organism is a gram-positive bacterium. Non-limiting examples include strains of *Streptomyces* (e.g., *S. lividans, S. coelicolor,* or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales,* or *Stigonematales*.

Exemplary Host Cells

A variety of host cells can be used to express isoprene synthase, DXS, IDI, and/or MVA pathway polypeptides and to produce isoprene in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041;WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 µL of these protoplasts or cells in an appropriate solution (e.g., 1.2 M sorbitol and 50 mM $CaCl_2$) are mixed with the desired DNA.

Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharids), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the carbon source is synthesized from carbon dioxide. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1). Thus the present invention provides methods for one or both of recycling carbon dioxide and reducing carbon dioxide emission during biological production of isoprene.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell media). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium) during this time period. In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$
Test Suite 3:
isoprene: 0 wt %-14 wt %
$O_2$: 6 wt %-21 wt %
$N_2$: 79 wt %-94 wt %
$CO_2$: 5 wt %-30 wt %
(2) Experimental Testing for Final Determination of Flammability Limits
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems*, 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm (OD600). In some embodiments, the isoprene amount is measured at the peak specific productivity time point. In some embodiments, the peak specific productivity for the cells is about any of the isoprene amounts per cell disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 µm; 0.25 µm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

Carbon Yield=(moles carbon in isoprene produced)/(moles carbon in carbon source)*100    Equation 1

For this calculation, yeast extract can be assumed to contain 50% w/w carbon. As an example, for the 500 liter described in Example 7, part VIII, the percent conversion of carbon into isoprene can be calculated as shown in Equation 2.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]* 100=0.042%    Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein. Example 10, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate)    Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.)    Equation 4

1 nmol isoprene/$g_{wcm}$/hr=68.1 ng isoprene/$g_{wcm}$/hr (given the molecular weight of isoprene)    Equation 5

1 nmol isoprene/$L_{gas}$ $O_2$/hr=90 nmol isoprene/$L_{broth}$/hr (at an $O_2$ flow rate of 90 L/hr per L of culture broth)    Equation 6

1 ug isoprene/$L_{gas}$ isoprene in off-gas=60 ug isoprene/
$L_{broth}$/hr at a flow rate of 60 $L_{gas}$ per $L_{broth}$ (1
vvm)  Equation 7

Units for Titer (Total and Specific)

1 nmol isoprene/mg cell protein=150 nmol isoprene/
$L_{broth}$/$OD_{600}$ (This conversion assumes that one
liter of broth with an $OD_{600}$ value of 1 has a total
cell protein of approximately 150 mg) (specific
productivity)  Equation 8

1 g isoprene/$L_{broth}$=14.7 mmol isoprene/$L_{broth}$ (total titer)  Equation 9

If desired, Equation 10 can be used to convert any of the units that include the wet weight of the cells into the corresponding units that include the dry weight of the cells.

Dry weight of cells=(wet weight of cells)/3.3  Equation 10

If desired, Equation 11 can be used to convert between units of ppm and ug/L. In particular, "ppm" means parts per million defined in terms of ug/g (w/w). Concentrations of gases can also be expressed on a volumetric basis using "ppmv" (parts per million by volume), defined in terms of uL/L (vol/vol). Conversion of ug/L to ppm (e.g., ug of analyte per g of gas) can be performed by determining the mass per L of off-gas (i.e., the density of the gas). For example, a liter of air at standard temperature and pressure (STP; 101.3 kPa (1 bar) and 273.15K) has a density of approximately 1.29 g/L. Thus, a concentration of 1 ppm (ug/g) equals 1.29 ug/L at STP (equation 11). The conversion of ppm (ug/g) to ug/L is a function of both pressure, temperature, and overall composition of the off-gas.

1 ppm (ug/g) equals 1.29 ug/L at standard temperature
and pressure (STP; 101.3 kPa (1 bar) and
273.15K).  Equation 11

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 $L \cdot atm\ K^{-1}\ mol^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

PV=nRT, where "P" is pressure, "V" is volume, "n" is
moles of gas, "R" is the Universal gas constant,
and "T" is temperature in Kelvin.  Equation 12

The amount of impurities in isoprene compositions are typically measured herein on a weight per volume (w/v) basis in units such as ug/L. If desired, measurements in units of ug/L can be converted to units of mg/m³ using equation 13.

1 ug/L=1 mg/m³  Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol) compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such as 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such as 1,3- cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, cis-pent-3-ene-1-yne, 3-hexen-1-ol, 3-hexen-1-yl acetate, limonene, geraniol (trans-3,7-dimethyl-2,6-octadien-1-ol) and citronellol (3,7-dimethyl-6-octen-1-ol)). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as pentyne-1, butyne-2, 2MB1-3yne, and 1-pentyne-4yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

In some embodiments encompassed by the invention, a cell comprising one or more heterologous nucleic acids encoding an isoprene synthase polypeptide, DXS polypeptide, IDI polypeptide, and/or MVA pathway polypeptide produces an amount of an isoprenoid compound (such as a compound with 10 or more carbon atoms that is formed from the reaction of one or more IPP molecules with one or more DMAPP molecules) that is greater than or about 2-fold, 3-fold, 5-fold, 10-fold, 25-fold, 50-fold, 100-fold, 150-fold, 200-fold, 400-fold, or greater than the amount of the isoprenoid compound produced from a corresponding cell grown under essentially the same conditions without the one or more heterologous nucleic acids.

Exemplary Isoprene Purification Methods

In some embodiments, any of the methods described herein further include recovering the isoprene. For example, the isoprene produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In particular embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

Exemplary Methods for Recycling Carbon Dioxide and For Reducing Carbon Dioxide Emission During Biological Production of Isoprene To meet the objective of developing ecologically friendly processes for the production of chemicals and fuels, it is critical to use renewable feedstocks. For instance, a dependable supply of isoprene is needed in billion(s) of pounds with a manufacturing cost target in the range of $0.50-0.70/lb. Isoprene is produced in nature by a variety of microbial, plant and animal species. Engineering biochemical pathways from a number of organisms, into microbial hosts permits the production of isoprene by fermentation. However, yield potential of isoprene produced from common fermentation feedstocks such as sugar (glucose, fructose, sucrose, galactose, lactose, xylose, arabinose) is lower than uncommon feedstocks such as methanol and glycerol.

As detailed in the experimental examples, the present invention provides methods, compositions and systems for production of isoprene by fermentation by using engineered microbes that can utilize uncommon carbon sources (e.g., alcohol) either alone or in combination with common carbon sources (e.g., sugar). These methods involve the: (1) rational design of pathways for utilization of uncommon carbon sources; (2) production of isoprene by fermentation; and (3) recovery of isoprene by continuous removal during fermentation via off-gas. In this way, polymer grade isoprene is produced in a manner that is less harmful to the environment than the processes that are currently employed for this purpose. In some embodiments, the cells are cultured in a culture medium comprising an uncommon carbon source, which in some preferred embodiments is selected from the group consisting of glycerol, cell mass, protein, alcohol (e.g., methanol, ethanol, etc.) and plant-derived oil or any combination thereof. In some embodiments, the carbon source is synthesized from carbon dioxide. In some embodiments, the culture medium does not contain glucose. In some embodiments, the isoprene produced as a percentage of off gas from the cultured cells is greater than 0.03% (greater than 0.04%, 0.05%, 0.06%, 0.07%, 0.08%, 0.09%, 0.10%, 0.11%, 0.12%, 0.14%, 0.15%, 0.3%, 0.6%, 0.9%, 1.2%, 1.5%, 5%, or 10%). In some embodiments, the ratio of carbon dioxide emitted per isoprene produced in off gas from the cultured cells is less than 800 (less than 700, 600, 500, 400, 300, 200, 100, 50, 40, 30, 20, 10, 5, or 1). Thus the present invention provides methods for one or both of recycling carbon dioxide and reducing carbon dioxide emission during biological production of isoprene.

Glycerol Feedstock

Isoprene production and carbon dioxide emitted was analyzed by culturing recombinant host cells in media containing either glucose or glycerol as the carbon source, in a bioreactor. In an exemplary embodiment, recombinant *E. coli* harboring the mevalonic acid pathway and isoprene synthase were utilized. However, the compositions and methods of the present invention for reducing carbone dioxide emission in biological processes for isoprene production are not limited to the use of this particular cell line. Other suitable compositions and methods for producing isoprene are provided by U.S. Application No. 61/134,094, filed Jul. 2, 2008, herein incorporated by reference in its entirety. The off-gas from the bioreactors was analyzed using an on-line Hiden HPR-20 mass spectrometer during the course of the experiment (20 hours). Masses corresponding to isoprene, carbon dioxide and other gasses naturally occurring in air were monitored. Concentration of isoprene and carbon dioxide was calculated as percentage of the off-gas. Accumulated isoprene and carbon dioxide was calculated by summing the concentration (in percent) of the respective gasses over time. Atmospheric carbon dioxide was subtracted from the total carbon dioxide in order to estimate the carbon dioxide released due to metabolic activity. This analysis revealed a significant production of isoprene and release of carbon dioxide during growth on the two different carbon sources (FIGS. 112A and 112B). The percentage of isoprene in the off-gas during growth on glycerol was significantly higher than during growth on glucose. Analysis of carbon dioxide in the off-gas from the bioreactors, which is a measure of metabolic activity, indicates that metabolic activity was independent from IPTG induction and isoprene production.

Calculation of the accumulated amount of isoprene and carbon dioxide (by adding the percent of the respective gasses in the off-gas released during the experiment) revealed that bacteria grown on glycerol produced significantly more isoprene (average of 0.122) when compared to bacteria grown on glucose (average of 0.026). Interestingly, only a small difference in the amount of carbon dioxide released during growth on the two different carbon sources (27.0 versus 24.3 during growth on glycerol and glucose respectively) was observed. However, calculation of the difference in the amount of carbon dioxide released per amount of isoprene produced as a consequence of growth on glucose versus growth on glycerol, showed that 4.2-fold less carbon dioxide was released during production of the same amount of isoprene when the bacteria were grown on glycerol as compared to glucose (See, Table 16-1). This indicates that carbon source selection provides the means to significantly reduce carbon dioxide emission during biological production of isoprene. Thus, a significant reduction in the amount of carbon dioxide released per amount of isoprene produced is achieved by growing recombinant bacterial host cells on glycerol instead of glucose.

Methanol Feedstock

Methanol for use in isoprene production can be obtained from carbon sources such as biomass, coal, natural gas, and petroleum. In addition, hydrogen produced by solar, wind, and geothermal energy sources can be used as a supplement to these carbon sources, for enhanced production of methanol. Further supplementation of methanol with sugar can increase the yield of isoprene obtained during fermentation of engineered microorganisms. In a preferred embodiment, chemical and biological catalytic steps are combined to produce isoprene from carbon dioxide and dihydrogen. Accordingly, the process outlined in Example 17 is estimated to recycle more than 3 lb $CO_2$ per lb isoprene by using 0.4-0.5 lb $H_2$, (e.g., $CO_2$ and $H_2$ are raw materials for isoprene production). Alternatively or additionally, chemical and biological catalytic steps are combined to produce isoprene from biomass, dioxide and dihydrogen. Electrolysis of water using alternate energy meets the demand for both $H_2$ and $O_2$, resulting in a substantial potential isoprene mass yield from biomass. Even if biomass cost is as high as $150/ton, isoprene production via this process would cost less than 30 cents/lb (equivalent to less than $2/gallon gasoline). Thus, isoprene is obtainable more cheaply via this process.

In order to tap methanol yield potential, multiple metabolic pathways are combined: methanol conversion to acetic acid; acetic acid conversion to mevalonic acid; and mevalonic acid conversion to isoprene via an isoprene synthase catalyzed reaction. As such it is estimated that an engineered organism could yield up to 40% isoprene from a methanol feedstock, whereas maximum yield on a sugar feedstock is estimated to be only 25%. For instance, the methylotrophic yeast, *Pichia pastoris*, is a suitable eukaryotic host for conversion of methanol to isoprene. Similarly, *Methylophilus methylotrophus* is a suitable prokaryotic host for conversion of methanol to isoprene (See, U.S. Pat. No. 4,652,527).

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *Escherichia coli* Expressing Recombinant Kudzu Isoprene Synthase I. Construction of Vectors for Expression of the Kudzu Isoprene Synthase in *E. coli*

Figure 2:
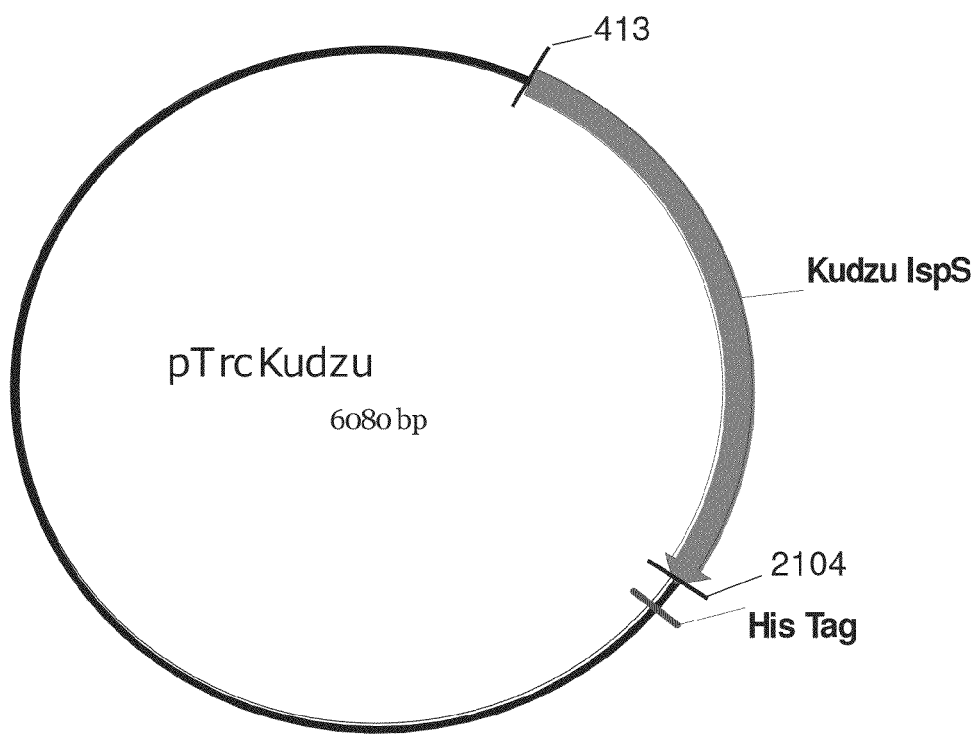
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
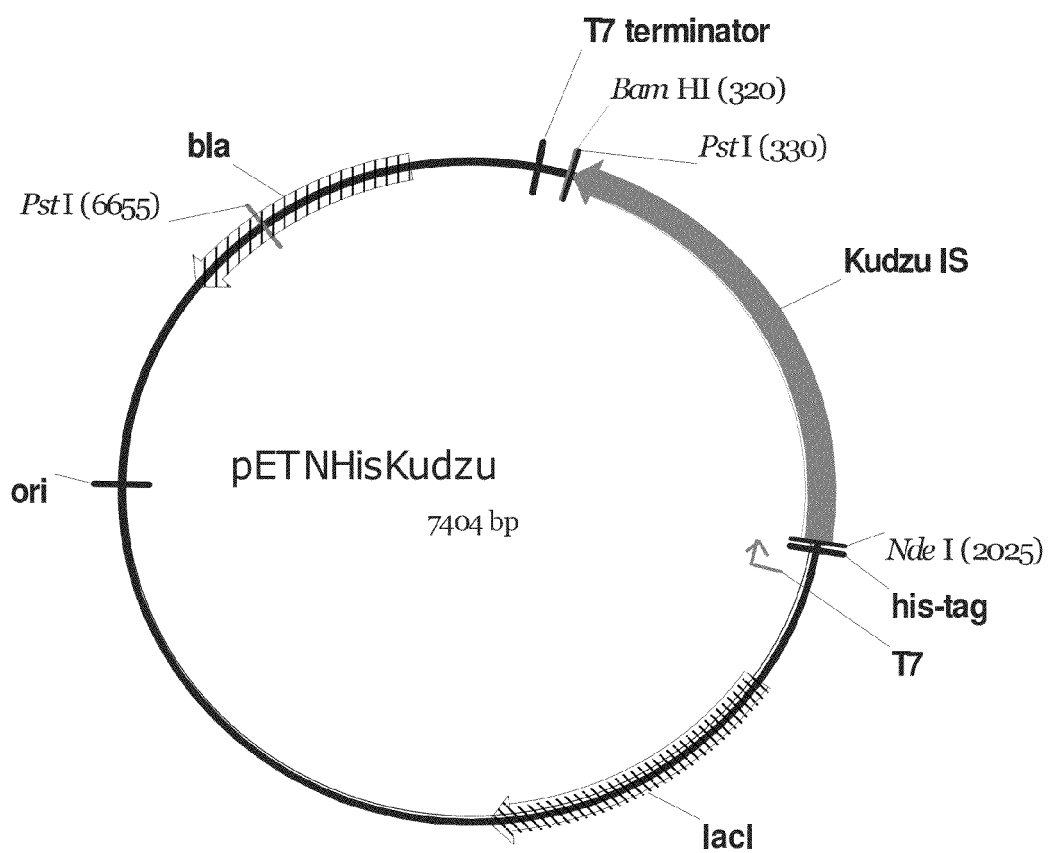
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGAT-CATATGTGTGCGACCTCTTCTCAATTTAC (SEQ ID NO:3) and pET-His-Kudzu-R: 5'-CGGTCGACGGATC-CCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 µl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

Figure 6:
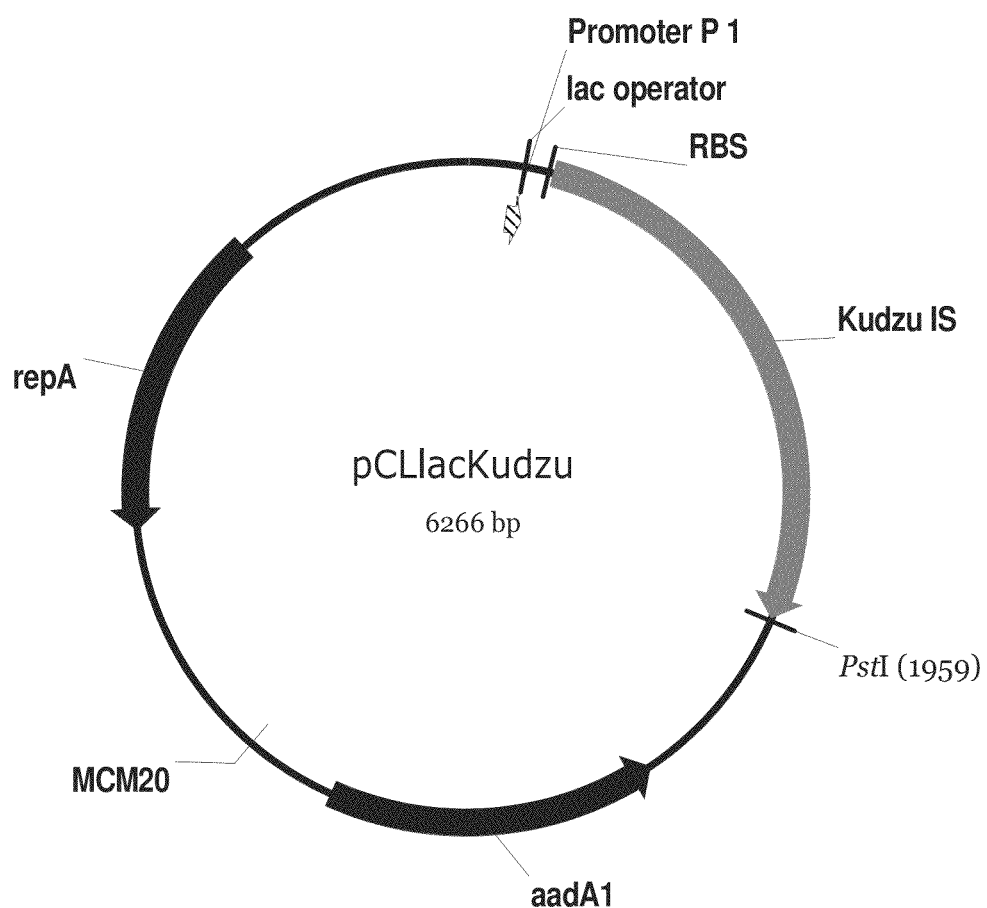
FIG. 6 is a map of pCL-lac-Kudzu.
Figure 8A:
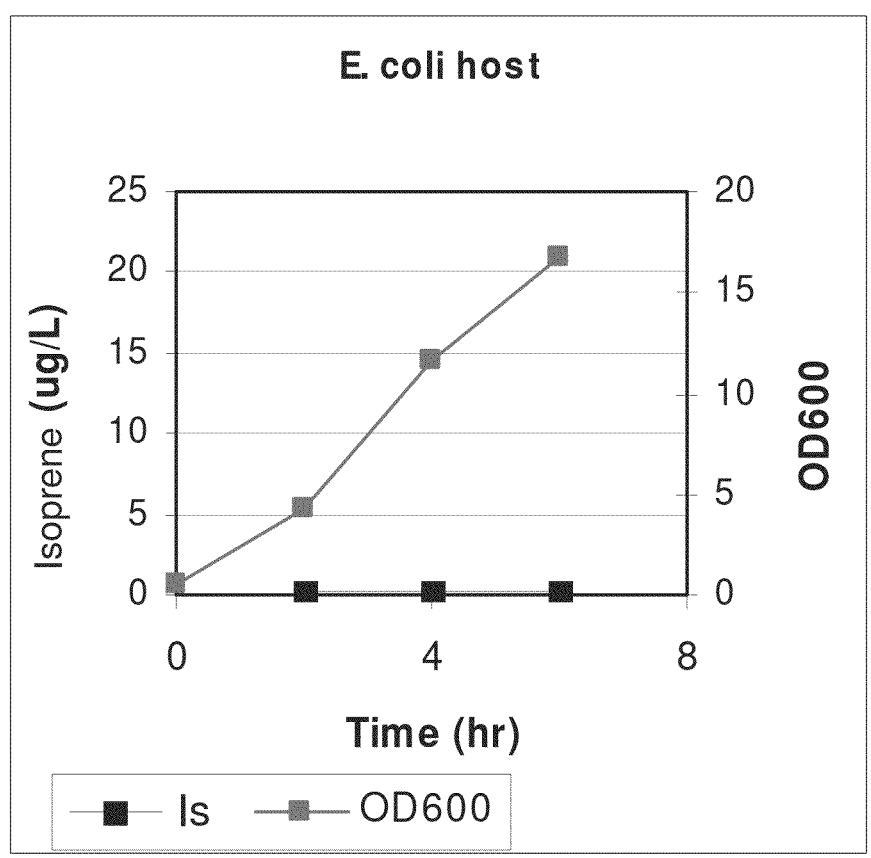
FIG. 8A is a graph showing the production of isoprene in *E. coli* BL21 cells with no vector.
Figure 8B:
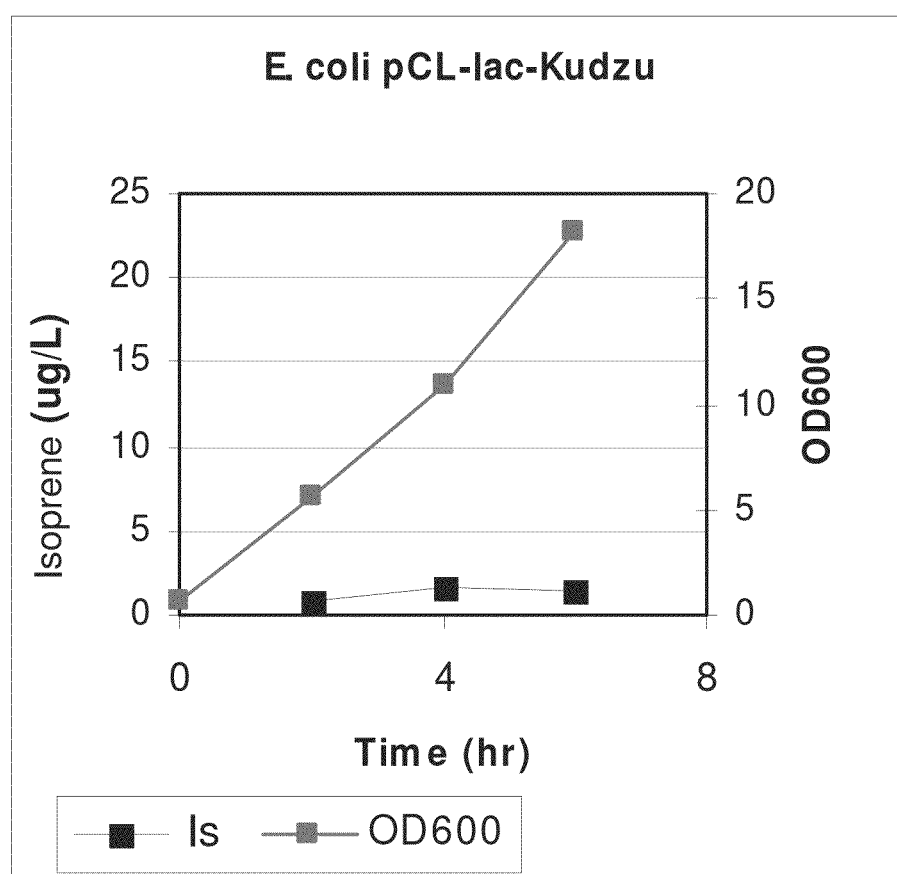
FIG. 8B is a graph showing the production of isoprene in *E. coli* BL21 cells with pCL-lac-Kudzu
Figure 8C:
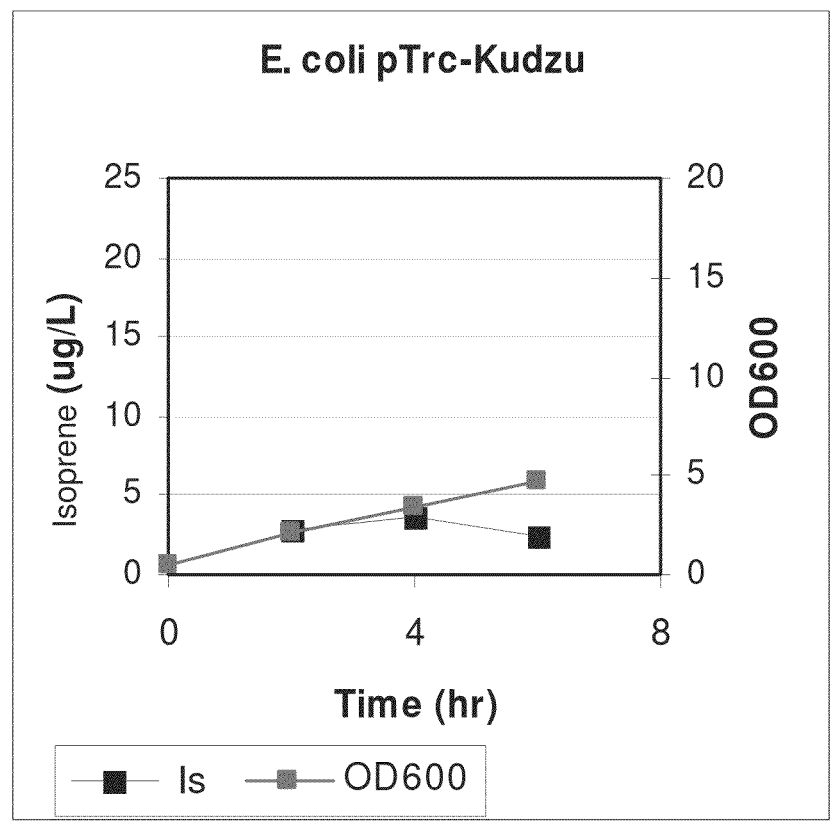
FIG. 8C is a graph showing the production of isoprene in *E. coli* BL21 cells with pTrcKudzu.
Figure 8D:
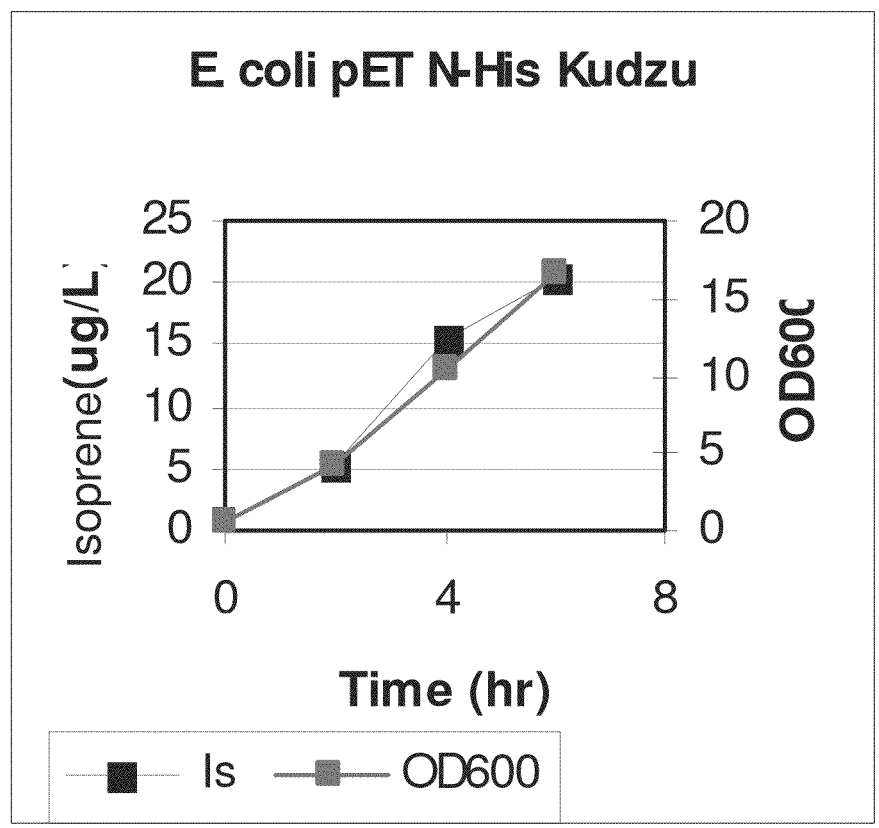
FIG. 8D is a graph showing the production of isoprene in *E. coli* BL21 cells with pETN-HisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATC-GATTAAATAAGGAGGAATAAACC (SEQ ID NO:6) and BamH1-Kudzu R:

5'-CGGTCGACGGATCCCTGCAGTTAGA-CATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7).

II. Determination of Isoprene Production

For the shake flask cultures, one ml of a culture was transferred from shake flasks to 20 ml CTC headspace vials (Agilent vial cat #5188 2753; cap cat #5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 2000 µg/L. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 µg/ml) to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in $diH_2O$. The pH was adjusted to 6.8 with potassium hydroxide (KOH) and q.s. to volume. The final product was filter sterilized with 0.22µ filter (only, do not autoclave).

The recipe for 1000× Modified Trace Metal Solution was as follows: citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component wa dissolved one at a time in $diH_2O$, pH to 3.0 with HCl/NaOH, then q.s. to volume and filter sterilized with a 0.22µ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 30:
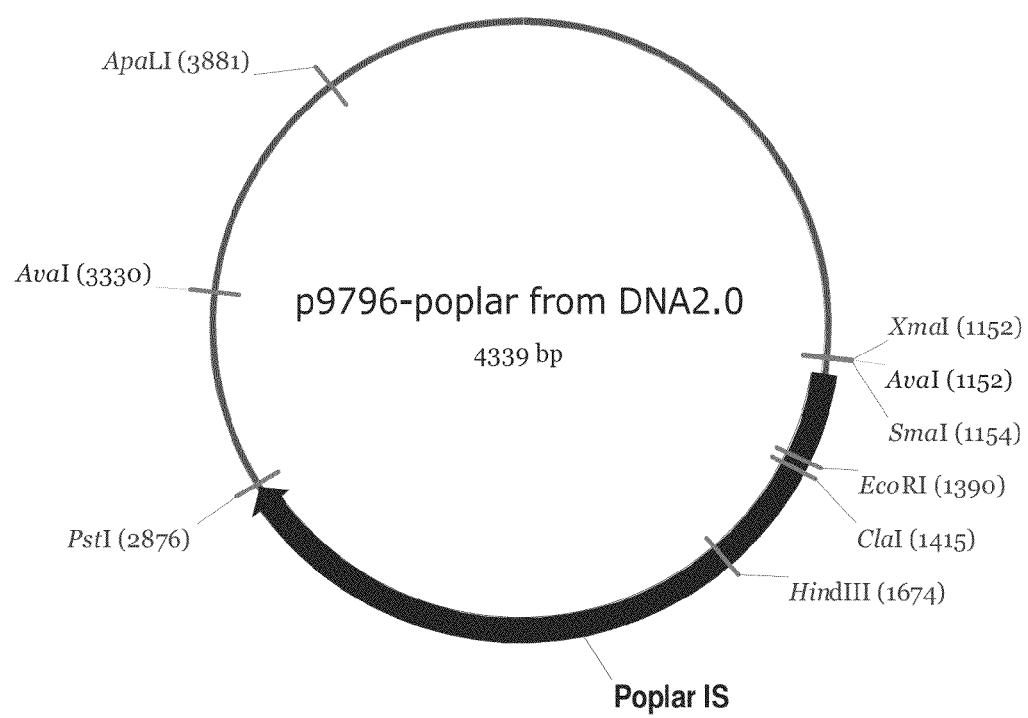
FIG. 30 is a map of p9796-poplar.
Figure 32:
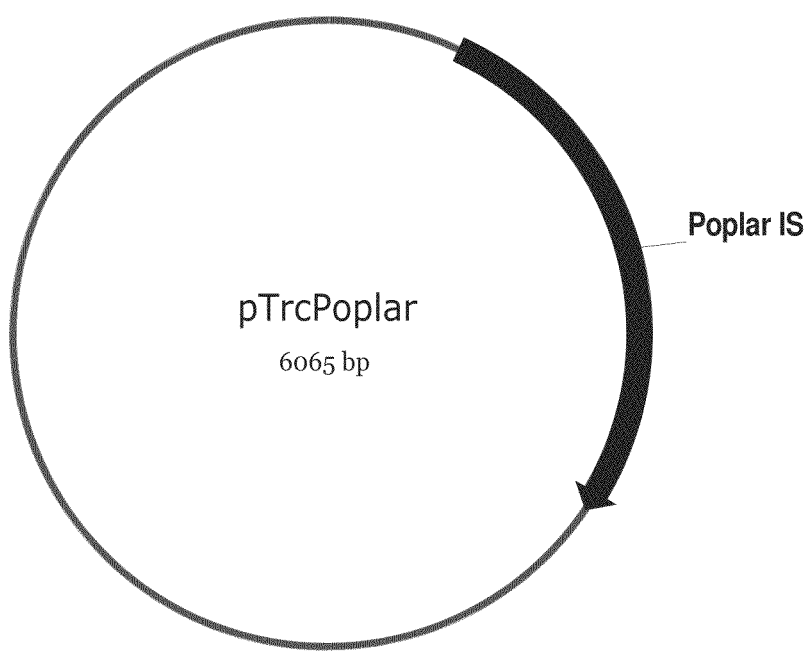
FIG. 32 is a map of pTrcPoplar.

Production of Isoprene in *Escherichia coli* Expressing Recombinant Poplar Isoprene Synthase The protein sequence for the poplar (*Populus alba×Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33), was verified by sequencing.

Example 3

Figure 10A:
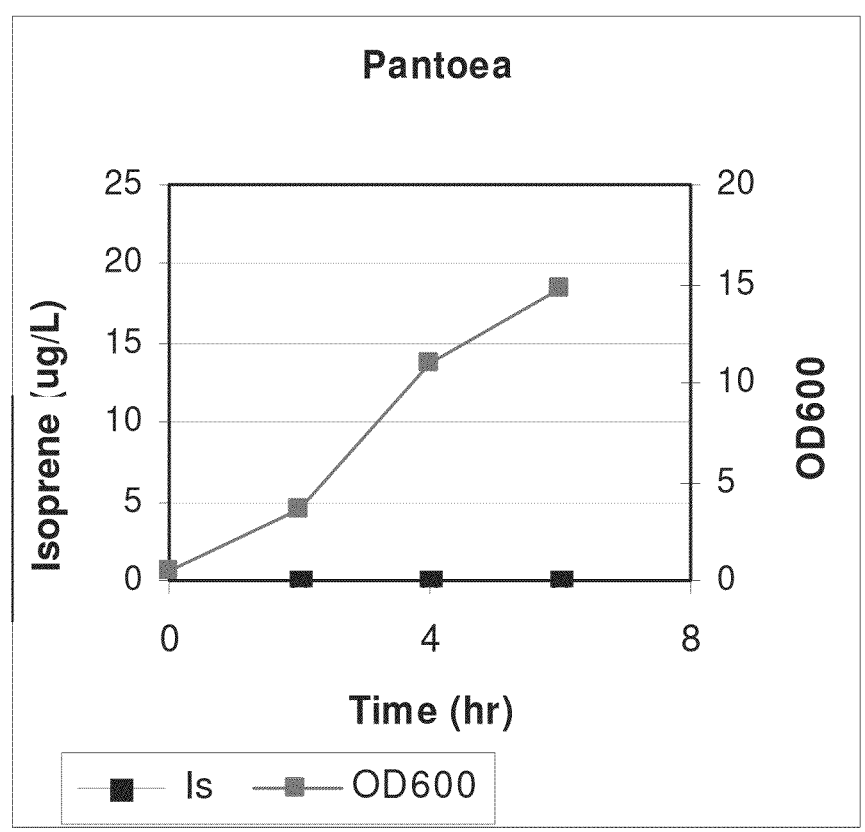
FIG. 10A is a graph showing the production of isoprene in *Panteoa citrea*. Control cells without recombinant kudzu isoprene synthase. Grey diamonds represent isoprene synthesis, black squares represent $OD_{600}$.
Figure 10B:
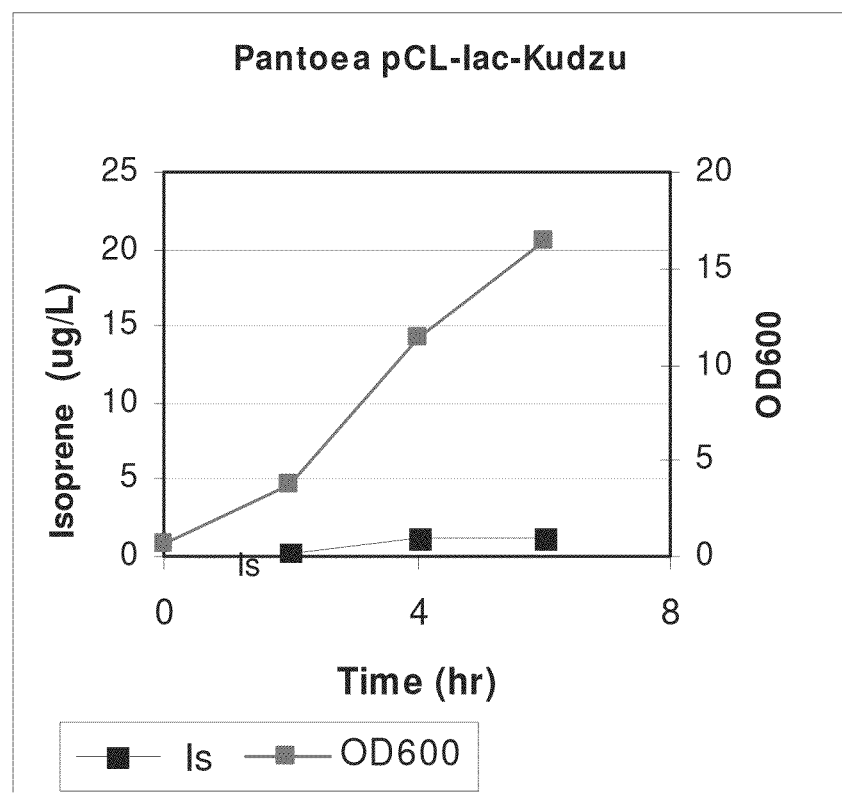
FIG. 10B is a graph showing the production of isoprene in *Panteoa citrea* expressing pCL-lac Kudzu. Grey diamonds represent isoprene synthesis, black squares represent $OD_{600}$.
Figure 10C:
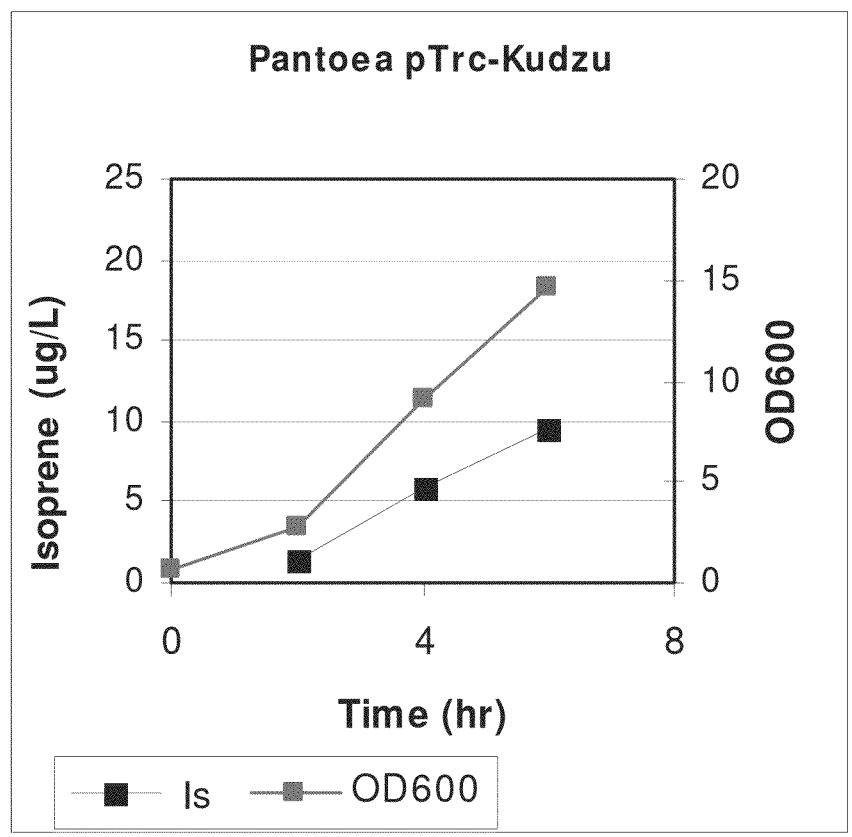
FIG. 10C is a graph showing the production of isoprene in *Panteoa citrea* expressing pTrcKudzu. Grey diamonds represent isoprene synthesis, black squares represent $OD_{600}$.

Production of Isoprene in *Panteoa citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Transformants were selected on LA containing carbenicillin (200 µg/ml) or spectinomycin (50 µg/ml) respectively. Production of isoprene from shake flasks and determination of the amount of isoprene produced was performed as described in Example 1 for *E. coli* strains expressing recombinant kudzu isoprene synthase. Results are shown in FIG. 10.

Example 4

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS19 and transformed into *B. subtilis*.

a) Amplification of the aprE Promoter

The aprE promoter was amplified from chromosomal DNA from *Bacillus subtilis* using the following primers:

```
CF 797 (+) Start aprE promoter MfeI
                                            (SEQ ID NO: 58)
5'-GACATCAATTGCTCCATTTTCTTCTGCTATC CF 07-43 (-) Fuse aprE promoter to Kudzu ispS
                                            (SEQ ID NO: 59)
5'-ATTGAGAAGAGGTCGCACACACTCTTTACCCTCTCCTTTTA
``` b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                            (SEQ ID NO: 60)
5'-TAAAAGGAGAGGGTAAAGAGTGTGTGCGACCTCTTCTCAAT CF 07-45 (-) Fuse the 3' end of kudzu isoprene
synthase gene to the terminator
                                            (SEQ ID NO: 61)
5'-CCAAGGCCGGTTTTTTTTAGACATACATCAGCTGGTTAATC
``` c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                   (SEQ ID NO: 62)
5'-GATTAACCAGCTGATGTATGTCTAAAAAAAACCGGCCTTGG CF 07-46 (-) End of B. amyliquefaciens terminator
(BamHI)
                                   (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                   (SEQ ID NO: 60)
5'-TAAAAGGAGAGGGTAAAGAGTGTGTGCGACCTCTTCTCAAT CF 07-46 (-) End of B. amyliquefaciens terminator
(BamHI)
                                   (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                   (SEQ ID NO: 64)
5'-GACATCAATTGCTCCATTTTCTTCTGCTATC CF 07-46 (-) End of B. amyliquefaciens terminator
(BamHI)
                                   (SEQ ID NO: 63)
5'-GACATGACGGATCCGATTACGAATGCCGTCTC
```

The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                   (SEQ ID NO: 65)
5'-GACATGAATTCCTCCATTTTCTTCTGC CF 847 (+) Sequence in pXX 049 (end of aprE
promoter)
                                   (SEQ ID NO: 66)
5'-AGGAGAGGGTAAAGAGTGAG CF 07-45 (-) Fuse the 3' end of kudzu
isoprene synthase to the terminator
                                   (SEQ ID NO: 61)
5'-CCAAGGCCGGTTTTTTTTAGACATACATCAGCTGGTTAATC CF 07-48 (+) Sequencing primer for kudzu
isoprene synthase
                                   (SEQ ID NO: 67)
5'-CTTTTCCATCACCCACCTGAAG CF 07-49 (+) Sequencing in kudzu isoprene synthase
                                   (SEQ ID NO: 68)
5'-GGCGAAATGGTCCAACAACAAAATTATC
```

Figure 52:
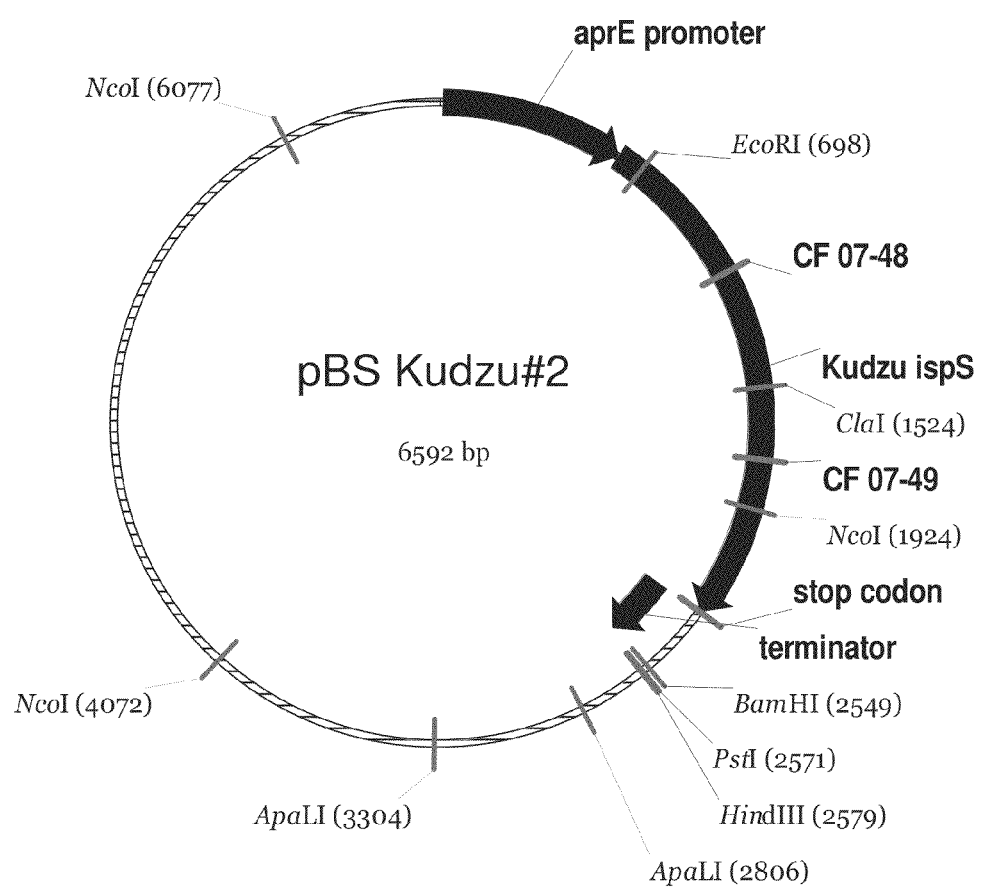
FIG. 52 is a map of pBS Kudzu #2.

The plasmid designated pBS Kudzu #2 (FIGS. 52 and 12) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

Figure 11:
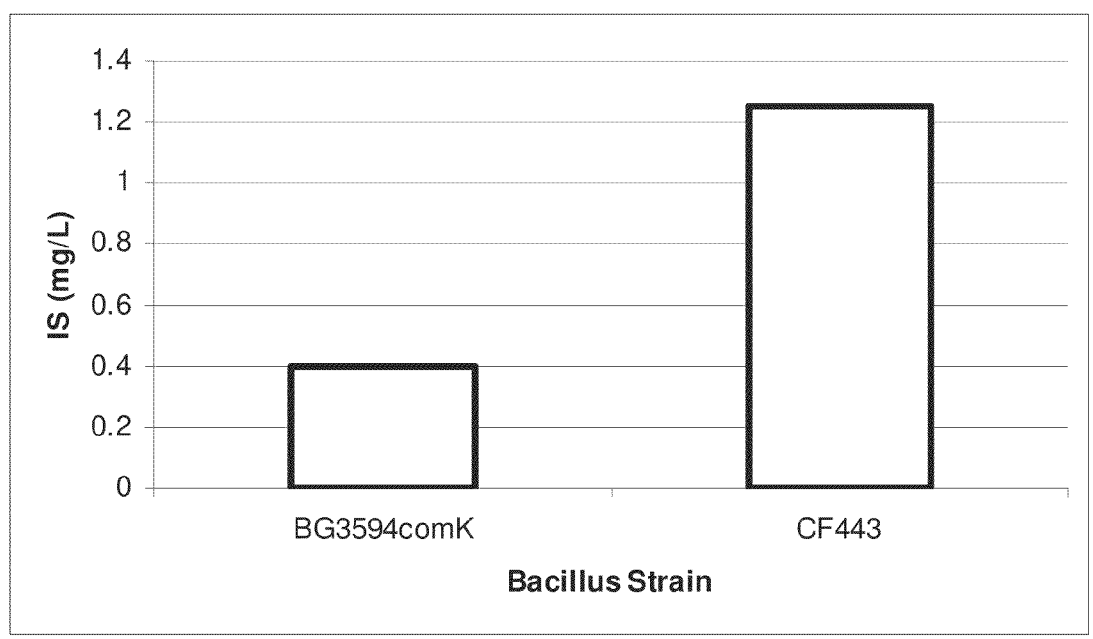
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA+Chloramphenicol (Cm, 25 μg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10× MOPS, q.s. to 1 L with $H_2O$, pH 7.2; 10× MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NACl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4*2H_2O$, q.s. to 1 L with $H_2O$. Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation

Figure 53A:
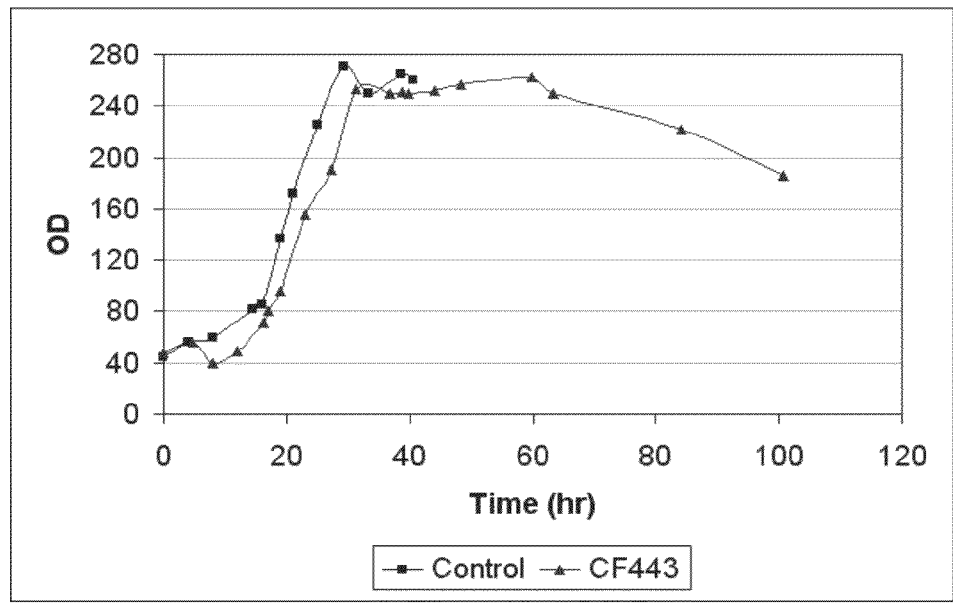
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).
Figure 53B:
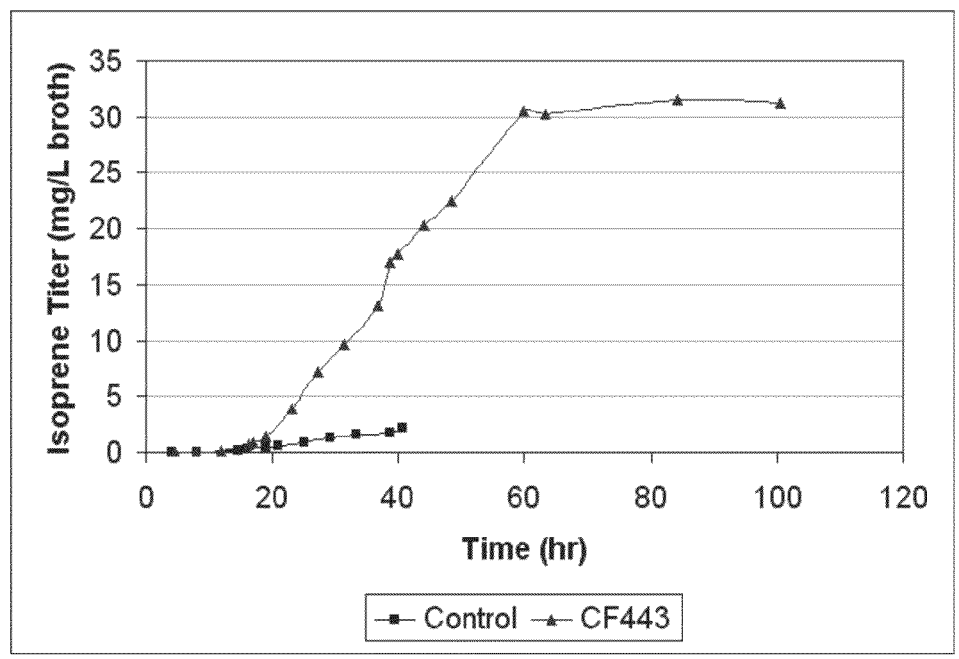
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Large scale production of isoprene from *B. subtilis* containing the recombinant kudzu isoprene synthase gene on a replication plasmid was determined from a fed-batch culture. Bacillus strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO%, airflow, and pressure were monitored throughout the entire process. The DO% is maintained above 20. Samples were taken over the time course of 36 hours and analyzed for cell growth (OD$_{550}$) and isoprene production. Results of these experiments are presented in FIGS. 53A and 53B.

IV. Integration of the Kudzu Isoprene Synthase (ispS) in *B. subtilis*.

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma reesei* Expressing Recombinant Kudzu Isoprene Synthase I. Construction of Vectors for Expression of the Kudzu Isoprene Synthase in *T. reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 µl plasmid template (20 ng/ul), 1 µl Primer EL-945 (10 uM) 5'-GCTTATGGATCCTCTAGACTATTA-CACGTACATCAATTGG (SEQ ID NO:9), 1 µl Primer EL-965 (10 uM) 5'-CACCATGTGTGCAACCTCCTC-CCAGTTTAC (SEQ ID NO:10), 1 µl dNTP (10 mM), 5 µl 10× PfuUltra II Fusion HS DNA Polymerase Buffer, 1 µl PfuUltra II Fusion HS DNA Polymerase, 40 µl water in a total reaction volume of 50 µl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 µl. The reaction was incubated at room temperature for 5 minutes. One microliter of TOPO reaction was transformed into TOP10 chemically competent *E. coli* cells. The transformants were selected on LA+50 µg/ml kanamycin plates. Several colonies were picked and each was inoculated into a 5 ml tube containing LB+50 µg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid encoding a *Y. lipolytica* codon-optimized kudzu isoprene synthase gene was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 µl. The reaction was incubated at room temperature for 1 hour and then 1 µl proteinase K solution was added and the incubation continued at 37° C. for 10 minutes. Then 1 µl of reaction was transformed into TOP10 chemically competent *E. coli* cells. The transformants were selected on LA+50 µg/ml carbenicillin plates. Several colonies were picked and each was inoculated into a 5 ml tube containing LB+50 µg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
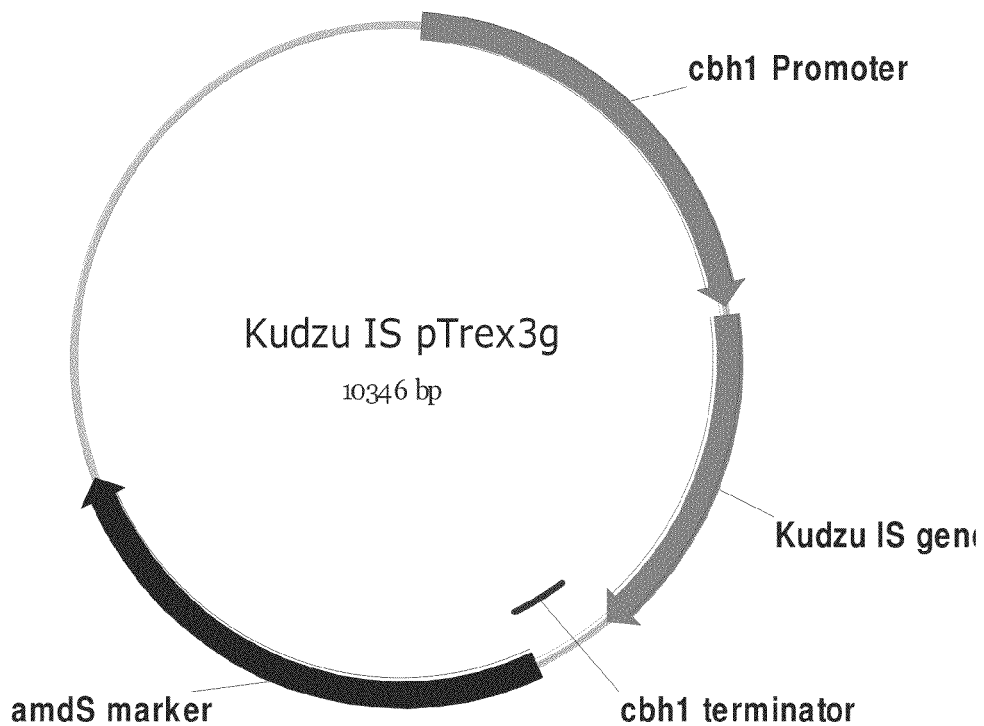
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 µg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia lipolytica* Expressing Recombinant Kudzu Isoprene Synthase I. Construction of Vectors for Expression of the Kudzu Isoprene Synthase in *Y. lipolytica*.

The starting point for the construction of vectors for the expression of the kudzu isoprene synthase gene in *Yarrowia lipolytica* was the vector pSPZ1 (MAP29Spb). The complete sequence of this vector (SEQ ID No:11) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                    (SEQ ID NO: 69)
5'-GGTGAATTCAGTCTACTGGGGATTCCCAAATCTATATATACTGCA
GGTGAC

ICL1 5
                                    (SEQ ID NO: 70)
5'-GCAGGTGGGAAACTATGCACTCC

XPR 3
                                    (SEQ ID NO: 71)
5'-CCTGAATTCTGTTGGATTGGAGGATTGGATAGTGGG

XPR 5
                                    (SEQ ID NO: 72)
5'-GGTGTCGACGTACGGTCGAGCTTATTGACC

XPRT3
```

-continued (SEQ ID NO: 73)
5'-GGTGGGCCCGCATTTTGCCACCTACAAGCCAG

XPRT 5
(SEQ ID NO: 74)
5'-GGTGAATTCTAGAGGATCCCAACGCTGTTGCCTACAACGG

Y18S3
(SEQ ID NO: 75)
5'-GGTGCGGCCGCTGTCTGGACCTGGTGAGTTTCCCCG

Y18S 5
(SEQ ID NO: 76)
5'-GGTGGGCCCATTAAATCAGTTATCGTTTATTTGATAG

YURA3
(SEQ ID NO: 77)
5'-GGTGACCAGCAAGTCCATGGGTGGTTTGATCATGG

YURA 50
(SEQ ID NO: 78)
5'-GGTGCGGCCGCCTTTGGAGTACGACTCCAACTATG

YURA 51
(SEQ ID NO: 79)
5'-GCGGCCGCAGACTAAATTTATTTCAGTCTCC

For PCR amplification the PfuUltraII polymerase (Stratagene), supplier-provided buffer and dNTPs, 2.5 µM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
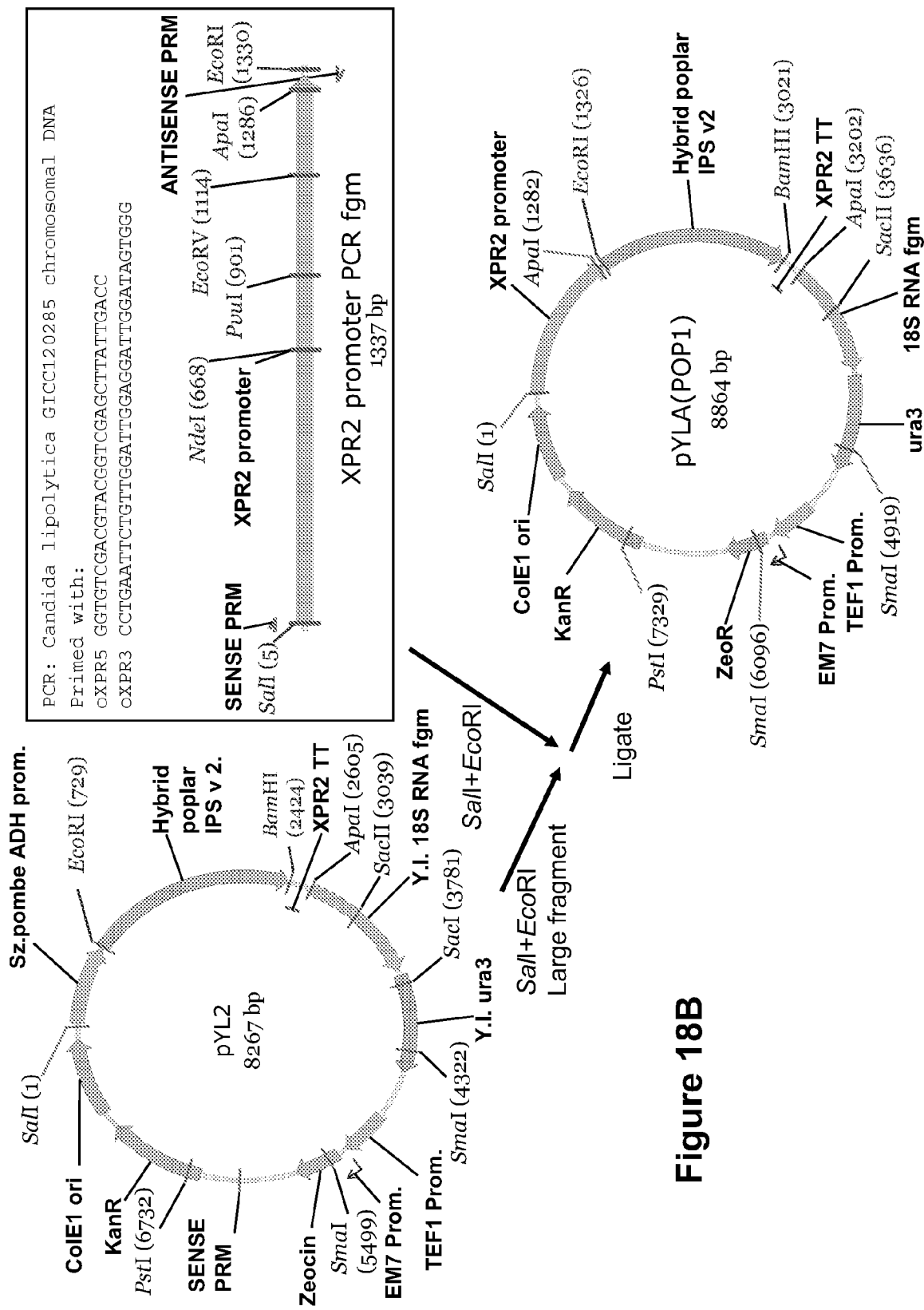
FIG. 18B shows a schematic outlining construction of the vector pYLA(POP1) (SEQ ID NO: 72, 73).
Figure 18C:
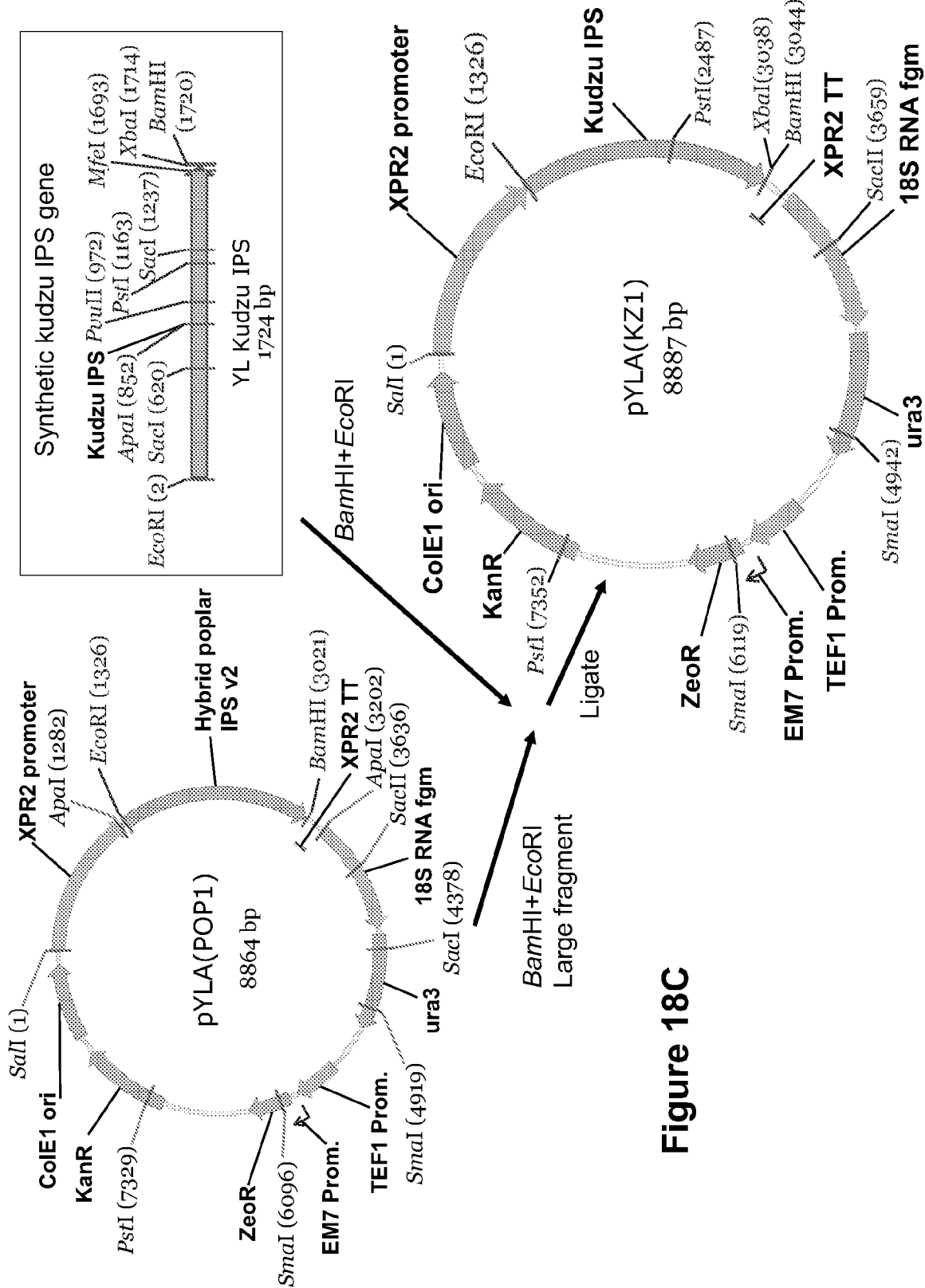
FIG. 18C shows a schematic outlining construction of the vector pYLA(KZ1)
Figure 18D:
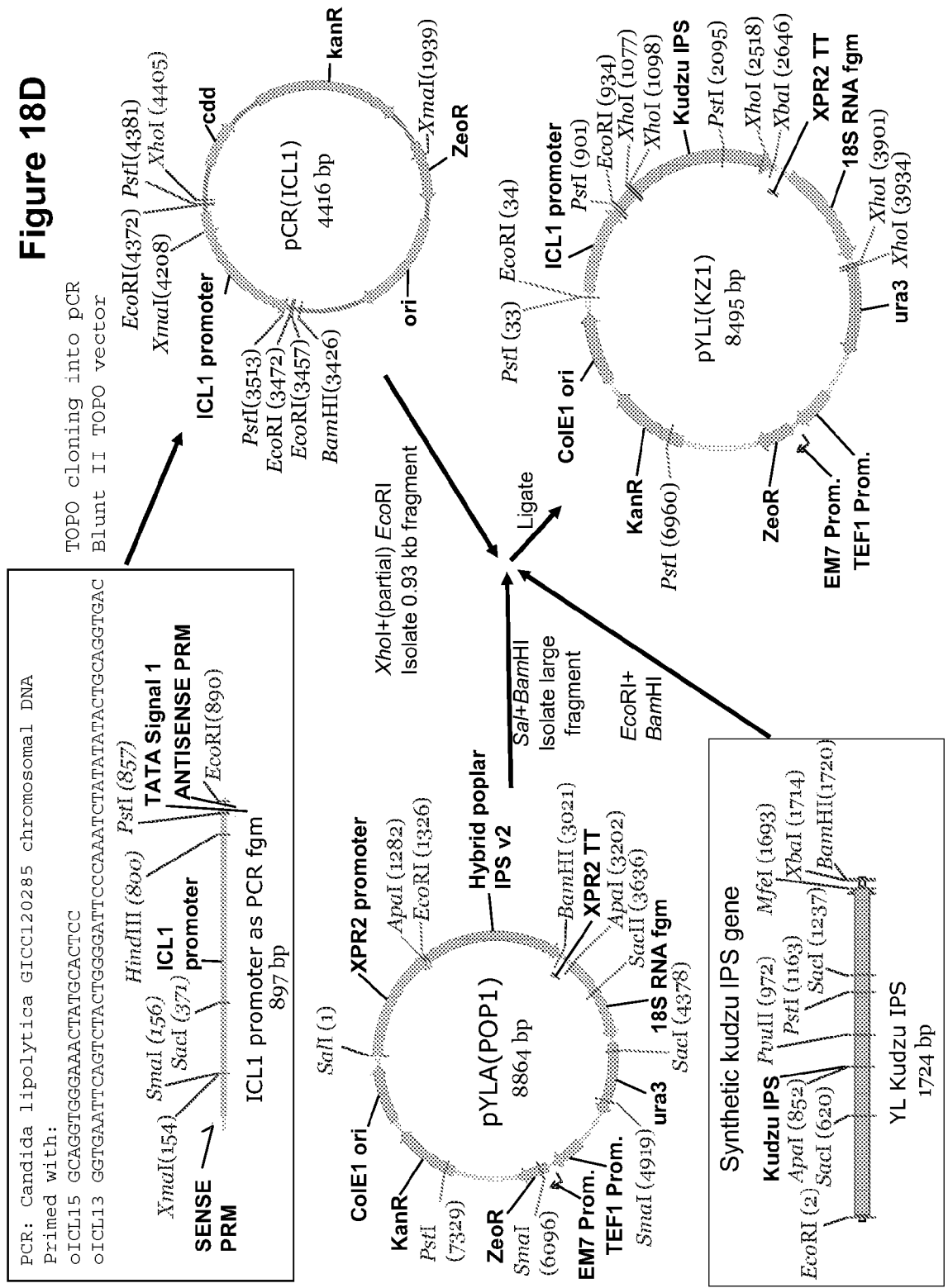
FIG. 18D shows a schematic outlining construction of the vector pYLI(KZ1) SEQ ID NO: 70, 71).
Figure 18E:
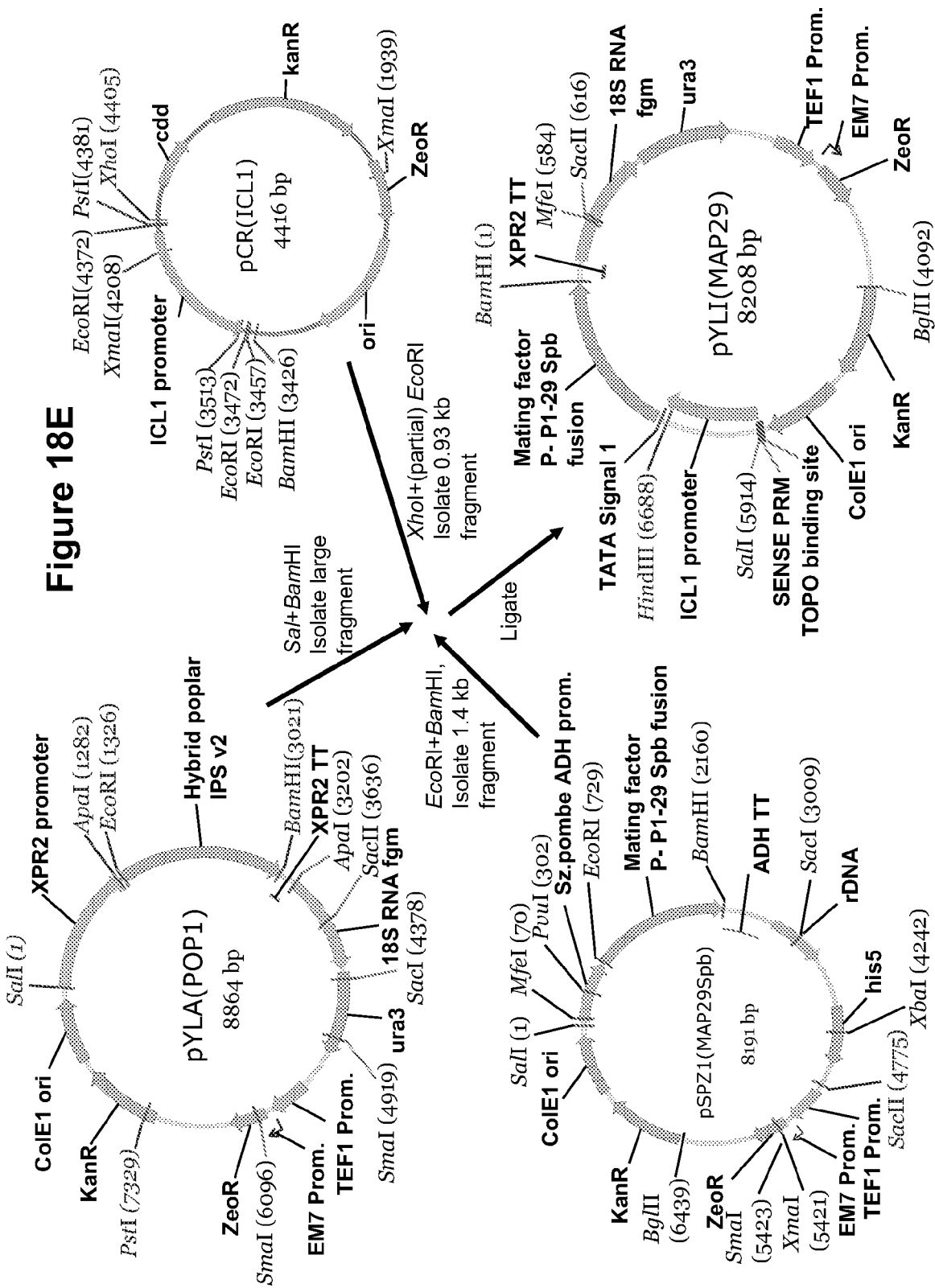
FIG. 18E shows a schematic outlining construction of the vector pYLI(MAP29)
Figure 18F:
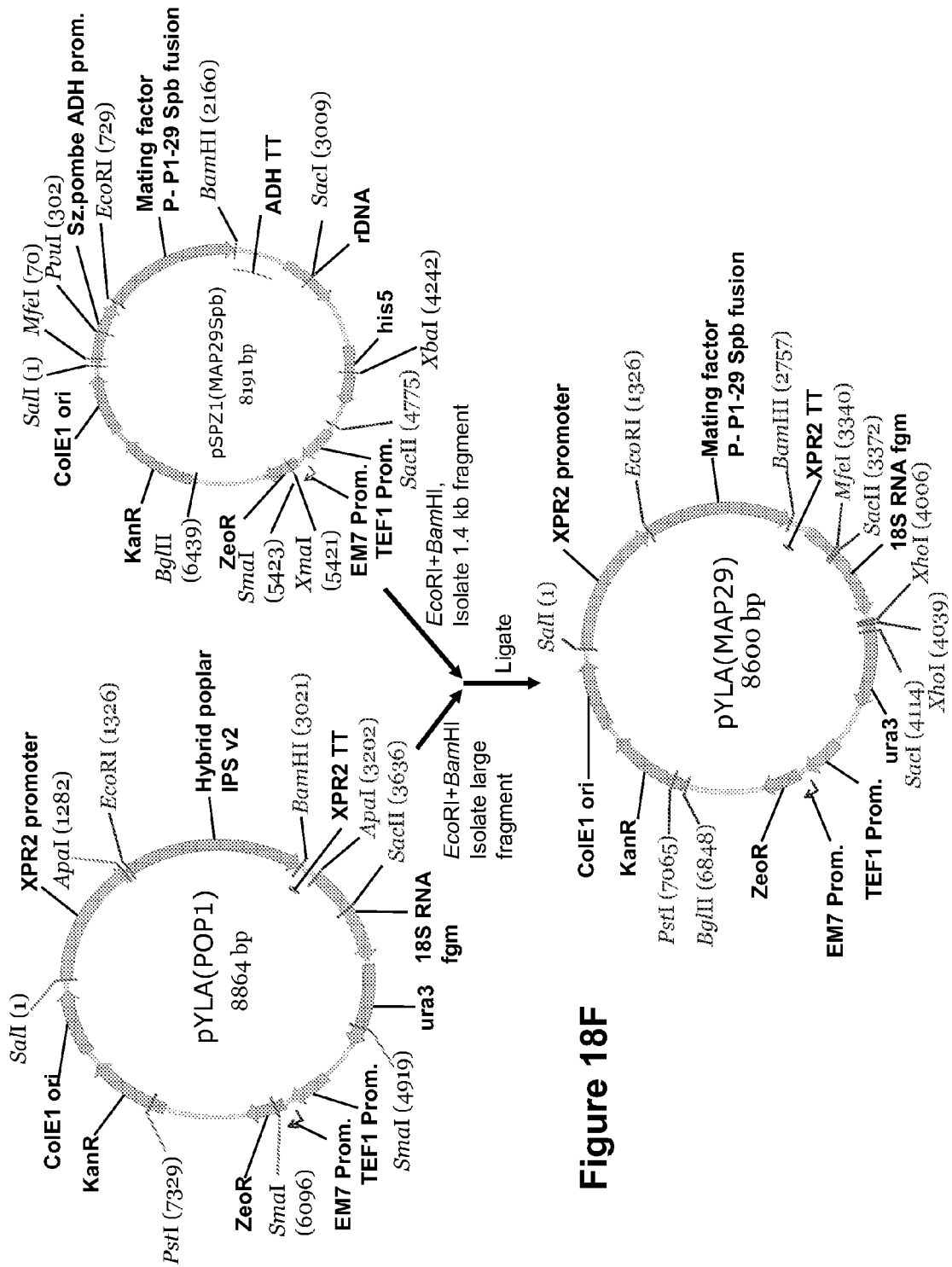
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba×Populus tremula*) isoprene synthase gene. The sequence of the poplar isoprene is described in Miller B. et al. (2001) *Planta* 213, 483-487 and shown in FIG. 17 (SEQ ID NO:13). A construction scheme for the generation of the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred µl aliquots of the cell suspension were mixed with linearized plasmid DNA solution (10-20 µg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Figure 20:
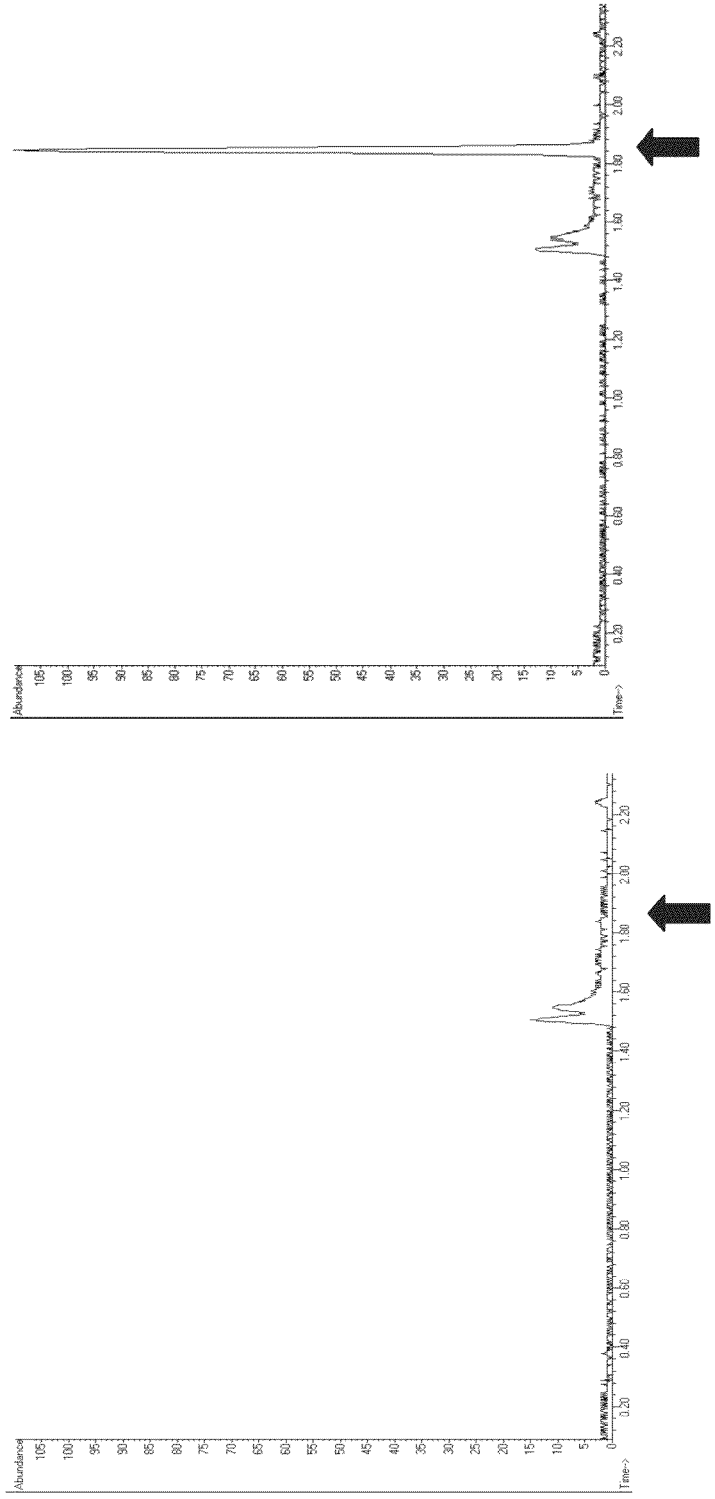
FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.
Figure 20A:
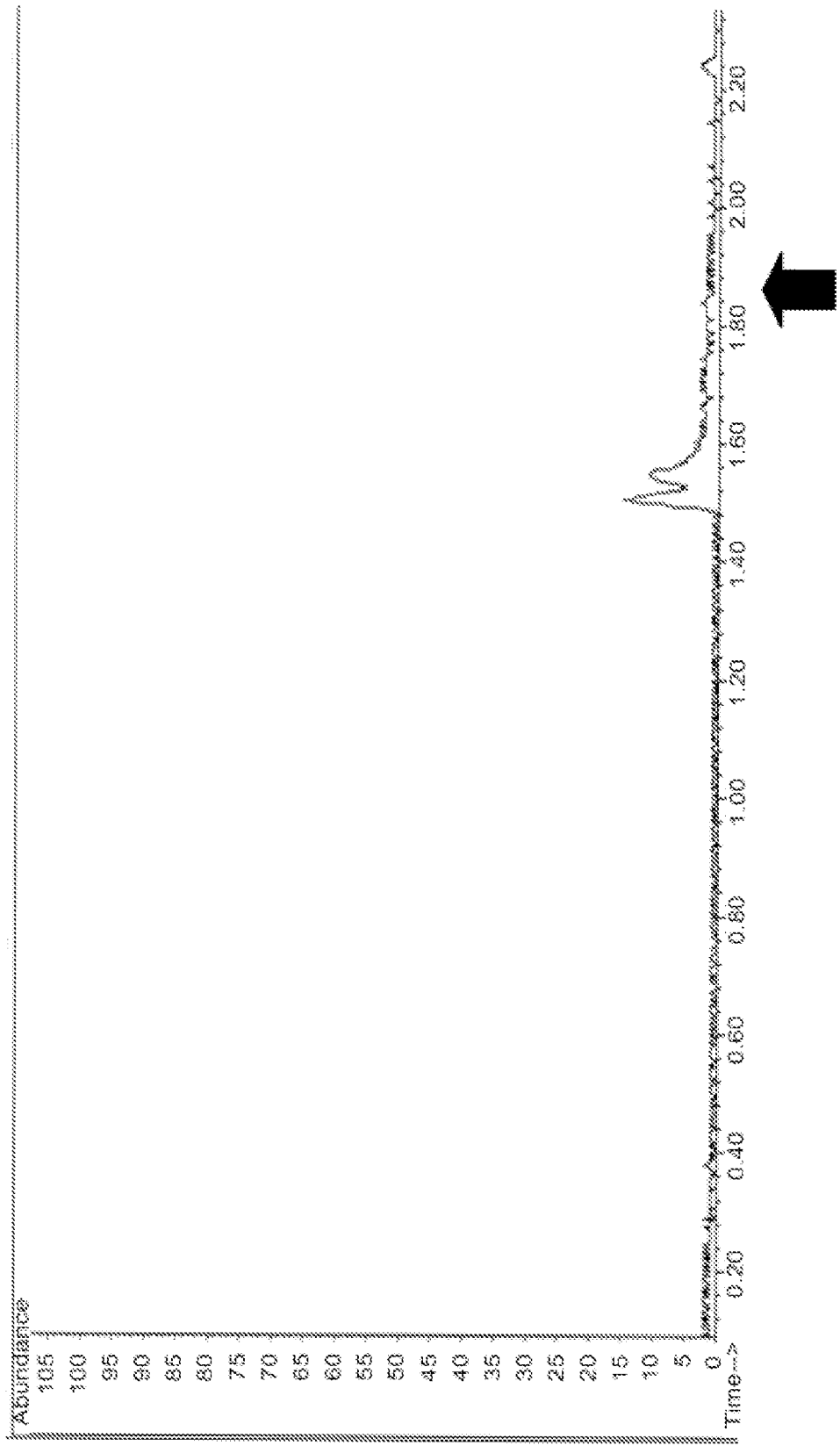
Figure 20B:
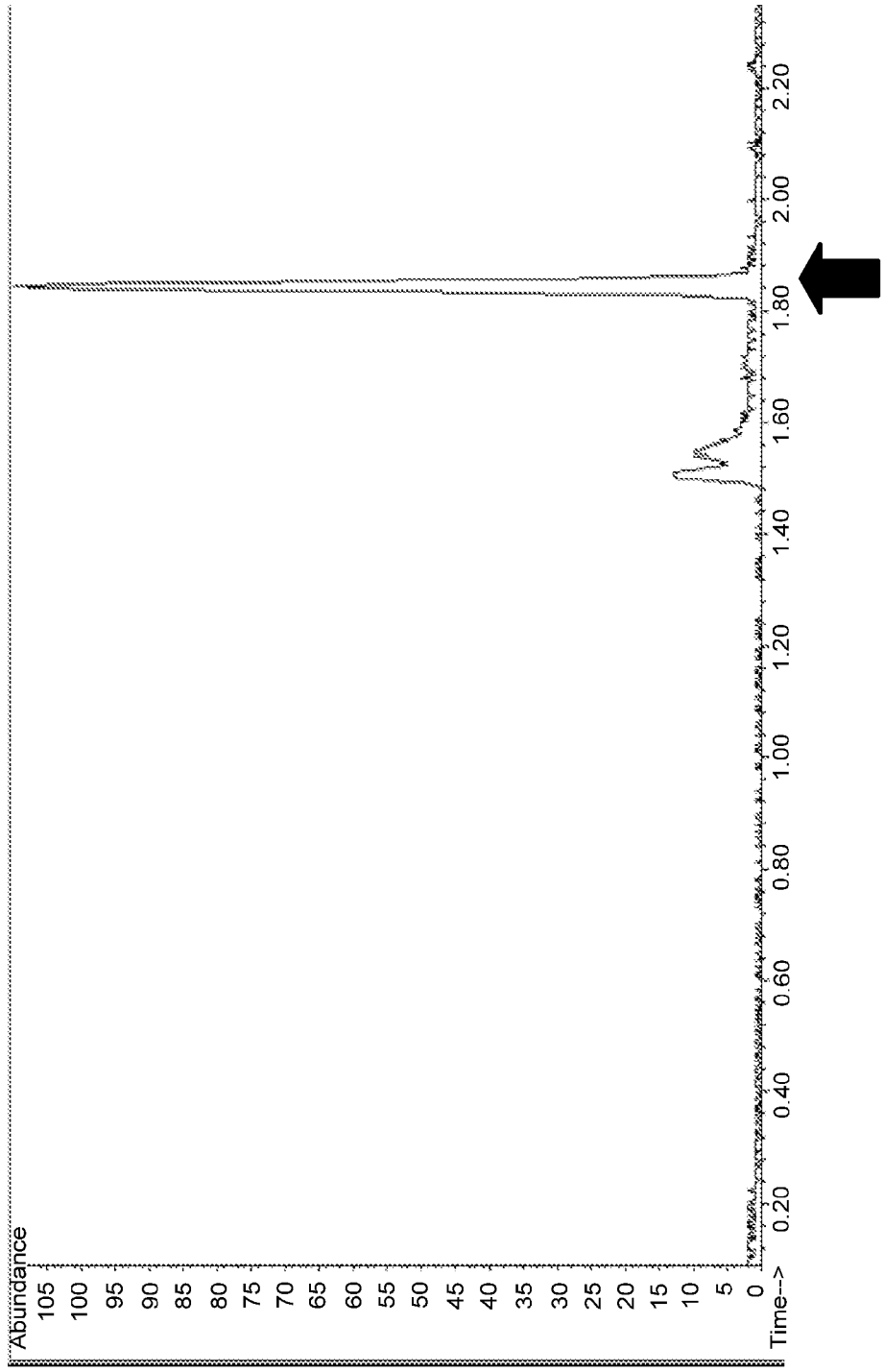

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 µg/L to 1 µg/L, FIG. 20). No isoprene was detected in the headspace of the control strains carrying phytase gene instead of an isoprene synthase gene.

Example 7

Figure 21:
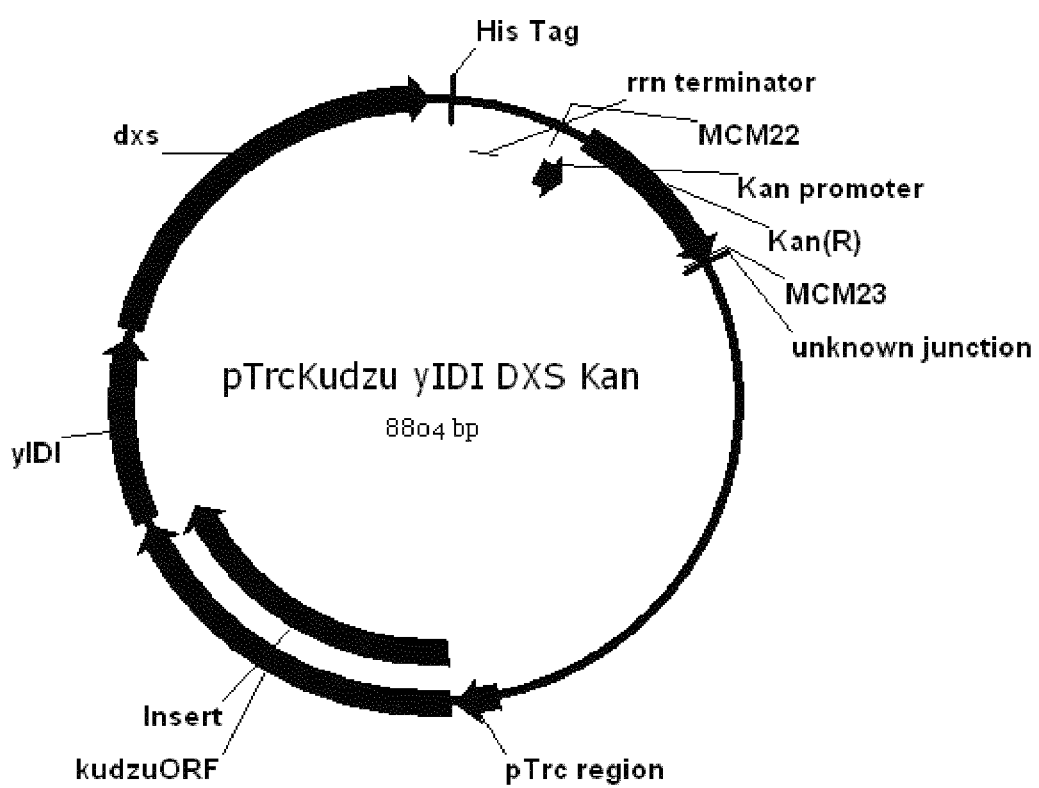
FIG. 21 is a map of pTrcKudzu yIDI DXS Kan.
Figure 34:
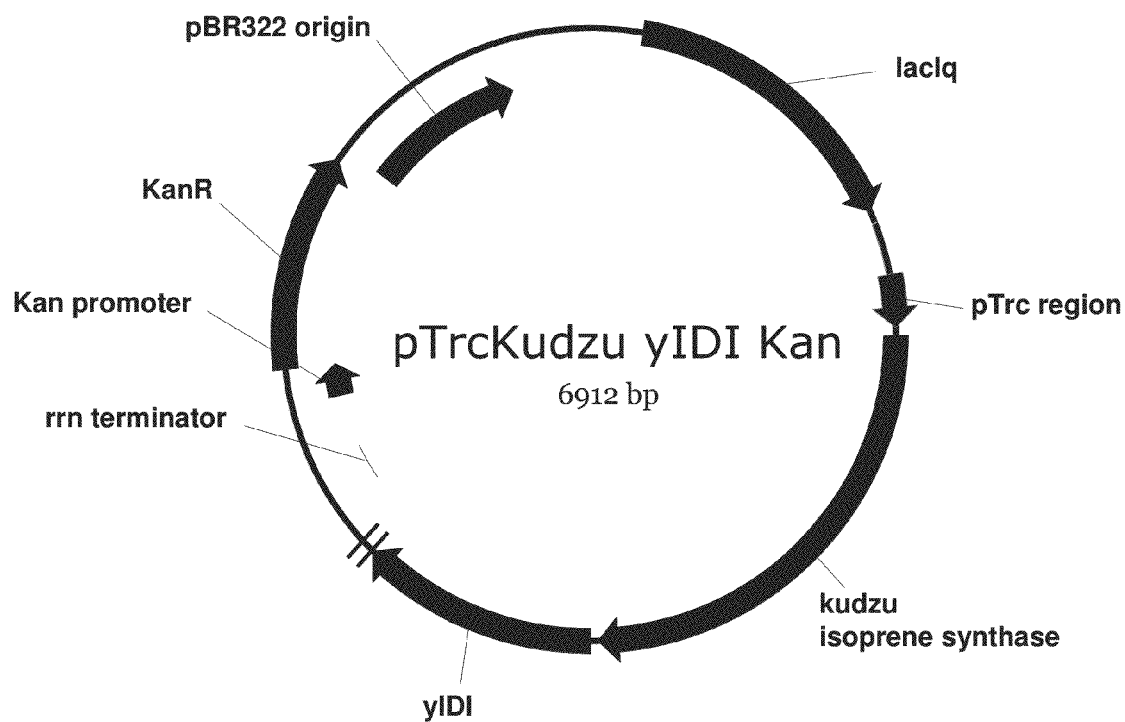
FIG. 34 is a map of pTrcKudzu yIDI Kan.
Figure 36:
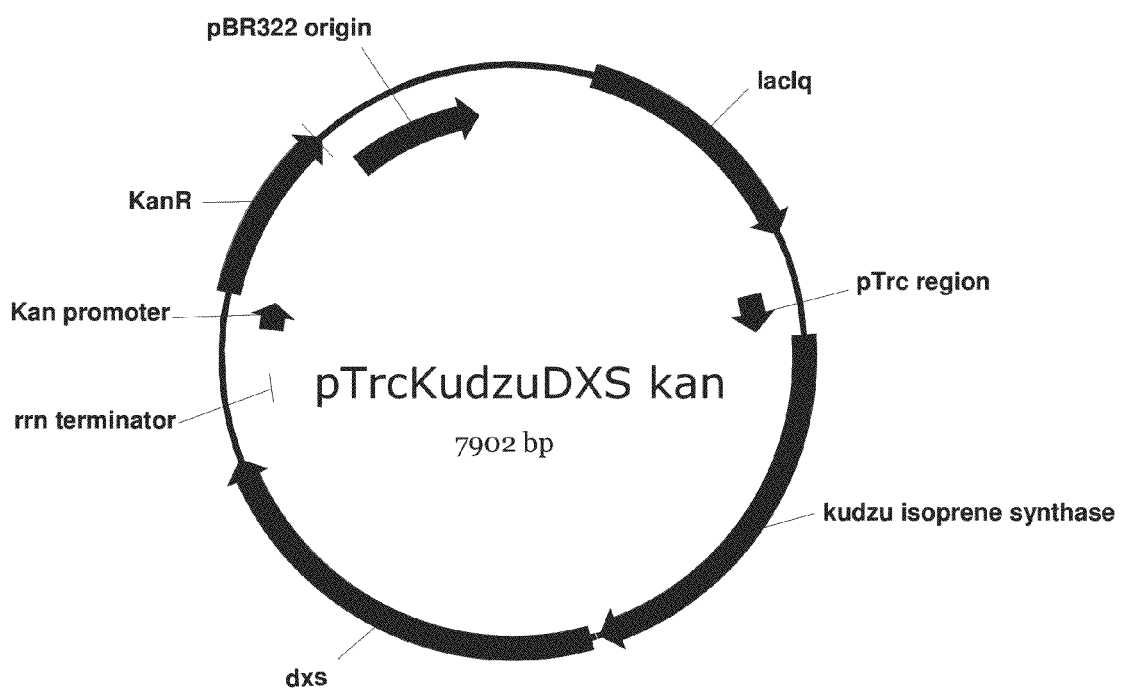
FIG. 36 is a map of pTrcKudzuDXS Kan.
Figure 38:
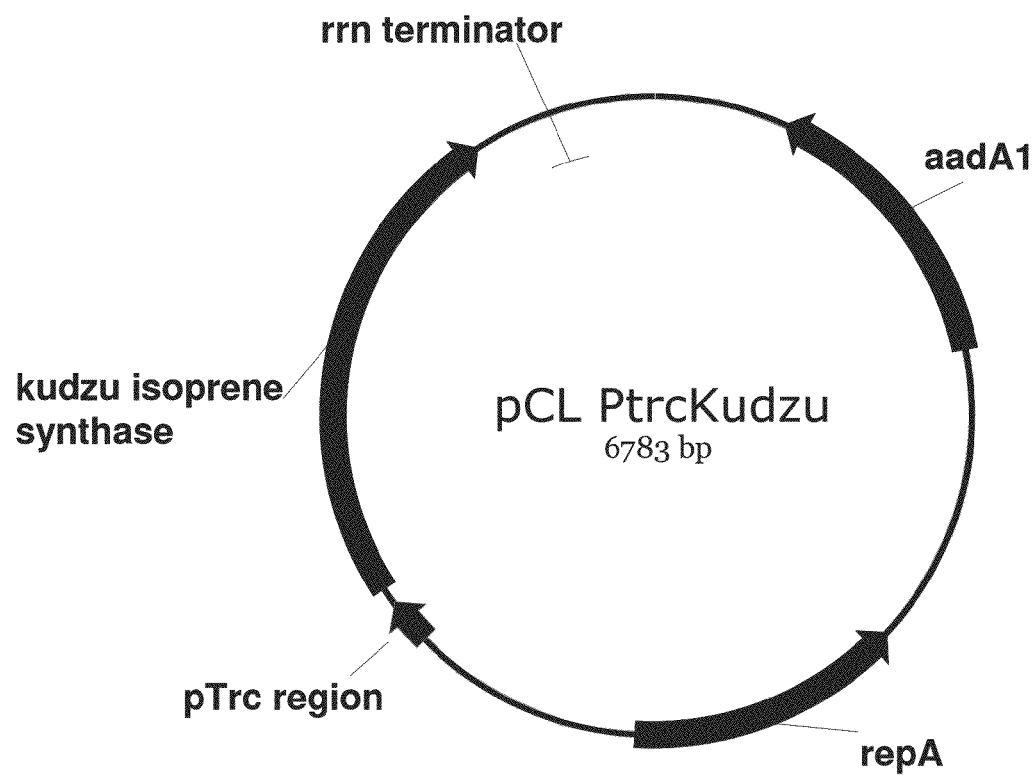
FIG. 38 is a map of pCL PtrcKudzu.
Figure 40:
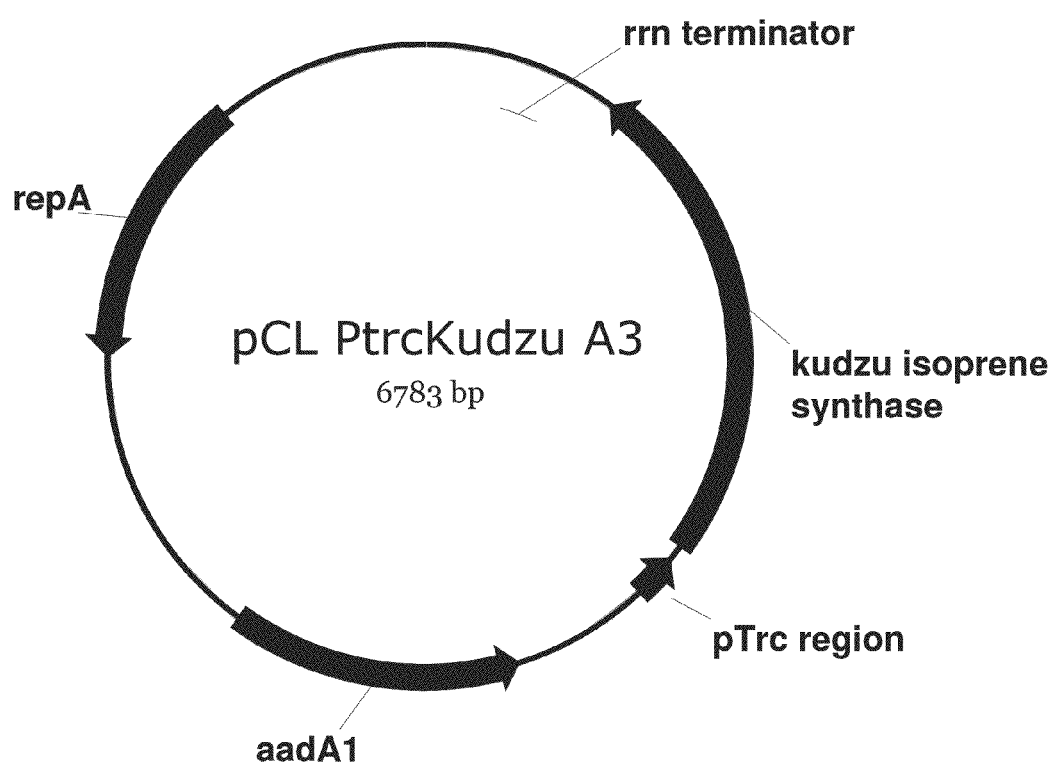
FIG. 40 is a map of pCL PtrcKudzu A3.

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli*
i) Construction of pTrcKudzuKan The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 µg/ml.
ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 µg/ml kanamycin. Several transformants were isolated and sequenced and the resulting plasmid was called pTrcKudzu-yIDI(kan) (FIGS. 34 and 35).
iii) Construction of pTrcKudzu DXS Kan Plasmid pTrcKudzuKan was digested with PstI, treated with SAP, heat killed and gel purified. It was ligated to a PCR product encoding dxs from *E. coli* with a synthetic RBS. The primers for PCR were MCM13 5'-GATCATGCATTCGCCCTTAGGAGGTAAAAAAACATGAGTTTTGATATTGCCAAATAC CCG (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 μg/ml. Several transformants were isolated and sequenced and the resulting plasmid was called pTrcKudzu-DXS(kan) (FIGS. 36 and 37).

iv) Construction of pTrcKudzu-yIDI-dxs (Kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGG-TAAAAAAACATGAGTTTTGATATTGCCAAATAC CCG (SEQ ID NO:18) and MCM14 5'-CATGCTGCAGTTATGC-CAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 μg/ml. Several clones were isolated and sequenced and two were selected. pCL PtrcKudzu and pCL PtrcKudzu (A3) have the insert in opposite orientations (FIGS. 38-41).

vi) Construction of pCL PtrcKudzu yIDI

Figure 42:
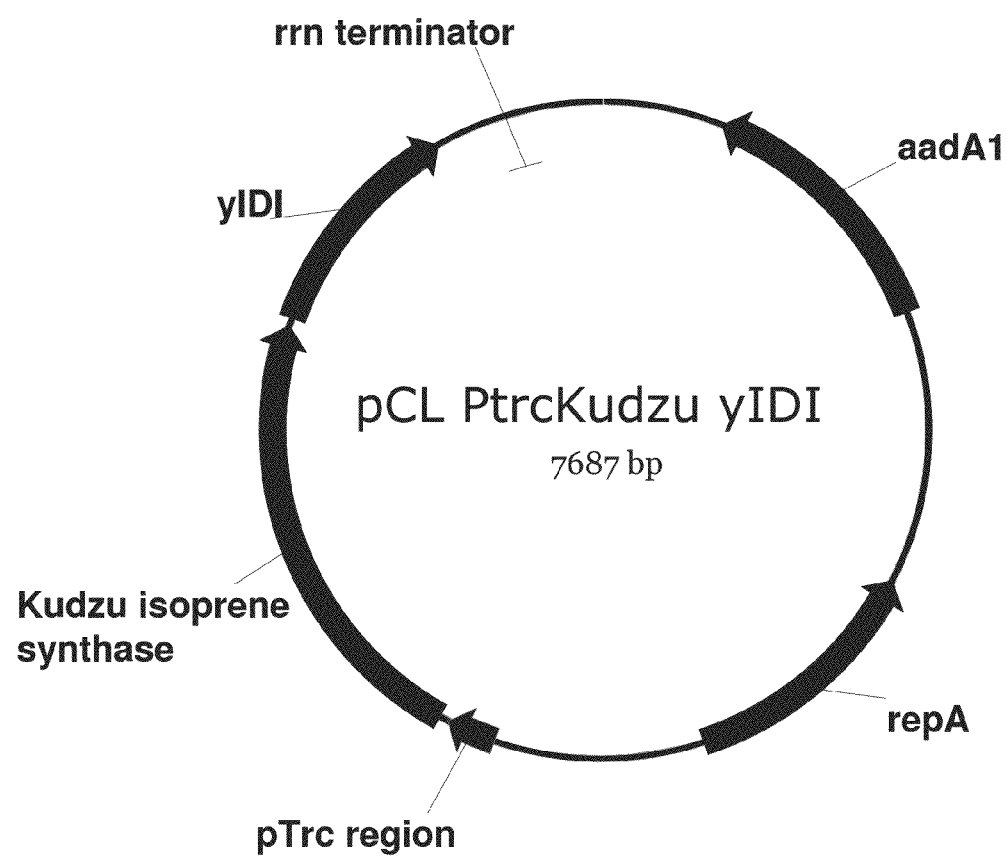
FIG. 42 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu yIDI (FIGS. 42 and 43).

vii) Construction of pCL PtrcKudzu DXS

Figure 44:
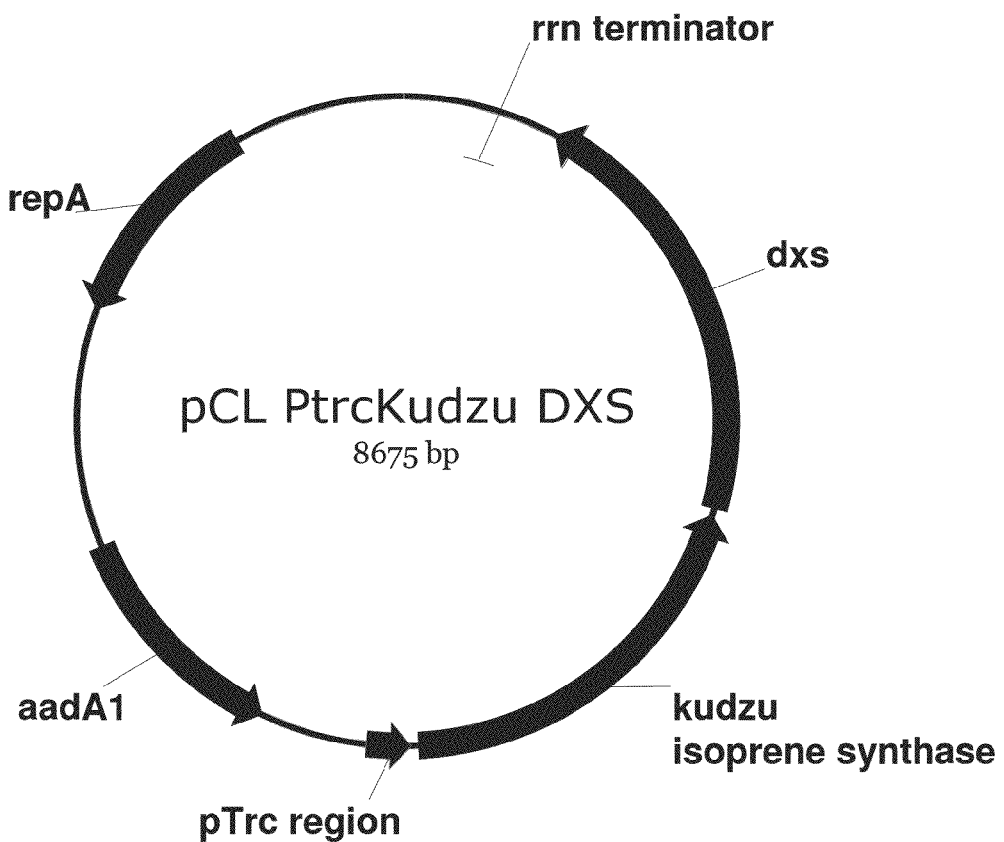
FIG. 44 is a map of pCL PtrcKudzu DXS.

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu DXS (FIGS. 44 and 45).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 μg/mL. Cultures of pCL PtrcKudzu (E), pCL PtrcKudzu, pCL PtrcKudzu-yIDI (F) and pCL PtrcKudzu-DXS (G) were grown in LB spectinomycin 50 μg/mL. Cultures were induced with 400 μM IPTG at time 0 ($OD_{600}$ approximately 0.5) and samples taken for isoprene headspace measurement (see Example 1). Results are shown in FIG. 23A-23G.

Figure 23A:
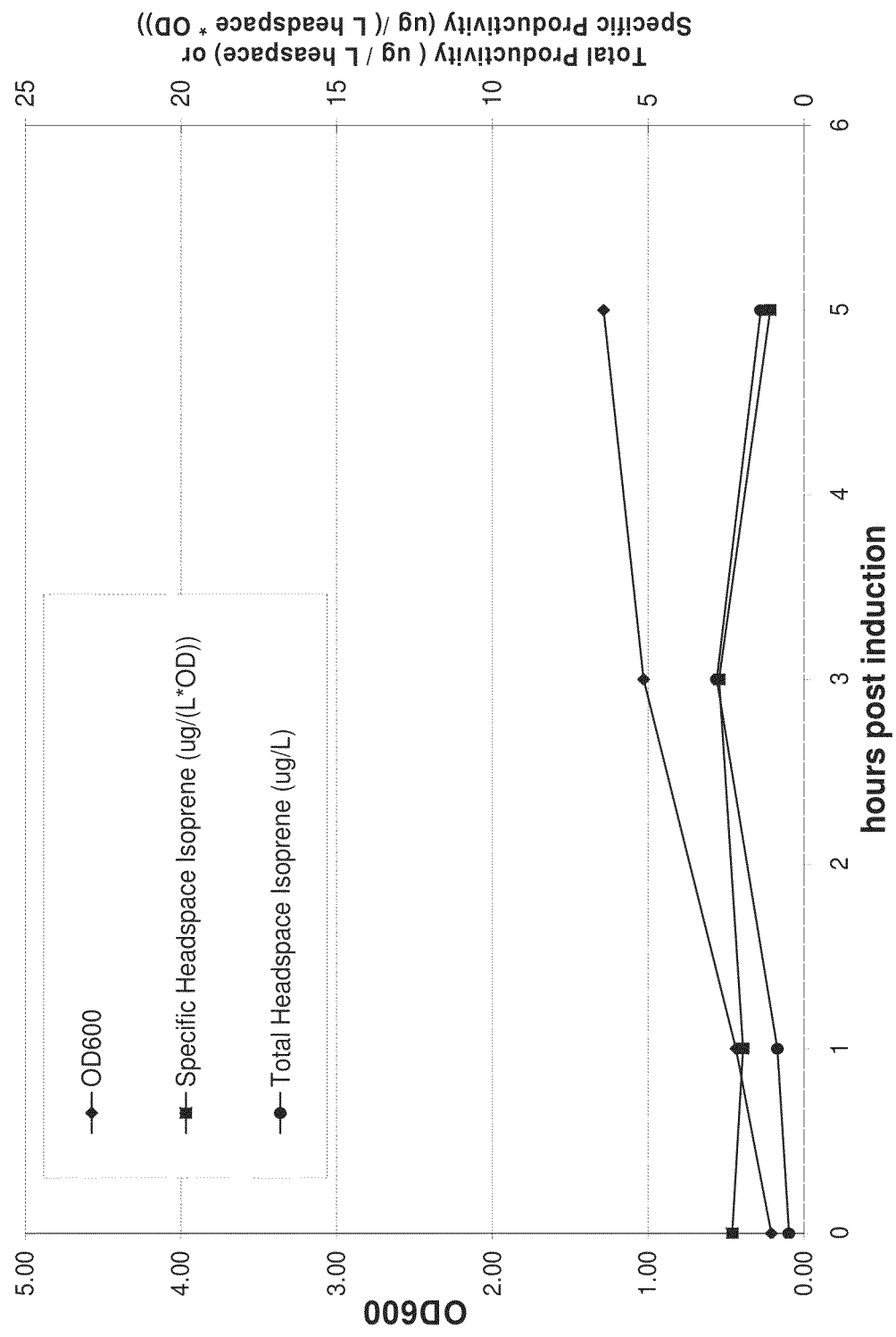
FIG. 23A is a graph showing production of isoprene from glucose in BL21/pTrcKudzukan. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23B:
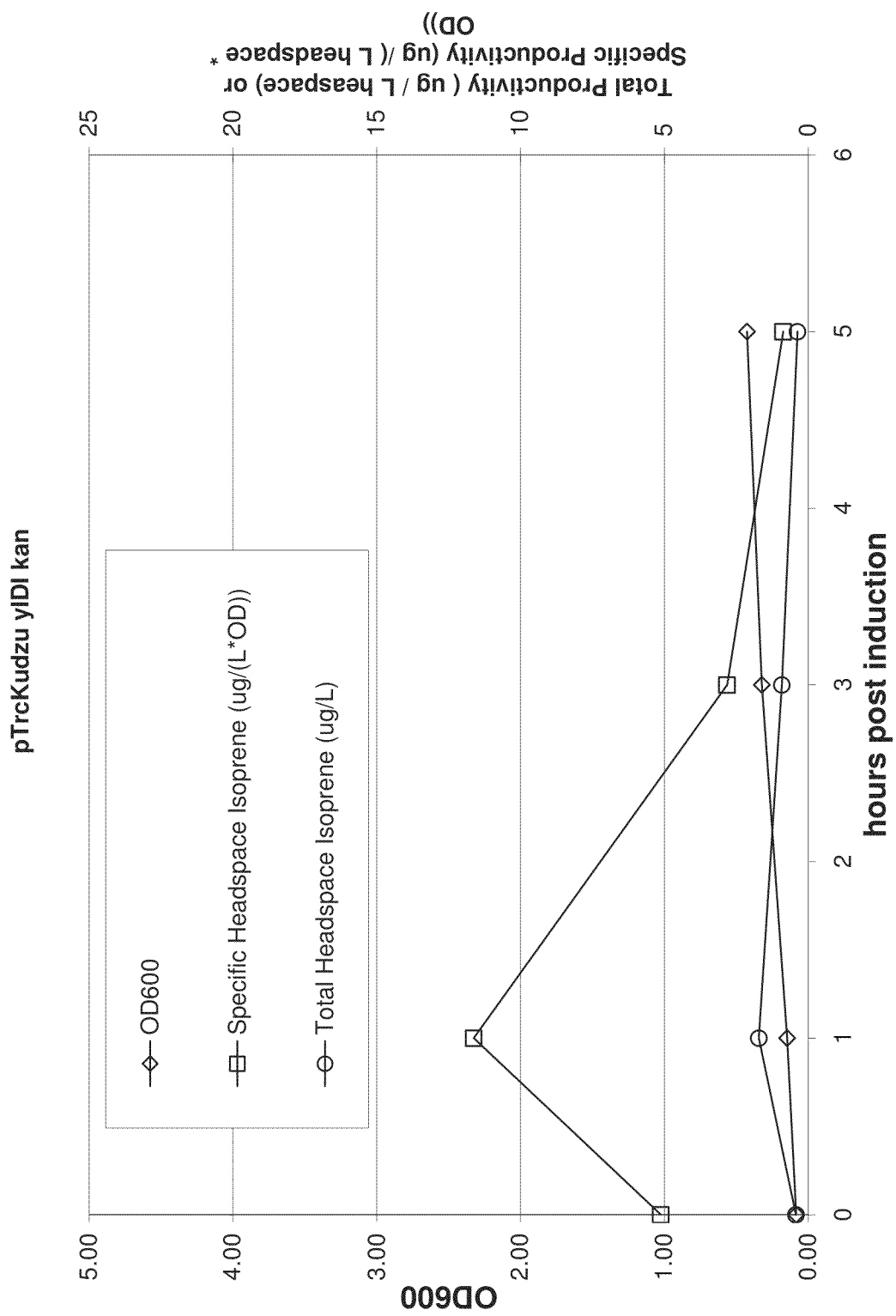
FIG. 23B is a graph showing production of isoprene from glucose in BL21/pTrcKudzu yIDI kan. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23D:
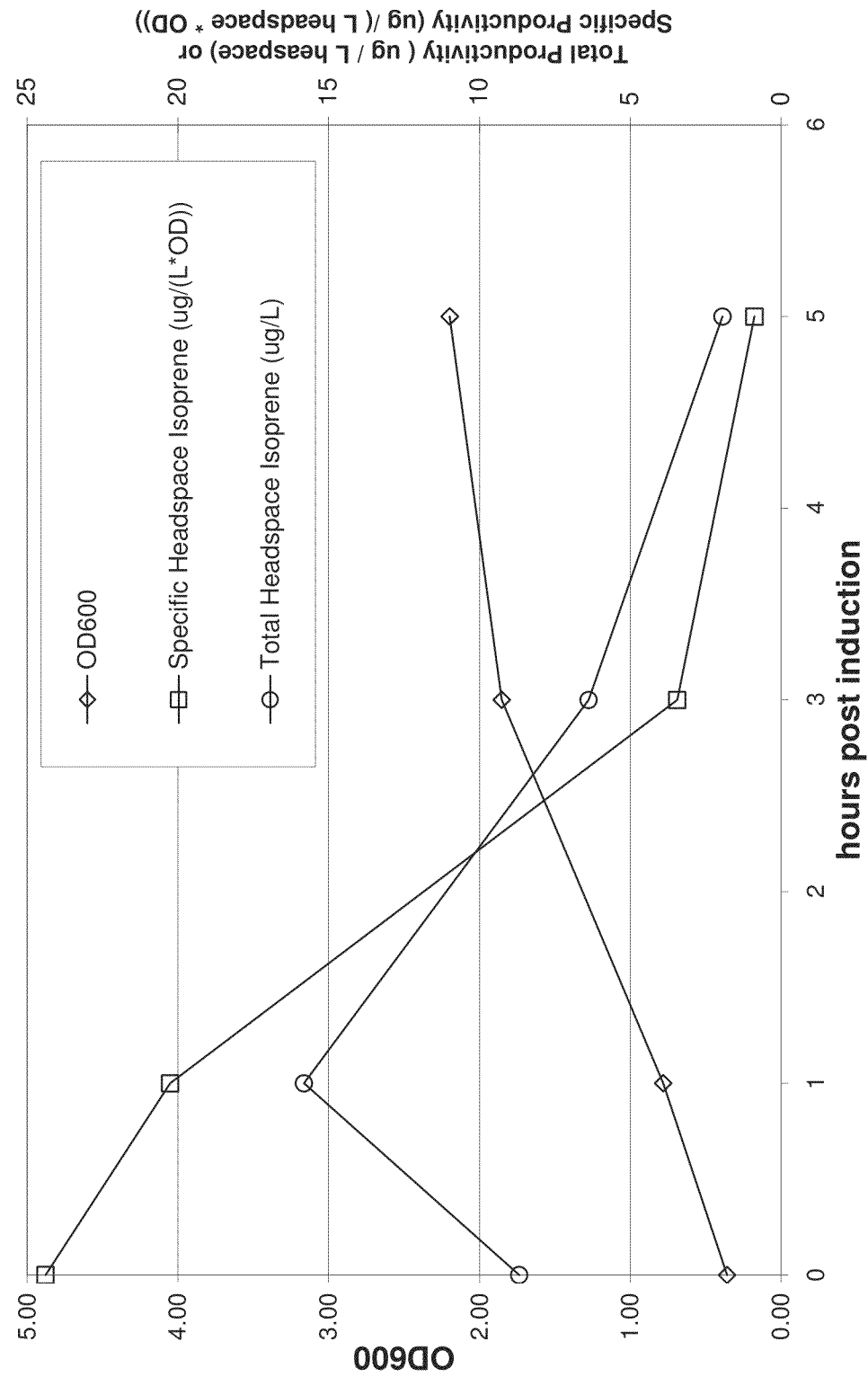
FIG. 23D is a graph showing production of isoprene from glucose in BL21/pTrcKudzu yIDI DXS kan. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23E:
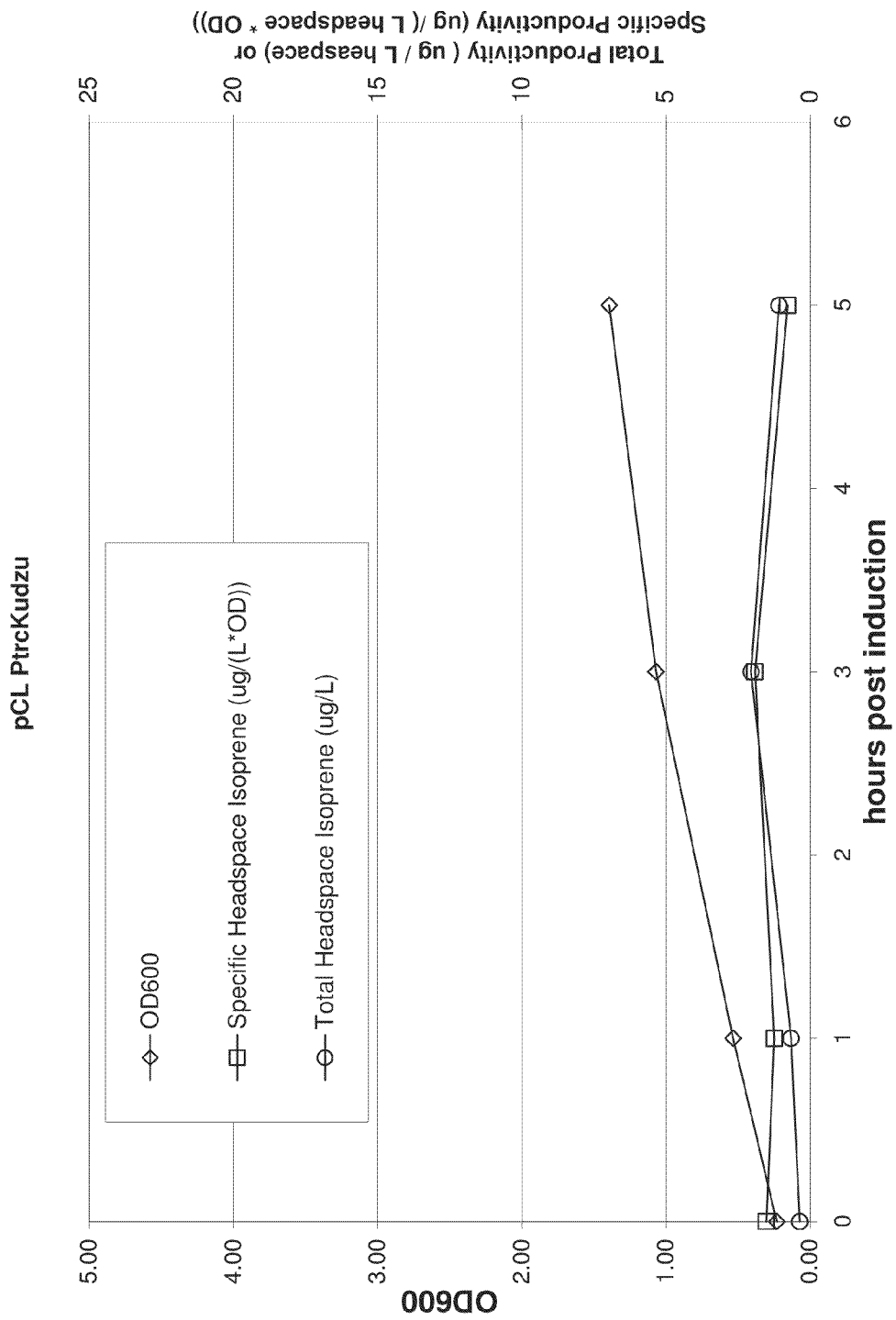
FIG. 23E is a graph showing production of isoprene from glucose in BL21/pCL PtrcKudzu. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23F:
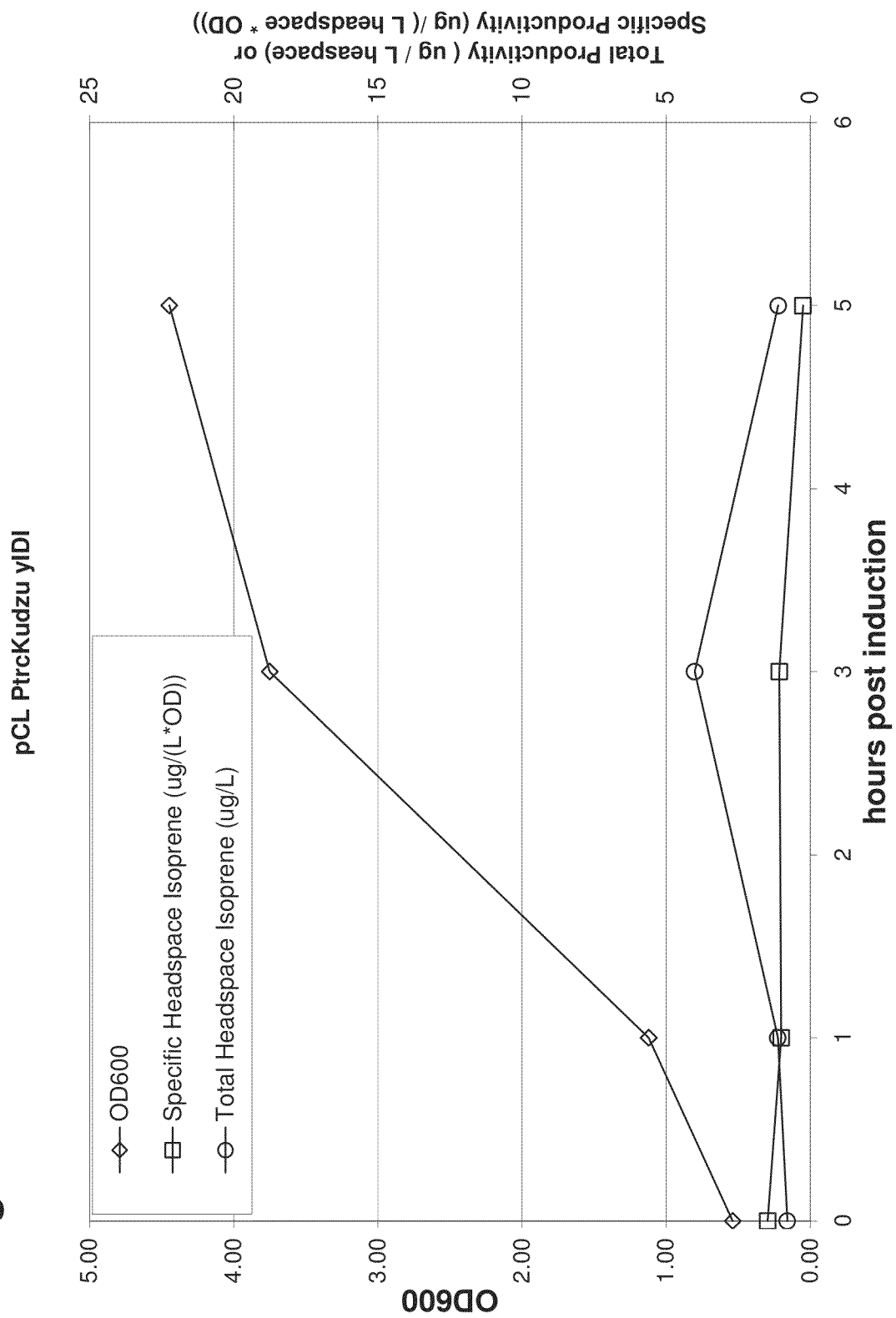
FIG. 23F is a graph showing production of isoprene from glucose in BL21/pCL PtrcKudzu yIDI. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23G:
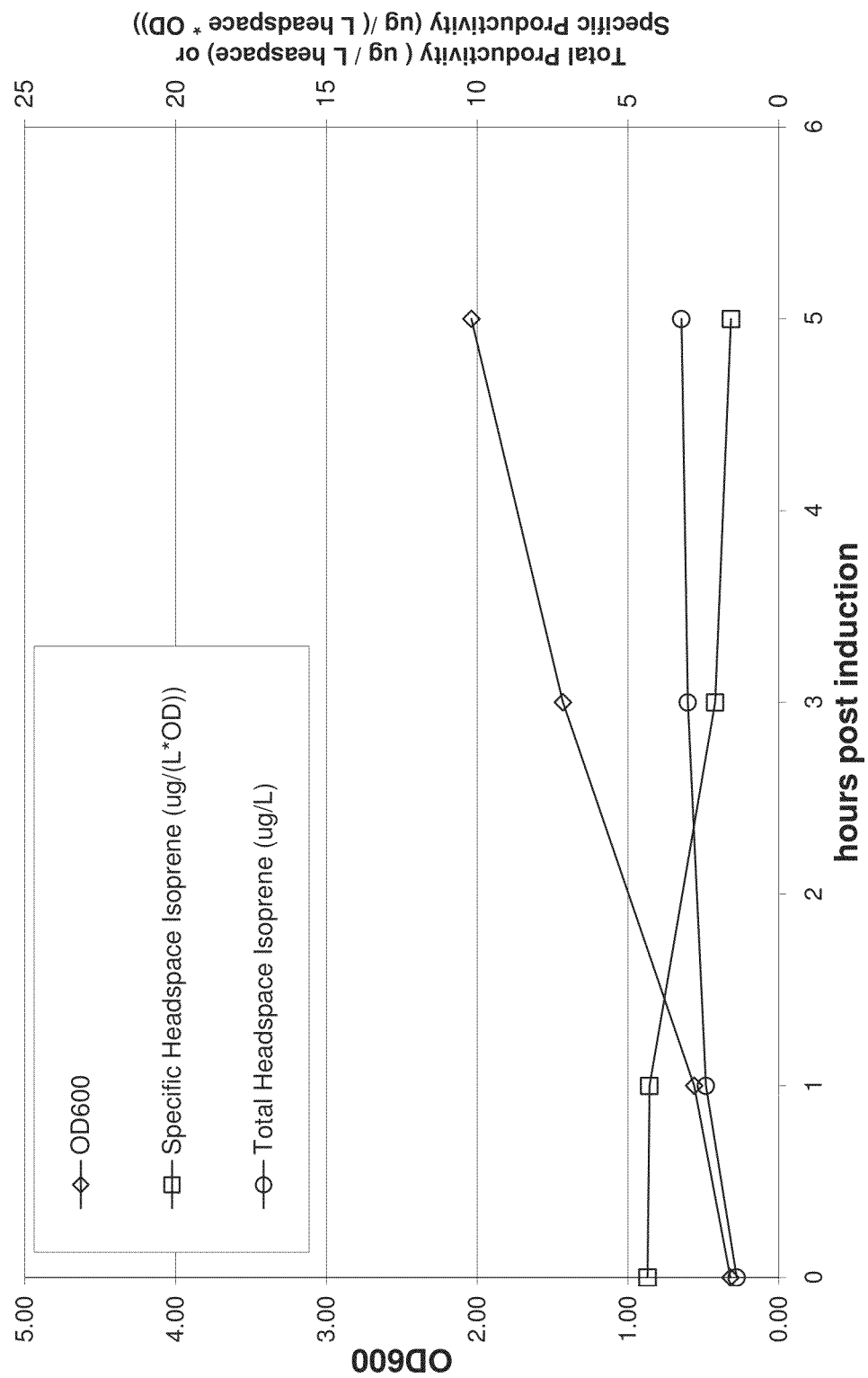
FIG. 23G is a graph showing production of isoprene from glucose in BL21/pCL PtrcKudzu DXS. Time 0 is the time of induction with IPTG (400 µmol). The x-axis is time after induction; the y-axis is $OD_{600}$ and the y2-axis is total productivity of isoprene (µg/L headspace or specific productivity (µg/L headspace/OD). Diamonds represent $OD_{600}$, circles represent total isoprene productivity (µg/L) and squares represent specific productivity of isoprene (µg/L/OD).
Figure 23H:
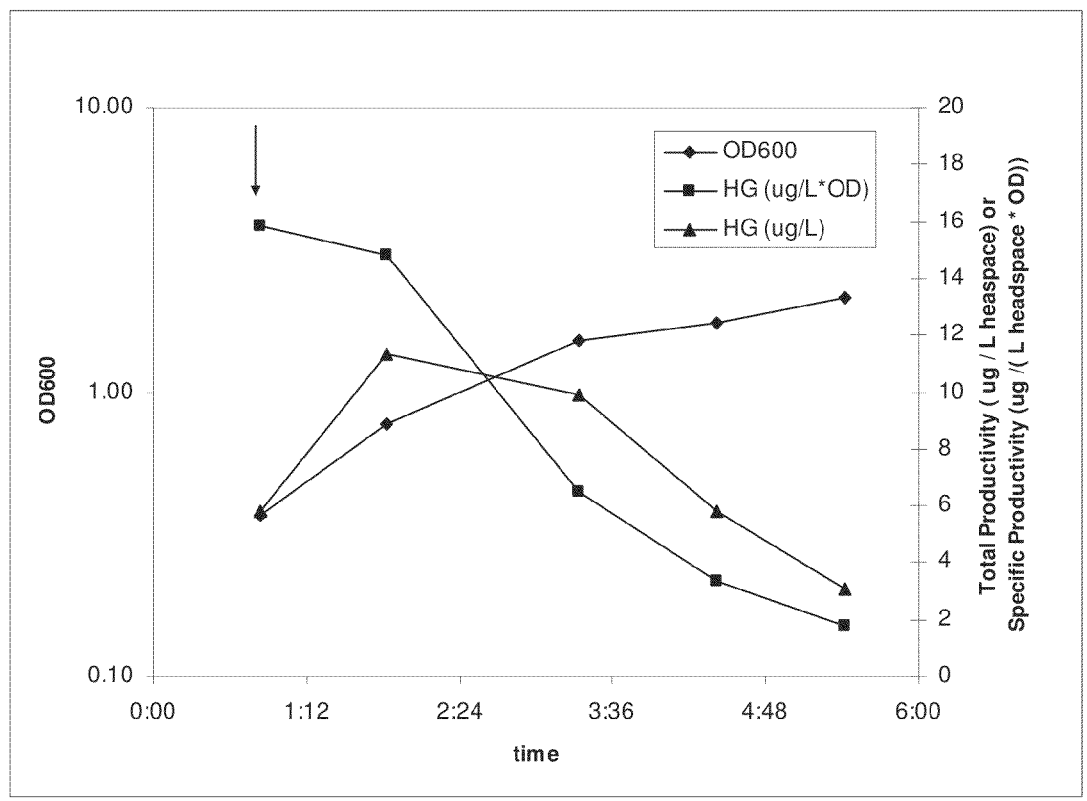
FIG. 23H is a graph showing production of isoprene from glucose in BL21/pTrcKudzuIDIDXSkan. The arrow indicates the time of induction with IPTG (400 µmol). The x-axis is time after inoculation; the y-axis is OD600 and the y2-axis is total productivity of isoprene (µg/L headspace or specific productivity (µg/L headspace/OD). Diamonds represent OD600, triangles represent total isoprene productivity (µg/L) and squares represent specific productivity of isoprene (µg/L/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 μg/ml) at 20° C. and used to inoculate shake flasks of TM3 (13.6 g $K_2PO_4$, 13.6 g $KH_2PO_4$, 2.0 g $MgSO_4*7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 μM IPTG. Samples were taken at various times after induction and the amount of isoprene in the head space was measured as described in Example 1. Results are shown in FIG. 23H.

III. Production of Isoprene from Biomass in *E. coli*/pTrcKudzu yIDI DXS

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. coli*/pTrcKudzuIDIDXS

A single colony from a plate freshly transformed cells of BL21 (λDE3)/pTrcKudzu yIDI DXS (kan) was used to inoculate 5 mL of LB+kanamycin (50 μg/ml). The culture was incubated overnight at 25° C. with shaking. The following day the overnight culture was diluted to an $OD_{600}$ of 0.05 in 25 ml of TM3+0.2% YE+1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI

A 500 liter fermentation of E. coli cells with a kudzu isoprene synthase, S. cerevisiae IDI, and E. coli DXS nucleic acids (E. coli BL21 (λDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of E. coli Grown in Fed-Batch Culture Medium Recipe (per liter fermentation medium): $K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution: citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with E. coli cells containing the pTrcKudzu yIDI DXS plasmid. This experiment was carried out to monitor isoprene formation from glucose and yeast extract at the desired fermentation pH 7.0 and temperature 30° C. An inoculum of E. coli strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
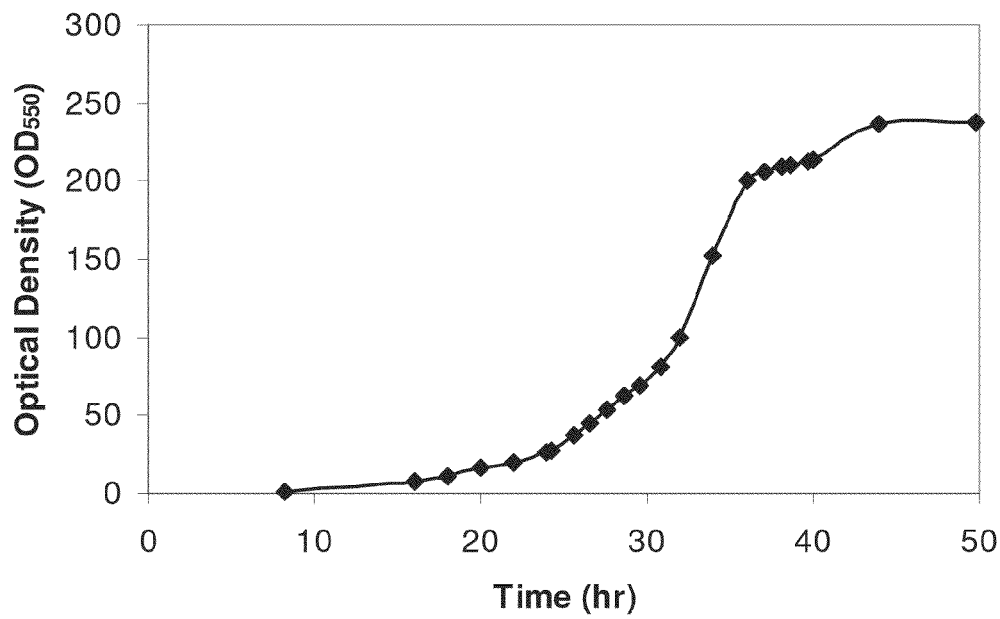
FIG. 49 shows graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
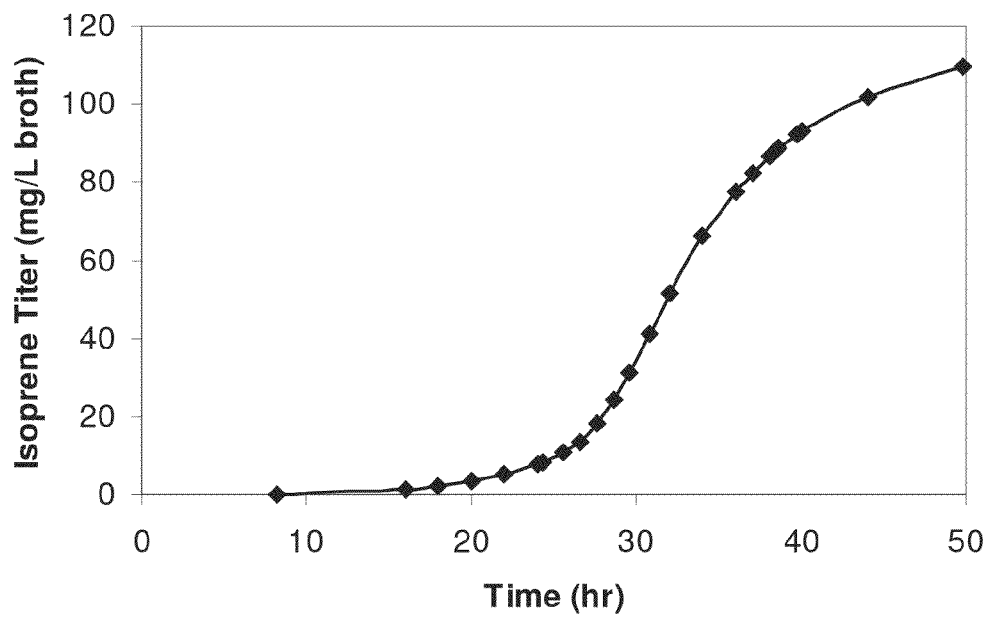
Figure 49C:
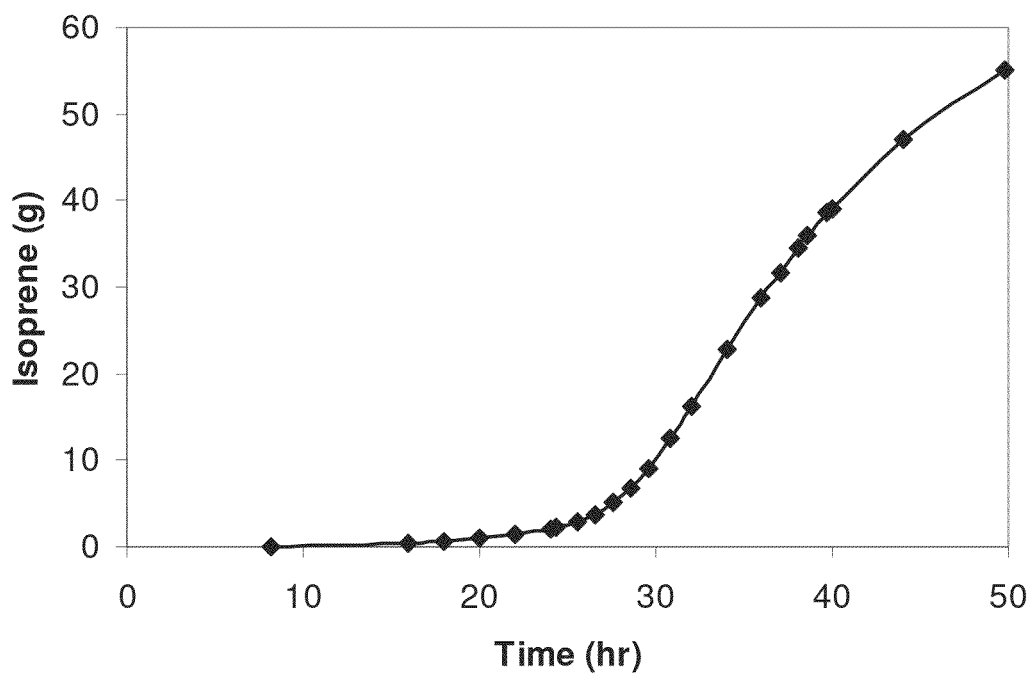

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in E. coli Expressing Heterologous Isoprene Synthase and Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from S. cerevisiae chromosomal DNA and cloned individually into the pCR BluntII TOPO plasmid (Invitrogen). In some cases, the idi gene was amplified from E. coli chromosomal DNA. The primers were designed such that an E. coli consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from S. cerevisiae S288C was obtained from ATCC (ATCC 204508D). The MVK gene was amplified from the chromosome of S. cerevisiae using primers MVKF (5'-AGGAGGTAAAAAAACATGTCATTAC-CGTTCTTAACTTCTGC, SEQ ID NO:21) and MVK-PstI-R (5'-ATGGCTGCAGGCCTATCGCAAATTAGCTT ATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and TaqI restriction endonucleases and the fragment was gel purified and ligated into pTrcHis2B digested with SacI and BstBI. The resulting plasmid was named pTrcMVK1.

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCAC-CCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTG-GAATTCGCCCTTCTGCAGC, SEQ ID NO:25) and NsiI-MVD 1 F (5'-GTAGATGCATGCAGAATTCGCCCTTAAG-GAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATG-CATCGCCCTTAGGAGGTAAAAAAAATGAC, SEQ ID NO:28) to amplify the yIDI gene. In some cases the IPP isomerase gene, idi from E. coli was used. To amplify idi from E. coli chromosomal DNA, the following primer set was used: PstI-CIDI 1 R (5'-GTGTGATGGATATCTGCAGAAT-TCG, SEQ ID NO:29) and NsiI-CIDI 1 F (5'-CATCAATG-CATCGCCCTTAGGAGGTAAAAAAACATG, SEQ ID NO:30). Template DNA was chromosomal DNA isolated by standard methods from E. coli FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and tranformants were grown at 37° C. overnight with selection on LA containing kanamycin (50 µg/ml). The transformants were verified by restriction enzyme digestion and one was frozen as a stock. The plasmid was designated pTrcKanKKDIy.

II. Cloning a Kudzu Isoprene Synthase Gene into pTrcKanKKDIy

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTT ACT (SEQ ID NO:31) and MCM53 5'-CGGTCGACGGATCCCT-GCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 µg/ml). The correct insertion of the fragment was verified by sequencing and this strain was designated MCM93.

Figure 24:
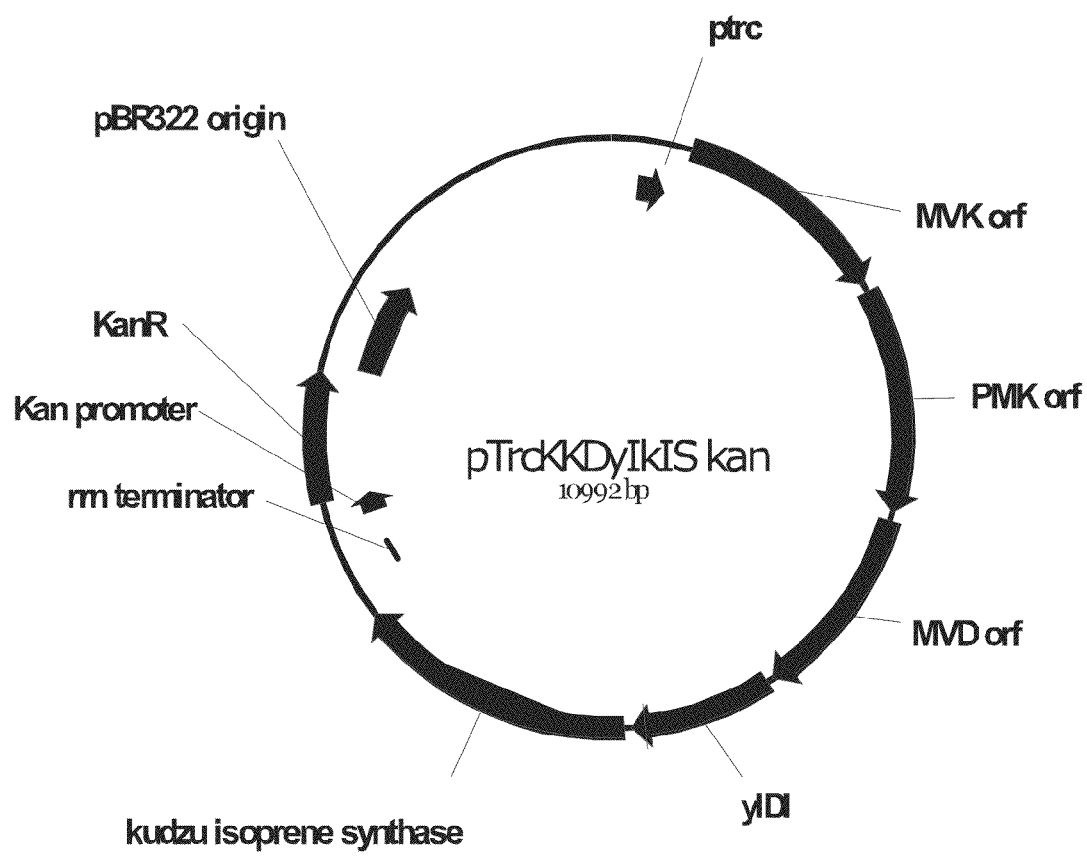
FIG. 24 is a map of pTrcKKDyIkIS kan.
Figure 26:
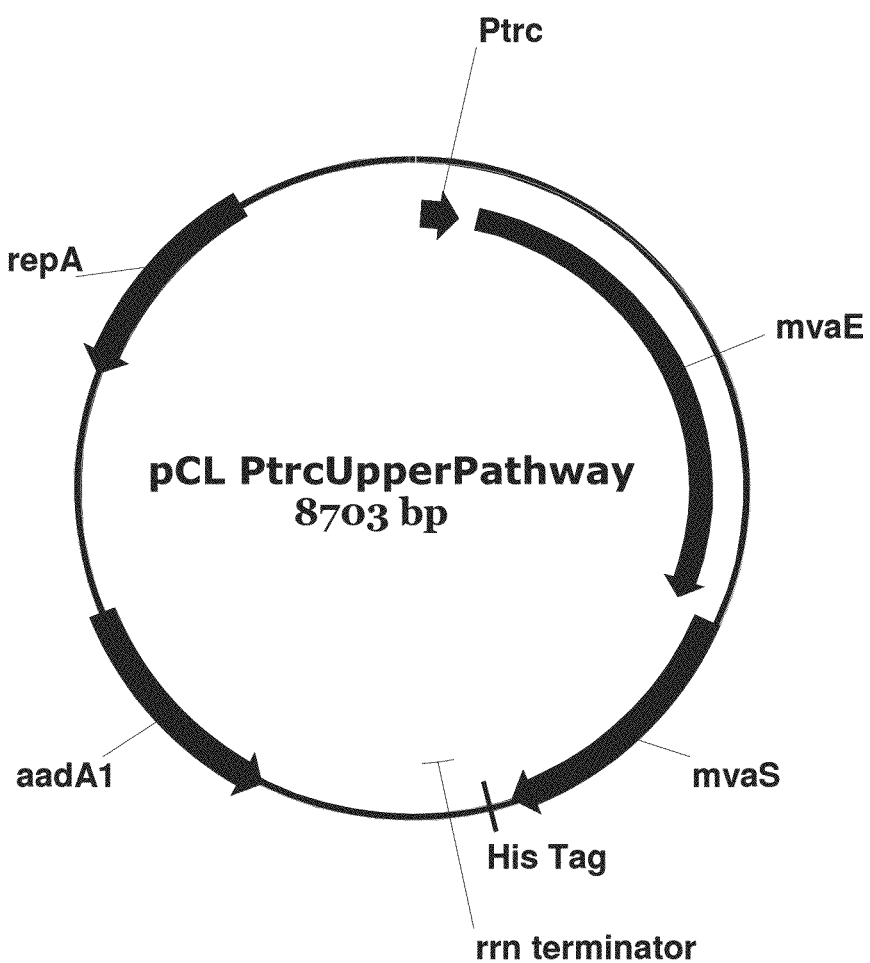
FIG. 26 is a map of pCL PtrcUpperPathway.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 µg/ml. The correct transformant was verified by restriction digestion and the plasmid was designated pTrcKKDyIkISKan (FIGS. 24 and 25). This plasmid was transformed into BL21(XDE3) cells (Invitrogen).

III. Isoprene Production from Mevalonate in *E. coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 µM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 1. Maximum production of isoprene was $6.67 \times 10^{-4}$ mol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

```
CF 07-60 (+) Start of mvaE w/ RBS + ATG
start codon SacI
                                   (SEQ ID NO: 34)
5'-GAGACATGAGCTCAGGAGGTAAAAAAACATGAAAACAGTA
GTTATTATTG CF 07-62 (-) Fuse mvaE to mvaS with RBS in between
                                   (SEQ ID NO: 35)
5'-TTTATCAATCCCAATTGTCATGTTTTTTTACCTCCTTTATTGT
TTTCTTAAATC
```

The mvaS gene was amplified from *E. faecalis* genomic DNA (ATCC 700802D-5) with a RBS and spacer from *E. coli* in front using the following primers:

```
CF 07-61 (+) Fuse mvaE to mvaS with RBS in between
                                   (SEQ ID NO: 36)
5'-GATTTAAGAAAACAATAAAGGAGGTAAAAAAACATGACAATT
GGGATTGATAAA CF 07-102 (-) End of mvaS gene BglII
                                   (SEQ ID NO: 37)
5'-GACATGACATAGATCTTTAGTTTCGATAAGAACGAACGGT
```

The PCR fragments were fused together with PCR using the following primers:

```
CF 07-60 (+) Start of mvaE w/ RBS + ATG start
codon SacI
                                   (SEQ ID NO: 34)
5'-GAGACATGAGCTCAGGAGGTAAAAAAACATGAAAACAGTAGTTAT
TATTG CF 07-102 (-) End of mvaS gene BglII
                                   (SEQ ID NO: 37)
5'-GACATGACATAGATCTTTAGTTTCGATAAGAACGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA+50 µg/ml carbenicillin plates. A total of six colonies were chosen and grown overnight in LB+50 µg/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                 (SEQ ID NO: 38)
5'-ATGAAAACAGTAGTTATTATTGATGC CF 07-59 (-) End of mvaE gene
                                 (SEQ ID NO: 39)
5'-ATGTTATTGTTTTCTTAAATCATTTAAAATAGC CF 07-82 (+) Start of mvaS gene
                                 (SEQ ID NO: 40)
5'-ATGACAATTGGGATTGATAAAATTAG CF 07-83 (-) End of mvaS gene
                                 (SEQ ID NO: 41)
5'-TTAGTTTCGATAAGAACGAACGGT CF 07-86 (+) Sequence in mvaE
                                 (SEQ ID NO: 42)
5'-GAAATAGCCCCATTAGAAGTATC CF 07-87 (+) Sequence in mvaE
                                 (SEQ ID NO: 43)
5'-TTGCCAATCATATGATTGAAAATC CF 07-88 (+) Sequence in mvaE
                                 (SEQ ID NO: 44)
5'-GCTATGCTTCATTAGATCCTTATCG CF 07-89 (+) Sequence mvaS
                                 (SEQ ID NO: 45)
5'-GAAACCTACATCCAATCTTTTGCCC
```

The plasmid called pTrcHis2AUpperPathway#1 was correct by sequencing and was transformed into the commercially available *E. coli* strain BL21. Selection was done on LA+50 µg/ml carbenicillin. Two transformants were chosen and grown in LB+50 µg/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

The plasmid pTrcHis2AUpperPathway was digested with the restriction endonuclease SspI to release a fragment containing pTrc-mvaE-mvaS-(His tag)-terminator. In this fragment, the His-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 µg/ml). A correct colony was identified by screening for the presence of the insert by PCR. The plasmid was designated pCL PtrcUpperPathway (FIGS. 26 and 27A-27D).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 µg/ml) and Spectinomycin (50 µg/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB+carbenicillin (100 µg/ml) and are grown overnight at 37° C. with shaking at 200 rpm. These cultures were diluted into 50 ml medium in 250 ml baffled flasks to an $OD_{600}$ of 0.1. The medium was TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 µM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli*.

VIII. Production of Isoprene from *E. coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21(XDE3) and the transformations were done by standard methods. Transformants were selected on L agar containing kanamycin (50 µg/ml) or kanamycin plus spectinomycin (both at a concentration of 50 µg/ml). Plates were grown at 37° C. The resulting strains were designated as follows:

Grown on Kanamycin Plus Spectinomycin (50 µg/ml each)
MCM127-pCL Upper MVA+pTrcKKDyIkIS (kan) in BL21 (λDE3)
MCM131-pCL1920+pTrcKKDyIkIS (kan) in BL21(λDE3)
MCM125-pCL Upper MVA+pTrcHis2B (kan) in BL21 (λDE3)

Grown on Kanamycin (50 µg/ml)
MCM64-pTrcKudzu yIDI DXS (kan) in BL21(λDE3)
MCM50-pTrcKudzu (kan) in BL21(λDE3)
MCM123-pTrcKudzu yIDI DXS DXR (kan) in BL21(λDE3)

The above strains were streaked from freezer stocks to LA+appropriate antibiotic and grown overnight at 37° C. A single colony from each plate was used to inoculate shake flasks (25 ml LB+the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB+the appropriate antibiotic. The cultures were then diluted into 25 ml LB+1% glucose+ the appropriate antibiotic to an $OD_{600}$ of 0.1. Two flasks for each strain were set up, one set for induction with IPTG (800 µM) the second set was not induced. The cultures were incubated at 37° C. with shaking at 250 rpm. One set of the cultures were induced after 1.50 hours (immediately following sampling time point 1). At each sampling time point, the OD$_{600}$ was measured and the amount of isoprene determined as described in Example 1. Results are presented in Table 8-1. The amount of isoprene made is presented as the amount at the peak production for the particular strain.

TABLE 8-1

Production of Isoprene in *E. coli* Strains

| Strain | Isoprene (μg/liter/OD/hr) |
|---|---|
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid

Mevalonolactone (1.0 g, 7.7 mmol) (CAS #503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 μl aliquot of supernatant to 900 μl of H$_2$O. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+column (300 mm by 7.0 mm) eluted with 5 mM sulfuric acid at 0.6 mL/min with refractive index (RI) detection. Under these conditions mevalonic acid eluted as the lactone form at 18.5 minutes.

X. Production of Isoprene from *E. coli* BL21 Containing the Upper MVA Pathway Plus Kudzu Isoprene Synthase A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 2.2 g/L of isoprene.

Medium Recipe (per liter fermentation medium): The medium was generated using the following components per liter fermentation medium: K$_2$HPO$_4$ 7.5 g, MgSO$_4$*7H$_2$O 2 g, citric acid monohydrate 2 g, ferric ammonium citrate 0.3 g, yeast extract 0.5 g, and 1000× modified trace metal solution 1 ml. All of the components were added together and dissolved in diH$_2$O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid*H$_2$O 40 g, MnSO$_4$*H$_2$O 30 g, NaCl 10 g, FeSO$_4$*7H$_2$O 1 g, CoCl$_2$*6H$_2$O 1 g, ZnSO$_4$*7H$_2$O 1 g, CuSO$_4$*5 H$_2$O 100 mg, H$_3$BO$_3$ 100 mg, and NaMoO$_4$*2H$_2$O 100 mg. Each component was dissolved one at a time in diH$_2$O, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperPathway (FIG. 26) and pTrcKKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into soytone-yeast extract-glucose medium. After the inoculum grew to OD 1.0 when measured at 550 nm, 500 mL was used to inoculate a 15-L bioreactor containing an initial working volume of 5 L.

Figure 54:
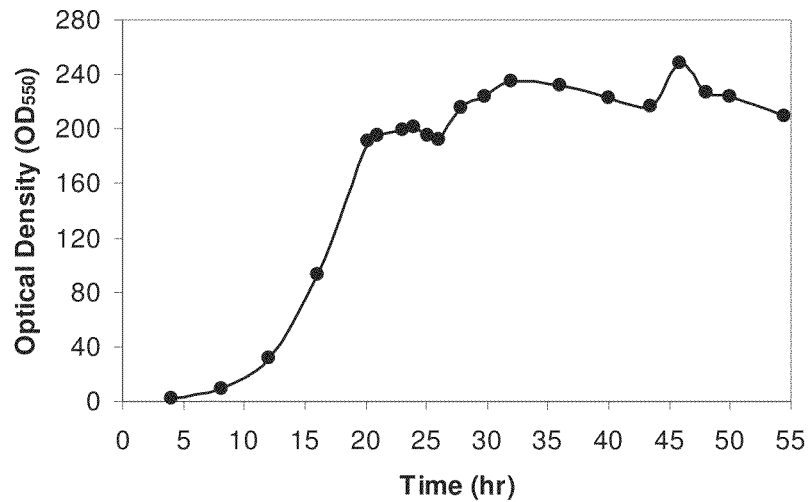
FIG. 54 is a time course of optical density within the 15-L bioreactor fed with glucose.
Figure 55:
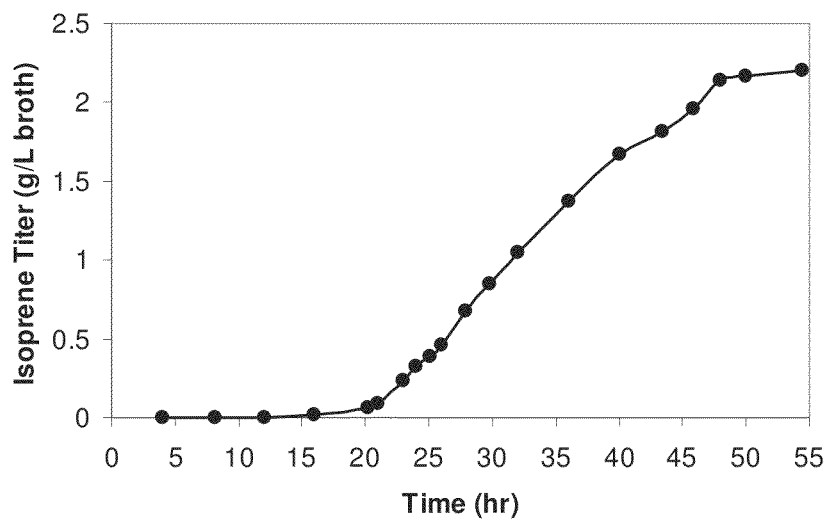
FIG. 55 is a time course of isoprene titer within the 15-L bioreactor fed with glucose. The titer is defined as the amount of isoprene produced per liter of fermentation broth.
Figure 56:
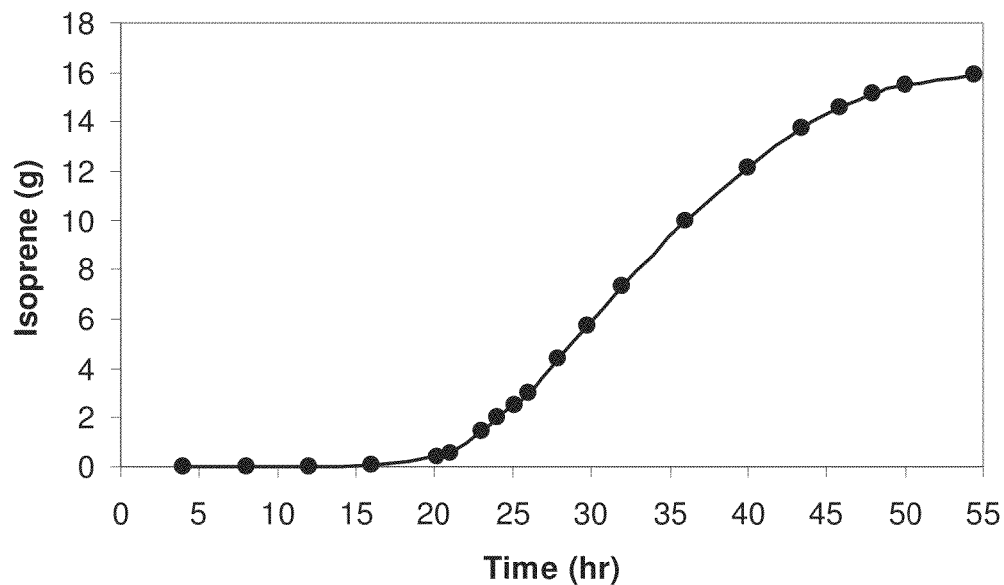
FIG. 56 is a time course of total isoprene produced from the 15-L bioreactor fed with glucose.
Figure 57:
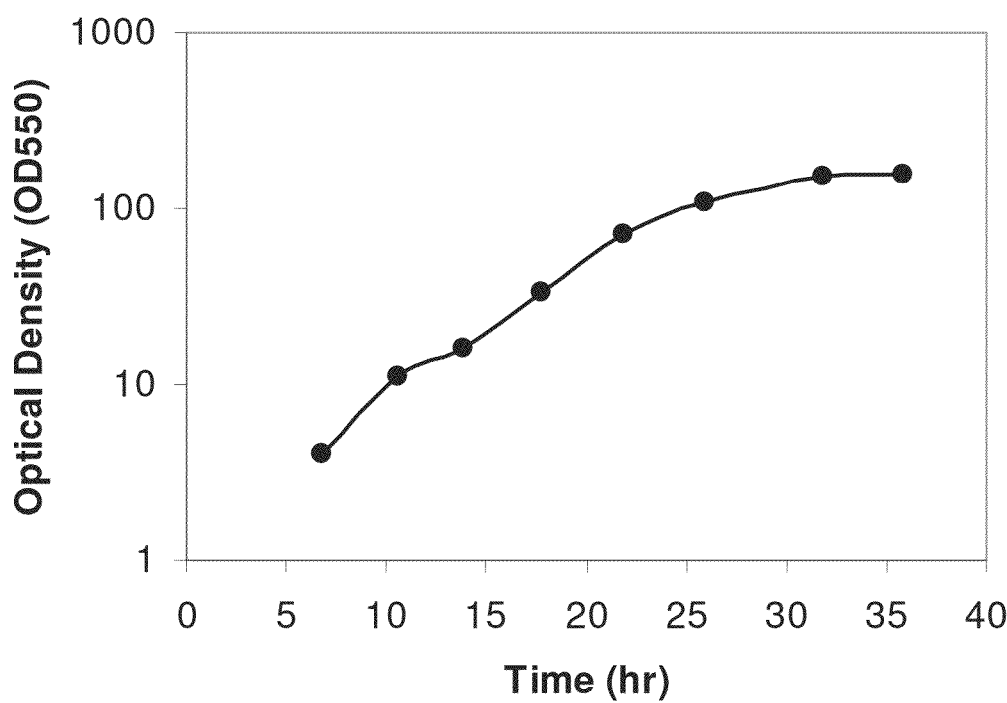
FIG. 57 is a time course of optical density within the 15-L bioreactor fed with glycerol.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 uM when the optical density at 550 nm (OD$_{550}$) reached a value of 10. The IPTG concentration was raised to 50 uM when OD$_{550}$ reached 190. IPTG concentration was raised to 100 uM at 38 hours of fermentation. The OD$_{550}$ profile within the bioreactor over time is shown in FIG. 54. The isoprene level in the off gas from the bioreactor was determined as described herein. The isoprene titer increased over the course of the fermentation to a final value of 2.2 g/L (FIG. 55). The total amount of isoprene produced during the 54 hour fermentation was 15.9 g, and the time course of production is shown in FIG. 56.

XI. Isoprene Fermentation from *E. coli* Expressing G from the Mevalonic Acid Pathway and Grown in Fed-Batch Culture at the 15-L Scale A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 3.0 g/L of isoprene.

Medium Recipe (per liter fermentation medium): The medium was generated using the following components per liter fermentation medium: K$_2$HPO$_4$ 7.5 g, MgSO$_4$*7H$_2$O 2 g, citric acid monohydrate 2 g, ferric ammonium citrate 0.3 g, yeast extract 0.5 g, and 1000× Modified Trace Metal Solution 1 ml. All of the components were added together and dissolved in diH$_2$O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid*H$_2$O 40 g, MnSO$_4$*H$_2$O 30 g, NaCl 10 g, FeSO$_4$*7H$_2$O 1 g, CoCl$_2$*6H$_2$O 1 g, ZnSO$_4$*7H$_2$O 1 g, CuSO$_4$*5 H$_2$O 100 mg, H$_3$BO$_3$ 100 mg, and NaMoO$_4$*2H$_2$O 100 mg. Each component was dissolved one at a time in diH$_2$O, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Figure 93:
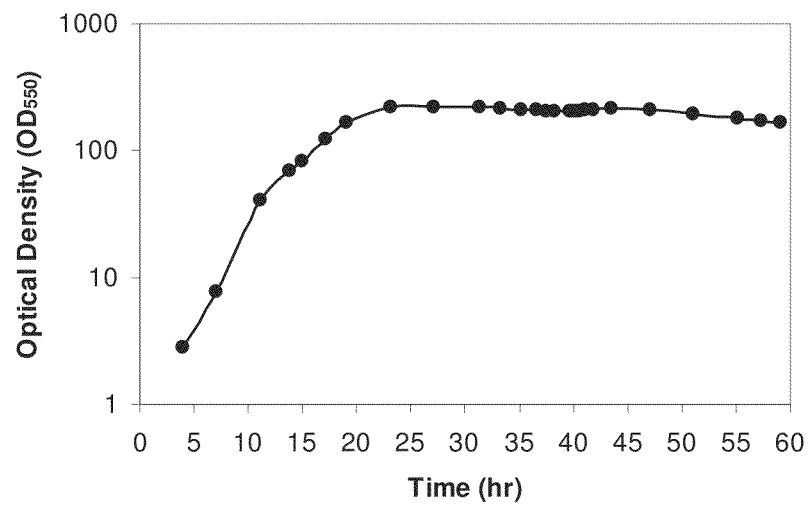
Figure 94:
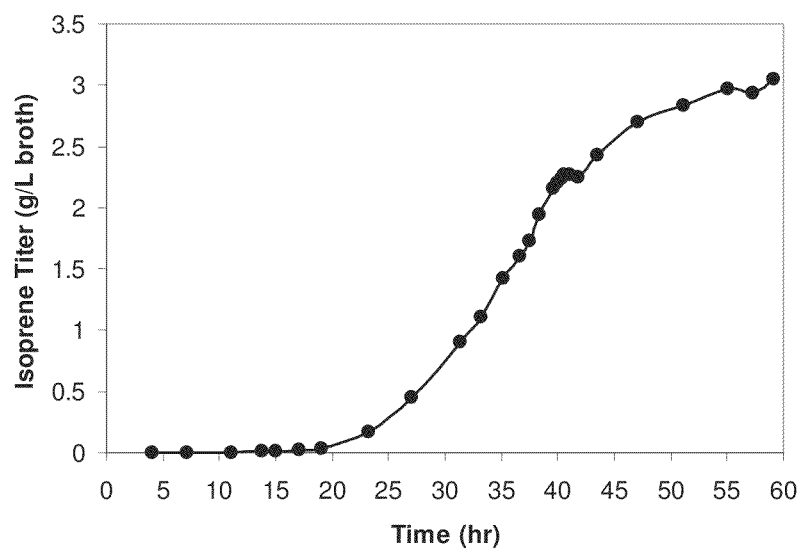
Figure 95:
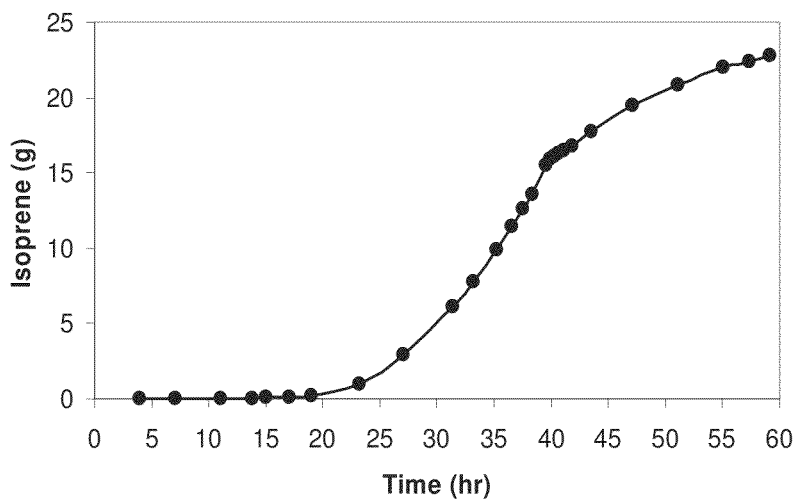

Glucose was fed at an exponential rate until cells reached the stationary phase. After this time, the glucose feed was decreased to meet metabolic demands. The total amount of glucose delivered to the bioreactor during the 59 hour fermentation was 2.2 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 93. The isoprene level in the off gas from the bioreactor was determined as described herein. The isoprene titer increased over the course of the fermentation to a final value of 3.0 g/L (FIG. 94). The total amount of isoprene produced during the 59 hour fermentation was 22.8 g, and the time course of production is shown in FIG. 95. The molar yield of utilized carbon that went into producing isoprene during fermentation was 2.2%. The weight percent yield of isoprene from glucose was 1.0%.

XII. Isoprene Fermentation from *E. coli* Expressing Genes from the Mevalonic Acid Pathway and Grown in Fed-Batch Culture at the 15-L Scale A 15-L scale fermentation of *E. coli* expressing mevalonic acid pathway polypeptides, *Puerearia lobata* isoprene synthase, and Kudzu isoprene synthase was used to produce isoprene from cells in fed-batch culture. This experiment demonstrates that growing cells under glucose limiting conditions resulted in the production of 3.3 g/L of isoprene.

i) Construction of pCLPtrcUpperPathwayHGS2

The gene encoding isoprene synthase from *Pueraria lobata* was PCR-amplified using primers NsiI-RBS-HGS F (CTTGATGCATCCTGCATTCGCCCTTAGGAGG, SEQ ID NO:88) and pTrcR (CCAGGCAAATTCTGTTTTAT-CAG, SEQ ID NO:89), and pTrcKKDyIkIS as a template. The PCR product thus obtained was restriction-digested with NsiI and PstI and gel-purified. The plasmid pCL PtrcUpperPathway was restriction-digested with PstI and dephosphorylated using rAPid alkaline phosphatase (Roche) according to manufacturer's instructions.

These DNA fragments were ligated together and the ligation reaction was transformed into *E. coli* Top10 chemically competent cells (Invitrogen), plated on L agar containing spectinomycin (50 μg/ml) and incubated overnight at 37° C. Plasmid DNA was prepared from 6 clones using the Qiaquick Spin Mini-prep kit. The plasmid DNA was digested with restriction enzymes EcoRV and MluI to identify a clone in which the insert had the right orientation (i.e., the gene oriented in the same way as the pTrc promoter).

The resulting correct plasmid was designated pCLPtrcUpperPathwayHGS2. This plasmid was assayed using the headspace assay described herein and found to produce isoprene in *E. coli* Top10, thus validating the functionality of the gene. The plasmid was transformed into BL21(LDE3) containing pTrcKKDyIkIS to yield the strain BL21/pCLPtrcUpperPathwayHGS2-pTrcKKDyIkIS. This strain has an extra copy of the isoprene synthase compared to the BL21/pCL PtrcUpperMVA and pTrc KKDyIkIS strain (Example 8, part XI). This strain also had increased expression and activity of HMGS compared to the BL21/pCL PtrcUpperMVA and pTrc KKDyIkIS strain used in Example 8, part XI.

ii) Isoprene Fermentation from *E. coli* Expressing pCLPtrcUpperPathwayHGS2-pTrcKKDyIkIS and Grown in Fed-Batch Culture at the 15-L Scale Medium Recipe (per liter fermentation medium): The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pCLPtrcUpperPathwayHGS2 and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0 measured at 550 nm, 500 mL was used to inoculate a 15-L bioreactor containing an initial working volume of 5 L.

Glucose was fed at an exponential rate until cells reached the stationary phase. After this time the glucose feed was decreased to meet metabolic demands. The total amount of glucose delivered to the bioreactor during the 58 hour fermentation was 2.1 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 170. The $OD_{550}$ profile within the bioreactor over time is shown in FIG. 104. The isoprene level in the off gas from the bioreactor was determined as described herein. The isoprene titer increased over the course of the fermentation to a final value of 3.3 g/L (FIG. 105). The total amount of isoprene produced during the 58 hour fermentation was 24.5 g and the time course of production is shown in FIG. 106. The molar yield of utilized carbon that went into producing isoprene during fermentation was 2.5%. The weight percent yield of isoprene from glucose was 1.2%. Analysis showed that the activity of the isoprene synthase was increased by approximately 3-4 times that compared to BL21 expressing CL PtrcUpperMVA and pTrc KKDyIkIS plasmids (data not shown).

XIII. Chromosomal Integration of the Lower Mevalonate Pathway in *E. coli*.

A synthetic operon containing mevalonate kinase, mevalonate phosphate kinase, mevalonate pyrophosphate decarboxylase, and the IPP isomerase was integerated into the chromosome of *E. coli*. If desired, expression may be altered by integrating different promoters 5' of the operon. Table 8-2 lists primers used for this experiment.

TABLE 8-2

PRIMERS

| Primer (Description) | Sequence |
| --- | --- |
| MCM78 (attTn7 up rev for integration construct) | gcatgctcgagcggccgcTTTTAATCAAACATCCTGCCAA CTC (SEQ ID NO: 91) |
| MCM79 (attTn7 down rev for integration construct) | gatcgaagggcgatcgTGTCACAGTCTGGCGAAACCG (SEQ ID NO: 92) |
| MCM88 (attTn7 up forw for integration construct) | ctgaattctgcagatatcTGTTTTTCCACTCTTCGTTCACTT T (SEQ ID NO: 93) |
| MCM89 (attTn7 down forw for integration construct) | tctagagggcccAAGAAAAATGCCCCGCTTACG (SEQ ID NO: 94) |
| MCM104 (GI1.2 promoter-MVK) | Gatcgcggccgcgcccttgacgatgccacatcctgagcaaataattcaaccac taattgtgagcggataacacaaggaggaaacagctatgtcattaccgttcttaact tc (SEQ ID NO: 95) |
| MCM105 (aspA terminator-yIDI) | Gatcgggccccaagaaaaaaggcacgtcatctgacgtgccttttttatttgtaga cgcgttgttatagcattcta (SEQ ID NO: 96) |
| MCM120 (forw of attTn7: attTn7 homology, GB marker homology) | aaagtagccgaagatgacggtttgtcacatggagttggcaggatgtttgattaaa agcAATTAACCCTCACTAAAGGGCGG (SEQ ID NO: 97) |
| MCM127 (Rev complement of 1.2 GI: GB marker homology (extra long), promoter, RBS, ATG) | AGAGTGTTCACCAAAAATAATAACCTTTCCCGG TGCAgaagttaagaacggtaatgacatagctgtttcctccttgtgttatccgct cacaattagtggttgaattatttgctcaggatgtggcatcgtcaagggcTAAT ACGACTCACTATAGGGCTCG (SEQ ID NO: 98) | i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 uL reaction with 1 uL 10 uM primers, 3 uL ddH2O, 45 uL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 uL PCR reactions containing 1 uL~10 ng/uL template, 1 uL each primer, 1.25 uL 10 mM dNTPs, 5 uL 10× buffer, 1 uL enzyme, and 39.75 uL ddH20. Reactions were pooled, purified on a Qiagen PCR cleanup column, and used to electroporate water-washed Pir1 cells containing plasmid MCM296. Electroporation was carried out in 2 mM cuvettes at 2.5 V and 200 ohms. Electroporation reactions were recovered in LB for 3 hr at 30° C. Transformant MCM330 was selected on LA with CMPS, Kan50 (FIGS. 107 and 108A-108C).

iii) Integration into E. coli Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4° C. ddH2O before electroporation with 2 uL of DNA. Integrants were selected on L agar with containing chloramphenicol (5 ug/ml) and subsequently confirmed to not grow on L agar+Kanamycin (50 ug/ml). BL21 integrant MCM331 and MG1655 integrant MCM333 were frozen.

iv) Construction of pET24D-Kudzu Encoding Kudzu Isoprene Synthase

The kudzu isoprene synthase gene was subcloned into the pET24d vector (Novagen) from the pCR2.1 vector (Invitrogen). In particular, the kudzu isoprene synthase gene was amplified from the pTrcKudzu template DNA using primers MCM50 5'-GATCATGCAT TCGCCCTTAG GAGG-TAAAAA AACATGTGTG CGACCTCTTC TCAATT-TACT (SEQ ID NO:99) and MCM53 5'-CGGTCGACGG ATCCCTGCAG TTAGACATAC ATCAGCTG (SEQ ID NO:100). PCR reactions were carried out using Taq DNA Polymerase (Invitrogen), and the resulting PCR product was cloned into pCR2.1-TOPO TA cloning vector (Invitrogen), and transformed into E. coli Top10 chemically competent cells (Invitrogen). Transformants were plated on L agar containing carbenicillin (50 µg/ml) and incubated overnight at 37° C. Five ml Luria Broth cultures containing carbenicillin 50 µg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu isoprene synthase fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into *E. coli* Top 10 chemically competent cells and plated on L agar containing kanamycin (50 μg/ml). The correct transformant was confirmed by sequencing and transformed into chemically competent BL21(λDE3)pLysS cells (Novagen). A single colony was selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:101) is shown in FIGS. 110A and 110B. Isoprene synthase activity was confirmed using a headspace assay.

v) Production Strains

Strains MCM331 and MCM333 were cotransformed with plasmids pCLPtrcupperpathway and either pTrcKudzu or pETKudzu, resulting in the strains shown in Table 8-3.

TABLE 8-3

Production Strains

| Background | Integrated Lower | Upper MVA plasmid | IpS plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 | vi) Isoprene Fermentation from *E. coli* Expressing Genes from the Mevalonic Acid Pathway and Grown in Fed-Batch Culture at the 15-L scale.

Medium Recipe (per liter fermentation medium): The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid *$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the gi1.2 integrated lower MVA pathway described above and the pCL PtrcUpperMVA and pTrcKudzu plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Glucose was fed at an exponential rate until cells reached the stationary phase. After this time, the glucose feed was decreased to meet metabolic demands. The total amount of glucose delivered to the bioreactor during the 57 hour fermentation was 3.9 kg. Induction was achieved by adding IPTG. The IPTG concentration was brought to 100 uM when the carbon dioxide evolution rate reached 100 mmol/L/hr. The $OD_{550}$ profile within the bioreactor over time is shown in FIG. 111A. The isoprene level in the off gas from the bioreactor was determined as described herein. The isoprene titer increased over the course of the fermentation to a final value of 1.6 g/L (FIG. 111B). The specific productivity of isoprene over the course of the fermentation is shown in FIG. 111C and peaked at 1.2 mg/OD/hr. The total amount of isoprene produced during the 57 hour fermentation was 16.2 g. The molar yield of utilized carbon that went into producing isoprene during fermentation was 0.9%. The weight percent yield of isoprene from glucose was 0.4%.

XIV. Production of Isoprene from *E. coli* BL21 Containing the Kudzu Isoprene Synthase Using Glycerol as a Carbon Source A 15-L scale fermentation of *E. coli* expressing Kudzu isoprene synthase was used to produce isoprene from cells fed glycerol in fed-batch culture. This experiment demonstrates that growing cells in the presence of glycerol (without glucose) resulted in the production of 2.2 mg/L of isoprene.

Medium Recipe (per liter fermentation medium): The medium was generated using the following components per liter fermentation medium: $K_2HPO_4$ 7.5 g, $MgSO_4*7H_2O$ 2 g, citric acid monohydrate 2 g, ferric ammonium citrate 0.3 g, and 1000× modified trace metal solution 1 ml. All of the components were added together and dissolved in diH2O. This solution was autoclaved. The pH was adjusted to 7.0 with ammonium hydroxide (30%) and q.s. to volume. Glycerol 5.1 g, thiamine*HCl 0.1 g, and antibiotics were added after sterilization and pH adjustment.

1000× Modified Trace Metal Solution: The medium was generated using the following components per liter fermentation medium: citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in diH2O, pH to 3.0 with HCl/NaOH, then q.s. to volume and filter sterilized with a 0.22 micron filter.

Fermentation was performed in a 15-L bioreactor with BL21 (DE3) *E. coli* cells containing the pTrcKudzu plasmid. This experiment was carried out to monitor isoprene formation from glycerol at the desired fermentation pH 7.0 and temperature 35° C. An inoculum of *E. coli* strain taken from a frozen vial was streaked onto an LA broth agar plate (with antibiotics) and incubated at 37° C. A single colony was inoculated into soytone-yeast extract-glucose medium and grown at 35° C. After the inoculum grew to OD 1.0, measured at 550 nm, 600 mL was used to inoculate a 7.5-L bioreactor.

Glycerol was fed at an exponential rate until cells reached an optical density at 550 nm ($OD_{550}$) of 153. The total amount of glycerol delivered to the bioreactor during the 36 hour fermentation was 1.7 kg. Other than the glucose in the inoculum, no glucose was added to the bioreactor. Induction was achieved by adding IPTG. The IPTG concentration was brought to 20 uM when the $OD_{550}$ reached a value of 50. The $OD_{550}$ profile within the bioreactor over time is shown in FIG.

Figure 58:
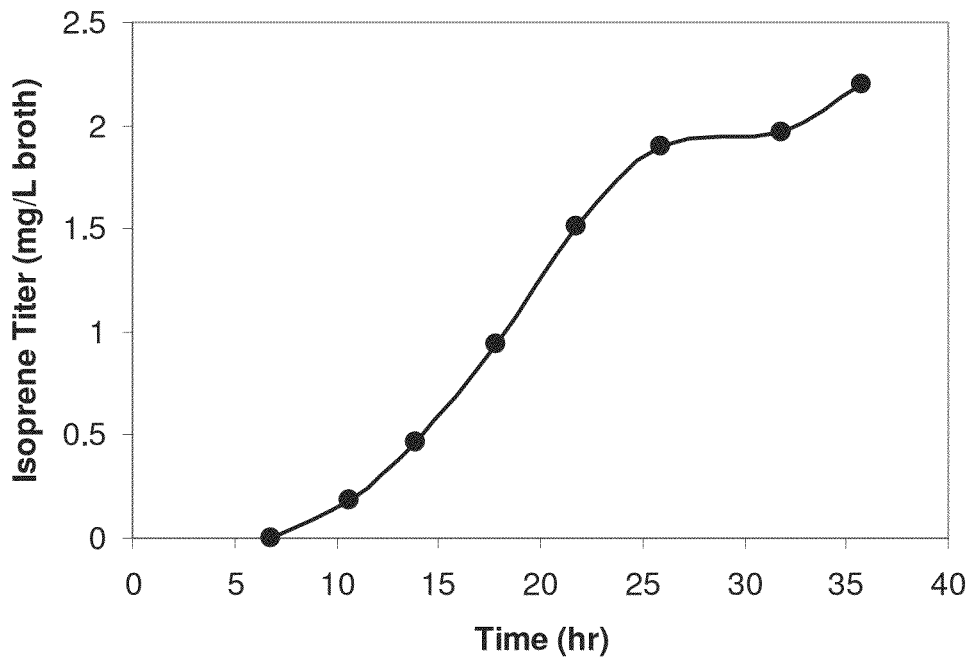
FIG. 58 is a time course of isoprene titer within the 15-L bioreactor fed with glycerol. The titer is defined as the amount of isoprene produced per liter of fermentation broth.
Figure 59:
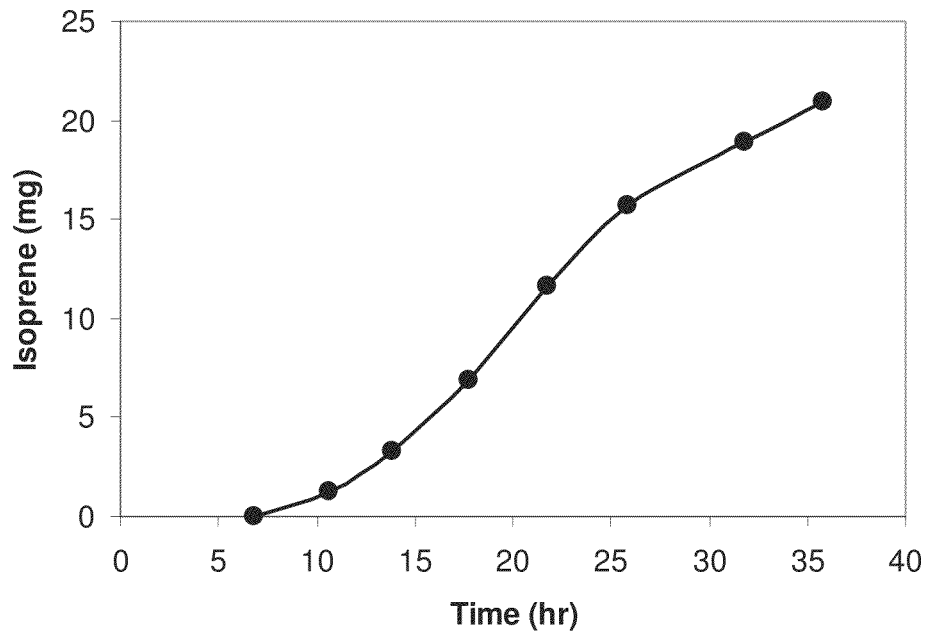
FIG. 59 is a time course of total isoprene produced from the 15-L bioreactor fed with glycerol.
Figure 60:
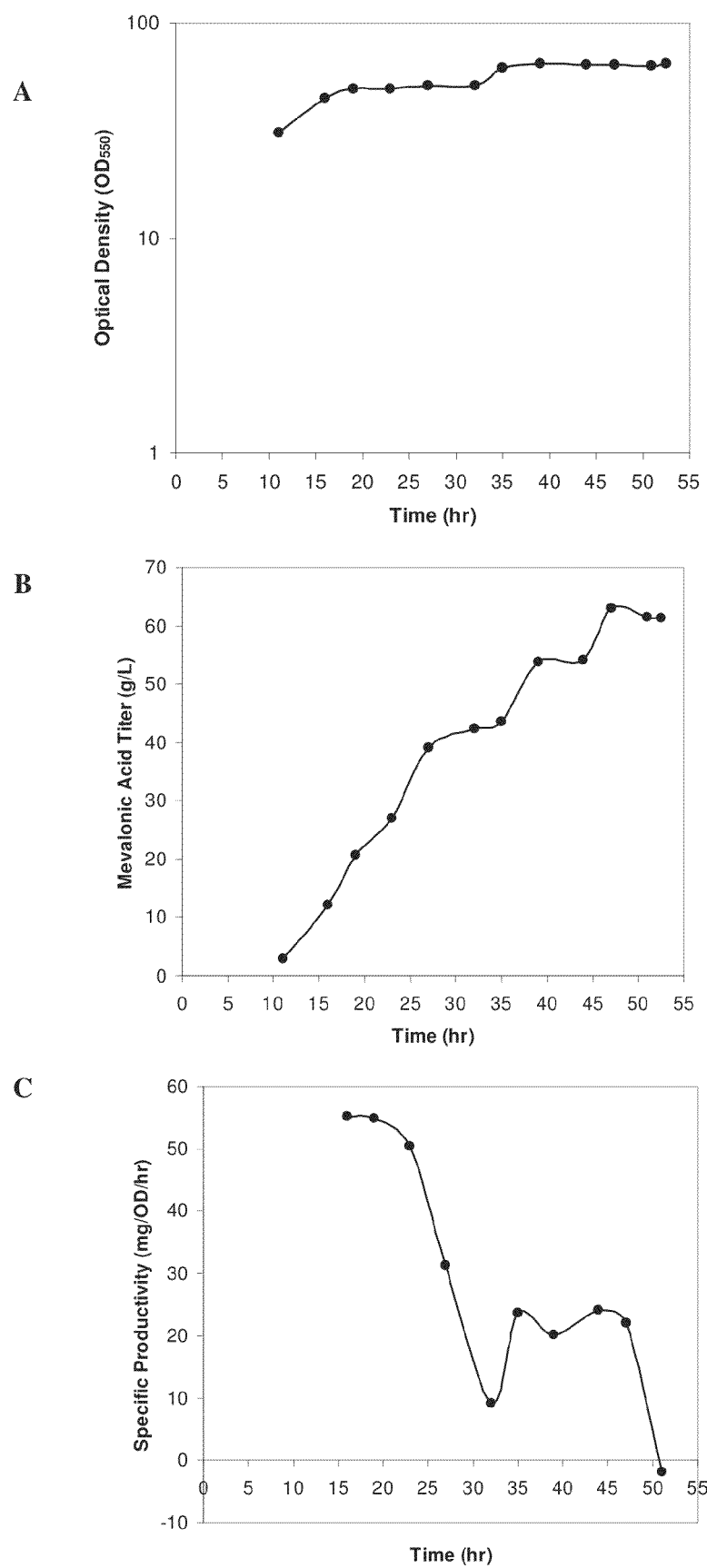
FIGS. 60A-60C are the time courses of optical density, mevalonic acid titer, and specific productivity within the 150-L bioreactor fed with glucose.
Figure 61:
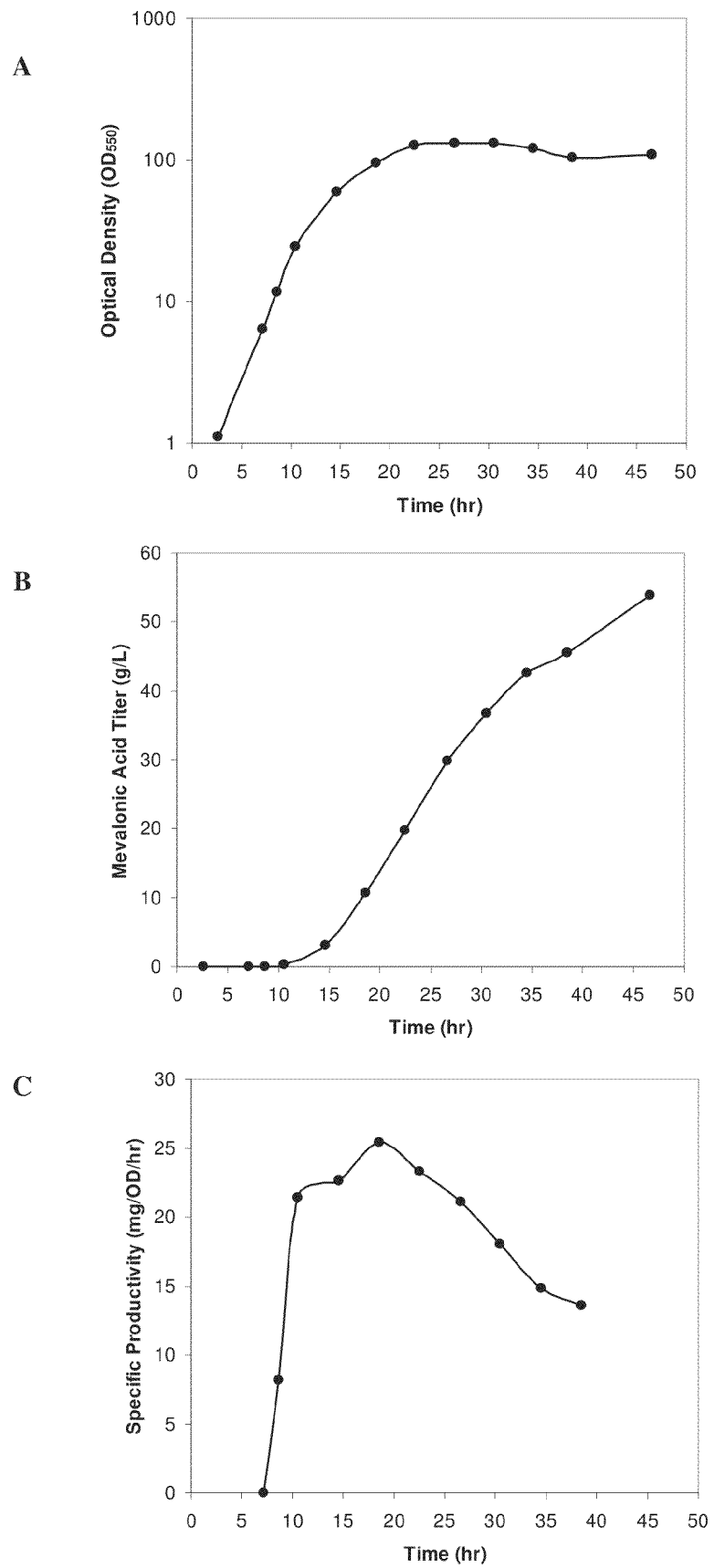
FIGS. 61A-61C are the time courses of optical density, mevalonic acid titer, and specific productivity within the 15-L bioreactor fed with glucose.
Figure 63:
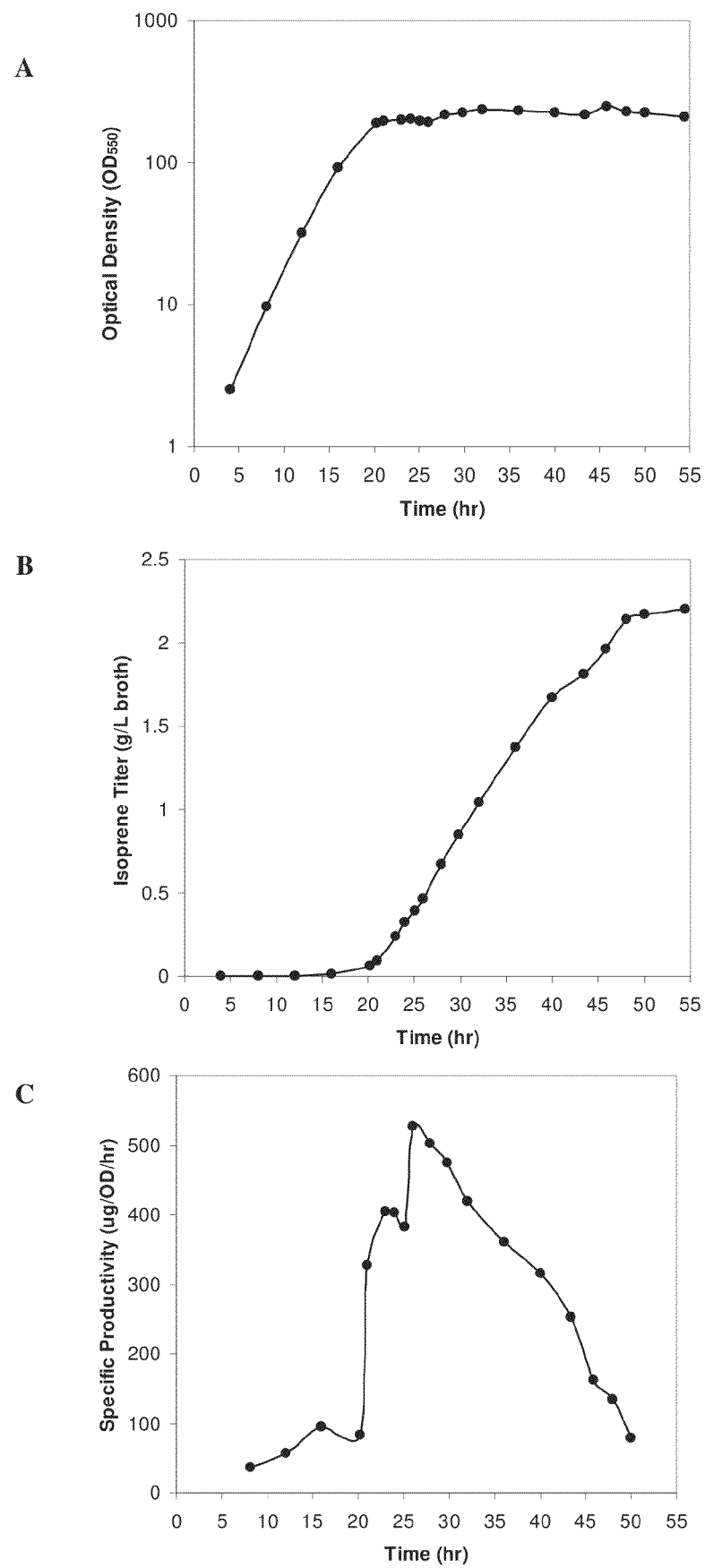
FIG. 63A-63C are the time courses of optical density, isoprene titer, and specific productivity within the 15-L bioreactor fed with glucose.
Figure 64:
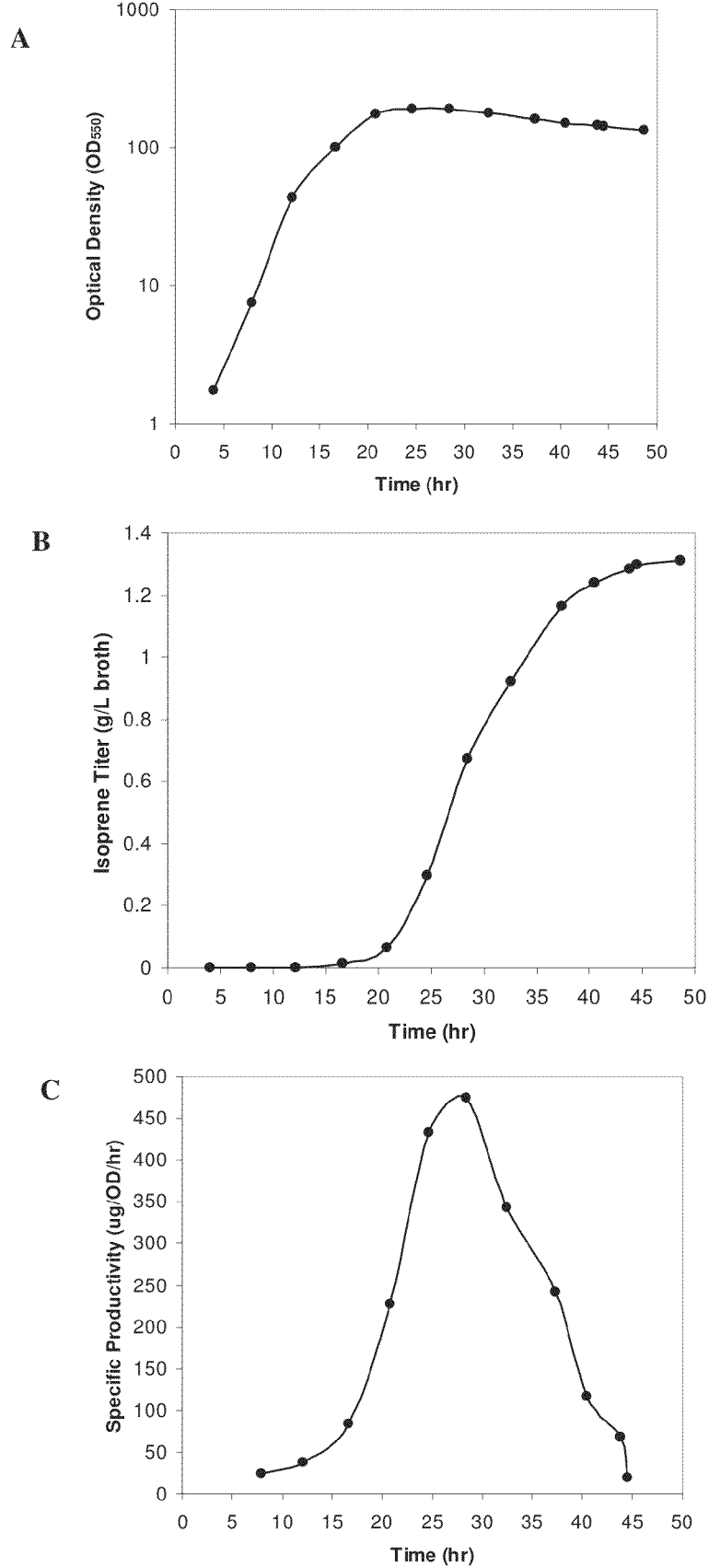
FIGS. 64A-64C are the time courses of optical density, isoprene titer, and specific productivity within the 15-L bioreactor fed with glucose.
Figure 67:
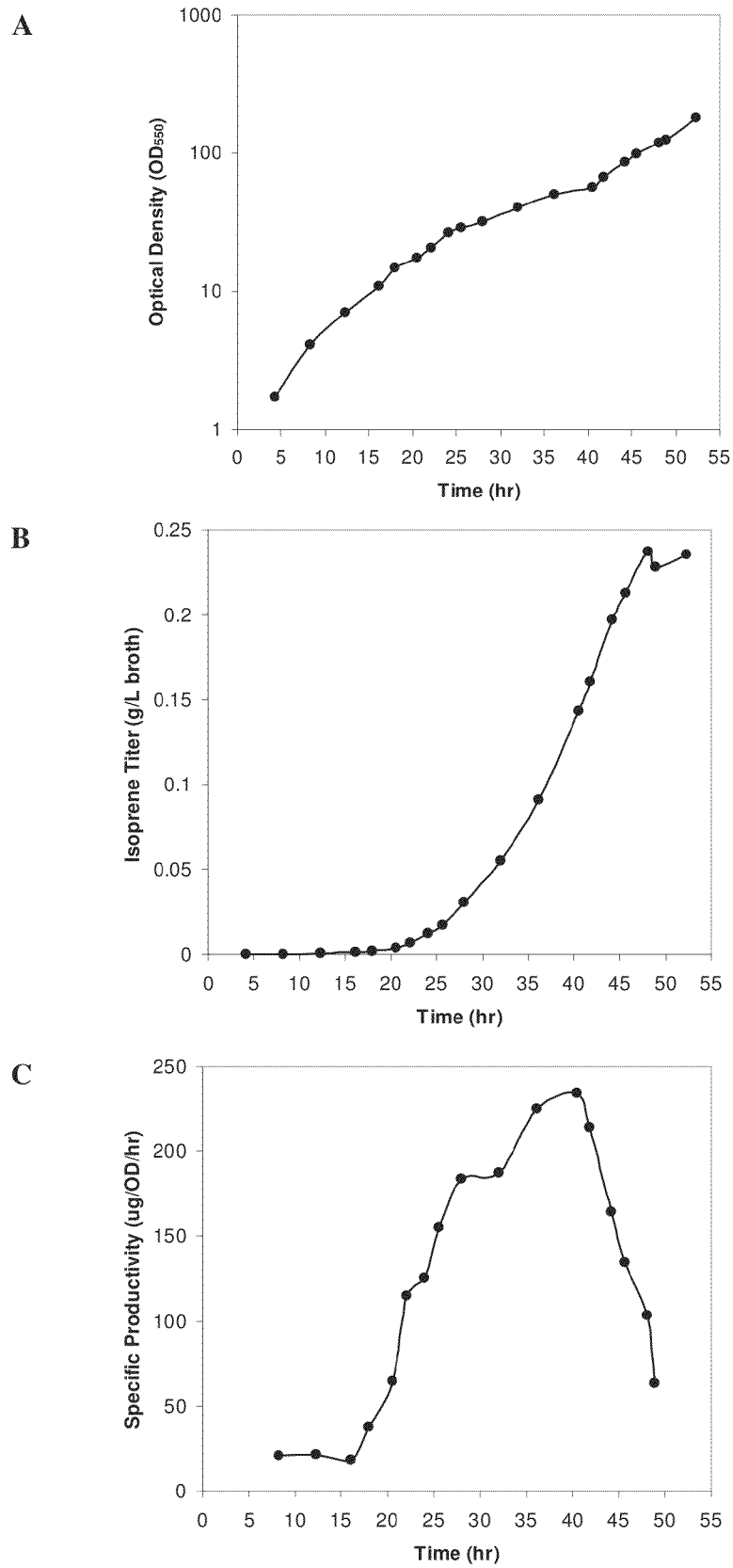
FIGS. 67A-67C are the time courses of optical density, isoprene titer, and specific productivity within the 15-L bioreactor fed with glucose.

57. The isoprene level in the off gas from the bioreactor was determined as described herein. The isoprene titer increased over the course of the fermentation to a final value of 2.2 mg/L (FIG. 58). The total amount of isoprene produced during the 54 hour fermentation was 20.9 mg, and the time course of production is shown in FIG. 59.

XV. Isoprene Fermentation from *E. coli* Expressing Genes from the Mevalonic Acid Pathway and Grown in Fed-Batch Culture at the 15-L Scale Using Invert Sugar as a Carbon Source A 15-L scale fermentation of *E. coli* expressing mevalonic acid pathway polypeptides and Kudzu isoprene synthase was used to produce isoprene from cells fed invert sugar in fed-batch culture. This experiment demonstrates that growing cells in the presence of invert sugar resulted in the production of 2.4 g/L of isoprene.

Medium Recipe (per liter fermentation medium): The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Invert sugar 10 g, thiamine*HCl 0.1 g, and antibiotics were added after sterilization and pH adjustment.

1000× Modified Trace Metal Solution: The 1000× modified trace metal solution was generated using the following components: citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from invert sugar at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Figure 96:
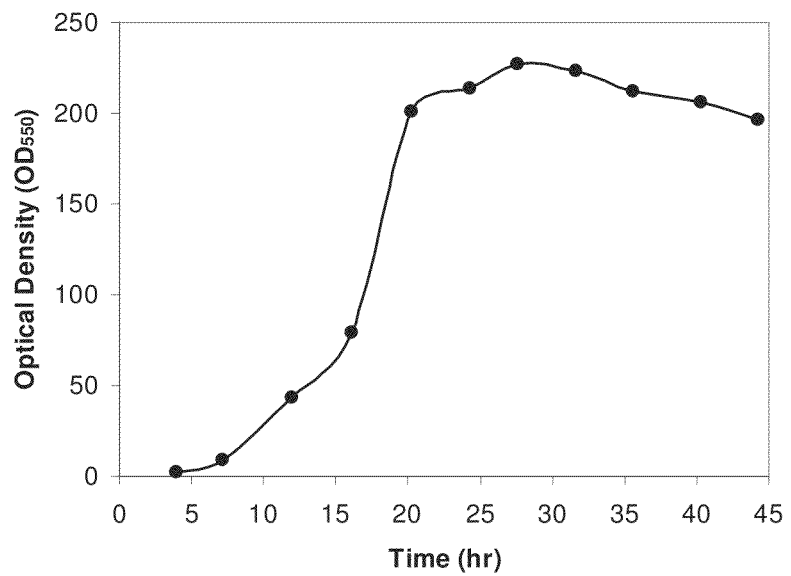
Figure 97:
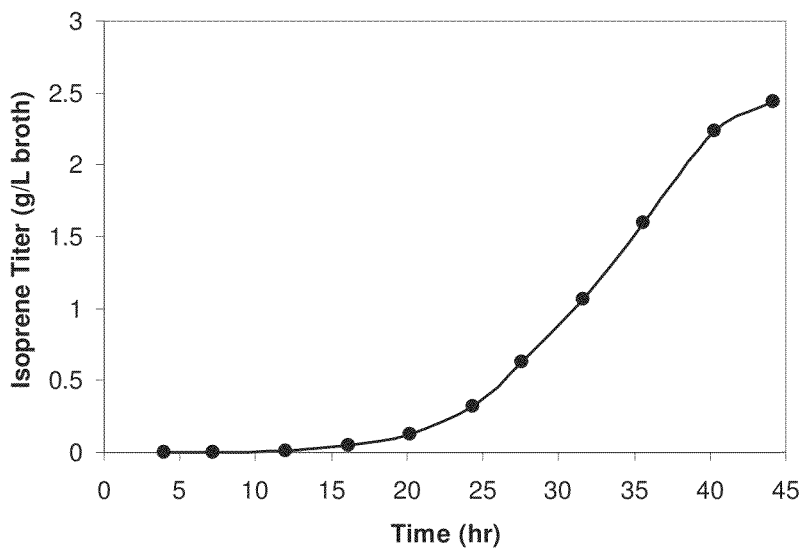
Figure 98:
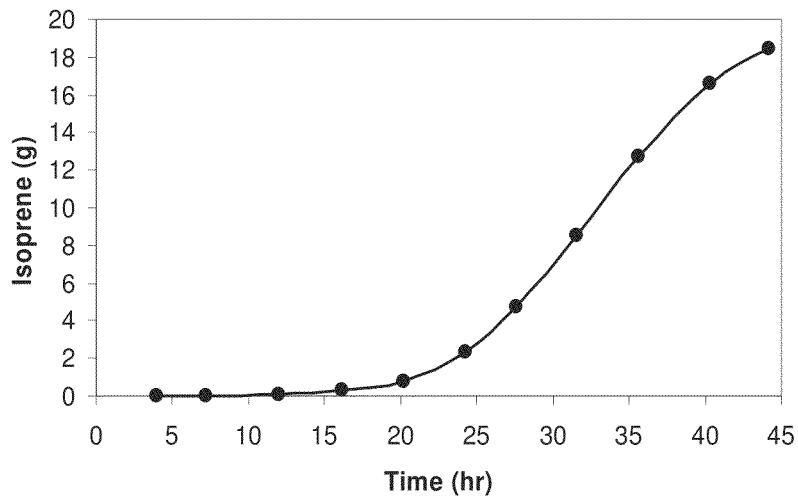

Invert sugar was fed at an exponential rate until cells reached the stationary phase. After this time the invert sugar feed was decreased to meet metabolic demands. The total amount of invert sugar delivered to the bioreactor during the 44 hour fermentation was 2.4 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 200. The $OD_{550}$ profile within the bioreactor over time is shown in FIG. 96. The isoprene level in the off gas from the bioreactor was determined as described herein. The isoprene titer increased over the course of the fermentation to a final value of 2.4 g/L (FIG. 97). The total amount of isoprene produced during the 44 hour fermentation was 18.4 g and the time course of production is shown in FIG. 98. The molar yield of utilized carbon that went into producing isoprene during fermentation was 1.7%. The weight percent yield of isoprene from glucose was 0.8%.

Example 9

Construction of the Upper and Lower MVA Pathway for Integration into *Bacillus subtilis*

I. Construction of the Upper MVA Pathway in *B. subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allow them to be fused together by a PCR reaction. PCR amplifications are carried out using Herculase polymerase according to manufacturer's instructions.

```
1. PaprE
CF 07-134 (+) Start of aprE promoter PstI
                                       (SEQ ID NO: 82)
5'-GACATCTGCAGCTCCATTTTCTTCTGC CF 07-94 (-) Fuse PaprE to mvaE
                                       (SEQ ID NO: 83)
5'-CAATAATAACTACTGTTTTCACTCTTTACCCTCTCCTTTTAA
Template: Bacillus subtilis chromosomal DNA 2. mvaE
CF 07-93 (+) fuse mvaE to the aprE promoter
(GTG start codon)
                                       (SEQ ID NO: 84)
5'-TTAAAAGGAGAGGGTAAAGAGTGAAAACAGTAGTTATTATTG CF 07-62 (-) Fuse mvaE to mvaS with RBS in between
                                       (SEQ ID NO: 35)
5'-TTTATCAATCCCAATTGTCATGTTTTTTTACCTCCTTTAT
TGTTTTCTTAAATC
Template: Enterococcus faecalis chromosomal
DNA (from ATCC)

3. mvaS
CF 07-61 (+) Fuse mvaE to mvaS with RBS in between
                                       (SEQ ID NO: 36)
5'-GATTTAAGAAAACAATAAAGGAGGTAAAAAAACATGACAATT
GGGATTGATAAA CF 07-124 (-) Fuse the end of mvaS to the
terminator
                                       (SEQ ID NO: 85)
5'-CGGGGCCAAGGCCGGTTTTTTTTAGTTTCGATAAGAACGAACGGT
Template: Enterococcus faecalis chromosomal DNA 4. B. amyliquefaciens alkaline serine
protease terminator
CF 07-123 (+) Fuse the end of mvaS to the
terminator
                                       (SEQ ID NO: 109)
5'-ACCGTTCGTTCTTATCGAAACTAAAAAAAACCGGCCTTGGCCCCG CF 07-46 (-) End of B. amyliquefaciens terminator
BamHI
                                       (SEQ ID NO: 63)
5'-GACATGACGGATCCGATTACGAATGCCGTCTC
Template: Bacillus amyliquefaciens chromosomal DNA
```

```
PCR Fusion Reactions
5. Fuse mvaE to mvaS
CF 07-93 (+) fuse mvaE to the aprE promoter
(GTG start codon)
                               (SEQ ID NO: 84)
5'-TTAAAAGGAGAGGGTAAAGAGTGAAAACAGTAGTTATTATTG CF 07-124 (-) Fuse the end of mvaS to the
terminator
                               (SEQ ID NO: 85)
5'-CGGGGCCAAGGCCGGTTTTTTTTAGTTTCGATAAGAACGAACGGT
Template: #2 and 3 from above 6. Fuse mvaE-mvaS to aprE promoter
CF 07-134 (+) Start of aprE promoter PstI
                               (SEQ ID NO: 82)
5'-GACATCTGCAGCTCCATTTTCTTCTGC CF 07-124 (-) Fuse the end of mvaS to the
terminator
                               (SEQ ID NO: 85)
5'-CGGGGCCAAGGCCGGTTTTTTTTAGTTTCGATAAGAACGAACGGT
Template #1 and #4 from above 7. Fuse PaprE-mvaE-mvaS to terminator
CF 07-134 (+) Start of aprE promoter PstI
                               (SEQ ID NO: 82)
5'-GACATCTGCAGCTCCATTTTCTTCTGC CF 07-46 (-) End of B. amyliquefaciens terminator
BamHI
                               (SEQ ID NO: 63)
5'-GACATGACGGATCCGATTACGAATGCCGTCTC
Template: #4 and #6
```

Figure 50:
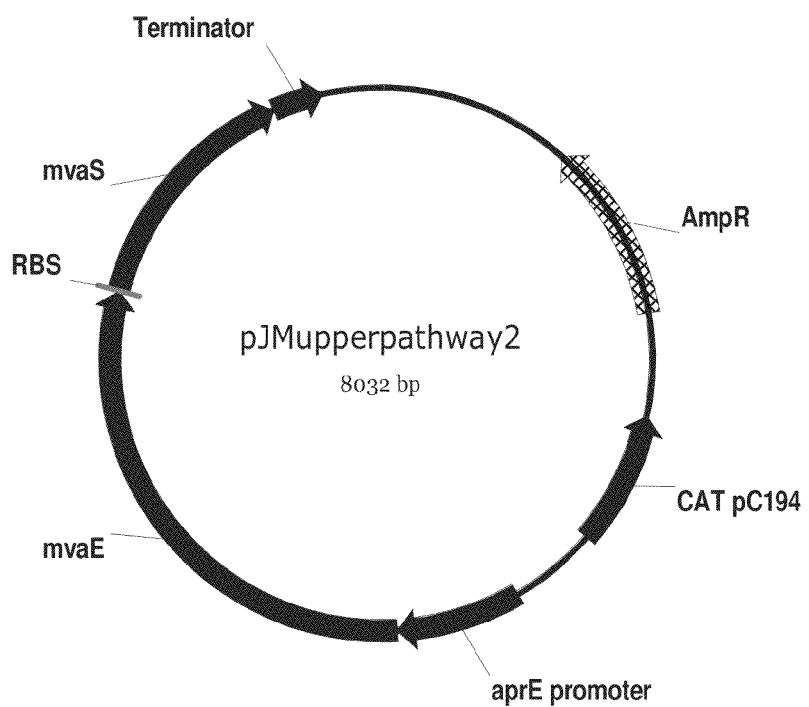
FIG. 50 is a map of pJMupperpathway2.

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 µg/ml). The correct plasmid is identified by sequencing and is designated pJMUpperpathway2 (FIGS. 50 and 51). Purified plasmid DNA is transformed into *Bacillus subtilis* aprEnprE PxylcomK and transformants are selected on L agar containing chloramphenicol (5 µg/ml). A correct colony is selected and is plated sequentially on L agar containing chloramphenicol 10, 15 and 25 µg/ml to amplify the number of copies of the cassette containing the upper pathway.

The resulting strain is tested for mevalonic acid production by growing in LB containing 1% glucose and 1%. Cultures are analyzed by GC for the production of mevalonic acid. This strain is used subsequently as a host for the integration of the lower mevalonic acid pathway.

The following primers are used to sequence the various constructs above.

```
Sequencing primers:
CF 07-134 (+) Start of aprE promoter PstI
                               (SEQ ID NO: 82)
5'-GACATCTGCAGCTCCATTTTCTTCTGC CF 07-58 (+) Start of mvaE gene
                               (SEQ ID NO: 38)
5'-ATGAAAACAGTAGTTATTATTGATGC CF 07-59 (-) End of mvaE gene
                               (SEQ ID NO: 39)
5'-ATGTTATTGTTTTCTTAAATCATTTAAAATAGC CF 07-82 (+) Start of mvaS gene
                               (SEQ ID NO: 40)
5'-ATGACAATTGGGATTGATAAAATTAG CF 07-83 (-) End of mvaS gene
                               (SEQ ID NO: 41)
5'-TTAGTTTCGATAAGAACGAACGGT CF 07-86 (+) Sequence in mvaE
                               (SEQ ID NO: 42)
5'-GAAATAGCCCCATTAGAAGTATC CF 07-87 (+) Sequence in mvaE
                               (SEQ ID NO: 43)
5'-TTGCCAATCATATGATTGAAAATC CF 07-88 (+) Sequence in mvaE
                               (SEQ ID NO: 44)
5'-GCTATGCTTCATTAGATCCTTATCG CF 07-89 (+) Sequence mvaS
                               (SEQ ID NO: 45)
5'-GAAACCTACATCCAATCTTTTGCCC
```

Transformants are selected on LA containing chloramphenicol at a concentration of 5 µg/ml. One colony is confirmed to have the correct integration by sequencing and is plated on LA containing increasing concentrations of chloramphenicol over several days, to a final level of 25 µg/ml. This results in amplification of the cassette containing the genes of interest. The resulting strain is designated CF 455: pJMupperpathway#1 X *Bacillus subtilis* aprEnprE Pxyl comK (amplified to grow on LA containing chloramphenicol 25 µg/ml).

II. Construction of the Lower MVA pathway in *Bacillus subtilis*

Figure 28:
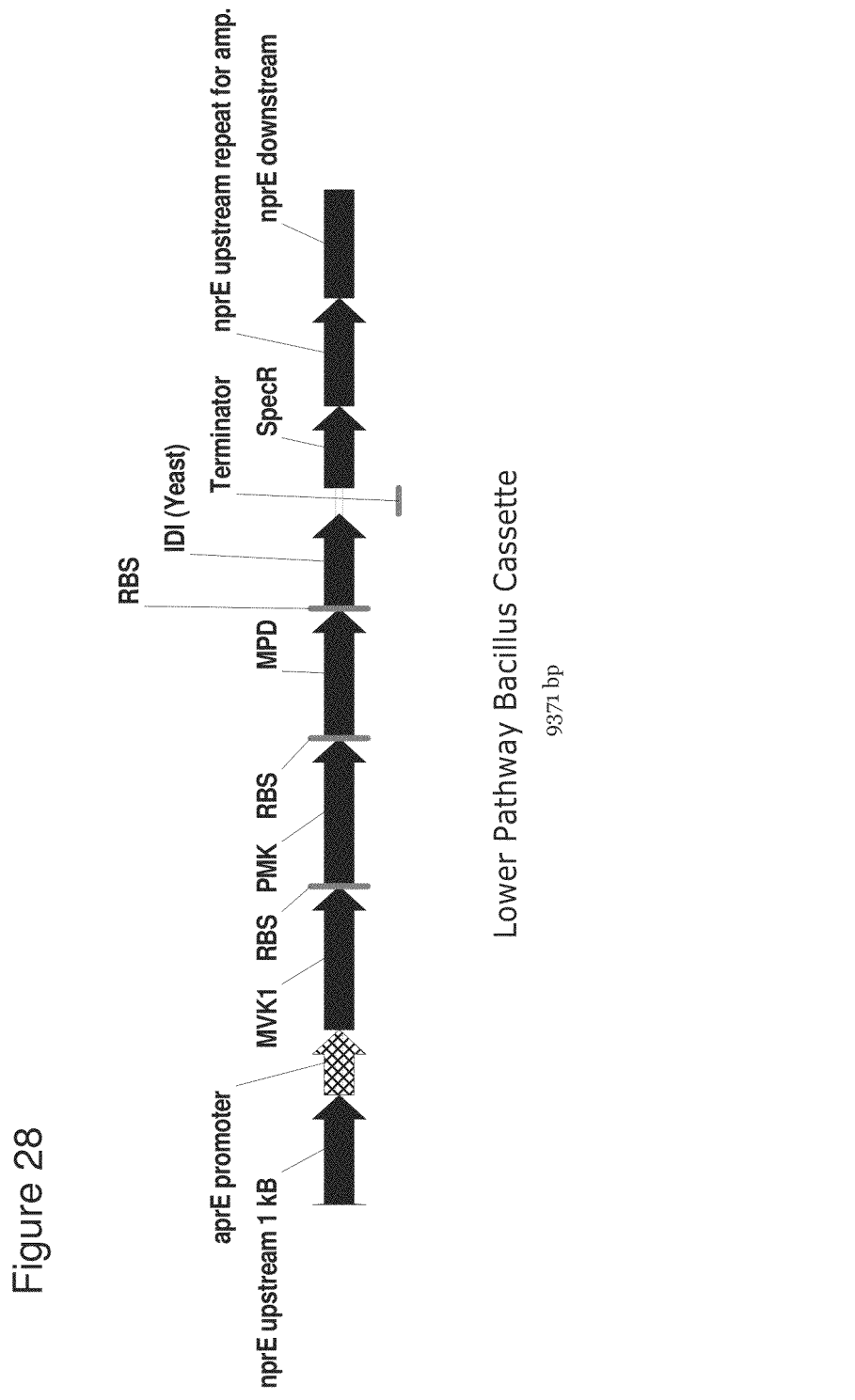
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvkl, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 4 and is transformed into the strain with both upper and lower pathways integrated.

Example 10

De-Coupling of Growth and Production of Isoprene in *E. coli* Expressing Genes of the Mevalonic Acid Pathway and Fermented in a Fed-Batch Culture This example illustrates the de-coupling of cell growth from mevalonic acid and isoprene production.

I. Fermentation Conditions

Medium Recipe (per liter fermentation medium): The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid*$H_2O$ 40 g, $MnSO_4*H_2O$ 30 g, NaCl 10 g, $FeSO_4*7H_2O$ 1 g, $CoCl2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in Di $H_2O$, pH to 3.0 with HCl/NaOH, then q.s. to volume, and filter sterilized with a 0.22 micron filter.

Fermentation was performed with *E. coli* cells containing the pTrcHis2AUpperPathway (also called pTrcUpperMVA, FIGS. 91 and 92A-92C) (50 µg/ml carbenicillin) or the pCL PtrcUpperMVA (also called pCL PtrcUpperPathway (FIG. 26)) (50 µg/ml spectinomycin) plasmids. For experiments in which isoprene was produced, the *E. coli* cells also contained the pTrc KKDyIkIS (50 µg/ml kanamycin) plasmid. These experiments were carried out to monitor mevalonic acid or isoprene formation from glucose at the desired fermentation pH 7.0 and temperature 30° C. An inoculum of an *E. coli* strain taken from a frozen vial was streaked onto an LA broth agar plate (with antibiotics) and incubated at 37° C. A single colony was inoculated into tryptone-yeast extract medium. After the inoculum grew to optical density 1.0 when measured at 550 nm, it was used to inoculate the bioreactor.

Glucose was fed at an exponential rate until cells reached the stationary phase. After this time the glucose feed was decreased to meet metabolic demands. Induction was achieved by adding IPTG. The mevalonic acid concentration in fermentation broth was determined by applying perchloric acid (Sigma-Aldrich #244252) treated samples (0.3 M incubated at 4° C. for 5 minutes) to an organic acids HPLC column (BioRad #125-0140). The concentration was determined by comparing the broth mevalonic acid peak size to a calibration curve generated from mevalonolacetone (Sigma-Aldrich #M4667) treated with perchloric acid to form D,L-mevalonate. The isoprene level in the off gas from the bioreactor was determined as described herein. The isoprene titer is defined as the amount of isoprene produced per liter of fermentation broth.

II. Mevalonic Acid Production from *E. coli* BL21 (DE3) Cells Expressing the pTrcUpperMVA Plasmid at a 150-L Scale BL21 (DE3) cells that were grown on a plate as explained above in part I were inoculated into a flask containing 45 mL of tryptone-yeast extract medium and incubated at 30° C. with shaking at 170 rpm for 5 hours. This solution was transferred to a 5-L bioreactor of tryptone-yeast extract medium, and the cells were grown at 30° C. and 27.5 rpm until the culture reached an $OD_{550}$ of 1.0. The 5 L of inoculum was seeded into a 150-L bioreactor containing 45-kg of medium. The IPTG concentration was brought to 1.1 mM when the $OD_{550}$ reached a value of 10. The $OD_{550}$ profile within the bioreactor over time is shown in FIG. 60A. The mevalonic acid titer increased over the course of the fermentation to a final value of 61.3 g/L (FIG. 60B). The specific productivity profile throughout the fermentation is shown in FIG. 60C and a comparison to FIG. 60A illustrates the de-coupling of growth and mevalonic acid production. The total amount of mevalonic acid produced during the 52.5 hour fermentation was 4.0 kg from 14.1 kg of utilized glucose. The molar yield of utilized carbon that went into producing mevalonic acid during fermentation was 34.2%.

III. Mevalonic Acid Production from *E. coli* BL21 (DE3) Cells Expressing the pTrcUpperMVA Plasmid at a 15-L Scale BL21 (DE3) cells that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 10. The $OD_{550}$ profile within the bioreactor over time is shown in FIG. 61A. The mevalonic acid titer increased over the course of the fermentation to a final value of 53.9 g/L (FIG. 61B). The specific productivity profile throughout the fermentation is shown in FIG. 61C and a comparison to FIG. 61A illustrates the de-coupling of growth and mevalonic acid production. The total amount of mevalonic acid produced during the 46.6 hour fermentation was 491 g from 2.1 kg of utilized glucose. The molar yield of utilized carbon that went into producing mevalonic acid during fermentation was 28.8%.

IV. Mevalonic Acid Production from *E. coli* FM5 Cells Expressing the pTrcUpperMVA Plasmid at a 15-L Scale FM5 cells that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 30. The $OD_{550}$ profile within the bioreactor over time is shown in FIG. 62A. The mevalonic acid titer increased over the course of the fermentation to a final value of 23.7 g/L (FIG. 62B). The specific productivity profile throughout the fermentation is shown in FIG. 62C and a comparison to FIG. 62A illustrates the de-coupling of growth and mevalonic acid production. The total amount of mevalonic acid produced during the 51.2 hour fermentation was 140 g from 1.1 kg of utilized glucose. The molar yield of utilized carbon that went into producing mevalonic acid during fermentation was 15.2%.

V. Isoprene Production from *E. coli* BL21 (DE3) Cells Expressing the pCL PtrcUpperMVA and pTrc KKDyIkIS Plasmids at a 15-L Scale BL21 (DE3) cells expressing the pCL PtrcUpperMVA and pTrc KKDyIkIS plasmids that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 25 µM when the $OD_{550}$ reached a value of 10. The IPTG concentration was raised to 50 uM when $OD_{550}$ reached 190. The IPTG concentration was raised to 100 uM at 38 hours of fermentation. The $OD_{550}$ profile within the bioreactor over time is shown in FIG. 63A. The isoprene titer increased over the course of the fermentation to a final value of 2.2 g/L broth (FIG. 63B). The specific productivity profile throughout the fermentation is shown in FIG.

63C and a comparison to FIG. 63A illustrates the de-coupling of growth and isoprene production. The total amount of isoprene produced during the 54.4 hour fermentation was 15.9 g from 2.3 kg of utilized glucose. The molar yield of utilized carbon that went into producing isoprene during fermentation was 1.53%.

VI. Isoprene Production from *E. coli* BL21 (DE3) Tuner Cells Expressing the pCL PtrcUpperMVA and pTrc KKDyIkIS Plasmids at a 15-L Scale BL21 (DE3) tuner cells expressing the pCL PtrcUpperMVA and pTrc KKDyIkIS plasmids that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 26 μM when the $OD_{550}$ reached a value of 10. The IPTG concentration was raised to 50 uM when $OD_{550}$ reached 175. The $OD_{550}$ profile within the bioreactor over time is shown in FIG. 64A. The isoprene titer increased over the course of the fermentation to a final value of 1.3 g/L broth (FIG. 64B). The specific productivity profile throughout the fermentation is shown in FIG. 64C and a comparison to FIG. 64A illustrates the de-coupling of growth and isoprene production. The total amount of isoprene produced during the 48.6 hour fermentation was 9.9 g from 1.6 kg of utilized glucose. The molar yield of utilized carbon that went into producing isoprene during fermentation was 1.34%.

VII. Isoprene Production from *E. coli* MG1655 Cells Expressing the pCL PtrcUpperMVA and pTrc KKDyIkIS Plasmids at a 15-L Scale MG1655 cells expressing the pCL PtrcUpperMVA and pTrc KKDyIkIS plasmids that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 24 μM when the $OD_{550}$ reached a value of 45. The $OD_{550}$ profile within the bioreactor over time is shown in FIG. 65A. The isoprene titer increased over the course of the fermentation to a final value of 393 mg/L broth (FIG. 65B). The specific productivity profile throughout the fermentation is shown in FIG. 65C and a comparison to FIG. 65A illustrates the de-coupling of growth and isoprene production. The total amount of isoprene produced during the 67.4 hour fermentation was 2.2 g from 520 g of utilized glucose. The molar yield of utilized carbon that went into producing isoprene during fermentation was 0.92%.

VIII. Isoprene Production from *E. coli* MG1655ack-pta Cells Expressing the pCL PtrcUpperMVA and pTrc KKDyIkIS Plasmids at a 15-L Scale MG1655ack-pta cells expressing the pCL PtrcUpperMVA and pTrc KKDyIkIS plasmids that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 30 μM when the $OD_{550}$ reached a value of 10. The $OD_{550}$ profile within the bioreactor over time is shown in FIG. 66A. The isoprene titer increased over the course of the fermentation to a final value of 368 mg/L broth (FIG. 66B). The specific productivity profile throughout the fermentation is shown in FIG. 66C and a comparison to FIG. 66A illustrates the de-coupling of growth and isoprene production. The total amount of isoprene produced during the 56.7 hour fermentation was 1.8 g from 531 g of utilized glucose. The molar yield of utilized carbon that went into producing isoprene during fermentation was 0.73%.

IX. Isoprene Production from *E. coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that were grown on a plate as explained above in part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 27 μM when the $OD_{550}$ reached a value of 15. The $OD_{550}$ profile within the bioreactor over time is shown in FIG. 67A. The isoprene titer increased over the course of the fermentation to a final value of 235 mg/L broth (FIG. 67B). The specific productivity profile throughout the fermentation is shown in FIG. 67C and a comparison to FIG. 67A illustrates the de-coupling of growth and isoprene production. The total amount of isoprene produced during the 52.3 hour fermentation was 1.4 g from 948 g of utilized glucose. The molar yield of utilized carbon that went into producing isoprene during fermentation was 0.32%.

Example 11

Production of Isoprene During the Exponential Growth Phase of *E. coli* Expressing Genes of the Mevalonic Acid Pathway and Fermented in a Fed-Batch Culture This example illustrates the production of isoprene during the exponential growth phase of cells.

Medium Recipe (per liter fermentation medium): The medium was generated using the following components per liter fermentation medium: $K_2HPO_4$ 7.5 g, $MgSO_4 \cdot 7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: The 1000× modified trace metal solution was generated using the following components: citric acid*$H_2O$ 40 g, $MnSO_4 \cdot H_2O$ 30 g, NaCl 10 g, $FeSO_4 \cdot 7H_2O$ 1 g, $CoCl2 \cdot 6H_2O$ 1 g, $ZnSO_4 \cdot 7H_2O$ 1 g, $CuSO_4 \cdot 5H_2O$ 100 mg, $H_3BO_3$ 100 mg, and $NaMoO_4 \cdot 2H_2O$ 100 mg. Each component is dissolved one at a time in Di $H2O$, pH to 3.0 with HCl/NaOH, then q.s. to volume and filter sterilized with 0.22 micron filter.

Fermentation was performed in a 15-L bioreactor with ATCC11303 *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Glucose was fed at an exponential rate until cells reached the stationary phase. After this time the glucose feed was decreased to meet metabolic demands. The total amount of glucose delivered to the bioreactor during the 50 hour fermentation was 2.0 kg. Induction was achieved by adding IPTG. The IPTG concentration was brought to 25 uM when the optical density at 550 nm ($OD_{550}$) reached a value of 10.

Figure 99:
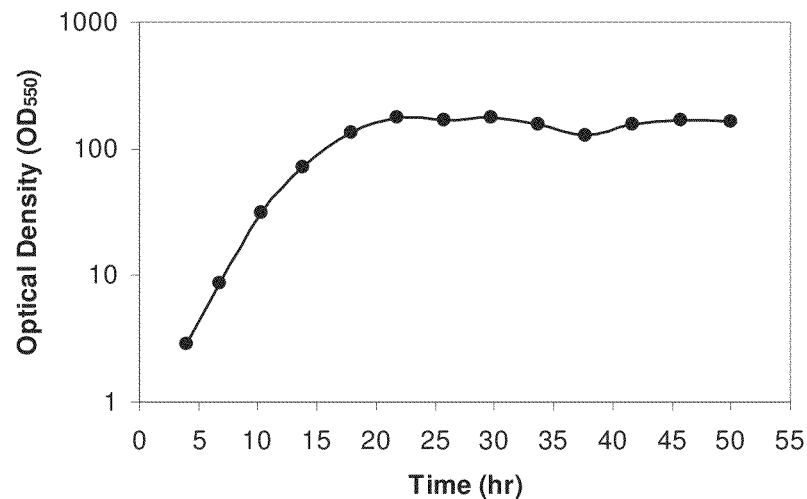
Figure 100:
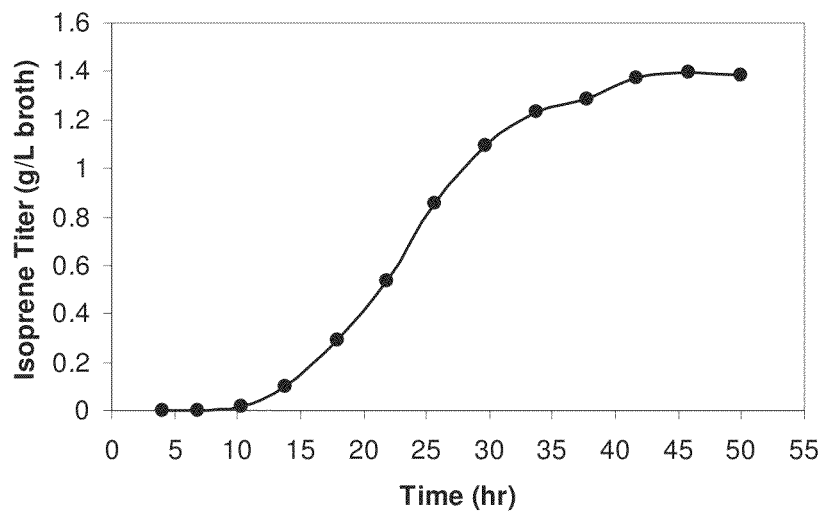
Figure 101:
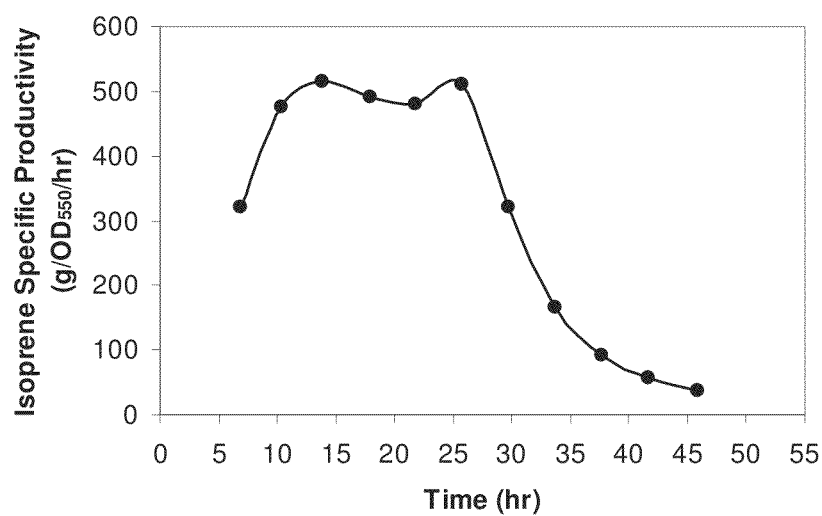
Figure 102:
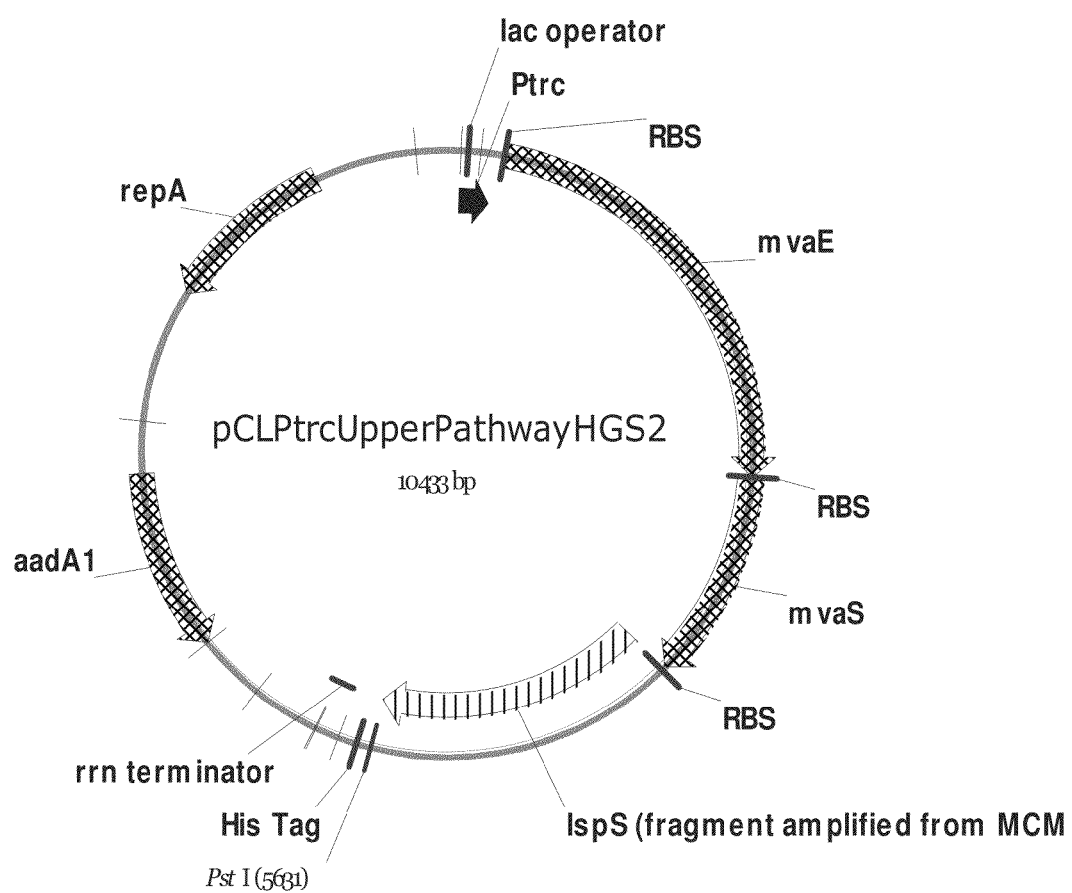

The IPTG concentration was raised to 50 uM when $OD_{550}$ reached 190. The $OD_{550}$ profile within the bioreactor over time is shown in FIG. 99. The isoprene level in the off gas from the bioreactor was determined as described herein. The isoprene titer increased over the course of the fermentation to a final value of 1.4 g/L (FIG. 100). The total amount of isoprene produced during the 50 hour fermentation was 10.0 g. The profile of the isoprene specific productivity over time within the bioreactor is shown in FIG. 101. The molar yield of utilized carbon that contributed to producing isoprene during fermentation was 1.1%. The weight percent yield of isoprene from glucose was 0.5%.

Example 12

Flammability Modeling and Testing of Isoprene

I. Summary of Flammability Modeling and Testing of Isoprene

Flammability modeling and experiments were performed for various hydrocarbon/oxygen/nitrogen/water/carbon dioxide mixtures. This modeling and experimental tested was aimed at defining isoprene and oxygen/nitrogen flammability curves under specified steam and carbon monoxide concentrations at a fixed pressure and temperature. A matrix of the model conditions is shown in Table 12-1, and a matrix of the experiments performed is shown in Table 12-2.

TABLE 12-1

Summary of Modeled Isoprene Flammability

| Series | Temperature (° C.) | Pressure (psig) | Steam Concentration (wt %) | $CO_2$ Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 12-2

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
|---|---|---|---|---|---|
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation were used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide were present in the program database. The program database did not have isoprene as a species; therefore the thermodynamic properties were incorporated manually.

The next step is to decide whether the initial pressure and temperature conditions that the combustion process is taking place in. In this model the pressure was 1 atmosphere (absolute) and the temperature was 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K was selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIGS. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIGS. 68 through 74. Additionally, the current form is not conducive to comparison with experimental data which is generally presented in terms of volume percent.

Figure 68:
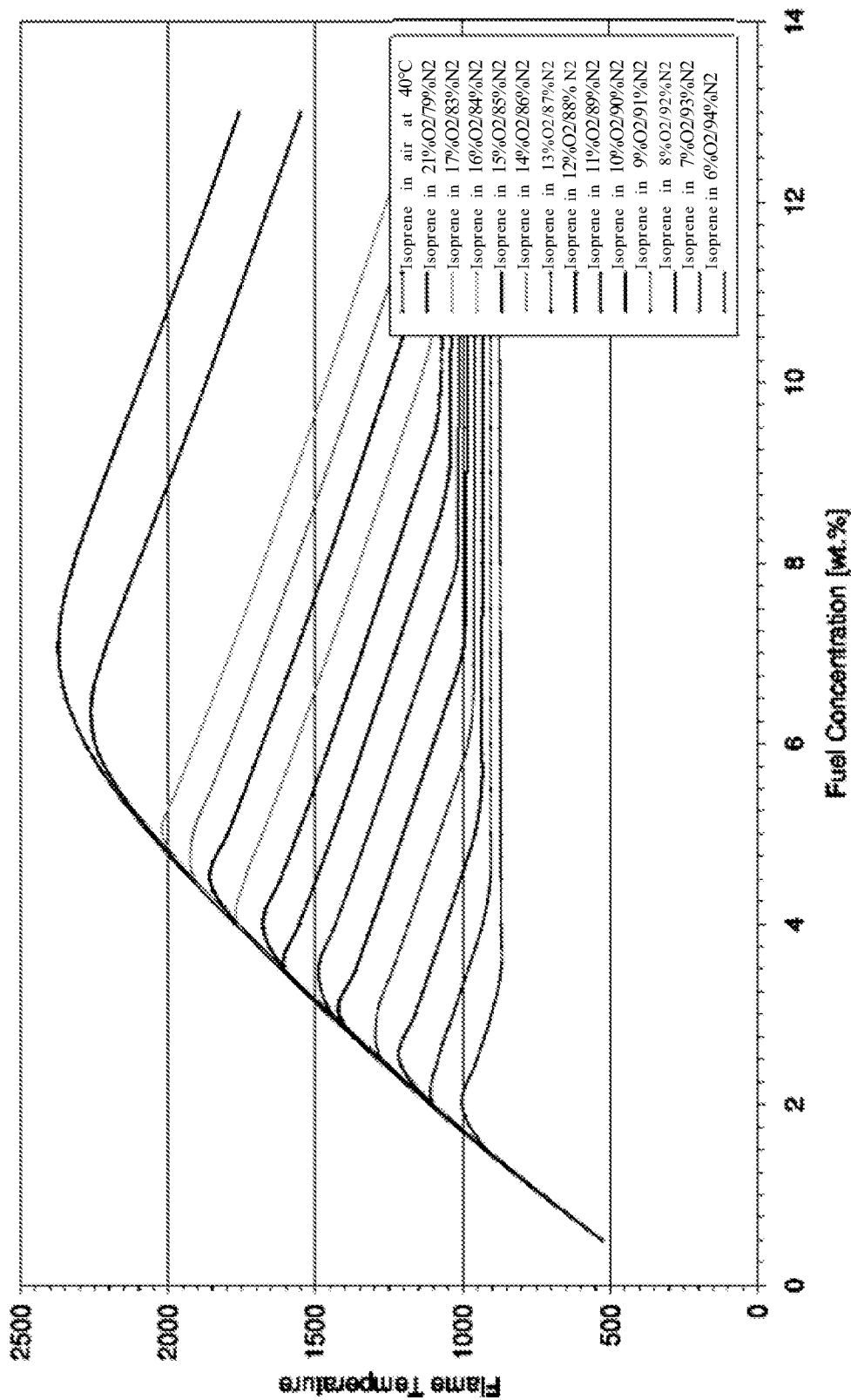
FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.
Figure 69:
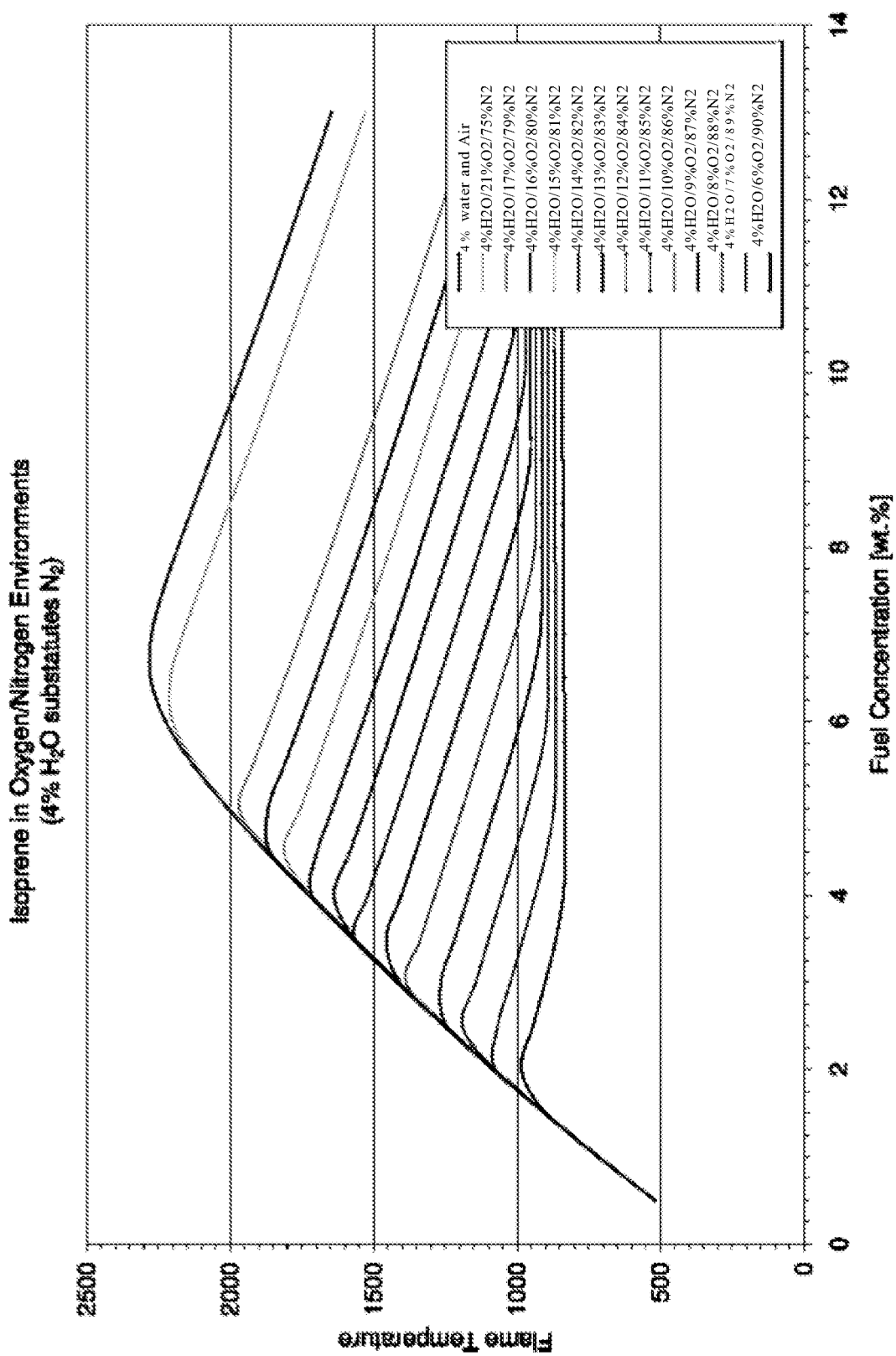
FIG. 69 is a graph of the calculated adiabatic flame temperatures for Series B as a function of fuel concentration for various oxygen levels with 4% water. The figure legend lists the curves in the order in which they appear in the graph.
Figure 70:
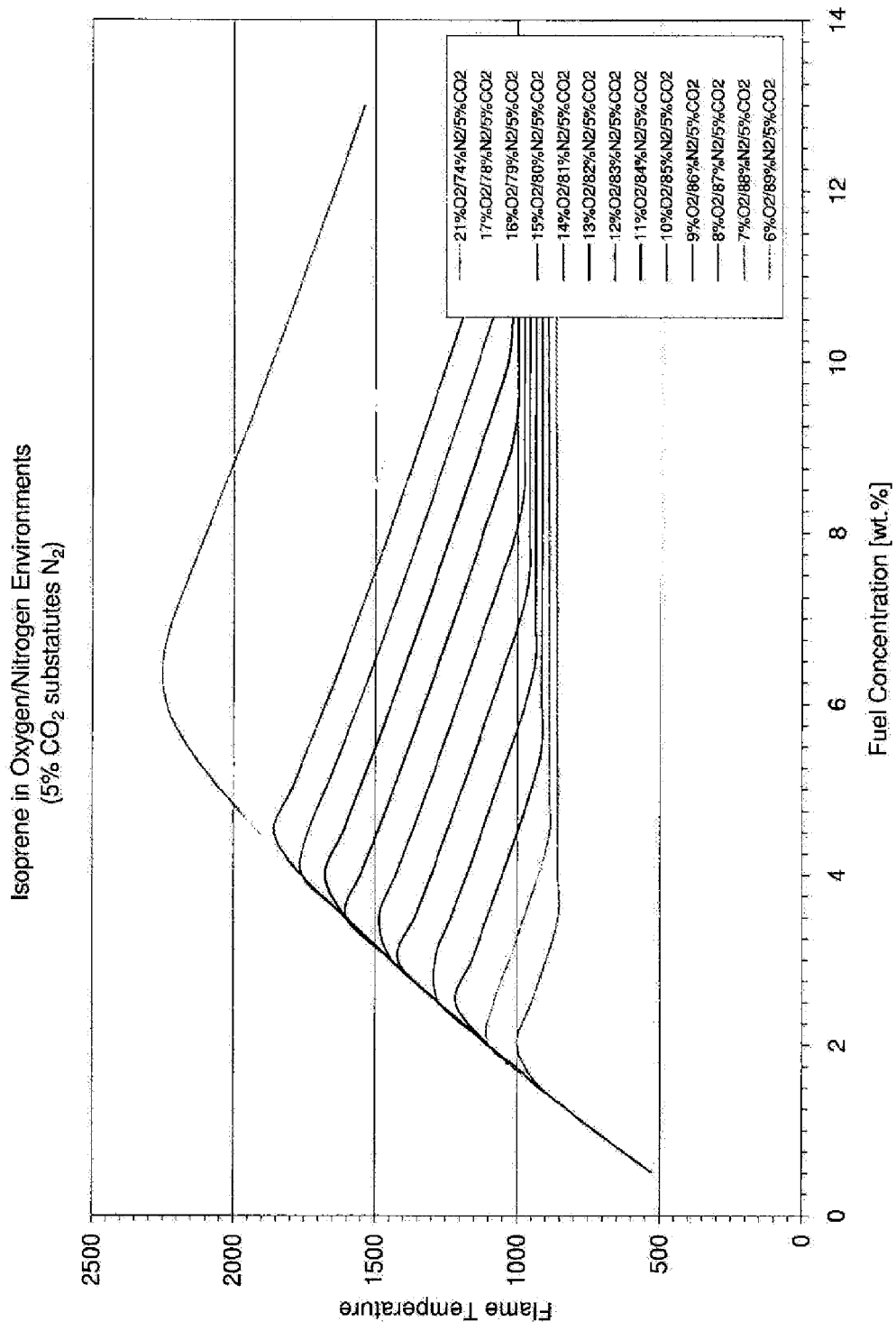
FIG. 70 is a graph of the calculated adiabatic flame temperatures for Series C as a function of fuel concentration for various oxygen levels with 5% $CO_2$. The figure legend lists the curves in the order in which they appear in the graph.
Figure 71:
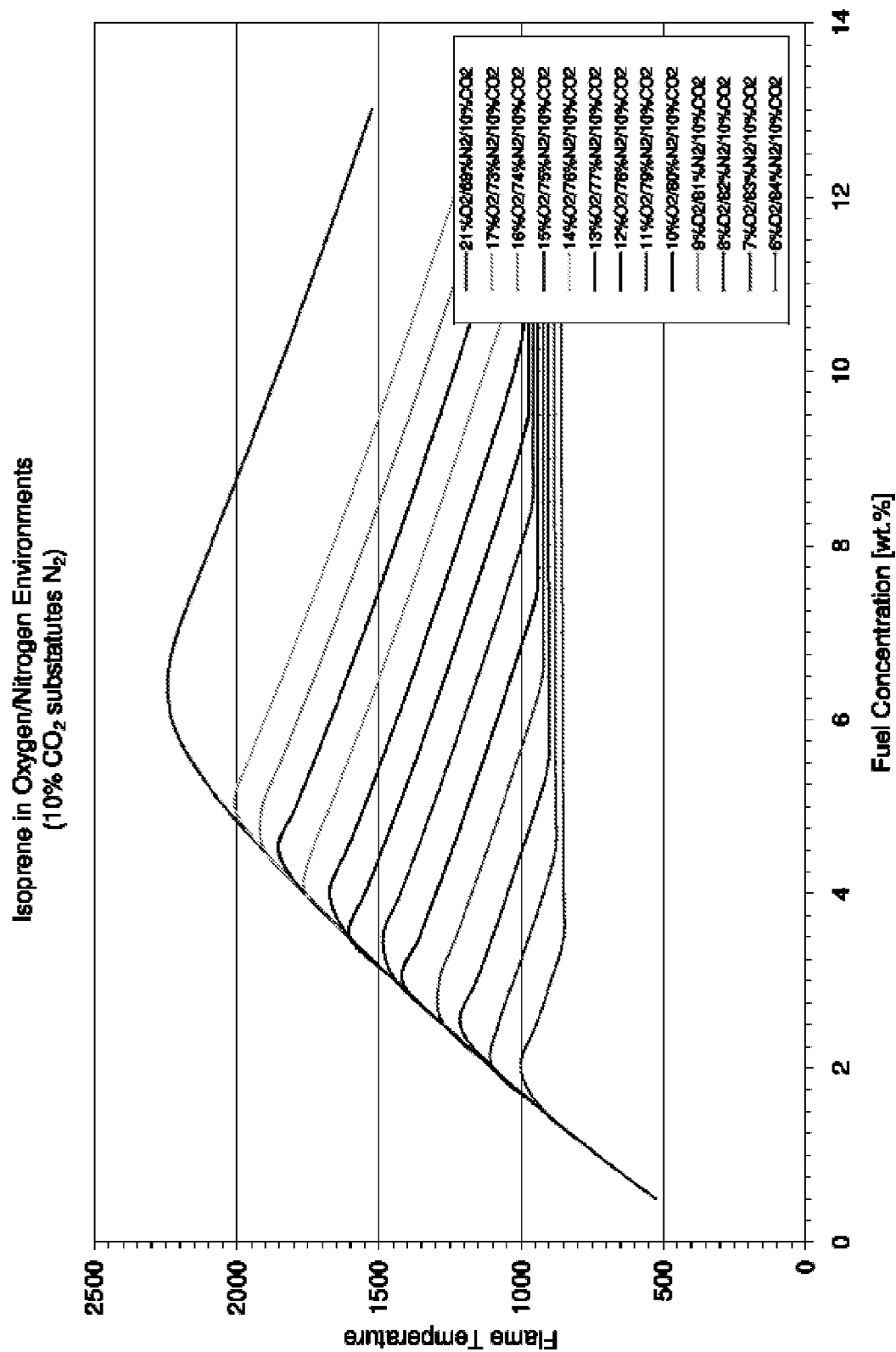
FIG. 71 is a graph of the calculated adiabatic flame temperatures for Series D as a function of fuel concentration for various oxygen levels with 10% $CO_2$. The figure legend lists the curves in the order in which they appear in the graph.
Figure 72:
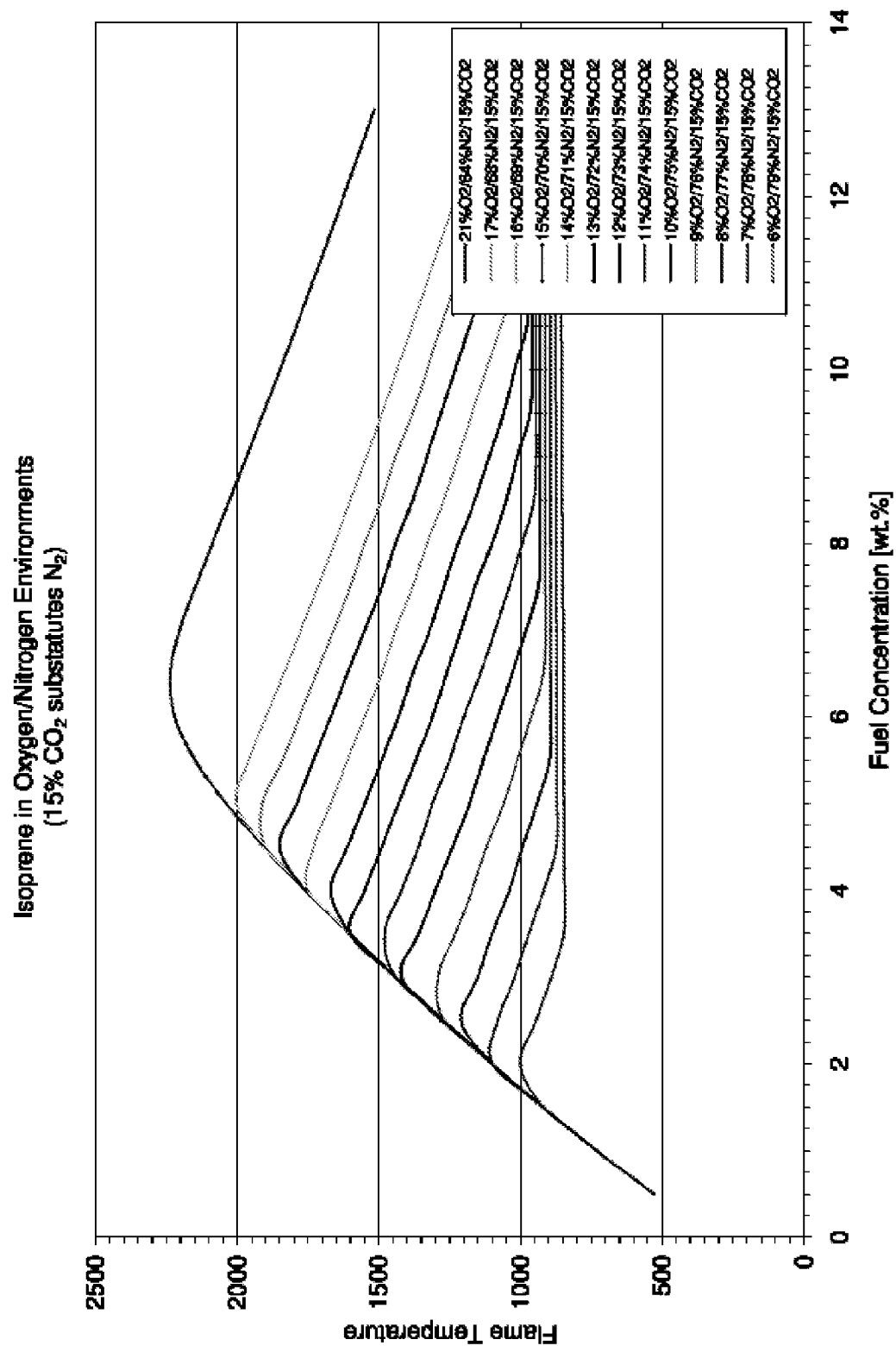
FIG. 72 is a graph of the calculated adiabatic flame temperatures for Series E as a function of fuel concentration for various oxygen levels with 15% $CO_2$. The figure legend lists the curves in the order in which they appear in the graph.
Figure 73:
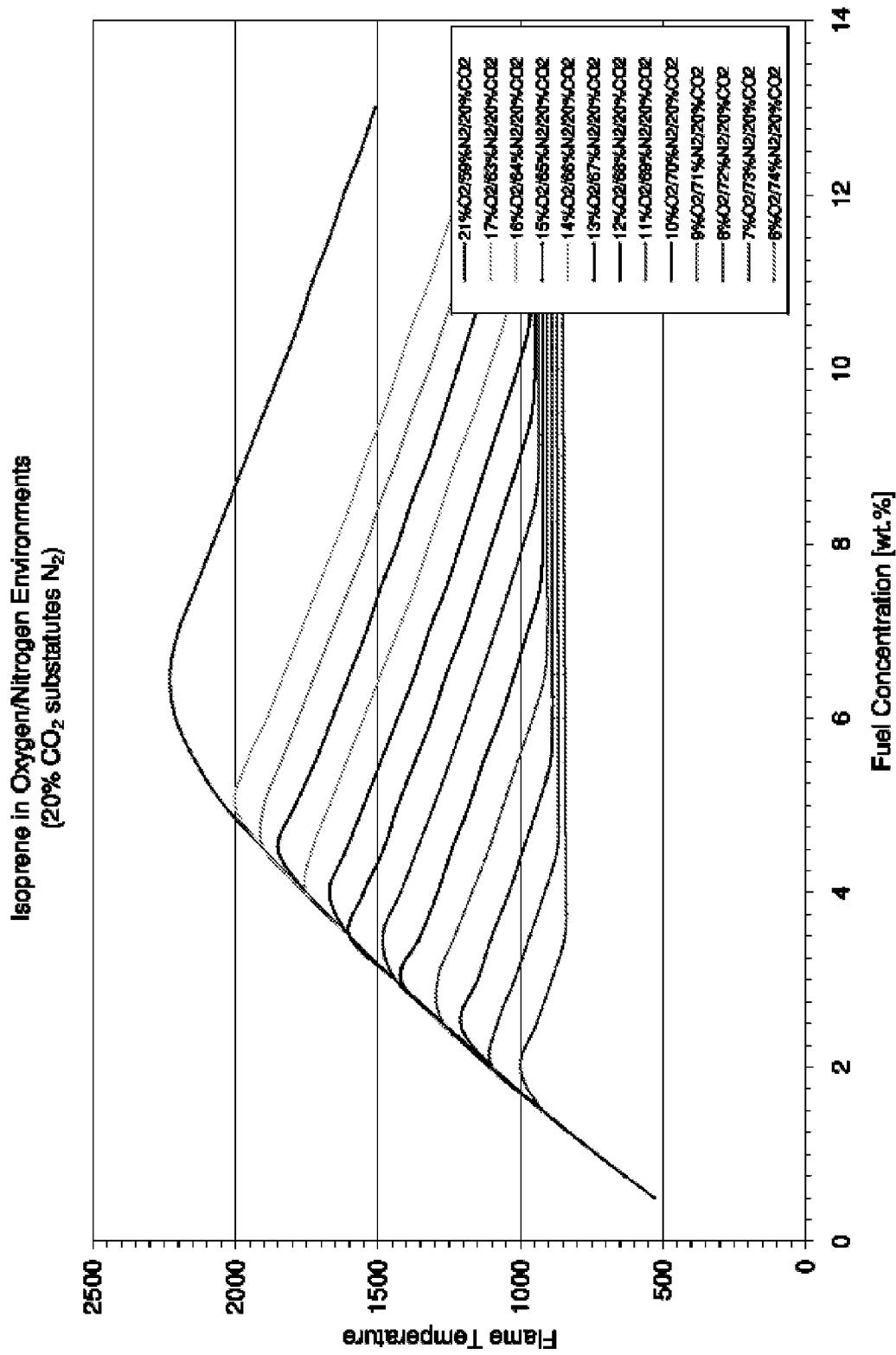
FIG. 73 is a graph of the calculated adiabatic flame temperatures for Series F as a function of fuel concentration for various oxygen levels with 20% $CO_2$. The figure legend lists the curves in the order in which they appear in the graph.
Figure 74:
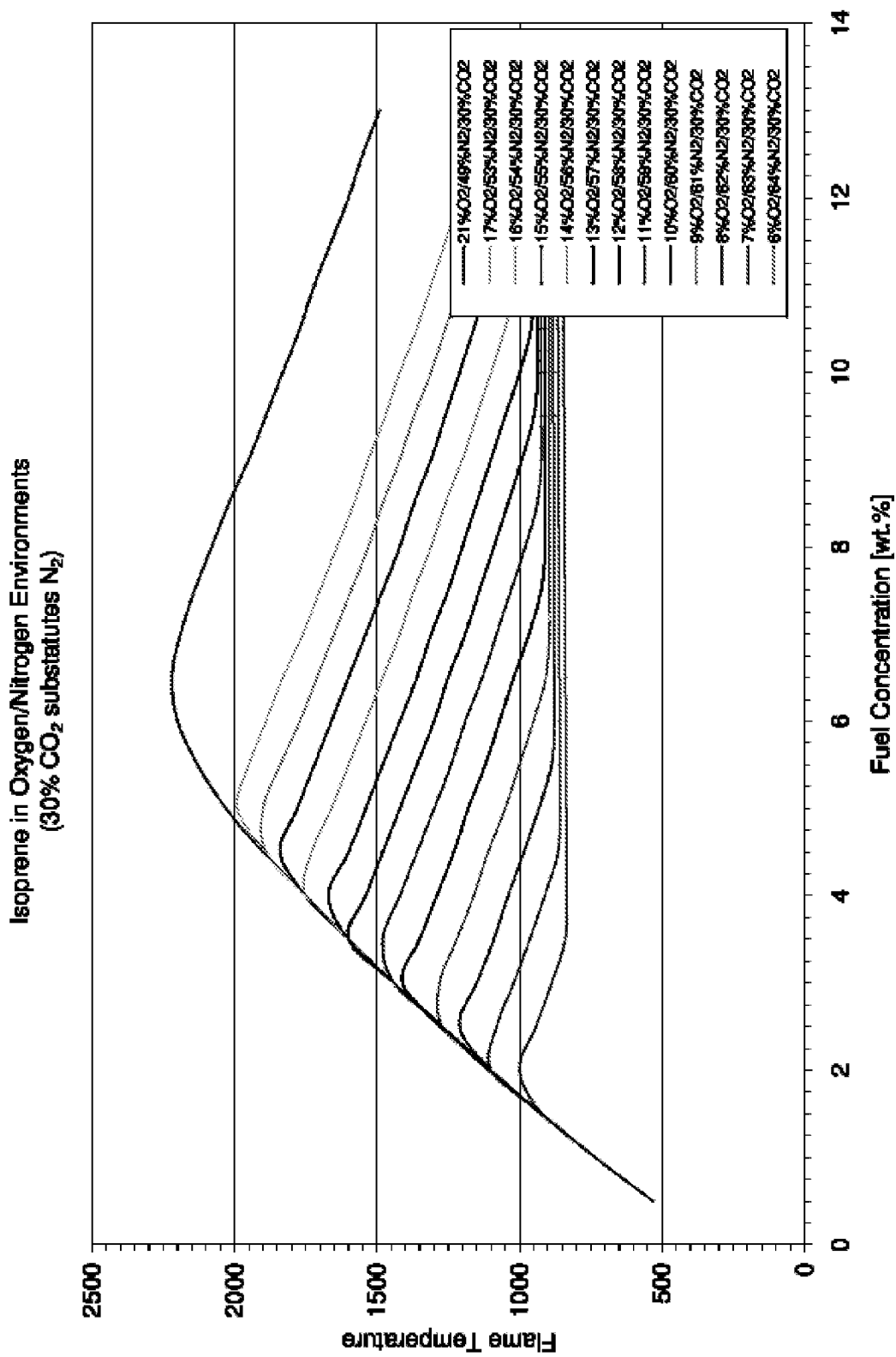
FIG. 74 is a graph of the calculated adiabatic flame temperatures for Series G as a function of fuel concentration for various oxygen levels with 30% $CO_2$. The figure legend lists the curves in the order in which they appear in the graph.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

Figure 75B:
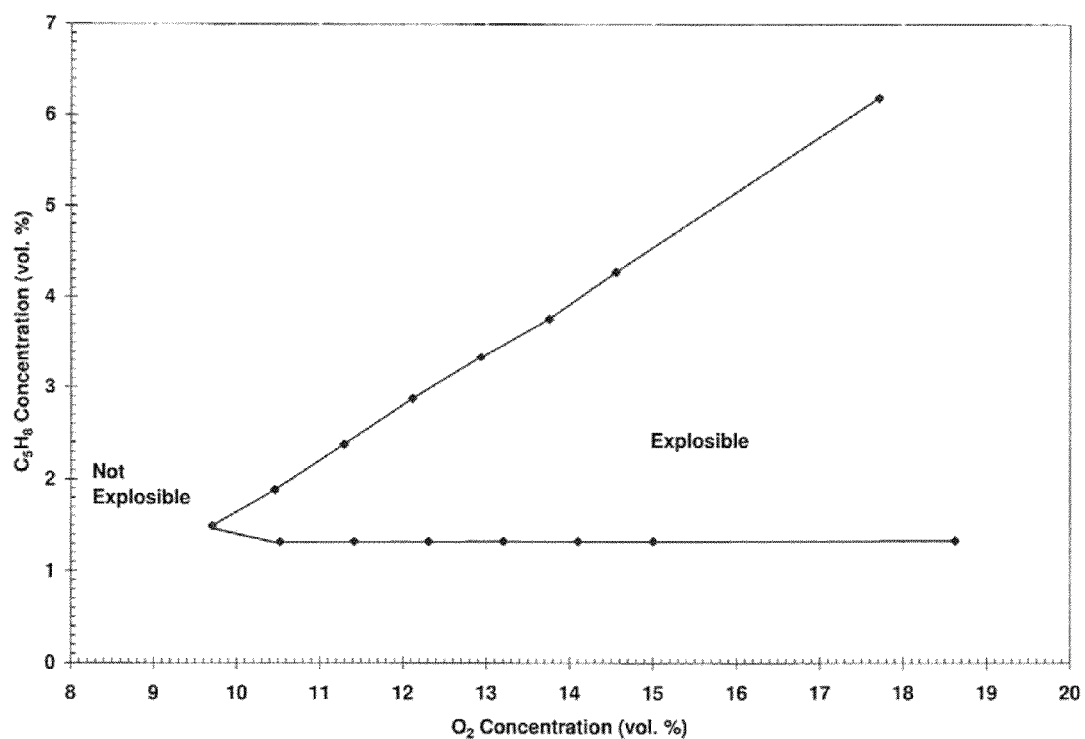
FIG. 75B is a graph of the flammability results from the CAFT model for Series A in FIG. 68 plotted as volume percent.
Figure 76B:
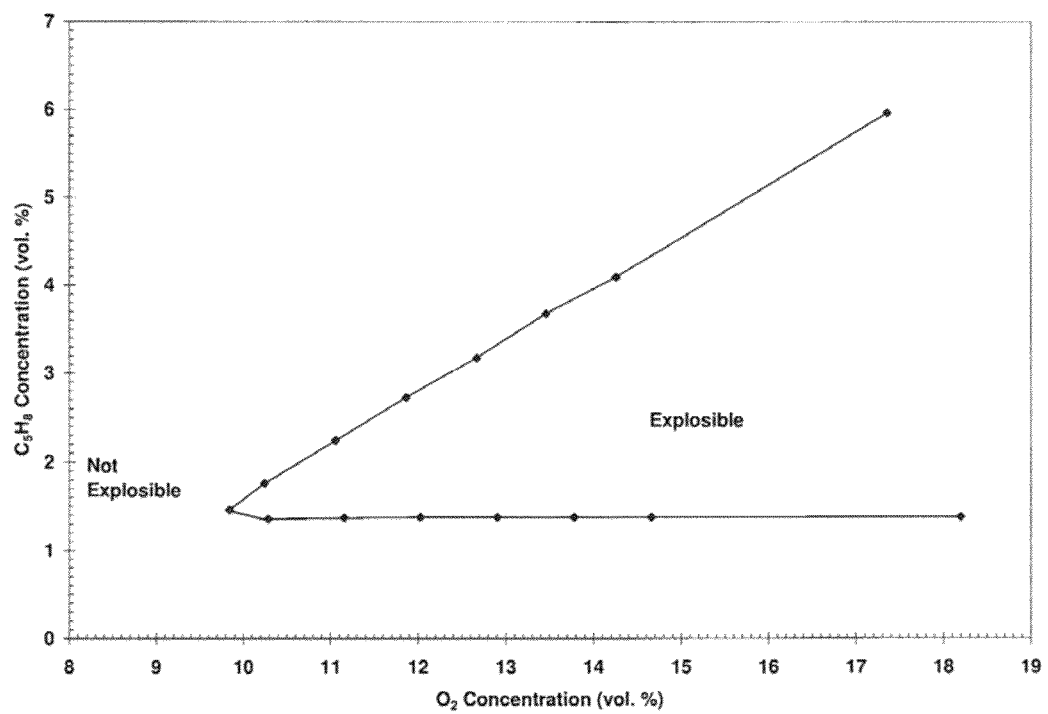
FIG. 76B is a graph of the flammability results from the CAFT model for Series B in FIG. 69 plotted as volume percent.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The "nose" of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Figure 77:
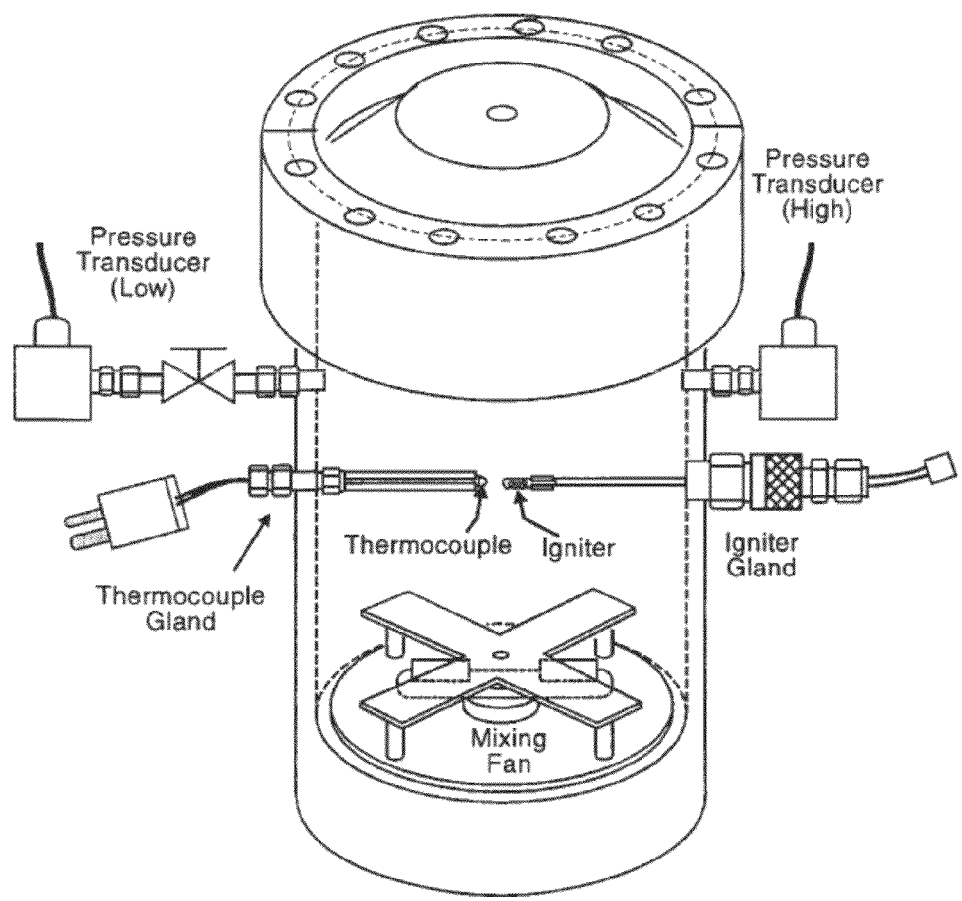
FIG. 77 is a figure of the flammability test vessel.

Flammability testing was conducted in a 4 liter high pressure vessel. The vessel was cylindrical in shape with an inner diameter of 6" and an internal height of 8.625". The temperature of the vessel (and the gases inside) was maintained using external heaters that were controlled by a PID controller. To prevent heat losses, ceramic wool and reflective insulation were wrapped around the pressure vessel. Type K thermocouples were used the measure the temperature of the gas space as well as the temperature of the vessel itself. FIG. 77 illustrates the test vessel.

Before a test was ran, the vessel was evacuated and purged with nitrogen to ensure that any gases from previous tests were removed. A vacuum was then pulled on the vessel. The pressure after this had been done was typically around 0.06 bar(a). Due to the nitrogen purging, the gas responsible for this initial pressure was assumed to be nitrogen. Using partial pressures, water, isoprene, nitrogen, and oxygen were then added in the appropriate amounts to achieve the test conditions in question. A magnetically driven mixing fan within the vessel ensured mixing of the gaseous contents. The gases were allowed to mix for about 2 minutes with the fan being turned off approximately 1 minute prior to ignition.

The igniter was comprised of a 1.5 ohm nicrome coil and an AC voltage source on a timer circuit. Using an oscilloscope, it was determined that 34.4 VAC were delivered to the igniter for 3.2 seconds. A maximum current of 3.8 amps occurred approximately halfway into the ignition cycle. Thus, the maximum power was 131 W and the total energy provided over the ignition cycle was approximately 210 J.

Deflagration data was acquired using a variable reluctance Validyne DP215 pressure transducer connected to a data acquisition system. A gas mixture was considered to have deflagrated if the pressure rise was greater than or equal to 5%.

V. Results of Flammability Testing

The first experimental series (Series 1) was run at 40° C. and 0 psig with no steam. Running tests at varying concentrations of isoprene and oxygen produced the flammability curve shown in FIG. 78A. The data points shown in this curve are only those that border the curve. A detailed list of all the data points taken for this series is shown in FIGS. 80A and 80B.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) was run at 40° C. and 0 psig with a fixed steam concentration of 4%. Running tests at varying concentrations of isoprene and oxygen produced the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits were tested. The addition of 4% steam to the test mixture did not significantly change the key limits of the flammability envelope. It should be noted that higher concentrations of steam/water and or other inertants may influence the flammability envelope.

Figure 79A:
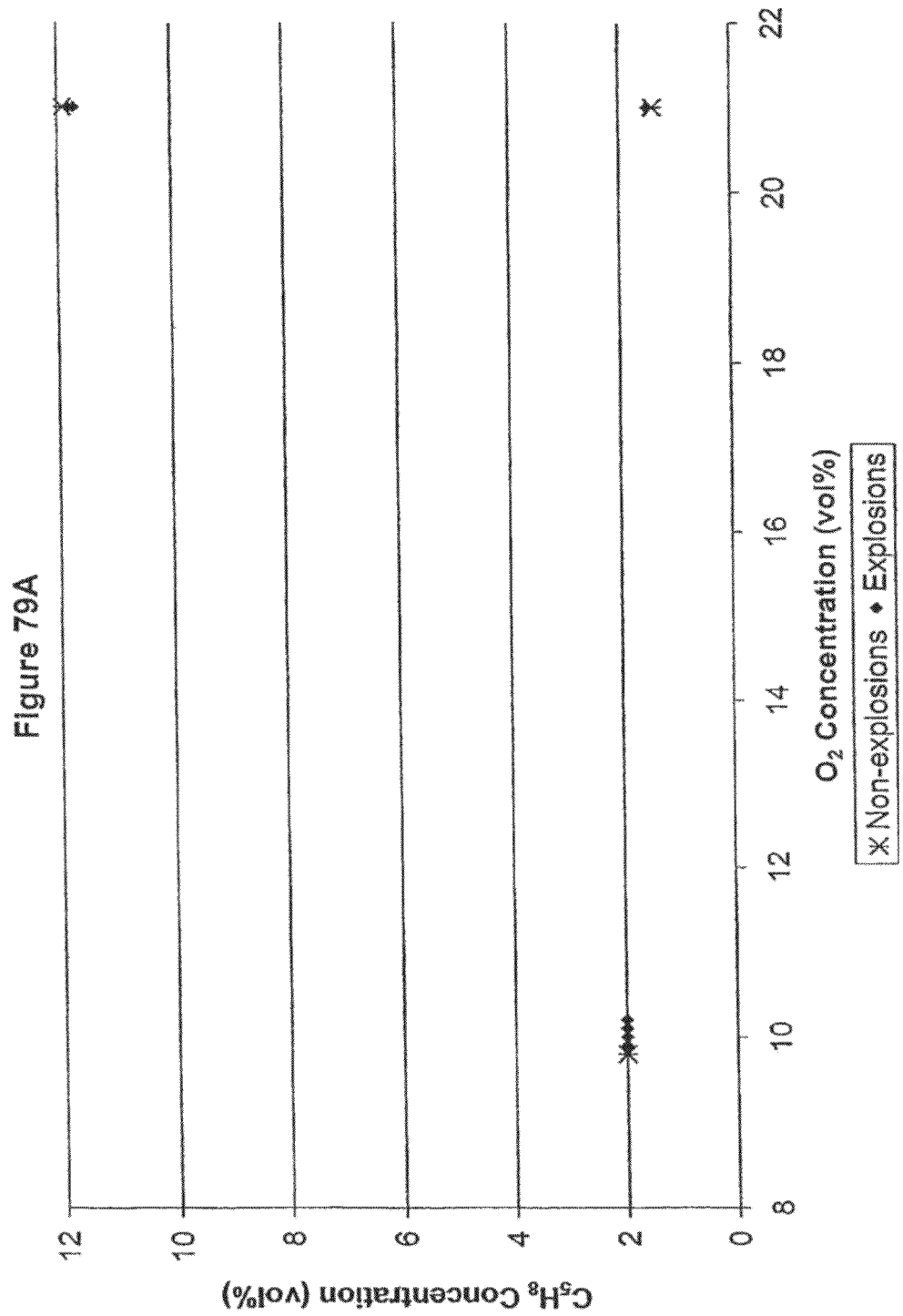
FIG. 79A is a graph of the flammability curve for Test Series 2: 4% Steam, 0 psig, and 40° C.
Figure 79C:
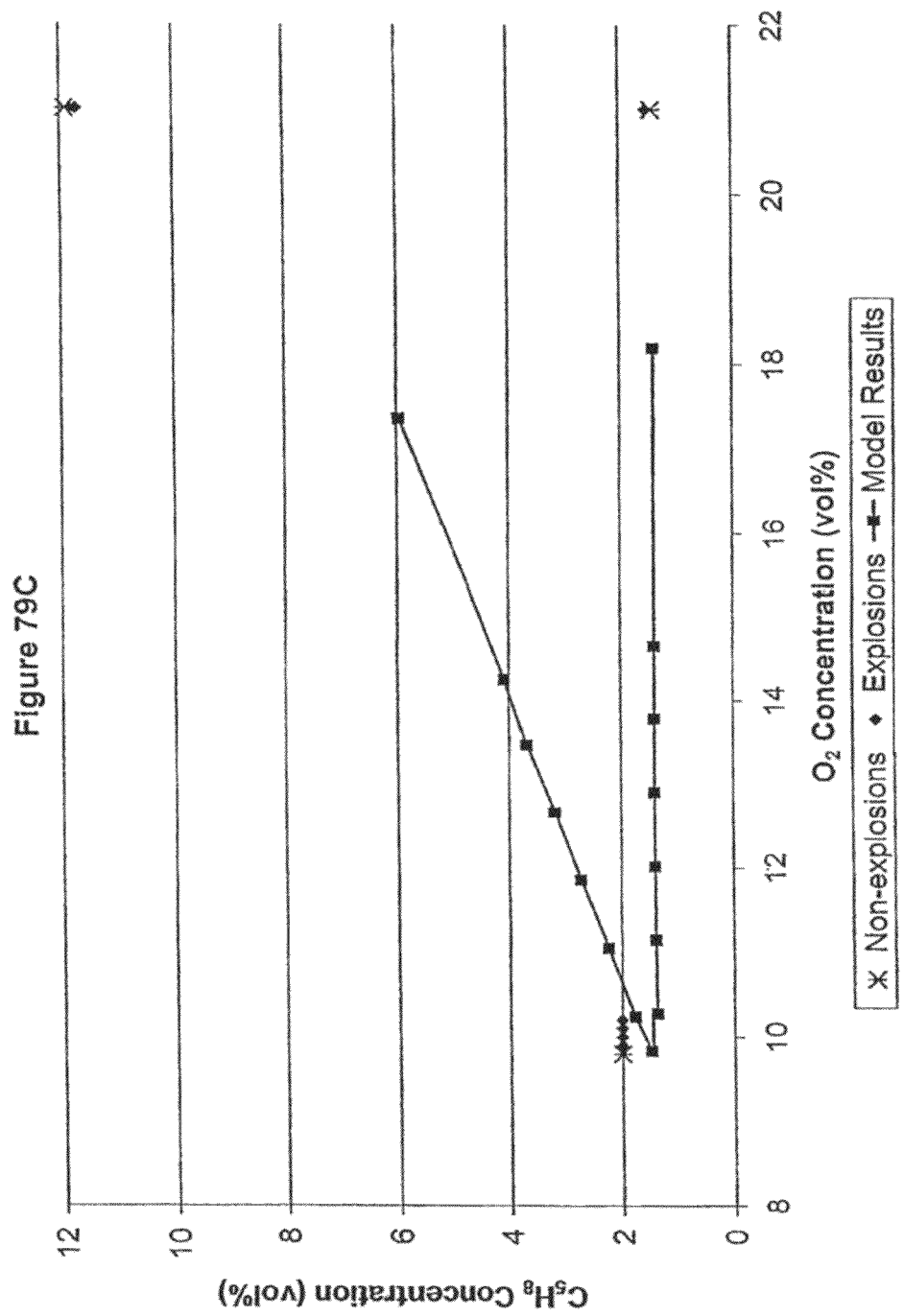
FIG. 79C is a graph of the flammability curve for Test Series 2 compared with the CAFT Model.

FIG. 79B summarizes the explosibility data points shown in FIG. 79A. FIG. 79C is a comparison of the experimental data with the CAFT model predicted flammability envelope. The model agrees very well with the experimental data. Discrepancies may be due to the same factors described in Series 1

V. Calculation of Flammability Limits of Isoprene in Air at 3 Atmospheres of Pressure The methods described in Example 12, parts I to IV were also used to calculate the flammability limits of isoprene at an absolute system pressure of 3 atmospheres and 40° C. These results were compared to those of Example 12, parts I to IV at an absolute system pressure of 1 atmosphere and 40° C. This higher pressure was tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, particular with respect to the calculation of flammability limits).

Figure 82:
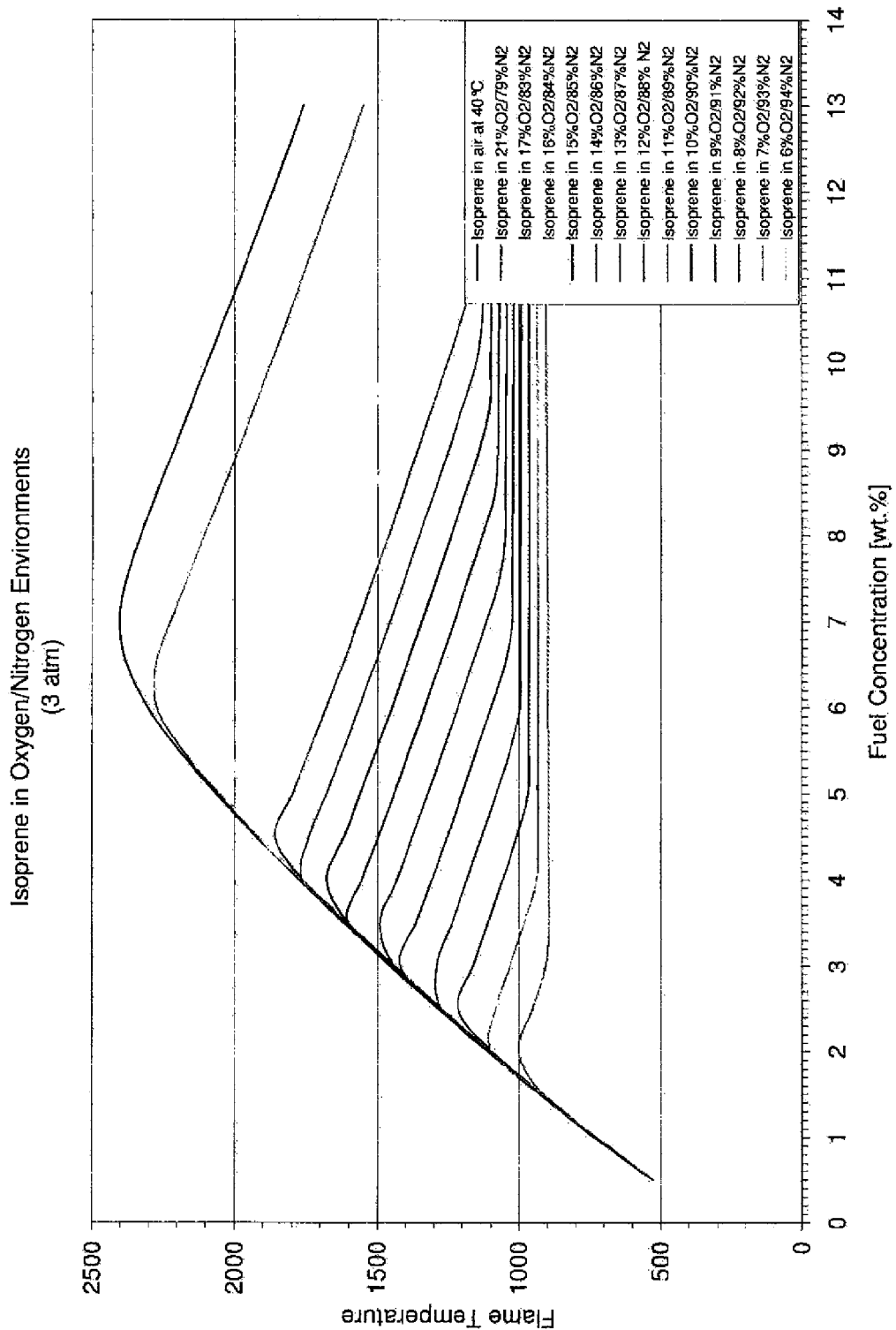
FIG. 82 is a graph of the calculated adiabatic flame temperature plotted as a function of fuel concentration for various nitrogen/oxygen ratios at 3 atmospheres of pressure.
Figure 83:
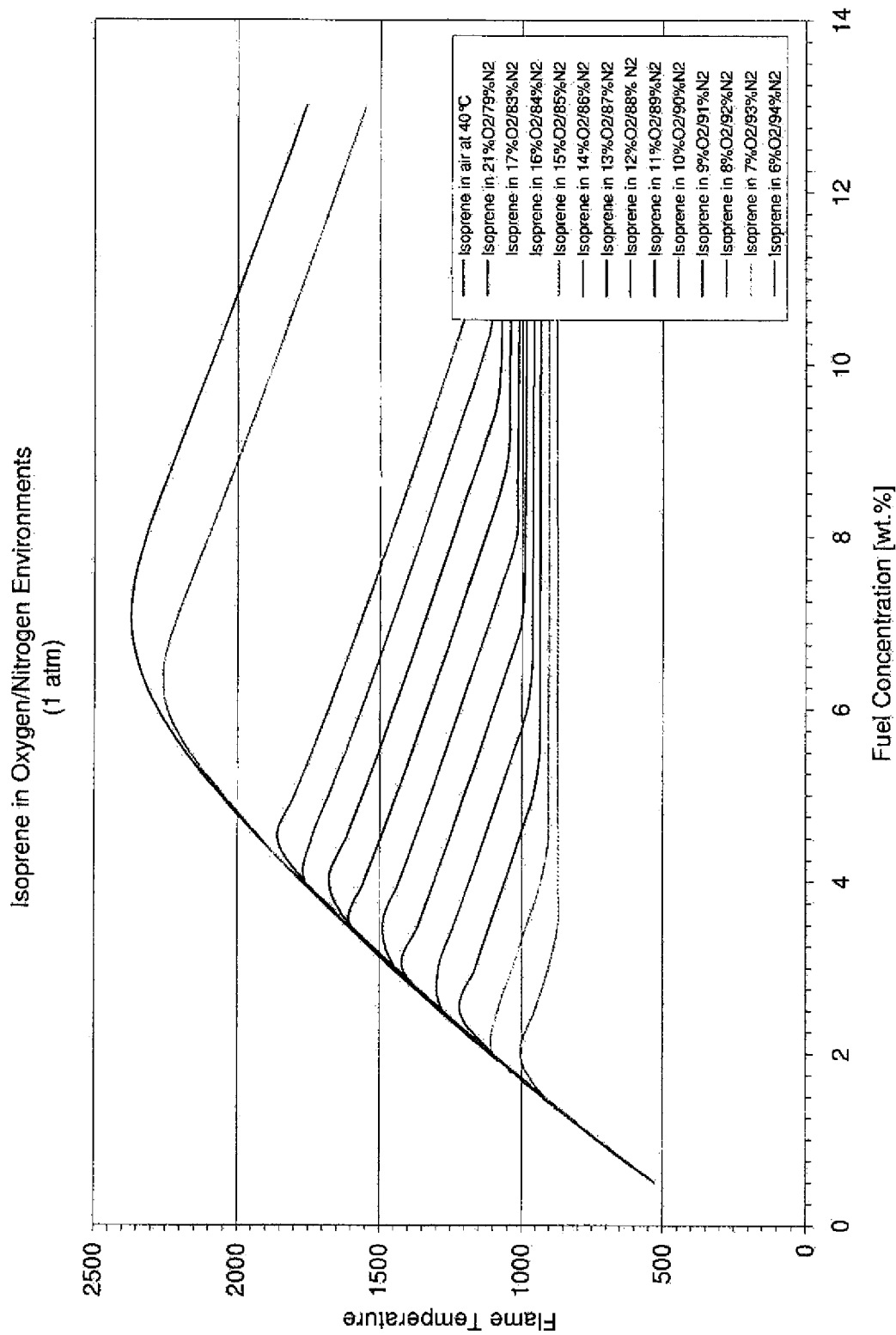
FIG. 83 is a graph of the calculated adiabatic flame temperature plotted as a function of fuel concentration for various nitrogen/oxygen ratios at 1 atmosphere of pressure.
Figure 84:
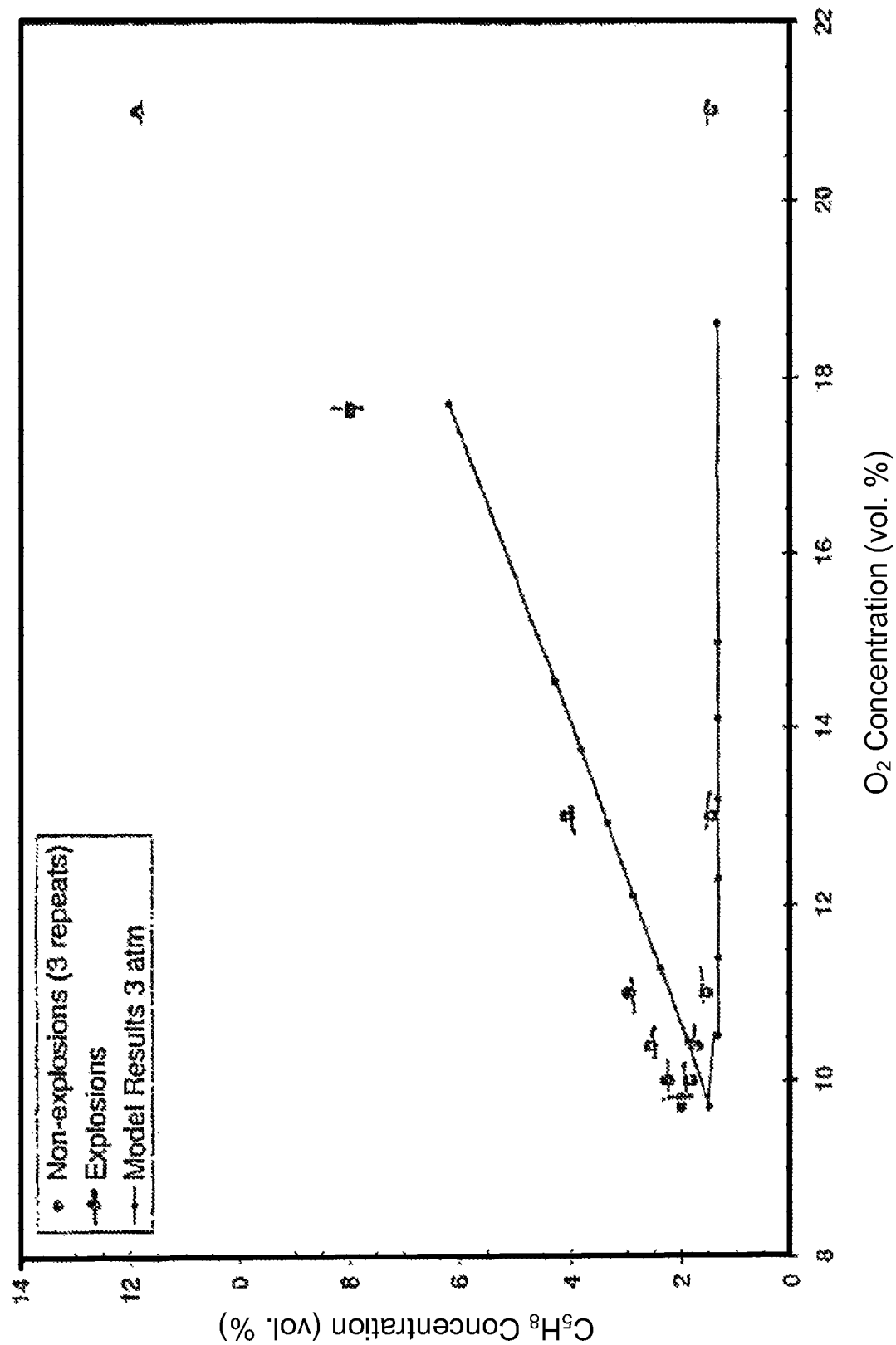
FIG. 84 is a graph of the flammability envelope constructed using data from FIG. 82 and following the methodology described in Example 12. The experimental data points (circles) are from tests described herein that were conducted at 1 atmosphere initial system pressure.
Figure 85:
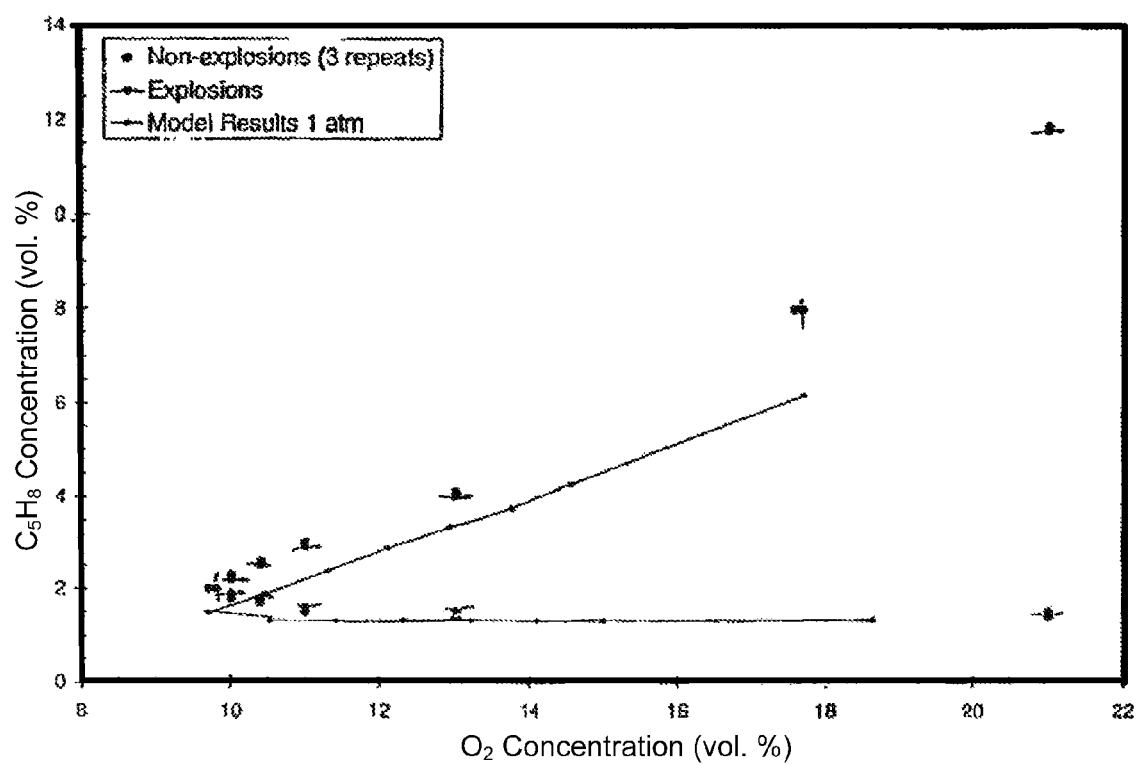
FIG. 85 is a graph of the flammability envelope constructed using data from FIG. 83 and following the methodology described in Example 12. The experimental data points (circles) are from tests described herein that were conducted at 1 atmosphere initial system pressure.

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model was developed for the flammability envelope of the isoprene/oxygen/nitrogen/water/carbon dioxide system at 40° C. and 0 psig. The CAFT model that was developed agreed well with the experimental data generated by the tests conducted in this work. The experimental results from Series 1 and 2 validated the model results from Series A and B.

Example 13

Archaeal Mevalonate Kinase Expression Constructs and Recombinant Bacterial Host Strains I. Construction of Plasmids Encoding Mevalonate Kinase.

Figure 87A:
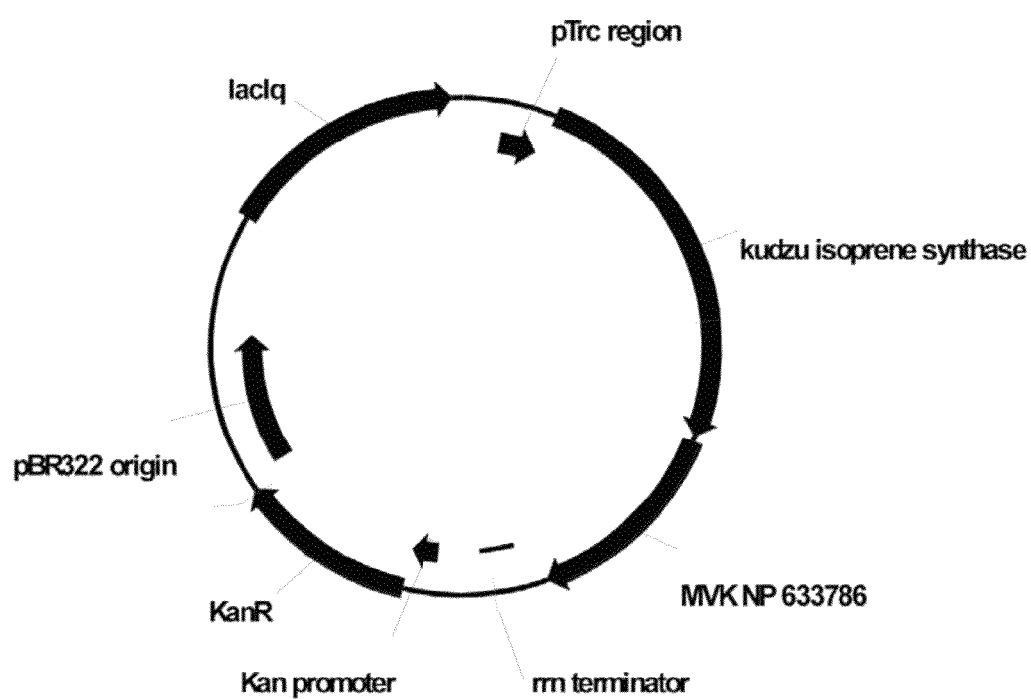
FIG. 87A provides a map of MCM382-pTrcKudzuMVK (mazei).

A construct encoding the *Methanosarcina mazei* lower MVA pathway (Accession numbers NC_003901.1, NC_003901.1, NC_003901.1, and NC_003901.1, which are each hereby incorporated by reference in their entireties) was synthesized with codon optimization for expression in *E. coli*. This construct is named *M. mazei* archaeal Lower Pathway operon (FIGS. 112A-112C) and encodes *M. mazei* MVK, decarboxylase, IPK, and IDI enzymes. The gene encoding MVK (Accession number NC_003901.1) was PCR amplified using primers MCM165 and MCM177 (Table 13-1) using the Strategene Herculase II Fusion kit according to the manufacturer's protocol using 30 cycles with an annealing temperature of 55° C. and extension time of 60 seconds. This amplicon was purified using a Qiagen PCR column and then digested at 37° C. in a 10 µL reaction with PmeI (in the presence of NEB buffer 4 and BSA). After one hour, NsiI and Roche buffer H were added for an additional hour at 37° C. The digested DNA was purified over a Qiagen PCR column and ligated to a similarly digested and purified plasmid MCM29 (also called pTrcKudzuKan) in an 11 uL reaction 5 uL Roche Quick Ligase buffer 1, 1 uL buffer 2, 1 uL plasmid, 3 uL amplicon, and 1 uL ligase (1 hour at room temperature). The ligation reaction was introduced into Invitrogen TOP10 cells and transformants selected on LA/kan50 plates incubated at 37° C. overnight. The MVK insert in the resulting plasmid MCM382 was sequenced (FIGS. 87A-87C).

TABLE 13-1

Oligonucleotides

| Primer (Description) | Sequence |
|---|---|
| MCM161 (*M. mazei* MVK for) | CACCATGGTATCCTGTTCTGCG (SEQ ID NO: 105) |
| MCM162 (*M. mazei* MVK rev) | TTAATCTACTTTCAGACCTTGC (SEQ ID NO: 106) |
| MCM165 (*M. mazei* MVK for w/RBS) | gcgaacgATGCATaaaggaggtaaaaaa acATGGTATCCTGTTCTGCGCCGGGTAA GATTTACCTG (SEQ ID NO: 107) |
| MCM177 (*M. mazei* MVK rev Pst) | gggcccgtttaaactttaactagact TTAATCTACTTTCAGACCTTGC (SEQ ID NO: 108) |

II. Creation of Strains Overexpressing Mevalonate Kinase and Isoprene Synthase.

Plasmid MCM382 was transformed into MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) that had been grown to midlog in LB medium and washed three times in iced, sterile water. 1 µL of DNA was added to 50 µL of cell suspension, and this mixture was electroporated in a 2 mm cuvette at 2.5 volts, 25 uFd followed immediately by recovery in 500 µL LB medium for one hour at 37° C. Transformant was selected on LA/kan50 and named MCM391. Plasmid MCM82 was introduced into this strain by the same electroporation protocol followed by selection on LA/kan50/spec50. The resulting strain MCM401 contains a cmp-marked chromosomal construct gi1.2KKDyI, kan-marked plasmid MCM382, and spec-marked plasmid MCM82 (which is pCL PtrcUpperPathway encoding *E. faecalis* mvaE and mvaS).

TABLE 13-2

Strains Overexpressing Mevalonate Kinase and Isoprene Synthase

| Strain | Genotype |
|---|---|
| MCM382 | *E. coli* BL21 (lambdaDE3) pTrcKudzuMVK (*M. mazei*) GI1.2KKDyI |
| MCM391 | MCM331 pTrcKudzuMVK (*M. mazei*) |
| MCM401 | MCM331 pTrcKudzuMVK (*M. mazei*) pCLPtrcUpperpathway |
| MCM396 | MCM333 pTrcKudzuMVK (*M. mazei*) |
| MCM406 | MCM333 pTrcKudzuMVK (*M. mazei*) pCLPtrcUpperpathway |

III. Construction of Plasmid MCM376—MVK from *M. mazei* Archeal Lower in pET200D.

Figure 86A:
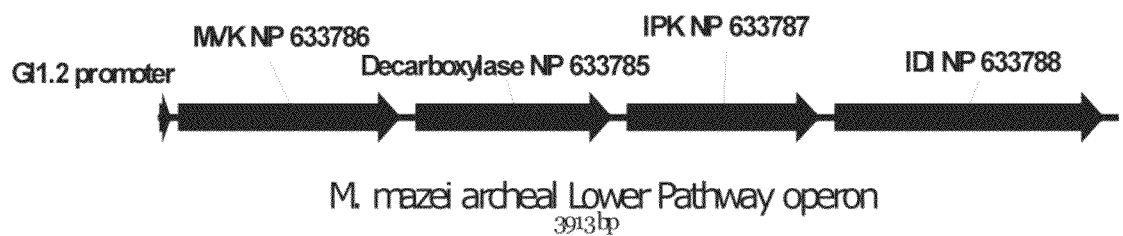
FIG. 86A provides a map of the *M. mazei* archeal lower pathway operon.
Figure 88A:
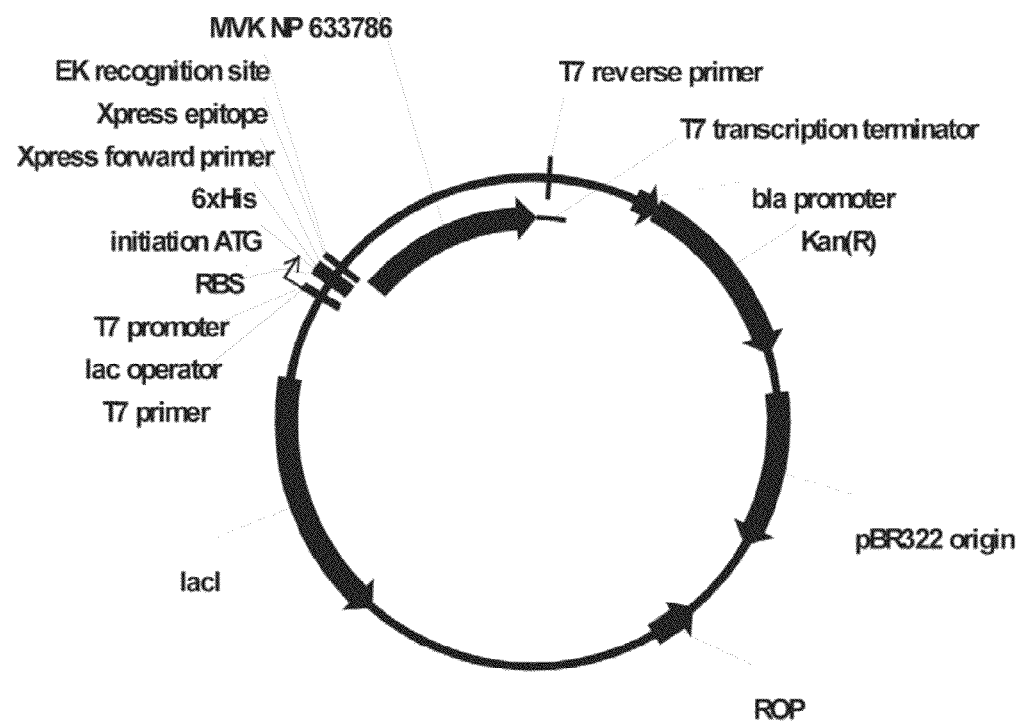
FIG. 88A provides a map of MCM376-MVK from *M. mazei* archeal Lowerin pET200D.

The MVK ORF from the *M. mazei* archeal Lower Pathway operon (FIGS. 86A-86C) was PCR amplified using primers MCM161 and MCM162 (Table 13-1) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00; 30 cycles of 94° C. for 0:30, 55° C. for 0:30; and 68° C. for 1:15; and then 72° C. for 7:00, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 88A-88C).

V. Creation of Expression Strain MCM378.

Plasmid MCM376 was transformed into Invitrogen BL21 (DE3) pLysS cells according to the manufacturer's protocol. Transformant MCM378 was selected on LA/kan50.

Example 14

Production of Isoprene by E. coli Expressing the Upper and Integrated Lower MVA Pathway, Mevalonate Kinase from M. mazei, and Isoprene Synthase from Kudzu Medium Recipe (per liter fermentation medium): Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution: 1000× Modified Trace Metal Solution contained citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) E. coli cells containing the upper mevalonic acid (MVA) pathway (pCL PtrcUpperPathway encoding E. faecalis mvaE and mvaS), the integrated lower MVA pathway (gi1.2KKDyI encoding S. cerevisiae mevalonate kinase, mevalonate phosphate kinase, mevalonate pyrophosphate decarboxylase, and IPP isomerase), and high expression of mevalonate kinase from M. mazei and isoprene synthase from Kudzu (pTrcKudzuMVK(M. mazei)). This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to innoculate 5-L of cell medium in the 15-L bioreactor. The liquid volume increases throughout the fermentation (such as to approximately 10 liters).

Figure 89A:
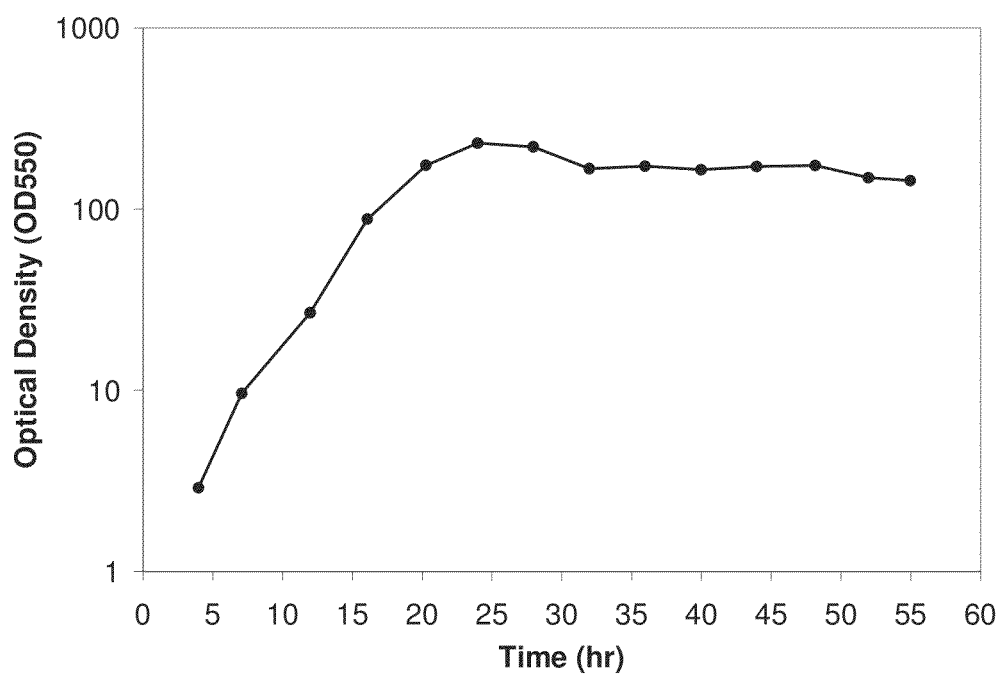
FIG. 89A provides a time course of optical density within the 15-L bioreactor fed with glucose.
Figure 89B:
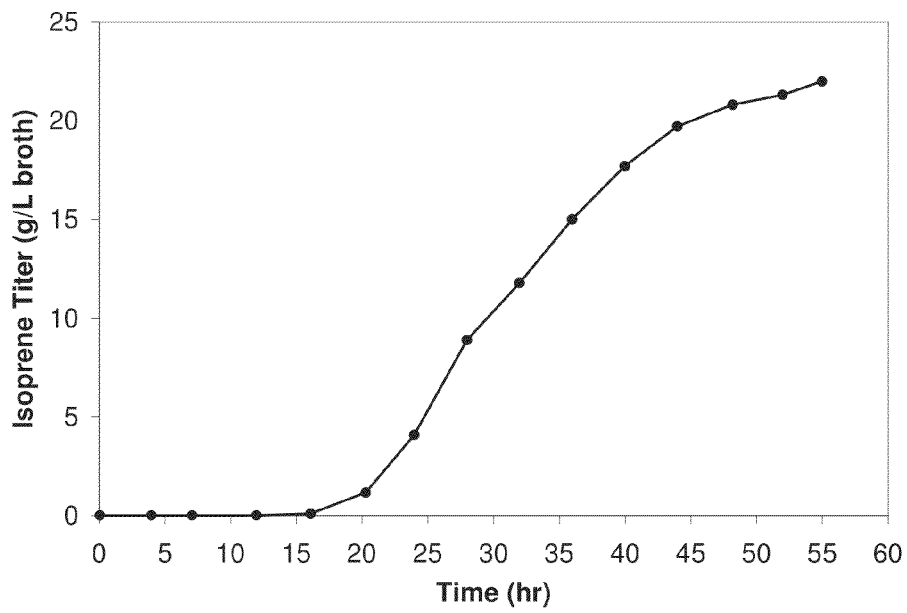
FIG. 89B provides a time course of isoprene titer within the 15-L bioreactor fed with glucose, in which titer is defined as the amount of isoprene produced per liter of fermentation broth.
Figure 89C:
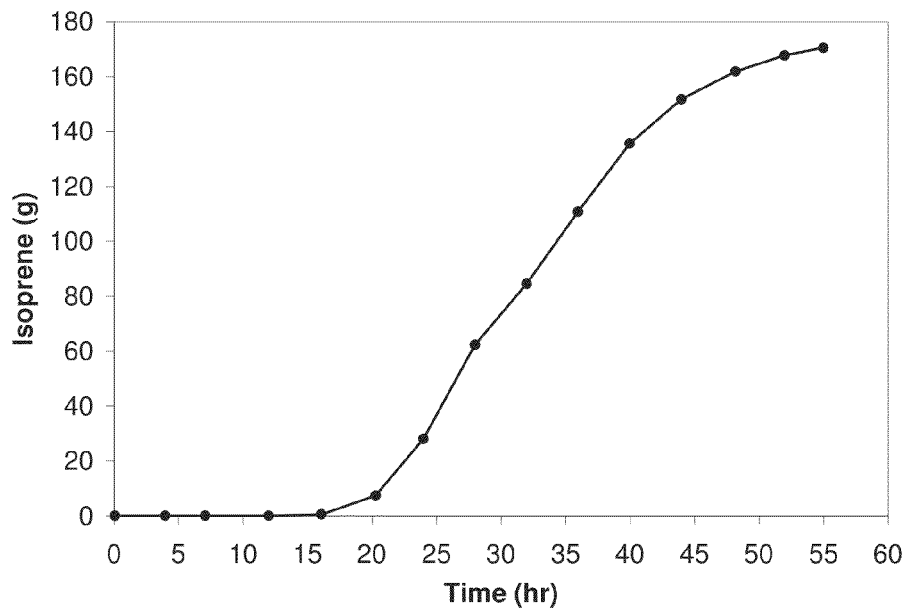
FIG. 89C provides a time course of total isoprene produced from the 15-L bioreactor fed with glucose.
Figure 91:
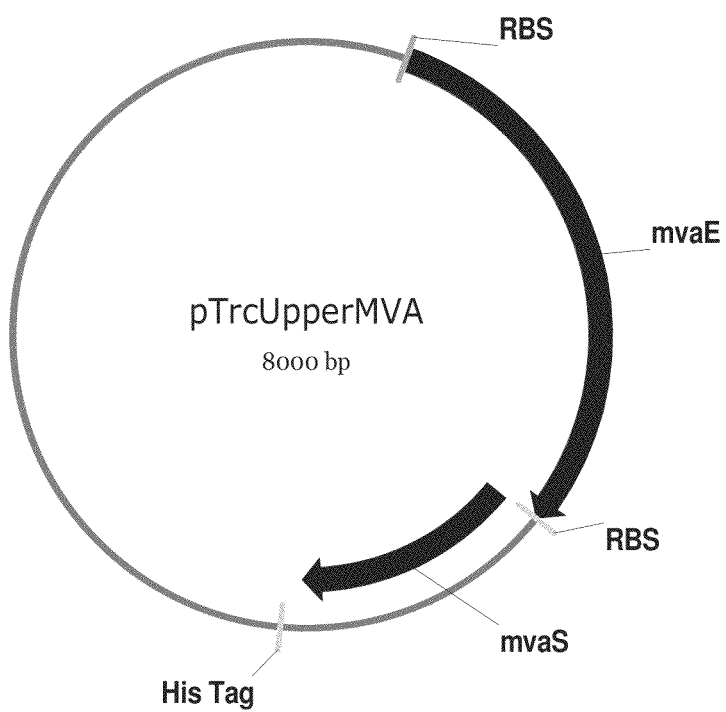
FIG. 91 is a map of pTrcHis2AUpperPathway (also called pTrcUpperMVA).

Glucose was fed at an exponential rate until cells reached the stationary phase. After this time the glucose feed was decreased to meet metabolic demands. The total amount of glucose delivered to the bioreactor during the 55 hour fermentation was 2.2 kg. Induction was achieved by adding IPTG. The IPTG concentration was brought to 51 uM when the optical density at 550 nm ($OD_{550}$) reached a value of 10. In addition to the IPTG spike, at $OD_{550}$=10 a constant feed began and delivered 164 mg of IPTG over 18 hours. The $OD_{550}$ profile within the bioreactor over time is shown in FIG. 89A. The isoprene level in the off gas from the bioreactor was determined using a Hiden mass spectrometer. The isoprene titer increased over the course of the fermentation to a final value of 22.0 g/L as shown in FIG. 89B. The total amount of isoprene produced during the 55 hour fermentation was 170.5 g and the time course of production is shown in FIG. 89C. The molar yield of utilized carbon that went into producing isoprene during fermentation was 16.6%. The weight percent yield of isoprene from glucose over the entire fermentation was 7.7%.

Example 15

Determination of Carbon Dioxide and Isoprene Yields from Various Feedstocks

As described herein, the maximum possible yield of isoprene on various carbon sources has been determined. Interestingly, the isoprene yield from nontraditional carbon sources such as alcohol (e.g., methanol, ethanol, etc.), glycerol, lipids/oils, proteins, and recycled cell mass, is higher than that from sugars.

TABLE 15-1

Carbon Dioxide and Isoprene Yield from Various Feedstocks

| Carbon Source | Reaction | $CO_2$/Isoprene |
|---|---|---|
| Sugar | $7C_6H_{12}O_6 \rightarrow 6C_5H_8 + 12CO_2 + 18H_2O$ | 2.0 |
| Glycerol | $2C_3H_8O_3 \rightarrow C_5H_8 + CO_2 + 4H_2O$ | 1.0 |
| Oil | $C_{57}H_{110}O_6 + 1.214CO_2 \rightarrow 11.643C_5H_8 + 8.429H_2O$ | 0 |
| Sugar + Oil | $0.71C_6H_{12}O_6 + C_{57}H_{110}O_6 \rightarrow 12.25C_5H_8 + 10.25H_2O$ | 0 |
| Cell mass | $7C_6H_{10.8}O_3N_{1.2} \rightarrow 0.9C_5H_8 + 1.5CO_2 + 1.2NH_3$ | 1.7 |
| Protein | $C_{235}H_{368}O_{75}N_{67} + 53.214H_2O \rightarrow 34.179C_5H_8 + 64.107CO_2 + 67NH_3$ | 1.9 |
| Methanol | $14CH_4O + CO_2 \rightarrow 3C_5H_8 + 16H_2O$ | 0 |

Based on the reactions listed above, the theoretical maximum isoprene yield potential of various carbon sources was determined. Carbon sources with a redox state (measure of reduced-oxidized extent of the chemical form) closer to that of isoprene (redox state 5.6) have higher isoprene yield potentials. Yield potential is defined as grams of isoprene formed per gram of carbon source.

TABLE 15-2

Maximum Isoprene Yield from Various Feedstocks

| Carbon Source | Chemical Formula | Redox | Yield Potential |
|---|---|---|---|
| Glucose or Fructose | $C_6H_{12}O_6$ | 4 | 32% |
| Xylose or Arabinose | $C_5H_{10}O_5$ | 4 | 32% |
| Glycerol | $C_3H_8O_3$ | 4.7 | 37% |
| Plant Oil | $C_{57}H_{110}O_6$ | 5.7 | 89% |
| Sugar + Oil | $C_6H_{12}O_6 + C_{57}H_{110}O_6$ | 5.6 | 82% |
| Cell mass | $C_6H_{10.8}O_3N_{1.2}$ | 4.2 | 41% |
| Protein | $C_{4.4}H_{6.9}O_{1.4}N_{1.25}$ | 4.1 | 44% |
| Methanol | $CH_4O$ | 6.0 | 46% |

Example 16

Relative Reduction in Carbon Dioxide Emission by Biological Production of Isoprene from Glycerol This example describes the determination of the ratio between emitted carbon dioxide and produced isoprene in recombinant *E. coli* harboring the mevalonic acid pathway and isoprene synthase. The host strain used was MCM127: BL21 (DE3) transformed with plasmids pCL-Upper, and pTrcKKDyIkIS. However, the compositions and methods of the present invention for reducing carbone dioxide emission in biological processes for isoprene production are not limited to the use of this particular cell line. Other suitable compositions and methods for producing isoprene are provided by U.S. Application No. 61/134,094, filed Jul. 2, 2008, herein incorporated by reference in its entirety. As detailed below, a significant reduction in the amount of carbon dioxide released per amount of isoprene produced is achieved by growing the bacterial host cells on glycerol instead of glucose.

Media Recipe (per liter fermentation media): $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)2SO_4$ 3.2 g, yeast extract 1 g, 1000× Trace Metal Solution 1 ml. All of the components were added together and dissolved in $diH_2O$. The pH was adjusted to 6.8 with ammonium hydroxide (30%) and brought to volume. Media was filter sterilized with a 0.22 micron vacuum filter. Either glucose or glycerol was added to the media, so that a final concentration of carbon from either glycerol or glucose in the media equaled 0.0833 mol carbon/L. Antibiotics were added after sterilization and pH adjustment.

1000× Trace Metal Solution (per liter fermentation media): citric acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in diH2O, pH to 3.0 with HCl/NaOH, and then brought to volume and filter sterilized with a 0.22 micron filter.

Isoprene production and carbon dioxide emitted was analyzed by growing the recombinant bacteria in 100 mL bioreactors with a 20 mL working volume at a temperature of 30° C. An inoculum of *E. coli* strain MCM127 taken from a frozen vial was streaked onto an LB broth agar plate (with antibiotics) and incubated at 30° C. A single colony was inoculated into media containing either glucose or glycerol as carbon source and grown overnight at 30° C. The bacteria were diluted into 20 mL of media to reach an optical density of 0.05 measured at 550 nm. The media contained either glucose or glycerol as the carbon source at concentrations so that an equal amount of carbon was present in both carbon sources (0.0833 mol carbon/L). The 100 mL bioreactors were sealed and air was pumped through at a rate of 8 mL/min. Adequate agitation of the media was obtained by stirring magnetic bars at 600 rpm. The off-gas from the bioreactors was analyzed using an on-line Hiden HPR-20 mass spectrometer. Masses corresponding to isoprene, carbon dioxide and other gasses naturally occurring in air were monitored. Concentration of isoprene and carbon dioxide was calculated as percentage of the off-gas. Accumulated isoprene and carbon dioxide was calculated by summing the concentration (in percent) of the respective gasses over time. Atmospheric carbon dioxide was subtracted from the total carbon dioxide in order to estimate the carbon dioxide released due to metabolic activity.

Isoprene production and carbon dioxide release from a strain expressing the full mevalonic acid (MVA) pathway and kudzu isoprene synthase (MCM127) was compared during growth in media containing either glycerol or glucose as a carbon source in 100 mL bioreactors. The bacteria were grown in duplicate in each media to an optical density of 0.4 measured at 550 nm. Expression of enzymes of the MVA pathway and of kudzu isoprene synthase was induced by adding isopropyl-beta-D-1-thiogalactopyranoside (IPTG) to a final concentration of 50 µM. The constitution in the off-gas was measured using online mass spectrometry during the course of the experiment (20 hours). This analysis revealed a significant production of isoprene and release of carbon dioxide during growth on the two different carbon sources (FIGS. 112A and 112B). The percentage of isoprene in the off-gas during growth on glycerol was significantly higher than during growth on glucose. Analysis of carbon dioxide in the off-gas from the bioreactors, which is a measure of metabolic activity, indicates that metabolic activity was independent from IPTG induction and isoprene production.

Calculation of the accumulated amount of isoprene and carbon dioxide (by adding the percent of the respective gasses in the off-gas released over time during the experiment) revealed that bacteria grown on glycerol produced significantly more isoprene (average of 0.122) when compared to bacteria grown on glucose (average of 0.026). Interestingly, only a small difference in the amount of carbon dioxide released during growth on the two different carbon sources (27.0 versus 24.3 during growth on glycerol and glucose respectively) was observed. However, calculation of the difference in the amount of carbon dioxide released per amount of isoprene produced as a consequence of growth on glucose versus growth on glycerol, showed that 4.2-fold less carbon dioxide was released during production of the same amount of isoprene when the bacteria were grown on glycerol as compared to glucose. This indicates that carbon source selection provides the means to significantly reduce carbon dioxide emission during biological production of isoprene.

TABLE 16-1

Compounds Produced During Growth of MCM127 On Media Containing Either Glycerol Or Glucose

| Carbon Source | $CO_2$ (%) | Isoprene (%) | $CO_2$/ Isoprene | Average $(CO_2/Isoprene)/$ $(CO_2/Isoprene)_{Glycerol}$ |
|---|---|---|---|---|
| Glycerol | 27.0 | 0.105 | 257.4 | 1.0 |
| Glycerol | 26.9 | 0.139 | 193.1 | |
| Glucose | 24.6 | 0.024 | 1039.2 | 4.2 |
| Glucose | 24.0 | 0.028 | 844.1 | |

Example 17

Reduction of Carbon Dioxide Emission by Biological Production of Isoprene from Methanol As described in Example 15, the maximum potential isoprene yield from methanol was determined to be higher than the maximum potential isoprene yield from C5 and C6 sugars. Methanol for use in isoprene production can be obtained from carbon sources such as biomass, coal, natural gas, and petroleum. In addition, hydrogen produced by solar, wind, and geothermal energy sources can be used as a supplement to these carbon sources, for enhanced production of methanol. Further supplementation of methanol with sugar can increase the yield of isoprene obtained during fermentation of engineered microorganisms.

I. Recycle $CO_2$ via $H_2$ from Alternate Energy Sources to Produce Methanol

A process which combines chemical and biological catalysis is advantageous for production of isoprene from carbon dioxide:

Carbon dioxide: $CO_2+3\ H_2 \rightarrow CH_3OH+H_2O$ (Chemical catalysis)

Ideal process: $14\ CH_3OH+CO_2 \rightarrow 3\ C_5H_8+16\ H_2O$ (Biocatalysis)

Commercial process: $16\ CH_3OH+3\ O_2 \rightarrow 3\ C_5H_8+CO_2+20\ H_2O$

Accordingly, this process recycles more than 3 lb $CO_2$ per lb isoprene by using 0.4-0.5 lb $H_2$, (e.g., $CO_2$ and $H_2$ are raw materials for isoprene production).

II. Recycle $CO_2$ via $CH_3OH$ from Biomass ($CH_{1.4}O_{0.6}$) and Supplemental Sources Such as Coal, Natural Gas and Petroleum to Produce Methanol A process which combines chemical and biological catalysis is advantageous for production of isoprene from biomass:

Biomass: $CH_{1.4}O_{0.6}+0.3\ H_2+0.2\ O_2 \rightarrow CH_3OH$ (Chemical catalysis)

Ideal process: $14\ CH_3OH+CO_2 \rightarrow 3\ C_5H_8+16\ H_2O$ (Biocatalysis)

Commercial process: $16\ CH_3OH+3\ O_2 \rightarrow 3\ C_5H_8+CO_2+20\ H_2O$

Electrolysis of water using alternate energy meets the demand for both $H_2$ and $O_2$, resulting in a substantially higher potential isoprene mass yield from biomass. Even if biomass cost is as high as $150/ton, isoprene production via this process would cost less than 30 cents/lb (equivalent to less than $2/gallon gasoline). Thus, isoprene is obtainable more cheaply via this process.

III. Rational Design of Metabolic Pathways for Production of Isoprene from Methanol via Biological Catalysis For instance, isoprene yield potential on methanol is estimated as shown below. In order to tap methanol yield potential, multiple metabolic pathways are combined: methanol conversion to acetic acid (Ace); acetic acid conversion to mevalonic acid; and mevalonic acid conversion to isoprene via an isoprene synthase catalyzed reaction. The reactions are as follows:

$4\ CH_3OH+2\ CO_2 \rightarrow 3\ CH_3COOH\ (Ace)+2\ H_2O$     (1):

$3\ Ace+3\ ATP \rightarrow 3\ AcP \rightarrow 3\ AcCoA+3\ Pi$     (2):

$3\ AcCoA+3\ ATP+2\ NAD(P)H \rightarrow C_5H_8\ (Isoprene)+CO_2$     (3):

$3\ Ace+6\ ATP+2\ NAD(P)H\ Isoprene+CO_2$     (4):

$Ace+O_2 \rightarrow 2\ NAD(P)H+6\ ATP$     (5):

$4\ Ace+O_2 \rightarrow Isoprene+3\ CO_2+4\ H_2O$     (6):

$4(1)+3(6): 16\ CH_3OH+3\ O2 \rightarrow 3\ Isoprene+CO_2+20\ H_2O$

Overall: $16\ CH_4O+3\ O_2 \rightarrow 3\ Isoprene+CO_2+20\ H_2O$

As such, it is estimated that an engineered organism could yield up to 40% isoprene from a methanol feedstock, whereas maximum yield on a sugar feedstock is estimated to be only 25%.

The methylotrophic yeast, *Pichia pastoris*, is a suitable eukaryotic host for conversion of methanol to isoprene. In one embodiment the *P. pastoris* would be mut+ so that utilization of methanol is fully enabled. Suitable promoters to drive isoprene synthase expression include the constitutive GAP promoter, and the methanol-induced AOX1 promoter. In another embodiment a phosphate-limited fermentation process is developed with isoprene synthase expression driven by a phosphate-starvation inducible promoter such as the Pho5 promoter. Use of the Pho5 promoter at limiting phosphate levels, after biomass had accumulated, would induce production of isoprene. Fermentations are then fed methanol, or a combination of glycerol and methanol. An online methanol sensor system is used to track the concentration of methanol in such a fermentation system.

Similarly, *Methylophilus methylotrophus* is a suitable prokaryotic host for conversion of methanol to isoprene (See, U.S. Pat. No. 4,652,527). The AS-1 (NCIB 10515; ATCC 53528) strain of *M. methylotrophus* was grown aerobically in an aqueous fermentation medium containing essential nutrients. This strain metabolized both methanol and glucose as carbon sources.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate Synthase Nucleic Acids and Polypeptides ATH: AT3G21500(DXPS1) AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479

ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Pat1_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csa1_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMCO352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)

MMS: mma_0331
NEU: NE1161(dxs)
NET: Neut_1501
NMU: Nmu1_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC 1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)

CCR: CC_2068
SIL: SP00247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)

SWO: Swo1_0582
CSC: Csac_1853
TTE: TTE1298(dxs)
MTA: Moth_1511
MPE: MYPE730
MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)
ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary acetyl-CoA-acetyltransferase Nucleic Acids and Polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639(MGC81256) 444457(MGC83664)
XTR: 394562(acat2)
DRE: 30643(acat2)
SPU: 759502(LOC759502)
DME: Dme1_CG10932 Dme1_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165C
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406

CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: S3052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)
XAC: XAC1348(atoB)
XOO: XOO1881(atoB)
XOM: XOO_1778(XOO1778)
VCH: VCA0690
VCO: VC0395_0630
VVU: VV2_0494 VV2_0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14_38630(atoB)
PPU: PP_2051(atoB) PP_2215(fadAx) PP_3754 PP_4636
PPF: Pput_2009 Pput_2403 Pput_3523 Pput_4498
PST: PSPTO_0957(phbA-1) PSPTO_3164(phbA-2)
PSB: Psyr_0824 Psyr_3031
PSP: PSPPH_0850(phbA1) PSPPH_2209(phbA2)
PFL: PFL_1478(atoB-2) PFL_2321 PFL_3066 PFL_4330(atoB-2) PFL_5283
PFO: Pfl_1269 Pfl_1739 Pfl_2074 Pfl_2868
PEN: PSEEN3197 PSEEN3547(fadAx) PSEEN4635(phbA)
PMY: Pmen_1138 Pmen_2036 Pmen_3597 Pmen_3662 Pmen_3820
PAR: Psyc_0252 Psyc_1169
PCR: Pcryo_0278 Pcryo_1236 Pcryo_1260
PRW: PsycPRwf_2011
ACI: ACIAD0694 ACIAD1612 ACIAD2516(atoB)
SON: SO_1677(atoB)
SDN: Sden_1943
SFR: Sfri_1338 Sfri_2063
SAZ: Sama_1375
SBL: Sbal_1495
SBM: Shew185_1489
SBN: Sbal195_1525
SLO: Shew_1667 Shew_2858
SPC: Sputcn32_1397
SSE: Ssed_1473 Ssed_3533
SPL: Spea_2783
SHE: Shewmr4_2597
SHM: Shewmr7_2664
SHN: Shewana3_2771
SHW: Sputw3181_2704
ILO: IL0872
CPS: CPS_1605 CPS_2626
PHA: PSHAa0908 PSHAa1454(atoB) PSHAa1586(atoB)
PAT: Patl_2923
SDE: Sde_3149
PIN: Ping_0659 Ping_2401
MAQ: Maqu_2117 Maqu_2489 Maqu_2696 Maqu_3162
CBU: CBU_0974
LPN: lpg1825(atoB)
LPF: lpl1789
LPP: lpp1788
NOC: Noc_1891
AEH: Mlg_0688 Mlg_2706
HHA: Hhal_1685
HCH: HCH_05299
CSA: Csal_0301 Csal_3068
ABO: ABO_0648(fadAx)
MMW: Mmwyl1_0073 Mmwyl1_3021 Mmwyl1_3053 Mmwyl1_3097 Mmwyl1_4182
AHA: AHA_2143(atoB)
CVI: CV_2088(atoB) CV_2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet_0106 Rmet_1357 Rmet_1362 Rmet_5156
BMA: BMA1316 BMA1321(phbA) BMA1436
BMV: BMASAVP1_A1805(bktB) BMASAVP1_A1810(phbA)
BML: BMA10299_A0086(phbA) BMA10299_A0091
BMN: BMA10247_1076(bktB) BMA10247_1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808_0519 Bcep1808_1717 Bcep1808_2877 Bcep1808_3594 Bcep1808_4015 Bcep1808_5507 Bcep1808_5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330(phbA) BURPS1710b_2453(atoB-2)

BPL: BURPS1106A_2197(bktB) BURPS1106A_2202 (phbA)
BPD: BURPS668_2160(bktB) BURPS668_2165(phbA)
BTE: BTH_I2144 BTH_I2256 BTH_I2261
PNU: Pnuc_0927
BPE: BPO447 BP0668 BP2059
BPA: BPP0608 BPP1744 BPP3805 BPP4216 BPP4361
BBR: BB0614 BB3364 BB4250 BB4804 BB4947
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(th1A)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(th1A)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbB) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD 3105 RPD_3306
RPE: RPE 0168 RPE_0248 RPE 3827
NWI: Nwi_3060
XAU: Xaut_3108 Xaut_4665
CCR: CC_0510 CC_0894 CC_3462
SIL: SP00142(bktB) SP00326(phbA) SP00773 SP03408
SIT: TM1040_0067 TM1040_2790 TM1040_3026 TM1040_3735
RSP: RSP_0745 RSP_1354 RSP 3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala 3158
SWI: Swit_0632 Swit_0752 Swit_2893 Swit_3602 Swit_4887 Swit_5019 Swit_5309
ELI: ELI 01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(th1) BCZK5044(atoB)
BCY: Bcer98_2722 Bcer98_3865
BTK: BT9727_3379(mmgA) BT9727_3765(th1) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABCO345 ABC2989 ABC3617 ABC3891(mmgA)
BAY: RBAM_022450
BPU: BPUM_2374(yhfS) BPUM_2941 BPUM_3373
OIH: OB0676 OB0689 OB2632 OB3013
GKA: GK1658 GK3397
SAU: SA0342 SA0534(vraB)
SAV: SAV0354 SAV0576(vraB)
SAM: MW0330 MW0531(vraB)
SAR: SAR0351(th1) SAR0581
SAS: SAS0330 SAS0534
SAC: SACOL0426 SACOL0622(atoB)
SAB: SAB0304(th1) SAB0526
SAA: SAUSA300_0355 SAUSA300_0560(vraB)

SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: LJ1609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CB03200(thl)
CBE: Cbei_0411 Cbei_3630
CKL: CKL_3696(thlA1) CKL_3697(thlA2) CKL_3698(thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred 1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c(fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053

DGE: Dgeo_0755 Dgeo_1305 Dgeo_1441 Dgeo_1883
TTH: TTC0191 TTC0330
TTJ: TTHA0559
TME: Tme1_1134
FNO: Fnod_0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pis1_0029 Pis1_1301
PCL: Pca1_0781
PAS: Pars_0309 Pars_1071
CMA: Cmaq_1941

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS 1)
SSC: 397673(CH242-38B5.1)
GGA: 396379(HMGCS1)
XLA: 380091(hmgcs1) 447204(MGC80816)
DRE: 394060(hmgcs1)
SPU: 578259(L00578259)
DME: Dme1_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG 01026
ANI: AN4923.2
AFM: AFUA_3G10660 AFUA_8G07210
AOR: AO090003000611 AO090010000487
CNE: CNCO5080 CNG02670
UMA: UM05362.1
ECU: ECU10_0510
DDI: DDBDRAFT_0217522 DDB_0219924(hgsA)
TET: TTHERM_00691190
TBR: Tb927.8.6110
YPE: YP01457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)
LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy_0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363

LCA: LSEI_1785
LGA: LGAS_1372
LRE: Lreu_0676
PPE: PEPE_0868
EFA: EF1363
OOE: OEOE_0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)
HMA: rrnAC1740(mvaS)
HWA: HQ2868A(mvaB)
NPH: NP2608A(mvaB_1) NP4836A(mvaB_2)

Exemplary hydroxymethylglutaryl-CoA Reductase
Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dme1_CG10367(Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VCO395_0662
VVU: VV2_0117
VVY: VVA0625
VPA: VPA0968
VFI: VFA0841
PAT: Pat1_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PTO1143
PAB: PAB2106(mvaA)
PFU: PF1848
TKO: TK0914
RCI: RCIX1027(hmgA) RC1X376(hmgA)
APE: APE_1869
IHO: Igni_0476
HBU: Hbut_1531
SSO: SSO0531
STO: ST1352
SAI: Saci_1359
PAI: PAE2182
PIS: Pis1_0814
PCL: Pca1_1085
PAS: Pars_0796

Exemplary Mevalonate Kinase Nucleic Acids and Polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(L00585785)
DME: Dme1_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lpl2017
LPP: lpp2022
BBA: Bd1027(lmbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425 (mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PT01352
PHO: PH1625
PAB: PAB0372(mvk)
PFU: PF1637(mvk)
TKO: TK1474
RCI: LRC399(mvk)
APE: APE_2439
HBU: Hbut_0877
SSO: SSO0383
STO: ST2185
SAI: Saci_2365(mvk)
MSE: Msed_1602
PAI: PAE3108
PIS: Pis1_0467
PCL: Pca1_1835

Exemplary Phosphomevalonate Kinase Nucleic
Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO_0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244

Exemplary Diphosphomevalonate Decarboxylase
Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226

SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PTO0478 PTO1356
SSO: SSO2989
STO: ST0977
SAI: Saci_1245(mvd)
MSE: Msed_1576

Exemplary Isopentenyl Phosphate Kinases (IPK) Nucleic Acids and Polypeptides

*Methanobacterium thermoautotrophicum* gi|2621082
*Methanococcus jannaschii* DSM 2661 gi|1590842;
*Methanocaldococcus jannaschii* gi|1590842
*Methanothermobacter thermautotrophicus* gi|2621082
*Picrophilus torridus* DSM9790 (IG-57) gi|48477569
*Pyrococcus abyssi* gi|14520758
*Pyrococcus horikoshii* OT3 gi|3258052
*Archaeoglobus fulgidus* DSM4304 gi|2648231

Exemplary Isopentenyl-Diphosphate Delta-Isomerase (IDI) Nucleic Acids and Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(L00586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)

ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937
SSN: SSON_3042 SSON_3489(yhfK)
SBO: SBO_3103
SDY: SDY_3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428 (fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)

MTC: MT1787(idi)
MBO: Mb1774c(idi)
MBB: BCG_1784c(idi)
MPA: MAP3079c
MAV: MAV_3894(fni)
MSM: MSMEG_1057(fni) MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCgl2223(cgl2305)
CGB: cg2531(idi)
CEF: CE2207
CDI: DIP1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi) GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G (crt_2) VNG7060 VNG7149
HMA: rrnAC3484(idi)
HWA: HQ2772A(idiA) HQ2847A(idiB)
NPH: NP0360A(idiB_1) NP4826A(idiA) NP5124A(idiB_2)

TAC: Ta0102
TVO: TVN0179
PTO: PT00496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SSO0063
STO: ST2059
SAI: Saci_0091
MSE: Msed_2136
PAI: PAE0801
PIS: Pisl_1093
PCL: Pcal_0017
PAS: Pars_0051
TPE: Tpen_0272

Exemplary Isoprene Synthase Nucleic Acids and Polypeptides

Genbank Accession Nos.
AY341431
AY316691
AY279379
AJ457070
AY182241

We claim:

1. A cell culture comprising cells capable of producing isoprene, wherein said cell culture comprises:
   (a) recombinant cells comprising a heterologous nucleic acid that encodes an isoprene synthase polypeptide in operable combination with a promoter;
   (b) culture medium comprising one or more uncommon carbon sources; and
   (c) culture conditions comprising an inlet air flow rate of less than or equal to 0.4 volume(air)/volume (culture medium)/minute (vvm);
   wherein said cell culture produces isoprene and carbon dioxide and the ratio of carbon dioxide emitted per isoprene produced in off gas from the cell culture is less than 500.

2. The cell culture of claim 1, wherein the uncommon carbon source is selected from the group consisting of glycerol, cell mass, protein, alcohol, and plant-derived oil.

3. The cell culture of claim 1, wherein the cells further comprise one or more heterologous nucleic acids that encode for an MVA pathway enzyme or a DXP pathway enzyme.

4. The cells of claim 3, wherein the MVA pathway enzyme is mevalonate kinase.

5. The cells of claim 4, wherein the mevalonate kinase is selected from the group consisting of feedback-resistant mevalonate kinase, archaeal mevalonate kinase, *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, and *Streptomyces* mevalonate kinase polypeptide, *Streptomyces* CL190 mevalonate kinase polypeptide.

6. The cell culture of claim 1, wherein at least a portion of the cells maintain the isoprene synthase nucleic acid for at least or about 5, 10, 20, 40, 50, 60, 65, or more cell divisions in a continuous culture.

7. The cell culture of claim 1, wherein the isoprene synthase polypeptide is from *Pueraria* or *Populus* or a hybrid, *Populus alba×Populus tremula*.

8. The cell culture of claim 7, wherein the isoprene synthase polypeptide is selected from the group consisting of *Pueraria montana* or *Pueraria lobata, Populus tremuloides, Populus alba, Populus nigra*, and *Populus trichocarpa*.

9. The cell culture of claim 1, wherein the cells are gram-positive bacterial cells, *Streptomyces* cells, gram-negative bacterial cells, *Escherichia cells, Pantoea* cells, fungal cells, filamentous fungal cells, *Trichoderma* cells, *Aspergillus* cells, or yeast cells.

10. The cell culture of claim 9, wherein the cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Yarrowia lipolytica* and *Saccharomyces cerevisieae*.

11. A composition for producing isoprene comprising the cell culture of claim 1.

12. A method of producing isoprene, the method comprising:
(a) culturing cells of claim 1 in culture medium under conditions suitable for the production of isoprene, wherein the culture medium comprises one or more uncommon carbon sources and the cells comprise a heterologous nucleic acid that encodes an isoprene synthase polypeptide in operable combination with a promoter; and
(b) producing isoprene, wherein the ratio of carbon dioxide emitted per isoprene produced in off gas from the cultured cells is less than 500.

13. The method of claim 12 wherein the uncommon carbon source is selected from the group consisting of glycerol, cell mass, protein, alcohol, and plant-derived oil.

14. The method of claim 13, wherein the alcohol comprises methanol.

15. The method of claim 12, wherein the isoprene produced as a percentage of off gas from the cultured cells is greater than 0.03%.

16. The method of claim 12, further comprising recovering the isoprene.

* * * * *